United States Patent [19]

Feldman

[11] Patent Number: 4,967,372

[45] Date of Patent: Oct. 30, 1990

[54] AUTOMATIC ORIENTATION AND INTERACTIVE ADDRESSING OF DISPLAY

[75] Inventor: Alfred P. Feldman, Columbia, Md.

[73] Assignee: The United States of America as represented by the Department of Health and Human Services, Washington, D.C.

[21] Appl. No.: 863,981

[22] Filed: May 16, 1986

[51] Int. Cl.$^5$ .............................................. G06F 15/66
[52] U.S. Cl. .................................. 364/518; 340/721; 400/110
[58] Field of Search ...................... 364/518, 521, 522; 346/139 R; 340/703, 923; 400/110, 484; 382/44–47

[56] References Cited

U.S. PATENT DOCUMENTS

| | | | |
|---|---|---|---|
| 2,666,515 | 1/1954 | Brumhill et al. | 400/82 |
| 3,256,422 | 6/1966 | Meyer et al. | 235/454 |
| 3,267,852 | 8/1966 | Gordon | 101/399 |
| 3,358,804 | 12/1967 | Feldman | 400/80 |
| 3,559,208 | 1/1971 | Giugno et al. | 240/711 |
| 3,623,068 | 11/1971 | Horgan et al. | 340/789 |
| 3,678,497 | 7/1972 | Watson et al. | 340/324 A |
| 3,786,478 | 1/1974 | King, Jr. | 340/324 AD |
| 3,927,752 | 12/1975 | Jones et al. | 400/487 |
| 4,063,232 | 12/1977 | Fernald | 340/324 AD |
| 4,085,443 | 4/1978 | Dubois et al. | 364/900 |
| 4,195,338 | 3/1980 | Freeman | 364/200 |
| 4,205,391 | 5/1980 | Ulyanov et al. | 364/900 |
| 4,473,890 | 9/1984 | Araki | 364/900 |
| 4,476,462 | 10/1984 | Feldman | 340/711 |
| 4,656,603 | 4/1987 | Dunn | 364/521 X |

FOREIGN PATENT DOCUMENTS 627746 3/1936 Fed. Rep. of Germany .

OTHER PUBLICATIONS

A. Feldman, D. B. Holland, D. P. Hacobus "The Automatic Encoding of Chemical Structures", J. Chem. Doc. 3, 187 (1963), pp. 187–189.

J. M. Mullen "Atom-by-Atom Typewriter Input for Computerized Storage and Retrieval of Chemical Structures", J. Chem. Do., 7,88 (1967), pp. 88–93.

A. Feldman "A Chemical Teletype", J. Chem. Doc. 13, 53 (1973), pp. 53–56.

Primary Examiner—H. R. Herndon
Assistant Examiner—H. R. Herndon
Attorney, Agent, or Firm—Glenna Hendricks; Marc A. Miller

[57] ABSTRACT

Automatic orientation of predefined chemical structures in conjunction with a computer terminal employs respective protocols corresponding to a system state. The system states can include a chain state, ring state, library state, and retrieve state. Upon orientation, the object is attached according to a specified attachment command to a parent graph. The protocols corresponding to connection of the object to the parent includes rules regarding angles at which the structures can be attached to one another, and another protocol governs rules respecting rotation of the stored object through predetermined angles. Nodes of the object recalled are automatically provided with markers in alphabetic order from the most recently used marker corresponding to a letter of alphabet. Multiple alphabet sequences are used. Specification of position is indicated by inputting the lower case letter of the alphabet corresponding to the location desired. Bonds can be specified between two markers.

21 Claims, 9 Drawing Sheets

| (NOT OBTAINED) | (OBTAINED) | (NOT OBTAINED) |
| --- | --- | --- |
| FIG. 5(a) | FIG. 5(b) | FIG. 5(c) |

| PARENT GRAPH | ENTER * | RESULT | |
| --- | --- | --- | --- |
| + | 3 | △ | } FIG. 7(a) |
| △₊ | 03 | △▽ | } FIG. 7(b) |
| △ | 03 | ⋈ | } FIG. 7(c) |
| △ | 03 | ▽△ | } FIG. 7(d) |

* FIRST DIGIT = $N_3$ CONNECTION CODE — SECOND DIGIT = $N_1$ IDENTIFICATION CODE.

| PARENT GRAPH | ENTER | RESULT | |
|---|---|---|---|
|  | 3 | 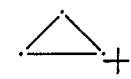 | } FIG. 8(a) |
|  | 13 OR 3 |  | } FIG. 8(b) |
| 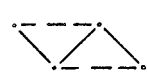 | 13 OR 3 |  | } FIG. 8(c) |
|  | 13 OR 3 | 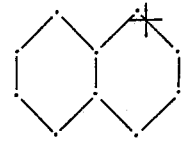 | } FIG. 8(d) |
| PARENT GRAPH | ENTER | RESULT | |
|---|---|---|---|
| 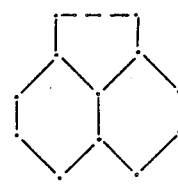 | 25 | 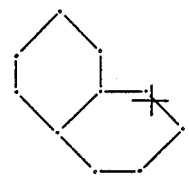 | } FIG. 9(a) |
| 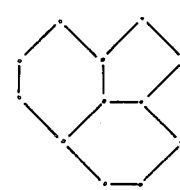 | 25 | 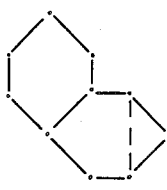 | } FIG. 9(b) |
| | | | } FIG. 9(c) |

| PARENT GRAPH | ENTER | RESULT | |
|---|---|---|---|
| + | 2 | .———. | FIG. 10(a) |
| .———+ | 1 | .———.———. | FIG. 10(b) |
| +——. | 1 | .———.———. | FIG. 10(c) |
| .———+——. | 1 | .———.———. (with vertical) | FIG. 10(d) |
| .———+——. | 1 | .———.———. (with vertical) | FIG. 10(e) |

| PARENT GRAPH | ENTER | RESULT | |
|---|---|---|---|
| + / F | 2 | C / C / F | FIG. 11(a) |
| + / F | 2 | C———C with F | FIG. 11(b) |
| F—+ | 2 | F—C———C | FIG. 11(c) |
| F\\+ | 2 | F\\C———C | FIG. 11(d) |
| + / F | 2 | F / C / C | FIG. 11(e) |
| +\\F | 2 | C———C\\F | FIG. 11(f) |
| +—F | 2 | C———C—F | FIG. 11(g) |
| +\\F | 2 | C———C\\F | FIG. 11(h) |

| PARENT GRAPH | ENTER * | RESULT | |
|---|---|---|---|
| ╬F | 03 OR 3 | ▽F | FIG. 12(a) |
| F╫ | 03 OR 3 | △F | FIG. 12(b) |
| F╪ | 03 OR 3 | F—△ | FIG. 12(c) |
| F╪ | 04 OR 4 | F—◇ | FIG. 12(d) |
| F╫ | 04 OR 4 | ▱F | FIG. 12(e) |
| ╬F | 05 OR 5 | ⬠F | FIG. 12(f) |
| ╪F | 05 OR 5 | ⬠—F | FIG. 12(g) |
| F╲╪ | 05 OR 5 | F—⬠ | FIG. 12(h) |
| ╬F | 06 OR 6 | ⬡F | FIG. 12(i) |
| F╫ | 06 OR 6 | ⬡F | FIG. 12(j) |
| F╪ | 06 OR 6 | F—⬡ | FIG. 12(k) |

| PARENT GRAPH | ENTER * | RESULT | |
|---|---|---|---|
|  | 15 | 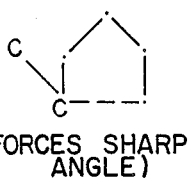 (FORCES SHARP ANGLE) | } FIG. 13(a) |
| 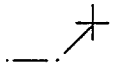 | 25 | 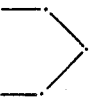 (FORCES NON-STANDARD ORIENTATION) | } FIG. 13(b) |
|  | 23 |  (FORCES USE OF ALTERNATIVE SHAPE) | } FIG. 13(c) |
| PARENT GRAPH | ENTER * | RESULT | |
|---|---|---|---|
| 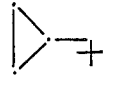 | 26 | 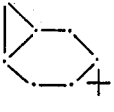 | } FIG. 14(a) |
|  | DE | 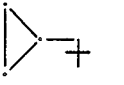 | } FIG. 14(b) |
|  | 26 | 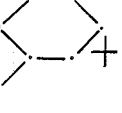 | } FIG. 14(c) |

FIG. 15(a)
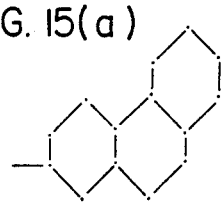
PREDEFINED OBJECT
FIG. 15(b)
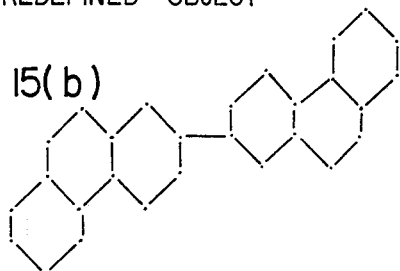
ATTACHED TO ITSELF WITHOUT FLIP
FIG. 15(c)
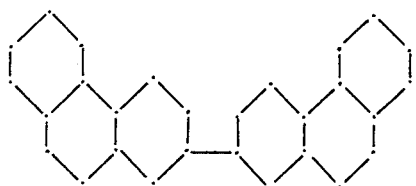
ATTACHED TO ITSELF WITH FLIP
FIG. 16
```
 a
 |
 b
 |
 c
```
FIG. 17
```
  a
  |
  b
  |
  c
```
FIG. 18
```
a
|
b—d—e—f—g
|
c
```
FIG. 19
```
a
|
b—d—e—f—g
|
c
```
FIG. 20
```
a
|
b
|
c
```
FIG. 21
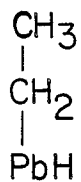
FIG. 22
```
CH3
|
CH2
|
PbH
```
FIG. 23
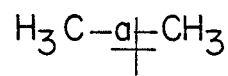
FIG. 24
```
a
|
b—d—e—f—g
|
c—h—i—j—k
```

AUTOMATIC ORIENTATION AND INTERACTIVE ADDRESSING OF DISPLAY

BACKGROUND OF THE INVENTION

1. The Technical Field

This invention is an improvement in display encoding, and deals in particular with the orientation of the objects by the addition of which a diagram is built up. As described herein, the invention relates to chemical structures, but the concept is usable with other applications, such as drafting and composition.

This invention is also to an improvement in display encoding, a technique for interactively entering graphic data into a computer. The improvement is due to a simplification in the orientation, marking, and display of structures on the screen of a CRT computer terminal. As described herein, the invention relates to chemical structures, but the concept is applicable to other types of diagrams, such as logical and electrical diagrams.

A computer may be used not only to process data, but also to facilitate the entry of these data into the computer With text input, for example, the user seemingly enters depictions of characters. In reality, he enters bit patterns, which are the codes that the computer needs. The machine translates these to graphic characters which are displayed. The input of visible graphics instead of arcane code is known as "display encoding". The term, however, is usually not applied to the input of common text, but is reserved for two-dimensional constructions, such as a diagram.

In display encoding, an entity is entered, as is text, by being assembled—on the face of a graphic computer 13 terminal—from smaller constituents. Ease of input, however, is not the sole advantage of display encoding. Throughout the process of assembly, the unfinished entity is visible, so that it can be determined, at a glance, what has been completed, and what remains to be done. The coupling between code and display further ensures that the visible structure accurately reflects the corresponding machine code. If one is correct, so will be the other. Any errors are apparent, and may be corrected prior to the entity's completion. A further, and not insignificant advantage, is that the input structure can be saved for re-display. Coded text is always translatable into visible, legible graphics; but with other applications, reconstruction of the display may require more than the data whose entry the display facilitated. Saving the code generating the display in addition to these data, will make it possible, in subsequent retrieval, to always view the graphic representation of these data, instead of their arcane codes.

A characteristic facilitating the graphic encoding of chemical structures is their flexibility. The appearance of a chemical structure bears as little resemblance to the shape of the molecule as does an electric wiring diagram to the layout of the actual wires This leaves such diagrams insensitive to the distortions, that are unavoidable in display encoding. There is, however, a limit. In FIG. 1, two diagrams are shown, representing the molecule, adamantane. Both diagrams are chemically correct, as they show all the atoms and all their bonds. But this identity will not be revealed by a casual glance, nor even by closer scrutiny. Considerable practice, or pencil and paper, will be required. This difficulty is normally circumvented by an artificial similarity, a "traditional" appearance, that has been adopted for many classes of chemical compounds. Very subtle, and often very personal considerations, determine what distortions are innocuous, and what distortions are objectionable.

Display encoding offers considerable latitude in the manner an entity is assembled. A diagram might wholly be constructed line by line. But it is more efficient to use simple lines only as a last resort, and to construct an entity, when possible, with larger building blocks. Indeed, the efficiency of the typewriter results from its capability of composing text with ready made and well formed characters, which are building blocks preassembled from simple lines.

A computer may be used not only to process data, but also to facilitate the entry of these data into the computer. This is commonly done for the input of graphic data, such as diagrams. The data are entered by seemingly being drawn on the face of the screen of a graphic computer terminal. This is an interactive process, in which the human user repeatedly issues commands, which the machine executes, and in so doing builds the diagram. Able to work with visible graphics instead of arcane code, the user's task is facilitated. Even so, the specification to the computer of the graphic elements (or objects) to be displayed, and of the location of these elements on the face of the screen, together with the orientation of these elements, is not a trivial matter. A variety of methods have been developed to facilitate these tasks. The present invention represents an improvement in two of these, namely orientation of these elements, and screen addressing.

The locations on a display can be specified precisely by means of Cartesian or other coordinates. This is one form of screen addressing. It would however be tedious to have to determine the value of these coordinates, and to have to key them in. Coordinates may, however, be obtained implicitly, thereby avoiding the necessity of keying them in, relieving even the operator from having to know their values. A number of approaches have been developed for obtaining coordinates implicitly. On a typewriter, for example, the type-guide indicates the location where a typed character will be printed. This location can be changed by depressing certain keys, called "function" keys: the space bar, the back space, the carriage-return, and others. On computer terminals, these same keys move a cursor. The cursor's coordinates can be determined by the computer's program as needed, without the human operator having to be importuned, or even being aware of this.

The drawing of a diagram, positioning all lines and characters by means of the above keys, would still be very cumbersome, even-though coordinates are obtained implicitly. The cause is the limited range of motions allowed by the above function keys. These permit the operator to progress only horizontally or vertically, usually in increments not exceeding the width or the height of a character. Graphic terminals, therefore, are often provided with additional function keys, called "cursor" keys. There are several of these, each engraved with an arrow, one pointing up, one down, one left and one right. If one is depressed, the cursor moves continuously, until the key is released, in the direction of the arrow.

More sophisticated yet is the "light pen". The computer senses the motion of the "pen" on the face of the terminal. Internally, it detects and computes the corresponding coordinates. It then displays a trace at the pen's location, the process being executed so rapidly that the input operator is under the impression of drawing free-hand. The user may also use the light pen to point at items (these are called "primitives" or "fragments" or "building blocks") on the screen, thereby selecting one of them, and even to drag it to another location on the screen While this goes on, the computer records, unobtrusively, both the identity and the new coordinates of the repositioned item.

Notwithstanding such sophistication, the light pen is not ideal. For example, keeping the hand raised to the screen for any length of time causes fatigue. Consequently, a number of alternatives to the light pen have developed: "Rand" or "graphic tablet", "joy stick", "mouse", "thumbwheel", "knee controls", "track ball", "touch pad", "touch screen", etc. The variety of these approaches is evidence of the effort to the facilitation of graphic input.

And yet, none of these devices overcomes all the problems inherent in the light pen. Because a character can be typed faster than it can be drawn with a pen, the keyboard cannot be dispensed with. Yet keyboard and light pen (or its equivalents) do not, from the ergonomics point of view, mix well. The alternation between light pen and keyboard taxes the operator. Typing, often done blindly, by "touch", must be interrupted to pick up the pen, requiring the typist to look away from the screen. The keyboard is a digital device, whereas the light pen is an analog device. Touch typists are able to type blindly because typewriter keys are located at fixed positions, evenly spaced, not too far apart yet sufficiently separated to be distinct. With the light pen, in contrast, the target that must be reached on the screen can have many positions It cannot be reached blindly; it requires hand-eye coordination. Unlike the keys, it cannot be reached with a simple motion. Studies in human factor analysis have revealed that subjects waver when pointing at an object. Initially, the target is overshot or undershot, requiring a number of adjustments to "zero in" on it with the required precision.

A difficulty in the construction of graphs from various predefined objects is the fitting of such objects to the parent graph. An object is not allowed to come too near, nor to touch, any part of the graph except through its point of attachment. Therefore, a fit may not always be possible, no matter what the object's orientation.

With complex graphs such as those used in chemistry, parameters can be used which are hereinafter referred to as N4 parameters, which define the orientation of objects to be attached to the parent graph, and are the most troublesome to specify. Commands such as 'rotate by 30 degrees' may not provide sufficient flexibility; if expanded to permit specification of the actual number of degrees, the user is generally unable to estimate that number, so that multiple trials may be necessary. Nudging an object with a light pen is slow and requires skill. The same object may be made available in different orientations, but, the larger the number of objects shown, the more extensive will be the menu wanderings required to locate any object. If, to reduce clutter, fewer objects are offered in menus, more of the input will have to be entered by means of simple lines or simple objects, thereby reducing the speed of the input process and rendering it more tedious. All these difficulties increase with the complexity of the graphs.

2. The Prior Art

U.S Pat. No. 4,085,443 to Dubois et al relates to a keyboard operated apparatus for coding and display of chemical structure and other graphical information. A cursor indicates on the display the part of a structural formula which is subject to the next keyboard operation. Alphanumeric characters identify atoms at nodes. The type of bond in any of eight directions from a node toward another node can be registered and displayed. Registering a bond at a particular node, by character and direction, causes the cursor to relocate to the node at the other end of the designated bond. Other movements of the cursor can be effected by the space bar, with the use of directional keyed instructions. FIG. 4 is noteworthy. This patent does suggest entering of graphical information on the keyboard of chemical structures, position by position, by operation of a direction key 5. This would evidently permit attachment of additional input figures, element-by-element, from a predetermined initial cursor position.

U.S Pat. No. 4,205,391 to Ulyano et al teaches inputting to a computer alphabetic as well as topological graphic data, and in particular, the structural formula of chemical compounds. An encoding tablet is provided, as well as an electronic writing means. FIG. 2 is noteworthy. In this device, graphical data is obtained by inputting the graphical data using a pickup sensor 5, symbol generator 17, coordinate pickup 4, and changeable writing member 38. The sensor 24 is used to check that the changeable writing member 38 touches the surface of the writing tablet 1. Other sensors 41,42 indicate axial position of the writing member 38.

U.S. Pat. No. 3,256,422 to Meyer et al relates to an apparatus for automatic encoding and retrieval of topological structures, such as chemical structures. In Meyer, as seen in FIG. 6, a scanning means is employed for coding the structures desired. A coded sheet having a standardized grid is required in order to encode the structures. Optical or light-sensitive scanning means are employed in this patent.

U.S Pat. No. 4,473,890 Araki, teaches a method and device for storing stereochemical information about chemical compounds. Three-dimensional structures of compounds are stored by supplying the coordinates of the atoms in a three-dimensional space represented by X,Y, and Z coordinates.

The entire disclosure of U.S. Pat. No. 4,476,462 to Feldman, issued Oct. 9, 1984 and filed on Nov. 16, 1981, which has been assigned to the U.S. Department of Health and Human Services, as described hereinabove, is expressly incorporated herein by reference in its entirety.

SUMMARY OF THE INVENTION

Automatic orientation is shown of chemical structures in conjunction with a computer terminal or the like. The invention is not limited to use with a computer terminal nor to use with chemical compounds, but can be extended to any computer-driven display for displaying any type of graphical information wherein graphical units (i.e. predetermined structures, such as for electrical diagrams, architectural diagrams, and the like) are stored, and detailed rules are provided regarding the angles at which such structures can be attached to one another. Such rules also determine the precise location at which additional structures can be added.

In this invention, each object specified has a "standard" orientation. Orientations are then automatically rotatable by 90 degrees as required for the computer to fit the object selected to the attachment points specified. All 90 degree rotations possible are tried by the computer before selection of a new, alternative shape for the structure will be specified. In chemistry especially, this is possible since there usually are a variety of ways of showing a particular chemical structure, other than the "standard" shape.

Furthermore, once a site has been selected for adding an object, a computer list is maintained of the angle pairs possible with the new structure. This permits precise determination of preferred orientations of chemical structures in readily identifiable standard manner. Automatic orientation takes into account all of the rules specified for each of the stored structures. Furthermore, user-defined structures are used within the program by reference thereto. Flipping of such structures is permitted to make mirror-images thereof.

Thus, a graphical display is made by positioning a cursor, whether by a light pen, cursor control from a keyboard, or the like, to move a cursor to a particular position, and an object is then selected. Automatically, the cursor is re-positioned at a predetermined point on the object specified. Alternatively, predetermined attachment points can be readily moved to by cursor control if necessary. From any predetermined attachment point, a new object can be specified and added, while being automatically oriented, without additional input from the user.

Another aspect of the invention shown herein relates to storage of icons or figures, each of which has labels thereon. Once recalled from storage, the stored figure permits positioning of the cursor thereon at selected locations thereof, by depression of a keyboard character, which corresponds to an identical character on the stored figure. Upon depression of the character, the cursor relocates there and permits attachment of the figure to another entity or figure selected. This permits precise attachment of one entity to the following entity, the attachment being automatic and precise.

This invention is particularly useful for specifying chemical structures, but is also useful in mechanical diagrams, electrical diagrams, and logical diagrams among many other uses.

An actual example of display encoding is the input of chemical structures. A chemical structure is a labeled graph, representing the architecture of a molecule in that each of its nodes represent an atom—each denoted by a chemical symbol—and each of its edges represents a chemical bond. It has been found that, in chemical structures, particular groupings of atoms tend to recur more frequently than others. Notable examples are rings and chains. These can be made into building blocks for the purpose of display encoding.

Dealing with a larger number of "objects" than the letters of the alphabet, dealing with two-dimensional space rather than with the linear arrangement of text, display encoding must surmount difficulties that can be far greater. These difficulties are reflected in the parameters that must be specified. These parameters define specific functions. They are listed below and numbered for later reference.

N1-This parameter defines identity. The potential variety of subassemblies or objects from which graphs may be constructed is very large. Furthermore, different sets of subassemblies are likely to be useful. To be selected in the construction of a diagram, these must all be identified.

N2-This parameter defines the intended location at which the above objects are to be placed. With text input, one letter usually follows the preceding one. In display encoding, the desired location must usually be specified explicitly. Requiring x- and y-coordinates, this is an example of a parameter using multiple items of data.

N3-This parameter defines the connection at the locus given by N2. Implied is the rigidity of the connection. The junction between the characters of text is rigid; only one orientation is acceptable. But the subassemblies of a graph can be connected with the parent graph through a single point, or by sharing a line, or in a number of other ways. There are degrees of rigidity, or degrees of attachment; several orientations may be compatible with the specified connection.

N4-This represents one or more parameters that indicate the orientation of the subassembly. In text, the normal orientation of a character is assumed. But if the character should be part, for example, of a caption that labels the y-coordinate of a graph, then its orientation will be changed by 90 degrees from the horizontal. This will have to be explicitly indicated.

Given a character, the purpose of its orientation is to make it agree with the orientation of the other characters on its line of text. In display encoding, as mentioned, the connection specified by N3 may be so rigid, that it allows for but a single orientation. But frequently, the connection specified by N3 is loose enough to allow for several orientations. The purpose of orientation then becomes different. Its purpose then is to fit the irregular contour of an object into the space available for it on the parent graph.

N5-This is required in systems that allow users to define objects for subsequent use. Such objects may be constructed normally, and may be identified with a N1 type parameter. But it is necessary to indicate, in addition, that they be stored for recall, and how they should attach to the parent graph. This requires additional parameters.

It is evident that the potential difficulties inherent in the specification of so many and so diverse a set of parameters may be formidable. Considerable ingenuity has been devoted to facilitate their specification.

The input of text is so common, that much of the logic required for the translation of key codes to character depictions is "hard wired" in terminals. So far, this has not been done for the capabilities required for display encoding. The required logic is normally implemented by means of programs running on a computer.

With simple displays, such as text, it is often possible to use "default" values for the required parameters. Default values are assigned beforehand, and take effect unless explicitly changed. Thus, in text, a character will always be placed to the right of the preceding character (parameter N2), unless a carriage-return, a tabulator, or similar command is used to override it.

Where the use of default values is impractical, other stratagems may be resorted to. A typewriter facilitates the selection of characters (parameter N1) by providing one key to each, and by further arranging these keys in such a manner that the most frequently used ones will be located in the most accessible part of the keyboard.

Because of their numbers, their variety, and their volatility, it is generally not practical to assign "dedicated" keys to all the objects used in the construction of a chemical structure or other graph. An alternative is to designate them by name or by code. A more ingenious approach is to allow the user to "pick" such objects from a "menu" that appears on the terminal's screen.

The N2 parameter may be specified by keying in actual coordinates. It may also be done by pointing at the desired location with a light pen, or by keying the symbol of a marker that has previously been positioned there.

The values used to specify the N4 parameters exhibit, perhaps, the widest variety. There are specific commands, such as "rotate" and "flip". An object may also be oriented by nudging it with the light pen, not unlike a tugboat maneuvering a large vessel into its berth. For a line whose starting point has been specified, both length and orientation are determined by its end point. And an object may appear on a menu in multiple orientations, so that one has to pick the desired object in the desired orientation.

One aspect of the invention is a method to facilitate the specification of one of the above parameters, namely N4, which specifies the orientation and to orient recalled objects with sequentially indicated nodes.

The orientation method performed automatically according to one aspect of the present invention has the following advantages.

The command structure, as described below, is simpler. With simpler and fewer commands, the encoding process is faster. Because of the symmetry inherent in automatic orientation, the layout of the graphs obtained with the method of the present invention tends to be more regular, hence more esthetically pleasing, than graphs generated by the usual methods.

The present inventive improvement in screen addressing takes advantage of the fact that, in display encoding, diagrams are constructed by attaching new entities to those already in place on the screen. A graph is begun by bringing up on the screen an entity, a character, a line, or any other building block. This first entity, of necessity a standalone, need not be positioned with the maximum precision afforded by the resolution of which the display is capable. Usually, the entity is placed roughly either in the center of the display, or in the top left quadrant. But the entities entered subsequently must be attached, and therefore need to be positioned with precision.

Another aspect of the present invention relates to marking of potential attachment sites, use of the markers for positioning of the cursor, and use of the markers for automatic replacement by a chemical symbol.

If an entity is to be attached to a point of the graph on display, then that point's coordinates are already known to the computer program that manages this display. As described below, the present invention implements a strategy for marking each potential attachment site. To attach an entity at a particular site on a diagram, it is then necessary only to identify that entity, and to specify the marker indicating the site of the attachment. That specifies the corresponding coordinates with precision.

The marker is a character, and it is selected by depressing, on the keyboard, the key bearing that character. Depressing this key will not, as is normal, cause that character to print. Instead, the computer program will cause the cursor to jump to the site marked with that character. The user next identifies the entity to be placed there. For example, if a four-atom chain is wanted, that chain—assuming everything else to be set up correctly—can be specified by entering the number 4. That will cause a four-atom chain to be drawn, attached at the site indicated by the cursor. In this manner, that chain (or other entity) is accomplished with precision, quickly, without wavering, without requiring the operator to remove either the hands from the keyboard, or the not least, the expensive hardware that is associated with the light pen, or, its equivalents, is superfluous.

The automatic system of the present invention is capable of fitting more objects into a graph than systems currently available for including chemical structure. This is due to the fact that, in the event of a failed test, the system of the present invention may make available an alternate object which, though diagramatically equivalent, has a different shape. The system will try to fit this by orienting it, as it did for the primary object. Therefore, the chances of achieving a fit are improved.

No manual system can practically have recourse to this solution, since even if objects were to be supplied in a menu in alternate shapes, it would be very difficult to translate and rotate an object mentally to gauge which shape, if any, and in what orientation, the shape is likely to fit.

Should the system of the present invention fail to fit an object onto the parent structure, an apologetic message will be issued. The user is still then able, by means of single bonds and atoms, to enter the object although in a distorted but chemically correct manner.

Although the orientation of objects is automatic, the system of the present invention produces structures in their traditional appearance. When generated directly from code, structures tend to lose their traditional appearance. That is because a structure's code, which is a connection table, is devoid of information concerning what constitutes a traditional appearance. The present inventive method works because it merely orients objects that tend to correspond to traditional subassemblies. It thereby retains the traditional appearance of chemical structures. FIG. 1 illustrates the difference.

FIG. 1 illustrates two equally correct representations of the molecule adamantane. FIG. 1(a) shows an unconventional but correct representation of the molecule; FIG. 1(b) illustrates a more conventional and recognizable representation of the same molecule. As discussed above, the identity of these two figures (a) and (b) is not apparent at a single glance.

The system of the present invention requires a "graphic" computer terminal, discussed in detail hereunder, of medium or high resolution. It does not require accessories such as a "light pen" or a "mouse", which are available on only some terminals, and then usually as expensive options.

The system of the present invention provides two types of objects for attachment to the parent graph. These are objects which are supplied by the system, and objects that have been created by the user which are stored in anticipation of future use. The objects supplied by the system include chains of atoms and rings of atoms. Some of the objects stored have alternate permissible shapes, which are also stored and selected by the system when the primary object will not fit, or cannot be fitted. The chains, at one of their extremities, have a bond, called the "merging" bond. That is, the bond is unattached at one end. Through this bond, these chains will connect to the parent graph.

Users can also create partial structures and store them in anticipation of future need, thereby increasing the variety of objects available for attaching to the parent graph. These are called "user-defined" or "predesigned" objects. These objects are of necessity entered with only a single orientation. This becomes their "standard orientation".

The system alters neither stored objects nor their orientation. In attempting to attach an object to the parent graph, it will manipulate only a copy of the object. The original remains available for subsequent use.

While system-supplied objects and user-defined objects differ in their origin. they do not differ in their interactions with the parent graph.

BRIEF DESCRIPTION OF THE DRAWINGS

FIGS. 5(a), (b), and (c) illustrate three similar angle-pairs which are obtained with different ring orientations or attachment points;

FIGS. 7(a)-(d) illustrate unconstrained orientation in the "ring" state where the object has no merging bond and the connection code is 0;

FIGS. 8(a)-(d) illustrate unconstrained orientation when the system is in the ring state where the object has no merging bond and the connection code is 1;

FIGS. 9(a)-(c) illustrate unconstrained orientation in the ring state where the object has no merging bond and the connection code is 2;

FIGS. 10(a)-(e) illustrate unconstrained orientation where the object has a merging bond in a chain state;

FIGS. 11(a)-(h) illustrate constrained orientation with a bond-interfacing object in a chain state;

FIGS. 13(a)-(c) illustrate constrained orientation in a ring state with an atom-interfacing object and a different connection code from FIG. 12;

FIGS. 14(a)-(c) illustrate correction of automatic orientation in a ring state;

FIGS. 15(a)-(c) illustrate use of a "flip" command;

FIG. 16 illustrates a chain before addition;

FIG. 17 illustrates movement of the cursor to marker "b";

FIG. 18 illustrates attachment of a four-atom chain at marker "b" of FIG. 17;

FIG. 19 illustrates connection of a line between two specified locations;

FIG. 20 shows addition of a bond to a marker;

FIG. 21 shows alteration of a diagram to include a chemical symbol;

FIG. 22 shows substitution of markers by atoms;

FIG. 23 shows assignment of markers upon request;

FIG. 24 shows automatic assignment of alphabetic letters to recalled chains.

DETAILED DESCRIPTION OF THE INVENTION

The present invention is disclosed in a preferred embodiment utilizing a standard version of the Model HP 2623A Graphics Terminal Keyboard manufactured by the Hewlett-Packard Company of Palo Alto, Calif. in conjunction with a DEC SYSTEM 10 computer manufactured by the Digital Equipment Corporation. A listing of instructions for a specific program embodying the present invention with the aforementioned equipment is provided in Appendix I attached hereto. It is to be understood that the equipment and program specifically described and illustrated herein are examples of a preferred embodiment only; in other words, the present invention can be performed with other equipment and other programs and should not be limited to the specific embodiment disclosed herein.

Figure 1A:
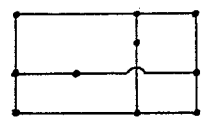
FIGS. 1(a)-(b) shows two representations of a molecule.
Figure 2A:
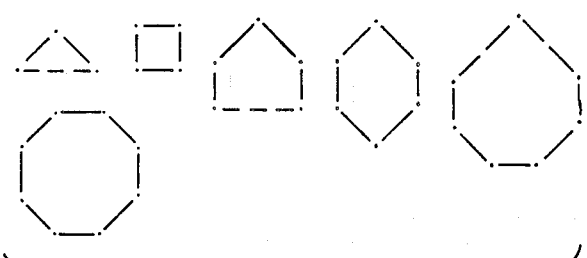
FIGS. 2(a)-(c) illustrates system-supplied objects.
Figure 1B:
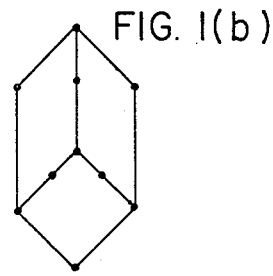

FIG. 2(a) illustrates system supplied objects having standard ring shapes. The number of atoms in a ring ranges from 3-8 atoms connected by corresponding bonds, and includes one element having seven atoms and two double-length bonds. Other ring-shaped objects could also be used, and the addition of any such ring-shaped objects as system supplied objects are contemplated as being within the scope of the present invention.

Figure 2B:
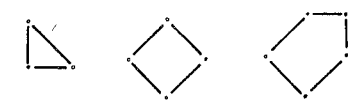

FIG. 2(b) illustrates secondary ring shapes for the three atom ring, the four atom ring, and the five atom ring. These secondary ring shapes are to be used by the computer in the present invention when the standard ring having the same number of atoms cannot be placed or added to the parent graph in a proper fashion, e.g. without touching other structures except at the connection point, or without going off the page, etc. Thus, it is seen that these secondary ring shapes are rotated through an angle relative to the corresponding shapes of the preceding FIG. 2(a).

Figure 2C:
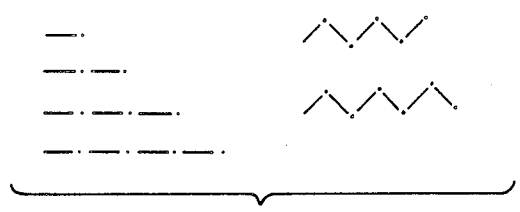

FIG. 2(c) illustrates system-supplied objects having chain form. Both short (linear) and long (jagged) chains are stored in the computer system. Upon recall, as described hereunder, the dots appearing between the dashed bonds would be replaced by alphanumeric characters. This replacement is discussed hereunder with respect to FIGS. 16-24.

Before an object can be attached to the parent graph, the common boundary between them, called an "interface", must be specified. A number of parameters must be specified, among them the N2 and N3 parameters.

Interfaces can range from simple to complex. The simplest ones consist of a bond, the more complex ones share one or more atoms. If the interface is constituted solely of a bond, then all the atoms of the parent graph lie to one extremity of this bond, and all the atoms of the object lie to its other extremity. If one or more atoms participate in the interface, then these atoms, as well as any bonds connecting them, will have belonged, before the connection was made, separately to both parent graph and object. The connection was made by overlapping, or "fusing" these atoms and bonds. Atom interfaces involving a single atom are referred to, in common chemical parlance, as "spiro"; atom interfaces involving two or more atoms are denoted as "fused".

TABLE I

| Interactions between objects and parent graphs | | | | |
|---|---|---|---|---|
| parent-graph interface | connection code | object interface | interface obtained | illustrated in FIG. |
| bond | — | bond | jointed | 11, 15 |
| atom | — | bond | jointed | 10 |
| bond | 0 | atom | jointed | 12 |
| atom | 1 or 2 | atom | hinged | 13, 14 |
| atom | 0 | atom | spiro | 7 |
| atom | 1 or 2 | atom | hinged | 8, 9 |

As for the site of the interface, the N2 parameter, it must be specified independently both for the parent graph, and for the stored object. For the stored object, this specification could be made either at the time it is used, or when it is stored. The former renders these objects more versatile, because any atom or bond then can serve as interface; the latter simplifies their use, because it avoids the necessity of specifying that interface when requesting the object. In the present system, the location of the interface—the N2 parameter—is specified when a predefined object is stored, but the nature of the interface—the N3 parameter—is specified when the object is used.

A. ORIENTATION OF OBJECTS

When recalled from storage, objects can be oriented. The number of potential orientations varies. It depends, in part, on what the specified interface, the N3 parameter, allows. Atom interfaces that consist of two points permit the object to be placed only against either one side or the other of the hinge line connecting these points. Bond and spiro interfaces, which consist of a point, accommodate orientations obtainable by rotating the object around this point. Rotations, however, are performed only in increments that are multiples of 90 degrees. Potential orientations are further limited by available space; as mentioned, an object is not allowed to come too near, nor to touch, any part of the graph except through its point of attachment. Automatic orientation consists of the selection of one orientation from these potential ones.

The system of the present invention selects one of the potential orientations on the basis of coupling rules. There are two such rules. One is applicable to objects that are rotated around a point or joint, hereafter called a "jointed" interface, the other is applicable to objects that have a "hinged" interface. Not all orientations are automatic. In addition to being rotated or hinged, objects may be changed into their mirror-images, or flipped, as illustrated in FIG. 15. The user accomplishes this by entering a "flip" command, as described hereunder. Flips, useful only with asymmetric objects, are rarely executed, however. Most orientations are automatic.

B. COUPLING RULES

B1. Coupling Rules for Jointed Interfaces

Figure 3A:
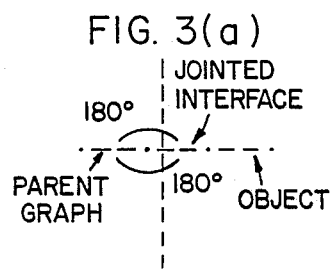
FIGS. 3(a)-(c) illustrates computation of angle-pairs.
Figure 3B:
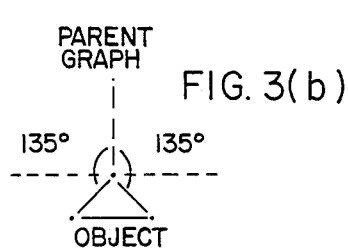
Figure 3C:
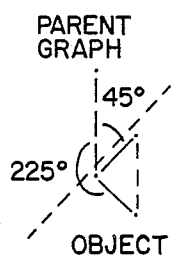

FIGS. 3(a)–(c) illustrate computation of angle-pairs. The order in which angle pairs are selected is governed by a preference list (protocol), as follows:

Preference List for angle-pairs (in degrees)

180,180
135,225 or 225,135
135,135
90,90
135,90 or 90,135
135,180 or 180,135

As an example, in FIGS. 3b and 3c, the two joints shown yield the angle-pairs 135,135 and 45,225, respectively. The former, being higher on the preference list, determines the corresponding orientation. This is an example of the use of a protocol.

If, because of an obstruction, the object, in the orientation determined from the preference list (protocol), cannot be fitted on the parent graph, then the system will attempt another orientation, provided it has the same angle-pairs. Failing that, it will attempt to use an alternate object, if available. Failing that, it will issue an apologetic message. Under no circumstance will it use an orientation with an angle-pair lower than the best.

With jagged chains, interpretation of the protocol becomes somewhat more complex, as the system will attempt not only to orient the chain in the appropriate direction, but will also try to keep the pucker regularly alternating, avoiding any discontinuities.

On system-supplied rings, the interface is not indicated. Any atom may be used, as they are all equal members of the rings. Nevertheless, because of graphic considerations, the appearance of the rings' sides and angles is uneven. The rings, consequently, can be oriented according to evaluation by the preference list. Should the same angle-pairs be obtained with different orientations, as in FIGS. 5 and 10(d), secondary considerations are deciding, namely equality of length of the adjoining sides (FIG. 5b) and, should that not suffice, the preference criteria of the list of rotations, below. Arbitrary considerations, based merely on aesthetics, may additionally be used (see FIG. 5).

B2. Coupling Rules for Hinged Interfaces

Hinged interfaces are obtained by rotating the object (a ring or ring system) until the designated side is lined up with the corresponding side of the parent graph.

The order in which successive orientations are attempted by the system is also governed by a preference list, which follows:

Preference list for rotations:
first, try standard orientation
rotate standard object by 180 degrees
rotate standard object by −90 degrees
rotate standard object by 135 degrees Note that the object may appear on either side of the hinge line (cf FIG. 14). In the absence of impediments, placement of the object against either side is at the system's discretion. If the wrong side was selected by the system, the user may remedy this with the retry command. The retry command, which is described below, rejects the current orientation, then allows the same rules to apply again while preventing rejected orientations from appearing.

C. THE COMMANDS

C1. Implied Commands

It is the burden of commands used in display encoding that not only must they convey the many parameters mentioned above, with their diversity, their multiple elements of data, and their complex definitions; but they must further do this efficiently, minimizing the inconvenience to the user.

The explicit specification of all necessary parameters is consequently intolerable. Prominent among the alternatives that have been devised is the already mentioned use of default values. Further, since the selection of an object is easier by pointing at it on a display than by alternative N1 specifications, many systems offer the use of a "light pen", or an equivalent.

With orientation being performed automatically, the parameter load according to the present invention is reduced. For the remaining conventional commands, default values are, of course, provided. In addition, the system of the present invention offers the use of "implied" commands.

Figure 6A:
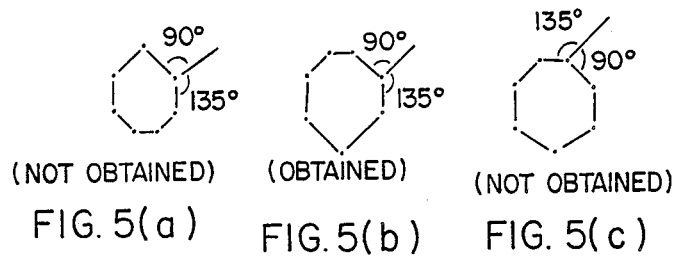
FIGS. 6(a) and (b) illustrate implied commands.
Figure 6B:

Implied commands are defined by the position of the cursor relative to an atom or a bond. They work as follows. If the cursor's position adjoins an atom, that expresses an "S1" command, resulting in a requested object becoming oriented in a particular manner. If the cursor's position adjoins the unattached end of a bond, that expresses an "S2" command, resulting in a requested object becoming oriented in a different manner (see FIG. 6). The S1 and S2 commands convey N4 parameters. Their meaning is explained hereunder.

To be executed, implied commands must be activated. They are activated by another command that requires depressing a key, such as a request for an object. This is also discussed hereunder.

These implied commands have been devised in the present invention because, on the average, they will require fewer keystrokes than conventional commands. If, for example, an N4 parameter—specified by implied command—requires the cursor to be located at the unattached end of a particular bond, it may not be necessary to place it there deliberately. The cursor may already be there, having gotten there as a consequence of entering that particular bond. If now this bond is to be used as a jointed interface to a chain, it will be necessary only to depress the key that calls the chain; no further command will have to be entered to specify its N4 parameter. Similarly, if the cursor is to be located next to an atom, there is at least a probability that it did not have to be placed there on purpose, but got there as a consequence of the preceding command. In these instances, the depression of a single key, to obtain, say, a system-supplied object, triggers a series of automatic operations that result in the assignment of default values to command, and consequently in the selection, interfacing, orientation and display of the requested object.

C2. Express Commands Requesting Objects

Inasmuch as one aspect of the present application is concerned with the orientation of objects, and not with an entire system of coding chemical compounds, detail on the N1 and other parameter specifications is provided here only insofar as it relates to the description of automatic orientation.

Basically, the system has a "Ground" state, a "Ring" state, a "Chain" state, a "Library" state, which is entered when an object is stored for future use, and a "Retrieve" state, which is entered when requesting a user-defined object.

A state is entered by depressing a particular key. The nature of this key is immaterial; on keyboards provided with these, it is preferably a programmable function key. On the HP-2623A computer terminal, for which this system is implemented, such keys are not available, because all the available programmable function keys are used for the entry of bonds. On this machine, a particular state is entered by depressing a particular key, which then does not print—the "meaning" of the key is changed—but causes the system to enter the particular state. The Library state, for example, is entered by depressing the "underline" (_) key, and the Retrieve state is entered by depressing the colon (:) key. Actuating the carriage-return key returns the system to the Ground state.

The interpretation of meanings that the system of the present invention gives to the keys is defined by the "state" of the system. In the same state, the same keystrokes produce the same results. In different states, at least one, and possibly more than one key, is interpreted differently. Typing the digits 3 through 8 in the Ring state produces a display of rings of corresponding sizes; in the Chain state, typing the digits 1 through 9 produces chains of corresponding lengths. In neither case are these digits displayed.

User defined objects are retrieved in a similar manner, except that the user defines the designations that recall the objects

C3. Commands Specifying the Connecting Site

The system of the present invention allows the use of "cursor" keys, which are usually provided on graphic terminals, and which allow the user to move the cursor to the locations where an object is to be placed. The present inventive system provides additionally a method of using "markers" to move the cursor to such positions. Either way, selection of the desired connecting site is indicated on the display by the vicinity of the cursor.

The N2 parameter must be specified for both the parent graph and the predefined objects. On the parent graph, this specification is made just before the object is requested; on the object, it is done prior to storage.

C4. Commands Specifying the Interface

The N3 parameter specifies the nature or degree of the interface joining object to parent graph. As already mentioned and as summarized in TABLE I, this interface can consist of a bond or of one or more shared atoms.

The N3 parameter is specified by means of a numerical code. With a value of "0" it specifies a bond or spiro attachment, with value "1" it specifies the fusion of one side, and with value "2" it specifies the fusion of at least two adjacent sides. FIGS. 7, 8, and 9 illustrate the use of these connection codes.

The N3 parameter is always entered immediately preceding the object3 s N1 specification, as shown in FIGS. 7-9. If omitted, a default value takes effect. Default values for the N3 parameter are 0 and 1, depending upon the N4 command, which is addressed next.

An explanation is useful about the extension of the interface. If jointed or spiro, the interface has no extension, but if fused, it will encompass two or more atoms. In the first instance, the position of the cursor, set by the N2 parameter, specifies the location of the interface adequately, but in the second instance, the cursor shows only one point along an interface with greater extension. This point, however, can be chosen so that it defines the entire interface. As also described in U.S. Pat. No. 4,476,462 to Feldman, the bonds in the present system have "direction". It is therein possible to distinguish the bonds leading into an atom, from those leading away from it. By placing the cursor next to the atom situated at the "base" of the interface—defined in the present system as the atom into which the interface bonds lead—the interface is specified. It may be specified ambiguously, as more than one bond may lead into the same atom. Such instance, however, are not too common. They can be resolved by using the retry command.

With an interface consisting of 3 atoms or more, the location of the interface is determined solely by the bond adjoining the base atom. The direction of the second bond is irrelevant. That again leaves room for ambiguity, as shown in FIG. 14. But, as this figure further illustrates, this too can be resolved by using the retry command.

C5. Commands Specifying the Orientation of Requested Objects

Since the objects in the system of the present invention are oriented automatically, the commands used to specify N4 parameters, in the main, serve not to orient objects, but to specify the degree of autonomy granted to the system. One command is used to flip objects. The following are the available N4 commands.

TABLE II

| Command | Operation |
| --- | --- |
| S1 | Orient object without constraints. |
| S2 | Orient object within the limits of certain constraints |
| S3 | Retry. Orient object in accordance with last specifications, but avoid orientations already attempted. |
| S4 | Flip. Transform object into its mirror image. |

S1 and S2 are implied commands. The "retry" command works through the "delete" key which, when depressed, erases the most recently entered object. The "delete" key is indicated throughout as the letter "DE". If next requested, that object will assume a different orientation. The flip command is made available when a user-defined object is requested. Use of the "flip" command is illustrated in FIG. 15.

Unconstrained orientation means that no restrictions are being imposed by the user. The system, of course, is subject to the several constraints already discussed: those imposed by the N3 parameter, and those resulting from the limits of the available space.

The (implied) S1 command is invoked by requesting an object while the cursor is either alone (i.e. located more than one space away from the nearest character or bond), or adjoins an atom of the parent graph.

Requesting an object with invocation of the S1 command has the following effect. If the requested object does not possess a merging bond, then a hinged interface will result, specified by the value of the N3 parameter. The object will be oriented according to the preference criteria of the list for rotations (FIGS. 7, 8, and 9). If the requested object has a merging bond, then that bond will participate in a jointed interface, and the object will be oriented according to the preference criteria of the list for angle-pairs (FIG. 10.). If the cursor is alone, then the object is displayed in its standard orientation, not connected to the parent graph, if any. If it possesses a merging bond, this bond will be lost.

With unconstrained orientation, the default value of the N3 parameter is 1. This means that typing 15, for example, would produce the same display as typing 5.

In the system of the present invention, automatic orientation can be partially or fully inhibited. This improves its versatility. In general, automatic systems are more flexible to the extent that their automatic features can be overridden.

Constrained orientation is invoked by means of the (implied) S2 command. This is activated when an object is requested while the cursor adjoins the unattached end of a bond. This bond is called a "pointer" bond. It is the direction of this bond that restricts the orientation that objects may assume.

The pointer bond can be used to connect with objects that either have a merging bond, or that do not have one. The effects are as follows.

When connecting with objects possessing a merging bond, this bond and the pointer bond must overlap. That will force a corresponding orientation of the object. As an object, however, can be rotated only in increments of 90 degrees, an incompatibility will exist where one of the bonds is horizontal or vertical, and the other bond diagonal. As shown in FIG. 11, this incompatibility is resolved in favor of the pointer bond, whose direction cannot change. The system rotates the merging bond, and the object attached to it, so as to minimize the difference with the pointer bond, discards the merging bond and connects the object to the pointer bond where the merging bond had been attached.

The object with the incompatible merging bond may be rotated so that this bond would have lain to one side or the other of the pointer bond. Consideration of fit will govern this choice which, otherwise, is resolved at the system's discretion.

If a connection needs to be made between a pointer bond and a merging bond whose lengths differ, the length of the pointer bond prevails; if their bond types differ (i.e. if the pointer bond is single, and the merging bond is double) then the merging bond type takes precedence. This is true whether the pointer bond overlaps the merging bond, or replaces it.

With constrained orientation, the default value of the N3 parameter is zero. The possession of a merging bond precludes objects from being connected to the parent graph except through a jointed interface. In the presence of a merging bond then, other N3 values are meaningless.

When a pointer bond connects with objects that do not possess a merging bond, and the value of the N3 parameter is zero, a jointed connected ensues, and the preference criteria of the list of angle-pairs govern the orientation of the object. FIG. 12 shows a number of examples. Other values of N3 produce a hinged interface, with the preference criteria of the list of rotations determining the orientation of the object.

As with overlapping pointer and merging bonds, the constraints imposed by such an interface are so severe, that it is meaningless to speak even of partially inhibited orientation. In fact, the hinged specification can be used to force an otherwise unattainable orientation, one, for example, that joins an object to the parent graph by a sharp angle, as illustrated in FIG. 13.

Whether it was automatic or constrained, the user can override the orientation selected by the system. This is done by depressing the "delete" key, which causes the latest single entry—a single atom, or a bond, or an entire object—to be deleted. If the user then repeats the last command, the system will attempt to orient the last addition in a different manner, using the applicable order of preference. This is illustrated in FIG. 14. After all alternatives have been exhausted, the system will issue an apologetic message. The user can then complete the graph in other ways.

The retry command is another instance of a N4 parameter specification characteristic of automatic orientation, in that its purpose is not to orient objects, but to restrict or, in this case, to revise, the autonomy granted to the system.

In the system of the present invention, system-supplied objects, being symmetrical, need only to be rotated. User-defined objects, however, may have to be rotated, or flipped. The Flip command is made available as an option when requesting a predefined object—which is done by entering the Retrieve state. The option is specified by typing either the letter "A" (for axial symmetry) or the letter "P" (for point symmetry). If the user then enters the letter P, the system will rotate the object in attempting a fit. If the user enters the letter A, the object first is flipped, i.e. its mirror-image is used. An example of a flipped object is shown in FIG. 15.

Figure 4A:
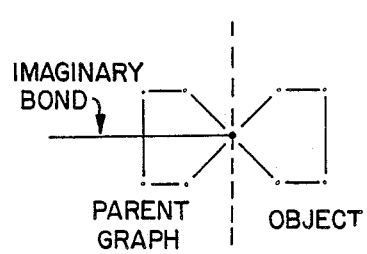
FIGS. 4(a) and (b) illustrate the imaginary bond of spiro connections.
Figure 4B:
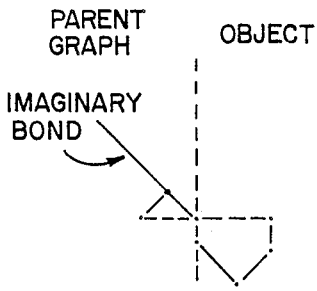

FIG. 4 illustrates the imaginary bond of spiro connections. FIG. 4(a) illustrates an imaginary line at right angles to an imaginary bond between a parent graph and an object which has been added. FIG. 4(b) shows an imaginary bond which overlaps one side of a parent graph, and a dotted line separating the parent graph from the object at the point of attachment and which is generally perpendicular to the imaginary bond line.

FIG. 11 illustrates constrained orientation with a bond-interfacing object. Here, the S2 command, while the system is in the chain state, uses the "pointer" bond. A number of examples are illustrated as FIGS. 11(a)–(h).

Figure 12I:
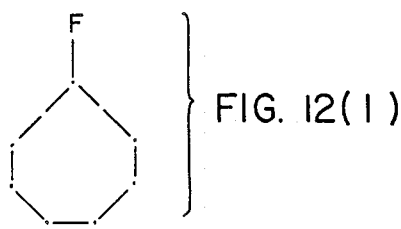
FIGS. 12(a)-(p) illustrate constrained orientation in a ring state with an atom-interfacing object.
Figure 12M:
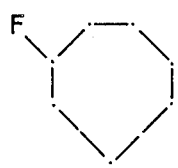
Figure 12N:
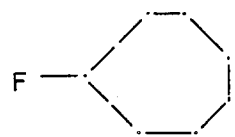
Figure 12O:
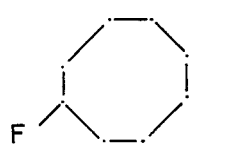
Figure 12P:
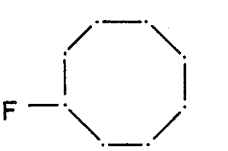

FIGS. 12(a)–(p) illustrate constrained orientation with an atom-interfacing object with the connection code being Zero (default value). Here, the system is in a ring state. As can be seen, in each of the figures (a)(p), the "pointer" bond from the parent graph orients the object which has been called or retrieved. The result is a connected graph in a conventional form.

D. INTERACTIVE ADDRESSING OF TWO-DIMENSIONAL COMPUTER DISPLAYS

The steps just described are illustrated in FIGS. 16, 17, and 18. FIG. 16 shows the diagram before the addition. The user, to specify the attachment site, depresses key 'b'. This causes the cursor to jump to marker 'b' (FIG. 17). The user next specifies the entity to be attached, a four-atom chain, by depressing key '4'. This causes a four-atom chain to attach itself at marker 'b' (FIG. 18).

In the context of chemical display encoding at least, all the operations that can be performed with the light pen, the drawing, the selecting, the dragging, can be performed by positioning the cursor in the above manner.

To draw an unusually placed or exceptional line, an instruction must be entered to indicate that, as the cursor jumps from one marker to another, a line (bond) is to be drawn. This function is not frequently necessary, as the system supplies bond lines where appropriate. This instruction is entered by typing of the character '%'. Thus, by typing 'e % a %', a line is drawn from marker 'e' (in FIGS. 18 and 19) to marker 'a'. FIG. 19 shows the result. The second '%' is required to confirm the last marker, since that marker may appear more than once if more than one alphabet series or character is used.

In chemical diagrams encoded as above, a marker always indicates the location of an atom. The markers are preferably lower-case letters of the alphabet. There is no need to mark the location of a bond, as each bond is always attached to at least one atom. This arrangement limits the number of markers, so that they do not clutter the screen, nor interfere with the visual apprehension of the diagram. If a bond is entered, it attaches to a marker (or to an atom); if an atomic symbol is entered, it replaces a marker if there is one at that site. At an atom location, there is thus either a marker or an atom symbol, never both. It is good practice to make all attachments first, and to replace the markers (with element symbols) last. Generally, it is not necessary to replace all markers. Once the diagram has been completed, the program replaces all remaining markers with the symbol of the atom most commonly occurring in diagrams, namely carbon. The markers thus represent a temporary feature, characteristic of a diagram under construction. In the final diagram, they won't be present.

FIG. 20 shows the addition of a bond to a marker. The original diagram is that of FIG. 16 in which the cursor is located at marker 'c'. When depressing a special key that is programmed to enter a horizontal bond directed to the right, the bond appears at the marker location, which is shown in FIG. 20. That bond can then either be lengthened, by again depressing the last key, or it can be followed by a marker or element symbol.

FIG. 21 shows the substitution of a marker by an atom. The original diagram again is tht of FIG. 16, with the cursor at marker 'c'. The key bearing the letters P, @ and b are depressed, resulting in the display of the chemical symbol "Pb".

If this is the last alteration, the letter Q is typed, indicating that the structure has been completed. This causes all remaining markers to be changed to carbon atoms, and H's to be added as illustrated in FIG. 22.

As markers, single lower case letters are used because, on a keyboard, there is a large number of keys bearing them, and because, in chemical diagrams, they are used rather infrequently. These letters need not be specified by the user. They are automatically assigned in sequence, as needed. After the end of the alphabet has been reached, the alphabet will repeat, the next letter being an 'a' again. The system resolves the ambiguity resulting from the presence of two or more alphabets by confining jumps to the last alphabet used. By actuating the same letter again, the preceding alphabet is accessed In this manner, all alphabets used are cycled through.

Until it is replaced, the operator may return to any marker as often as desired.

Although lower case characters have relatively little use in chemical structures, there are times when they must be printed. To preclude a lower case character from causing a jump when intending to let it print, such a character must be preceded by a specific code. This is the character @. It was typed, when obtaining the diagram in FIG. 21 above, to avoid jumping to marker 'b'.

The foregoing describes the use of markers. It remains now to indicate how they are created, and how they are placed into their strategic locations.

Entities that are entered on the screen, either as standalones or as attachments, are either primitives or composites. A primitive is a single, a double or a triple line (or bond), or the symbol of a chemical element. A composite, which may be a chain or a ring or a more complex fragment of a structure, is composed of a number of primitives. The operator may enter chemical symbols directly, or markers, which will be converted to chemical symbols later. To request a marker, the operator types a particular symbol, preferably the symbol '#'. The program will thereupon supply the next available marker, displaying it at the current cursor location. As already mentioned, markers are assigned by the program in alphabetical order. If the last assigned marker was an 'a', the marker next to be assigned will be a 'b'.

FIG. 23 shows the assignment of markers upon request. The user types a 'C', then depresses the key printing a horizontal right-oriented bond, whereupon the program inserts the necessary hydrogens. The user then types a '#' whereupon the program prints an 'a'. The user than types another bond then another 'C'. Wishing to return to the marker, the user then types an 'a'. This causes the necessary hydrogens to be added to the last C, and the cursor to jump to marker 'a'. The user can then either attach another bond at this site, or replace the marker, and go on.

If composites are used, the library, which supplies these, cannot predict where branch points may occur. Because of this, a composite, upon being displayed on the diagram, will have all its atoms represented by markers. That is illustrated in FIG. 18. (Exceptions—atoms represented as elements are, of course, readily accomodated). The same composite, requested a second time, will receive different markers. For example, if, in FIG. 18, the cursor is jumped to marker 'c' (by depressing key 'c'), and another four-atom chain is requested (by depressing key '4'), that chain will have the markers h through k, as shown in FIG. 24.

Figure 25:
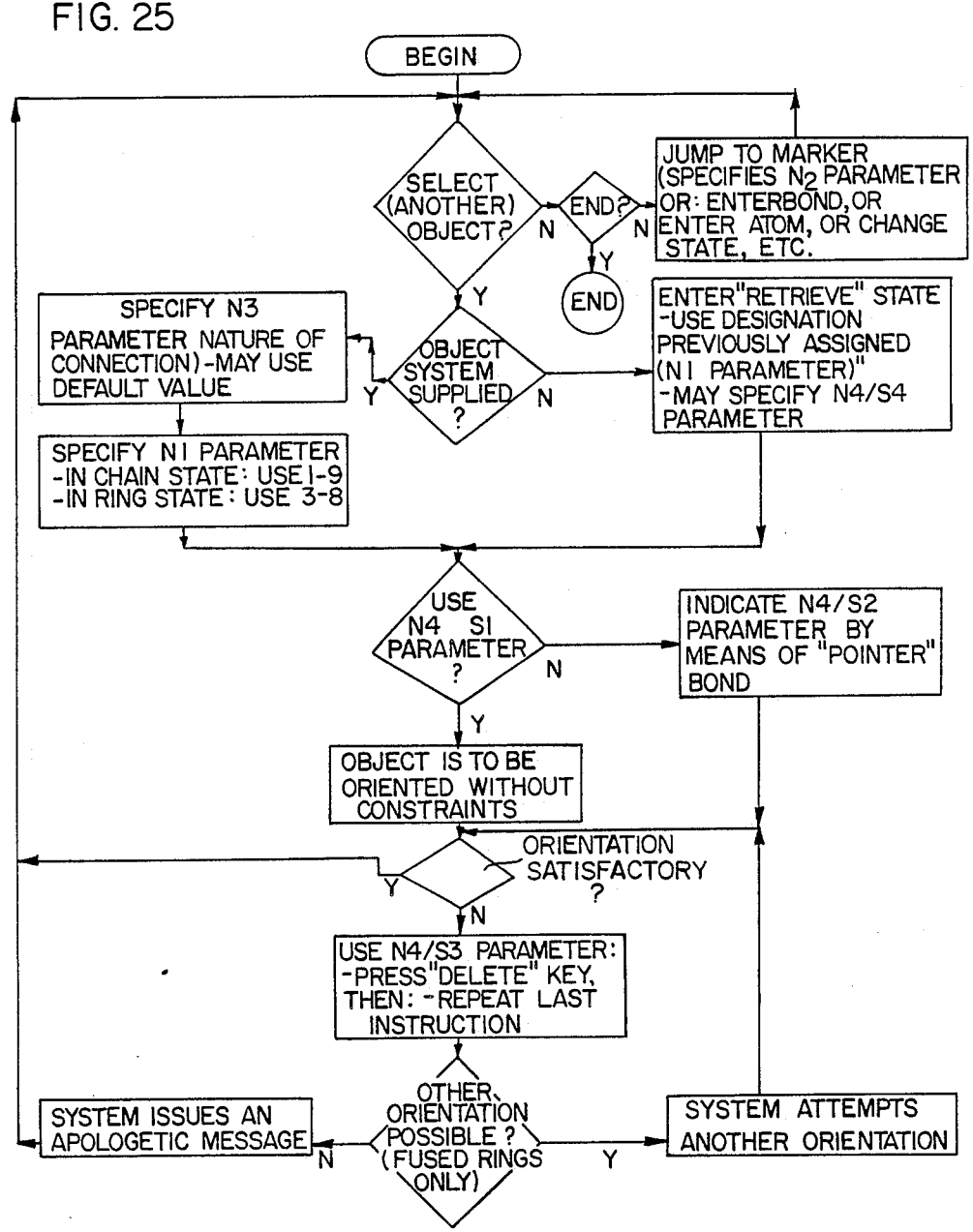
FIG. 25 shows a flowchart illustrating the choices available to the user.

The flowchart of FIG. 25 shows the choices available to a user. Specification of required parameters permits automatic orientation of objects.

While preferred embodiments have been shown and discussed, it will be understood that the present invention is not limited thereto, but may otherwise be embodied within the scope of the following claims.

APPENDIX I

```
!         HPCHEM - VERSION 0.5 - DATE APRIL 6, 1986
!
$STORAGE:2
      BLOCK DATA
      IMPLICIT INTEGER*2 (A-Z)
      INTEGER*2 IELEM1(126,2),IELEM2(126,3)
      INTEGER*4 MM,IDTPIX
      REAL A
      CHARACTER*1 KAN
      COMMON /ELECHR/ IELEM(126,5)
      COMMON /STRPIX/ LPIX,MM(90,38),LBLEN,LNGBND(100,5)
      COMMON /STRED/ IDTPIX(90,38),LABL(260,2),MRKCHN(260)
      COMMON /CD/ MAXX,MAXY
        COMMON /ITERM/ITER
        COMMON /IOFFST/IOFF
        COMMON /HP/IHP    !IHP = 1 if terminal is HP else IHP = -1
      COMMON /SIZZE/ MULTX,MULTY
      COMMON /CHARS/IES,IDOT,ITAG,JUMP,LBOND,KAN,ISPACE
      COMMON /KEYS/ ICODE(8)
      COMMON /IPLUS/ IHIGH(14,2)
      COMMON /BONDS/ A(5,3,4,4),B(2,3,4)
      COMMON /XBOND/ GOODB(2,9)
      COMMON /RCAN/ CAN(10,10)
      COMMON /XRNG/ NORDRW(8,8,2),SOFAR
      EQUIVALENCE (IELEM(1,1),IELEM1),(IELEM(1,3),IELEM2)
      DATA IELEM1 /67,79,78,83,67,70,80,66,73,83,65,72,65,66,65,66,83,
     *   65,83,67,86,67,70,77,80,83,65,76,75,78,71,67,63,90,87,65,66,
     *   65,69,69,69,68,68,66,78,78,78,
     *   78,78,78,67,67,77,77,66,77,76,76,67,76,75,65,73,73,67,90,72,
     *   89,89,88,67,72,85,84,84,84,84,84,84,84,84,84,83,72,83,72,
     *   71,83,67,71,82,82,82,82,82,82,80,80,80,80,80,80,70,80,70,79,
     *   74,68,68,68,68,68,68,68,68,68,77,77,77,77,77,77,77,77,77,99,
     *   0,0,0,0,108,0,0,114,0,105,115,103,99,0,103,105,110,108,
     *   98,97,0,117,101,103,98,101,114,105,0,97,100,111,0,110,0,109,
     *   107,117,117,115,114,121,0,101,112,111,105,101,100,98,115,
     *   114,111,110,97,100,117,114,109,97,114,116,114,110,102,114,
     *   111,98,0,101,101,102,0,109,108,105,104,101,99,98,97,0,114,
     *   101,109,0,101,99,100,97,117,110,104,101,98,97,117,116,114,
     *   111,109,100,114,97,109,115,0,112,113,114,115,116,117,118,
     *   119,120,112,113,114,115,116,117,118,119,120,0/
      DATA IELEM2
     *   /4,2,3,2,1,1,3,1,1,4,3,1,3,3,1,3,2,3,3,2,5,1,2,2,2,
     *   2,1,1,1,1,3,2,1,2,6,3,3,3,2,3,3,3,1,2,3,2,2,0,3,3,1,2,6,4,2,
     *   2,3,3,3,3,0,1,3,3,3,4,3,2,3,0,3,4,4,3,1,4,4,2,4,3,5,1,2,0,2,
     *   1,2,3,2,3,3,0,3,4,1,2,4,2,3,2,3,2,1,4,3,8,1,
     *   1,1,1,1,1,1,1,1,1,1,1,1,1,1,1,1,1,4,
     *   0,0,5,4,2,2,5,2,2,0,0,2,0,0,0,5,4,0,5,0,0,2,3,0,4,
     *   4,0,0,0,0,0,3,2,0,0,4,4,0,3,0,0,0,0,0,4,3,3,0,0,5,0,3,0,0,0,
     *   3,0,0,0,0,2,4,0,0,0,0,3,0,0,4,0,5,0,3,0,0,4,6,0,0,0,0,0,3,
     *   0,4,0,0,0,0,0,6,0,0,5,4,0,4,0,4,0,5,0,0,0,
     *   2,2,2,2,2,2,2,2,2,2,2,2,2,2,2,2,2,2,0,
     *   0,0,0,6,7,7,0,7,7,0,0,0,0,0,0,0,0,0,0,0,0,0,0,
     *   6,0,0,0,0,0,0,3,0,0,5,0,0,0,0,0,0,0,0,5,0,0,0,0,0,0,6,0,0,0,
     *   0,0,0,0,0,0,7,0,0,0,0,0,0,0,0,6,0,0,0,0,6,7,0,0,0,0,0,0,
     *   0,0,0,0,0,0,0,7,0,0,6,0,0,0,0,0,0,0,0,0,
     *   3,3,3,3,3,3,3,3,3,3,3,3,3,3,3,3,3,3,0/
      DATA IES/"33/
      DATA IHP/1/
      DATA IDOT/46/,ITAG/35/,JUMP/36/,LBOND/37/,KAN/'^'/,ISPACE/32/
```

```
      DATA MAXX,MAXY /73,38/
      DATA MULTX,MULTY /7,10/
        DATA ITER/1/
        DATA IOFF/0/       !Set IOFF to 0 to disable offset
                           !IOFF = 0 for HP
                           !IOFF = 1 FOR IBM
      DATA MM /3420*0/, IDTPIX /3420*0/
      DATA ICODE /22,23,24,25,31,30,29,28/
      DATA IHIGH /-2,-1,0,1,2,-2,-1,1,2,-2,-1,0,1,2,
     *  -1,-1,-1,-1,-1,0,0,0,0,1,1,1,1,1/
      DATA A /3.5,2.5,1.5,3.5,1.,0.,4.5,3.5,6.,6.,0.,0.,5.5,1.,3.5,0.,
     *  -1.,-2.,0.,2.,0.,8.,7.,9.,7.,0.,0.,2.,6.,-2.,0.,0.,
     *  0.,1.,0.,0.,7.,7.,6.,6.,0.,0.,0.,6.,0.,0.,-1.,-2.,
     *  0.,-2.,0.,8.,7.,9.,2.,0.,0.,2.,5.,7.,0.,0.,0.,0.,
     *  0.,0.,10.,10.,10.,0.,0.,0.,0.,10.,10.,0.,1.,2.,0.,-2.,
     *  0.,9.,10.,8.,10.,0.,0.,-2.,12.,2.,5.,4.,3.,5.,2.,0.,
     *  6.,5.,2.,5.,0.,0.,7.,8.,8.,10.,9.,8.,10.,8.,0.,1.,
     *  0.,2.,12.,0.,0.,12.,-2.,0.,3.5,2.5,1.5,6.,6.,0.,4.5,3.5,
     *  1.,3.5,0.,0.,5.5,3.5,1.,7.,6.,5.,9.,7.,0.,1.,0.,6.,
     *  -2.,0.,0.,9.,0.,2.,7.,7.,7.,6.,6.,0.,0.,0.,6.,0.,
     *  0.,0.,7.,1.,0.,7.,6.,5.,9.,2.,0.,1.,0.,5.,7.,0.,
     *  0.,9.,0.,-2.,10.,10.,10.,10.,0.,0.,0.,0.,10.,10.,0.,0.,
     *  10.,0.,0.,10.,11.,12.,8.,10.,0.,-1.,0.,12.,2.,0.,0.,8.,
     *  0.,-2.,5.,4.,3.,2.,5.,0.,6.,5.,8.,8.,0.,0.,7.,5.,
     *  2.,0.,-1.,-2.,2.,12.,0.,11.,10.,-2.,0.,0.,0.,2.,10.,8./
      DATA B /4,1,1,1,4,7,
     *        1,4,7,7,7,4,
     *        2,2,10,2,2,2,
     *        10,10,10,2,10,10/
      DATA GOODB /4,3,5,5,6,7,3,3,10,10,7,7,2,3,1,1,8,7/
      DATA CAN(1,3),CAN(2,3),CAN(3,3) /11,2,3/
      DATA CAN(1,4),CAN(2,4),CAN(3,4),CAN(4,4) /2,2,2,2/
      DATA CAN(1,5),CAN(2,5),CAN(3,5),CAN(4,5),CAN(5,5)/1,2,1,2,10/
      DATA CAN(1,6),CAN(2,6),CAN(3,6),CAN(4,6),CAN(5,6),CAN(6,6)
     *  /1,1,2,1,1,2/
      DATA CAN(1,7),CAN(2,7),CAN(3,7),CAN(4,7),CAN(5,7),CAN(6,7),
     *  CAN(7,7) /6,5,1,1,1,1,1/
      DATA CAN(1,8),CAN(2,8),CAN(3,8),CAN(4,8),CAN(5,8),CAN(6,8),
     *  CAN(7,8),CAN(8,8) /1,1,1,1,1,1,1,1/
      DATA CAN(1,9),CAN(2,9),CAN(3,9) /3,3,2/
      DATA CAN(1,10),CAN(2,10),CAN(3,10),CAN(4,10),CAN(5,10)
     *  /1,2,1,2,2/
      DATA NORDRW /128*0/,SOFAR /0/
      END
$STORAGE:2
C         MAIN ROUTINE OF XTCHEM
C
      IMPLICIT INTEGER*2 (A-Z)
      INTEGER*4 MM,IDTPIX,DSKMEM
      REAL A
      LOGICAL*2 IEDIT,FIRST,EXIST,OPENED,OPSTD,OPED,DELAY,ALPHID
      CHARACTER*12 HLOID
      CHARACTER*10 ID,GETID,INID,FILE,STDFIL,INFILE,POUND,BLNK10,
     *  ZERO10
      CHARACTER*8 LIBRET
      CHARACTER*82 BLNK90
      CHARACTER*6 FNAME
      CHARACTER*20 DIRECT
      CHARACTER*1 KAN
      CHARACTER*1 AAA
      CHARACTER*1 AAAA
      CHARACTER*1 SSK
      CHARACTER*5 NSC(2),FSC
      CHARACTER*3 QUALIF
      CHARACTER*10 DIG10E
      CHARACTER*1 NAMSTR(10)
      CHARACTER*12 HALOE
      CHARACTER*4 HLOD2E
      CHARACTER*3 HLOE
      CHARACTER*1 NSC10(10),ID10(10),HALO(12),HLO(3),LIBR8(8,640),
     *  FNAM6(6),DIGIT(8),DIGI10(10),HLOD12(12),REPATM,HLOD2(4)
      EQUIVALENCE (NSC(1),FILE),(NSC(1),NSC10(1)),(ID10(1),GETID),
     *  (LIBRET,LIBR8),(FNAME,FNAM6),(DIGIT(1),DIGI10(2)),
     *  (GETID,HLOD12(2)),(HLOID,HLOD12(1))
      EQUIVALENCE (HLOE,HLO(1))
```

```
      EQUIVALENCE (HLOD2E,HLOD2(1))
      EQUIVALENCE (DIG10E,DIGI10(1))
      EQUIVALENCE (HALOE,HALO(1))

COMMON /LIB/ LIBRET(640),NLIBS
      COMMON /ELECHR/ IELEM(126,5)
      COMMON /CD/ MAXX,MAXY
      COMMON /SIZZE/ MULTX,MULTY
      COMMON /HP/IHP
      COMMON /KEYS/ ICODE(8)
      COMMON /IPLUS/ IHIGH(14,2)
      COMMON /BONDS/ A(5,3,4,4),B(2,3,4)
      COMMON /XBOND/ GOODB(2,9)
      COMMON /RCAN/ CAN(10,10)
      COMMON /STRDEF/ NNODE,TABLE(255,43)
      COMMON /CHARS/IES, IDOT,ITAG,JUMP,LBOND,KAN,ISPACE
      COMMON /STRPIX/ LPIX,MM(90,38),LBLEN,LNGBND(100,5)
      COMMON /STRED/ IDTPIX(90,38),LABL(260,2),MRKCHN(260)
      COMMON /HEAD/ MW(12),ISTATE,PAGE
      COMMON /LABELS/ NR,NJLAST,NJNEXT
      COMMON /PARAMS/ JBDIR,NOCHG,LASTN,MCHAR,JCHAR,NLARGE,LEVEL
      COMMON /MODES/ JBTYPE,ICHR,IBDIR,IBTYPE,ISMART,MODE,ISKILL,ISP
      COMMON /PROB/ IPROB,JPROB
      COMMON /IIDD/ IONDX,ID,FILE,INID(2500)
      COMMON /IIDD0/ INFILE(2500),PLACE
      COMMON /IIDD1/ RECNO(2500),NUMIDS,TOTIDS
      COMMON /BLANK/BLNK90
      COMMON /OLD/ IOX,IOY
      COMMON /H/ MOBILE(255,2)
      COMMON /D1/ IDNUM,IDS(9,6),NBD1,DSCNC(6,50)
      COMMON /M1/ MNUM,IMS(90,5)
      COMMON /NDE/ NODE(255,3),IATOM
      COMMON /CONNCT/ IBOND(255,16),KBOND(255,16)
      COMMON /KHARGE/ ICHRGE(50,4),NCHG
      COMMON /CUR/ ICUR
      COMMON /FUSE/ ITIMES
      COMMON /CHN/ CLARGE,CHBITS(65)
      COMMON /TRNS/ TRANS(200)
      COMMON /RANGE/ LOX,HIX,LOY,HIY
      COMMON /FROM/ LCHAR
      COMMON /XRNG/ NORDRW(8,8,2),SOFAR
      COMMON /QTVLNC/ OERR,CHER
      COMMON /ORECS/ OU,OREC
      COMMON /IRECS/ IU,IREC,TOPREC,BOTREC
      COMMON /ALPHID/ ALPHID
      COMMON /RET/ SYM,FSC(2)
      COMMON /DFAULT/ REPATM(2)
      COMMON /MOD/MODEL            !VAA version
      COMMON /CINFO/ NDIRS(4),BDIRS(8,3)
      DIMENSION HPDIR(4),IBMDIR(4),BDHP(8,3),BDIBM(8,3)
      DATA HPDIR/3,7,1,5/
      DATA IBMDIR/3,7,5,1/
      DATA BDIBM/31,25,23,23,25,31,31,29,23,23,25,25,29,29,29,
    * 31,22,24,24,24,28,30,30,30/
      DATA BDHP/23,25,25,23,29,31,29,29,31,23,23,25,25,29,31,31,
    * 22,24,24,24,28,30,30,30/
      DATA POUND /'          '/, BLNK10 /'          '/,
    *    ZERO10 /'0000000000'/

!     This section does some HP terminal dependent chores
!     HNDOFF = Sets handshake type
!     DEVICE = Gets HP terminal model number   (2623A or 2647A)
!     DOWNLO = Loads the function keys CALL HNDOFF            !VAA version
      CALL DEVICE(MODEL)     !VAA version
      CALL DOWNLO            !VAA version BLNK90(1:1)='^'
      DO 919 I=2,81
      BLNK90(I:I)=' '
919   CONTINUE
      BLNK90(82:82)='^'
      IF (IHP .EQ. 1) THEN
      DO 456 I=1,4
```

```
156         NDIRS(I)=HPDIR(I)         !Set chain values for HP terminal
            DO 567 I=1,8
            DO 567 J=1,3
            BDIRS(I,J)=BDHP(I,J)
567         CONTINUE
            ELSE
            DO 678 I=1,4
678         NDIRS(I)=IBMDIR(I)        !Set chain values for IBM terminal
            DO 789 I=1,8
            DO 789 J=1,3
            BDIRS(I,J)=BDIBM(I,J)
789         CONTINUE
            ENDIF
C
C
C
C           The substructure library list file is read.
            NLIBS = 0
            LIO = 1
            INQUIRE(FILE='LIB.RET',EXIST=EXIST)
            IF (EXIST) THEN
                OPEN(LIO,FILE='LIB.RET',STATUS='OLD')
                IF (IHP .EQ. 1) THEN    !Handle DEC10 LIB.RET format here
                    DO 505 I=1,645
                    READ (LIO, 444,END=666) DIRECT
444                 FORMAT(A20)
                    J=INDEX(DIRECT,':')
                    K=INDEX(DIRECT,'.')
                    FNAME='       '
                    FNAME=DIRECT(J+1:K-1)
                    NLIBS = NLIBS+1
                    LIBR8(1,NLIBS) = '^'
                    DO 4040 J=1,6
                    LIBR8(J+1,NLIBS)=FNAM6(J)
4040                CONTINUE
                    LIBR8(8,NLIBS)='^'
505                 CONTINUE
666                 CONTINUE
                    CLOSE(LIO)
                ELSE
                    DO 50 I = 1,645
                    READ(LIO,39,END=60) FNAME,QUALIF
39                  FORMAT(A6,3X,A3)
                    IF (QUALIF.EQ.'STR') THEN
                        NLIBS = NLIBS + 1
                        LIBR8(1,NLIBS) = '^'
                        DO 40 J = 1,6
                            LIBR8(J+1,NLIBS) = FNAM6(J)
40                      CONTINUE
                        LIBR8(8,NLIBS) = '^'
                    ENDIF
50                  CONTINUE
60                  CONTINUE
                    CLOSE(LIO)
                ENDIF
            ELSE
                STOP 'TO EXECUTE PROGRAM ENTER COMMAND -RUN-'
            ENDIF
C
C           Initializations are made.
            FSC(1) = '       '
            FSC(2) = '       '
            OU = 30

IU = 31
            OREC = 0
            IREC = 0
            TOPREC = 0
            BOTREC = 0
            IONDX = 32
            NUMIDS = 0
            TOTIDS = 0
            FILE = POUND
            STDFIL = POUND
            OPENED = .FALSE.
            OPSTD = .FALSE.
```

```
            OPED = .FALSE.
            HALO(1) = KAN
            HALO(12) = KAN
            HLOD2(1) = KAN
            HLOD2(4) = KAN
            HLO(1) = KAN
            HLO(3) = KAN
            HLOD12(1) = KAN
            HLOD12(12) = KAN
            CHER = 0
            FIRST = .TRUE.
            DELAY = .FALSE.
            ID = ZERO10
            The index file is read.
            INQUIRE(FILE='IDS.NDX',EXIST=EXIST)
            IF (EXIST) THEN
                OPEN(IONDX,FILE='IDS.NDX',STATUS='OLD',ACCESS='DIRECT',
       *            FORM='FORMATTED',RECL=80)
                DO 100 I = 1,2500
                    NUMIDS = I - 1
                    READ(IONDX,99,REC=I,END=110) INID(I),INFILE(I),RECNO(I)
                    IF (INID(I).EQ.BLNK10) GO TO 110
100             CONTINUE
99              FORMAT(A10,A10,I6)
110             CONTINUE
                CLOSE(IONDX)
            ENDIF
            TOTIDS = NUMIDS
            FRSTID = NUMIDS
            CALL RESET(IX,IY,FIRST)
            CALL SETSCR(1)
            PAGE = 1
            CALL DISPLA(1)
C
            INQUIRE(FILE='XTCHEM.SPC',EXIST=EXIST)
            IF (EXIST) THEN
                OPEN(LIO,FILE='XTCHEM.SPC',STATUS='OLD')
                READ(LIO,149) AAA,SSK,(REPATM(I),I=1,2)
149             FORMAT(A1,1X,A1,1X,2A1)
                IF (AAA .EQ.'A') THEN
                    ALPHID = .TRUE.
                ELSE
                    ALPHID = .FALSE.
                ENDIF
                IF (SSK .EQ.'G') THEN
                    ISKILL = 2
                ELSE
                    ISKILL = 1
                ENDIF
                CLOSE(LIO)
            ELSE
                ALPHID = .FALSE.
                AAA = 'N'
                ISKILL = 2
                SSK = 'G'
                REPATM(1) = 'N'
                REPATM(2) = CHAR(0)
            ENDIF
61          CONTINUE
            CALL FTSIZE(2,18)
            CALL FTLOCA(6,22)
            CALL FTEXT('^Automatic chemical input generator...^')
            CALL FTLOCA(8,22)
            IF (ALPHID) THEN
                CALL FTEXT('^IDs are: ALPHANUMERIC^')
            ELSE
                CALL FTEXT('^IDs are: NUMERIC^')
            ENDIF
            CALL FTLOCA(9,22)
            IF (ISKILL.EQ.2) THEN
                CALL FTEXT('^Screen headers are: GUIDED^')
            ELSE
                CALL FTEXT('^Screen headers are: SOLO^')
```

```
              ENDIF
              CALL FTLOCA(10,22)
              CALL FTEXT('^The REPEAT STATE default replacement atom is: ^')
              HLOD2(2) = REPATM(1)
              HLOD2(3) = REPATM(2)
              CALL FTEXT(HLOD2E)
62        CONTINUE
              CALL FTLOCA(11,22)
              CALL FTEXT('^Do you want to change program parameters (Y/N)?^')
              CALL REDO(L,89,78,13,0,0,0)
              IF (L.EQ.89) THEN
88                CALL FTLOCA(8,23)
                  CALL FTEXT('^Enter "A" for alphanumeric IDs -or-^')
                  CALL FTLOCA(9,23)
                  CALL FTEXT('^Enter "N" for numeric IDs with incremental defau
     *lts -or-^')
                  CALL FTLOCA(10,23)
                  HLO(2) = AAA
                  CALL FTEXT('^Enter CR for current status of: ^')
                  CALL FTEXT(HLOE)
                  CALL REDO(AA,65,78,13,0,0,0)
                  CALL FTLOCA(8,26)
                  IF (AA.EQ.65) THEN
                      CALL FTEXT('^IDs are ALPHANUMERIC.  Is this OK (Y/N)?^')
                  ELSE IF (AA.EQ.78) THEN
                      CALL FTEXT('^IDs are NUMERIC.  Is this OK (Y/N)?^')
                  ENDIF
                  IF (AA.NE.13) THEN
                      L = GETCHR()
                      CALL SETCOL(0)
                      CALL CLR
                      CALL SETCOL(1)
                      IF ((L.NE.89).AND.(L.NE.121)) THEN
                          CALL SETCOL(0)
                          CALL CLR
                          CALL SETCOL(1)
                          GO TO 88
                      ENDIF
                      IF (AA.EQ.65) THEN
                          ALPHID = .TRUE.
                      ELSE
                          ALPHID = .FALSE.
                      ENDIF
                  ELSE
                      CALL SETCOL(0)
                      CALL CLR
                      CALL SETCOL(1)
                      AA = ICHAR(AAA)
                  ENDIF
                  CALL FTLOCA(8,24)
                  CALL FTEXT('^Enter "G" if you need HEADER guidance -or-^')
                  CALL FTLOCA(9,24)
                  CALL FTEXT('^Enter "S" if you wish to solo -or-^')
                  CALL FTLOCA(10,24)
                  CALL FTEXT('^Enter CR for current status of: ^')
                  HLO(2) = SSK
                  CALL FTEXT(HLOE)
                  CALL REDO(SK,71,83,13,0,0,0)
                  IF (SK.EQ.71) THEN
                      ISKILL = 2
                  ELSE IF (SK.EQ.83) THEN
                      ISKILL = 1
                  ELSE
                      SK = ICHAR(SSK)
                  ENDIF
63            CONTINUE
                  CALL FTLOCA(8,22)
                  CALL FTEXT('^Enter REPEAT STATE default replacement atom: ^')
                  CALL FTLOCA(9,22)
                  CALL FTEXT('^(CR for current: ^')
                  CALL FTEXT(HLOD2E)
                  CALL FTEXT('^)^')
                  R1 = ICHAR(REPATM(1))
                  R2 = ICHAR(REPATM(2))
                  IF (IHP .EQ. 1) THEN
                      CALL ALPCUR
```

```
                ACCEPT 695, REPATM(1),REPATM(2)
695     FORMAT(2A1)
        ELSE
            REPATM(1) = CHAR(GETCHR())
        ENDIF
            CALL FTLOCA(9,22)
            CALL FTEXT('^                                          ^')
            CALL FTLOCA(1,1)
            CALL FTEXT('^                                          ^')
            CALL FTLOCA(8,67)
            IF(ICHAR(REPATM(1)).EQ.13.OR. ICHAR(REPATM(1)) .EQ. 32) THEN
                REPATM(1) = CHAR(R1)
                REPATM(2) = CHAR(R2)
                HLO(2) = REPATM(1)
                CALL FTEXT(HLOE)
                HLO(2) = REPATM(2)
                CALL FTEXT(HLOE)
                GO TO 77
            ELSE
                HLO(2) = REPATM(1)
                CALL FTEXT(HLOE)
                HLO(2) = ' '
                CALL FTEXT(HLOE)
                IF ((ICHAR(REPATM(1)).LT.65).OR.(ICHAR(REPATM(1)).GT.
     *              90)) THEN
                    GO TO 73
                ENDIF
                IF (IHP .NE. 1) REPATM(2) = CHAR(GETCHR())
                IF ((ICHAR(REPATM(2)).EQ.13).OR.(ICHAR(REPATM(2)).EQ.32))
     *              THEN
                    REPATM(2) = CHAR(0)
                ELSE
                    CALL FTLOCA(8,68)
                    HLO(2) = REPATM(2)
                    CALL FTEXT(HLOE)
                ENDIF
            ENDIF
67          CONTINUE
            DO 72 I = 1,107
                IF ((ICHAR(REPATM(1)).EQ.IELEM(I,1)).AND.(ICHAR(REPATM(2))
     *              .EQ.IELEM(I,2))) GO TO 74
72          CONTINUE
73          CONTINUE
            CALL FTLOCA(1,1)
            CALL FTEXT('^ELEMENT DOES NOT EXIST IN THE ELEMENT TABLE^')
            REPATM(1) = CHAR(R1)
            REPATM(2) = CHAR(R2)
            GO TO 63
74          CONTINUE
            CALL FTLOCA(9,22)
            CALL FTEXT('^Is default replacement atom OK (Y/N)?^')
            CALL REDO(L,89,78,0,0,0,0)
            IF (L.NE.89) THEN
                REPATM(1) = CHAR(R1)
                REPATM(2) = CHAR(R2)
                GO TO 63
            ENDIF
77          OPEN(LIO,FILE='XTCHEM.SPC')
            AAAA=CHAR(AA)
            SSK=CHAR(SK)
            WRITE(LIO,149) AAAA,SSK,(REPATM(I),I=1,2)
            CLOSE(LIO)
            CALL SETCOL(0)
            CALL CLR
            CALL SETCOL(1)
        ENDIF
        GO TO 9
1       CONTINUE
C
C
C       The program is called.
        CALL STRINP(IX,IY,IEDIT,FIRST)
        FIRST = .FALSE.
        CALL SETSCR(1)
```

```
            PAGE = 1
            CALL DISPLA(1)
 9          CALL FTSIZE(2,18)
            IF (IHP .NE. 1) THEN
            CALL MEMDSK(CLUSTS,CPDISK,BPSECT,SPCLUS)
            DSKMEM = CLUSTS * BPSECT * SPCLUS
            CALL FTLOCA(1,1)
            CALL REPNUM(DSKMEM,NDGT,DIGIT)
            CALL FTEXT('^Number of free bytes on disk: ^')
            DIGI10(1) = '^'
            DIGI10(10) = '^'
            CALL FTEXT(DIG10E)
            ENDIF
C
10          CONTINUE
C
C           The operator is prompted for next instruction.
            IEDIT = .FALSE.
            CHER = 0
            CALL FTSIZE(2,18)
            CALL FTLOCA(7,18)
            CALL FTEXT('^N TO ENTER NEXT COMPOUND - I TO EDIT NEXT COMPOUND
           *-^')
            CALL FTLOCA(8,15)
            CALL FTEXT('^P TO EDIT PREVIOUS COMPOUND - V TO VIEW PREVIOUS CO
           *MPOUND -^')
            CALL FTLOCA(9,20)
            CALL FTEXT('^'' TO VIEW LIST OF COMPOUNDS ON DISK - Q TO QUIT^')
            CALL REDO(L,78,73,80,81,86,39)
C
.1

IF (((L.EQ.86).OR.(L.EQ.80)).AND.(FIRST.OR.(NUMIDS.EQ.FRSTID)))
           *    GO TO 10
            IF (L.EQ.39) THEN
               IF (NUMIDS.GT.0) THEN
                   CALL VIDNDX
               ELSE
                   CALL FTLOCA(1,1)
                   CALL FTEXT('^NO INDEX TABLE YET EXISTS^')
               ENDIF
               GO TO 10
            ENDIF
            IF (L.EQ.86) THEN
               CALL SETSCR(2)
               PAGE = 2
               CALL DISPLA(2)
               CALL FTSIZE(2,18)
               CALL FTLOCA(1,1)
               CALL FTEXT('^PRESS RETURN TO RETURN TO MENU^')
               AA = GETCHR()
               CALL SETSCR(1)
               PAGE = 1
               CALL DISPLA(1)
                   IF (IHP .EQ. 1) THEN
                      CALL FTLOCA(1,1)
                      CALL FTEXT('^                                    ^')
                      CALL GRAOFF
                   ENDIF
               GO TO 10
            ENDIF
C
            IF (IHP .NE. 1) THEN
            IF (DSKMEM.LE.(36864+(80*TOTIDS))) THEN
               CALL FTLOCA(1,1)
               CALL FTEXT('^WARNING: Insufficient number of bytes on disk:^
           *')
               CALL FTEXT(DIG10E)
               CALL FTEXT('^ PROGRAM TERMINATING^')
               L = 81
            ENDIF
            ENDIF
C
```

```
C       This section closes the program.
        IF (L.EQ.81) THEN
            OPEN(IONDX,FILE='IDS.NDX',ACCESS='DIRECT',
     *          FORM='FORMATTED',RECL=80)
            OCOUNT = 0
            DO 200 I = 1,NUMIDS
                IF (INFILE(I).NE.POUND) THEN
                    OCOUNT = OCOUNT + 1
                    WRITE(IONDX,99,REC=OCOUNT) INID(I),INFILE(I),RECNO(I)
                ENDIF
200         CONTINUE
            DO 210 I = OCOUNT+1,OCOUNT+6
                WRITE(IONDX,289,REC=I) BLNK10
210         CONTINUE
289         FORMAT(A10)
            CLOSE(IONDX)
            IF (OPENED) THEN
                WRITE(OU,29,REC=1) OREC
                CLOSE(OU)

ENDIF
        CALL CLOSEG
        IF (IHP .EQ. 1) CALL ALPCON      !Turn on alpha cursor
        IF (IHP .EQ. 1) STOP
            IF (DSKMEM.LE.(36864+(80*TOTIDS))) THEN
                STOP 'UPLOAD OR CLEAR DISK SPACE BEFORE USING XTCHEM'
            ELSE
                STOP
            ENDIF C
C
C       THIS SECTION OPENS AN INPUT CONNECTION TABLE AND ITS FILE
C       FOR EDITING.
        ELSE IF ((L.EQ.73).OR.(L.EQ.80)) THEN
            IEDIT=.TRUE.
            IF (L.EQ.80) THEN
                OPED = .FALSE.
                IU = OU
                GETID = INID(NUMIDS)
                ID = GETID
                DO 554 I = 1,10
                    HALO(I+1) = ID10(I)
554             CONTINUE
                CALL FTLOCA(8,23)
                CALL FTEXT('^PREVIOUS STRUCTURE TO BE VIEWED: ^')
                CALL FTEXT(HALOE)
                FILE = INFILE(NUMIDS)
                IREC = RECNO(NUMIDS)
                PLACE = NUMIDS
                DO 555 I = 1,10
                    HALO(I+1) = NSC10(I)
555             CONTINUE
            ELSE
                FY = 10
                IF (FIRST) DELAY = .TRUE.
565             CONTINUE
                IF (ALPHID) THEN
                    GETID = BLNK10
                ELSE
                    GETID = ZERO10
                ENDIF
                CALL FTLOCA(9,28)
                IF (ALPHID) THEN
                    CALL FTEXT('^Enter (1-10) character ID^')
                ELSE
                    CALL FTEXT('^Enter (1-10) digit ID^')
                ENDIF
C               Input structure ID
11445           J = 0
        IF (IHP .EQ. 1) THEN
            CALL ALPCUR
            ACCEPT 691, (NAMSTR(I),I=1,10)
691         FORMAT(10A1)
        ENDIF
```

```
                DO 4445 I = 1,100
                    J = J + 1
                    FX = 27 + J
1445            CONTINUE
                IF (IHP .EQ. 1) THEN
                    AA=ICHAR(NAMSTR(J))

ELSE
                    AA = GETCHR()
        ENDIF
                IF (AA.EQ.13 .OR. AA .EQ. 32) THEN
                    FIN = J - 1
                    GO TO 4447
                ENDIF
                IF (AA.EQ.8) THEN
                    IF (J.GT.1) J = J - 1
                    FX = 27 + J
                    CALL FTLOCA(FY,FX)
                    CALL FTEXT('^ ^')
                    IF (ALPHID) THEN
                        ID10(J) = ' '
                    ELSE
                        ID10(J) = '0'
                    ENDIF
                    GO TO 1445
                ENDIF
                IF (((AA.GE.48).AND.(AA.LE.57)).OR.(AA.EQ.32)) THEN
                    HLO(2) = CHAR(AA)
                    IF (AA.EQ.32) AA = 48
                IF (IHP .NE. 1) THEN
                    CALL FTLOCA(FY,FX)
                    CALL FTEXT(HLOE)
                ENDIF
                    ID10(J) = CHAR(AA)
                ELSE IF ((ALPHID).AND.(((AA.GE.65).AND.(AA.LE.90)).OR.
 *                  ((AA.GE.97).AND.(AA.LE.122)))) THEN
                    IF (AA.GE.97) AA = AA - 32
                    HLO(2) = CHAR(AA)
                IF (IHP .NE. 1) THEN
                    CALL FTLOCA(FY,FX)
                    CALL FTEXT(HLOE)
                ENDIF
                    ID10(J) = CHAR(AA)
                ELSE
                    HLO(2) = CHAR(AA)
                    CALL FTLOCA(1,1)
                    PAGE = 0
                    CALL FTEXT(HLOE)
                    CALL FTEXT('^ IS ILLEGAL INPUT. ENTER DIGITS OR SPAC
    *ES AND CR^')
        IF (IHP .EQ. 1) THEN
        CALL FTLOCA(9,49)
        CALL FTEXT('^                ^')
        CALL FTLOCA(9,49)
        GO TO 11445
        ENDIF
                    GO TO 1445
                ENDIF
                IF (J.EQ.10) THEN
                    FIN = 10
                    GO TO 4447
                ENDIF
4445        CONTINUE
4447        CONTINUE
            CALL SETCOL(0)
            CALL CLR
            CALL SETCOL(1)
            IF ((GETID.EQ.ZERO10).OR.(GETID.EQ.BLNK10)) THEN
                IF (FIRST) DELAY = .FALSE.
                GO TO 10
            ENDIF
            IF (FIN.LT.10) THEN
                J = 10 - FIN
                DO 8689 I = FIN,1,-1
```

```
                        ID10(I+J) = ID10(I)
                     IF (ALPHID) THEN
                        ID10(I) = ' '
                     ELSE
                        ID10(I) = '0'
                     ENDIF
8689              CONTINUE
               ENDIF
               DO 8334 I = 1,10
                  HALO(I+1) = ID10(I)
8334           CONTINUE
               CALL FTLOCA(7,23)
               CALL FTEXT('^Seeking ID NUMBER: ^')
               CALL FTEXT(HALOE)
               DO 8335 I = 1,NUMIDS
                  IF ((GETID.EQ.INID(I)).AND.(INFILE(I).NE.POUND)) THEN
                     IF (FILE.NE.INFILE(I)) THEN
                        IF (.NOT.FIRST) THEN
                           WRITE(OU,29,REC=1) OREC
                           CLOSE(OU)
                           OPENED = .FALSE.
                        ENDIF
                        OPED = .TRUE.
                        OU = IU
                     ELSE
                        OPED = .FALSE.
                        IU = OU
                     ENDIF
                     FILE = INFILE(I)
                     IREC = RECNO(I)
                     PLACE = I
                     GO TO 8336
                  ENDIF
8335           CONTINUE
               CALL FTLOCA(7,23)
               CALL FTEXT('^                                    ^')
               CALL FTLOCA(7,36)
               CALL FTEXT('^ID NUMBER: ^')
               CALL FTEXT(HALOE)
               CALL FTLOCA(1,1)
               CALL FTEXT('^ID NUMBER NOT FOUND IN DIRECTORY^')
               IF (FIRST) DELAY = .FALSE.
               GO TO 10
8336           CONTINUE
               CALL FTLOCA(8,23)
               CALL FTEXT('^Input from file: ^')
               DO 8837 I = 1,10
                  HALO(I+1) = NSC10(I)
8837           CONTINUE
               CALL FTEXT(HALOE)
            ENDIF
            CALL FTLOCA(9,23)
            CALL FTEXT('^Edited structure will be appended to file: ^')
            CALL FTEXT(HALOE)
            CALL FTLOCA(10,23)
            CALL FTEXT('^Press RETURN to clear screen^')
            AA = GETCHR()
            CALL SETCOL(0)
            CALL CLR
            CALL SETCOL(1)
            IF (OPED) THEN
               INQUIRE(FILE=FILE,EXIST=EXIST)
            ELSE
               EXIST = .TRUE.
            ENDIF
            IF (.NOT.EXIST) THEN
               OPED = .FALSE.
               CALL FTLOCA(1,1)
               CALL FTEXT('^FILE IS NOT ON DISK^')
               IF (FIRST) DELAY = .FALSE.
               GO TO 10
            ELSE
```

```
              IF (OPED) THEN
                 OPEN(IU,FILE=FILE,STATUS='OLD',ACCESS='DIRECT',
     *              FORM='FORMATTED',RECL=80)
                 OPENED = .TRUE.
                 READ(IU,29,REC=1) OREC
              ENDIF
              ID = GETID
           ENDIF
           GO TO 1
C
C
C          THIS SECTION OPENS THE STANDARD CONNECTION TABLE OUTPUT FILE.
           ELSE IF ((FIRST.AND.(.NOT.IEDIT)).OR.(DELAY.AND.(.NOT.IEDIT)
     *        .AND.(.NOT.FIRST))) THEN
              IF (DELAY) THEN
                 WRITE(IU,29,REC=1) OREC
                 CLOSE(IU)
                 OPED = .FALSE.
                 OPENED = .FALSE.
                 OU = 30
                 IU = 31
                 DELAY = .FALSE.
              ENDIF
44            CONTINUE
              FILE = POUND
              TOPREC = 0
              BOTREC = 0
              CALL SETCOL(0)
              CALL CLR
              CALL SETCOL(1)
              CALL FTLOCA(9,20)
              CALL FTEXT('^Enter (1-6) character connection table output fi
     *le name^')
C             Request file name
C             Read file name
              J = 0
           IF (IHP .EQ. 1) THEN
                 CALL ALPCUR
                 ACCEPT 691,(NAMSTR(I),I=1,6)
           ENDIF
              DO 4444 I = 1,60
                 J = J + 1
                 FX = 19 + J
1444             CONTINUE
           IF (IHP .EQ. 1) THEN
           AA=ICHAR(NAMSTR(J))
           IF (AA .GT. 97) AA=AA-32
           ELSE
                 AA = GETCHR()
           ENDIF
                 IF (AA.EQ.13 .OR. AA .EQ. 32) GO TO 4446
                 IF (AA.EQ.8) THEN
                    IF (J.GT.1) J = J - 1
                    FX = 19 + J
                    CALL FTLOCA(10,FX)
                    CALL FTEXT('^ ^')
                    NSC10(J) = ' '
                    GO TO 1444
                 ENDIF
                 IF (AA .GE. 97) AA = AA-32
                 HLO(2) = CHAR(AA)
                 CALL FTLOCA(10,FX)
                 IF (((AA.GE.48).AND.(AA.LE.57)).OR.((AA.GE.65).AND.
     *              (AA.LE.90)).OR.((AA.GE.97).AND.(AA.LE.122))) THEN
                    NSC10(J) = CHAR(AA)
                 ELSE
                    NSC10(J) = ' '
                 ENDIF
                 IF (IHP .NE. 1)CALL FTEXT(HLOE)
                 IF (J.EQ.6) GO TO 4446
4444          CONTINUE
4446          CALL SETCOL(0)
              CALL CLR
              CALL SETCOL(1)
```

```
              IF (NSC(1) .EQ. '     ') GO TO 44
443           FORMAT(2A5)
              NSC10(7) = '.'
              NSC10(8) = 'T'
              NSC10(9) = 'B'
              NSC10(10) = 'L'
              DO 8686 I = 1,10
                  HALO(I+1) = NSC10(I)
8686          CONTINUE
              CALL FTLOCA(8,21)
              CALL FTEXT('^All non-edited structures will output to file: ^
     *')
              CALL FTEXT(HALOE)
              CALL FTLOCA(9,21)
              CALL FTEXT('^All edited structures will be appended to their
     *input file^')
              CALL FTLOCA(10,21)
              CALL FTEXT('^Is file name OK (Y/N)?^')
              AA = GETCHR()
              CALL SETCOL(0)
              CALL CLR
              CALL SETCOL(1)
              IF ((AA.NE.89).AND.(AA.NE.121)) GO TO 44
              INQUIRE(FILE=FILE,EXIST=EXIST)
              IF (.NOT.EXIST) GO TO 404
              DO 8888 I = 1,NUMIDS
                  IF (FILE.EQ.INFILE(I)) GO TO 466
8888          CONTINUE
              GO TO 404
C             File exists - Do you wish to append it (Y/N)?
466           CONTINUE
              CALL FTLOCA(8,23)
              CALL FTEXT('^File exists - Do you wish to append it (Y/N)?^'
     *)
              IKAR = GETCHR()
              CALL SETCOL(0)
              CALL CLR
              CALL SETCOL(1)
              IF (IKAR.EQ.78 .OR. IKAR.EQ.110) GO TO 44
C             If no - go get new file name
              IF (IKAR .EQ. 89 .OR. IKAR .EQ. 121) THEN
                  OPEN(OU,FILE=FILE,STATUS='OLD',ACCESS='DIRECT',FORM=
     *               'FORMATTED',RECL=80)
                  OPENED = .TRUE.
                  OPSTD = .TRUE.
                  STDFIL = FILE
                  READ(OU,29,REC=1) OREC
                  GO TO 55
              ENDIF
              CALL FTLOCA(10,23)
              CALL FTEXT('^Invalid response:^')
              HLO(2) = CHAR(IKAR)
              CALL FTEXT(HLOE)
C             Invalid response - go try new entry
              GO TO 466
404           OPEN(OU,FILE=FILE,STATUS='NEW',ACCESS='DIRECT',FORM=
     *           'FORMATTED',RECL=80)
              OPENED = .TRUE.
              OPSTD = .TRUE.
              STDFIL = FILE
              OREC = 1
              WRITE(OU,29,REC=OREC) OREC
C
C
C       THIS SECTION REQUESTS THE STANDARD OUTPUT FILE TO RECEIVE ITS
C       NEXT STRUCTURE.
              ELSE
                  IEDIT = .FALSE.
                  TOPREC = 0
                  BOTREC = 0
                  IF ((FILE.NE.STDFIL).OR.(OU.EQ.11)) THEN
                      WRITE(IU,29,REC=1) OREC
29                    FORMAT(I5)
                      CLOSE(IU)
                      FILE = STDFIL
                      OU = 30
```

```
              IU = 31
              OPEN(OU,FILE=FILE,STATUS='OLD',ACCESS='DIRECT',FORM=
     *          'FORMATTED',RECL=80)
              READ(OU,29,REC=1) OREC
              OPENED = .TRUE.
              OPED = .FALSE.
              OPSTD = .TRUE.
          ELSE
              CLOSE(OU)
              OPEN(OU,FILE=FILE,STATUS='OLD',ACCESS='DIRECT',FORM=
     *          'FORMATTED',RECL=80)
          ENDIF
      ENDIF
C
C
C     ENTER ID NUMBER OF NEXT INPUT STRUCTURE.
55    CONTINUE
      CALL SETCOL(0)
      CALL CLR
      CALL SETCOL(1)
      IF (.NOT.IEDIT) THEN
          IF (ALPHID) THEN
              GETID = BLNK10
              MX = 32
              CALL FTLOCA(8,MX)
              CALL FTEXT('^Enter (1-10) character ID^')
          ELSE
              GETID = ZERO10
              MX = 28
              CALL FTLOCA(7,MX)
              CALL FTEXT('^Enter CR for default ID increment -or-^')
              CALL FTLOCA(8,MX)
              CALL FTEXT('^Enter (1-10) digit ID^')
          ENDIF
11555     J = 0
          IF (IHP .EQ. 1) THEN
              CALL ALPCUR
              ACCEPT 691, (NAMSTR(I),I=1,10)
          ENDIF
          DO 5555 I = 1,100
              J = J + 1
              FX = MX + J - 1
1555      CONTINUE
          IF (IHP .EQ. 1) THEN
          AA=ICHAR(NAMSTR(J))
          ELSE
              AA = GETCHR()
          ENDIF
              IF (AA.EQ.13 .OR. AA .EQ. 32) THEN IF ((GETID.EQ.ZERO10).OR.(GETID.EQ.BLNK10)) THEN
                      IF (ALPHID) GO TO 55
                      GETID = ID
                      IF ((NUMIDS.EQ.0).OR.((NUMIDS.GT.0).AND.
     *                    (ID.EQ.INID(NUMIDS))).OR.(FIRST)) THEN
5530                      DO 5535 K = 10,1,-1
                              ID10(K) = CHAR(ICHAR(ID10(K)) + 1)
                              IF (ID10(K).EQ.':') THEN
                                  ID10(K) = '0'
                                  IF (K.EQ.1) THEN
                                      GETID = '0000000001'
                                      GO TO 5536
                                  ENDIF
                              ELSE
                                  GO TO 5536
                              ENDIF
5535                      CONTINUE
5536                      CONTINUE
                          FIN = 10
                          DO 5566 K = 1,NUMIDS
                              IF (GETID.EQ.INID(K)) GO TO 5530
5566                      CONTINUE
                          IF (IHP .NE. 1) THEN
                          CALL FTLOCA(9,28)
```

```
                    CALL FTEXT(HLOID)
                  ENDIF
                  GO TO 5556
                ELSE
                  FIN = 10
                    IF (IHP .NE. 1) THEN
                    CALL FTLOCA(9,28)
                    CALL FTEXT(HLOID)
                      ENDIF
                  GO TO 6667
                ENDIF
              ELSE
                FIN = J - 1
                GO TO 5556
              ENDIF
            ENDIF
            IF (AA.EQ.8) THEN
                IF (J.GT.1) J = J - 1
                FX = MX + J - 1
                CALL FTLOCA(9,FX)
                CALL FTEXT('^ ^')
                IF (ALPHID) THEN
                   ID10(J) = ' '
                ELSE
                   ID10(J) = '0'
                ENDIF
                GO TO 1555
            ENDIF
            IF (((AA.GE.48).AND.(AA.LE.57)).OR.(AA.EQ.32)) THEN
               HLO(2) = CHAR(AA)
               IF (AA.EQ.32) AA = 48
               IF (IHP .NE. 1) THEN
               CALL FTLOCA(9,FX)
               CALL FTEXT(HLOE)
               ENDIF
               ID10(J) = CHAR(AA)
            ELSE IF ((ALPHID).AND.(((AA.GE.65).AND.(AA.LE.90)).OR.
*              ((AA.GE.97).AND.(AA.LE.122)))) THEN
               IF (AA.GE.97) AA = AA - 32
               HLO(2) = CHAR(AA)
               IF (IHP.NE.1)  THEN
               CALL FTLOCA(9,FX)
               CALL FTEXT(HLOE)
               ENDIF
               ID10(J) = CHAR(AA)
            ELSE
               HLO(2) = CHAR(AA)
               CALL FTLOCA(1,1)
               PAGE = 0
               CALL FTEXT(HLOE)
               CALL FTEXT('^ IS ILLEGAL INPUT. ENTER DIGITS OR SPAC
     *ES AND CR^')
               IF (IHP .EQ. 1) THEN
               CALL FTLOCA(9,49)
               CALL FTEXT('^              ^')
               CALL FTLOCA(9,49)
               GO TO 11555
               ENDIF
                GO TO 1555
              ENDIF
              IF (J.EQ.10) THEN
                 FIN = 10
                 GO TO 5556
              ENDIF
5555       CONTINUE
5556       CONTINUE
           IF ((GETID.EQ.ZERO10).OR.(GETID.EQ.BLNK10)) GO TO 55
           IF (FIN.LT.10) THEN
             J = 10 - FIN
             DO 6663 I = FIN,1,-1
                ID10(I+J) = ID10(I)
                IF (ALPHID) THEN
                   ID10(I) = ' '
                ELSE
                   ID10(I) = '0'
                ENDIF
```

```
6663            CONTINUE
             ENDIF
             DO 6666 I = 1,NUMIDS
                IF (GETID.EQ.INID(I)) THEN
                   CALL FTLOCA(10,MX)
                   CALL FTEXT('^WARNING - ID already exists on current file
     *s - ^')
                   CALL FTLOCA(11,MX)
                   CALL FTEXT('^Upload existing structure prior to new entr
     *y^')
                   CALL FTLOCA(12,MX)
                   CALL FTEXT('^Press RETURN to continue^')
                   AA = GETCHR()
                   GO TO 55
                ENDIF
6666         CONTINUE
6667         CONTINUE
             CALL FTLOCA(10,MX)
             CALL FTEXT('^Output ID: ^')
             CALL FTEXT(HLOID)
             CALL FTLOCA(11,MX)
             CALL FTEXT('^Is ID OK (Y/N)?^')
             IKAR = GETCHR()
C            If no - go get new ID
             IF (IKAR.NE.89 .AND. IKAR.NE.121) GO TO 55
             ID = GETID
             CALL SETCOL(0)
             CALL CLR
             CALL SETCOL(1)
          ENDIF
C
          GO TO 1
          END
C
C
C
C     SUBROUTINE VCONTB writes the file format image of the input for
C     edit connection table to the screen.
C
C     ORI   Paul Broderick    April, 1985
      SUBROUTINE VCONTB
      IMPLICIT INTEGER*2(A-Z)
      CHARACTER*82 LINE
      CHARACTER*12 IDHLO
      CHARACTER*10 ID,FILE,INID,PASSID
      CHARACTER*1 CONTBL,LINE82(82),ID12(12)
      EQUIVALENCE (LINE;LINE82),(ID,ID12(2)),(IDHLO,ID12(1))
      COMMON /CONTBL/ CONTBL(80,258),LTBL
      COMMON /IIDD/ IONDX,PASSID,FILE,INID(2500)
C
      ID = PASSID
      CALL SETSCR(1)
      PAGE = 1
      CALL DISPLA(1)
      LINE82(1) = '^'
      LINE82(82) = '^'
      ID12(1) = '^'
      ID12(12) = '^'
      LOW = 1
      PASSES = LTBL / 32
      IF (MOD(LTBL,32).GT.0) PASSES = PASSES + 1
      IF (LTBL.GT.32) THEN
         HIGH = 32
      ELSE
         HIGH = LTBL
      ENDIF
C
      DO 300 I = 1,PASSES
         CALL FTSIZE(1,10)
         FY = 1
         CALL FTLOCA(FY,1)
         CALL FTEXT(IDHLO)
         DO 200 J = LOW,HIGH
            DO 100 K = 1,80
               LINE82(K+1) = CONTBL(K,J)
100         CONTINUE
```

```
                FY = FY + 1
                CALL FTLOCA(FY,1)
                CALL FTEXT(LINE)
200         CONTINUE
                FY = FY + 1
                CALL FTLOCA(FY,1)
                CALL FTSIZE(2,18)
                CALL FTEXT('^Press RETURN to continue^')
                KHAR = GETCHR()
                LOW = LOW + 32
                IF (PASSES.EQ.(I+1)) THEN
                    HIGH = HIGH + LTBL - (I * 32)
                ELSE IF (PASSES.GT.1) THEN
                    HIGH = HIGH + 32
                ENDIF
                CALL SETCOL(0)
                CALL CLR
                CALL SETCOL(1)
300         CONTINUE
C
            CALL SETSCR(2)
            PAGE = 2
            CALL DISPLA(2)
            CALL FTSIZE(1,10)
            RETURN
            END
C
C
C
C       SUBROUTINE VIDNDX
C
C       ORI   Paul Broderick   April, 1985
C
        SUBROUTINE VIDNDX
        IMPLICIT INTEGER*2(A-Z)
        INTEGER*4 VAL
        CHARACTER*12 OID,OFILE
          CHARACTER*9 DIGT9E
          EQUIVALENCE (DIGT9E,DIGIT9(1))
        CHARACTER*10 INID,INFILE,ID,FILE,PID,PFILE
        CHARACTER*1 ID12(12),FILE12(12),DIGIT(7),DIGIT9(9)
        EQUIVALENCE (PID,ID12(2)),(OID,ID12(1)),(PFILE,FILE12(2)),
     *      (OFILE,FILE12(1)),(DIGIT(1),DIGIT9(2))
        COMMON /IIDD/ IONDX,ID,FILE,INID(2500)
          COMMON /HP/IHP
        COMMON /IIDD0/ INFILE(2500),PLACE
        COMMON /IIDD1/ RECNO(2500),NUMIDS,TOTIDS
C
        ID12(1) = '^'
        ID12(12) = '^'
        FILE12(1) = '^'
        FILE12(12) = '^'
        NUMCNT = 0
          IF (IHP .EQ. 1) THEN              !Set ID's/line to 3 for HP
                ILINE=3
          ELSE
                ILINE=4                      !Set ID's/line to 4 for IBM PC
          ENDIF
        PASSES = NUMIDS / 128
        IF (MOD(NUMIDS,128).GT.0) PASSES = PASSES + 1
        LOW = 1
        IF (NUMIDS.GT.128) THEN
            HIGH = 32
        ELSE
            HIGH = NUMIDS / ILINE
            IF (MOD(NUMIDS,ILINE).GT.0) HIGH = HIGH + 1
        ENDIF
        VAL = TOTIDS
        CALL REPNUM(VAL,NDGT,DIGIT)
        DIGIT9(1) = '^'
        DIGIT9(9) = '^'
        FY = 1
        CALL FTSIZE(1,10)
        CALL FTLOCA(FY,1)
        CALL FTEXT('^Number of structures in index: ^')
        CALL FTEXT(DIGT9E)
```

```
          DO 300 I = 1,PASSES
              DO 200 J = LOW,HIGH
                  FY = FY + 1
                  FX = 1
                  DO 100 K = 1,ILINE
                      NUMCNT = NUMCNT + 1
                      IF (NUMCNT.GT.NUMIDS) GO TO 201
                      PID = INID(NUMCNT)
                      PFILE = INFILE(NUMCNT)
                      DO 50 L = 2,7
                          IF ((FILE12(L).GE.'a').AND.(FILE12(L).LE.'z'))
     *                        FILE12(L) = CHAR(ICHAR(FILE12(L)) - 32)
50                    CONTINUE
                      CALL FTLOCA(FY,FX)
                      CALL FTEXT(OID)
                      CALL FTEXT('^ ^')
                      CALL FTEXT(OFILE)
                      FX = FX + 23
100               CONTINUE
200           CONTINUE
201           CONTINUE
              FY = FY + 1
              CALL FTLOCA(FY,1)
              CALL FTSIZE(2,18)
              CALL FTEXT('^Enter CR to break or C and CR to continue^')
              KHAR = GETCHR()
              IF (KHAR.NE.13 .AND. KHAR .NE. 32) THEN
                  LOW = LOW + 32
                  IF (PASSES.EQ.I+1) THEN
                      HIGH = HIGH + (NUMIDS / ILINE) - (I * 32)
                      IF (MOD(NUMIDS,ILINE).GT.0) HIGH = HIGH + 1
                  ELSE IF (PASSES.GT.1) THEN
                      HIGH = HIGH + 32
                  ENDIF
                  CALL SETCOL(0)
                  CALL CLR
                  CALL SETCOL(1)
              ELSE
                  CALL SETCOL(0)
                  CALL CLR
                  CALL SETCOL(1)
                  RETURN
              ENDIF
              CALL FTSIZE(1,10)
              FY = 0
300       CONTINUE
          RETURN
          END
C
          SUBROUTINE QUIT(IRESET,KAR,KX,KY)
          IMPLICIT INTEGER*2 (A-Z)
          INTEGER*4 MM,IDTPIX,VAL
          LOGICAL*2 RTNMSG
          CHARACTER*82 BLNK90
          CHARACTER*10 ID,INID,FILE,INFILE
          CHARACTER*12 HALOE
          CHARACTER*1 NSC10(10),HALO(12),HLO(3),RET(7),DIGIT(9)
          CHARACTER*1 KAN
          EQUIVALENCE (ID,NSC10),(RET(1),DIGIT(2))
          EQUIVALENCE (HALOE,HALO(1))
          COMMON /STRDEF/ NNODE,TABLE(255,43)
          COMMON /CD/ MAXX,MAXY
          COMMON /SIZZE/ MULTX,MULTY
          COMMON /RANGE/ LOX,HIX,LOY,HIY
          COMMON /STRPIX/ LPIX,MM(90,38),LBLEN,LNGBND(100,5)
          COMMON /HP/IHP
          COMMON /PARAMS/ JBDIR,NOCHG,LASTN,MCHAR,JCHAR,NLARGE,LEVEL
          COMMON /MODES/ JBTYPE,ICHR,IBDIR,IBTYPE,ISMART,MODE,ISKILL,ISP
          COMMON /CHARS/IES, IDOT,ITAG,JUMP,LBOND,KAN,ISPACE
          COMMON/BLANK/BLNK90
          COMMON /HEAD/ MW(12),ISTATE,PAGE
          COMMON /STRED/ IDTPIX(90,38),LABL(260,2),MRKCHN(260)
          COMMON /LABELS/ NR,NJLAST,NJNEXT
          COMMON /PROB/ IPROB,JPROB
          COMMON /CUR/ ICUR
```

```
      COMMON /QTVLNC/ OERR,CHER
      COMMON /WARN/ ERR
      COMMON /DARK/ OCUR
      COMMON /IRECS/ INU,IREC,TOPREC,BOTREC
      COMMON /IIDD/ IONDX,ID,FILE,INID(2500)
      COMMON /IIDD0/ INFILE(2500),PLACE
      COMMON /IIDD1/ RECNO(2500),NUMIDS,TOTIDS
      COMMON /M1/ MNUM,IMS(90,5)
      COMMON /D1/ IDNUM,IDS(9,6),NBD1,DSCNC(6,50)
      COMMON /LNGOUT/ LNGNDE(100,2)
      COMMON /DTDS/ DTN,DTX(30),DTY(30),DTN1(30),DTN2(30)
      COMMON /GPRNT/ KHAR
      IBLANK=' '
C If IRESET=1, arrays are to be reset in subrout RESET.
      HALO(1) = KAN
      DO 7 I = 1,10
          HALO(I+1) = NSC10(I)
 7    CONTINUE
      HALO(12) = KAN
      HLO(1) = KAN
      HLO(3) = KAN
      NLARGE = 1
      OCUR = 1
      IRESET=0
      KAR=13
      CALL SETSCR(1)
      CALL DISPLA(1)
      IF (IHP .EQ. 1) CALL GRAOFF
      CALL SETCOL(0)
      CALL CLR
      CALL SETCOL(1)
      IF (PAGE.EQ.0) THEN
          RTNMSG = .TRUE.
          RR = ERR
          CHER = 2
          CALL MYERR(RR,32,32)
          CHER = 0
      ELSE
          RTNMSG = .FALSE.
      ENDIF
 11   CONTINUE
      CALL FTSIZE(2,18)
      PAGE = 1
C
C Short menu only
 824     IF (ISKILL.EQ.1) GOTO 10
C
      CALL FTLOCA(6,18)
      CALL FTEXT('^You are now in END OF STRUCTURE MODE^')
      CALL FTLOCA(7,18)
      CALL FTEXT('^C--Allows you to continue building current structure^
     *')
      CALL FTLOCA(8,18)
      CALL FTEXT('^H--Makes hard copy & returns to this menu^')
      CALL FTLOCA(9,18)
      CALL FTEXT('^X--Cancels current structure & prepares for re-entry^
     *')
      CALL FTLOCA(10,18)
      CALL FTEXT('^S--Generates connection table and exits^')
      CALL FTLOCA(11,18)
      CALL FTEXT('^G--Makes hard copy, generates connection table and ex
     *its^')
      CALL FTLOCA(12,18)
      CALL FTEXT('^D--Deletes the existing connection table on file^')
      CALL FTLOCA(13,18)
      CALL FTEXT('^Q--Exits with no output^').
 10   CONTINUE
      IF (ISKILL.EQ.1) THEN
          CALL FTLOCA(8,30)
      ELSE
          CALL FTLOCA(14,18)
      ENDIF
      CALL FTEXT('^Enter C, H, X, S, G, D, or Q: ^')
      KHAR = GETCHR()
C
```

```fortran
C Convert lc to cap
      IF ((KHAR.GE.97).AND.(KHAR.LE.122)) KHAR=KHAR-32
C
C C=continue same structure
      IF (KHAR.EQ.67) GOTO 67
C H=hard copy
      IF (KHAR.EQ.72) GOTO 72
C X=kill this structure
      IF (KHAR.EQ.88) GOTO 88
      IF(KHAR .EQ. 81) GO TO 81
C S=make connection table
      IF (KHAR.EQ.83) GOTO 83
C G=make hard copy and connection table
      IF (KHAR.EQ.71) GO TO 83
C D=delete existing structure on file
      IF (KHAR.EQ.68) GO TO 68
C If KHAR is not in above list.
      CALL SETCOL(0)
      CALL CLR
      CALL SETCOL(1)
      CALL ERRMSG(KHAR)
      CALL FTSIZE(2,18)
      GO TO 824
C
C Return to same structure
68    CONTINUE
      CALL FTLOCA(16,18)
      CALL FTEXT('^Are you sure you want structure on file deleted (Y/
     *N)?^')
      KHAR = GETCHR()
      CALL SETCOL(0)
      CALL CLR
      CALL SETCOL(1)
      IF ((KHAR.NE.89).AND.(KHAR.NE.121)) GO TO 824
      IF (TOPREC.GT.0) THEN
         INFILE(PLACE) = '            '
         DO 5 I = TOPREC,BOTREC
            WRITE(INU,9,REC=I) BLANK
9           FORMAT(A1)
5        CONTINUE
         TOPREC = 0
         TOTIDS = TOTIDS - 1
      ELSE
         CALL FTLOCA(1,1)
         CALL FTEXT('^NO INPUT STRUCTURE IS ON DISK - NO DELETION POSS
     *IBLE^')
      ENDIF
      GO TO 824
67    CONTINUE
      CALL SETCOL(0)
      CALL CLR
      CALL SETCOL(1)
6677  CONTINUE
      MODE=1
C return to ground state
      LASTN=0
C Allows us to rewrite header
      DO 999 I=1,12
         MW(I)=999
999   CONTINUE
C Graphic display on
      CALL SETSCR(2)
      PAGE = 2
      CALL DISPLA(2)
      CALL FTSIZE(1,10)
      CALL HEADER
      RETURN
C
C     HARD COPY OPTION
C
72    CONTINUE
      CALL SETCOL(0)
      CALL CLR
      CALL SETCOL(1)
      CALL SETSCR(2)
```

```
              PAGE = 2
              CALL FTSIZE(1,10)
              CALL FTLOCA(1,1)
              CALL FTEXT(BLNK90)
              CALL FTLOCA(2,1)
              CALL FTEXT(BLNK90)
              CALL FTLOCA(3,1)
              CALL FTEXT(BLNK90)
              IF (IHP .NE. 1) THEN
              CALL FTLOCA(2,1)
              CALL FTEXT('^Structure ID: ^')
              CALL FTEXT(HALOE)
              ENDIF
              ICUR = 0
              IF (IHP .NE. 1)          CALL CURSOR(IX,IY)
              CALL DISPLA(2)
              CALL GPRINT
              IF (IHP .EQ. 1) THEN
              CALL FTLOCA(1,1)
              CALL FTEXT('^    ^')
              ENDIF
              CALL SETSCR(1)
              CALL GRAOFF
              PAGE = 1
              CALL DISPLA(1)
              CALL FTSIZE(2,18)
              DO 9331 I = 1,12
                 MW(I) = 999
9331          CONTINUE
C      Return to menu
              GOTO 11
C
C CLEAR SCREEN
83            CONTINUE
              CHER = 1
              CALL SETCOL(0)
              CALL CLR
              CALL SETCOL(1)
              CALL SETSCR(2)
              CALL FTSIZE(1,10)
              PAGE = 2
              CALL DISPLA(2)
              CALL FTLOCA(1,1)
              CALL FTEXT(BLNK90)
              CALL FTLOCA(2,1)
              CALL FTEXT(BLNK90)
              CALL FTLOCA(3,1)
              CALL FTEXT(BLNK90)
              CALL FTLOCA(2,1)
              CALL FTEXT('^Structure ID: ^')
              CALL FTEXT(HALOE)
              CALL FTSIZE(2,18)
              CALL FTLOCA(3,1)
              CALL FTEXT('^CONNECTION TABLE IS BEING PROCESSED^')
              CALL FTSIZE(1,10)
              IF (RTNMSG) CALL MYERR(RR,32,32)
C
C Following code writes out MM array & Text common to files:
C
C         GO MAKE CONNECTION TABLE
C
              CALL FTSIZE(1,10)
              DO 603 I = 1,NJNEXT+1
              OERR = 0
605           CONTINUE
              IF ((LABL(I,1).LE.0).OR.(LABL(I,1).GT.MAXX).OR.(LABL(I,2).LE.0)
     *          .OR.(LABL(I,2).GT.MAXY)) GO TO 603
              IF (MM(LABL(I,1),LABL(I,2)).NE.46) GOTO 603
C If no chain marker go to 607
              IF (MRKCHN(I) .EQ. 0) GO TO 607
C ASCII 'C'
              IX = LABL(I,1)
              IY = LABL(I,2)
              FX = IX + 1
              FY = IY
```

```
            JCHAR = 2
            CALL DEL(46,FX,FY,0,0,0)
            HLO(2) = 'C'
            CALL CURSOR(IX,IY)
            CALL TEXT(HLO)
            MM(IX,IY) = 67
            LABL(I,1) = -999
            LABL(I,2) = -999
            GO TO 603
607         CONTINUE
C Blank out marker with space
            IX = LABL(I,1)
            IY = LABL(I,2)
            FX = IX + 1
            FY = IY
            JCHAR = 2
            CALL DEL(46,FX,FY,0,0,0)
            MM(IX,IY) = 46
            JX = IX * MULTX - 6
            JY = IY * MULTY - 4
            J3X = JX + 3
            J3Y = JY - 3
            CALL BAR(JX,JY,J3X,J3Y)
            LABL(I,1)=-999
            LABL(I,2)=-999
C Undoes cursor move done in DOT
C       CHECK VALENCE
603         CONTINUE
C
            IF (KHAR.EQ.71) THEN
               CALL FTSIZE(2,18)
               IF ((RTNMSG).OR.(PAGE.EQ.0)) THEN
                  CALL FTLOCA(1,1)
                  CALL FTEXT(BLNK90)
                  IF (LOY.LE.2) THEN
                     DO 1153 I = LOX,HIX+6,6
                        LX = MINO(I,MAXX)
                        CALL REPLCE(LX,1,1,1,0,0,2)
 53                  CONTINUE
                     CALL RELONG
                  ENDIF
               ENDIF
               CALL FTLOCA(3,1)
               CALL FTEXT(BLNK90)

E.EQ.1) THEN
                     SETSCR(2)
                      ISPLA(2)

PAGE = 2
            IF (RTNMSG) CALL MYERR(RR,32,32)
            CHER = 2

CALL BOND(IERR,KX,KY)

CALL FTSIZE(2,18)
            CALL FTLOCA(3,1)
            CALL FTEXT(BLNK90)
            CALL FTSIZE(1,10)
            IF (IERR.EQ.0) GO TO 5353
               IF (IERR.EQ.100) THEN
                  CALL SETSCR(1)
                  PAGE = 1
                  CALL DISPLA(1)
                  CALL FTSIZE(2,18)
                  CALL FTLOCA(1,1)
                  CALL FTEXT('^INSUFFICIENT DISK SPACE FOR STRUCTURE^')
                  IERR = 18
                  CALL MYERR(IERR,KAR,KAR)
                  CHER = 0
                  PAGE = 0
```

```
              IRESET = 3
              RETURN
           ENDIF
           DO 50 L1 = 1,DTN
              MM(DTX(L1),DTY(L1)) = 42
              DTX(L1) = 0
              DTY(L1) = 0
              DTN1(L1) = 0
              DTN2(L1) = 0
50         CONTINUE
           DO 55 L1 = 1,2
              DO 55 L2 = 1,LBLEN
                 LNGNDE(L2,L1) = 0
55         CONTINUE
           DO 66 L2 = 1,NBD1
              DSCNC(1,L2) = 0
66         CONTINUE
           DO 86 L2 = 1,MNUM
              IF (IMS(7,L2).GT.0) THEN
                 VAL = IMS(7,L2)
                 CALL REPNUM(VAL,NDGT,RET)
                 DO 74 L0 =  NDGT,1,-1
                    MM(IMS(3,L2)-L0,IMS(4,L2)) = ICHAR(RET(NDGT+1-L0))
74               CONTINUE
                 L1 = NDGT + 1
                 MM(IMS(3,L2)-L1,IMS(4,L2)) = 47
              ELSE
                 L1 = 0
              ENDIF
              IF (IMS(1,L2).GT.1) THEN
                 VAL = IMS(1,L2)
                 CALL REPNUM(VAL,NDGT,RET)
                 DO 76 L0 =  NDGT,1,-1
                    MM(IMS(3,L2)-L0-L1,IMS(4,L2)) =
     *                 ICHAR(RET(NDGT+1-L0))
76               CONTINUE
                 MM(IMS(3,L2)-(NDGT+1+L1),IMS(4,L2)) = 42

MM(IMS(3,L2),IMS(4,L2)) = 77
                 MM(IMS(3,L2)+1,IMS(4,L2)) = IMS(2,L2)
              ELSE
                 MM(IMS(3,L2)-1,IMS(4,L2)) = 42
                 MM(IMS(3,L2),IMS(4,L2)) = 77
                 MM(IMS(3,L2)+1,IMS(4,L2)) = IMS(2,L2)
              ENDIF
              DO 80 L1 = 0,IMS(6,L2)
                 IF ((IMS(8+L1,L2).EQ.43).OR.(IMS(8+L1,L2).EQ.45)) THEN
                    MM(IMS(3,L2)+2+L1,IMS(4,L2)) = (8 * 2**13) +
     *                 IMS(8+L1,L2)
                 ELSE
                    MM(IMS(3,L2)+2+L1,IMS(4,L2)) = IMS(8+L1,L2)
                 ENDIF
                 IMS(8+L1,L2) = 0
80            CONTINUE
              DO 84 L1 = 1,7
                 IMS(L1,L2) = 0
84            CONTINUE
86         CONTINUE
           DO 1066 I = 1,12
              MW(I) = 999
1066       CONTINUE
           IF (IERR.EQ.12) THEN
              MODE=1
C             Return to ground state
C             Allows us to rewrite header
              CALL HEADER
              MCHAR = 0
              JCHAR = 2
              RETURN
           ENDIF
           CALL SETSCR(1)
           PAGE = 1
           CALL DISPLA(1)
           IF (IERR.EQ.41) THEN
              JCHAR = 1
           ELSE
```

```
              JCHAR = 2
           ENDIF
           IERR = 18
           CALL MYERR(IERR,IERR,IERR)
C          SET ERR = BAD DATA
           JPROB = 1
           CHER = 0
           OERR = -1
           MCHAR = 0
        IF (IHP .EQ. 1) CALL CLEAR
        RETURN
5353    CONTINUE
        IF (IHP .EQ. 1) CALL CLEAR

CALL GRAOFF
        CHER = 0
        PAGE = 2
        IRESET = 3
        RETURN
C
C Kill structure & reset
88      IRESET=1
        RETURN
1       IRESET=3
        RETURN
        END SUBROUTINE REPNUM assigns the ASCII representation of a passed
   decimal integer value of 1 - 7 digits.

ORI   Paul Broderick   April, 1985

SUBROUTINE REPNUM(VALUE,NDGT,RET)
        IMPLICIT INTEGER*2 (A-Z)
        INTEGER*4 VALUE,VAL
        CHARACTER*1 DIGIT(8),RET(8)

IF ((VALUE.GT.99999999).OR.(VALUE.LT.-9999999)) RETURN
        VAL = IABS(VALUE)
        DO 100 I = 1,8
           DIVD = MOD(VAL,10)
           VAL = VAL / 10
           DIGIT(I) = CHAR(DIVD + 48)
           NDGT = I
           IF (VAL.EQ.0) GO TO 110
100     CONTINUE
110     CONTINUE
C
        IF (VALUE.LT.0) THEN
           NDGT = NDGT + 1
           DIGIT(NDGT) = '-'
        ENDIF
        N = 0
        DO 200 I = NDGT,1,-1
           N = N + 1
           RET(N) = DIGIT(I)
200     CONTINUE
        N = N + 1
        DO 300 I = N,8
           RET(I) = ' '
300     CONTINUE
C
        RETURN
        END
C
        SUBROUTINE HEADER
        IMPLICIT INTEGER*2 (A-Z)
        LOGICAL*2 FIRST
        CHARACTER*1 RET(3),HALO(3),MWB1(16),MWB2(36),MWB3(36),MWB4(13),
     *     MWB6(13),MWB7(90),MWB9(90),MWB107(90),MWB109(90),
     *     MWB11(90),MWB13(90),MWB14(90),MWB15(90),MWB16(90),
     *     MWB17(90),MWB18(90),IDHLO(12),ID10(10),MWB19(18),MWB20(6),
     *     KSC10(10),HCMD,HLO(4),MWB21(90),MWB111(90),
     *     MWB113(90),MWB115(90),MWB116(90),MWB117(90),MWB118(90)
```

```
      CHARACTER*1 KAN
      CHARACTER*3 HALOE
      CHARACTER*4 HLOE
      CHARACTER*1 ISTAT
      CHARACTER*5 KSC
      CHARACTER*6 MW20
      CHARACTER*7 IPNT,IAXE
      CHARACTER*10 ID2,FILE,INID
      CHARACTER*12 IDH12
      CHARACTER*13 MW4,MW6
      CHARACTER*16 MW1
      CHARACTER*36 MW2,MW3
      CHARACTER*18 MW19
      CHARACTER*90 MW7,MW9,MW11,MW13,MW14,MW15,MW16,MW17,
     *   MW18,MW21,MW107,MW109,MW111,MW113,MW115,MW116,MW117,MW118
      COMMON /IIDD/ IONDX,ID2,FILE,INID(2500)
      COMMON /HEAD/ MW(12),ISTATE,PAGE
      COMMON /ISTATE/ ISTAT
      COMMON /CHARS/IES, IDOT,ITAG,JUMP,LBOND,KAN,ISPACE
      COMMON /PARAMS/ JBDIR,NOCHG,LASTN,MCHAR,JCHAR,NLARGE,LEVEL
      COMMON /MODES/ JBTYPE,ICHAR,IBDIR,IBTYPE,ISMART,MODE,ISKILL,ISP
      COMMON /RET/ SYM,KSC(2)
      COMMON /QTVLNC/ OERR,CHER
      COMMON /REP/ HCMD(2)
      EQUIVALENCE (ID2,ID10),(KSC,KSC10),(MW1,MWB1),(MW2,MWB2),
     *   (MW3,MWB3),(MW4,MWB4),(MW6,MWB6),(MW7,MWB7),(MW9,MWB9),
     *   (MW11,MWB11),(MW13,MWB13),(MW14,MWB14),(MW15,MWB15),
     *   (MW16,MWB16),(MW17,MWB17),(MW18,MWB18),(MW19,MWB19),
     *   (MW20,MWB20),(MW21,MWB21),(MWB107,MW107),(MWB109,MW109),
     *   (MWB111,MW111),(MWB113,MW113),(MWB115,MW115),(MWB116,MW116),
     *   (MWB117,MW117),(MWB118,MW118),(IDHLO,IDH12)
      EQUIVALENCE (HALOE,HALO(1))
      EQUIVALENCE (HLOE,HLO(1))
      DATA MW1 /'^Structure ID: ^'/
      DATA MW2 /'^Terminal is DUMB                    ^'/
      DATA MW3 /'^Terminal is SMART .                 ^'/
      DATA MW7 /'?GND:UC  lc  Bd  No  -+ sp/bksp  &   !   ^   _   :
     *  #  %  a  *  DEL  Q       ?'/
      DATA MW107/'^   el jmp bd bdtp chg dumb  nlrg chn rng lib ret
     * mrk lgbd rep dotdis del quit   ^'/
      DATA MW11 /'^RING:No UC  lc Bd sp/bksp ESC  &    !   _   :   #
     *%  a  |  -+ DEL  Q  CR ^'/
      DATA MW111/'^    size el jmp bnd  dumb  rec nlrg chn lib ret
     * mrk lgbd rep num chg del quit rtn  ^'/
      DATA MW9 /'?CHAIN:No UC lc  Bd sp/bksp &    ESC  ^   _   :
     * #  %  a  |  -+ DEL  Q  CR ?'/
      DATA MW109/'^    size el jmp bd  dumb   nlrg rec rng lib ret
     * mrk lbnd rep num chg del quit rtn  ^'/
      DATA MW4 /'^Bond=        ^'/
      DATA MW6 /'^Enlrge=      ^'/
      DATA MW13 /'^LONG BOND:  lc   #       No      %     CR    Q
     *                          ^'/
      DATA MW113/'^                jmp  mrkr  bndtype  draw   rtn  quit
     *                         ^'/
      DATA MW14 /'^DUMB MODE:  Bd to return to SMART MODE
     *                          ^'/
      DATA MW15 /'^REPEAT:  No       UC      lc    ''    UC$lc     Bd     CR
     *                        ^'/
      DATA MW115/'^              bndtyp  elem  jump  draw  setelem  bond  rtn
     *                        ^'/
      DATA MW16 /'^DOT DISCONNECT: No  "  /    UC/lc -+  sp  Q     HCl   Na
     * Na+  Cl  Cl-  H+  Mx:        ^'/
      DATA MW116/'^                       mult frac elem  chg rtn quit
     *                         ^'/
      DATA MW17 /'^LIBRARY: lc    Bd    No      DEL E    S     ESC
     *  CR                       ^'/
      DATA MW117/'^              jump bond  bndtyp del attach cursor rec
     *   rtn                    ^'/
      DATA MW18 /'^RETRIEVE:sp/bksp   ''   ESC  #  DEL  Bd   lc    L     F
     *  V   A    P   CR  Q           ^'/
      DATA MW118/'^            dumb  draw rec mrk del bond jump list file
     * view axial point rtn quit        ^'/
      DATA MW19 /'^ File name=            ^'/
      DATA MW20 /'^Sym=^'/
      DATA MW21 /'^ENLARGE: num(set bond enlargement factor), &(exit)
     *                         ^'/
```

```
              DATA IOST /71/
              DATA IPNT /'^Point^'/
              DATA IAXE /'^Axial^'/
              DATA FIRST /.TRUE./
C
              IF (CHER.GT.0) RETURN
              IF (PAGE.NE.2) THEN
                  CALL SETSCR(2)
                  PAGE = 0
                  CALL FTSIZE(1,10)
              ENDIF
              IF (FIRST) THEN
                  HALO(1) = KAN
                  HALO(3) = KAN
                  IDHLO(1) = KAN
                  IDHLO(12) = KAN
                  HLO(1) = KAN
                  HLO(4) = KAN
                  FIRST = .FALSE.
              ENDIF
              IF (ISTATE.EQ.0) THEN
                  IF (MODE.EQ.1) THEN
                      ISTTT = 71
                  ELSE IF (MODE.EQ.2) THEN
                      ISTTT = 78
                  ENDIF
              ELSE IF (ISTATE.NE.0) THEN
                  ISTTT=ICHAR(ISTAT)
              ENDIF
C     SOLO, NO CHANGE
              IF ((MW(1).NE.999).AND.(ISKILL.EQ.1).AND.(ISTTT.EQ.IOST)) RETURN
C ISTAT = SINGLE CHAR CODE FOR STATE - USED IN SOLO MODE
              IOST=ISTTT
              CALL MEMOFF     !HP code - unlock memory
              CALL HOME       !HP code - move alpha cursor home
C
C         MW(1)= displayed ID(structure number)
C           2        terminal smartness; 1=smart
C           3        ISTATE OR (MODE IF ISTATE= 0)
C           4        last numeral entered
C           5        last bond type
C           6        Enlargement factor (NLARGE)
C
C         ISTATE=1  Don't use--USE MODE=1 instead
C               2    "    "   "    "   =2   "
C               3   Chain state
C               4   Chain/number entry
C               5   Ring
C               6   Ring/number entry
C               7   Long bond
C               8   Dumb mode
C               9   Repeat state
C              10   Dot disconnect mode
C              11   Library
C              12   Retrieve
C              13   Enlarge
C         Following only displays changed infor on screen:
              IF (MW(1).EQ.999) THEN
                  DO 2 I = 1,10
                      IDHLO(I+1) = ID10(I)
2                 CONTINUE
                  MW(1) = 0
                  IF (ISKILL.EQ.2) THEN
                      CALL FTLOCA(1,1)
                      CALL FTEXT(MW1)
                  ELSE
                      CALL FTLOCA(2,1)
                  ENDIF
                  CALL FTEXT(IDH12)
                  CALL FTEXT('^     ^')
              ENDIF
              IF (ISKILL.EQ.1) GOTO 19
              IF (ISTATE.EQ.9) THEN
                  IF (MW(3).NE.9) THEN
                      CALL FTLOCA(2,1)
```

```
                  CALL FTEXT(MW15)
                  CALL FTLOCA(3,1)
                  CALL FTEXT(MW115)
              ENDIF
              CALL FTLOCA(1,54)
              DO 140 I = 1,2
                  HLO(I+1) = HCMD(I)
140           CONTINUE
              IF (HLO(3) .EQ. '0') HLO(3)=' '
              CALL FTEXT('^ATOM ACTIVE=^')
              CALL FTEXT(HLOE)
              CALL FTEXT('^      ^')
              MW(3) = 9
          ELSE IF (ISTATE.EQ.12) THEN
              IF (MW(3).NE.12) THEN
                  CALL FTLOCA(2,1)
                  CALL FTEXT(MW18)
                  CALL FTLOCA(3,1)
                  CALL FTEXT(MW118)
              ENDIF
              MW(6) = 999
              MW(9) = SYM
              CALL FTLOCA(1,52)
              CALL FTEXT(MW20)
              IF (SYM.EQ.2) THEN
                  CALL FTEXT(IPNT)
              ELSE IF (SYM.EQ.1) THEN
                  CALL FTEXT(IAXE)
              ENDIF
              CALL FTEXT('^      ^')
              DO 292 I = 1,6
                  MWB19(12+I) = KSC10(I)
292           CONTINUE
              CALL FTEXT(MW19)
              MW(3) = 12
              GO TO 17
      ENDIF
      IF (ISMART.NE.MW(2)) THEN
          MW(2)=ISMART
          IF (ISMART.EQ.1) THEN
              CALL FTLOCA(1,52)
              CALL FTEXT('^      ^')
              CALL FTEXT(MW3)
          ELSE
              IF (MW(3).NE.ISTATE) THEN
                  MW(5) = 999
                  MW(6) = 999
                  CALL FTLOCA(1,30)
                  CALL FTEXT('^
                  CALL FTEXT('^                              ^')
                  CALL FTLOCA(1,54)
                  CALL FTEXT(MW2)
                  CALL FTLOCA(2,1)
                  CALL FTEXT(MW14)
                  CALL FTLOCA(3,1)
          CALL FTEXT('^
          CALL FTEXT('^
                  MW(3) = ISTATE
                  GO TO 190
              ELSE
                  GO TO 190
              ENDIF
          ENDIF
      ENDIF
      IF (ISTATE.NE.MW(3)) THEN
          CALL FTLOCA(2,1)
          IF ((ISTATE.EQ.1).OR.(ISTATE.EQ.0)) THEN
              CALL FTEXT(MW7)
              CALL FTLOCA(3,1)
              CALL FTEXT(MW107)
          ELSE IF (ISTATE.EQ.3) THEN
              CALL FTEXT(MW9)
              CALL FTLOCA(3,1)
              CALL FTEXT(MW109)
          ELSE IF (ISTATE.EQ.5) THEN
```

```fortran
              CALL FTEXT(MW11)
              CALL FTLOCA(3,1)
              CALL FTEXT(MW111)
           ELSE IF (ISTATE.EQ.7) THEN
              CALL FTEXT(MW13)
              CALL FTLOCA(3,1)
              CALL FTEXT(MW113)
           ELSE IF (ISTATE.EQ.10) THEN
              CALL FTEXT(MW16)
              CALL FTLOCA(3,1)
              CALL FTEXT(MW116)
           ELSE IF (ISTATE.EQ.11) THEN
              CALL FTEXT(MW17)
              CALL FTLOCA(3,1)
              CALL FTEXT(MW117)
           ELSE IF (ISTATE.EQ.13) THEN
              CALL FTEXT(MW21)
              CALL FTLOCA(3,1)
           CALL FTEXT('^
           CALL FTEXT('^
           ENDIF
           MW(3) = ISTATE
        ENDIF
17      CONTINUE
        IF (NLARGE.NE.MW(6)) THEN
           DO 310 I = 9,11
              MWB6(I) = ' '
310        CONTINUE
           PAS = NLARGE
           CALL NUMCHR(PAS,RET,NDGT)
           DO 300 I = 1,NDGT
              MWB6(I+8) = RET(I)
300        CONTINUE
           MW(6)=NLARGE
           CALL FTLOCA(1,41)
           CALL FTEXT(MW6)
        ENDIF
        IF (IBTYPE.EQ.MW(5)) GO TO 190
           I = IBTYPE + 48
           MWB4(7) = CHAR(I)
           CALL FTLOCA(1,30)
           CALL FTEXT(MW4)
           MW(5) = IBTYPE
C
C       THIS NEXT CODE FOOLS THE HEADER ROUTINE INTO THINKING
C       THAT IBTYPE HAS BEEN SWITCHED FROM NON-PERMANENT TO 1
C       BEFORE IT HAS ACTUALLY HAPPENED.
C       I DIDN'T WANT TO ACTUALLY RESET IBTYPE BECAUSE IT HAS
C       TOO MANY REPERCUSSIONS.
C
19         IF (ISKILL .EQ. 2) GO TO 190
           HALO(2) = CHAR(ISTTT)
           CALL FTLOCA(3,1)
           IF (ISTATE.EQ.5) THEN
              HALO(1) = ';'
              HALO(3) = ';'
              CALL FTEXT(HALOE)
              HALO(1) = '^'
              HALO(3) = '^'
           ELSE
              CALL FTEXT(HALOE)
           ENDIF
           GO TO 119
190     IF ((ISTATE.EQ.9).OR.(ISTATE.EQ.13)) GO TO 119
        IF (.NOT.(ICHAR.EQ.1 .AND.
     1  (IBTYPE.EQ.2 .OR. IBTYPE.EQ.3 .OR. IBTYPE.EQ.5
     2  .OR. IBTYPE.EQ.6 .OR. IBTYPE.EQ.7))) GO TO 119
           IFOOL=1
           MW(5) = 999
           MWB4(7) = '1'
119     CONTINUE
        CALL LINE4       !HP code - move to line 4
        CALL MEMON       !HP code - lock memory
        RETURN
        END
```

```
$STORAGE:2
C
C         THIS SUBROUTINE WILL MAKE A LIBRARY ENTRY
C
          SUBROUTINE LIBRA(IX,IY,KAR)
          IMPLICIT INTEGER*2 (A-Z)
          INTEGER*4 MM,IDTPIX,IFIRST,ONE,DSKMEM
          INTEGER*2 CGINFO(10,4)
          LOGICAL*2 EXIST,OVRWRT
          CHARACTER*10 FILE,LFILE,LSC
          CHARACTER*8 LIBRET
          CHARACTER*5 NSC
          CHARACTER*1 KAN
          CHARACTER*1 NAMSTR(6)
          CHARACTER*1 ISTAT
          CHARACTER*1 NSC10(10),HALO(12),HLO(3),LIBR8(8,640)
          CHARACTER*12 HALOE
          CHARACTER*3 HLOE
          EQUIVALENCE (HALOE,HALO(1))
          EQUIVALENCE (HLOE,HLO(1))
          EQUIVALENCE (NSC,FILE),(NSC,NSC10),(LIBRET,LIBR8)
          COMMON /RET/ SYM,NSC(2)
          COMMON /BAKLIB/ LSC
          COMMON /LIB/ LIBRET(640),NLIBS
          COMMON /CD/ MAXX,MAXY
          COMMON /IPLUS/ IHIGH(14,2)
          COMMON /MKSKP/ ISKIP
          COMMON /RANGE/ LOX,HIX,LOY,HIY
          COMMON /ISTATE/ ISTAT
          COMMON /STRPIX/ LPIX,MM(90,38),LBLEN,LNGBND(100,5)
          COMMON /MODES/ JBTYPE,ICHAR,IBDIR,IBTYPE,ISMART,MODE,ISKILL,ISP
          COMMON /CHARS/IES, IDOT,ITAG,JUMP,LBOND,KAN,ISPACE
          COMMON /HEAD/ MW(12),ISTATE,PAGE
          COMMON /CUR/ ICUR
          COMMON /PARAMS/ JBDIR,NOCHG,LASTN,MCHAR,JCHAR,NLARGE,LEVEL
          COMMON /STRED/ IDTPIX(90,38),LABL(260,2),MRKCHN(260)
          COMMON /FROM/ LCHAR
          COMMON /IIDD1/ RECNO(2500),NUMIDS,TOTIDS
          COMMON /D1/ IDNUM,IDS(9,6),NBD1,DSCNC(6,50)
          COMMON /HP/IHP
          COMMON /RETLIB/OVRWRT
          DATA OU /35/
C*****************************************************************
C This section initializes some parameters and calls HEADER
C*****************************************************************
          IF (IHP .NE. 1) THEN
          CALL MEMDSK(CLUSTS,CPDISK,BPSECT,SPCLUS)
          DSKMEM = CLUSTS * BPSECT * SPCLUS
          IF (DSKMEM.LE.(36864+(80*TOTIDS))) THEN
             PAGE = 0
             CALL FTSIZE(2,18)
             CALL FTLOCA(1,1)
             CALL FTEXT('^INSUFFICIENT DISK SPACE FOR ADDITIONAL SUBSTRUCT
         *URES-MAY ATTEMPT CONNECTION TABLE^')
             CALL FTSIZE(1,10)
             GO TO 409
          ENDIF
          ENDIF
          HLO(1) = KAN
          HLO(3) = KAN
          HALO(1) = KAN
          LFILE = FILE
1         CONTINUE
          OVRWRT = .FALSE.
          DOT = 0
          ISKIP = 1
          ISTAT = '_'
          MODE=1
          ISTATE=11
          KAR=13
          DBONDX=0
          DBONDY=0
C         Set attaching bond coordinates to 0
C         They will remain 0 if we have a stand alone structure
          DO 786 I = 1,10
```

```
              DO 786 J = 1,4
                 CGINFO(I,J) = 0
786           CONTINUE
              DVAL=0
              BLEN=0
C             Set attaching bond length and bond direction to 0
C             They will remain 0 if we have a stand alone structure
              CALL HEADER
61            CONTINUE
C             Abort if input=A
              ONE = MM(IX,IY)
C Picture value at cursor when LIBRA was entered
              IF (ONE .EQ. 42) GO TO 5050
C If we are at a * don't call valence or clear hydrogen
              CALL CLRHYD(IX-1,IY)
              CALL VALNCE(2,IX-1,IY,0,0)
C Clear valence hydrogens and replace as needed
              ICUR = 1
              CALL CURSOR(IX,IY)
C***************************************************************
C This section looks for a Dot Disconnected structure - If a pure dot disconnec
C detected then "merging and exit bond" prompts are ignored and the
C final cursor position is set to the *
C A dot dis is stored with DOT = 1 - Charges are not stored separately
C and valence hydrogens are not removed
C If a mixture of dotdis and regular structure is found - the structure
C is disallowed and the command is rejected
C***************************************************************
5050          IFIRST=0
              DO 345 I = LOX,HIX
              DO 345 J = LOY,HIY
              IF (IFIRST .NE. 0) GO TO 42
              IF (MM(I,J) .NE. 0) IFIRST=MM(I,J)
2             IF (MM(I,J) .NE. 42) GO TO 345
              DOT = 1
              LBONDX=I
              LBONDY=J
              IF (IFIRST .EQ. 42 .AND. ONE .EQ. 42) GO TO 731
C Test for unmixed DOT DIS
              IERR = 52
              CALL MYERR(IERR,KAR,KAR)
              ICNT=ICNT+1
              GO TO 409
731           CONTINUE
              CALL FTSIZE(2,18)
              CALL FTLOCA(6,1)
              CALL FTEXT('^DOTDIS structure detected^')
              CALL DELAY
              CALL FTSIZE(1,10)
              PAGE = 0
              ICNT=ICNT+1
              GO TO 800
345           CONTINUE
C***************************************************************
C This section obtains the connecting site
C Make sure connecting site is a marker or bond
C***************************************************************
56            CONTINUE
              CALL FTSIZE(2,18)
              CALL FTLOCA(6,1)
              CALL FTEXT('^Move cursor to connecting site - Type E to finalize
     *  position         ^')
              PAGE = 0
              AKAR=69
C Primary terminator character = E
              BKAR=83
              REST = 1
C Alternate terminator character = S
              CALL SITE(IX,IY,AKAR,BKAR,TER,ICNT,REST)
              IF (REST.EQ.131) GO TO 1
C Get connecting site
              IF (TER .EQ. 13) GO TO 409
C Abort if return from SITE was CR
C Cursor should be at a marker or bond - Find out which
              KIX=IX
```

```
              KIY=IY
              IVAL=LMM(IX,IY)
              IF (IVAL .NE. 46) GO TO 2002
              IX=IX+1
C Cursor right on marker - placed there by moving the cursor
C Save DBONDX AND DBONDY and call CURSOR
              ICUR = 1
              CALL CURSOR(IX,IY)
              GO TO 2003
 2002         IF (LMM(IX-1,IY) .NE. 46) GO TO 2001
 2003         DBONDX=IX
C We are at a marker
              DBONDY=IY
              BLEN=0
              DVAL=0
              GO TO 2000
 2001         IF (IVAL .EQ. 0) GO TO 47
C        Spot is empty - Are we at the end of a bond?
              IF (IVAL .LT. 256 .OR. IVAL .GT. 2**13) GOTO 64
              GO TO 480
 47           CALL FINDB(IBDIR,KBDIR,IX,IY)
C        See if we are at the end of a bond
              IF (IBDIR .EQ. -1) GO TO 64
C        -1 means we are not at the end of a bond
              DVAL = KBDIR
C        Find end of bond
              CALL DELTA(DVAL,KNCX,KNCY)
              INCX=KNCX
              INCY=KNCY
              KIX=KIX-INCX
              KIY=KIY-INCY
              IVAL=MM(KIX,KIY)
              GO TO 53
 480          DVAL=IVAL/256
              DVAL=IVAL-DVAL*256
              CALL DELTA(DVAL,INCX,INCY)
 53           DO 73   K=1,2
              DO 72   I=1,20
              KIX=KIX+INCX
              KIY=KIY+INCY
              LVAL=LMM(KIX,KIY)
              IF (LVAL .EQ. 0) GO TO 71
              IF (LVAL .NE. IVAL) GO TO 75
 72           CONTINUE
 75           INCX=-INCX
              INCY=-INCY
              KIX=IX
              KIY=IY
 73           CONTINUE
 64           CONTINUE
              CALL FTSIZE(2,18)
              CALL FTLOCA(4,1)
              CALL FTEXT('^Cursor not at a bond or a marker^')
              PAGE = 0
              CALL FTSIZE(1,10)
              GO TO 66
 71           DBONDX=KIX-INCX
              DBONDY=KIY-INCY
C        Get length of attaching bond
              KIX=DBONDX
              KIY=DBONDY
              DO 67 I=1,20
                 II = I
                 KIX=KIX-KNCX
                 KIY=KIY-KNCY
                 IF (LMM(KIX,KIY) .NE. IVAL) GO TO 68
 67           CONTINUE
              GO TO 64
C        Something funny with bond length - issue error message and try again
 68           BLEN=II
C***********************************************************************
C This section assigns an output channel, gets the file name, checks
C to see if the name already exists, asks if an existing file is to
C be overwritten, aborts the command if the file is not to be over-
C written, opens the file, writes the file, closes the file and releases
```

```
C the output channel
C***************************************************************
        IX=DBONDX+KNCX
        IY=DBONDY+KNCY
        ICUR = 1
        CALL CURSOR(IX,IY)
C Set X and Y and call CURSOR
2000    CONTINUE
        IF (TER .NE. BKAR) GO TO 777
        LBONDX=IX
        IF (MM(IX,IY).EQ.0 .AND. MM(IX-1,IY).EQ.46) LBONDX = LBONDX - 1
C If TER = S then skip entry of exit site data
        LBONDY=IY
C and use connecting site data for exit data
        GO TO 800
C***************************************************************
C This section obtains the exit site
C Make sure exit site is a marker or bond
C***************************************************************
777     AKAR=83
C Set terminator to S
77      ICNT=ICNT+1
        CALL FTSIZE(2,18)
        CALL FTLOCA(6,1)
        CALL FTEXT('^Move cursor to exit site - Type S to finalize posit
     *ion       ^')
        PAGE = 0
        REST = 2
        CALL SITE(IX,IY,AKAR,BKAR,TER,ICNT,REST)
        IF (REST.EQ.131) GO TO 1
C Get exit site
        IF (TER .EQ. 13) GO TO 409
C Terminator was CR - bail out
        IBDIR=0
        IVAL=LMM(IX,IY)
        IF (IVAL .NE.46) GO TO 6002
        IX=IX+1
C Cursor is right on marker - Adjust X and go on
        GO TO 6003
6002    IF (LMM(IX-1,IY) .EQ. 46) GO TO 6003
C We are at a marker - go on
        IF (IVAL .EQ. 0) CALL FINDB(IBDIR,KBDIR,IX,IY)
C We are at an empty spot - See if we are at the end of a bond
        IF ((IBDIR .NE. -1 .AND. IVAL .EQ. 0) .OR. IVAL .GE. 256)
     1  GO TO 6003
C We are at a bond - go to 6003
        ICNT=ICNT+1
C Not at a bond or marker - try again
        GO TO 77
        ICUR = 1
6003    CALL CURSOR(IX,IY)
        LBONDX=IX
        IF (MM(IX,IY).EQ.0 .AND. MM(IX-1,IY).EQ.46) LBONDX = LBONDX - 1
C Set final cursor postion
        LBONDY=IY
C***************************************************************
C This section deletes all valence hydrogens before the file is stored on disk
C MM is copied to IDTPIX - Valence H's are removed from IDTPIX
C***************************************************************
800     CONTINUE
!       Trap for " on 2 letter element - Bail out if you find one
!
        IF (NBD1 .EQ. 0) GO TO 962
        DO 963 I=1,NBD1
        LX=DSCNC(3,I)
        LY=DSCNC(4,I)
        MX=DSCNC(5,I)
        MY=DSCNC(6,I)
        IF (MM(MX,MY) .NE."34) GO TO 963
        M1=MM(LX,LY)
        M2=MM(LX+1,LY)
        IF ((M1 .GE. 65 .AND. M1 .LE. 90) .AND.
     *  (M2 .GE. 97 .AND. M2 .LE. 122)) THEN
        IERR=61
        CALL MYERR(IERR,IERR,IERR)
```

```
              GO TO 409
              ENDIF
963           CONTINUE
962           CONTINUE
!
!       Trap for charges on 2 letter elements
!
              IF (DOT .EQ. 1) GO TO 842        !Skip if DOTDIS
              DO 617 I=LOX,HIX
              DO 617 J=LOY,HIY
              IF (LMM(I,J) .NE. 43 .AND. LMM(I,J).NE.45) GO TO 617
              LOC = IHMM(I,J)
              IF (LOC .EQ. 0) GO TO 617
              ITX=I-IHIGH(LOC,1)
              ITY=J+IHP*IHIGH(LOC,2)
              M1=LMM(ITX,ITY)
              M2=LMM(ITX+1,ITY)
              IF ((M1 .GE. 65 .AND. M1 .LE.90) .AND. (M2 .GE. 97
           *    .AND. M2 .LE. 122)) THEN
              IERR=61
              CALL MYERR(IERR,IERR,IERR)
              GO TO 409
              ENDIF
617           CONTINUE
842           DO 81 I = LOX,HIX
              DO 81 J = LOY,HIY
              IDTPIX(I,J)=MM(I,J)
81            CONTINUE
              IF (DOT .EQ. 1) GO TO 589
C Skip CLEARH if this is a DOTDIS
              DO 80 I = LOX,HIX
              DO 80 J = LOY,HIY
              II = I
              JJ = J
              IF (IDTPIX(I,J).GE.65 .AND. IDTPIX(I,J) .LE. 97
           1    .AND. (IDTPIX(I,J) .NE. 72 .OR. (IDTPIX(I,J) .EQ. 72
           2    .AND. IDTPIX(I+1,J) .GE. 97 .AND. IDTPIX(I+1,J) .LE. 122)))
           3    CALL CLEARH(2,II,JJ)
80            CONTINUE
589           CONTINUE
44            ICNT = ICNT +1
              IF (PAGE.NE.1) THEN
                  CALL SETSCR(1)
                  PAGE = 1
                  CALL DISPLA(1)
                  CALL FTSIZE(2,18)
              ENDIF
              IF (IHP .EQ. 1) THEN
              CALL LINE4        !Partial clear for HP
              CALL ACLEAR
              ELSE
              CALL SETCOL(0)
              CALL CLR
              CALL SETCOL(1)
              ENDIF
              FILE = '         '

CALL FTLOCA(7,20)
              CALL FTEXT('^Enter designation for structure (1-6 alphanumerics)
           *  ^')
444           CONTINUE
              J = 0
              IF (IHP .EQ. 1) THEN
              CALL ALPCUR
              ACCEPT 691, (NAMSTR(I),I=1,6)
691           FORMAT(6A1)
              ENDIF
              DO 4444 I = 1,60
                  J = J + 1
                  FX = 19 + J
4444          CONTINUE
              IF (IHP .EQ. 1) THEN
              A=ICHAR(NAMSTR(J))
              IF (A .GE. 97) A=A-32
              ELSE
```

```
                  A = GETCHR()
              ENDIF
              IF (A.EQ.13 .OR. A .EQ. 32) GO TO 4446
              IF (A.EQ.8) THEN
                  IF (J.GT.1) J = J - 1
                  FX = 19 + J
                  CALL FTLOCA(8,FX)
                  CALL FTEXT('^ ^')
                  NSC10(J) = ' '
                  GO TO 1444
              ENDIF
              HLO(2) = CHAR(A)
          IF (IHP .NE. 1) THEN
              CALL FTLOCA(8,FX)
              CALL FTEXT(HLOE)
          ENDIF
              IF (((A.GE.48).AND.(A.LE.57)).OR.((A.GE.65).AND.
       *         (A.LE.90)).OR.((A.GE.97).AND.(A.LE.122))) THEN
                  NSC10(J) = CHAR(A)
              ELSE
                  NSC10(J) = ' '
              ENDIF
              IF (J.EQ.6) GO TO 4446
 4444     CONTINUE
 4446     CONTINUE
          IF (IHP .EQ. 1) THEN
          CALL LINE4
          CALL ACLEAR     !Partial clear for HP
          ELSE
          CALL SETCOL(0)
          CALL CLR
          CALL SETCOL(1)
          ENDIF
C         NULL FILE NAME IMPLIES ABORT COMMAND.
          IF (NSC(1) .EQ. '  ') GO TO 409
C         CONCATENATE .STR EXTENSION TO FILE NAME
          NSC10(7) = '.'
          NSC10(8) = 'S'
          NSC10(9) = 'T'
          NSC10(10) = 'R'
          DO 8686 I = 1,10
              HALO(I+1) = NSC10(I)
 8686     CONTINUE
          HALO(12) = KAN
          CALL FTLOCA(7,26)
          CALL FTEXT('^Output to file: ^')
          CALL FTEXT(HALOE)
          CALL FTLOCA(8,26)
          CALL FTEXT('^Press RETURN to clear screen^')
          A = GETCHR()
          IF (IHP .EQ. 1) THEN
          CALL LINE4
          CALL ACLEAR     !Partial clear for HP
          ELSE
          CALL SETCOL(0)
          CALL CLR
          CALL SETCOL(1)
          ENDIF
          INQUIRE(FILE=FILE,EXIST=EXIST)
          IF (.NOT.EXIST) GO TO 404
C
C File exists - Do you wish to replace it (Y/N)?
          CALL FTLOCA(7,23)
          CALL FTEXT('^File exists - Do you wish to replace it (Y/N)?^')
 460      CONTINUE
          IKAR = GETCHR()
          IF (IHP .EQ. 1) THEN
          CALL LINE4       !Partial clear for HP
          CALL ACLEAR
          ELSE
          CALL SETCOL(0)
          CALL CLR
          CALL SETCOL(1)
          ENDIF
```

```
            IF (IKAR.EQ.95) THEN
                IERR = 39
                CALL MYERR(IERR,IERR,IERR)
                GO TO 460
            ELSE IF (IKAR.EQ.13 .OR. IKAR.EQ.78 .OR. IKAR.EQ.110) THEN
                GO TO 44
C If no - go get new file name
            ELSE IF (IKAR .EQ. 89 .OR. IKAR .EQ. 121) THEN
                OVRWRT = .TRUE.
                GO TO 404
            ENDIF
            CALL FTLOCA(8,23)
            CALL FTEXT('^Invalid response: ^')
            HLO(2) = CHAR(IKAR)
            CALL FTEXT(HLOE)
C Invalid response - go try new entry
            GO TO 460
404         OPEN(OU,FILE=FILE)
            IF (DOT .EQ. 1) GO TO 912
C Skip charge processing for DOTDIS
C       Get charges
            LENC = 0
            DO 85 I = LOX,HIX
            DO 85 J = LOY,HIY
            IF(LMM(I,J) .NE. 43 .AND. LMM(I,J) .NE. 45) GO TO 85
            LENC=LENC+1
            IF (LENC .GT. 10) GO TO 1234
C Too many charges - bail out
            LOC = IHMM(I,J)
C Get index if IHIGH so we can determine the
C coordinates of the associated node
            IF (LOC .NE. 0) GO TO 86
            CGINFO(LENC,1)=I
C Delocalized charge - X value
            CGINFO(LENC,2)=J
C Delocalized charge - y value
            GO TO 87
86          CGINFO(LENC,1)=I-IHIGH(LOC,1)
C X value
            CGINFO(LENC,2)=J+IHP*IHIGH(LOC,2)
C Y value
87          CGINFO(LENC,3)=LMM(I,J)
C + OR -
            IDTPIX(I,J)=0
            CGINFO(LENC,4)=0
            IF(MM(I+1,J).GE.50.AND.MM(I+1,J).LE.57) CGINFO(LENC,4)=MM(I+1,J)
C Digit following sign
            IF (CGINFO(LENC,4) .NE. 0) IDTPIX(I+1,J)=0
85          CONTINUE
C
C       D1 data is prepared for output.
            LEND = 0
            DO 300 I = 1,NBD1
                MX = DSCNC(5,I)
                MY = DSCNC(6,I)
                IF (MM(MX,MY).NE.34) GO TO 300
                LEND = LEND + 1
                IDTPIX(MX,MY) = 0
300         CONTINUE
C
C       THE FOLLOWING CODE GETS THE LENGTHS OF THE ARRAYS
C       MM - LABL - MRKCHN - AND LNGBND
C       SO THAT WE CAN COMPRESS THE DISK FILES
            LOX = MAX0(LOX,1)
            LOY = MAX0(LOY,1)
            HIX = MIN0(HIX,MAXX)
            HIY = MIN0(HIY,MAXY)
912         LENP=0
            DO 45 I= LOX,HIX
            DO 45 J= LOY,HIY
            IF (IDTPIX(I,J) .NE. 0) LENP=LENP+1
45          CONTINUE
            LENM=0
            FLENM = 0
            DO 46 I=1,260
```

```
              IF ((LABL(I,1).NE.0).AND.(LABL(I,2).NE.0)) THEN
                 FLENM = FLENM + 1
                 IF ((LABL(I,1).GT.0).AND.(LABL(I,2).GT.0)) LENM = LENM + 1
              ELSE
                 GO TO 4466
              ENDIF
46         CONTINUE
4466       CONTINUE
C
           LENL = LBLEN
C
100        FORMAT(7I4)
           WRITE(OU,100) DBONDX,DBONDY,DVAL,BLEN,DOT,LBONDX,LBONDY
           WRITE(OU,100) LENP
           DO 49 I= LOX,HIX
           DO 49 J= LOY,HIY
              IF (IDTPIX(I,J) .NE. 0) WRITE (OU,400) I,J,IDTPIX(I,J)
49         CONTINUE
400        FORMAT(2I4,I10)
C
           WRITE(OU,100) LENM
           IF (LENM .EQ. 0) GO TO 406
           DO 401 I=1,FLENM
              IF ((LABL(I,1).GT.0).AND.(LABL(I,2).GT.0))
     *           WRITE(OU,100) LABL(I,1),LABL(I,2), MRKCHN(I)
401        CONTINUE
C
406        WRITE (OU,100) LENL
           IF (LENL .EQ. 0) GO TO 4077
           DO 403 I=1,LENL
              WRITE(OU,100) (LNGBND(I,J),J=1,5)
403        CONTINUE
C
4077       WRITE(OU,100) LENC
           DO 4033 I = 1,LENC
              WRITE(OU,100) (CGINFO(I,J),J=1,4)
4033       CONTINUE
           WRITE(OU,100) LEND
           DO 310 I = 1,NBD1
              MX = DSCNC(5,I)
              MY = DSCNC(6,I)
              IF (MM(MX,MY).EQ.34) WRITE(OU,100) (DSCNC(J,I),J=3,4)
310        CONTINUE
           IF (.NOT.OVRWRT) THEN
              NLIBS = NLIBS + 1
              IF (NLIBS.GT.640) THEN
                 CALL FTLOCA(4,1)
                 CALL FTEXT('^WARNING-MORE THAN 640 SUBSTRUCTURE FILES EXIS
     *T-NOT ALL NAMES CAN BE LISTED IN RETRIEVE^')
                 PAGE = 0
                 GO TO 407
              ENDIF
              LIBR8(1,NLIBS) = '^'
              DO 4088 I = 1,6
                 LIBR8(I+1,NLIBS) = NSC10(I)
4088          CONTINUE
              LIBR8(8,NLIBS) = '^'
           ENDIF
407        CLOSE (OU)
C          RELEASE CHANNEL
C**********************************************************************
C This section clears the dialog from the screen, positions the cursor,
C sets some return variables, calls HEADER and returns
C**********************************************************************
409        CONTINUE
           IF (IHP .EQ. 1) THEN
           CALL LINE4
           CALL ACLEAR      !Do partial clear for HP
           ENDIF
           IF (PAGE.EQ.1) THEN
              CALL SETCOL(0)

IF (IHP .NE. 1)   CALL CLR
              CALL SETCOL(1)
              CALL SETSCR(2)
```

```
                PAGE = 2
                CALL DISPLA(2)
                CALL FTSIZE(1,10)
            ENDIF
            ICUR = 1
            CALL CURSOR(IX,IY)
C       Position cursor correctly and set parameters accordingly
            ISTATE=0
            IF (FILE.EQ.'         ') THEN
                FILE = LFILE
            ELSE
                LSC = LFILE
            ENDIF
            IF ((LCHAR.EQ.12).OR.(LCHAR.EQ.13)) GO TO 3000
            LEVEL=0
            CALL HEADER
            ISKIP = 0
C       SET LEVEL AND ISTATE TO GROUND AND CALL HEADER
            RETURN
3000        CONTINUE
            LFLAG = 1
            LEVEL = 1
            ICHAR = LCHAR
            IF (ICHAR.EQ.12) KAR = 94
            IF (ICHAR.EQ.13) KAR = 33
            ISKIP = 0
            CALL HEADER
            RETURN
1234        IERR = 51
            CALL MYERR(IERR,KAR,KAR)
            GO TO 407
            END
C
C       SUBROUTINE REFORM creates from connection table input the graphics
C       image in arrays MM and LNGBND.  SUBROUTINE GETLIN is called to
C       return a record of connection table input and SUBROUTINE CHRNUM
C       called to convert strings of numeric digits to integer values.
C
C       ORI   Paul Broderick   December, 1984
C
        SUBROUTINE REFORM(STATUS)
        IMPLICIT INTEGER*2 (A-Z)
        INTEGER*4 MM
        DIMENSION NODE(2),MULT(2),BOND(255,16),BTYPE(255,16),X(255),
     *   Y(255),NCON(255)
        CHARACTER*1 LINE,COMMA,APOST,STAR,BLANK,CONTBL,SLASH
        COMMON /STRPIX/ LPIX,MM(90,38),LBLEN,LNGBND(100,5)
        COMMON /TRANS/ LINE(160)
        COMMON /CD/ MAXX,MAXY
        COMMON /RANGE/ LOX,HIX,LOY,HIY
        COMMON /QTVLNC/ OERR,CHER
        COMMON /D1/ IDNUM,IDS(9,6),NBD1,DSCNC(6,50)
        COMMON /IRECS/ IU,IREC,TOPREC,BOTREC
        COMMON /CONTBL/ CONTBL(80,258),LTBL
        COMMON /HP/ IHP
        DATA COMMA /','/,APOST /''''/,STAR /'*'/,CANCEL /24/,
     *   BLANK/' '/,SLASH /'/'/
C
        STATUS = 0
        TOPREC = IREC
        LTBL = 0
        LONODE = 1
        HINODE = 0
C
C       The header record is input.
10      CONTINUE
        CALL TTYGET(LENGTH,STATUS)
        POS = 1
        CALL CHRNUM(RECNO,BEG,POS)
        IF ((RECNO.NE.0).OR.(STATUS.NE.0)) THEN
            CHER = 2
            CALL MYERR(37,37,37)
            CALL FTSIZE(2,18)
            CALL FTLOCA(1,35)
            CALL FTEXT('^-OR-IN FILE VERSION-INPUT RECORD OUT OF ORDER^')
```

```
      STATUS = 1
      RETURN
   ENDIF
   PRVREC = RECNO
C
C  The number of records to follow is identified.
   POS = 3
   CALL CHRNUM(NRECS,BEG,POS)
C
C  Each node is processed into the picture array.
   DO 1000 I = 1,NRECS
      CALL TTYGET(LENGTH,STATUS)
C
C     The record number is identified.
      POS = 1
      CALL CHRNUM(RECNO,BEG,POS)
      IF ((RECNO.NE.PRVREC+1).OR.(STATUS.NE.0)) THEN
         CHER = 2
         CALL MYERR(37,37,37)
         CALL FTSIZE(2,18)
         CALL FTLOCA(1,35)
         CALL FTEXT('^-OR-IN FILE VERSION-INPUT RECORD OUT OF ORDER^'
   *)
         STATUS = 1
         RETURN
      ENDIF
      PRVREC = RECNO
C
C     The chemical symbol is identified.
      POS = POS + 1
      IF (LINE(POS).NE.'c') THEN
         NODE(1) = ICHAR(LINE(POS))
      ELSE
         NODE(1) = 46
      ENDIF
      NOD = 1
      POS = POS + 1
      IF (LINE(POS).NE.BLANK) THEN
         NODE(2) = ICHAR(LINE(POS))
         NOD = 2
      ENDIF
C
C     The x and y coordinates are identified.
      POS = POS + 2
      CALL CHRNUM(VAL,BEG,POS)
      X(I) = VAL
      IF (X(I).LT.LOX) THEN
         LOX = X(I)
      ELSE IF (X(I).GT.HIX) THEN
         HIX = X(I)
      ENDIF
      POS = POS + 1
      CALL CHRNUM(VAL,BEG,POS)
      Y(I) = VAL
      IF (Y(I).LT.LOY) THEN
         LOY = Y(I)
      ELSE IF (Y(I).GT.HIY) THEN
         HIY = Y(I)
      ENDIF
C
      POS = POS + 1
C     If the node is a dot-disconnect marker, it is processed.
      IF (NODE(1).EQ.42) THEN
         MM(X(I),Y(I)) = NODE(1)
         IF ((ICHAR(LINE(POS)).GE.49).AND.(ICHAR(LINE(POS)).LE.57)) THEN
            KNT = 0
            CALL CHRNUM(VAL,BEG,POS)
            DO 30 RNT = BEG,POS-1
               KNT = KNT + 1
               MM(X(I)+KNT,Y(I)) = ICHAR(LINE(RNT))
30          CONTINUE
            KNT = KNT + 1
            POS = POS + 1
```

```
            IF ((ICHAR(LINE(POS)).GT.48).AND.(ICHAR(LINE(POS)).LE.57)) THEN
                MM(X(I)+KNT,Y(I)) = ICHAR(SLASH)
                GO TO 20
              ENDIF
            ENDIF
            LONODE = LONODE + 1
C
C           If the node is a non-localized charge, it is processed.
          ELSE IF ((NODE(1).EQ.43).OR.(NODE(1).EQ.45)) THEN
            DO 50 J = 1,NOD
              IF (NODE(J).NE.49) MM(X(I)-1+J,Y(I)) = NODE(J)
 50         CONTINUE
            HINODE = 1
C
C           If the node is a D structure, it is processed.
          ELSE
            IF ((NODE(1).EQ.68).AND.(NODE(2).GE.49).AND.(NODE(2).LE.
     *        57)) THEN
              NODE(2) = NODE(2) + 63
              MUL = 1
              MULT(1) = ICHAR(LINE(POS))
              POS = POS + 1
              IF ((ICHAR(LINE(POS))).GE.48).AND.(ICHAR(LINE(POS)).LE.57)) THEN
                MULT(2) = ICHAR(LINE(POS))
                MUL = 2
                POS = POS + 1
              ENDIF
              POS = POS + 1
              IF ((MULT(1).GE.50).OR.(MUL.EQ.2)) THEN
                K = 1
                DO 100 J = MUL,1,-1
                  MM(X(I)-J,Y(I)) = MULT(K)
                  K = MUL
 100            CONTINUE
              ELSE
                MUL = 0
              ENDIF
              DO 200 J = 1,NOD
                MM(X(I)-1+J,Y(I)) = NODE(J)
 200          CONTINUE
C
C             If the node is an *M structure, it is processed.
            ELSE IF ((NODE(1).EQ.77).AND.(NODE(2).GE.49).AND.(NODE(2)
     *        .LE.57)) THEN
              NODE(2) = NODE(2) + 63
              DO 300 J = 1,NOD
                MM(X(I)-1+J,Y(I)) = NODE(J)
 300          CONTINUE
C
C             If the node is an atom node, it is processed.
            ELSE
              IF ((NODE(1).EQ.72).AND.(NOD.EQ.1)) NODE(1) = 74
              DO 400 J = 1,NOD
                MM(X(I)-1+J,Y(I)) = NODE(J)
 400          CONTINUE
C
C             The charge or possible D1 bond site is identified.
              CALL CHRNUM(CHG,BEG,POS)
              LOW = BEG
              HIGH = POS - 1
C
C             The relative charge or bond site position is identified.
              POS = POS + 1
              CALL CHRNUM(RELCGP,BEG,POS)
              IF (CHG.NE.0) THEN
                IF (RELCGP.EQ.1) THEN
                  IGH = 3
                  INKX = 0
                  INKY = IHP
                ELSE IF (RELCGP.EQ.2) THEN
                  IGH = 4
                  INKX = 1
                  INKY = IHP
                ELSE IF (RELCGP.EQ.12) THEN
                  IGH = 5
                  INKX = 2
                  INKY = IHP
```

```
      ELSE IF (RELCGP.EQ.3) THEN
         IGH = 8
         INKX = 1
         INKY = 0
      ELSE IF (RELCGP.EQ.13) THEN
         IGH = 9
         INKX = 2
         INKY = 0
      ELSE IF (RELCGP.EQ.4) THEN
         IGH = 13
         INKX = 1
         INKY = -IHP
      ELSE IF (RELCGP.EQ.14) THEN
         IGH = 14
         INKX = 2
         INKY = -IHP
      ELSE IF (RELCGP.EQ.5) THEN
         IGH = 12
         INKX = 0
         INKY = -IHP
      ELSE IF (RELCGP.EQ.6) THEN
         IGH = 11
         INKX = -1
         INKY = -IHP
      ELSE IF (RELCGP.EQ.16) THEN
         IGH = 10
         INKX = -2
         INKY = -IHP
      ELSE IF (RELCGP.EQ.7) THEN
         IGH = 7
         INKX = -1
         INKY = 0
      ELSE IF (RELCGP.EQ.17) THEN
         IGH = 6
         INKX = -2
         INKY = 0
      ELSE IF (RELCGP.EQ.8) THEN
         IGH = 2
         INKX = -1
         INKY = IHP
      ELSE IF (RELCGP.EQ.18) THEN
         IGH = 1
         INKX = -2
         INKY = IHP
      ENDIF
      IF (CHG.LT.100) THEN
         IMPLUS = 0
         IF ((CHG.GT.0).AND.(ICHAR(LINE(J)).NE.43)) THEN
            MM(X(I)+INKX,Y(I)+INKY) = 43
            IMPLUS = 1
         ENDIF
         DO 600 J = LOW,HIGH
            L = J - LOW + IMPLUS
            IF (ICHAR(LINE(J)).NE.49)
               MM(X(I)+INKX+L,Y(I)+INKY) = ICHAR(LINE(J))
         CONTINUE
         MM(X(I)+INKX,Y(I)+INKY) = MM(X(I)+INKX,Y(I)+INKY)
     +      + IGH * 2**13
      ELSE
         NBD1 = NBD1 + 1
            MM(X(I)+INKX,Y(I)+INKY) = ICHAR(APOST)
            DSCNC(2,NBD1) = RELCGP
            DSCNC(3,NBD1) = X(I)
            DSCNC(4,NBD1) = Y(I)
            DSCNC(5,NBD1) = X(I) + INKX
            DSCNC(6,NBD1) = Y(I) + INKY
      ENDIF
      ENDIF
C
C     The number of attached hydrogens is identified.
      POS = POS + 1
      CALL CHRNUM(HYDS,BEG,POS)
      LOW = BEG
      HIGH = POS - 1
C
```

```
C           The relative hydrogen position is identified.
            POS = POS + 1
            CALL CHRNUM(RLHYDP,BEG,POS)
            IF (HYDS.GT.0) THEN
                IF ((RLHYDP.GE.2).AND.(RLHYDP.LE.4)) THEN
                    INKX = NOD
                ELSE IF ((RLHYDP.EQ.1).OR.(RLHYDP.EQ.5)) THEN
                    INKX = 0
                ELSE
                    IF (HYDS.EQ.1) THEN
                        INKX = -1
                    ELSE
                        INKX = -2
                    ENDIF
                ENDIF
                IF ((RLHYDP.EQ.3).OR.(RLHYDP.EQ.7)) THEN
                    INKY = 0
                ELSE IF ((RLHYDP.EQ.8).OR.(RLHYDP.LE.2)) THEN
                    INKY = - 1
                ELSE
                    INKY = 1
                ENDIF
                MM(X(I)+INKX,Y(I)+INKY) = 72
                IF (HYDS.GT.1) THEN
                    DO 700 J = LOW,HIGH
                        L = J - LOW + 1
                        MM(X(I)+INKX+L,Y(I)+INKY) = ICHAR(LINE(J))
  700               CONTINUE
                ENDIF
            ENDIF
C
C           The abnormal mass is identified.
            POS = POS + 1
            CALL CHRNUM(MS,BEG,POS)
            POS = POS + 1
        ENDIF
C
C           The number of connections from the node is identified.
            CALL CHRNUM(VAL,BEG,POS)
            NCON(I) = VAL
C
C           Each connection and bond type is stored for bond tracing.
            DO 800 J = 1,NCON(I)
                POS = POS + 1
                CALL CHRNUM(VAL,BEG,POS)
                BOND(I,J) = VAL
                POS = POS + 1
                CALL CHRNUM(VAL,BEG,POS)
                IF (VAL.LE.3) THEN
                    BTYPE(I,J) = VAL
                ELSE
                    BTYPE(I,J) = VAL + 1
                ENDIF
  800       CONTINUE
        ENDIF
 1000 CONTINUE
C
C       Bonds are drawn.
        DO 2000 I = LONODE,NRECS-HINODE
            DO 1500 J = 1,NCON(I)
                DX = X(BOND(I,J)) - X(I)
                DY = Y(BOND(I,J)) - Y(I)
C
C               If a bond does not fit a normal bond direction, it is
C               assumed to be a long bond.
C
                IF ((IABS(DX).NE.IABS(DY)).AND.(DX.NE.0).AND.(DY.NE.0)) THEN
                    LBLEN = LBLEN + 1
                    LNGBND(LBLEN,1) = X(I)
                    LNGBND(LBLEN,2) = Y(I)
                    LNGBND(LBLEN,3) = X(BOND(I,J))
                    LNGBND(LBLEN,4) = Y(BOND(I,J))
                    LNGBND(LBLEN,5) = BTYPE(I,J)
C
```

```
C       The bonds directional increments and directional code are
C       computed
        ELSE
            IF (DX.NE.0) THEN
                INKX = DX / IABS(DX)
            ELSE
                INKX = 0
            ENDIF
            IF (DY.NE.0) THEN
                INKY = DY / IABS(DY)
            ELSE
                INKY = 0
            ENDIF
            IF (INKX.EQ.0) THEN
                LOW = 1
                HIGH = IABS(Y(BOND(I,J)) - Y(I)) - 1
                INK = INKY
                IF (INKY.EQ.1) THEN
                    BIDIR = 5
                ELSE
                    BIDIR = 1
                ENDIF
            ELSE IF (INKX.EQ.1) THEN
                LOW = 1
                HIGH = IABS(X(BOND(I,J)) - X(I)) - 1
                INK = INKX
                IF (INKY.EQ.1) THEN
                    BIDIR = 4
                ELSE IF (INKY.EQ.0) THEN
                    BIDIR = 3
                ELSE IF (INKY.EQ.-1) THEN
                    BIDIR = 2
                ENDIF
            ELSE
                LOW = 1
                HIGH = IABS(X(BOND(I,J)) - X(I)) - 1
                INK = INKX
                IF (INKY.EQ.-1) THEN
                    BIDIR = 8
                ELSE IF (INKY.EQ.0) THEN
                    BIDIR = 7
                    IF (NOD.EQ.2) HIGH = HIGH - 1
                ELSE
                    BIDIR = 6
                ENDIF
            ENDIF
C
C       Normal bonds are traced into the picture array.
C
        DO 1100 K = LOW,HIGH,INK
            LO = K
            AX = X(I) + (K * INKX)
            AY = Y(I) + (K * INKY)
            IF ((MM(AX,AY).EQ.0).OR.(MM(AX,AY).GE.256)) GO TO 115
1100    CONTINUE
1150    CONTINUE
        DO 1300  K = LO,HIGH,INK
            KX = K * INKX + X(I)
            KY = K * INKY + Y(I)
            IF (MM(KX,KY).GT.0) THEN
C
C               If the bond crosses a node or other bond, it is
C               reassessed as a long bond.
                IF ((LMM(KX,KY).LT.48).OR.
     *              ((MM(KX,KY).GT.57).AND.(MM(KX,KY).NE.72).AND.
     *              (MM(KX,KY).LE.96)).OR.(LMM(KX,KY).GE.256))
                    GO TO 1175
                IF (((MM(LX,LY).EQ.46).OR.(MM(LX,LY).EQ.63).OR.
     *              ((MM(LX,LY).GE.65).AND.(MM(LX,LY).LE.90))).AND.
     *              ((X(BOND(I,J)).NE.LX).OR.(Y(BOND(I,J)).NE.LY)))
                    GO TO 1175
                IF (((MM(LX,LY).GE.97).AND.(MM(LX,LY).LE.122).AND.
     *              ((X(BOND(I,J)).NE.LX+INKX).OR.(Y(BOND(I,J))
     *              .NE.LY)))) GO TO 1175
                GO TO 1400
```

```
1175              CONTINUE
                  DO 1200 L = LO,K-1
                      KX = L * INKX
                      KY = L * INKY
                      MM(X(I)+KX,Y(I)+KY) = 0
1200              CONTINUE
                  LBLEN = LBLEN + 1
                  LNGBND(LBLEN,1) = X(I)
                  LNGBND(LBLEN,2) = Y(I)
                  LNGBND(LBLEN,3) = X(BOND(I,J))
                  LNGBND(LBLEN,4) = Y(BOND(I,J))
                  LNGBND(LBLEN,5) = BTYPE(I,J)
                  GO TO 1400
C                 If a bond stumbles across an attached hydrogen or
C                 charge bond extension ceases.
              ELSE
                  MM(KX,KY) = (BTYPE(I,J) * 256) + BIDIR
              ENDIF
1300      CONTINUE
1400      CONTINUE
      ENDIF
1500  CONTINUE
2000 CONTINUE
C
C     The trailer record is processed.
      CALL TTYGET(LENGTH,STATUS)
      POS = 1
      CALL CHRNUM(RECNO,BEG,POS)
      IF ((RECNO.NE.-1).OR.(STATUS.GT.0)) THEN
          CHER = 2
          CALL MYERR(37,37,37)
          CALL FTSIZE(2,18)
          CALL FTLOCA(1,35)
          CALL FTEXT('^-OR-IN FILE VERSION-INPUT RECORD OUT OF ORDER^')
          STATUS = 1
          RETURN
      ENDIF
      DELEMS = 0
      POS = 3
2100  CONTINUE
      IF (LINE(POS).EQ.COMMA) DELEMS = DELEMS + 1
      POS = POS + 1
      IF ((DELEMS.GE.11).OR.(ICHAR(LINE(POS)).EQ.48))   GO TO 3100
          IF ((ICHAR(LINE(POS)).GE.49).AND.(ICHAR(LINE(POS)).LE.57)) THEN
              CALL CHRNUM(NOD,BEG,POS)
              POS = POS + 1
              CALL CHRNUM(XM,BEG,POS)
              IF (XM.LT.LOX) THEN
                  LOX = XM
              ELSE IF (XM+NOD.GT.HIX) THEN
                  HIX = XM + NOD
              ENDIF
              POS = POS + 1
              CALL CHRNUM(YM,BEG,POS)
              IF (YM.LT.LOY) THEN
                  LOY = YM
              ELSE IF (YM.GT.HIY) THEN
                  HIY = YM
              ENDIF
              POS = POS + 1
              IF (ICHAR(LINE(POS)).NE.77) THEN
                  CALL CHRNUM(MUL,BEG,POS)
                  IF (LINE(POS).EQ.SLASH) THEN
                      POS = POS + 1
                      CALL CHRNUM(MUL,DUM,POS)
                  ENDIF
                  LSHFT = POS - BEG
                  K = 0
                  DO 2200 J = LSHFT,1,-1
                      MM(XM-J,YM) = ICHAR(LINE(BEG+K))
                      K = K + 1
2200              CONTINUE
                  POS = POS + 1
              ELSE
                  LSHFT = 0
```

```
            ENDIF
            MM(XM,YM) = ICHAR(LINE(POS))
            POS = POS + 1
            MM(XM+1,YM) = ICHAR(LINE(POS)) + 63
            POS = POS + 1
            MM(XM-(LSHFT+1),YM) = ICHAR(STAR)
            PLACE = POS
            DO 2500 J = PLACE,LENGTH
                POS = J
                IF (LINE(POS).EQ.COMMA) THEN
                    DELEMS = DELEMS + 1
                    IF (ICHAR(LINE(POS+1)).EQ.48) THEN
                        GO TO 3100
                    ELSE
                        POS = POS + 1
                        GO TO 2100
                    ENDIF
                ENDIF
                K = J + 2 - PLACE
                IF (XM+K.GT.HIX) HIX = XM + K
                IF ((ICHAR(LINE(POS)).EQ.43).OR.(ICHAR(LINE(POS)).EQ.45))
     *          THEN
                    MM(XM+K,YM) = (8 * 2**13) + ICHAR(LINE(POS))
                ELSE
                    MM(XM+K,YM) = ICHAR(LINE(POS))
                ENDIF
 2500       CONTINUE
            ENDIF
            IF (POS.GE.LENGTH) GO TO 3100
            GO TO 2100
 3100   CONTINUE
        LOX = MAX0(LOX-2,1)
        HIX = MIN0(HIX+3,MAXX)
        LOY = MAX0(LOY-1,1)
        HIY = MIN0(HIY+1,MAXY)
        RETURN
        END
C
C       SUBROUTINE CHRNUM returns the integer value that is represented
C       by a string of digits that is delemited by either commas or
C       horizontal bars.
C
C       ORI     Paul Broderick   December, 1984
        SUBROUTINE CHRNUM(VAL,BEG,POS)
        IMPLICIT INTEGER*2 (A-Z)
        CHARACTER*1 LINE,COMMA,BAR,NEGA,POSI,SLASH
        COMMON /TRANS/ LINE(160)
        DATA COMMA /','/, BAR /'|'/, NEGA /'-'/, POSI /'+'/, SLASH /'/'/
C
        BEG = POS
        VAL = 0
        POW = 1
C
        IF (LINE(POS).EQ.NEGA) THEN
            SIGN = -1
            POS = POS + 1
        ELSE IF (LINE(POS).EQ.POSI) THEN
            SIGN = 1
            POS = POS + 1
        ELSE
            SIGN = 1
        ENDIF
 10     CONTINUE
        IF ((LINE(POS).NE.COMMA).AND.(LINE(POS).NE.BAR).AND.
     *      LINE(POS).NE.SLASH) THEN
            VAL = (VAL * POW) + (ICHAR(LINE(POS)) - 48)
            POW = 10
            POS = POS + 1
            GO TO 10
        ENDIF
C
        VAL = VAL * SIGN
        RETURN
        END
C
```

```
C     SUBROUTINE TTYGET is used to input a line of the connection table.
      SUBROUTINE TTYGET(LENGTH,STATUS)
      IMPLICIT INTEGER*2(A-Z)
      LOGICAL*2 TERMN
      CHARACTER*1 LINE,CONTBL
      COMMON /TRANS/ LINE(160)
      COMMON /IRECS/ IU,IREC,TOPREC,BOTREC
      COMMON /CONTBL/ CONTBL(80,258),LTBL
      DATA POS /80/
C
      STATUS = 0
      DO 10 I = 1,POS
          LINE(I) = CHAR(0)
10    CONTINUE
      IREC = IREC + 1
      READ(IU,999,REC=IREC,END=40) (LINE(L),L=1,80)
40    CONTINUE
      LMAX = 80
      BOTREC = IREC
      LTBL = LTBL + 1
      TERMN = .FALSE.
      DO 400 I = 1,80
          CONTBL(I,LTBL) = LINE(I)
          IF ((((ICHAR(LINE(I)).EQ.32).AND.((I.GT.6).OR.(LINE(1)
     *        .EQ.'0'))).OR.(I.EQ.80)).AND.(.NOT.TERMN)) THEN
              IF (I.EQ.80) THEN
                  LENGTH = I
                  IF ((ICHAR(LINE(1)).EQ.45).AND.(ICHAR(LINE(2)).EQ.49))
     *            THEN
                      IREC = IREC + 1
                      DO 100 L = 81,160
                          LINE(L) = CHAR(0)
100                   CONTINUE
                      READ(IU,999,REC=IREC,END=110) (LINE(L),L=81,160)
110                   LTBL = LTBL + 1
                      LMAX = 160
                      BOTREC = IREC
                      DO 200 L = 81,160
                          CONTBL(L-80,LTBL) = LINE(L)
                          LENGTH = L
                          IF (ICHAR(LINE(L)).EQ.32) GO TO 410
200                   CONTINUE
                  ENDIF
              ELSE
                  LENGTH = I - 1
              ENDIF
              TERMN = .TRUE.
          ENDIF
400   CONTINUE
410   IF (LENGTH.LT.LMAX) POS = LENGTH + 1
999   FORMAT(80A1)
      RETURN
      END
C
C
C     SUBROUTINE TBLCHR prepares connection table data for transmission by
C     transforming the numeric elements of the connection table to
C     character representation, inserts commas between the elements,
C     and heads each record string with SOH and appends the string with
C     its computed check digit and CR, LF.
C
C     ORI   Paul Broderick   July, 1984
      SUBROUTINE TBLCHR(IERR)
      IMPLICIT INTEGER*2 (A-Z)
      INTEGER*4 DSKMEM
      LOGICAL*2 EXIST,NEWNME,ALPHID
      CHARACTER*10 ID,FILE,INID,INFILE,BLNK10,GETID,ZERO10
      CHARACTER*1 NAMSTR(10)
      CHARACTER*12 HLOID
      CHARACTER*1 ID10(10),HLOD12(12),HLO(3)
      CHARACTER*3 HLOE
      EQUIVALENCE (HLOE,HLO(1))
      EQUIVALENCE (ID10(1),GETID),(GETID,HLOD12(2)),(HLOID,HLOD12(1))
      CHARACTER*1 TRANS,CHK,RET(3),BLANK
      CHARACTER*1 COMMA
      COMMON /STRDEF/ NNODE,TABLE(255,43)
```

```
      COMMON /TRNS/ TRANS(80)
       COMMON /HP/IHP
      COMMON /ORECS/ OU,OUTREC
      COMMON /IRECS/ IU,INREC,TOPREC,BOTREC
      COMMON /IIDD/ IONDX,ID,FILE,INID(2500)
      COMMON /IIDD0/ INFILE(2500),PLACE
      COMMON /IIDD1/ RECNO(2500),NUMIDS,TOTIDS
C
C     Variable MNUM the number of *M structures and array
C     IMS contains the following items for each *M structure:
C         1 - Multiplier of the structure.
C         2 - *M identifying ordinal value.
C         3,4 - X and Y coordinates of the M.
C         5 - Length of connection table entry for the *M structure.
C         6 - Length of the formula to follow.
C         7 - Divisor of multiplier.
C         8 thru 90 - The molecular formula of the *M structure.
      COMMON /M1/ MNUM,IMS(90,5)
      COMMON /ALPHID/ ALPHID
      COMMON /DTDS/ DTN,DTX(30),DTY(30),DTN1(30),DTN2(30)
      DATA COMMA /','/, BLANK /' '/, BLNK10/'          '/
      DATA ZERO10 /'0000000000'/
C
      IF (IHP .NE.1) THEN
      CALL MEMDSK(CLUSTS,CPDISK,BPSECT,SPCLUS)
      DSKMEM = CLUSTS * BPSECT * SPCLUS
      IF ((DSKMEM.LE.((TOTIDS+NNODE+80)*80))) THEN
         IERR = 100
         WRITE(OU,89,REC=1) OUTREC
89       FORMAT(I6)
         CLOSE(OU)
         OPEN(IONDX,FILE='IDS.NDX',STATUS='NEW',ACCESS='DIRECT',
     *      FORM='FORMATTED',RECL=80)
         DO 13 I = 1,NUMIDS
            IF (INFILE(I).NE.'          ') WRITE(IONDX,79,REC=I)
     *         INID(I),INFILE(I),RECNO(I)
13       CONTINUE
         CLOSE(IONDX)
         CALL CLOSEG
      ENDIF
      ENDIF
C
C     The original copy of the edited structure is deleted from the
C     file.
      IF (TOPREC.GT.0) THEN
         CALL SETSCR(1)
         PAGE = 1
         CALL DISPLA(1)
55       CONTINUE
         CALL SETCOL(0)
         CALL CLR
         CALL SETCOL(1)
         CALL FTSIZE(2,18)
         CALL FTLOCA(8,24)
         CALL FTEXT('^Do you want to replace edited version (Y/N)?^')
         AA = GETCHR()
         CALL FTLOCA(8,24)
         CALL FTEXT('^                                              ^')
         IF ((AA.NE.89).AND.(AA.NE.121)) THEN
            IF (ALPHID) THEN
               GETID = BLNK10
               MX = 32
               CALL FTLOCA(8,MX)
               CALL FTEXT('^Enter (1-10) character ID^')
            ELSE
               GETID = ZERO10
               MX = 28
               CALL FTLOCA(7,MX)
               CALL FTEXT('^Enter CR for default ID increment -or-^')
               CALL FTLOCA(8,MX)
               CALL FTEXT('^Enter (1-10) digit ID ^')
            ENDIF
```

```
                  J = 0
11555       IF (NUMIDS+1.LE.2500) INID(NUMIDS+1) = ID
            IF (IHP .EQ. 1) THEN
            CALL ALPCUR
            ACCEPT 691,(NAMSTR(I),I=1,10)
691         FORMAT(10A1)
            ENDIF
            DO 5555 I = 1,100
              J = J + 1
              FX = MX + J - 1
1555        CONTINUE
            IF (IHP .EQ. 1) THEN
              AA=ICHAR(NAMSTR(J))
            ELSE
              AA = GETCHR()
            ENDIF
            IF (AA.EQ.13 .OR. AA .EQ. 32) THEN
                IF ((GETID.EQ.ZERO10).OR.(GETID.EQ.BLNK10)) THEN
                    IF (ALPHID) GO TO 55
                    GETID = ID
                    IF (NUMIDS.GT.0) THEN
5530                    DO 5535 K = 10,1,-1
                            ID10(K) = CHAR(ICHAR(ID10(K)) + 1)
                            IF (ID10(K).EQ.':') THEN
                                ID10(K) = '0'
                                IF (K.EQ.1) THEN
                                    GETID = '00000000001'
                                    GO TO 5536
                                ENDIF
                            ELSE
                                GO TO 5536
                            ENDIF
5535                    CONTINUE
5536                    CONTINUE
                        FIN = 10
                        DO 5566 K = 1,NUMIDS+1
                            IF (GETID.EQ.INID(K)) GO TO 5530
5566                    CONTINUE
                        IF (IHP .NE.1) THEN
                          CALL FTLOCA(9,28)
                          CALL FTEXT(HLOID)
                        ENDIF
                        GO TO 5556
                    ELSE
                        IF (IHP .NE. 1) THEN
                          CALL FTLOCA(9,28)
                          CALL FTEXT(HLOID)
                        ENDIF
                        FIN = 10
                        GO TO 6667
                    ENDIF
                ELSE
                    FIN = J - 1
                    GO TO 5556
                ENDIF
            ENDIF
            IF (AA.EQ.8) THEN
                IF (J.GT.1) J = J - 1
                FX = MX + J - 1
                CALL FTLOCA(9,FX)
                IF (ALPHID) THEN
                    CALL FTEXT('^ ^')
                    ID10(J) = ' '
                ELSE
                    CALL FTEXT('^0^')
                    ID10(J) = '0'
                ENDIF
                GO TO 1555
            ENDIF
            IF (((AA.GE.48).AND.(AA.LE.57)).OR.(AA.EQ.32)) THEN
                HLO(2) = CHAR(AA)
                IF (AA.EQ.32) AA = 48
                    IF (IHP .NE. 1) THEN
```

```
              CALL FTLOCA(9,FX)
              CALL FTEXT(HLOE)
                ENDIF
              ID10(J) = CHAR(AA)
            ELSE IF ((ALPHID).AND.(((AA.GE.65).AND.(AA.LE.90)).OR.
     *      ((AA.GE.97).AND.(AA.LE.122)))) THEN
              IF (AA.GE.97) AA = AA - 32
              HLO(2) = CHAR(AA)
                IF (IHP .NE. 1) THEN
              CALL FTLOCA(9,FX)
              CALL FTEXT(HLOE)
                ENDIF
              ID10(J) = CHAR(AA)
            ELSE
                HLO(2) = CHAR(AA)
                CALL FTLOCA(1,1)
                PAGE = 0
                CALL FTEXT(HLOE)
                CALL FTEXT('^ IS ILLEGAL INPUT. ENTER DIGITS OR SPAC
     *E AND CR^')
                IF (IHP .EQ. 1) THEN
                CALL FTLOCA(8,49)
                CALL FTEXT('^                    ^')
                CALL FTLOCA(8,49)
                GO TO 11555
                ENDIF
              ENDIF
            IF (J.EQ.10) THEN
                FIN = J
                GO TO 5556
              ENDIF
 5555       CONTINUE
 5556       CONTINUE
            IF ((GETID.EQ.ZERO10).OR.(GETID.EQ.BLNK10)) GO TO 55
            IF (FIN.LT.10) THEN
              J = 10 - FIN
              DO 6664 I = FIN,1,-1
                ID10(I+J) = ID10(I)
                IF (ALPHID) THEN
                    ID10(I) = ' '
                ELSE
                    ID10(I) = '0'
                ENDIF
 6664         CONTINUE
            ENDIF
            DO 6666 I = 1,NUMIDS+1
              IF (GETID.EQ.INID(I)) THEN
                  CALL FTLOCA(10,MX)
                  CALL FTEXT('^WARNING - ID already exists on current
     *iles - ^')
                  CALL FTLOCA(11,MX)
                  CALL FTEXT('^Upload existing structure prior to new
     *ntry^')
                  CALL FTLOCA(12,MX)
                  CALL FTEXT('^Press RETURN to continue^')
                  AA = GETCHR()
                  GO TO 55
              ENDIF
 6666       CONTINUE
 6667       IF (NUMIDS+1.LE.2500) INID(NUMIDS+1) = ZERO10
            NEWNME = .TRUE.
          ELSE
            GETID = ID
            NEWNME = .FALSE.
            MX = 32
          ENDIF
          CALL FTLOCA(9,MX)
          CALL FTEXT('^Output ID: ^')
          CALL FTEXT(HLOID)
          CALL FTLOCA(10,MX)
          CALL FTEXT('^Is ID OK (Y/N)?^')
          IKAR = GETCHR()
```

```
C           If no - go get new ID
            IF (IKAR.NE.89 .AND. IKAR.NE.121) GO TO 55
            CALL SETCOL(0)
            CALL CLR
            CALL SETCOL(1)
            CALL SETSCR(2)
            PAGE = 2
            CALL DISPLA(2)
            CALL FTSIZE(1,10)
            IF (NEWNME) THEN
                ID = GETID
                TOPREC = 0
                    IF (IHP .NE. 1) THEN
                CALL FTLOCA(331)
                CALL FTEXT('^Structure ID: ^')
                CALL FTEXT(HLOID)
                    ENDIF
            ENDIF
        ENDIF
C
        IF (TOPREC.GT.0) THEN
            INFILE(PLACE) = '             '
            DO 2 I = TOPREC,BOTREC
                WRITE(IU,9,REC=I) BLANK
2           CONTINUE
        ELSE
            TOTIDS = TOTIDS + 1
            IF (TOTIDS.GT.2500) THEN
                WRITE(OU,89,REC=1) OUTREC
                OPEN(IONDX,FILE='IDS.NDX',STATUS='NEW',ACCESS='DIRECT',
     *              FORM='FORMATTED',RECL=80)
                DO 3 I = 1,NUMIDS
                    IF (INFILE(I).NE.'              ') WRITE(IONDX,79,REC=I)
     *                  INID(I),INFILE(I),RECNO(I)
79              FORMAT(A10,A10,I6)
3               CONTINUE
                CLOSE(IONDX)
                CALL CLOSEG
            STOP 'CANNOT EXCEED 2500 STRUCTURES. NULL CONNECTION TABLE.'
            ENDIF
        ENDIF
C
C       The structure id number is output to the output file.
        OUTREC = OUTREC + 1
        WRITE(OU,999,REC=OUTREC) ID,OUTREC
999     FORMAT(A10,1X,I10)
C       The structure id number, file name, and record number are output
C       to the index file.
        NUMIDS = NUMIDS + 1
        PLNTID = NUMIDS
        IF (NUMIDS.GT.2500) THEN
            DO 6 I = 1,2500
                IF (INFILE(I).EQ.'             ') THEN
                    PLNTID = I
                    IF (I.LT.2500) THEN
                        DO 4 J = I,2499
                            INID(J) = INID(J+1)
                            INFILE(J) = INFILE(J+1)
                            RECNO(J) = RECNO(J+1)
4                       CONTINUE
                    ENDIF
                    NUMIDS = NUMIDS - 1
                    GO TO 7
                ENDIF
6           CONTINUE
        ENDIF
7       CONTINUE
        INID(PLNTID) = ID
        INFILE(PLNTID) = FILE
        RECNO(PLNTID) = OUTREC
C
C       The header transmission record string is prepared.
        POS = 1
```

```
              OREC = 1
              TRANS(POS) = '0'
              POS = POS + 1
              TRANS(POS) = COMMA
        C
        C     The number of node records to follow is assigned.
              VAL = NNODE
              CALL NUMCHR(VAL,RET,NDGT)
              DO 10 I = 1,NDGT
                  POS = POS + 1
                  TRANS(POS) = RET(I)
      10      CONTINUE
              POS = POS + 1
              TRANS(POS) = COMMA
        C
        C     The header string's check character is computed and assigned.
              CALL CHKGEN(POS,CHK)
              POS = POS + 1
              TRANS(POS) = CHK
        C
        C     The number of header characters is assigned to define the length
        C     of header transmission.
              OUTN = POS
        C
        C     The string is uploaded.
              RESULT = SEND(TRANS,OUTN)
        C
        C     A transmission string for each node in the structure is prepared.
              DO 500 IREC = 1,NNODE
                  OREC = IREC + 1
        C
        C     The number of items in the connection table record is
        C     assessed.
              IF (TABLE(IREC,2).EQ.42) THEN
                  LNG = 7
              ELSE IF ((TABLE(IREC,2).EQ.43).OR.(TABLE(IREC,2).EQ.45)) THEN
                  LNG = 5
              ELSE IF ((TABLE(IREC,2).EQ.68).AND.((TABLE(IREC,3).GE.112)
           *      .AND.(TABLE(IREC,3).LE.120))) THEN
                  LNG = 7 + (TABLE(IREC,7) * 2)
              ELSE IF ((TABLE(IREC,2).EQ.77).AND.((TABLE(IREC,3).GE.112)
           *      .AND.(TABLE(IREC,3).LE.120))) THEN
                  LNG = 6 + (TABLE(IREC,6)*2)
              ELSE
                  LNG = 11 + (TABLE(IREC,11) * 2)
              ENDIF
        C
              POS = 0
        C     The record node number is assigned.
              VAL = TABLE(IREC,1)
              CALL NUMCHR(VAL,RET,NDGT)
              DO 100 I = 1,NDGT
                  POS = POS + 1
                  TRANS(POS) = RET(I)
      100     CONTINUE
              POS = POS + 1
              TRANS(POS) = COMMA
        C
        C     The element symbol is assigned.
              POS = POS + 1
              TRANS(POS) = CHAR(TABLE(IREC,2))
              POS = POS + 1
              TRANS(POS) = CHAR(TABLE(IREC,3))
```

```
C              Any *D or *M identifying ordinal value is converted from
C              letter to digit.
               IF (((TABLE(IREC,2).EQ.68).OR.(TABLE(IREC,2).EQ.77))
     *           .AND.((TABLE(IREC,3).GE.112).AND.(TABLE(IREC,3).LE.
     *           120))) TRANS(POS) = CHAR(TABLE(IREC,3) - 63)
               POS = POS + 1
               TRANS(POS) = COMMA
C
C              The x-coordinate, the y-coordinate, the charge value,
C              the relative charge position, the number of hydrogens,
C              the hydrogen's relative graphic position, the abnormal
C              mass, the number of the node's connections, the connected
C              node's numbers and the connection's bond types are assigned
C              to the string.
               DO 200 I = 4,LNG
                  VAL = TABLE(IREC,I)
                  CALL NUMCHR(VAL,RET,NDGT)
                  DO 110 J = 1,NDGT
                     POS = POS + 1
                     TRANS(POS) = RET(J)
110               CONTINUE
                  POS = POS + 1
                  TRANS(POS) = COMMA
200            CONTINUE
C
C              The transmission string's check character is computed and
C              assigned.
               CALL CHKGEN(POS,CHK)
               POS = POS + 1
               TRANS(POS) = CHK
C
C              The number of transmission string characters is passed to
C              define the length of record transmission.
               OUTN = POS
C
               RESULT = SEND(TRANS,OUTN)
500         CONTINUE
C
C           The trailer record is assembled.
            TRANS(1) = '-'
            TRANS(2) = '1'
            TRANS(3) = COMMA
            POS = 3
C
C           Any of up to 5 *M structure formulas along with multipliers and x,y
C           coordinates of the formula definition is positionally inserted into
C           the trailer.
            DO 900 IMSPOS = 1,MNUM
C
               VAL = IMS(5,IMSPOS)
               CALL NUMCHR(VAL,RET,NDGT)
               DO 730 I = 1,NDGT
                  POS = POS + 1
                  IF (POS.EQ.81) CALL MCONT(POS,TRANS)
                  TRANS(POS) = RET(I)
730            CONTINUE
               POS = POS + 1
               IF (POS.EQ.81) CALL MCONT(POS,TRANS)
               TRANS(POS) = COMMA
C
C              X and Y coordinates are assigned.
               VAL = IMS(3,IMSPOS)
               CALL NUMCHR(VAL,RET,NDGT)
               DO 770 I = 1,NDGT
                  POS = POS + 1
                  IF (POS.EQ.81) CALL MCONT(POS,TRANS)
                  TRANS(POS) = RET(I)
770            CONTINUE
               POS = POS + 1
               IF (POS.EQ.81) CALL MCONT(POS,TRANS)
               TRANS(POS) = '|'
               VAL = IMS(4,IMSPOS)
               CALL NUMCHR(VAL,RET,NDGT)
               DO 790 I = 1,NDGT
                  POS = POS + 1
```

```
            IF (POS.EQ.81) CALL MCONT(POS,TRANS)
            TRANS(POS) = RET(I)
790     CONTINUE
        POS = POS + 1
        IF (POS.EQ.81) CALL MCONT(POS,TRANS)
        TRANS(POS) = '|'
C
C       The multiplier of the *M structure is assigned.
        IF (IMS(1,IMSPOS).GT.1) THEN
            VAL = IMS(1,IMSPOS)
810         CALL NUMCHR(VAL,RET,NDGT)
            DO 840 I = 1,NDGT
                POS = POS + 1
                IF (POS.EQ.81) CALL MCONT(POS,TRANS)
                TRANS(POS) = RET(I)
840         CONTINUE
            POS = POS + 1
            IF (POS.EQ.81) CALL MCONT(POS,TRANS)
            IF (IMS(7,IMSPOS).GT.0) THEN
                TRANS(POS) = '/'
                VAL = IMS(7,IMSPOS)
                IMS(7,IMSPOS) = 0
                GO TO 810
            ENDIF
            TRANS(POS) = '|'
        ENDIF
C
        POS = POS + 1
        IF (POS.EQ.81) CALL MCONT(POS,TRANS)
        TRANS(POS) = 'M'
        POS = POS + 1
        IF (POS.EQ.81) CALL MCONT(POS,TRANS)
        TRANS(POS) = CHAR(IMS(2,IMSPOS) - 63)
C
C       Molecular formula of *M structure.
        DO 850 I = 1,IMS(6,IMSPOS)
            POS = POS + 1
            IF (POS.EQ.81) CALL MCONT(POS,TRANS)
            TRANS(POS) = CHAR(IMS(7+I,IMSPOS))
850     CONTINUE
        POS = POS + 1
        IF (POS.EQ.81) CALL MCONT(POS,TRANS)
        TRANS(POS) = COMMA
C
900     CONTINUE
C
C       The trailer's positional fillers rather than *M structure formula
C       strings are assigned.
        DO 1000 I = MNUM+1,5
            POS = POS + 1
            IF (POS.EQ.81) CALL MCONT(POS,TRANS)
            TRANS(POS) = '0'
            POS = POS + 1
            IF (POS.EQ.81) CALL MCONT(POS,TRANS)
            TRANS(POS) = COMMA
            POS = POS + 1
            IF (POS.EQ.81) CALL MCONT(POS,TRANS)
            TRANS(POS) = COMMA
1000    CONTINUE
C
C       The trailer's check digit is computed and assigned.
        CALL CHKGEN(POS,CHK)
        POS = POS + 1
        IF (POS.EQ.81) CALL MCONT(POS,TRANS)
        TRANS(POS) = CHK
C
C       The number of trailer string characters is assigned to define
C       length of trailer transmission.
        OUTN = POS
C
C       The molecular strucure is passed for transmission.
        ONODES = NNODE + 2
        RESULT = SEND(TRANS,OUTN)
C
```

```fortran
      DO 2000 I = OUTREC+1,OUTREC+6
          WRITE(OU,9,REC=I) BLANK
2000  CONTINUE
      INQUIRE(FILE='IDS.NDX',EXIST=EXIST)
      IF (EXIST) THEN
          OPEN(IONDX,FILE='IDS.NDX',STATUS='OLD',ACCESS='DIRECT',
     *        FORM='FORMATTED',RECL=80)
        ELSE
          OPEN(IONDX,FILE='IDS.NDX',STATUS='NEW',ACCESS='DIRECT',
     *        FORM='FORMATTED',RECL=80)
      ENDIF
      WRITE(IONDX,79,REC=PLNTID) ID,FILE,OUTREC
      DO 2010 I = NUMIDS+1,NUMIDS+6
          WRITE(IONDX,189,REC=I) BLNK10
2010  CONTINUE
      CLOSE(IONDX)
9     FORMAT(A1)
189   FORMAT(A10)
      RETURN
      END
C
C     FUNCTION SEND outputs the transmission strings of each molecular
C     structure.
C
C     ORI   Paul Broderick   July, 1984
C
      INTEGER*2 FUNCTION SEND(TRANS,OUTN)
      IMPLICIT INTEGER*2 (A-Z)
      CHARACTER*1 TRANS(80)
      COMMON /ORECS/ OU,OREC
C
      IF (OUTN.NE.80) THEN
          OUTN = OUTN + 1
          TRANS(OUTN) = CHAR(32)
      ENDIF
C
C     Output transmission string.
      OREC = OREC + 1
      WRITE(OU,999,REC=OREC) (TRANS(L),L=1,OUTN)
C
      SEND = 1
      RETURN
999   FORMAT(80A1)
      END
C
C
      SUBROUTINE MCONT(POS,TRANS)
      IMPLICIT INTEGER*2 (A-Z)
      CHARACTER*1 TRANS(80)
C
      OUTN = POS -1
      RESULT = SEND(TRANS,OUTN)
      POS = 1
      RETURN
      END
$STORAGE:2
C
C         XTCHEM: VERSION 1 - MARCH, 1984
C
C         ADAPTED FROM HPCHEM: VERSION 5 - APRIL 25,1984
C               through HPCHEM: VERSION 8 - FEB 5, 1985
C
      SUBROUTINE STRINP(IX,IY,IEDIT,FIRST)
      IMPLICIT INTEGER*2 (A-Z)
      REAL A
      INTEGER*4 MM,IDTPIX
      LOGICAL*2 FIRST,IEDIT
      CHARACTER*1 ISTAT
      COMMON /ELECHR/ IELEM(126,5)
      COMMON /STRDEF/ NNODE,TABLE(255,43)
      COMMON /STRPIX/ LPIX,MM(90,38),LBLEN,LNGBND(100,5)
C Input program for chem structures. Version 4Apr83. Includes setting
C setting markers with'#',jump to marker by typing lowercase letter,
C typing second letter of 2-letter element with '$' precedence code.
C No changing of previously-entered markers. GMK
      COMMON /KEYS/ ICODE(8)
```

```
          COMMON /CD/ MAXX,MAXY
          COMMON /PARAMS/ JBDIR,NOCHG,LASTN,MCHAR,JCHAR,NLARGE,LEVEL
          COMMON /MODES/ JBTYPE,ICHAR,IBDIR,IBTYPE,ISMART,MODE,ISKILL,ISP
          COMMON /CHARS/IES, IDOT,ITAG,JUMP,LBOND,KAN,ISPACE
          COMMON /HEAD/ MW(12),ISTATE,PAGE
          COMMON /PROB/ IPROB,JPROB
C Line segments to draw bonds(see SUB DRAW)
          COMMON /BONDS/ A(5,3,4,4),B(2,3,4)
C X,Y of up to 10
          COMMON /LABELS/ NR,NJLAST,NJNEXT
C         alphabets of lowercase label locations (0 if unused,
C         -999 if used but erased). NR is the last line of LABL
C         which has been jumped to, NJLAST is the last lowercase
C         label which has been jumped to minus 96, and NJNEXT is
C         the last line number where XY coordinates were added to
C         the list in LABL by subroutine MARK.
          COMMON /SIZZE/ MULTX,MULTY
          COMMON /ISTATE/ ISTAT
          COMMON /STRED/ IDTPIX(90,38),LABL(260,2),MRKCHN(260)
          COMMON /CUR/ ICUR
C Subroutine CHAIN; includes some which may have been already changed
          COMMON /IPLUS/ IHIGH(14,2)
          COMMON /RANGE/ LOX,HIX,LOY,HIY
          COMMON /MKSKP/ ISKIP
          COMMON /WARN/ ERR
          COMMON /QTVLNC/ OERR,CHER
          COMMON /FROM/ LCHAR C
C THIS PROGRAM GENERATES A CHARACTER MATRIX FOR CHEMICAL STRUCTURES.
C THE PROGRAM FACILITATES TYPING BY GENERATING ATOMIC SYMBOLS WHERE
C THESE ARE MANDATORY.
C
C         MCHAR is last character entered.
C         LASTN is last numeral entered.
C SET RETURN = OK UNTIL OTHERWISE KNOWN
          LFLAG = 0
          ISKIP = 0
          LPIX = MAXX * MAXY
          ISTAT = ' '
          IPROB=0
          JPROB=0
          IRESET = 0
          INCX = 0
          INCY = 0
          IF (FIRST) THEN
              LOX = 26
              HIX = 26
              LOY = 15
              HIY = 15
          ELSE
              CALL RESET(IX,IY,FIRST)
          ENDIF
C
100       IF (IRESET.EQ.1) CALL RESET(IX,IY,FIRST)
          CALL SETSCR(2)
          PAGE = 2
          CALL DISPLA(2)
          CALL FTSIZE(1,10)
          CALL INITHC(3,3,1)
          ICUR = 1
          CALL CURSOR(IX,IY)
C
C Go on if we are not in EDIT mode
          IF (.NOT.IEDIT) GO TO 50
              CALL REFORM(STATUS)
              IF (STATUS.NE.0) RETURN
              CALL REMARK(IERR)
C             Call STRDRW with markers displayed as markers
              ISWIT=1
C             Display old picture
              CALL STRDRW(ISWIT)
C Sense cursor position after displaying picture
          DO 61 J = LOY,HIY
```

```
              DO 60 I = LOX,HIX
                II = I
                JJ = J
                M = LMM(I,J)
                IF (M.EQ.42) GO TO 61
                IF ((M.EQ.46).OR.(((M.GE.65).AND.(M.LE.90)
     *            .AND.(.NOT.((M.EQ.72).AND.((MM(IX+1,J).LT.97).OR.
     *            (MM(IX+1,J).GT.122)))))) GO TO 65
60            CONTINUE
61            CONTINUE
              IX = 26
              IY = 15
              GO TO 66
65            IX = II+1
C Set cursor position
              IY = JJ
              ICHAR = 2
              JCHAR = 2
              KAR = M
              MCHAR = KAR
66            CALL CURSOR(IX,IY)
C
50            IEDIT=.FALSE.
C When IRESET=1, done with a structure; recycle to 100
              IRESET=0
C Display status info on top of screen
              ICUR = 1
              CALL HEADER
1             CONTINUE
              LEVEL = 0
              LCHAR = 0
              CALL INPUTX(KAR,IX,IY)
3             CALL IDENT(KAR,IX,IY,INCX,INCY,IRESET)
              IF ((KAR.EQ.13).OR.(KAR.EQ.127)) THEN
                 ICUR = 1
                 CALL CURSOR(IX,IY)
              ENDIF
              IF (LEVEL.EQ.1) THEN
                 IF (ICHAR.EQ.33) THEN
                    CALL LIBRA(IX,IY,KAR)
                 ELSE IF (ICHAR.EQ.12) THEN
                    CALL RING(KAR,IX,IY,INCX,INCY,IRESET,LFLAG)
                    IF ((LCHAR.EQ.13).AND.(LFLAG.EQ.0).AND.(JPROB.EQ.0)) THEN
                       KAR = 33
                       LCHAR = 0
                       GO TO 3
                    ENDIF
                 ELSE IF (ICHAR.EQ.13) THEN
                    CALL CHAIN(KAR,IX,IY,INCX,INCY,IRESET,LFLAG)
                    IF ((LCHAR.EQ.12).AND.(LFLAG.EQ.0).AND.(JPROB.EQ.0)) THEN
                       KAR = 94
                       LCHAR = 0
                       GO TO 3
                    ENDIF
                 ELSE IF (ICHAR.EQ.14) THEN
                    CALL REPEAT(KAR,IX,IY,INCX,INCY,IRESET,LFLAG)
                 ELSE IF (ICHAR.EQ.16) THEN
                    CALL DOTDIS(KAR,IX,IY,IRESET,LFLAG)
                 ELSE IF (ICHAR.EQ.21) THEN
                    CALL GETIT(IX,IY,LFLAG,KAR)
                 ENDIF
                 ICUR = 1
                 CALL CURSOR(IX,IY)
              ENDIF
C EXIT TO DIS WITH GOOD OR BAD RETURN
              IF ((KAR.EQ.17).OR.(KAR.EQ.18)) GO TO 850
              IF (JPROB .NE. 0) GO TO 70
              IF (LFLAG .NE. 1) GO TO 2
              LFLAG=0
              GO TO 3
2             IF (IRESET.EQ.1) THEN
                 FIRST = .FALSE.
                 GO TO 100
              ENDIF
              IF (IRESET .EQ. 3) RETURN
              GO TO 1
```

```
 70      IF(JPROB .EQ. 1) GO TO 72
         CALL FTSIZE(2,18)
            IF (PAGE.NE.1) THEN
               CALL SETSCR(1)
               PAGE = 1
               CALL DISPLA(1)
            ENDIF
         CALL FTLOCA(8,20)
         CALL FTEXT('^ Do you wish to^')
         CALL FTLOCA(9,20)
         CALL FTEXT('^ (R)enter new structure or (E)xit - (data will b
     *e lost)^')
         CALL FTLOCA(10,20)
         CALL FTEXT('^ Type R or E: ^')
 799     CONTINUE
         ERR = 100
         CALL INPUTX(L,IX,IY)
         ERR = 0
         JCHAR = 2
C     HE WANTS TO REENTER
         IF (L.EQ. 82 .OR. L .EQ. 114) GO TO 800
C     HE WANTS TO ABORT
         IF(L.EQ. 69 .OR. L .EQ.101) GO TO 850
         CALL SETCOL(0)
         CALL CLR
         CALL SETCOL(1)
         CALL FTLOCA(8,20)
         CALL FTEXT('^ You should have typed R or E - Please try again:^'
     *   )
         GO TO 799
 800     IRESET=1
         JPROB=0
         GO TO 100
 850     CONTINUE
         CALL SETCOL(0)
         CALL CLR
         CALL SETCOL(1)
         RETURN
 72      CONTINUE
         CALL SETSCR(1)
         PAGE = 1
         CALL FTSIZE(2,18)
         CALL DISPLA(1)
         CALL FTLOCA(8,20)
         CALL FTEXT('^ Do you wish to^')
         CALL FTLOCA(9,20)
         CALL FTEXT('^ (C)ontinue structure or (E)xit -(data will be los
     *t)^')
         CALL FTLOCA(10,20)
         CALL FTEXT('^ Type C or E: ^')
 888     CONTINUE
         ERR = 100
         CALL INPUTX(L,IX,IY)
         ERR = 0
         IF (L.EQ.67 .OR. L.EQ.99) GO TO 805
         IF (L.EQ.69 .OR. L .EQ.101) GO TO 850
         CALL SETCOL(0)
         CALL CLR
         CALL SETCOL(1)
         CALL FTLOCA(8,20)
         CALL FTEXT('^ You should have typed C or E - Please try again:^'
     *   )
         GO TO 888
 805     CONTINUE
         JPROB=0
         CALL SETCOL(0)
         CALL CLR
         CALL SETCOL(1)
         MODE=1
         LASTN=0
         DO 999 I=1,12
            MW(I)=999
 999     CONTINUE
```

```
      IF (OERR.EQ.-1) THEN
          OERR = 0
          CALL SETSCR(2)
          CALL SETCOL(0)
          CALL CLR
          CALL SETCOL(1)
          PAGE = 2
          CALL DISPLA(2)
      CALL CLR
          CALL REMARK(IERR)
          ISWIT = 1
          CALL STRDRW(ISWIT)
      ELSE
          CALL SETSCR(2)
          PAGE = 2
          CALL DISPLA(2)
      ENDIF
      CALL FTSIZE(1,10)
      CALL HEADER
      ICUR = 1
      CALL CURSOR(IX,IY)
      GO TO 1
      END
C
      SUBROUTINE REDO(L,I1,I2,I3,I4,I5,I6)
      IMPLICIT INTEGER*2 (A-Z)
      CHARACTER*1 HALO(3)
      CHARACTER*1 KAN
      CHARACTER*3 HALOE
      COMMON /CHARS/IES, IDOT,ITAG,JUMP,LBOND,KAN,ISPACE
      EQUIVALENCE (HALOE,HALO(1))
C
C SUBROUTINE MONITORS FOR CORRECTNESS OF SPECIFIED INPUT CHARACTER.
C
      HALO(1) = KAN
      HALO(3) = KAN
5     CONTINUE
C
      L = GETCHR()
      HALO(2) = CHAR(L)
C
C Lower case ok too.
      IF (L.GT.95) L=L-32
      CALL SETCOL(0)
      CALL CLR
      CALL SETCOL(1)
      IF ((L.EQ.I1).OR.(L.EQ.I2).OR.(L.EQ.I3).OR.(L.EQ.I4).OR.
     *    (L.EQ.I5).OR.(L.EQ.I6)) RETURN
C
      CALL FTLOCA(7,26)
      CALL FTEXT('^ NO! YOU TYPED: ^')
      CALL FTEXT(HALOE)
      CALL FTLOCA(8,26)
      HALO(2) = CHAR(I1)
      CALL FTEXT('^ YOU SHOULD HAVE TYPED: ^')
      CALL FTEXT(HALOE)
      FY = 9
      IF (I2.EQ.0) GO TO 900
          HALO(2) = CHAR(I2)
          CALL FTLOCA(9,45)
          CALL FTEXT('^ OR: ^')
          CALL FTEXT(HALOE)
          FY = 10
      IF (I3.EQ.0) GO TO 900
          HALO(2) = CHAR(I3)
          CALL FTLOCA(10,45)
          CALL FTEXT('^ OR: ^')
          CALL FTEXT(HALOE)
          FY = 11
      IF (I4.EQ.0) GO TO 900
          HALO(2) = CHAR(I4)
          CALL FTLOCA(11,45)
          CALL FTEXT('^ OR: ^')
          CALL FTEXT(HALOE)
          FY = 12
```

```
              IF (I5.EQ.0) GO TO 900
              HALO(2) = CHAR(I5)
              CALL FTLOCA(12,45)
              CALL FTEXT('^ OR: ^')
              CALL FTEXT(HALOE)
              FY = 13
              IF (I6.EQ.0) GO TO 900
              HALO(2) = CHAR(I6)
              CALL FTLOCA(13,45)
              CALL FTEXT('^ OR: ^')
              CALL FTEXT(HALOE)
              FY = 14
900           CONTINUE
C
              CALL FTLOCA(FY,26)
              CALL FTEXT('^ PLEASE TRY AGAIN. ^')
              GO TO 5
              END
C
              SUBROUTINE RESET(IX,IY,FIRST)
              IMPLICIT INTEGER*2 (A-Z)
              INTEGER*4 MM,IDTPIX
              LOGICAL*2 FIRST,NOMSG,BONDEL,BAR,CNTX
              CHARACTER*1 ISTAT
              COMMON /CD/ MAXX,MAXY
              COMMON /RANGE/ LOX,HIX,LOY,HIY
              COMMON /STRPIX/ LPIX,MM(90,38),LBLEN,LNGBND(100,5)
              COMMON /PARAMS/ JBDIR,NOCHG,LASTN,MCHAR,JCHAR,NLARGE,LEVEL
              COMMON /MODES/ JBTYPE,ICHAR,IBDIR,IBTYPE,ISMART,MODE,ISKILL,ISP
              COMMON /CHARS/IES, IDOT,ITAG,JUMP,LBOND,KAN,ISPACE
              COMMON /HEAD/ MW(12),ISTATE,PAGE
              COMMON /ISTATE/ ISTAT
              COMMON /LABELS/ NR,NJLAST,NJNEXT
              COMMON /STRDEF/ NNODE,TABLE(255,43)
              COMMON /STRED/ IDTPIX(90,38),LABL(260,2),MRKCHN(260)
              COMMON /RETLIB/OVRWRT
              COMMON /H/ MOBILE(255,2)
              COMMON /CUR/ ICUR
              COMMON /DARK/ OCUR
              COMMON /D1/ IDNUM,IDS(9,6),NBD1,DSCNC(6,50)
              COMMON /M1/ MNUM,IMS(90,5)
              COMMON /KHARGE/ ICHRGE(50,4),NCHG
              COMMON /CONNCT/ IBOND(255,16),KBOND(255,16)
              COMMON /TEMP/ LLBOND(100,5),LLABL(260,2),MCHN(260)
              COMMON /FROM/ LCHAR
              COMMON /QTVLNC/ OERR,CHER
              COMMON /LNGOUT/ LNGNDE(100,2)
              COMMON /VLNPRV/ MLARGE
              COMMON /LEAPER/ NOMSG
              COMMON /DELBND/ BONDEL
              COMMON /BTPDIR/ BAR
              COMMON /CNTX/ CNTX
              COMMON /DTDS/ DTN,DTX(30),DTY(30),DTN1(30),DTN2(30)
              DATA OVRWRT/.FALSE./
C
C CURSOR HOME
C       (ERASE GRAPHICS MEMORY, TURN ON ALPHA DISPLAY, TURN ON
C        GRAPHICS DISPLAY, TURN OFF GRAPHICS TEXT MODE)
              IF (.NOT.FIRST) CALL CLOSEG
              CALL INITGR(0)
C
              CALL SETSCR(1)
              CALL SETGPR(1)
              CALL SETCOL(1)
              CALL FTINIT
              CALL FTSIZE(2,18)
              CALL FTCOLO(0,1)
C
              CALL SETSCR(2)
              CALL SETCOL(1)
              PAGE = 2
              CALL DISPLA(2)
              CALL STARTG(0)
              CALL SETGPR(1)
              CALL SETIEE(1)
              CALL SETDEG(1)
```

```
            CALL INITTC(0,0,0)
            CALL SETTEX(1,1,0,0)
            CALL SETTCL(1,0)
C
            IX = 26
            IY = 15
            NOMSG = .FALSE.
            BAR = .FALSE.
            BONDEL = .FALSE.
            CNTX = .FALSE.
            ISTAT=' '
            ICUR = 0
            OCUR = 1
            CALL CURSOR(IX,IY)
C           (INITIALIZE CURSOR)
            MCHAR=0
            JCHAR=0
            LASTN=0
C ISP = 0 IMPLIES WE HAVE NOT JUST RETURNED FROM SPACE
            ISP=0
C THIS VARIABLE IS USED TO KEEP US FROM CALLING VALNCE
C AFTER RETURN FROM SPACE AND JUST BEFORE CALL TO LEAP
C TERMINAL SMART=1, DUMB=0
            ISMART=1
            IBDIR=3
            IBTYPE=1
C 1 means chain or ring state
            LEVEL=0
            MODE=1
            NLARGE=1
            MLARGE = NLARGE
            CHER = 0
            NR=1
            NBD1 = 0
            LBLEN = 0
            IDNUM = 0
            NJNEXT = 0
            NJLAST=0
            ISTATE = 0
            LCHAR = 0
            DO 200 I=1,9
               DO 100 J = 1,6
                  IDS(I,J) = 0
100            CONTINUE
               MW(I)=999
200         CONTINUE
            DO 400 I = 10,12
               DO 300 J = 1,6
                  IDS(I,J) = 0
300            CONTINUE
400         CONTINUE
            DO 500 I = LOX,HIX
            DO 500 J = LOY,HIY
               MM(I,J)=0
               IDTPIX(I,J)=0
500         CONTINUE
            LOX = IX
            HIX = IX
            LOY = IY
            HIY = IY
            DO 2000 I = 1,50
               DO 1100 J = 1,2
                  MOBILE(I,J) = 0
                  IBOND(I,J) = 10000
                  KBOND(I,J) = 10000
                  DSCNC(J,I) = 0
                  IMS(I,J) = 0
                  ICHRGE(I,J) = 10000
                  LNGBND(I,J) = 0
                  LLBOND(I,J) = 0
                  LNGNDE(I,J) = 0
                  LABL(I,J) = 0
                  LLABL(I,J) = 0
1100           CONTINUE
               DO 1500 J = 3,4
```

```
                IBOND(I,J) = 10000
                KBOND(I,J) = 10000
                IMS(I,J) = 0
                ICHRGE(I,J) = 10000
                LNGBND(I,J) = 0
                LLBOND(I,J) = 0
                DSCNC(J,I) = 0
1500       CONTINUE
           DSCNC(5,I) = 0
           DSCNC(6,I) = 0
           IMS(I,5) = 0
           MRKCHN(I)=0
           MCHN(I) = 0
           IBOND(I,5) = 10000
           KBOND(I,5) = 10000
           LNGBND(I,5)=0
           LLBOND(I,5) = 0
           DO 1800 J = 6,16
                IBOND(I,J) = 10000
                KBOND(I,J) = 10000
1800       CONTINUE
           IF (I.LE.30) THEN
                DTX(I) = 0
                DTY(I) = 0
                DTN1(I) = 0
                DTN2(I) = 0
           ENDIF
2000    CONTINUE
C
        DO 3000 I=51,90
           MRKCHN(I)=0
           MCHN(I) = 0
           DO 2200 J=1,2
                MOBILE(I,J) = 0
                IBOND(I,J) = 10000
                KBOND(I,J) = 10000
                LNGBND(I,J)=0
                LLBOND(I,J) = 0
                LNGNDE(I,J) = 0
                LABL(I,J) = 0
                LLABL(I,J) = 0
                IMS(I,J) = 0
2200       CONTINUE
           DO 2300 J = 3,5
                IBOND(I,J) = 10000
                KBOND(I,J) = 10000
                LNGBND(I,J)=0
                LLBOND(I,J) = 0
                IMS(I,J) = 0
2300       CONTINUE
           DO 2400 J = 6,16
                IBOND(I,J) = 10000
                KBOND(I,J) = 10000
2400       CONTINUE
3000    CONTINUE
        DO 4000 I = 91,100
           MRKCHN(I)=0
           MCHN(I) = 0
           DO 3100 J=1,2
                MOBILE(I,J) = 0
                IBOND(I,J) = 10000
                KBOND(I,J) = 10000
                LNGBND(I,J)=0
                LLBOND(I,J) = 0
                LNGNDE(I,J) = 0
                LABL(I,J)=0
                LLABL(I,J)=0
3100       CONTINUE
           DO 3200 J = 3,5
                IBOND(I,J) = 10000
                KBOND(I,J) = 10000
                LNGBND(I,J)=0
                LLBOND(I,J) = 0
3200       CONTINUE
           DO 3300 J = 6,16
                IBOND(I,J) = 10000
                KBOND(I,J) = 10000
```

```
      3300        CONTINUE
      4000        CONTINUE
                  DO 5000 I=101,255
                      MRKCHN(I)=0
                      MCHN(I) = 0
                      DO 4100 J=1,2
                          MOBILE(I,J) = 0
                          IBOND(I,J) = 10000
                          KBOND(I,J) = 10000
                          LABL(I,J) = 0
                          LLABL(I,J) = 0
      4100        CONTINUE
                      DO 4200 J = 3,16
                          IBOND(I,J) = 10000
                          KBOND(I,J) = 10000
      4200        CONTINUE
      5000        CONTINUE
                  DO 5500 I=256,260
                      MRKCHN(I)=0
                      MCHN(I) = 0
                      DO 5100 J=1,2
                          LABL(I,J) = 0
                          LLABL(I,J) = 0
      5100        CONTINUE
      5500        CONTINUE
      7000        CONTINUE
                  RETURN
                  END
C
            SUBROUTINE IDENT(KAR,IX,IY,INCX,INCY,IRESET)
            IMPLICIT INTEGER*2 (A-Z)
            INTEGER*4 MM
            LOGICAL*2 BONDEL,DELTED,BAR
            CHARACTER*1 ISTAT
            COMMON /CD/ MAXX,MAXY
            COMMON /CHARS/IES, IDOT,ITAG,JUMP,LBOND,KAN,ISPACE
            COMMON /MODES/ JBTYPE,ICHAR,IBDIR,IBTYPE,ISMART,MODE,ISKILL,ISP
            COMMON /PARAMS/ JBDIR,NOCHG,LASTN,MCHAR,JCHAR,NLARGE,LEVEL
            COMMON /OLD/ IOX,IOY
            COMMON /STRPIX/ LPIX,MM(90,38),LBLEN,LNGBND(100,5)
            COMMON /ISTATE/ ISTAT
            COMMON /HEAD/ MW(12),ISTATE,PAGE
            COMMON /PROB/ IPROB,JPROB
            COMMON /FROM/ LCHAR
            COMMON /WARN/ ERR
            COMMON /IRECS/ IU,IREC,TOPREC,BOTREC
CXT         BONDEL = TRUE indicates that a bond has been drawn between 2
CXT         nodes so subsequent deletion should delete the bond, not a node.
            COMMON /DELBND/ BONDEL
CXT         BAR is used in conjunction with NOCHG and LASTN to control
CXT         bond type determination in relation to default bond types.
            COMMON /BTPDIR/ BAR
C
C     This subroutine identifies input characters and sets modes and states
C     accordingly.
C     Previous mode(state)
CXT   DELTED = TRUE after SUBROUTINE DEL is called.
            DELTED = .FALSE.
      16    JMODE=MODE
C Assume reset to bondtype 1
            IF ((KAR.NE.58).AND.(ISTATE.NE.12).AND.(ISTATE.NE.3).AND.
           *    (ISTATE.NE.5).AND.(KAR.NE.94).AND.(KAR.NE.33)) THEN
                IF ((LASTN.NE.IBTYPE).AND.(ISTATE.NE.9)) NOCHG = 0
            ELSE IF ((KAR.EQ.58).OR.(KAR.EQ.33).OR.(KAR.EQ.94)) THEN
                BAR = .TRUE.
            ENDIF
            LASTN = 0
            ITEMP=0
            IF (KAR.NE.127) BONDEL = .FALSE.
            IF (ICHAR.EQ.30) ITEMP=30
            IF ((ICHAR.EQ.18).OR.(ICHAR.EQ.25)) ITEMP=18
C character type
            ICHAR=0
            JJJ=IX
```

```
              DO 428 I=0,-3,-1
              IF (((MM(IX+I,IY).GE.65).AND.(MM(IX+I,IY).LE.90).AND.
     2        (MM(IX+I,IY).NE.72)).OR.((MM(IX+I,IY).EQ.72).AND.
     3        (MM(IX+I+1,IY).GE.97).AND.(MM(IX+I+1,IY).LE.122))) THEN
                JJJ=IX+I
                GO TO 427
              ENDIF
428           CONTINUE
427           IF(KAR .EQ. 81) GO TO 966
C GOTO if not ground state
              IF (KAR.EQ.21) THEN
                ISMART = 0
                CALL SPACE(IX,IY)
                MCHAR = 0
                JCHAR = 2
                RETURN
              ENDIF
CXT           IF (MODE.GT.1) GOTO 20
              IF ((KAR.GE.48).AND.(KAR.LE.57).AND.(ITEMP.NE.30)) THEN
                ICHAR = 29
                CALL NUMBER(KAR,IX,IY)
                MCHAR = KAR
                RETURN
              ENDIF
C
C                     Ground state:
C
C Select bonds
              IF (KAR.EQ.124) RETURN
              IF ((KAR.LT.22) .OR. (KAR.GT.31)) GOTO 1
C bonds
18            ICHAR=1
C set bond direction
              IBDIR = KAR-21
              IF (IBDIR.GT.4) IBDIR=IBDIR-2
              GOTO 4400
C 81=Q--quit
1             IF (KAR.NE.81) GOTO 2
966           ICHAR=20
              IF (ITEMP.NE.18) CALL CLRHYD(JJJ,IY)
              IF (ITEMP.NE.18) CALL VALNCE(2,JJJ,IY,0,0)
              IF (JPROB.NE.0) RETURN
              CALL QUIT(IRESET,KAR,IX,IY)
              IF ((MM(JJJ,IY).NE.0).AND.(ERR.NE.18).AND.(ERR.NE.12)) JCHAR = 2
              IF ((PAGE.EQ.2).AND.(IRESET.EQ.0)) THEN
                ICUR = 1
                CALL CURSOR(IX,IY)
              ENDIF
              IF ((PAGE.NE.2).AND.(JPROB.NE.1)) THEN
                CALL SETCOL(0)
                CALL CLR
                CALL SETCOL(1)
              ENDIF
              IF ((IRESET.NE.3).OR.(IRESET.EQ.1)) THEN
                CALL SETSCR(2)
                PAGE = 0
                CALL FTSIZE(1,10)
              ENDIF
C WE ARE DONE - EXIT
              IF ((IRESET.EQ.1).OR.(IRESET.EQ.3)) RETURN
              MODE = 1
              RETURN
C             GO TO 4400
C             Seperate UC; '?'; and '.'
2             IF (((KAR.LT.65) .OR. (KAR.GT.90)) .AND. (KAR.NE.63) .AND.
     2        (KAR.NE.46))  GOTO 3
C UC after '$'--2nd letter of elem symb
              IF (ITEMP.NE.30) GOTO 35
C             Convert UC to LC
              KAR=KAR+32
              GOTO 3
35            ICHAR = 2
              GOTO 4400
C separate lowercase
C LINE FOOLS PROGRAM INTO ACCEPTING D1'S AND M1'S.
```

```
3       IF ((KAR.GT.48).AND.(KAR.LT.58).AND.(ITEMP.EQ.30))
*          GO TO 44
        IF ((KAR.LT.97).OR.(KAR.GT.122)) GO TO 4
C       If lc is second letter of element
44      IF (ITEMP.EQ.30) ICHAR = 4
        ITEMP=0
C jump to marker
        IF (ICHAR.NE.4)  ICHAR=31
        IF (ICHAR.EQ.31) CALL CLRHYD(JJJ,IY)
        GOTO 4400
C sign+-
4       CONTINUE
C % ring mode
5       IF (KAR.NE.94) GOTO 6
        ICHAR=12
        LEVEL=1
        GOTO 4400
C chain mode
6       IF (KAR.NE.33) GOTO 7
        ICHAR=13
        LEVEL=1
        GOTO 4400
C a repeat mode
7       IF (KAR.NE.64) GOTO 88
        ICHAR=14
        LEVEL=1
        GOTO 4400
88      IF(KAR.NE.42) GO TO 8
        ICHAR=16
        LEVEL=1
        GO TO 4400
C % long bond
8       IF (KAR.NE.LBOND) GOTO 11
        ICHAR=17
        GOTO 4400
C & enlarge state
11      IF (KAR.NE.38) GOTO 12
        ICHAR=15
        GOTO 4400
C delete state
12      IF (KAR.NE.127) GOTO 13
        ICHAR=19
        GOTO 4400
C backspace
13      IF (KAR.NE.8) GOTO 14
        ICHAR=18
        ISMART=0
        GOTO 4400
C space
14      IF (KAR.NE.ISPACE) GOTO 15
        ICHAR=25
        GOTO 4400
C Carriage return--return to gnd state
15      IF (KAR.NE.13) GOTO 19
        ICHAR=26
        MODE=1
        GOTO 4400
C '$':2nd letter of element symbol next
19      IF (KAR.NE.JUMP) GOTO 33
C WE MISTAKENLY CHANGED A H
        IF(MCHAR .NE. 74) GO TO 1119
C TO A J - NOW CHANGE IT BACK
        MM(IX-1,IY)=72
1119    ICHAR=30
        GOTO 4400
C '#'set a marker
33      IF (KAR.NE.ITAG) GOTO 341
        ICHAR=28
        GOTO 4400
```

```
C   Library
341       IF (KAR.NE.95) GO TO 3004
          ICHAR = 33
          LEVEL = 1
          GO TO 4400
C : Retrieve
3004      IF (KAR.NE.58) GO TO 3404
          ICHAR = 21
          LEVEL = 1
          GO TO 4400
C D1 " indeterminant bond site marker
3404      IF (KAR.NE.34) GO TO 34
          ICHAR = 9
          GO TO 4400
C Chg+-=
34        IF ((KAR.NE.43).AND.(KAR.NE.45)) GOTO 4455
          ICHAR = 6
          IF (JCHAR.NE.6) THEN
              HCHAR = JCHAR
              NCHRG = 1
          ELSE IF ((KAR.EQ.MCHAR).AND.(NCHRG.LT.9)) THEN
              NCHRG = NCHRG + 1
          ELSE
              CALL MYERR(55,55,55)
              CALL DEL(KAR,IX,IY,INCX,INCY,0)
              IF (JCHAR .EQ. 6) JCHAR=2
              DELTED = .TRUE.
              JCHAR = HCHAR
              GO TO 4444
          ENDIF
          GO TO 4400
C Types the connection table of input structure to screen from GND
4455      IF ((KAR.NE.39).OR.(TOPREC.EQ.0)) GO TO 45
          CALL VCONTB
          ICUR = 1
          CALL CURSOR(IX,IY)
          RETURN
C Unrecognized character for this mode
45        CALL ERRMSG(KAR)
          RETURN
C draw printable char
4400      IF (ICHAR.LT.10) THEN
CXT           IF (ERR.EQ.45) ERR = 0
              IF (ICHAR.EQ.6) THEN
                  CALL CHARGE(KAR,IX,IY,NCHRG)
              ELSE IF (ICHAR.EQ.9) THEN
                  IDRAW = 0
                  CALL IND1(KAR,IX,IY,IDRAW,IERR)
              ELSE
                  CALL DRAW (KAR,IX,IY,INCX,INCY)
              ENDIF
C backspace
          ELSE IF (ICHAR.EQ.18) THEN
              CALL BKSPCE(IX,IY)
              JCHAR = 2
              MCHAR = 0
C delete
          ELSE IF (ICHAR.EQ.19) THEN
              CALL DEL(KAR,IX,IY,INCX,INCY,0)
              DELTED = .TRUE.
          ENDIF
          CALL HEADER
C save last printable character
          ISP = 0
          IF (ICHAR.LE.10) THEN
              MCHAR=KAR
C save last char type
              JCHAR=ICHAR
          ELSE IF (ICHAR.EQ.28) THEN
              CALL MARK(KAR,IX,IY,IERR)
          ELSE IF (ICHAR.EQ.25) THEN
              IX = IX - 1
              CALL CURSOR(IX,IY)
              CALL CLRHYD(IX,IY)
              CALL VALNCE(2,IX,IY,0,0)
```

```
              IF (JPROB.EQ.1) RETURN
              IX = JJJ
              CALL SPACE(IX,IY)
              JCHAR = 2
              MCHAR = 0
          ELSE IF (ICHAR.EQ.15) THEN
              CALL SETLRG
          ELSE IF (ICHAR.EQ.16) THEN
              IF (JCHAR.EQ.2.OR.JCHAR.EQ.4) THEN
                  CALL CLRHYD(IOX-1,IOY)
                  CALL VALENCE BEFORE DOTDIS
                  CALL VALNCE(2,IOX-1,IOY,0,0)
              ENDIF
          ELSE IF (ICHAR.EQ.31) THEN
              IF ((MM(JJJ,IY).NE.46).AND.(MM(JJJ-1,IY).NE.46))
     *            CALL VALNCE(2,JJJ,IY,0,0)
              CALL LEAP(KAR,IX,IY)
C             LEAP to label KAR
          ELSE IF (ICHAR.EQ.17) THEN
              CALL LONG(KAR,IX,IY)
              IF (KAR.EQ.81) GO TO 966
          ENDIF
C         RETURNED FROM LONG BOND WITH Q - GO TO QUIT
          IF ((DELTED).OR.(ICHAR.EQ.18).OR.(ICHAR.EQ.25)) GO TO 4444
          JBTYPE=IBTYPE
          JBDIR=IBDIR
4444      CONTINUE
          IF (LEVEL.NE.1) LCHAR = 0
          RETURN
          END
C
C
C     This subroutine replaces most of the number entry section of IDENT.
C     This subroutine sets bondtype and draws a bond of the new type
C                                  or
C     sets  charge value and displays the charge.
C
          SUBROUTINE NUMBER(KAR,IX,IY)
          IMPLICIT INTEGER*2 (A-Z)
          LOGICAL*2 BAR
          CHARACTER*1 ISTAT
          COMMON /MODES/  JBTYPE,ICHAR,IBDIR,IBTYPE,ISMART,MODE,ISKILL,ISP
          COMMON /PARAMS/ JBDIR,NOCHG,LASTN,MCHAR,JCHAR,NLARGE,LEVEL
          COMMON /OLD/    IOX,IOY
          COMMON /ISTATE/ ISTAT
          COMMON /HEAD/   MW(12),ISTATE,PAGE
CXT       BAR is used in conjunction with NOCHG and LASTN to control
CXT       bond type determination in relation to default bond types.
          COMMON /BTPDIR/ BAR
          LASTN = 0
C
C         If KAR = | discard it.
          IF ((KAR.GE.48).AND.(KAR.LE.57)) THEN
              BAR = .FALSE.
              GO TO 100
          ENDIF
          BAR = .TRUE.
50        CALL INPUTX(KAR,IX,IY)
          IF ((KAR.GE.48).AND.(KAR.LE.57)) THEN
              GO TO 100
          ELSE IF (KAR.EQ.124) THEN
              GO TO 400
          ELSE IF (KAR.EQ.13) THEN
              GO TO 600
          ELSE IF (KAR.EQ.81) THEN
              GO TO 700
          ELSE
              GO TO 800
          ENDIF
C
C         Digit processing
100       LASTN = KAR - 48
          IBTYPE = LASTN
```

```
          CALL HEADER
          IF (IBTYPE.EQ.9) GO TO 500
          NOCHG = 1
          RETURN
C
C     Already in current state
400       IERR = 39
          CALL MYERR(IERR,IERR,IERR)
          GO TO 50
C
C     Bad bond type or charge value - cmd rejected - get new cmd
500       IERR = 55
          CALL MYERR(IERR,IERR,IERR)
          IBTYPE = 1
          LASTN = 0
          CALL HEADER
          RETURN
C
C     Return with CR or Q
600       ICHAR = 26
700       MODE = 1
          NOCHG = 0
          LASTN = 0
          IBTYPE = 1
          CALL HEADER
          RETURN
800       IERR = 5
          CALL MYERR(IERR,IERR,IERR)
          GO TO 50
          END
$STORAGE:2
C
C     SUBROUTINE MOVE moves the cursor 1 unit in any of the 8 defined
C     directions while the program is in the dumb mode. MOVE is called
C     from SUBROUTINES SPACE and BKSPCE.
C
C     ORI   Paul Broderick   October, 1984
      SUBROUTINE MOVE(KHAR,IX,IY)
      IMPLICIT INTEGER*2(A-Z)
      COMMON /CD/ MAXX,MAXY
      COMMON /CUR/ ICUR
C
      IF (KHAR.EQ.22) THEN
         IY = IY - 1
      ELSE IF (KHAR.EQ.23) THEN
         IX = IX + 1
         IY = IY - 1
      ELSE IF (KHAR.EQ.24) THEN
         IX = IX + 1
      ELSE IF (KHAR.EQ.25) THEN
         IX = IX + 1
         IY = IY + 1
      ELSE IF (KHAR.EQ.28) THEN
         IY = IY + 1
      ELSE IF (KHAR.EQ.29) THEN
         IX = IX - 1
         IY = IY + 1
      ELSE IF (KHAR.EQ.30) THEN
         IX = IX - 1
      ELSE IF (KHAR.EQ.31) THEN
         IX = IX - 1
         IY = IY - 1
      ENDIF
      IF (IX.GT.MAXX) THEN
         IX = MAXX
      ELSE IF (IX.LT.1) THEN
         IX = 1
      ENDIF
      IF (IY.GT.MAXY) THEN
         IY = MAXY
      ELSE IF (IY.LT.1) THEN
         IY = 1
      ENDIF
```

```
C
            ICUR = 1
            CALL CURSOR(IX,IY)
            RETURN
            END
C
            SUBROUTINE CURSOR(IX,IY)
            IMPLICIT INTEGER*2 (A-Z)
            COMMON /SIZZE/ MULTX,MULTY
            COMMON /CUR/ ICUR
            COMMON /HEAD/ MW(12),ISTATE,PAGE
            COMMON /DARK/ OCUR
            DATA XCUR /-1/
C
C           CONVERT COORDINATES TO RASTER
            IF (PAGE.LE.1) CALL SETSCR(2)
            INTX = (IX*MULTX)
            INTY = (IY*MULTY)
            CALL MOVTCA(INTX,INTY)
            IF (OCUR.EQ.1) THEN
               IF (ICUR.NE.XCUR) CALL INITHC(3,3,ICUR)
               HINTX = INTX - 1
               HINTY = INTY + 1
               IF (ICUR.NE.0) CALL MOVHCA(HINTX,HINTY)
            ENDIF
            XCUR = ICUR
            IF (PAGE.EQ.1) CALL SETSCR(1)
            RETURN
            END
C
            SUBROUTINE INPUTX(KAR,IX,IY)
            IMPLICIT INTEGER*2 (A-Z)
            CHARACTER*82 BLNK90
            COMMON /CHARS/IES, IDOT,ITAG,JUMP,LBOND,KAN,ISPACE
            COMMON /SIZZE/ MULTX,MULTY
            COMMON /OLD/ IOX,IOY
            COMMON /HEAD/ MW(12),ISTATE,PAGE
            COMMON /MODES/ JBTYPE,ICHAR,IBDIR,IBTYPE,ISMART,MODE,ISKILL,ISP
            COMMON /PARAMS/ JBDIR,NOCHG,LASTN,MCHAR,JCHAR,NLARGE,LEVEL
            COMMON /CUR/ ICUR
            COMMON /ISTATE/ ISTAT
            COMMON /PROB/ IPROB,JPROB
            COMMON /BLANK/BLNK90
            COMMON /CD/ MAXX,MAXY
            COMMON /RANGE/ LOX,HIX,LOY,HIY
            COMMON /WARN/ ERR
            IOX=IX
C           SAVE OLD COORDINATES FOR VALENCE CALL PRIOR TO DOTDIS
            IOY=IY
1           CONTINUE
            CALL GETCR(KAR,IX,IY)
            IF (((KAR.EQ.74).AND.(ISTATE.NE.8)).OR.(KAR.GE.128)) THEN
               IF (KAR.EQ.131) THEN
                  IF (((LEVEL.EQ.1).AND.(ISTATE.GE.3).AND.(ISTATE.LE.7))
         *           .OR.(ISTATE.EQ.11).OR.(ISTATE.EQ.12)) THEN
                     GO TO 2
                  ELSE
                     KAR = 13
                     GO TO 2
                  ENDIF
               ENDIF
               CALL ERRMSG(KAR)
               GO TO 1
            ENDIF
2           CONTINUE
            IF (PAGE.EQ.0) THEN
               IF (IY.LE.2) THEN
                  ICUR = 0
                  CALL CURSOR(IX,IY)
                  ICUR = 1
               ENDIF
               CALL FTSIZE(2,18)
               CALL FTLOCA(4,1)
               CALL FTEXT(BLNK90)
               PAGE = 2
               CALL FTSIZE(1,10)
```

```
            IF (LOY.LE.2) THEN
               DO 10 I = LOX,HIX+6,6
                  KX = MINO(I,MAXX)
                  CALL REPLCE(KX,1,1,1,0,0,2)
10             CONTINUE
               CALL RELONG
               CALL CURSOR(IX,IY)
            ENDIF
         ELSE IF (PAGE.LE.1) THEN
            CALL SETCOL(0)
            CALL CLR
            CALL SETCOL(1)
            IF (ERR.NE.100) THEN
               PAGE = 2
               CALL SETSCR(2)
               CALL DISPLA(2)
               CALL FTSIZE(1,10)
            ENDIF
         ENDIF
         RETURN
         END
$STORAGE:2
         SUBROUTINE CONTEX(KAR,IX,IY,INCX,INCY,IERR)
         IMPLICIT INTEGER*2 (A-Z)
         INTEGER*4 MM,IDTPIX
         LOGICAL*2 BAR,CNTX
         COMMON /CD/ MAXX,MAXY
         COMMON /CHARS/IES, IDOT,ITAG,JUMP,LBOND,KAN,ISPACE
         COMMON /PARAMS/ JBDIR,NOCHG,LASTN,MCHAR,JCHAR,NLARGE,LEVEL
         COMMON /MODES/ JBTYPE,ICHAR,IBDIR,IBTYPE,ISMART,MODE,ISKILL,ISP
         COMMON /STRPIX/ LPIX,MM(90,38),LBLEN,LNGBND(100,5)
         COMMON /SIZZE/ MULTX,MULTY
         COMMON /LABELS/ NR,NJLAST,NJNEXT
         COMMON /STRED/ IDTPIX(90,38),LABL(260,2),MRKCHN(260)
         COMMON /PROB/ IPROB,JPROB
         COMMON /WARN/ ERR
CXT      CHER indicates to which HALO page error messages are to be written.
         COMMON /QTVLNC/ OERR,CHER
         COMMON /CUR/ ICUR
         COMMON /HEAD/ MW(12),ISTATE,PAGE
CXT      BAR, in conjunction with NOCHG controls bond typ settings in
CXT      in relation to bond type defaults.
         COMMON /BTPDIR/ BAR
CXT      CNTX acts to inform SUBROUTINE MARKER that is being called by
CXT      SUBROUTINE CONTEX and to set parameters accordingly.
         COMMON /CNTX/ CNTX
C
C           This routine determines the corrected location for the next
C position.  Subroutine DRAW has already TENTATIVELY selected an IX,IY
C to the right of a character or Luhn dot, or one grid space beyond the
C end of a bond (in the bond's direction).  For this 'a priori' context
C analysis are the current and previous character (KAR,MCHAR), current
C and previous character type(ICHAR,JCHAR).
C
         ICUR = 1
C Insert dot if first input is a bond:
         IF (ICHAR.EQ.1) THEN
CXT         Edge of screen problems are precluded.
            IF (IX.GE.MAXX) THEN
               IX = MAXX
               X1 = 0
               NX1 = 1
            ELSE IF (IX.LE.1) THEN
               IX = 1
               NX1 = 0
               X1 = 1
            ELSE
               X1 = 1
               NX1 = 1
            ENDIF
```

```
              IF (IY.GE.MAXY) THEN
                  IY = MAXY
                  Y1 = 0
                  NY1 = 1
              ELSE IF (IY.LE.1) THEN
                  IY = 1
                  NY1 = 0
                  Y1 = 1
              ELSE
                  Y1 = 1
                  NY1 = 1
              ENDIF
              IF ((MM(IX-NX1,IY)+MM(IX,IY)+
     2            MM(IX+X1,IY)+MM(IX-NX1,IY-NY1)+MM(IX,IY-NY1)+
     3            MM(IX+NX1,IY-NY1)+MM(IX-NX1,IY+Y1)+MM(IX,IY+Y1)+
     4            MM(IX+X1,IY+Y1).EQ.0)) THEN
                  CNTX = .TRUE.
                  CALL MARK(KAR,IX,IY,IERR)
                  CNTX = .FALSE.
              ENDIF
          ENDIF
C
C Replace Luhn dot with uppercase if typed immed after it
          IF ((KAR.EQ.46).OR.(ICHAR.EQ.1)) GOTO 1
          IX = IX - 1
          IF ((MM(IX,IY).NE.46).OR.(IX.EQ.0)) THEN
              IX = IX + 1
              GO TO 1
          ENDIF
          MM(IX,IY) = 0
          CALL REPLCE(IX,IY,0,0,0,0,1)
C
C The following code, through label 41, determines, if the Luhn dot is
C being replaced by an uppercase, whether you are in fact replacing a
C lower case marker with an uppercase element symbol. If so, the marker
C is removed from the list of markers in LABL and replaced in LABL
C with negative numbers, indicating availability for reuse.
C
          DO 40 I=1,260
C End of markers in use
              IF (LABL(I,1)+LABL(I,2).EQ.0) GOTO 41
C No match
              IF ((LABL(I,1).NE.IX) .OR. (LABL(I,2).NE.IY)) GOTO 40
C Neg value indicates discarded marker available for reuse (see MARK).
              LABL(I,1)=-999
              LABL(I,2)=-999
C Jump out of loop
              GOTO 41
40        CONTINUE
41        CONTINUE
C Reset cursor to exact corner, else char is offset to insert new character
          ICUR = 1
          CALL CURSOR(IX,IY)
          RETURN
C
C
.C
.C Character after character: tentative position OK:
1         IF((JCHAR.LT.11) .AND. (ICHAR.LT.11).AND. (JCHAR.GT.1) .AND.
     2      (ICHAR.GT.1))   RETURN
C Character after a bond--tentative position is OK:
          IF ((ICHAR.EQ.1) .OR. (JCHAR.NE.1)) GOTO 2
          RETURN
C
C Bond after character--move left to nearest uppercase(or .or?) &
C proceed one unit in bond direction.
2         IF ((JCHAR.LE.1) .OR. (ICHAR.NE.1)) GOTO 4
          DO 3 I=0,5
C Look left
              MX=IX-I
              IF (MX.LE.0) GO TO 3
              LL = LMM(MX,IY)
C (Non-uppercase or . or ?)
              IF ((LL.NE.46).AND.(LL.NE.63).AND.((LL.LT.65).OR.(LL.GT.90)))
     2            GOTO 3
C Skip over H which is not He, Hg, etc.
```

```
          IF((LL.EQ.72).AND.((MM(MX+1,IY).LE.97).OR.(MM(MX+1,IY).GE.122
     2   ))) GOTO 3
          IX = IX-I
          LL=0
          GOTO 7
   3      CONTINUE
C Position bond correctly wrt character
   7      IX=IX + INCX
          IY=IY + INCY
          RETURN
C
C
C 2 similar bonds in a row:
   4      IF ((ICHAR.NE.1) .OR. (JCHAR.NE.1)) GOTO 5
C Same bond direction--tentative location is OK
          IF (IBDIR.NE.JBDIR) GO TO 9
C Bonds in same dir, diff type get dot
          IF (IBTYPE.NE.JBTYPE) GO TO 6
C Keep bond type unchanged
          NOCHG=1
          ICUR = 0
          RETURN
C Opposite direction
   9      CONTINUE
          IF (IABS(IBDIR-JBDIR).NE.4) THEN
             IF ((ISTATE.EQ.3).OR.(ISTATE.EQ.5).OR.(ISTATE.EQ.12)) THEN
                IF (.NOT.BAR) NOCHG = 0
                BAR = .FALSE.
             ENDIF
             GO TO 6
          ENDIF
C Return to end of bond
  10      IX=IX+INCX
          IY=IY+INCY
C         Follow back bond to node
          IF ((LMM(IX,IY).GT.256).OR.((IBTYPE.EQ.0).AND.(MM(IX,IY).EQ.0))
     1   .OR. ((MM(IX,IY).GE.50).AND.
     2   (MM(IX,IY).LE.57)) .OR. ((MM(IX,IY).GE.97).AND.
     3   (MM(IX,IY).LE.122)).OR.((MM(IX,IY).EQ.72).AND.((MM(IX+1,IY)
     4   .LT.97).OR.(MM(IX+1,IY).GT.122)))) GOTO 10
          IX=IX+1
          ICUR = 1
          CALL CURSOR (IX,IY)
C Flag to line 4900 of draw
          MCHAR=-999
          KAR=MCHAR
          JCHAR=ICHAR
          ICHAR=2
C Keep bond type unchanged
          NOCHG=1
          RETURN
C Automatically drawn dot, then. . .
   6      CNTX = .TRUE.
          CALL MARK(KAR,IX,IY,IERR)
          CNTX = .FALSE.
C         Keep NOCHG what it was: zero unless set to one in number state
C         to introduce new bond type.
C . . .continue as above--bond after character.
          IF (IERR.NE.48) GOTO 2
          RETURN
C Initial letter
   5      IF (MCHAR.EQ.0) RETURN
          IERR=13
C Contex error
          CHER = 2
          CALL MYERR(IERR,MCHAR,MCHAR)
          CHER = 0
          JPROB = 1
          RETURN
          END
C
          SUBROUTINE MARK(KAR,IX,IY,IERR)
          IMPLICIT INTEGER*2 (A-Z)
          INTEGER*4 MM,IDTPIX
```

```
      LOGICAL*2 NOMSG,CNTX
      CHARACTER*1 HALO(3)
      CHARACTER*1 KAN
      COMMON /CD/ MAXX,MAXY
      COMMON /RANGE/ LOX,HIX,LOY,HIY
      COMMON /STRPIX/ LPIX,MM(90,38),LBLEN,LNGBND(100,5)
      COMMON /CHARS/IES, IDOT,ITAG,JUMP,LBOND,KAN,ISPACE
      COMMON /PARAMS/ JBDIR,NOCHG,LASTN,MCHAR,JCHAR,NLARGE,LEVEL
      COMMON /MODES/ JBTYPE,ICHAR,IBDIR,IBTYPE,ISMART,MODE,ISKILL,ISP
      COMMON /LABELS/ NR,NJLAST,NJNEXT
      COMMON /STRED/ IDTPIX(90,38),LABL(260,2),MRKCHN(260)
C     What is displayed; State of line 2
      COMMON /HEAD/ MW(12),ISTATE,PAGE
      COMMON /CUR/ ICUR
      COMMON /OLD/ IOX,IOY
      COMMON /LEAPER/ NOMSG
      COMMON /CNTX/ CNTX
C
C This routine puts the next available marker on the screen.  It
C stores the last line number used as NJNEXT.  NJNEXT is incremented to
C the next line, where LABL(NJNEXT,*)=0.  Previously used but deleted
C labels (where LABL(J,*)=-999are not reused to avoid confusion on
C where a jump will take p.) The program puts
C IX & IY into LABL on the new line, prints the appropriate label on the
C screen, inserts IDOT=46 (Luhn dot) into MM(IX,IY), moves the cursor to
C IX+1,IY, and sets KAR to IDOT=46 and ICHAR to 2, as if a Luhn dot
C were typed in directly.
C
      ICUR = 1
      IF ((IX.LT.1).OR.(IX.GT.MAXX).OR.(IY.LT.1).OR.(IY.GT.MAXY))
     *    THEN
         IX = IOX
         IY = IOY
         ICUR = 1
         CALL CURSOR(IX,IY)
         CALL MYERR(36,KAR,KAR)
         RETURN
      ENDIF
      HALO(1) = KAN
      HALO(3) = KAN
C
C Line # for next marker--Don't reuse old ones because
C too much confusion in where you're jumping.
      IF (MM(IX,IY).EQ.0) GO TO 10
      IERR = 48
      GO TO 11
C Check adjacent nodal values.
10        DO 1122 I = -1,1
         MX = IX + I
         IF ((MX.LE.0).OR.(MX.GT.MAXX)) GO TO 1122
         DO 12 J = -1,1
            MY = IY + J
            IF ((MY.LE.0).OR.(MY.GT.MAXY)) GO TO 12
            L = LMM(MX,MY)
            IF ((L.EQ.0).OR.(L.GE.256)) GO TO 12
            IF ((MM(MX,MY).GT.2**13).OR.
     *         ((L.GE.50).AND.(L.LE.57).AND.((MM(MX-1,MY).GT.
     *         2**13).OR.((IABS(I+J).NE.1)
     *         .AND.(MM(MX-1,MY).EQ.72))).AND.(MX-1.GT.0))
     *         .OR. (L .EQ. 34))GO TO 12
            IF (NOMSG) GO TO 13
            IERR = 48
            IF (CNTX) GO TO 13
            GO TO 11
12       CONTINUE
1122     CONTINUE
C
      NJNEXT=NJNEXT+1
      IF (NJNEXT.LE.260) GO TO 99
      IERR=16
C Issue message - decrement counter and return
      NJNEXT=NJNEXT-1
```

```
C We've used up all labels
11      CALL MYERR(IERR,KAR,KAR)
13      RETURN
C
99      LINE=NJNEXT
C Letter to be typed
        NR = NJNEXT
        LET=MOD(LINE,26)
C Label 'z'
        IF (LET.EQ.0) LET=26
C ASCII equivalent
        LET=LET+96
C
C Insert coordinates into table of labels.
        LABL(LINE,1)=IX
        LABL(LINE,2)=IY
C Luhn dot into data table
        MM(IX,IY)=IDOT
        HALO(2) = CHAR(LET)
        IF (IX.LT.LOX) THEN
            LOX = IX
        ELSE IF (IX.GT.HIX) THEN
            HIX = IX
        ENDIF
        IF (IY.LT.LOY) THEN
            LOY = IY
        ELSE IF (IY.GT.HIY) THEN
            HIY = IY
        ENDIF
        CALL CURSOR(IX,IY)
        CALL TEXT(HALO)
C Cursor to next location
        IX=IX+1
C As if dot or uppercase were just typed in JCHAR=2
        IF (.NOT.CNTX) THEN
            ICHAR=2
            IF ((ISTATE.NE.9).AND.(IBTYPE.NE.0).AND.(IBTYPE.NE.4).AND.
2               (IBTYPE.NE.8)) IBTYPE=1
        ENDIF
        CALL HEADER
        KAR=IDOT
        MCHAR=IDOT
        ICUR = 1
        CALL CURSOR(IX,IY)
        RETURN
        END
C
        SUBROUTINE DOT(IX,IY,IERR)
        IMPLICIT INTEGER*2 (A-Z)
        INTEGER*4 MM
        COMMON /STRPIX/ LPIX,MM(90,38),LBLEN,LNGBND(100,5)
        COMMON /PARAMS/ JBDIR,NOCHG,LASTN,MCHAR,JCHAR,NLARGE,LEVEL
        COMMON /MODES/ JBTYPE,ICHAR,IBDIR,IBTYPE,ISMART,MODE,ISKILL,ISP
        COMMON /CHARS/IES, IDOT,ITAG,JUMP,LBOND,KAN,ISPACE
        COMMON /SIZZE/ MULTX,MULTY
        COMMON /CD/ MAXX,MAXY
        COMMON /RANGE/ LOX,HIX,LOY,HIY
C
C This subroutine generates 'automatic' Luhn dots & updates position
C and parameters as if generated by keyboard entry.
        IF (IX.GT.MAXX) THEN
            IX = MAXX
        ELSE IF (IX.LT.1) THEN
            IX = 1
        ENDIF
        IF (IY.GT.MAXY) THEN
            IY = MAXY
        ELSE IF (IY.LT.1) THEN
            IY = 1
        ENDIF
        IERR = 0
```

```
              IF (MM(IX,IY).NE.0) GO TO 1144
C Check adjacent nodal values.
        DO 12 I = -1,1
           MX = IX + I
           IF ((MX.LE.0).OR.(MX.GT.MAXX)) GO TO 12
           DO 1122 J = -1,1
              MY = IY + J
              IF ((MY.LE.0).OR.(MY.GT.MAXY)) GO TO 1122
              L = LMM(MX,MY)
              IF ((L.EQ.0).OR.(L.GE.256)) GO TO 1122
              IF ((MM(MX,MY).GT.2**13).OR.
     *           ((L.GE.50).AND.(L.LE.57).AND.((MM(MX-1,MY).GT.2**13)
     *           .OR.((IABS(I+J).NE.1)
     *           .AND.(MM(MX-1,MY).EQ.72))).AND.(MX-1.GT.0)) .OR.
     *           (L.EQ.34)) GO TO 1122
              GO TO 1144
1122       CONTINUE
12      CONTINUE
C Draw a Luhn dot.
        JX = IX * MULTX - 6
        JY = IY * MULTY - 4
        J3X = JX + 3
        J3Y = JY - 3
        CALL BAR(JX,JY,J3X,J3Y)
        MM(IX,IY)=IDOT
C Expand picture boundaries.
        IF (IX.LT.LOX) THEN
           LOX = IX
        ELSE IF (IX.GT.HIX) THEN
           HIX = IX
        ENDIF
        IF (IY.LT.LOY) THEN
           LOY = IY
        ELSE IF (IY.GT.HIY) THEN
           HIY = IY
        ENDIF
        MCHAR=IDOT
        JCHAR=2
        IX=IX+1
        RETURN
1144    CONTINUE
        IERR = 48
        RETURN
        END
C
        SUBROUTINE LEAP (KAR,IX,IY)
        IMPLICIT INTEGER*2 (A-Z)
        INTEGER*4 MM,IDTPIX
        LOGICAL*2 NOMSG
        COMMON /STRPIX/ LPIX,MM(90,38),LBLEN,LNGBND(100,5)
        COMMON /CHARS/IES, IDOT,ITAG,JUMP,LBOND,KAN,ISPACE
        COMMON /PARAMS/ JBDIR,NOCHG,LASTN,MCHAR,JCHAR,NLARGE,LEVEL
        COMMON /MODES/ JBTYPE,ICHAR,IBDIR,IBTYPE,ISMART,MODE,ISKILL,ISP
        COMMON /LABELS/ NR,NJLAST,NJNEXT
        COMMON /MKSKP/ ISKIP
        COMMON /STRED/ IDTPIX(90,38),LABL(260,2),MRKCHN(260)
        COMMON /CUR/ ICUR
        COMMON /HEAD/ MW(12),ISTATE,PAGE
        COMMON /LEAPER/ NOMSG
C
C This routine moves the cursor to the location of a given lower case
C label. A counter NR is placed at the line of the last label jumped
C to, and is used as a starting point for the next jump. When all al-
C phabets have been used, NR returns to the top. When a previously-
C deleted label is addressed (LABL < 0), the next alphabet down is
C addressed.
C
C This subroutine is called by the operator by typing a lower case
C letter without the '$' precedance code.
```

```
C
        ICUR = 1
C Flag for how many times you have gone to top this jump
10      ITEST=0
C Sequence number within the lowercase alphabet
        NJ=KAR-96
C Same label twice: next alphabet.
        IF (NJ.EQ.NJLAST) GOTO 1
C The alphabet # where currently located.
30      NALPH=(NR+25)/26
C Tentative line in LABL of desired coords.
        NQ=NJ+(NALPH-1)*26
C End of array--go to top.
        IF (NQ.GT.260) GOTO 2
C Tentative X coord of label
        JX=LABL(NQ,1)
        JY=LABL(NQ,2)
        IF (JX+JY) 1,2,3
C Discarded marker: try next alphabet
1       NR=NR+26
        GOTO 30
C Beyond end of useful data: try top
2       NR=1
C Started at top again in this CALL MARK.
        ITEST=ITEST+1
C No such label
        IF (ITEST.GT.1) THEN
            CALL ERRMSG(KAR)
C No such label
            RETURN
        ENDIF
        GOTO 30
C Relocate cursor as if dot were typed here.
3       IF ((ISKIP.NE.1).AND.(JCHAR.EQ.1)) THEN
            NOMSG = .TRUE.
            CALL MARK(ZAR,IX,IY,IERR)
            NOMSG = .FALSE.
        ENDIF
        IX=JX+1
        IY=JY
        CALL CURSOR (IX,IY)
        KAR=IDOT
        JCHAR=2
        ICHAR=2
        MCHAR=IDOT
        NJLAST=NJ
        RETURN
        END
C
        SUBROUTINE CHARGE(KAR,IX,IY,NCHRG)
        IMPLICIT INTEGER*2 (A-Z)
        INTEGER*4 MM,M
        LOGICAL*2 NONLOC
        CHARACTER*1 HALO(3)
        CHARACTER*1 KAN
        COMMON /MODES/ JBTYPE,ICHAR,IBDIR,IBTYPE,ISMART,MODE,ISKILL,ISP
        COMMON /PARAMS/ JBDIR,NOCHG,LASTN,MCHAR,JCHAR,NLARGE,LEVEL
        COMMON /CD/ MAXX,MAXY
        COMMON /RANGE/ LOX,HIX,LOY,HIY
        COMMON /CHARS/IES, IDOT,ITAG,JUMP,LBOND,KAN,ISPACE
        COMMON /STRPIX/ LPIX,MM(90,38),LBLEN,LNGBND(100,5)
        COMMON /HEAD/ MW(12),ISTATE,PAGE
        COMMON /HP/IHP
        COMMON /IPLUS/ IHIGH(14,2)
        COMMON /CUR/ ICUR
        DATA NONLOC /.FALSE./
C
C This subroutine, called when an initial + or - sign is entered, searches
C for a diagonal location for the charge, and types it in. When subsequent
C + or - signs are entered, respectively, the previous charge value is
C increments by 1.
        IF ((JCHAR.EQ.6).AND.(NCHRG.GT.1)) THEN
            IF (NONLOC) THEN
                GO TO 5402
```

```
              ELSE
                  GO TO 4501
              ENDIF
          ENDIF
          HALO(1) = KAN
          HALO(3) = KAN
          ICUR = 0
          IC=0
C Search back for the node, if any:
          JJJ=0
          DO 428 I=0,-3,-1
          IF (IX+I.LE.0) GO TO 428
          IF (((MM(IX+I,IY).GE.65).AND.(MM(IX+I,IY).LE.90).AND.(MM(IX+I,
     2        IY).NE.72)) .OR. ((MM(IX+I,IY).EQ.72).AND.(MM(IX+I+1,IY).GE.
     3        97).AND.(MM(IX+I+1,IY).LE.122)).OR.(MM(IX+I,IY).EQ.46)) THEN
              JJJ=IX+I
              GO TO 117
          ENDIF
428       CONTINUE
C Delocalized charge
117       IF (JJJ.LE.0) GOTO 430
C
C Look for space for charge up & to the right:
          IF ((JJJ+2.GT.MAXX).OR.(IY+2*IHP.LE.0).OR.(IY+2*IHP.GT.MAXY))
     *        GO TO 431
          IF (MM(JJJ+1,IY+IHP)+MM(JJJ+2,IY+IHP)+MM(JJJ+2,IY+2*IHP)+
     *        MM(JJJ+1,IY+2*IHP).NE.0) GOTO 431
          IF (JJJ+3.LE.MAXX) THEN
              IF (MM(JJJ+3,IY+IHP).NE.0) GO TO 431
          ENDIF
          JX=JJJ+1
          JY = IY + 1 *IHP
          IC=4
          GOTO 450
C
C Look down & right:
431       IF ((JJJ+2.GT.MAXX).OR.(IY-2*IHP.GT.MAXY)
     *        .OR. (IY-2*IHP.LE.0)) GO TO 118
          IF (MM(JJJ+1,IY-IHP)+MM(JJJ+2,IY-IHP)+MM(JJJ+2,IY-2*IHP)+
     *        MM(JJJ+1,IY-2*IHP).NE.0) GOTO 118
          IF (JJJ+3.LE.MAXX) THEN
              IF (MM(JJJ+3,IY-IHP).NE.0) GO TO 118
          ENDIF
          JX=JJJ+1
          JY = IY -1*IHP
          IC=13
          GOTO 450
C
C Look up & left:
118       IF ((JJJ-2.LE.0).OR.(IY+2*IHP.LE.0)
     *        .OR. (IY+2*IHP.GT.MAXY)) GO TO 433
          IF (MM(JJJ-2,IY+IHP)+MM(JJJ-1,IY+IHP)+MM(JJJ-2,IY+2*IHP)+
     *        MM(JJJ-1,IY+2*IHP).NE.0) GOTO 433
          IF (JJJ-3.GT.0) THEN
              IF (MM(JJJ-3,IY+IHP)+MM(JJJ-3,IY+2*IHP).NE.0) GO TO 433
          ENDIF
          JX = JJJ - 1
          JY = IY + 1*IHP
          IC=2
          GOTO 450
C
C Look down and left:
433       IF ((JJJ-2.LE.0).OR.(IY-2*IHP.GT.MAXY)
     *        .OR. (IY-2*IHP.LE.0)) GO TO 434
          IF (MM(JJJ-2,IY-IHP)+MM(JJJ-1,IY-IHP)+MM(JJJ-1,IY-2*IHP)
     *        +MM(JJJ-2,IY-2*IHP).NE.0) GOTO 434
          IF (JJJ-3.GT.0) THEN
              IF (MM(JJJ-3,IY-IHP)+MM(JJJ-3,IY-2*IHP).NE.0) GO TO 434
          ENDIF
          JX = JJJ - 1
          JY = IY - 1*IHP
CXT       IC=10
CXT       IF (NCHRG.LE.1) THEN
```

```
CXT      JX=JX+1
         IC=11
CXT      ENDIF
         GOTO 450
C
434      CONTINUE
C No room exists for the charge on the diagonals.
         PAGE = 0
         CALL FTSIZE(2,18)
         CALL FTLOCA(4,1)
         CALL FTEXT('^NO ROOM FOR CHARGES. TRY DUMB MODE. ^')
         NCHRG=0
         KAR = 13
         ICHAR = JCHAR
         CALL FTSIZE(1,10)
         ICUR = 1
         CALL CURSOR(IX,IY)
         RETURN
C
C Draw charges in:
450      CONTINUE
CXT The existance of a previous charge on the node is checked.
         ICNT = 0
         DO 400 I = -2,2
           IF ((JJJ+I.GT.MAXX).OR.(JJJ+I.LE.0)) GO TO 400
           DO 300 J = -1,1
             IF ((IY+J.GT.MAXY).OR.(IY+J.LE.0)) GO TO 300
             IF ((LMM(JJJ+I,IY+J).NE.43).AND.(LMM(JJJ+I,IY+J).NE.45))
     *         GO TO 300
             ILC = IHMM(JJJ+I,IY+J)
             IF (ILC.EQ.0) GO TO 300
             IF ((I.NE.IHIGH(ILC,1)).OR.(J.NE.(-IHP)*IHIGH(ILC,2)))
     *         GO TO 300
             ICNT = ICNT + 1
300        CONTINUE
400      CONTINUE
         IF (ICNT.EQ.0) GO TO 4500
         IERR = 38
         CALL MYERR(IERR,IERR,IERR)
         ICHAR = JCHAR
         KAR = 13
         NCHRG = 0
         RETURN
4500     CONTINUE
CXT The charges sign is drawn with the first entry of a + or -.
         NONLOC = .FALSE.
         HALO(2) = CHAR(KAR)
         CALL CURSOR (JX,JY)
         CALL TEXT(HALO)
         SHFKAR = KAR
         IF (JX.LT.LOX) LOX = JX
         IF (JX+1.GT.HIX) HIX = JX + 1
         IF (JY.LT.LOY) THEN
           LOY = JY
         ELSE IF (JY.GT.HIY) THEN
           HIY = JY
         ENDIF
4501     CONTINUE
         IF (NCHRG.EQ.2) THEN
           IF ((IC.EQ.2).OR.(IC.EQ.11)) THEN
             IF (IC.EQ.2) THEN
               IC = 1
             ELSE IF (IC.EQ.11) THEN
               IC = 10
             ENDIF
             CALL FTLOCA(JY,JX)
             CALL FTEXT('^ ^')
             MM(JX,JY) = 0
             HALO(2) = CHAR(SHFKAR)
             JX = JX - 1
             CALL CURSOR(JX,JY)
             CALL TEXT(HALO)
```

```
              ENDIF
              FX = JX + 1
          ELSE IF (NCHRG.GT.2) THEN
              CALL FTLOCA(JY,FX)
              CALL FTEXT('^ ^')
          ENDIF
C Store location of charge in high order part of MM.
          MM(JX,JY)=KAR +IC * 2**13
          IF (NCHRG.LE.1) GOTO 60
          CALL CURSOR(JX+1,JY)
          KHAR=NCHRG+48
C Type integer digit
          HALO(2) = CHAR(KHAR)
          CALL TEXT(HALO)
          MM(JX+1,JY)=KHAR
60        IX=JJJ+1
CXT       NCHRG=1
          ICUR = 1
          CALL CURSOR(IX,IY)
CXT       IF (MM(IX-1,IY) .EQ. 46) KAR=46
          RETURN
C
C Delocalized charge--find clear area:
430       JJJ=IX
          NONLOC = .TRUE.
493       M=0
          DO 223 I=JJJ-1,JJJ+2
          DO 223 J=IY-1,IY+1
          M = M + MM(I,J)
223       CONTINUE
          IF (M.LE.0) GOTO 4320
          IF (JJJ+2.GT.MAXX) GO TO 434
          JJJ=JJJ+1
          GO TO 493
CXT When the clear area is found, the existance of any other non-local
CXT is checked - only 1 non-local charge per structure.
4320      DO 4345 I = LOX,HIX
          DO 4345 J = LOY,HIY
              IF ((MM(I,J).NE.45).AND.(MM(I,J).NE.43)) GO TO 4345
              IF (MM(I-1,J).NE.42) GO TO 4300
4345      CONTINUE
          GO TO 432
4300      CONTINUE
          IERR = 4
          CALL MYERR(IERR,IERR,IERR)
          ICHAR = JCHAR
          KAR = 13
          NCHRG = 0
          RETURN
432       CONTINUE
C The charge sign is entered.
          HALO(2) = CHAR(KAR)
          CALL CURSOR(JJJ,IY)
          CALL TEXT(HALO)
CXT Picture boundaries are expanded.
          IF (JJJ.LT.LOX) LOX = JJJ
          IF (JJJ+1.GT.HIX) HIX = JJJ + 1
          IF (IY.LT.LOY) THEN
              LOY = IY
          ELSE IF (IY.GT.HIY) THEN
              HIY = IY
          ENDIF
CXT The successive charge increment is entered and drawn.
5402      MM(JJJ,IY)=KAR
          IF (NCHRG.LE.1) GOTO 60
          KHAR=NCHRG+48
          IF (NCHRG.EQ.2) THEN
              FX = JJJ + 1
          ELSE
              CALL FTLOCA(IY,FX)
              CALL FTEXT('^ ^')
          ENDIF
          CALL CURSOR (FX,IY)
```

```
          HALO(2) = CHAR(KHAR)
          CALL TEXT(HALO)
          MM(JJJ+1,IY)=KHAR
          GOTO 60
          END
C
C      SUBROUTINE IND1 is called to enter undetermined bond site
C      markers in smart mode.  The marker is drawn in the first
C      available corner cell.  The default corners are first upper
C      left, then lower left, then upper right, and lower right last.
       SUBROUTINE IND1(KAR,IX,IY,IDRAW,IERR)
       IMPLICIT INTEGER*2 (A-Z)
       INTEGER*4 MM
       CHARACTER*1 HALO(3)
       CHARACTER*1 KAN
       COMMON /CD/ MAXX,MAXY
       COMMON /RANGE/ LOX,HIX,LOY,HIY
       COMMON /CHARS/IES, IDOT,ITAG,JUMP,LBOND,KAN,ISPACE
       COMMON /STRPIX/ LPIX,MM(90,38),LBLEN,LNGBND(100,5)
       COMMON /HEAD/ MW(12),ISTATE,PAGE
       COMMON /CUR/ ICUR
       COMMON /HP/IHP
       COMMON /D1/ IDNUM,IDS(9,6),NBD1,DSCNC(6,50)
C
       HALO(1) = KAN
       HALO(3) = KAN
       ICUR = 0
C Search back for the node, if any:
       JJJ=0
       DO 428 I=0,-3,-1
       IF (IX+I.LE.0) GO TO 428
       IF(((MM(IX+I,IY).GE.65).AND.(MM(IX+I,IY).LE.90).AND.(MM(IX+I,
     2   IY).NE.72)) .OR. ((MM(IX+I,IY).EQ.72).AND.(MM(IX+I+1,IY).GE.
     3   97).AND.(MM(IX+I+1,IY).LE.122)).OR.(MM(IX+I,IY).EQ.46)) THEN
       JJJ=IX+I
       GO TO 117
       ENDIF
428    CONTINUE
C If no node found, jump to error message.
117    IF (JJJ.LE.0) GOTO 434
C      Check for duplicate "s.
       IF (NBD1.EQ.0) GO TO 4511
       DO 527 I = 1,NBD1
       IF ((JJJ.EQ.DSCNC(3,I)).AND.(IY.EQ.DSCNC(4,I))) GO TO 892
527    CONTINUE
       GO TO 4511
892    IERR = 47
       IF (IDRAW.EQ.1) RETURN
       CALL MYERR(IERR,IERR,IERR)
       RETURN
4511   CONTINUE
C
C Look for space for " up & to the right:
       IF ((JJJ+1.GT.MAXX).OR.(IY+IHP.LE.0).OR.(IY+IHP.GT.MAXY))
     *   GO TO 431
       IF (MM(JJJ+1,IY+IHP).NE.0) GOTO 431
       JX=JJJ+1
       JY = IY +IHP
       NBD1 = NBD1 + 1
       DSCNC(2,NBD1) = 2
       DSCNC(3,NBD1) = JJJ
       DSCNC(4,NBD1) = IY
       DSCNC(5,NBD1) = JX
       DSCNC(6,NBD1) = JY
       GOTO 450
C
C Look down & right:
431    IF ((JJJ+1.GT.MAXX).OR.(IY-IHP.GT.MAXY).OR. (IY-IHP.LE.0))
     *   GO TO 118
       IF (MM(JJJ+1,IY-IHP).NE.0) GO TO 118
       JX=JJJ+1
       JY = IY -IHP
       NBD1 = NBD1 + 1
```

```
            DSCNC(2,NBD1) = 4
            DSCNC(3,NBD1) = JJJ
            DSCNC(4,NBD1) = IY
            DSCNC(5,NBD1) = JX
            DSCNC(6,NBD1) = JY
            GOTO 450
C
C Look up & left:
118         IF ((JJJ-1.LE.0).OR.(IY+IHP.LE.0).OR. (IY+IHP .GT. MAXY))
     *      GO TO 433
            IF (MM(JJJ-1,IY+IHP).NE.0) GOTO 433
            JX=JJJ-1
            JY = IY + IHP
            NBD1 = NBD1 + 1
            DSCNC(2,NBD1) = 8
            DSCNC(3,NBD1) = JJJ
            DSCNC(4,NBD1) = IY
            DSCNC(5,NBD1) =.JX
            DSCNC(6,NBD1) = JY
            GOTO 450
C
C Look down and left:
433         IF ((JJJ-1.LE.0).OR.(IY-IHP.GT.MAXY).OR. (IY-IHP .LE.0))
     *      GO TO 119
            IF (MM(JJJ-1,IY-IHP).NE.0) GOTO 119
            JX=JJJ-1
            JY = IY -IHP
            NBD1 = NBD1 + 1
            DSCNC(2,NBD1) = 6
            DSCNC(3,NBD1) = JJJ
            DSCNC(4,NBD1) = IY
            DSCNC(5,NBD1) = JX
            DSCNC(6,NBD1) = JY
            GOTO 450
C
C No node was found.
119         CONTINUE
            IERR = 57
            IF (IDRAW.EQ.1) RETURN
            PAGE = 0
            CALL FTSIZE(2,18)
            CALL FTLOCA(4,1)
            CALL FTEXT('^NO ROOM FOR UNDETERMINED BOND SITE MARKER. TRY D
     *UMB MODE. ^')
            CALL FTSIZE(1,10)
            ICUR = 1
            CALL CURSOR(IX,IY)
            RETURN
434         CONTINUE
            IERR = 34
            IF (IDRAW.EQ.1) RETURN
            CALL MYERR(IERR,IERR,IERR)
            RETURN
C
C Draw bond site marker in:
450         CONTINUE
            IF (JX.LT.LOX) LOX = JX
            IF (JX+1.GT.HIX) HIX = JX + 1
            IF (JY.LT.LOY) THEN
                LOY = JY
            ELSE IF (JY.GT.HIY) THEN
                HIY = JY
            ENDIF
            MM(JX,JY)=KAR
            IF (IDRAW.EQ.1) RETURN
            HALO(2) = CHAR(KAR)
            CALL CURSOR (JX,JY)
            CALL TEXT(HALO)
60          IX=JJJ+1
            ICUR = 1
            CALL CURSOR(IX,IY)
            IF (MM(IX-1,IY) .EQ. 46) KAR=46
            RETURN
            END
```

```
$STORAGE:2
C
        SUBROUTINE VALNCE(II,IX,IY,INCX,INCY)
        IMPLICIT INTEGER*2 (A-Z)
        INTEGER*4 MM,IDTPIX
        CHARACTER*1 HALO(3)
        CHARACTER*1 KAN
        COMMON /ELECHR/ IELEM(126,5)
        COMMON /CD/ MAXX,MAXY
        COMMON /RANGE/ LOX,HIX,LOY,HIY
        COMMON /STRPIX/ LPIX,MM(90,38),LBLEN,LNGBND(100,5)
C       MM(I,J) CONTAINS BOND OR ATOM TYPE, & BOND DIRECTION
C       FOR EACH OF MAXX * MAXY LOCATIONS.
        COMMON /CHARS/IES, IDOT,ITAG,JUMP,LBOND,KAN,ISPACE
        COMMON /PARAMS/ JBDIR,NOCHG,LASTN,MCHAR,JCHAR,NLARGE,LEVEL
        COMMON /MODES/ JBTYPE,ICHAR,IBDIR,IBTYPE,ISMART,MODE,ISKILL,ISP
        COMMON /PROB/ IPROB,JPROB
        COMMON /IPLUS/ IHIGH(14,2)
        COMMON /LABELS/ NR,LJLAST,NJNEXT
        COMMON /STRED/ IDTPIX(90,38),LABL(260,2),MRKCHN(260)
        COMMON /CUR/ ICUR
        COMMON /HP/IHP
CXT     If CHER = 2, error messages are output on HALO screen page 1,
CXT     otherwise they are output to page 2. If CHER = 1, SUBROUTINE
CXT     NOD is calling VALNCE.
        COMMON /QTVLNC/ OERR,CHER
CXT     MLARGE is used to mark distance to node whose valence is being
CXT     computed.
        COMMON /VLNPRV/ MLARGE
CXT     ELENOD carries the current element position code to SUBROUTINE NOD.
        COMMON /ELENOD/ IELT
        HALO(1) = KAN
        HALO(3) = KAN
        MAR=0
C Filler atoms not triggered by bond.
        IF (II.GT.2) THEN
            JX = IX
            JY = IY
            IF (CHER.EQ.1) THEN
                IF (MM(JX,JY).EQ.46) THEN
                    IELT = 126
                    GO TO 800
                ENDIF
                GO TO 87
            ENDIF
C If element is in DOTDIS compute no valence.
            DO 444 JJ = 0,MAXX
                IF ((MM(JX-JJ,JY).EQ.0).OR.(LMM(JX-JJ,JY).GE.256).OR.
     *              (JX-JJ.LE.0)) THEN
                    GO TO 445
                ELSE IF (MM(JX-JJ,JY).EQ.42) THEN
                    RETURN
                ENDIF
444         CONTINUE
445         CONTINUE
            GO TO 1000
        ELSE IF (II.EQ.1) THEN
C Look at grid space BEFORE bond.
            JX=IX-(MLARGE+1)*INCX
C (NLARGE+1) removes incrementing done in DRAW.
            JY=IY-(MLARGE+1)*INCY
CXT
        ELSE IF (II.EQ.2) THEN
C If overdrawing an existing bond, II=2.
            JX=IX-INCX
            JY=IY-INCY
        ENDIF
C If to right of element, skip back over lower case second letter:
23      IF ((MM(JX,JY).GT.96) .AND. (MM(JX,JY).LT.123)) JX=JX-1
C If bond didn't originate at a (non-dot) node (i.e. cap letter), return
        IF(MM(JX,JY).EQ.46) GO TO 63
        IF ((MM(JX,JY).LT.65) .OR. (MM(JX,JY).GT.90)) THEN
```

```
              MLARGE = NLARGE
              RETURN
           ENDIF
           IF (((MM(JX,JY).EQ.68).OR.(MM(JX,JY).EQ.77)).AND.
     *        (MM(JX+1,JY).GE.112).AND.(MM(JX+1,JY).LE.120)) THEN
              MLARGE = NLARGE
              RETURN
           ENDIF
C If element is in DOTDIS compute no valence.
           DO 1444 JJ = 0,MAXX
              IF ((MM(JX-JJ,JY).EQ.0).OR.(LMM(JX-JJ,JY).GE.256).OR.(JX-JJ
     *             .LE.0)) THEN
                 GO TO 1445
              ELSE IF (MM(JX-JJ,JY).EQ.42) THEN
                 MLARGE = NLARGE
                 RETURN
              ENDIF
1444       CONTINUE
1445       CONTINUE
           GO TO 87
C IS THIS A MARKER OR FAT DOT
63         DO 64 I=1,NJNEXT
              IF (JX.EQ.LABL(I,1).AND.JY.EQ.LABL(I,2)) THEN
                 MLARGE = NLARGE
                 RETURN
              ENDIF
64         CONTINUE
           MAR=1
C IF FAT DOT SET PARAMS FOR CARBON
           LET1=67
           LET2=0
           IELT=1
           GO TO 800
C First letter of symbol
87         LET1=LMM(JX,JY)
           LET2=0
C Second letter, if 2-letter symbol
           IF ((MM(JX+1,JY).GE.97) .AND. (MM(JX+1,JY).LE.122))
     2        LET2=MM(JX+1,JY)
C Dont check H2,ETC
CXT        IF ((LET1.EQ.72) .AND. (LET2.EQ.0)) THEN
CXT           MLARGE = NLARGE
CXT           RETURN
CXT        ENDIF
C count of OCCUPIED valence positions
           IVALNC=0
C Element number of node at JX,JY
           IELT=0
C
C search for element in element table
           DO 1 I=1,125
              IF ((LET1.NE.IELEM(I,1)) .OR. (LET2.NE.IELEM(I,2)))
     2           GOTO 1
C Records row number of correct element
              IELT=I
C No valence in table
              IF (IELEM(IELT,3).EQ.0) THEN
                 MLARGE = NLARGE
                 RETURN
              ENDIF
              GOTO 2
1          CONTINUE
C
2          IF (IELT.NE.0) GO TO 800
C ELEMENT NOT FOUND - ISSUE MESSAGE AND CONTINUE
           IERR=11
           CALL MYERR(IERR,LET1,LET2)
C BEWARE I DON'T KNOW ALL THE IMPLICATIONS OF THIS RETURN
           MLARGE = NLARGE
           RETURN
C
C Now search around node for bonds, charges, for 'valence users'.
C
C Indicates presence(=1) or absence(=0) of bond on left
800        CONTINUE
```

```
C                     where to put filler H's if there is room on both sides.
C         BEWARE - VAA MODIFIED LOOP 3 - THE MODIFICATION IS TO DETECT
C         CHARGES ON THE RIGHT DIAGONALS OF THE SECOND LETTER OF A 2
C         LETTER ELEMENT NAME
C Count of bonds 'used'.
      IVALNC=0
C search around node - LOOP CHANGED TO 2 BY VAA
      DO 3 IDIRX=-1,2
      DO 3 IDIRY=-1,1
      IF ((IDIRX.EQ.0) .AND. (IDIRY.EQ.0)) GOTO 3
      IF((IDIRX .EQ. 2) .AND. (IDIRY .EQ.0)) GO TO 3
C WE DON'T NEED TO CHECK THIS ONE
C WE WILL CATCH A CHARGE AT THIS LOCATION
C WHEN X=1 AND Y=0
C Nearby array location to look for bonds
      NEWX=JX + IDIRX
      NEWY=JY + IDIRY
C Off the edge
7     IF ((NEWX.LT.1) .OR. (NEWX.GT.MAXX)) GOTO 3
      IF ((NEWY.LT.1) .OR. (NEWY.GT.MAXY))  GOTO 3
C Blank space
      IF (MM(NEWX,NEWY).EQ.0) GOTO 3
C Bonds are >256
      IF (LMM(NEWX,NEWY).LT.256)  GOTO 4
C WE ARE ONLY LOOKING
      IF (IDIRX .EQ. 2) GO TO 3
C FOR CHARGES AT THIS PLACE - NOT BONDS
C Bond extracted for type
      JBOND=LMM(NEWX,NEWY)/2**8
C  Following 5 lines skip bonds not pointed to node being analyzed:
C Direction of bond
      JDIR=LMM(NEWX,NEWY)-JBOND*2**8
      IF ((IDIRX*IDIRY.EQ.-1).AND.(MOD(JDIR,4).NE.2)) GOTO 3
      IF ((IDIRX*IDIRY.EQ.1).AND.(MOD(JDIR,4).NE.0)) GOTO 3
      IF ((IDIRX.EQ.0) .AND. (MOD(JDIR,4).NE.1)) GOTO 3
      IF ((IDIRY.EQ.0) .AND. (MOD(JDIR,4).NE.3)) GOTO 3
C Useful for bondtypes 1-3 others revised below
      IVAL = JBOND
C Stereo bonds are single.
      IF (JBOND.GT.3) IVAL=1
      IVALNC = IVALNC + IVAL
C Used below at label 41 to determine where to put H's. Set here
C only if a valence-using bond is on this side.
      GOTO 3
C Charges
4     IF ((LMM(NEWX,NEWY).NE.43) .AND. (LMM(NEWX,NEWY).NE.45))GOTO 5
4444  LOC=IHMM(NEWX,NEWY)
      IFX=NEWX-IHIGH(LOC,1)
      IFY=NEWY+IHP*IHIGH(LOC,2)
C IS CHARGE ASSOCIATED
      IF(JX.NE.IFX .OR.JY.NE.IFY) GO TO 5
C WITH THIS NODE
C Set the sign from ASCII char
      ISIGN = 44 - LMM(NEWX,NEWY)
      IF ((MM(NEWX+1,NEWY).LT.50).OR.(MM(NEWX+1,NEWY).GT.57)) GOTO 6
C     Number of charges>1
      ISIGN = ISIGN * (LMM(NEWX+1,NEWY) - 48)
C     Correct # of valencies used for chg
6     IVALNC=IVALNC + IABS(ISIGN)
      ISIGN=0
C Used below at label 41 to deter-
CXT       IF ((IDIRX.EQ.1).AND.(IDIRY.EQ.0)) JRIGHT=1
C mine where to put H's. Set here
CXT       IF ((IDIRX.EQ.-1).AND.(IDIRY.EQ.0)) JLEFT=1
C         only if a valence-using bond is on this side.
      GOTO 3
C
C  H, lowercase, numerals, etc, keep looking
5     NEWX = NEWX + IDIRX
C H, lc, OR NUMERAL CAN'T
      IF (IDIRX .EQ. 0) GO TO 3
C CONTRIBUTE TO VALENCE IN THIS LOC
C BEWARE CHANGED BY VAA - TO FIX
C ENDLESS LOOP FOUND BY GREG
      GOTO 7
```

```fortran
C Close loop of looking around each node.
3         CONTINUE
C
C Following code (through label 200) adds to IVALNC those bonds 'used'
C by long bonds:
C Beginning & ending nodes of long bond
          DO 200 I=0,2,2
C Up to 100 long bonds stored
          DO 201 J=1,100
C Done with this column of node
          IF (LNGBND(J,I+1).EQ.0) GOTO 200
C   Check if current nodeJX,JY is listed as a node of a long bond:
          IF ((LNGBND(J,I+1).NE.JX) .OR. (LNGBND(J,I+2).NE.JY)) GOTO 201
C    Use of valence from this long bond
          IVAL = 1
          IF (LNGBND(J,5).EQ.2) IVAL=2
          IF (LNGBND(J,5).EQ.3) IVAL=3
          IVALNC = IVALNC + IVAL
201       CONTINUE
200       CONTINUE
C
C Number of H's required at this node. neg no for test
          IHYD=-7
C elect smallest valence from IELEM which would
              DO 10 M=3,5
C                                satisfy all existing bonds.
              IF(IELEM(IELT,M).LT.IVALNC) GOTO 10
              IHYD = IELEM(IELT,M) - IVALNC
              GOTO 11
10            CONTINUE
C Now draw hydrogens
11            CONTINUE
          IF (IHYD.GE.0 .AND. MAR .EQ. 0)  GO TO 1000
          IF (IHYD.GE.0 .AND. MAR.EQ.1) THEN
              MLARGE = NLARGE
              RETURN ENDIF
C TOO MANY BONDS FOR VALENCY
          IERR=12
          OERR = IERR
          CALL MYERR(IERR,IVALNC,KAR)
1000      CONTINUE
          IF (MM(JX,JY).EQ.46) THEN
              MLARGE = NLARGE
              RETURN
          ENDIF
C
C Now look left & right to determine where filler atoms can fit:
C
C Done if no filler atoms needed.
          IF (IHYD) 111,111,30
C =1 means there IS room for H('s) on left
30        ILEFT=1
C similarly
          IRIGHT=1
C
C         two-letter symbol
          IF (LET2.GT.0) THEN
              MX=JX+2
              NX = JX + 1
          ELSE
C         MX is first position to right of node.
              MX=JX+1
              NX = JX
          ENDIF
C Look right to see if there is room for H('s):
C number of chars needed for H('s):=1 or 2
          KHYD=1
          IF (IHYD.GT.1) KHYD = 2
C
C         Edge of screen problems are checked.
          IF (NX+2.GT.MAXX) THEN
              DO 31 I = 1,KHYD+1
                  DG = LMM(JX-I,JY)
```

```
                   IF (((DG.LT.256).AND.(DG.GT.0)).OR.((DG.GE.256).AND.
    *                 (MOD(IDIR(DG),4).NE.3))) GO TO 9394
31             CONTINUE
               GO TO 42
           ELSE IF (JX-2.LT.1) THEN
               DO 32 I = 1,KHYD+1
                   DG = LMM(NX+I,JY)
                   IF (((DG.LT.256).AND.(DG.GT.0)).OR.((DG.GE.256).AND.
    *                 (MOD(IDIR(DG),4).NE.3))) GO TO 9394
32             CONTINUE
               GO TO 43
           ENDIF
C
C       If CHER = 1, SUBROUTINE NOD is converting chain markers to "C"s
           IF (CHER.EQ.1) THEN
               IF (KHYD.EQ.2) THEN
                   SHF = 1
               ELSE
                   SHF = 0
               ENDIF
               DG1 = LMM(NX+KHYD+1,JY)
               DG2 = LMM(NX+KHYD-SHF,JY)

DG3 = LMM(NX+KHYD,JY)
               U1 = LMM(NX+KHYD+1,JY-1)
               U2 = LMM(NX+KHYD-SHF,JY-1)
               U3 = LMM(NX+KHYD,JY-1)
               L1 = LMM(NX+KHYD+1,JY+1)
               L2 = LMM(NX+KHYD-SHF,JY+1)
               L3 = LMM(NX+KHYD,JY+1)
               IF (((DG1.GT.0).AND.(DG1.LT.256)).OR.((DG2.GT.0).AND.
    *             (DG2.LT.256)).OR.((DG3.GT.0).AND.(DG3.LT.256))) GO TO 402
               IF (((DG1.GE.256).AND.(MOD(IDIR(DG1),4).NE.3)).OR.
    *             ((DG2.GE.256).AND.(MOD(IDIR(DG2),4).NE.3)).OR.
    *             ((DG3.GE.256).AND.(MOD(IDIR(DG3),4).NE.3))) GO TO 402
               IF ((U1.EQ.46).OR.((U1.GE.65).AND.(U1.LE.122)).OR.
    *             ((U1.GE.50).AND.(U1.LE.57).AND.(U3.NE.43).AND.
    *             (U3.NE.45))) GO TO 402
               IF ((L1.EQ.46).OR.((L1.GE.65).AND.(L1.LE.122)).OR.
    *             ((L1.GE.50).AND.(L1.LE.57).AND.(L3.NE.43).AND.
    *             (L3.NE.45))) GO TO 402
               IF ((U3.EQ.46).OR.((U3.GE.65).AND.(U3.LE.122)).OR.
    *             ((U3.GE.50).AND.(U3.LE.57).AND.(LMM(NX+KHYD-1,JY-1)
    *             .NE.43).AND.(LMM(NX+KHYD-1,JY-1).NE.45))) GO TO 402
               IF ((L3.EQ.46).OR.((L3.GE.65).AND.(L3.LE.122)).OR.
    *             ((L3.GE.50).AND.(L3.LE.57).AND.(LMM(NX+KHYD-1,JY+1)
    *             .NE.43).AND.(LMM(NX+KHYD-1,JY+1).NE.45))) GO TO 402
               IF (SHF.EQ.1) THEN
                   IF ((U2.EQ.46).OR.((U2.GE.65).AND.(U2.LE.122)).OR.
    *                 ((U2.GE.50).AND.(U2.LE.57).AND.(LMM(NX+KHYD-2,JY-1)
    *                 .NE.43).AND.(LMM(NX+KHYD-2,JY-1).NE.45))) GO TO 402
                   IF ((L2.EQ.46).OR.((L2.GE.65).AND.(L2.LE.122)).OR.
    *                 ((L2.GE.50).AND.(L2.LE.57).AND.(LMM(NX+KHYD-2,JY+1)
    *                 .NE.43).AND.(LMM(NX+KHYD-2,JY+1).NE.45))) GO TO 402
               ENDIF
               GO TO 43
402        CONTINUE
           DG1 = LMM(JX-KHYD-1,JY)
           DG2 = LMM(JX-KHYD+SHF,JY)
           DG3 = LMM(JX-KHYD,JY)
           U1 = LMM(NX-KHYD-1,JY-1)
           U2 = LMM(NX-KHYD+SHF,JY-1)
           U3 = LMM(NX-KHYD,JY-1)
           L1 = LMM(NX-KHYD-1,JY+1)
           L2 = LMM(NX-KHYD+SHF,JY+1)
           L3 = LMM(NX-KHYD,JY+1)
           IF (((DG1.GT.0).AND.(DG1.LT.256)).OR.((DG2.GT.0).AND.
    *         (DG2.LT.256)).OR.((DG3.GT.0).AND.(DG3.LT.256)).OR.
    *         ((DG1.GE.256).AND.(MOD(IDIR(DG1),4).NE.3)).OR.
    *         ((DG2.GE.256).AND.(MOD(IDIR(DG2),4).NE.3)).OR.
    *         ((DG3.GE.256).AND.(MOD(IDIR(DG3),4).NE.3))) GO TO 9394
           IF ((U3.EQ.46).OR.((U3.GE.65).AND.(U3.LE.122)).OR.
    *         ((U3.GE.50).AND.(U3.LE.57).AND.(U1.NE.43).AND.
    *         (U1.NE.45))) GO TO 9394
           IF ((L3.EQ.46).OR.((L3.GE.65).AND.(L3.LE.122)).OR.
```

```
     *          ((L3.GE.50).AND.(L3.LE.57).AND.(L1.NE.43).AND.
     *          (L1.NE.45))) GO TO 9394
                IF (SHF.EQ.1) THEN
                    IF ((U2.EQ.46).OR.((U2.GE.65).AND.(U2.LE.122)).OR.
     *              ((U2.GE.50).AND.(U2.LE.57).AND.(U3.NE.43)
     *              .AND.(U3.NE.45))) GO TO 9394
                    IF ((L2.EQ.46).OR.((L2.GE.65).AND.(L2.LE.122)).OR.
     *              ((L2.GE.50).AND.(L2.LE.57).AND.(L3.NE.43)
     *              .AND.(L3.NE.45))) GO TO 9394
                ENDIF
                IF ((U1.EQ.46).OR.((U1.GE.65).AND.(U1.LE.122)).OR.
     *          ((U1.GE.50).AND.(U1.LE.57).AND.(LMM(NX-KHYD-2,JY-1)
     *          .NE.43).AND.(LMM(NX-KHYD-2,JY-1).NE.45))) GO TO 9394
                IF ((L1.EQ.46).OR.((L1.GE.65).AND.(L1.LE.122)).OR.
     *          ((L1.GE.50).AND.(L1.LE.57).AND.(LMM(NX-KHYD-2,JY+1)
     *          .NE.43).AND.(LMM(NX-KHYD-2,JY+1).NE.45))) GO TO 9394
                GO TO 42
            ENDIF
C
C           Check for bad bonds coming in on the left diagonals.
            L1 = LMM(MX-1,JY-1)
            L2 = LMM(MX-1,JY+1)
            IF (((L1.EQ.0).OR.((L1.GT.256).AND.(MOD(IDIR(L1),4).NE.0)))
     *      .AND.((L2.EQ.0).OR.((L2.GT.256).AND.(MOD(IDIR(L2),4).NE.
     *      2)))) GO TO 522
            IRIGHT = 0
            GO TO 34
C
C The actual search-right algorithm loop.
522         DO 33 I=0,KHYD
                IF (MM(MX+I,JY).EQ.0) THEN
                    GO TO 330
                ELSE IF (LMM(MX+I,JY) .LT. 256) THEN
                    GO TO 400
                ENDIF
                ITEST=LMM(MX+I,JY)/256
                ITEST=LMM(MX+I,JY)-ITEST*256
C               CHECK FOR BOND IN LEFT OR RIGHT DIR
                IF (ITEST.EQ.3 .OR. ITEST.EQ.7) GO TO 330
C If non-blank or non-bond on right within
400             IRIGHT=0
C KHYD+1 to right of node, can't put H('s)there
                GOTO 34
330             CONTINUE
                L1 = LMM(MX+I,JY-1)
                L2 = LMM(MX+I,JY+1)
                L3 = LMM(MX+I-1,JY-1)
                L4 = LMM(MX+I-1,JY+1)
                IF ((L1.EQ.0).AND.(L2.EQ.0)) GO TO 33
                IF (I.LE.2) THEN
                    IF (((L1.EQ.46).OR.((L1.GE.65).AND.(L1.LE.122))).OR.
     *              ((L1.GE.50).AND.(L1.LE.57).AND.(L3.NE.43).AND.
     *              (L3.NE.45))) GO TO 400
                    IF (((L2.EQ.46).OR.((L2.GE.65).AND.(L2.LE.122))).OR.
     *              ((L2.GE.50).AND.(L2.LE.57).AND.(L4.NE.43).AND.
     *              (L4.NE.45))) GO TO 400
                ENDIF
                IF ((I.EQ.KHYD).AND.(((L1.GT.256).AND.
     *          (MOD(IDIR(L1),4).EQ.2)).OR.((L2.GT.256)
     *          .AND.(MOD(IDIR(L2),4).EQ.0)))) GO TO 400
                IF ((KHYD.EQ.1).AND.(I.EQ.0).AND.((
     *          (L1.GE.256).AND.(MOD(IDIR(L1),4).EQ.1)).OR.(
     *          (L2.GT.256).AND.(MOD(IDIR(L2),4).EQ.1)))) GO TO 400
                IF ((KHYD.EQ.2).AND.(I.EQ.0).AND.((
     *          (L1.GE.256).AND.((MOD(IDIR(L1),4).EQ.1).OR.
     *          (MOD(IDIR(L1),4).EQ.0))).OR.(
     *          (L2.GT.256).AND.((MOD(IDIR(L2),4).EQ.1).OR.
     *          (MOD(IDIR(L2),4).EQ.2)))) GO TO 400
                IF ((KHYD.EQ.2).AND.(I.EQ.1).AND.((
     *          (L1.GE.256).AND.((MOD(IDIR(L1),4).EQ.1).OR.
     *          (MOD(IDIR(L1),4).EQ.2))).OR.(
     *          (L2.GT.256).AND.((MOD(IDIR(L2),4).EQ.1).OR.
     *          (MOD(IDIR(L2),4).EQ.0)))) GO TO 400
33          CONTINUE
```

```
              IF (IRIGHT.EQ.1) GO TO 36
C Now look left to see if filler atoms can be put there:
C Look left for non-blank,non-bonds.
34            L1 = LMM(JX,JY-1)
              L2 = LMM(JX,JY+1)
              IF (((L1.EQ.0).OR.((L1.GT.256).AND.(MOD(IDIR(L1),4).NE.2)))
     *            .AND.((L2.EQ.0).OR.((L2.GT.256).AND.(MOD(IDIR(L2),4)
     *            .NE.0)))) GO TO 3441
              ILEFT = 0
              GO TO 36
3441          DO 35 I=1,KHYD+1
              IF (MM(JX-I,JY).EQ.0) GOTO 3555
              IF(LMM(JX-I,JY) .LT. 256) GO TO 401
              ITEST=LMM(JX-I,JY)/256
              ITEST=LMM(JX-I,JY)-ITEST*256
              IF (ITEST.EQ.3 .OR. ITEST.EQ.7) GO TO 3555
401           ILEFT=0
              GOTO 36
3555          L1 = LMM(JX-I,JY-1)
              L2 = LMM(JX-I,JY+1)
              L3 = LMM(JX-I-1,JY-1)
              L4 = LMM(JX-I-1,JY+1)
              IF ((L1.EQ.0).AND.(L2.EQ.0)) GO TO 35
              IF (((L1.EQ.46).OR.((L1.GE.65).AND.(L1.LE.122))).OR.
     *            ((L1.GE.50).AND.(L1.LE.57).AND.(L3.NE.43).AND.
     *            (L3.NE.45))) GO TO 401
              IF (((L2.EQ.46).OR.((L2.GE.65).AND.(L2.LE.122))).OR.
     *            ((L2.GE.50).AND.(L2.LE.57).AND.(L4.NE.43).AND.
     *            (L4.NE.45))) GO TO 401
              IF ((I.EQ.KHYD+1).AND.(((L1.GT.256).AND.
     *            (MOD(IDIR(L1),4).EQ.0)).OR.((L2.GT.256)
     *            .AND.(MOD(IDIR(L2),4).EQ.2)))) GO TO 401
              IF ((KHYD.EQ.1).AND.(I.EQ.1).AND.(((L1.GE.256)
     *            .AND.(MOD(IDIR(L1),4).EQ.1)).OR.((L2.GT.256)
     *            .AND.(MOD(IDIR(L2),4).EQ.1)))) GO TO 401
              IF ((KHYD.EQ.2).AND.(I.EQ.2).AND.(((L1.GE.256)
     *            .AND.((MOD(IDIR(L1),4).EQ.1).OR.
     *            (MOD(IDIR(L1),4).EQ.0))).OR.((L2.GT.256)
     *            .AND.((MOD(IDIR(L2),4).EQ.1).OR.
     *            (MOD(IDIR(L2),4).EQ.2)))) GO TO 401
              IF ((KHYD.EQ.2).AND.(I.EQ.1).AND.(((L1.GE.256)
     *            .AND.((MOD(IDIR(L1),4).EQ.1).OR.
     *            (MOD(IDIR(L1),4).EQ.2)).OR.((L2.GT.256)
     *            .AND.((MOD(IDIR(L2),4).EQ.1).OR.
     *            (MOD(IDIR(L2),4).EQ.0)))) GO TO 401
35            CONTINUE
C
C See if ILEFT, IRIGHT, or both equal 1. If one is, insert H('s) there.
C If both equal 1, use criteria to decide which side to put H('s) on.
C If neither equals 1, call error message that there is no room for H.
C
36            CONTINUE
              IF (ILEFT+IRIGHT.NE.0) THEN
                 IF (IRIGHT.EQ.0) THEN
                    GO TO 42
                 ELSE
                    GO TO 43
                 ENDIF
              ENDIF
CXT           IF (ILEFT+IRIGHT.GT.0) GO TO 38
9394          CONTINUE
CXT
CXT           Vertical positioning of attached hydrogens to nodes is attempted.
              MBOND = 0
              DO 9395 IN = IHP,-IHP,-IHP*2
              FY = JY + IN
              IF (((MM(JX,FY).EQ.0).OR.(LMM(JX,FY).GE.256)).AND.(FY.GT.0)
     *            .AND.(FY.LE.MAXY)) THEN
CXT              Check adjacent cells.
                 DO 939 KK = -1,2
                 IF ((KK.EQ.2).AND.(KHYD.LE.1)) GO TO 939
                 DO 938 JJ = 0,1
                    IL = JX + KK
                    JL = FY + (JJ * IN)
```

```
            IF (((MM(IL,JL).GT.0).AND.(LMM(IL,JL).LT.256).AND.
  *             (MM(IL,JL).NE.34).AND.(LMM(IL,JL).NE.43).AND.
  *             (LMM(IL,JL).NE.45)) GO TO 9395
938           CONTINUE
939         CONTINUE
CXT
            IF (KHYD.GT.1) THEN
               FX = JX + 1
               IF (MM(FX,FY).EQ.0) THEN
                  IF (LMM(JX,FY).GT.256) THEN
                     MBOND = MM(JX,FY)
                     MM(JX,FY) = 0
                     CALL REPLCE(JX,FY,0,1,0,0,1)
                     IF (IN.EQ.1) CALL REPLCE(JX,JY,0,1,0,0,1)
                  ENDIF
                  MM(JX,FY) = 72
                  MM(FX,FY) = IHYD + 48
                  HALO(2) = 'H'
                  ICUR = 0
                  CALL CURSOR(JX,FY)
                  CALL TEXT(HALO)
                  HALO(2) = CHAR(MM(FX,FY))
                  CALL CURSOR(FX,FY)
                  CALL MOVTCR(0,2)
                  CALL TEXT(HALO)
                  CALL MOVTCR(0,-2)
                  IF (((ICHAR.EQ.1).AND.(INCY.EQ.IN)).OR.(CHER.EQ.1))
 *                 THEN
                     IF (CHER.NE.1) THEN
                        INC = (IN * NLARGE) + IN
                        IX = JX + (NLARGE * INCX) + INCX
                        IF ((NLARGE.EQ.1).AND.(INCX.EQ.0)) INC=INC+IN
                        IY = JY + INC
                     ENDIF
                     IF (MBOND.GT.256) THEN
                        FY = FY + IN
                        CALL DRAW2(JX,FY,MBOND)
                        ICHAR = 1
                     ENDIF

IF (FX.GT.HIX) HIX = FX
                  GO TO 9396
               ELSE
                  GO TO 9395
               ENDIF
            ELSE
               IF (LMM(JX,FY).GT.256) THEN
                  MBOND = MM(JX,FY)
                  MM(JX,FY) = 0
                  CALL REPLCE(JX,FY,0,1,0,0,1)
                  IF (IN.EQ.1) CALL REPLCE(JX,JY,0,1,0,0,1)
               ENDIF
               MM(JX,FY) = 72
               HALO(2) = 'H'
               ICUR = 0
               CALL CURSOR(JX,FY)
               CALL TEXT(HALO)
               IF (((ICHAR.EQ.1).AND.(INCY.EQ.IN)).OR.(CHER.EQ.1))
 *                 THEN
                  IF (CHER.NE.1) THEN
                     INC = (IN * NLARGE) + IN
                     IX = JX + (NLARGE * INCX) + INCX
                     IF ((NLARGE.EQ.1).AND.(INCX.EQ.0)) INC=INC+IN
                     IY = JY + INC
                  ENDIF
                  IF (MBOND.GE.256) THEN
                     FY = FY + IN
                     CALL DRAW2(JX,FY,MBOND)
                     ICHAR = 1
                  ENDIF
               ENDIF
               GO TO 9396
            ENDIF
         ENDIF
9395     CONTINUE
```

```
              GO TO 9397
9396      CONTINUE
              IF (IY.LT.LOY) THEN
                  LOY = IY
              ELSE IF (IY.GT.HIY) THEN
                  HIY = IY
              ENDIF
              ICUR = 1
              CALL CURSOR(IX,IY)
              MLARGE = NLARGE
              RETURN
9397      IERR=14
          JPROB=1
C ERROR IN DECIDING WHERE TO PUT H'S
              CHER = 2
              CALL MYERR(IERR,KAR,KAR)
              CHER = 0
              MLARGE = NLARGE
              RETURN
C         41 IF BOTH 1; 42 OK LEFT; 43 OK RIGHT ONLY
C
C Selection of left vs right for filler H's if there is room on either
C side. JLEFT & JRIGHT, calculated during the valence count in the DO 3
C loop above, represent the presenc(1) or absence(0) of bonds on the
C left & right sides of the node. Select the right if there are
C bonds on the left, or bonds on neither left or right, or bonds on
C both sides. Otherwise, select the left(i.e. bonds on right,none left)
C
C         Draw H on left:
C Saved for possible extension of bond
42        MBOND=LMM(JX-1,JY)
              IF (MBOND.GE.256) THEN
                  FX = JX - KHYD
                  CALL FTLOCA(JY,FX)
                  CALL FTEXT('^ ^')
              ENDIF
C Move to H location
              CALL CURSOR(JX-KHYD,JY)
C ASCII H into array
              MM(JX-KHYD,JY)=72
C Insert H here
              HALO(2) = 'H'
              IF ((JX-2).LT.LOX) LOX = MIN0(JX-2,1)
              CALL TEXT(HALO)
C Skip subscript if not necessary.
              IF (KHYD.LE.1) GOTO 45
              IF (MBOND.GE.256) THEN
                  FX = JX - 1
                  CALL FTLOCA(JY,FX)
                  CALL FTEXT('^ ^')
              ENDIF
C Move to cursor position: one left of node.
              ICUR = 0
              CALL CURSOR(JX-1,JY)
C ASCII for typing
              IJ=IHYD+48
C backspace
              IBACK=8
C Drop down, type subscript, raise up
              HALO(2) = CHAR(IJ)
              CALL MOVTCR(0,2)
              CALL TEXT(HALO)
              CALL MOVTCR(0,-2)
C ASCII of numeral into array
              MM(JX-1,JY)=IJ
C
C If blank now to the left of H, extend whatever bond was covered over
C by the H and/or subscript,if any.(If MBOND=0,there was no bond there):
45            IF (MM(JX-KHYD-1,JY).NE.0) GOTO 111
              CALL DRAW2(JX-KHYD-1,JY,MBOND)
C Move cursor
              IF ((IBDIR.EQ.7) .AND. (ILEFT.EQ.1)) IX=JX-KHYD-2
              IF (MBOND.GT.256) ICHAR=1
C beyond the end of the extended bond.
```

```
C Done with valence after left insertion.
        ICUR = 1
        CALL CURSOR (IX,IY)
111     CONTINUE
        MLARGE = NLARGE
        RETURN
C
C  Insert (H's) on right:
C Position for H on right of node
43      MX = JX + 1
        IF (LET2.GT.0) MX=JX+2
C Save for possible bond extension.
        MBOND = LMM(MX,JY)
        IF (MBOND.GE.256) THEN
            CALL FTLOCA(JY,MX)
            CALL FTEXT('^ ^')
        ENDIF
        CALL CURSOR(MX,JY)
C Insert H.
        HALO(2) = 'H'
        IF ((JX+2).GT.HIX) HIX = MAX0(JX+2,MAXX)
        CALL TEXT(HALO)
C ASCII H into array
        MM(MX,JY)=72
C No subscript needed
        IF (KHYD.LE.1) GOTO 44
        IF (MBOND.GE.256) THEN
            FX = MX + 1
            CALL FTLOCA(JY,FX)
            CALL FTEXT('^ ^')
        ENDIF
C Position of subscript
        ICUR = 0
        CALL CURSOR(MX+1,JY)
C ASCII for subscript
        IJ=IHYD+48
        IBACK=8
C Type blank, drop down, type sub, raise
        HALO(2) = CHAR(IJ)
        CALL MOVTCR(0,2)
        CALL TEXT(HALO)
        CALL MOVTCR(0,-2)
C ASCII of numeral into array
        MM(MX+1,JY)=IJ
C If H and subscript covered over all of bond (if any), replace with one
C length of bond, using DRAW2:
44      IF (MM(MX+KHYD,JY).EQ.0) CALL DRAW2(MX+KHYD,JY,MBOND)
        IF ((IBDIR.EQ.3).AND.(IRIGHT.EQ.1)) THEN
            IF (IBTYPE.EQ.0) THEN
                IX = MX + KHYD + MLARGE
            ELSE IF (NLARGE.EQ.1) THEN
                IX = MX + KHYD + 1
            ELSE
                IX = MX + MLARGE
            ENDIF
        ENDIF
        ICUR = 1
        CALL CURSOR(IX,IY)
        MLARGE = NLARGE
C Completed with insertion of H on right
        RETURN
        END
C
        SUBROUTINE CLRHYD(KX,KY)
        IMPLICIT INTEGER*2 (A-Z)
        INTEGER*4 MM,ITEMP1
        COMMON /CD/ MAXX,MAXY
        COMMON /SIZZE/ MULTX,MULTY
        COMMON /CHARS/IES, IDOT,ITAG,JUMP,LBOND,KAN,ISPACE
        COMMON /STRPIX/ LPIX,MM(90,38),LBLEN,LNGBND(100,5)
        COMMON /CUR/ ICUR
        COMMON /HP/IHP
C This subroutine clears valence hydrogens from the vicinity of nodes
C and extends bonds as needed, before re-calculation of valences.
C      In earlier versions, this code was contained in DRAW. 3/16/83 GMK
```

```
C
C       DO NOTHING IF AT A MARKER OR DOT
1       IF ((MM(KX-1,KY).EQ.46).OR.(MM(KX,KY).EQ.46)) RETURN
        ICUR = 0
C     Look right for H's & subscripts & eliminate them:
C     Increment for looking across for H & subscripts
        INC=1
        MBOND=0
C     2 let element
        IF( (MM(KX+1,KY).GE.97) .AND. (MM(KX+1,KY).LE.122)) INC=2
        IF (MM(KX+INC,KY).NE.72) GOTO 40
C     Bond on rt of H
        MBOND=MAX0 (LMM(KX+INC+1,KY),LMM(KX+INC+2,KY))
        LBLOB=MOD(MBOND,256)
        IF (LBLOB .NE. 3 .AND. LBLOB .NE. 7) MBOND=0
        CALL CURSOR(KX+INC,KY)
C     Undraw H
        FX = KX + INC
        CALL FTLOCA(KY,FX)
        CALL FTEXT('^ ^')
        MM(KX+INC,KY)=0
C     Reinstall bond
        CALL DRAW2(KX+INC,KY,MBOND)
        IF ((MM(KX+INC+1,KY).LT.50).OR.(MM(KX+INC+1,KY).GT.57)) GOTO43
C     Erase subscript on right
        CALL CURSOR (KX+INC+1,KY)
C     Erase bond
        FX = KX + INC + 1
        CALL FTLOCA(KY,FX)
        CALL FTEXT('^ ^')
        CALL CURSOR(KX+INC+1,KY)
        ITEMP1 = MM(KX+INC+1,KY)
        FX = KX + INC + 1
        CALL FTLOCA(KY,FX)
        CALL FTEXT('^ ^')
        IF (IHP .NE. 1) THEN
        IF (MOD((KY*10),40).EQ.0) THEN
           IF ((KY.EQ.8).OR.(KY.EQ.28).OR.(KY.EQ.16)) THEN
              FY = ((KY * 10) / 11) + 1
              CALL FTSIZE(1,11)
           ELSE
              FY = ((KY * 10) / 9) + 1
              CALL FTSIZE(1,9)
           ENDIF
        ELSE
           FY = ((KY * 10) / 8) + 1
           CALL FTSIZE(1,8)
        ENDIF
        CALL FTLOCA(FY,FX)
        CALL FTEXT('^ ^')
        ENDIF
        CALL FTSIZE(1,10)
        MM(KX+INC+1,KY)=0
        IF (MM(KX+INC+1,KY+1).NE.0) CALL REPLCE(KX+INC+1,KY+1,0,0,0,0,0)
        CALL DRAW2(KX+INC+1,KY,MBOND)
C Here completh undrawing H's & subscripts on right
        GOTO 43
C
C  Now look on left for H & subscripts:
40      MBOND=0
C Look left for H, subscript, MBOND to copy
        DO 42 INC=-3,-1
        IF ((MM(KX-1,KY).LT.50) .OR. (MM(KX-1,KY).GT.72)) GOTO 43
        IF (LMM(KX+INC,KY).GT.256) MBOND=MM(KX+INC,KY)
C
        IF (LMM(KX+INC,KY).NE.72) GOTO 42
        CALL CURSOR (KX+INC,KY)
C Untype H
        FX = KX + INC
        CALL FTLOCA(KY,FX)
        CALL FTEXT('^ ^')
        MM(KX+INC,KY)=0
        LBLOB=MOD(MBOND,256)
        IF (LBLOB .NE. 3 .AND. LBLOB .NE. 7) MBOND=0
```

```
C Replace H with bond
        CALL DRAW2(KX+INC,KY,MBOND)
C  Look for number to right of H, on left of node
        IF ((MM(KX+INC+1,KY).LT.50) .OR. (MM(KX+INC+1,KY).GT.57))
     2      GOTO 43
C If no number,skip out of loop: done here
        CALL CURSOR(KX+INC+1,KY)
C Erase bond
        FX = KX + INC + 1
        CALL FTLOCA(KY,FX)
        CALL FTEXT('^ ^')
        CALL CURSOR(KX+INC+1,KY)
C Untype subscript
        ITEMP1 = MM(KX+INC+1,KY)
        FX = KX + INC + 1
        CALL FTLOCA(KY,FX)
        CALL FTEXT('^ ^')
        IF (IHP .NE. 1) THEN
        IF (MOD((KY*10),40).EQ.0) THEN
            IF ((KY.EQ.8).OR.(KY.EQ.28).OR.(KY.EQ.16)) THEN
                FY = ((KY * 10) / 11) + 1
                CALL FTSIZE(1,11)
            ELSE
                FY = ((KY * 10) / 9) + 1
                CALL FTSIZE(1,9)
            ENDIF
        ELSE
            FY = ((KY * 10) / 8) + 1
            CALL FTSIZE(1,8)
        ENDIF
        CALL FTLOCA(FY,FX)
        CALL FTEXT('^ ^')
        CALL FTSIZE(1,10)
        ENDIF
        MM(KX+INC+1,KY)=0
        IF (MM(KX+INC+1,KY+1).NE.0) CALL REPLCE(KX+INC+1,KY+1,0,0,0,0,0)
        CALL DRAW2(KX+INC+1,KY,MBOND)
C At this point, filler H's are removed
42      CONTINUE
43      CONTINUE
C
C       Look above and below to remove H's.

DO 50 I = -1,1,2
            FY = KY + I
            IF (MM(KX,FY).EQ.72) THEN
                MM(KX,FY) = 0
                CALL FTLOCA(FY,KX)
                CALL FTEXT('^ ^')
                FX = KX + 1
                IF ((MM(FX,FY).GE.50).AND.(MM(FX,FY).LE.57)) THEN
                    MM(FX,FY) = 0
                    CALL REPLCE(FX,FY,0,0,0,0,1)
                ENDIF
                MBOND = LMM(KX,FY+I)
                IF ((MBOND.GE.256).AND.(MOD(IDIR(MBOND),4).EQ.1))
     *              CALL DRAW2(KX,FY,MBOND)
            ENDIF
50      CONTINUE
        ICUR = 1
C
        RETURN
        END
$STORAGE:2
C
        SUBROUTINE SPACE(IX,IY)
        IMPLICIT INTEGER*2 (A-Z)
        INTEGER*4 MM,IDTPIX
        LOGICAL*2 FOUND
        CHARACTER*1 HALO(3),HLO(3)
        CHARACTER*3 HALOE
        EQUIVALENCE (HALOE,HALO(1))
        CHARACTER*1 KAN
        CHARACTER*1 ISTAT
        COMMON /CD/ MAXX,MAXY
```

```
      COMMON /HP/IHP
      COMMON /RANGE/ LOX,HIX,LOY,HIY
      COMMON /HEAD/ MW(12),ISTATE,PAGE
      COMMON /STRPIX/ LPIX,MM(90,38),LBLEN,LNGBND(100,5)
      COMMON /STRED/ IDTPIX(90,38),LABL(260,2),MRKCHN(260)
      COMMON /ISTATE/ ISTAT
      COMMON /MODES/ JBTYPE,ICHAR,IBDIR,IBTYPE,ISMART,MODE,ISKILL,ISP
      COMMON /CHARS/IES, IDOT,ITAG,JUMP,LBOND,KAN,ISPACE
      COMMON /IPLUS/ IHIGH(14,2)
      COMMON /D1/ IDNUM,IDS(9,6),NBD1,DSCNC(6,50)
      COMMON /CUR/ ICUR
C
      HALO(1) = KAN
      HALO(3) = KAN
C
C  This routine moves right until the cursor is in a 'clear' area, i.e.
C  one with nothing around current cursor location.
C
      LEFT2 = 0
      ICUR = 1
      ISTAT='S'
      ISP=1
      IF (ICHAR.EQ.25) IX = IX + 1
      CALL CURSOR(IX,IY)
C
C  Following code is for terminal going 'dumb' after a space.  Exactly
C  the same as in subroutine BKSPCE.
475   ISMART=0
      KHAR=0
      ISTATE=8
      CALL HEADER
100   CALL INPUTX(KHAR,IX,IY)
      IF ((LEFT2.NE.0).AND.((KHAR.LT.50).OR.(KHAR.GT.57))) THEN
CXT      If a charge has been entered to the left of a node and no
CXT      digit attaches it to the node, its validity as a standalone
CXT      charge is determined, and the operator warned.
         DO 20 I = LOX,HIX
            DO 20 J = LOY,HIY
               IF ((MM(I,J).EQ.43).OR.(MM(I,J).EQ.45)) THEN
                  IERR = 4
                  CALL MYERR(IERR,IERR,IERR)
                  MM(OX,OY) = 0
                  CALL FTLOCA(OY,OX)
                  CALL FTEXT('^ ^')
                  GO TO 30
               ENDIF
20       CONTINUE
         IERR = 28
         CALL MYERR(IERR,IERR,IERR)
         MM(OX,OY) = LEFT2
         LEFT2 = 0
         IX = IX - 1
         CALL CURSOR(IX,IY)
         GO TO 100
      ENDIF
30    CONTINUE
      LEFT2 = 0
      IF (IHP .EQ. 1 .AND. ((KHAR .GE. 22) .AND. (KHAR .LE. 31)))
     1 GO TO 200       !Exit if this is a bond and we are using an HP
CXT      If F1 is entered return to calling state.
      IF (KHAR.EQ.21) GO TO 200
      IF ((KHAR.LE.31).AND.(KHAR.GE.22).AND.(KHAR.NE.26).AND.
     *    (KHAR.NE.27)) THEN
C        The cursor moves freely.
         CALL MOVE(KHAR,IX,IY)
         MCHAR = 0
         GO TO 100
      ENDIF
      IF ((KHAR.GT.32).AND.(KHAR.NE.127)) THEN
C
C        The character is put to the screen.
         IF (KHAR.EQ.94) THEN
            HLO(1) = '/'
            HLO(2) = CHAR(KHAR)
```

```
              HLO(3) = '/'
              CALL TEXT(HLO)
          ELSE
              HALO(2) = CHAR(KHAR)
              CALL TEXT(HALO)
          ENDIF
C         New picture boundaries are expanded.
          IF (IX.LT.LOX) THEN
              LOX = IX
          ELSE IF (IX.GT.HIX) THEN
              HIX = IX
          ENDIF
          IF (IY.LT.LOY) THEN
              LOY = IY ELSE IF (IY.GT.HIY) THEN
              HIY = IY
          ENDIF
      ENDIF
      IF (KHAR .NE. 43.AND.KHAR .NE. 45) GO TO 199
C
C     WE FOUND A + OR -    ... NOW FIND ITS NODE
C
C     The logical variable FOUND is set to TRUE when a node adjacent
C     to the charge is found.  The loop that searches for adjacent
C     nodes is continued until all positions adjacent to the charge
C     are checked to ensure the charge placement is not ambiguous.
C     If a second adjacent node is found, the charge is erased, an
C     error message prompting the user to use another position is
C     issued, and the loop is exited.
      FOUND = .FALSE.
C LOOK AROUND FOR NODE
      DO 50 I=-2,2
      DO 50 J=-1,1
C DON'T CHECK THIS BOX
      IF(I.EQ.0 .AND. J .EQ. 0) GO TO 50
      IIX=IX+I
      IIY=IY - J
      IF (((MM(IIX,IIY).GE.65).AND.(MM(IIX,IIY).LE.90)).OR.
     *    (MM(IIX,IIY).EQ.46)) GO TO 47
C CHECK FOR UC LETTER - IF WE FIND ONE - THEN CHECK
C FOR OTHER REQUIREMENTS
C ITS NOT A UC - CAN'T BE A NODE
      GO TO 50
C IF X = -2 THEN WE NEED UC FOLLOWED BY lc
47    IF ((I.EQ.-2).AND.(MM(IIX+1,IIY).GE. 97
     1   .AND. MM(IIX+1,IIY) .LE.122)) THEN
          IF (FOUND) THEN
              IERR = 42
              CALL MYERR(IERR,IERR,IERR)
              CALL FTLOCA(IY,IX)
              CALL FTEXT('^ ^')
              GO TO 999
          ENDIF
          II = -I
          JJ = J
          NIX = IIX
          NIY = IIY
          FOUND = .TRUE.
          GO TO 50
      ENDIF
C IF X=2 WE NEED DIGIT TO RIGHT OF CHARGE
      IF (I.EQ.-2) GO TO 50
49    IF (MM(IIX,IIY).NE.72) THEN
          IF (FOUND) THEN
              IERR = 42
              CALL MYERR(IERR,IERR,IERR)
              CALL FTLOCA(IY,IX)
              CALL FTEXT('^ ^')
              GO TO 999
          ENDIF
          II = -I
          JJ = J
          NIX = IIX
          NIY = IIY
```

```
                    FOUND = .TRUE.
                    GO TO 50
                ENDIF
                IF (MM(IIX+1,IIY).GE.97.AND.MM(IIX+1,IIY).LE.122) THEN
                    IF (FOUND) THEN
                        IERR = 42
                        CALL MYERR(IERR,IERR,IERR)
                        CALL FTLOCA(IY,IX)
                        CALL FTEXT('^ ^')
                        GO TO 999
                    ENDIF
                    II = -I
                    JJ = J
                    NIX = IIX
                    NIY = IIY
                    FOUND = .TRUE.
                    GO TO 50
                ENDIF
C IF UC = H IT MUST BE FOLLOWED BY 1c
50          CONTINUE
            IF (FOUND) GO TO 55
C CAN'T FIND NODE - CALL IT DELOCALIZED CHARGE
C       Check that there is only 1 delocalized charge.
            DO 4345 I = LOX,HIX
                DO 4345 J = LOY,HIY
                    IF ((MM(I,J).NE.45).AND.(MM(I,J).NE.43)) GO TO 4345
                    IF (MM(I-1,J).NE.42) GO TO 4300
4345        CONTINUE
            GO TO 51
4300        IERR = 4
            CALL MYERR(IERR,IERR,IERR)
            CALL FTLOCA(IY,IX)
            CALL FTEXT('^ ^')
            IX = IX - 1
            GO TO 999
C CAN'T FIND NODE - CALL IT DELOCALIZED CHARGE
51          IERR=28
            CALL MYERR(IERR,KHAR,MAR)
            LEFT2 = 0
            GO TO 99
55          CONTINUE
            ICNT = 0
            DO 300 I = -2,2
                DO 300 J = -1,1
                    IF ((LMM(NIX+I,NIY+J).NE.43).AND.(LMM(NIX+I,NIY+J).NE.45))
     *                  GO TO 300
                    ILC = IHMM(NIX+I,NIY+J)
                    IF (ILC.EQ.0) GO TO 300
                    IF ((I.NE.IHIGH(ILC,1)).OR.(J.NE.(-IHP)*IHIGH(ILC,2)))
     *                  GO TO 300
                    ICNT = ICNT + 1
                    PREX = NIX + I
                    PREY = NIY + J
300         CONTINUE
            IF (ICNT.EQ.0) GO TO 4500
            IERR = 38
            CALL MYERR(IERR,IERR,IERR)
            CALL FTLOCA(IY,IX)
            IF ((IX.NE.PREX).OR.(IY.NE.PREY)) THEN
                CALL FTEXT('^ ^')
                MM(IX,IY) = 0
            ELSE IF (LMM(IX,IY).EQ.43) THEN
                CALL FTEXT('^+^')
            ELSE
                CALL FTEXT('^-^')
            ENDIF
            IX = IX - 1
            GO TO 999
4500        CONTINUE
            DO 56 I=1,14
                KK = I
                IF (IHIGH(I,1).EQ.II.AND.(-IHP)*IHIGH(I,2).EQ.JJ) THEN
                    IF (II.EQ.-2) THEN
```

```
                LEFT2 = KHAR
                OX = IX
                OY = IY
              ENDIF
              GO TO 57
           ENDIF
C LOOK UP NODE ASSOCIATOR IN IHIGH
56         CONTINUE
C COULDN'T FIND ONE - CALL IT DELOCALIZED
           GO TO 51
C STORE SIGN WITH NODE ASSOCIATOR
57         CONTINUE
           IF ((MM(IX,IY).EQ.43).OR.(MM(IX,IY).EQ.45)) THEN
              CALL FTLOCA(IY,IX)
              HALO(2) = CHAR(KHAR)
              CALL FTEXT(HALOE)
              CALL FTSIZE(2,18)
              CALL FTLOCA(4,1)
              PAGE = 0
              CALL FTEXT('^CHARGE IS NOW LOCAL^')
              CALL FTSIZE(1,10)
           ENDIF
           MM(IX,IY) = KHAR + KK*2**13
           GO TO 999
C
199        CONTINUE
C
C          UNDETERMINED BOND SITE MARKERS ARE ENTERED.
C
           IF (KHAR.NE.34) GO TO 99
C  The logical variable FOUND is set to TRUE when a node adjacent
C  to the marker is found.  The loop that searches for adjacent
C  nodes is continued until all positions adjacent to the marker
C  are checked to ensure the marker placement is not ambiguous.
C  If a second adjacent node is found, the marker is erased, an
C  error message prompting the user to use another position is
C  issued, and the loop is exited.
           FOUND = .FALSE.
           DO 150 I=-2,1
           DO 150 J=-1,1
C DON'T CHECK THIS BOX
           IF (I.EQ.0 .AND. J .EQ. 0) GO TO 150
           IIX = IX+I
           IIY = IY - J
           IF (((MM(IIX,IIY).GE.65).AND.(MM(IIX,IIY).LE.90)).OR.
     *         (MM(IIX,IIY).EQ.46)) GO TO 147
C CHECK FOR UC LETTER - IF WE FIND ONE - THEN CHECK
C FOR OTHER REQUIREMENTS
C ITS NOT A UC - CAN'T BE A NODE
C          IF X = -2 THEN WE NEED UC FOLLOWED BY 1c
           GO TO 150
147        IF ((I.EQ.-2).AND.(MM(IIX+1,IIY).GE. 97
     1        .AND. MM(IIX+1,IIY) .LE.122)) THEN
              IF (FOUND) THEN
                 IERR = 42
                 CALL MYERR(IERR,IERR,IERR)
                 CALL FTLOCA(IY,IX)
                 CALL FTEXT('^ ^')
                 GO TO 999
              ENDIF
              II = -I
              JJ = J
              NIX = IIX
              NIY = IIY
              FOUND = .TRUE.
              GO TO 150
           ENDIF
           IF (I.EQ.-2) GO TO 150
149        IF (MM(IIX,IIY).NE.72) THEN
              IF (FOUND) THEN
                 IERR = 42
                 CALL MYERR(IERR,IERR,IERR)
                 CALL FTLOCA(IY,IX)
                 CALL FTEXT('^ ^')
                 GO TO 999
```

```
              ENDIF
              II = -I
              JJ = J
              NIX = IIX
              NIY = IIY
              FOUND = .TRUE.
              GO TO 150
          ENDIF
          IF (MM(IIX+1,IIY).GE.97.AND.MM(IIX+1,IIY).LE.122) THEN
              IF (FOUND) THEN
                  IERR = 42
                  CALL MYERR(IERR,IERR,IERR)
                  CALL FTLOCA(IY,IX)
                  CALL FTEXT('^ ^')
                  GO TO 999
              ENDIF
              II = -I
              JJ = J
              NIX = IIX
              NIY = IIY
              FOUND = .TRUE.
              GO TO 150
          ENDIF
C IF UC = H IT MUST BE FOLLOWED BY 1c
150       CONTINUE
          IF (FOUND) GO TO 155
C         CAN'T FIND NODE
151       IERR = 34
          CALL MYERR(IERR,IERR,IERR)
          CALL FTLOCA(IY,IX)
          CALL FTEXT('^ ^')
          IX = IX - 1
          GO TO 999
155       CONTINUE
          IF (NBD1.EQ.0) GO TO 157
C         Check for " already on this node.
          DO 527 I = 1,NBD1
              KK = I
              IF ((NIX.EQ.DSCNC(3,I)).AND.(NIY.EQ.DSCNC(4,I))) GO TO 892
527       CONTINUE
          GO TO 157
892       IERR = 47
          CALL MYERR(IERR,IERR,IERR)
          IF ((IX.NE.DSCNC(5,KK)).OR.(IY.NE.DSCNC(6,KK))) THEN
              CALL FTLOCA(IY,IX)
              CALL FTEXT('^ ^')
          ENDIF
          GO TO 999
C STORE SIGN WITH NODE ASSOCIATOR
157       MM(IX,IY) = KHAR
          NBD1 = NBD1 + 1
          DSCNC(3,NBD1) = NIX
          DSCNC(4,NBD1) = NIY
          DSCNC(5,NBD1) = IX
          DSCNC(6,NBD1) = IY
          IF (II.GE.1) THEN
              IF (JJ.EQ.IHP) THEN
                  DSCNC(2,NBD1) = 2
              ELSE IF (JJ.EQ.0) THEN
                  DSCNC(2,NBD1) = 3
              ELSE
                  DSCNC(2,NBD1) = 4
              ENDIF
          ELSE IF (II.EQ.0) THEN
              IF (JJ.EQ.-IHP) THEN
                  DSCNC(2,NBD1) = 5
              ELSE
                  DSCNC(2,NBD1) = 1
              ENDIF
          ELSE
              IF (JJ.EQ.-IHP) THEN
                  DSCNC(2,NBD1) = 6
              ELSE IF (JJ.EQ.0) THEN
```

```
                    DSCNC(2,NBD1) = 7
                ELSE
                    DSCNC(2,NBD1) = 8
                ENDIF
            ENDIF
        ENDIF
        GO TO 999
C Put KHAR into data array.
C TRANSLATE FOR D1'S AND M1'S.
 99     IF ((KHAR.GE.49).AND.(KHAR.LE.57).AND.
     *      ((MM(IX-1,IY).EQ.68).OR.(MM(IX-1,IY).EQ.77)))
     *      KHAR = KHAR + 63
        IF ((KHAR.GT.32).AND.(KHAR.NE.127)) THEN
            IF (MM(IX,IY).EQ.46) THEN
                DO 505 I = 1,260
                    IF ((IX.EQ.LABL(I,1)).AND.(IY.EQ.LABL(I,2))) THEN
                        LABL(I,1) = -999
                        LABL(I,2) = -999
                        GO TO 506
                    ENDIF
505             CONTINUE
            ENDIF
506         CONTINUE
            MM(IX,IY) = KHAR
        ENDIF
C Non-printing characters
C ERASE CHAR - WE HAD A DEL
C DEL WAS ENTERED
        IF (((KHAR.EQ.127).OR.(KHAR.EQ.32).OR.(KHAR.EQ.8)).AND.
     *      (MM(IX,IY).NE.0)) THEN
            ICUR = 0
            CALL CURSOR(IX,IY)
            IF ((LMM(IX,IY).GE.256).AND.(MOD(IDIR(IX,IY),2).EQ.0)) THEN
                FX = IX - 1
      IF (IHP .EQ. 1) THEN
      CALL BERASE(IX,IY)
      ELSE
                CALL FTLOCA(IY,FX)
                CALL FTEXT('^   ^')
      ENDIF
                IF (MM(FX,IY).NE.0) CALL REPLCE(FX,IY,0,0,0,0,0)
                FX = IX + 1
                IF (MM(FX,IY).NE.0) CALL REPLCE(FX,IY,0,0,0,0,0)
                INKX = 1
                INKY = 1
            ELSE
                CALL FTLOCA(IY,IX)
                CALL FTEXT('^ ^')
                INKX = 0
                INKY = 0
            ENDIF
            IF ((MM(IX,IY).EQ.46).OR.(LMM(IX,IY).GE.256).OR.(MM(IX,IY)
     *          .EQ.44).OR.((MM(IX,IY).GE.50).AND.(MM(IX,IY).LE.57).AND.
     *          (LMM(IX-1,IY).NE.43).AND.(LMM(IX-1,IY).NE.45)).OR.
     *          (MM(IX,IY).EQ.103).OR.(MM(IX,IY).EQ.106).OR.(MM(IX,IY).EQ
     *          .112).OR.(MM(IX,IY).EQ.113).OR.(MM(IX,IY).EQ.121).OR.
     *          (MM(IX,IY).EQ.95).OR.(MM(IX,IY).EQ.59)) THEN
                IF (MOD((IY*10),40).EQ.0) THEN
                    IF ((IY.EQ.8).OR.(IY.EQ.28).OR.(IY.EQ.16)) THEN
                        FY = ((IY * 10) / 11) + 1
                        CALL FTSIZE(1,11)
                    ELSE
                        FY = ((IY * 10) / 9) + 1
                        CALL FTSIZE(1,9)
                    ENDIF
                ELSE
                    FY = ((IY * 10) / 8) + 1
                    CALL FTSIZE(1,8)
                ENDIF
                IF ((LMM(IX,IY).GE.256).AND.(MOD(IDIR(IX,IY),2).EQ.0))THEN
                    FX = IX - 1
      IF (IHP .EQ. 1) THEN
      CALL BERASE(IX,IY)
      ELSE
```

```
                  CALL FTLOCA(FY,FX)
                  CALL FTEXT('^   ^')
                  CALL FTSIZE(1,10)
            ENDIF
                  FY = IY + 1
                  IF (MM(FX,FY).NE.0) CALL REPLCE(FX,FY,0,0,0,0,0)
                  IF (MM(IX,FY).NE.0) CALL REPLCE(IX,FY,0,0,0,0,0)
                  FX = IX + 1
                  IF (MM(FX,FY).NE.0) CALL REPLCE(FX,FY,0,0,0,0,0)
            ELSE
      IF (IHP .EQ.1) THEN
      CALL BERASE(IX,IY)
      ELSE
                  CALL FTLOCA(FY,IX)
                  CALL FTEXT('^   ^')
                  CALL FTSIZE(1,10)
            ENDIF
                  FY = IY + 1
                  IF (MM(IX,FY).NE.0) CALL REPLCE(IX,FY,0,0,0,0,0)
               ENDIF
            ENDIF
            IF (LMM(IX,IY).GE.256) THEN
               MM(IX,IY) = 0
               FY = IY - 1
               CALL REPLCE(IX,FY,INKX,INKY,0,0,1)
            ELSE
               IF (MM(IX,IY).EQ.46) THEN
                  DO 515 I = 1,260
                     IF ((IX.EQ.LABL(I,1)).AND.(IY.EQ.LABL(I,2))) THEN
                        LABL(I,1) = -999
                        LABL(I,2) = -999
                        GO TO 516
                     ENDIF
515               CONTINUE
               ENDIF
516            CONTINUE
               IF (MM(IX,IY).EQ.34) THEN
                  DO 519 I = 1,NBD1
                     IF ((DSCNC(5,I).EQ.IX).AND.(DSCNC(6,I).EQ.IY)) THEN
                        DO 518 K = I,NBD1
                           DO 517 J = 1,6
                              IF (K.LT.50) THEN
                                 DSCNC(J,K) = DSCNC(J,K+1)
                              ELSE
                                 DSCNC(J,K) = 0
                              ENDIF
517                        CONTINUE
                           IF (DSCNC(K,2).EQ.0) THEN
                              NBD1 = NBD1 - 1
                              GO TO 520
                           ENDIF
518                     CONTINUE
                     ENDIF
519               CONTINUE
520               CONTINUE
               ENDIF
               MM(IX,IY) = 0
            ENDIF
         ENDIF
999      IX=IX+1
         IF (KHAR.EQ.8) IX=IX-2
C BACKUP ONE SPACE IF A DEL
         IF (KHAR.EQ.127) IX=IX-1
         IF (IX.LT.1) IX = 1
         ICUR = 1
         CALL CURSOR(IX,IY)
C Next character
         GOTO 100
200      ISMART=1
         ISTATE=0
C End graphics text mode
         CALL HEADER
         RETURN
         END
```

```
      SUBROUTINE BKSPCE(IX,IY)
      IMPLICIT INTEGER*2 (A-Z)
      INTEGER*4 MM,IDTPIX
      LOGICAL*2 FOUND
      CHARACTER*1 HALO(3),HLO(3)
      CHARACTER*3 HALOE
      EQUIVALENCE (HALOE,HALO(1))
      CHARACTER*1 KAN
      CHARACTER*1 ISTAT
      COMMON /CD/ MAXX,MAXY
      COMMON /RANGE/ LOX,HIX,LOY,HIY
      COMMON /STRPIX/ LPIX,MM(90,38),LBLEN,LNGBND(100,5)
      COMMON /STRED/ IDTPIX(90,38),LABL(260,2),MRKCHN(260)
      COMMON /HEAD/ MW(12),ISTATE,PAGE
      COMMON /CHARS/IES, IDOT,ITAG,JUMP,LBOND,KAN,ISPACE
      COMMON /MODES/ JBTYPE,ICHAR,IBDIR,IBTYPE,ISMART,MODE,ISKILL,ISP
      COMMON /HP/IHP
      COMMON /ISTATE/ ISTAT
      COMMON /IPLUS/ IHIGH(14,2)
      COMMON /SIZZE/ MULTX,MULTY
      COMMON /D1/ IDNUM,IDS(9,6),NBD1,DSCNC(6,50)
      COMMON /CUR/ ICUR
C
C  This routine, called when a backspace (Ctl-H, or ASCII 8) is typed
C  in.  Free text is entered onto he graphics screen and into the data
C  array MM. Any bond key 11 return you to regular input. Input of a *
C  will be interpreted in the analysis program as preceeding a dot-
C  disconnected substructure.
C
C Input character ASCII equiv; distinct from KAR.
      LEFT2 = 0
      ICUR = 1
      KHAR=0
      ISTAT='B'
      ISTATE=8
      CALL HEADER
      IX=IX-1
      IF (IX.LT.1) IX = 1
      CALL CURSOR(IX,IY)
      HALO(1) = KAN
      HALO(3) = KAN
10    CALL INPUTX(KHAR,IX,IY)
      IF ((LEFT2.NE.0).AND.((KHAR.LT.50).OR.(KHAR.GT.57))) THEN
          DO 2 I = LOX,HIX
             DO 2 J = LOY,HIY
                IF ((MM(I,J).EQ.43).OR.(MM(I,J).EQ.45)) THEN
                   IERR = 4
                   CALL MYERR(IERR,IERR,IERR)
                   MM(OX,OY) = 0
                   CALL FTLOCA(OY,OX)
                   CALL FTEXT('^ ^')
                   GO TO 3
                ENDIF
2         CONTINUE
          IERR = 28
          CALL MYERR(IERR,IERR,IERR)
          MM(OX,OY) = LEFT2
          LEFT2 = 0
          IX = IX - 1
          CALL CURSOR(IX,IY)
          GO TO 10
      ENDIF
3     CONTINUE
      LEFT2 = 0
      IF (IHP .EQ. 1 .AND. ((KHAR .GE. 22) .AND. (KHAR .LE. 31)))
     1   GO TO 20
      IF (KHAR.EQ.21) GO TO 20
      IF ((KHAR.LE.31).AND.(KHAR.GE.22).AND.(KHAR.NE.26).AND.(KHAR.NE.
     *   27)) THEN
          CALL MOVE(KHAR,IX,IY)
          MCHAR = 0
          GO TO 10
```

```
            ENDIF
            IF ((KHAR.GT.32).AND.(KHAR.NE.127)) THEN
                IF (MM(IX,IY).NE.0) THEN
                    ICUR = 0
                    CALL CURSOR(IX,IY)
                    HALO(2) = ' '
                    IF ((LMM(IX,IY).GE.256).AND.(MOD(IDIR(IX,IY),2).EQ.0))
     *              THEN
                        FX = FX - 1
      IF (IHP .EQ. 1) THEN
      CALL ERASE(IX,IY)
      ELSE
                        CALL FTLOCA(IY,FX)
                        CALL FTEXT('^    ^')
      ENDIF
                    IF (MM(FX,IY).NE.0) CALL REPLCE(FX,IY,0,0,0,0,0)
                    FX = IX + 1
                    IF (MM(FX,IY).NE.0) CALL REPLCE(FX,IY,0,0,0,0,0)
                    INKX = 1
                    INKY = 1
                ELSE
                    CALL FTLOCA(IY,IX)
                    CALL FTEXT(HALOE)
                    INKX = 0
                    INKY = 0
                ENDIF
                IF ((MM(IX,IY).EQ.46).OR.(LMM(IX,IY).GE.256).OR.
     *             ((MM(IX,IY).GE.50).AND.(MM(IX,IY).LE.57)).AND.
     *             ((LMM(IX-1,IY).NE.43).AND.(LMM(IX-1,IY).NE.45)).OR.
     *             (MM(IX,IY).EQ.103).OR.(MM(IX,IY).EQ.106).OR.(MM(IX,IY)
     *             .EQ.112).OR.(MM(IX,IY).EQ.113).OR.(MM(IX,IY).EQ.121)
     *             .OR.(MM(IX,IY).EQ.95).OR.(MM(IX,IY).EQ.44).OR.
     *             (MM(IX,IY).EQ.59)) THEN
                    IF (MOD((IY*10),40).EQ.0) THEN
                        IF ((IY.EQ.8).OR.(IY.EQ.28).OR.(IY.EQ.16)) THEN
                            FY = ((IY * 10) / 11) + 1
                            CALL FTSIZE(1,11)
                        ELSE
                            FY = ((IY * 10) / 9) + 1
                            CALL FTSIZE(1,9)
                        ENDIF
                    ELSE
                        FY = ((IY * 10) / 8) + 1
                        CALL FTSIZE(1,8)
                    ENDIF
                ENDIF
                IF ((LMM(IX,IY).GE.256).AND.(MOD(IDIR(IX,IY),2).EQ.0))
     *          THEN
                    FX = IX - 1
      IF (IHP .EQ. 1) THEN
      CALL ERASE(IX,IY)
      ELSE
                    CALL FTLOCA(FY,FX)
                    CALL FTEXT('^    ^')
                    CALL FTSIZE(1,10)
      ENDIF
                    FY = IY + 1
                    IF (MM(FX,FY).NE.0) CALL REPLCE(FX,FY,0,0,0,0,0)
                    IF (MM(IX,FY).NE.0) CALL REPLCE(IX,FY,0,0,0,0,0)
                    FX = IX + 1
                    IF (MM(FX,FY).NE.0) CALL REPLCE(FX,FY,0,0,0,0,0)
                ELSE
      IF (IHP .EQ. 1) THEN
      CALL ERASE(IX,IY)
      ELSE
                    CALL FTLOCA(FY,IX)
                    CALL FTEXT('^ ^')
                    CALL FTSIZE(1,10)
      ENDIF
                    FY = IY + 1
                    IF (MM(IX,FY).NE.0) CALL REPLCE(IX,FY,0,0,0,0,0)
                ENDIF
```

```
            ENDIF
            IF (LMM(IX,IY).GE.256) THEN
                MM(IX,IY) = 0
                FY = IY - 1
                CALL REPLCE(IX,FY,INKX,INKY,0,0,1)
            ENDIF
            ICUR = 1
            CALL CURSOR(IX,IY)
            IF (KHAR.GT.32) THEN
                IF (IX.LT.LOX) THEN
                    LOX = IX
                ELSE IF (IX.GT.HIX) THEN
                    HIX = IX
                ENDIF
                IF (IY.LT.LOY) THEN
                    LOY = IY
                ELSE IF (IY.GT.HIY) THEN
                    HIY = IY
                ENDIF
            ENDIF
            IF (KHAR.EQ.94) THEN
                HLO(1) = '/'
                HLO(2) = CHAR(KHAR)
                HLO(3) = '/'
                CALL TEXT(HLO)
            ELSE
                HALO(2) = CHAR(KHAR)
                CALL TEXT(HALO)
            ENDIF
        ENDIF
C
        IF (KHAR .NE. 43.AND.KHAR .NE. 45) GO TO 199
C
C       WE FOUND A + OR -    ... NOW FIND ITS NODE
C
C
C       The logical variable FOUND is set to TRUE when a node adjacent
C       to the charge is found.  The loop that searches for adjacent
C       nodes is continued until all positions adjacent to the charge
C       are checked to ensure the charge placement is not ambiguous.
C       If a second adjacent node is found, the charge is erased, an
C       error message prompting the user to use another position is
C       issued, and the loop is exited.
        FOUND = .FALSE.
C LOOK AROUND FOR NODE
        DO 50 I=-2,2
        DO 50 J=-1,1
C DON'T CHECK THIS BOX
        IF(I.EQ.0 .AND. J .EQ. 0) GO TO 50
        IIX=IX+I
        IIY=IY - J
        IF (((MM(IIX,IIY).GE.65).AND.(MM(IIX,IIY).LE.90)).OR.
     *      (MM(IIX,IIY).EQ.46)) GO TO 47
C CHECK FOR UC LETTER - IF WE FIND ONE - THEN CHECK
C FOR OTHER REQUIREMENTS
C ITS NOT A UC - CAN'T BE A NODE
        GO TO 50
C IF X = -2 THEN WE NEED UC FOLLOWED BY lc
47      IF ((I.EQ.-2).AND.(MM(IIX+1,IIY).GE. 97
     1   .AND. MM(IIX+1,IIY) .LE.122)) THEN
            IF (FOUND) THEN
                IERR = 42
                CALL MYERR(IERR,IERR,IERR)
                CALL FTLOCA(IY,IX)
                CALL FTEXT('^ ^')
                GO TO 999
            ENDIF
            II = -I
            JJ = J
            NIX = IIX
            NIY = IIY
            FOUND = .TRUE.
            GO TO 50
```

```
              ENDIF
C IF X=2 WE NEED DIGIT TO RIGHT OF CHARGE
              IF (I.EQ.-2) GO TO 50
49            IF (MM(IIX,IIY).NE.72) THEN
                  IF (FOUND) THEN
                      IERR = 42
                      CALL MYERR(IERR,IERR,IERR)
                      CALL FTLOCA(IY,IX)
                      CALL FTEXT('^ ^')
                      GO TO 999
                  ENDIF
                  II = -I
                  JJ = J
                  NIX = IIX
                  NIY = IIY
                  FOUND = .TRUE.
                  GO TO 50
              ENDIF
              IF (MM(IIX+1,IIY).GE.97.AND.MM(IIX+1,IIY).LE.122) THEN
                  IF (FOUND) THEN
                      IERR = 42
                      CALL MYERR(IERR,IERR,IERR)
                      CALL FTLOCA(IY,IX)
                      CALL FTEXT('^ ^')
                      GO TO 999
                  ENDIF
                  II = -I
                  JJ = J
                  NIX = IIX
                  NIY = IIY
                  FOUND = .TRUE.
                  GO TO 50
              ENDIF
C IF UC = H IT MUST BE FOLLOWED BY lc
50            CONTINUE
              IF (FOUND) GO TO 55
C CAN'T FIND NODE - CALL IT DELOCALIZED CHARGE
C         Check that there is only 1 delocalized charge.
              DO 4345 I = LOX,HIX
                  DO 4345 J = LOY,HIY
                      IF ((MM(I,J).NE.45).AND.(MM(I,J).NE.43)) GO TO 4345
                      IF (MM(I-1,J).NE.42) GO TO 4300
4345          CONTINUE
              GO TO 51
4300          IERR = 4
              CALL MYERR(IERR,IERR,IERR)
              CALL FTLOCA(IY,IX)
              CALL FTEXT('^ ^')
              IX = IX - 1
              GO TO 999
C CAN'T FIND NODE - CALL IT DELOCALIZED CHARGE
51            IERR=28
              CALL MYERR(IERR,KHAR,MAR)
              LEFT2 = 0
              GO TO 99
55            CONTINUE
              ICNT = 0
              DO 300 I = -2,2
                  DO 300 J = -1,1
                      IF ((LMM(NIX+I,NIY+J).NE.43).AND.(LMM(NIX+I,NIY+J).NE.45))
     *                    GO TO 300
                      ILC = IHMM(NIX+I,NIY+J)
                      IF (ILC.EQ.0) GO TO 300
                      IF ((I.NE.IHIGH(ILC,1)).OR.(J.NE.(-IHP)*IHIGH(ILC,2)))
     *                    GO TO 300
                      ICNT = ICNT + 1
                      PREX = NIX + I
                      PREY = NIY + J
300           CONTINUE
              IF (ICNT.EQ.0) GO TO 4500
              IERR = 38
              CALL MYERR(IERR,IERR,IERR)
              CALL FTLOCA(IY,IX)
```

```
              IF ((IX.NE.PREX).OR.(IY.NE.PREY)) THEN
                  CALL FTEXT('^ ^')
                  MM(IX,IY) = 0
              ELSE IF (LMM(IX,IY).EQ.43) THEN
                  CALL FTEXT('^+^')
              ELSE
                  CALL FTEXT('^-^')
              ENDIF
              IX = IX - 1
              GO TO 999
 4500         CONTINUE
              DO 56 I=1,14
                  KK = I
                  IF (IHIGH(I,1).EQ.II.AND.(-IHP)*IHIGH(I,2).EQ.JJ) THEN
                      IF (II.EQ.-2) THEN
                          LEFT2 = KHAR
                          OX = IX
                          OY = IY
                      ENDIF
                      GO TO 57
                  ENDIF
C LOOK UP NODE ASSOCIATOR IN IHIGH
 56           CONTINUE
C COULDN'T FIND ONE - CALL IT DELOCALIZED
              GO TO 51
C STORE SIGN WITH NODE ASSOCIATOR
 57           CONTINUE
              IF ((MM(IX,IY).EQ.43).OR.(MM(IX,IY).EQ.45)) THEN
                  CALL FTLOCA(IY,IX)
                  HALO(2) = CHAR(KHAR)
                  CALL FTEXT(HALOE)
                  CALL FTSIZE(2,18)
                  CALL FTLOCA(1,1)
                  PAGE = 0
                  CALL FTEXT('^CHARGE IS NOW LOCAL^')
                  CALL FTSIZE(1,10)
              ENDIF
              MM(IX,IY) = KHAR + KK*2**13
              GO TO 999
C
 199          CONTINUE
C
C             UNDETERMINED BOND SITE MARKER ENTRY.
C
              IF (KHAR.NE.34) GO TO 99
C The logical variable FOUND is set to TRUE when a node adjacent
C to the marker is found.  The loop that searches for adjacent
C nodes is continued until all positions adjacent to the marker
C are checked to ensure the charge placement is not ambiguous.
C If a second adjacent node is found, the marker is erased, an
C error message prompting the user to use another position is
C issued, and the loop is exited.
              FOUND = .FALSE.
              DO 150 I=-2,1
              DO 150 J=-1,1
C DON'T CHECK THIS BOX
              IF (I.EQ.0 .AND. J .EQ. 0) GO TO 150
              IIX=IX+I
              IIY=IY - J
              IF (((MM(IIX,IIY).GE.65).AND.(MM(IIX,IIY).LE.90)).OR.
     *            (MM(IIX,IIY).EQ.46)) GO TO 147
C CHECK FOR UC LETTER - IF WE FIND ONE - THEN CHECK
C FOR OTHER REQUIREMENTS
C ITS NOT A UC - CAN'T BE A NODE
C ITS NOT A UC - CAN'T BE A NODE
C             IF X = -2 THEN WE NEED UC FOLLOWED BY 1c
              GO TO 150
 147          IF ((I.EQ.-2).AND.(MM(IIX+1,IIY).GE. 97
     1          .AND. MM(IIX+1,IIY) .LE.122)) THEN
                  IF (FOUND) THEN
                      IERR = 42
                      CALL MYERR(IERR,IERR,IERR)
                      CALL FTLOCA(IY,IX)
```

```
                    CALL FTEXT('^ ^')
                    GO TO 999
                ENDIF
                II = -I
                JJ = J
                NIX = IIX
                NIY = IIY
                FOUND = .TRUE.
                GO TO 150
            ENDIF
            IF (I.EQ.-2) GO TO 150
149         IF (MM(IIX,IIY).NE.72) THEN
                IF (FOUND) THEN
                    IERR = 42
                    CALL MYERR(IERR,IERR,IERR)
                    CALL FTLOCA(IY,IX)
                    CALL FTEXT('^ ^')
                    GO TO 999
                ENDIF
                II = -I
                JJ = J
                NIX = IIX
                NIY = IIY
                FOUND = .TRUE.
                GO TO 150
            ENDIF
            IF (MM(IIX+1,IIY).GE.97.AND.MM(IIX+1,IIY).LE.122) THEN
                IF (FOUND) THEN
                    IERR = 42
                    CALL MYERR(IERR,IERR,IERR)
                    CALL FTLOCA(IY,IX)
                    CALL FTEXT('^ ^')
                    GO TO 999
                ENDIF
                II = -I
                JJ = J
                NIX = IIX
                NIY = IIY
                FOUND = .TRUE.
                GO TO 150
            ENDIF
C IF UC = H IT MUST BE FOLLOWED BY lc
150         CONTINUE
            IF (FOUND) GO TO 155
C CAN'T FIND NODE
151         IERR = 34
            CALL MYERR(IERR,IERR,IERR)
            CALL FTLOCA(IY,IX)
            CALL FTEXT('^ ^')
            IX = IX - 1
            GO TO 999
155         CONTINUE
C STORE SIGN WITH NODE ASSOCIATOR
            IF (NBD1.EQ.0) GO TO 157
C           Check for " already on this node.
            DO 527 I = 1,NBD1
                KK = I
                IF ((NIX.EQ.DSCNC(3,I)).AND.(NIY.EQ.DSCNC(4,I))) GO TO 892
527         CONTINUE
            GO TO 157
892         IERR = 47
            CALL MYERR(IERR,IERR,IERR)
            IF ((IX.NE.DSCNC(5,KK)).OR.(IY.NE.DSCNC(6,KK))) THEN
                CALL FTLOCA(IY,IX)
                CALL FTEXT('^ ^')
            ENDIF
            CALL FTLOCA(IY,IX)
            CALL FTEXT('^ ^')
            GO TO 999
157         MM(IX,IY) = KHAR
            NBD1 = NBD1 + 1
            DSCNC(3,NBD1) = NIX
            DSCNC(4,NBD1) = NIY
```

```
                DSCNC(5,NBD1) = IX
                DSCNC(6,NBD1) = IY
                IF (II.GE.1) THEN
                    IF (JJ.EQ.IHP) THEN
                        DSCNC(2,NBD1) = 2
                    ELSE IF (JJ.EQ.0) THEN
                        DSCNC(2,NBD1) = 3
                    ELSE
                        DSCNC(2,NBD1) = 4
                    ENDIF
                ELSE IF (II.EQ.0) THEN
                    IF (JJ.EQ.-IHP) THEN
                        DSCNC(2,NBD1) = 5
                    ELSE
                        DSCNC(2,NBD1) = 1
                    ENDIF
                ELSE
                    IF (JJ.EQ.-IHP) THEN
                        DSCNC(2,NBD1) = 6
                    ELSE IF (JJ.EQ.0) THEN
                        DSCNC(2,NBD1) = 7
                    ELSE
                        DSCNC(2,NBD1) = 8
                    ENDIF
                ENDIF
                GO TO 999
C Put KHAR into data array.
C TRANSLATE D1'S AND M1'S.
 99         IF ((KHAR.EQ.47).AND.(KHAR.LE.57).AND.((MM(IX-1,IY)
     *          .EQ.68).OR.(MM(IX-1,IY).EQ.77))) KHAR = KHAR + 63
            IF ((KHAR.GT.32).AND.(KHAR.NE.127)) THEN
                IF (MM(IX,IY).EQ.46) THEN
                    DO 505 I = 1,260
                        IF ((IX.EQ.LABL(I,1)).AND.(IY.EQ.LABL(I,2))) THEN
                            LABL(I,1) = -999
                            LABL(I,2) = -999
                            GO TO 506
                        ENDIF
 505                CONTINUE
                ENDIF
 506            CONTINUE
                MM(IX,IY) = KHAR
            ENDIF C Non printing chars
C ERASE CHAR - WE HAD A DEL
            IF (((KHAR.EQ.127).OR.(KHAR.EQ.32).OR.(KHAR.EQ.8)).AND.
     *          (MM(IX,IY).NE.0)) THEN
                ICUR = 0
                CALL CURSOR(IX,IY)
                HALO(2) = ' '
                IF ((LMM(IX,IY).GE.256).AND.(MOD(IDIR(IX,IY),2).EQ.0)) THEN
                    FX = IX - 1
                IF (IHP .EQ.1) THEN
                CALL ERASE(IX,IY)
                ELSE
                    CALL FTLOCA(IY,FX)
                    CALL FTEXT('^   ^')
                ENDIF
                    IF (MM(FX,IY).NE.0) CALL REPLCE(FX,IY,0,0,0,0,0)
                    FX = IX + 1
                    IF (MM(FX,IY).NE.0) CALL REPLCE(FX,IY,0,0,0,0,0)
                    INKX = 1
                    INKY = 1
                ELSE
                    CALL FTLOCA(IY,IX)
                    CALL FTEXT(HALOE)
                    INKX = 0
                    INKY = 0
                ENDIF
                IF ((MM(IX,IY).EQ.46).OR.(LMM(IX,IY).GE.256).OR.
     *              ((MM(IX,IY).GE.50).AND.(MM(IX,IY).LE.57)).AND.
     *              ((LMM(IX-1,IY).NE.43).AND.(LMM(IX-1,IY).NE.45)).OR.
     *              (MM(IX,IY).EQ.103).OR.(MM(IX,IY).EQ.106).OR.(MM(IX,IY)
     *              .EQ.112).OR.(MM(IX,IY).EQ.113).OR.(MM(IX,IY).EQ.121).OR.
```

```
*             (MM(IX,IY).EQ.95).OR.(MM(IX,IY).EQ.44).OR.(MM(IX,IY).EQ.
*        59)) THEN
             IF (MOD((IY*10),40).EQ.0) THEN
                 IF ((IY.EQ.8).OR.(IY.EQ.28).OR.(IY.EQ.16)) THEN
                     FY = ((IY * 10) / 11) + 1
                     CALL FTSIZE(1,11)
                 ELSE
                     FY = ((IY * 10) / 9) + 1
                     CALL FTSIZE(1,9)
                 ENDIF
             ELSE
                 FY = ((IY * 10) / 8) + 1
                 CALL FTSIZE(1,8)
             ENDIF
          ENDIF
          IF ((LMM(IX,IY).GE.256).AND.(MOD(IDIR(IX,IY),2).EQ.0))
*        THEN
             FX = IX - 1
      IF (IHP .EQ. 1) THEN
      CALL ERASE(IX,IY)
      ELSE
             CALL FTLOCA(FY,FX)
             CALL FTEXT('^    ^')
             CALL FTSIZE(1,10)
      ENDIF
             FY = IY + 1
             IF (MM(FX,FY).NE.0) CALL REPLCE(FX,FY,0,0,0,0,0)
             IF (MM(IX,FY).NE.0) CALL REPLCE(IX,FY,0,0,0,0,0)
             FX = IX + 1
             IF (MM(FX,FY).NE.0) CALL REPLCE(FX,FY,0,0,0,0,0)
          ELSE
      IF (IHP .EQ. 1) THEN
      CALL ERASE(IX,IY)
      ELSE
             CALL FTLOCA(FY,IX)
             CALL FTEXT(HALOE)
             CALL FTSIZE(1,10)
      ENDIF
             FY = IY + 1
             IF (MM(IX,FY).NE.0) CALL REPLCE(IX,FY,0,0,0,0,0)
          ENDIF
          IF (LMM(IX,IY).GE.256) THEN
             MM(IX,IY) = 0
             FY = IY - 1
             CALL REPLCE(IX,FY,INKX,INKY,0,0,1)
          ELSE
             IF (MM(IX,IY).EQ.46) THEN
                DO 515 I = 1,260
                   IF ((IX.EQ.LABL(I,1)).AND.(IY.EQ.LABL(I,2))) THEN
                      LABL(I,1) = -999
                      LABL(I,2) = -999
                      GO TO 516
                   ENDIF
515             CONTINUE
             ENDIF
516          CONTINUE
             IF (MM(IX,IY).EQ.34) THEN
                DO 519 I = 1,NBD1
                   IF ((DSCNC(5,I).EQ.IX).AND.(DSCNC(6,I).EQ.IY)) THEN
                      DO 518 K = I,NBD1
                         DO 517 J = 1,6
                            IF (K.LT.50) THEN
                               DSCNC(J,K) = DSCNC(J,K+1)
                            ELSE
                               DSCNC(J,K) = 0
                            ENDIF
517                      CONTINUE
                         IF (DSCNC(K,2).EQ.0) THEN
                            NBD1 = NBD1 - 1
                            GO TO 520
                         ENDIF
518                   CONTINUE
                   ENDIF
```

```
519            CONTINUE
520            CONTINUE
            ENDIF
            MM(IX,IY) = 0
         ENDIF
      ENDIF
C DEL WAS ENTERED
999   IX=IX+1
      IF (KHAR.EQ.8 ) IX=IX-2
C BACKUP ONE IF DEL
      IF (KHAR .EQ. 127) IX=IX-1
      IF (IX.LT.1) IX = 1
      ICUR = 1
      CALL CURSOR(IX,IY)
C Next char
      GOTO 10
20    ISMART=1
      ISTATE=0
      CALL HEADER
      RETURN
      END
$STORAGE:2
C
      SUBROUTINE REDRAW(IX,IY,INCX,INCY,NBTYPE)
      IMPLICIT INTEGER*2 (A-Z)
      REAL A
      INTEGER*4 MM,IDTPIX
      LOGICAL*2 RDBACK,SKIP,RETR
      CHARACTER*1 HALO(3)
      COMMON /CD/ MAXX,MAXY
      COMMON /IOFFST/IOFF
      COMMON /CHARS/IES, IDOT,ITAG,JUMP,LBOND,KAN,ISPACE
      COMMON /SIZZE/ MULTX,MULTY
      COMMON /MODES/ JBTYPE,ICHAR,IBDIR,IBTYPE,ISMART,MODE,ISKILL,ISP
      COMMON /STRPIX/ LPIX,MM(90,38),LBLEN,LNGBND(100,5)
      COMMON /BONDS/ A(5,3,4,4),B(2,3,4)
      COMMON /STRED/ IDTPIX(90,38),LABL(260,2),MRKCHN(260)
      COMMON /CUR/ ICUR
      COMMON /HP/IHP
CXT   RDBACK = TRUE indicates bond is being patched by SUBROUTINE DRAW.
      COMMON /PTCH/ RDBACK
CXT   SKIP = TRUE indicates a bond of type 0 is to skim over existing
CXT   bond.
      COMMON /BOSKIP/ SKIP
CXT   RETR is set in SUBROUTINE RETRIEVE to ensure proper screen
CXT   replacement activity with respect to arrays MM and IDTPIX.
      COMMON /RETDRW/ RETR
C
C This subroutine replaces existing bonds with bonds of a new type code.
C The parameter NBTYPE is the type of the old bond, the IBTYPE is that
C of the new one.  This routine is only called by DRAW when attempting
C to retrace an existing bond with one of a new bondtye.
C
C Existing bond direction.
      IF (RETR) THEN
         SKIP = .FALSE.
         RDBACK = .FALSE.
      ENDIF
      LX=IX
      LY=IY
      ICUR = 0
      CALL CURSOR(LX,LY)
C
C     Undraw existing bond:
100   CONTINUE
      IF ((.NOT.RDBACK).AND.(.NOT.SKIP)) THEN
         IF (IABS(INCX*INCY).EQ.1) THEN
      IF (IHP .EQ. 1) THEN
      CALL BERASE(LX,LY)
      ELSE
         FX = LX - 1
         CALL FTLOCA(LY,FX)
         CALL FTEXT('^    ^')
```

```
              ENDIF
          ELSE
              FX = LX
              CALL FTLOCA(LY,FX)
              CALL FTEXT('^ ^')
          ENDIF
      ENDIF
      CALL FTSIZE(1,10)
C
C     Close NLINES loop
C     If NBTYPE = 0 REDRAW just skims existing bond to next node
C     (IBTYPE = 0 and starting node is not a marker).
      IF (.NOT.SKIP) THEN
          IF (MM(LX,LY).GT.256) MM(LX,LY) = MM(LX,LY) * (-1)
          IF (MM(LX+INCX,LY+INCY).GT.256) MM(LX+INCX,LY+INCY) =
     *        MM(LX+INCX,LY+INCY) * (-1)
          CALL REPLCE(LX,LY,INCX,INCY,0,0,1)
      ENDIF
      LX = LX + INCX
      LY = LY + INCY
      IF (IABS(LMM(LX,LY)).GT.256) GO TO 100
      IF (SKIP) GO TO 645
      IF (INCY.NE.0) THEN
          FX = IX - INCX
          FY = IY - INCY
          CALL REPLCE(FX,FY,INCX,INCY,0,0,1)
          CALL REPLCE(LX,LY,INCX,INCY,0,0,1)
      ENDIF
      LX = IX
      LY = IY
200   CONTINUE
      IF (IBTYPE.EQ.0) GOTO 635
C
C     number of line segments req'd to draw bond--max 3
      NLINES=3
C     double bond needs 2 line segments
      IF (IBTYPE.EQ.2)    NLINES=2
      IF (IBTYPE.EQ.4) NLINES = 1
C     single or stereo
      IF ((MOD(IBTYPE,4).EQ.1)) NLINES=1
      define & select dashed line--stereo
      IF (IBTYPE.EQ.5) CALL SETLNS(2)
C
C     Conversion of bond type to first A array coordinate value IBOND:
      IBOND=1
      IF (IBTYPE.LE.3)    IBOND=IBTYPE
      IF (IBTYPE.EQ.4) IBOND = 1
      IF (IBTYPE.EQ.6)    IBOND=4
      IF (IBTYPE .EQ. 8) IBOND=3
      IF (IBTYPE.EQ.7)    IBOND=5
C
      JKL=IBDIR
      JKM = IBDIR
      IF (JKL.GT.4) JKL=JKL-4
      IF ((IBOND.GE.4).AND.(IBDIR.GT.4)) IBOND=9-IBOND
C
C
C     Start drawing the bond:
      NX=LX*MULTX - 8*IOFF
C     Screen coordinates of lower left corner of 7x10 area
      NY=LY*MULTY - 11*IOFF
C     Draw each segment separately
      DO 1153 J=1,NLINES
          IF (IBTYPE.EQ.8) THEN
              IF (J.EQ.1) THEN
                  CALL SETLNS(2)
              ELSE IF (J.EQ.2) THEN
                  CALL SETLNS(1)
              ELSE IF (J.EQ.3) THEN
                  CALL SETLNS(3)
              ENDIF
          ENDIF
```

```
C             Calc plotting coords
              IF (MOD(JKM,2).EQ.1) THEN
                  JKJ = JKL
                  IF ((IBOND.EQ.5).AND.(JKM.EQ.1)) THEN
                      BND = 4
                  ELSE IF ((IBOND.EQ.4).AND.(JKM.EQ.1)) THEN
                      BND = 5
                  ELSE
                      BND = IBOND
                  ENDIF
              ELSE
                  BND = IBOND
                  IF (JKL.EQ.2) THEN
                      JKJ = 4
                  ELSE IF (JKL.EQ.4) THEN
                      JKJ = 2
                  ENDIF
              ENDIF
              IF ((JKM.EQ.5).AND.((IBOND.EQ.4).OR.(IBOND.EQ.5))) THEN
                  IF (IBOND.EQ.4) THEN
                      BND = 2
                  ELSE
                      BND = 1
                  ENDIF
                  I1X = NX + B(BND,J,1)
                  I2X = NX + B(BND,J,2)
                  I1Y = NY + B(BND,J,3)
                  I2Y = NY + B(BND,J,4)
              ELSE
                  I1X = NX + A(BND,J,JKJ,1)
C                 I1X,I1Y = start
                  I2X = NX + A(BND,J,JKJ,3)
C                 I2X,I2Y = end
                  I1Y = NY + A(BND,J,JKJ,2)
                  I2Y = NY + A(BND,J,JKJ,4)
              ENDIF
C             Do the actual drawing here:
              CALL MOVABS(I1X,I1Y)
              CALL LNABS(I2X,I2Y)
C         Close NLINES loop
1153      CONTINUE
C         Replace old data in array.
CXT       Directional defaults for wedge bonds are set.
          IF ((IBTYPE.EQ.6).AND.((INCX.LT.0).OR.(INCX+INCY.LT.0)).AND.
     *        (.NOT.RDBACK)) THEN
              ZBTYPE = 7
              ZBDIR = IBDIR + 4
              IF (ZBDIR.GT.8) ZBDIR = ZBDIR - 8
          ELSE IF ((IBTYPE.EQ.7).AND.((INCX.LT.0).OR.(INCX+INCY.LT.0))
     *        .AND.(.NOT.RDBACK)) THEN
              ZBTYPE = 6
              ZBDIR = IBDIR + 4
              IF (ZBDIR.GT.8) ZBDIR = ZBDIR - 8
          ELSE
              ZBTYPE = IBTYPE
              ZBDIR = IBDIR
          ENDIF
          MM(LX,LY)=2**8*ZBTYPE + ZBDIR
          CALL SETLNS(1)
C         Return to solid linetype
635       CONTINUE
          IF (IBTYPE.EQ.0) MM(LX,LY) = 0
          LX=LX+INCX
          LY=LY+INCY
          IF (MM(LX,LY).LE.-256) GO TO 200
C         Do next piece of bond.
645       IF (RETR) THEN
              CALL VLNCE(1,IX,IY,0,0,IERR)
          ELSE
              CALL VALNCE(1,IX,IY,0,0)
          ENDIF
          IX = LX
          IY = LY
```

```
      IF (LBLEN.GT.0) CALL RELONG
      ICUR = 0
      CALL CURSOR(IX,IY)
      SKIP = .FALSE.
      RETURN
      END
C
      SUBROUTINE DRAW2(LX,LY,MBOND)
      IMPLICIT INTEGER*2 (A-Z)
      REAL A
      INTEGER*4 MM
      COMMON /CD/ MAXX,MAXY
C     LX represents MX, MX+1, NX, etc. as location of former H or subscript.
      COMMON /STRPIX/ LPIX,MM(90,38),LBLEN,LNGBND(100,5)
      COMMON /CHARS/IES, IDOT,ITAG,JUMP,LBOND,KAN,ISPACE
      COMMON /RANGE/ LOX,HIX,LOY,HIY
      COMMON /SIZZE/ MULTX,MULTY
      COMMON /IOFFST/IOFF
C     Line segments to draw bonds--see DRAW.
      COMMON /BONDS/ A(5,3,4,4),B(2,3,4)
C
C  This routine draws in individual bond segments at location LX,LY,
C  and of the form of bond MBOND.
C  It is patterned after the drawing routines in subroutine DRAW, but is
C  simplified, and is used primarily to fill in gaps in bonds of length
C  3 or more made when an H or numerical subscript is erased when
C  drawing a bond from a node in subroutine DRAW.
C
C  The type and direction of bond to be used as filler is supplied as
C  MBOND by the calling program.
C
C     END DRAWing if it isn't a bond.
      IF (MBOND.LT.256) RETURN
      IF (LX.LT.LOX) THEN
          LOX = LX
      ELSE IF (LX.GT.HIX) THEN
          HIX = LX
      ENDIF
      IF (LY.LT.LOY) THEN
          LOY = LY
      ELSE IF (LY.GT.HIY) THEN
          HIY = LY
      ENDIF
C     Extract bond type
      KBTYPE = MBOND/2**8
C     Extract bond direction
      KBDIR = MBOND - KBTYPE*2**8
C     Put data in permanent array
      MM(LX,LY) = MBOND
C
C  Conversion of bond type to the first coordinate of 'A' (drawing coordin-
C  ate array:
      IBOND=1
C     IBOND is 1st coord of A; max 5
      IF (KBTYPE.LE.3) IBOND=KBTYPE
C     Wedges:
      IF ((KBTYPE.EQ.6) .OR. (KBTYPE.EQ.7)) IBOND=KBTYPE-2
C
C     Number of line segments req'd to draw the bond-Max 3
      NLINES=3
C     single=1; double=2 line segments
      IF (IBOND.LE.2) NLINES=IBOND
C
C     Set line type if necessary to change:
C     Go to solid line type first
      CALL SETLNS(1)
C     Set dashed line for stereo down
      IF (KBTYPE.EQ.5) CALL SETLNS(2)
C
C     Correct direction error for wedge bond inherent in A array in DRAW:
      JKL=KBDIR
      JKM = KBDIR
      IF (JKL.GT.4) JKL=JKL-4
      IF ((IBOND.GE.4) .AND. (KBDIR.GT.4)) IBOND= 9 - IBOND
C
C     Start drawing the bond:
      NX=LX*MULTX - 8*IOFF
```

```
C       Screen coordinates of lower left corner of 7x10 area
        NY=LY*MULTY - 11*IOFF
        IF (KBTYPE.EQ.8) GO TO 40
C       Draw each segment separately
        DO 153 J=1,NLINES
            IF (MOD(JKM,2).EQ.1) THEN
                JKJ = JKL
                IF ((IBOND.EQ.5).AND.(JKM.EQ.1)) THEN
                    BND = 4
                ELSE IF ((IBOND.EQ.4).AND.(JKM.EQ.1)) THEN
                    BND = 5
                ELSE
                    BND = IBOND
                ENDIF
            ELSE
                BND = IBOND
                IF (JKL.EQ.2) THEN
                    JKJ = 4
                ELSE IF (JKL.EQ.4) THEN
                    JKJ = 2
                ENDIF
            ENDIF
            IF ((JKM.EQ.5).AND.((IBOND.EQ.4).OR.(IBOND.EQ.5))) THEN
                IF (IBOND.EQ.4) THEN
                    BND = 2
                ELSE
                    BND = 1
                ENDIF
                I1X = NX + B(BND,J,1)
                I2X = NX + B(BND,J,2)
                I1Y = NY + B(BND,J,3)
                I2Y = NY + B(BND,J,4)
            ELSE
C               Calc plotting coords
                I1X = NX + A(BND,J,JKJ,1)
C               I1X,I1Y = start
                I2X = NX + A(BND,J,JKJ,3)
C               I2X,I2Y = end
                I1Y = NY + A(BND,J,JKJ,2)
                I2Y = NY + A(BND,J,JKJ,4)
            ENDIF
C           Do the actual drawing here:
            CALL MOVABS(I1X,I1Y)
            CALL LNABS(I2X,I2Y)
C       Close NLINES loop
153     CONTINUE
        GO TO 70
C       DRAWING OF TYPE 8 BOND - WIGGLY LINE
C       draw each segment separately
40      DO 66 J=1,3
            IF (J.EQ.1) CALL SETLNS(2)
            IF (J.EQ.2) CALL SETLNS(1)
            IF (J.EQ.3) CALL SETLNS(3)
C           Calculate plotting
            IF (MOD(JKM,2).EQ.1) THEN
                JKJ = JKL
            ELSE
                IF (JKL.EQ.2) THEN
                    JKJ = 4
                ELSE IF (JKL.EQ.4) THEN
                    JKJ = 2
                ENDIF
            ENDIF
            I1X = NX + A(3,J,JKJ,1)
C           Coodinates;1=start
            I2X = NX + A(3,J,JKJ,3)
C           2=end
            I1Y = NY + A(3,J,JKJ,2)
            I2Y = NY + A(3,J,JKJ,4)
            CALL MOVABS(I1X,I1Y)
            CALL LNABS(I2X,I2Y)
66      CONTINUE
```

```
 70        CONTINUE
C          Return to solid linetype
           CALL SETLNS(1)
           RETURN
           END
C
           SUBROUTINE DRAW(KAR,IX,IY,INCX,INCY)
           IMPLICIT INTEGER*2 (A-Z)
           REAL A
           INTEGER*4 MM,IDTPIX,LLUP,LLDN
           LOGICAL*2 NEWO,PCROS,XCROS,RDBACK,BONDEL,SKIP,BARR,RETR,NEWDIR
           CHARACTER*1 HALO(3)
           CHARACTER*1 KAN
           CHARACTER*3 HALOE
           COMMON /CD/ MAXX,MAXY
           COMMON /IOFFST/ IOFF
           COMMON /RANGE/ LOX,HIX,LOY,HIY
           COMMON /CHARS/IES, IDOT,ITAG,JUMP,LBOND,KAN,ISPACE
           COMMON /SIZZE/ MULTX,MULTY
           COMMON /MODES/ JBTYPE,ICHAR,IBDIR,IBTYPE,ISMART,MODE,ISKILL,ISP
           COMMON /PARAMS/ JBDIR,NOCHG,LASTN,MCHAR,JCHAR,NLARGE,LEVEL
           COMMON /STRPIX/ LPIX,MM(90,38),LBLEN,LNGBND(100,5)
C          Relative coords for dwg bonds in 7x10 areas
           COMMON /BONDS/ A(5,3,4,4),B(2,3,4)
C          0,0 in lower left corner.
C          1st coord is bondtype (1=single,2=double,3=triple,4=wedge in,5=Out)
C          2nd coord is line segment # for dwg each bond (eg triple has 3segments)
C          3rd coord is bond direction, modulo 4 (up=1)
C          4th coord is Xstart,Ystart,Xend,Yend drawing coordinates.
           COMMON /LABELS/ NR,NJLAST,NJNEXT
           COMMON /HEAD/ MW(12),ISTATE,PAGE
           COMMON /STRED/ IDTPIX(90,38),LABL(260,2),MRKCHN(260)
           COMMON /WARN/ ERR
           COMMON /ITERM/ ITER
           COMMON /CUR/ ICUR
           COMMON /OLD/ IOX,IOY
CXT        OCUR is set by SUBROUTINES RING and CHAIN to darken cursor and
CXT        facilitate ring and chain bond drawing.
           COMMON /DARK/ OCUR
           COMMON /ELECHR/ IELEM(126,5)
CXT        RDBACK = TRUE indicates to SUBROUTINE REDRAW that a bond is
CXT        being patched.
           COMMON /PTCH/ RDBACK
CXT
CXT        NEWBND is set by SUBROUTINE REPEAT to indicate the drawing of a
CXT        new bond.
           COMMON /REPBND/ NEWBND
CXT
CXT        MLARGE is passed to SUBROUTINE VALNCE to note the distance between
CXT        the cursor and the node whose valence hydrogens are computed.
           COMMON /VLNPRV/ MLARGE
CXT
CXT        BONDEL = TRUE if a bond has been drawn between 2 nodes so a
CXT        subsequent deletion will delete the bond, not a node.
           COMMON /DELBND/ BONDEL
CXT
CXT        SKIP informs SUBROUTINE REDRAW that a retracing, not a replacing
CXT        of a bond with a bond of type 0 occurs.
           COMMON /BOSKIP/ SKIP
CXT
CXT        BARR in used in conjunction with NOCHG to set bond types in
CXT        relation to their defaults.
           COMMON /BTPDIR/ BARR
CXT
CXT        RETR is set by SUBROUTINE RETRIEVE to replace screen values
CXT        with SUBROUTINE REPLCE involving both array MM and array IDTPIX.
           COMMON /RETDRW/ RETR
C
           EQUIVALENCE (HALOE,HALO(1))
           HALO(1) = KAN
           HALO(3) = KAN
           IERR = 0
```

```
C Skip following code if not a bond.
      IF (ICHAR.NE.1) GO TO 10
      BEGX = IX
      BEGY = IY
      RETR = .FALSE.
      SKIP = .FALSE.
      RDBACK = .FALSE.
      NEWDIR = .FALSE.
      IF (MM(IX,IY).EQ.42) THEN
          IERR = 25
          CALL MYERR(IERR,IERR,IERR)
          ICHAR = JCHAR
          KAR = MCHAR
          IBDIR = JBDIR
          RETURN
      ENDIF
C X & Y increment depend on bond direction.
      INCY = -1*ITER
      IF ((IBDIR.GE.4).AND.(IBDIR.LE.6)) INCY = 1*ITER
      IF (MOD(IBDIR,4).EQ.3)   INCY=0
      INCX=1
      IF ((IBDIR.GE.6) .AND. (IBDIR.LE.8)) INCX=-1
      IF (MOD(IBDIR,4).EQ.1) INCX=0
C
      CALL CONTEX(KAR,IX,IY,INCX,INCY,IERR)
      IF (IERR.NE.48) GO TO 11448
      CALL MYERR(IERR,IERR,IERR)
      DBDIR = JBDIR
      CALL DELTA(DBDIR,INCX,INCY)
      IX = IOX
      IY = IOY
      IF (LMM(IX-INCX,IY-INCY).GE.256) THEN
          JCHAR = 1
          CALL DEL(KAR,IX,IY,INCX,INCY,0)
          JCHAR = 2
      ENDIF
      CALL CURSOR(IX,IY)
      ICHAR = JCHAR
      KAR = MCHAR
      IBDIR = JBDIR
      RETURN
C
11448 IF ((ICHAR.EQ.2).AND.(MCHAR.LT.0)) RETURN
      JIX = IX - INCX
      JIY = IY - INCY
      IF (MM(JIX,JIY).NE.0) GO TO 11446
      CALL MARK(KAR,JIX,JIY,IERR)
      IF (IERR.NE.48) GO TO 11446
          CALL MYERR(IERR,IERR,IERR)
          ICUR = 1
      IX=IOX
      IY=IOY
          CALL CURSOR(IX,IY)
          ICHAR = JCHAR
          KAR = MCHAR
          IBDIR = JBDIR
          RETURN
11446 CONTINUE
      NEWX = IX + INCX
      NEWY = IY + INCY
      IF ((NEWX.LE.0).OR.(NEWX.GT.MAXX).OR.(NEWY.LE.0).OR.
     *    (NEWY.GT.MAXY)) THEN
          IERR = 36
          CALL MYERR(IERR,KAR,KAR)
          IX = IOX
          IY = IOY
          CALL CURSOR(IX,IY)
          ICHAR = JCHAR
          KAR = MCHAR
          IBDIR = JBDIR
          RETURN
      ELSE IF ((MM(IX,IY).EQ.46).OR.((MM(IX,IY).GE.65).AND.
     *    (MM(IX,IY).LE.90).AND.(MM(IX,IY).NE.72).OR.
     *    ((MM(IX+1,IY).GE.97).AND.(MM(IX+1,IY).LE.122)))))
```

```
    *      THEN
           IERR = 40
           CALL MYERR(IERR,KAR,KAR)
           IX = IOX
           IY = IOY
           ICUR = 1
           CALL CURSOR(IX,IY)
           ICHAR = JCHAR
           KAR = MCHAR
           IBDIR = JBDIR
           RETURN
         ELSE IF (IBTYPE.EQ.0) THEN
           KX = IX
           KY = IY
987        IF (MM(KX,KY).EQ.0) THEN
             NEWO = .TRUE.
             GO TO 804
           ELSE IF (LMM(KX,KY).GT.256) THEN
             DIR = MM(KX,KY)
             IF (MOD(IDIR(DIR),4).EQ.MOD(IBDIR,4)) THEN
               NEWO = .FALSE.
             ELSE
               NEWO = .TRUE.
             ENDIF
           ELSE
             KX = KX + INCX
             KY = KY + INCY
             GO TO 987
           ENDIF
         ELSE
           NEWO = .FALSE.
         ENDIF
C     Ret bondtype to 1
         IF ((NOCHG.EQ.0).AND.(IBTYPE.NE.0).AND.(IBTYPE.NE.4).AND.
     2       (IBTYPE.NE.8)) IBTYPE=1
C            or newly-entered number
C
         IBOND = 1
         NLINES = 1
C number of line segments req'd to draw bond--max 3
         IF (IBTYPE.EQ.3) THEN
           NLINES=3
           IBOND = 3
C double bond needs 2 line segments
         ELSE IF (IBTYPE.EQ.2) THEN
           NLINES=2
           IBOND = 2
         ELSE IF (IBTYPE.EQ.6) THEN
           IBOND=4
           NLINES = 3
         ELSE IF (IBTYPE.EQ.7) THEN
           IBOND=5
           NLINES = 3
C single or stereo
         ELSE IF (IBTYPE.EQ.4) THEN
           GOTO 805
         ENDIF
C Following code (thru label 804) handles bond type 4:
C
C Conversion of bond type to first A array coordinate value IBOND:
C
         JKL=IBDIR
         JKM = IBDIR
         IF (JKL.GT.4) JKL=JKL-4
         IF ((IBOND.GE.4).AND.(IBDIR.GT.4)) IBOND=9-IBOND
         GOTO 804
805      KX=IX-INCX
         KY=IY-INCY
C Search around node
         DO 3 IDIRX=-1,1
         DO 3 IDIRY=-1,1
         IF ((IDIRX.EQ.0) .AND. (IDIRY.EQ.0)) GOTO 3
C Nearby array location to look for bonds
         NEWX=KX + IDIRX
         NEWY=KY + IDIRY
```

```
C Off the edge
802     IF ((NEWY.LT.1) .OR. (NEWY.GT.MAXY))  GOTO 3
        IF ((NEWX.LT.1) .OR. (NEWX.GT.MAXX))  GOTO 3
C Blank space
        IF (MM(NEWX,NEWY).EQ.0) GOTO 3
C Bonds are >256
        IF (LMM(NEWX,NEWY).GT.256)   GOTO 806
C Look beyond characters
        NEWY=NEWY+IDIRY
        NEWX=NEWX+IDIRX
        GOTO 802
C Bond extracted for type
806     JBOND=LMM(NEWX,NEWY)/2**8
C Not a double bond
        IF ((JBOND.NE.2).AND.(JBOND.NE.3)) GOTO 3
C Following 5 lines skip bonds not pointed to node being analyzed:
C Direction of bond
        JDIR=LMM(NEWX,NEWY)-JBOND*2**8
        IF ((IDIRX*IDIRY.EQ.-1).AND.(MOD(JDIR,4).NE.2)) GO TO 3
        IF ((IDIRX*IDIRY.EQ.1).AND.(MOD(JDIR,4).NE.0)) GO TO 3
        IF ((IDIRX.EQ.0)  .AND. (MOD(JDIR,4).NE.1)) GOTO 3
        IF ((IDIRY.EQ.0)  .AND. (MOD(JDIR,4).NE.3)) GOTO 3
        NLINES=1
        IBOND=1
        JKL = IBDIR
        JKM = IBDIR
        IF (JKL.GT.4) JKL = JKL - 4
        GOTO 803
3       CONTINUE
C
C See if there exists a double or triple longbond at this node
C
        DO 40 I=0,2,2
        DO 4141 J=1,100
        IF (LNGBND(J,I+1) .EQ. 0) GO TO 40
        IF ((LNGBND(J,I+1) .NE. KX) .OR.
     1  (LNGBND(J,I+2) .NE. KY)) GO TO 4141
        IF (LNGBND(J,5) .NE. 2 .AND. LNGBND(J,5) .NE. 3) GO TO 4343
        IBOND=1
        NLINES=1
        GO TO 44
4141    CONTINUE
40      CONTINUE
C
4343    IBOND=2
        NLINES=2
44      JKL=IBDIR
        JKM = IBDIR
        IF (JKL.GT.4) JKL=JKL-4
803     IF (LMM(IX-INCX,IY-INCY).LE.256) GOTO 804
C Bond type of immediate preceeding.
        IBT4=LMM(IX-INCX,IY-INCY)/2**8
C       bond, if no dot or marker interposed.
        IBOND=IBT4
        NLINES=IBT4
C Check for DOTDIS structure.
804     CONTINUE
        DO 444 JJ = 1,MAXX
        IF ((MM(BEGX-JJ,BEGY).EQ.0).OR.(LMM(BEGX-JJ,BEGY).GE.256).OR.
     *  (BEGX-JJ.LE.0)) THEN
            GO TO 445
        ELSE IF (MM(BEGX-JJ,BEGY).EQ.42) THEN
            IERR = 25
            CALL MYERR(IERR,IERR,IERR)
            IX = IOX
            IY = IOY
            KAR = MCHAR
            ICHAR = JCHAR
            IBDIR = JBDIR
            CALL SETLNS(1)
            ICUR = 1
            CALL CURSOR(IX,IY)
            RETURN
        ENDIF
```

```
444     CONTINUE
445     CONTINUE
C
C
C Start drawing bonds:
C Enlargement factor NLARGE
        DO 5 I = 1,NLARGE
            II = I
            ICUR = 0
            CALL CURSOR(IX,IY)
C Don't do any redrawing if retracing your path.
C Null bond type
        IF ((IBTYPE.EQ.0).AND.(.NOT.NEWO)) THEN
            IF (I.EQ.1) THEN
                KX = IX - INCX
                KY = IY - INCY
                CALL CLRHYD(KX,KY)
            ENDIF
            GO TO 7777
        ENDIF
C Only eliminate H's once.
        IF (I.GT.1) GO TO 1236
C Erease all H's & subscripts.
        KX=IX-INCX
        KY=IY-INCY
C Only a nodes
        IF ((MM(KX,KY).LT.65) .OR. (MM(KX,KY).GT.90)) GOTO 43
C
        CALL CLRHYD(KX,KY)
C
C At this point filler H's are removed; IX and IY are
C poised at first position for new (or retraced) bond. If MM(IX,IY)=0,
C skip to 41 & just draw the bond.  If not, glide along it to next
C node or empty space, reset ICHAR accordingly, and leave this subroutine:
C Move one right if 2-letter element & bond dir=3
43      IF ((IBDIR.EQ.3).AND.(MM(IX,IY).GE.97).AND.(MM(IX,IY).LE.122))
     2    IX=IX+1
        IXX=IX
        IYY=IY
        IF (MM(IX,IY).EQ.0) GOTO 1232
C Save first position of bond being traced over
C Existing bond type
        DIR = LMM(IX,IY)
CXT
CXT
        IF ((DIR.LT.256).OR.(MOD(IBDIR,4).NE.MOD(IDIR(DIR),4))) GO TO 52
CXT
        NBTYPE=DIR/2**8
C Following line takes care of wedge in-from looks like wedge out-to.
        IF ((NBTYPE*IBTYPE.EQ.36).OR.(NBTYPE*IBTYPE.EQ.49)) GOTO 75
C Don't redraw if same bondtype
        IF ((NBTYPE.EQ.IBTYPE).OR.((OCUR.EQ.0).AND.(.NOT.BARR))) THEN
            IF (OCUR.EQ.0) NEWDIR = .TRUE.
            GOTO 52
        ENDIF
        IF (IBTYPE.EQ.4 .AND.(NBTYPE.EQ.2.OR.NBTYPE.EQ.1))GOTO 52
C Don't redraw if bondtype = alternating and existing bond is single or
C double.
C These 4 lines of code allow change of bond
75      DO 123 K=1,260
C Type only if starting a marker.
        IF (LABL(K,1).EQ.0) GOTO 52
        IF ((KX.EQ.LABL(K,1)).AND.(KY.EQ.LABL(K,2))) GOTO 74
123     CONTINUE
C Redraw new bond 'over' old
74      CONTINUE
        IF (LMM(KX+INCX,KY+INCY).GE.256) THEN
            CALL REDRAW(IX,IY,INCX,INCY,NBTYPE)
            IF (OCUR.EQ.1) NOCHG = 0
C Don't increment past first bond segment first time.
            GOTO 52
        ELSE
            IX = KX
            IY = KY
        ENDIF
```

```
C Track along bond till its end
51         CONTINUE
           IX=IX+INCX
           IY=IY+INCY
C Shorthand for seeing what is on bond's track
52         CONTINUE
           LL=LMM(IX,IY)
           L2=LMM(IX+1,IY)
      IF ((LL.EQ.43).OR.(LL.EQ.45).OR.(LL.EQ.34).OR.
     *    ((LL.GE.49).AND.(LL.LE.57).AND.((MOD(IBDIR,4).NE.3).OR.
     *    (MM(IX-1,IY).NE.72)))) THEN
           IERR = 45
           CALL MYERR(IERR,IERR,IERR)
           IF (LMM(IX-INCX,IY-INCY).GE.256) THEN
               JCHAR = 1
               CALL DEL(KAR,IX,IY,INCX,INCY,0)
               JCHAR = 2
           ELSE
               IX = IOX
               IY = IOY
           ENDIF
           ICUR = 1
           CALL CURSOR(IX,IY)
           KAR = MCHAR
           ICHAR = JCHAR
           IBDIR = JBDIR
           CALL SETLNS(1)
           RETURN
       ENDIF
825    CONTINUE
C See if bond intersection is on bond path.
       IF ((LL.GT.256).AND.(MOD(IBDIR,4).NE.MOD(IDIR(LL),4))) THEN
           IERR = 23
           CALL MYERR(IERR,IERR,IERR)
           IF ((LMM(IX-INCX,IY-INCY).GE.256).AND.
     *         ((LMM(IX,IY).GE.256).OR.(MM(IX,IY).EQ.0))) THEN
               JCHAR = 1
               CALL DEL(KAR,IX,IY,INCX,INCY,0)
               JCHAR = 2
           ELSE
               IX = IOX
               IY = IOY
           ENDIF
           KAR = MCHAR
           ICHAR = JCHAR
           IBDIR = JBDIR
           CALL SETLNS(1)
           ICUR = 1
           CALL CURSOR(IX,IY)
           RETURN
       ENDIF
C Following line bypasses bond segments, numerals, lowercase, and H's
C not followed by lowercases, inorder to find the 'other' end of bond:
       IF (((LL.NE.0).AND.(LL.NE.46).AND.(LL.NE.63).AND.(LL.LT.65))
     *     .OR.(LL.GT.90).OR.((LL.EQ.72).AND.((L2.LT.97).OR.
     *     (L2.GT.122)))) GO TO 51
       CALL VALNCE(2,IXX,IYY,INCX,INCY)
       ICUR = 1
       CALL CURSOR(IX,IY)
C Bond tracked to empty slot.
       IF (MM(IX,IY).EQ.0) THEN
           CALL SETLNS(1)
           RETURN
       ENDIF
C New location is already a node
       ICHAR=2
       IF (IBTYPE.NE.0) BONDEL = .TRUE.
C This part of code simulates IDENT.
       KAR=LMM(IX,IY)
C Tentative location, as if after typing uppercase.
       IX=IX+1
       CALL CURSOR(IX,IY)
       CALL SETLNS(1)
       RETURN
C Back to jam mode
```

```
1232    CONTINUE
        DISTX = NLARGE * INCX + IX
        DISTY = NLARGE * INCY + IY
        IF ((DISTX.GE.2).AND.(DISTX.LT.MAXX).AND.(DISTY.GE.2).AND.
     *      (DISTY.LT.MAXY)) GO TO 1235
        IF (((IX.LE.1).AND.(IBDIR.GE.6)).OR.((IY.GE.MAXY).AND.
     *      (IBDIR.GE.4).AND.(IBDIR.LE.6)).OR.((IY.LE.1).AND.
     *      ((IBDIR.LE.2).OR.(IBDIR.EQ.8))).OR.((IX.GE.MAXX).AND.
     *      (IBDIR.GE.2).AND.(IBDIR.LE.4)).OR.
     *      (DISTX.GT.MAXX).OR.(DISTX.LT.1).OR.(DISTY.GT.MAXY).OR.
     *      (DISTY.LT.1)) THEN
            IF (((MM(IOX,IOY).LT.256).AND.(NLARGE.EQ.1).AND.
     *          (DISTX.LT.1).AND.(IOX.EQ.2).AND.(IBDIR.GE.6)).OR.
     *          ((DISTY.LT.1).AND.(IY.LE.2).AND.((IBDIR.LE.2).OR.
     *          (IBDIR.EQ.8)))) THEN
                GO TO 1233
            ELSE IF ((NLARGE.EQ.1).AND.(JCHAR.EQ.1).AND.
     *          (IBDIR.EQ.JBDIR).AND.(IBTYPE.EQ.JBTYPE)) THEN
                IF ((IBDIR.GE.4).AND.(IBDIR.LE.6).AND.
     *              (DISTY.LE.MAXY)) GO TO 1234
                IF ((DISTX.LT.1).OR.(DISTX.GE.MAXX).OR.(DISTY.LT.1)
     *              .OR.(DISTY.GT.MAXY)) GO TO 1233
            ENDIF
            IF ((IY.LE.1).AND.((DISTX.LE.1).OR.(DISTX.GE.MAXX)))
     *          THEN
                GO TO 1233
            ELSE IF ((IY.GE.MAXY).AND.((DISTX.LE.1).OR.
     *          (DISTX.GE.MAXX))) THEN
                GO TO 1233
            ELSE IF ((IX.LE.1).AND.((DISTY.LE.1).OR.(DISTY.GE.MAXY)))
     *          THEN
                GO TO 1233
            ELSE IF ((IX.GE.MAXX).AND.((DISTY.LE.1).OR.
     *          (DISTY.GE.MAXY))) THEN
                GO TO 1233
            ENDIF
            IF (((IX.GE.MAXX).OR.(IX.LE.1)).AND.(INCX.EQ.0))
     *          GO TO 1234
            IF (((IY.GE.MAXY).OR.(IY.LE.1)).AND.(INCY.EQ.0))
     *          GO TO 1234
1233        CALL MYERR(36,KAR,KAR)
            IX = IOX
            IY = IOY
            ICUR = 1
            CALL CURSOR(IX,IY)
            ICHAR = JCHAR
            KAR = MCHAR
            IBDIR = JBDIR
            CALL SETLNS(1)
            RETURN
1234        CONTINUE
        ENDIF
1235    CONTINUE
C
C The drawing of overlapping bonds is prevented.
        GIX = IX
        GIY = IY
        XCROS = .FALSE.
        PCROS = .FALSE.
1237    CONTINUE
        GOX = GIX + 1
        NOX = GIX - 1
        GOY = GIY + 1
        NOY = GIY - 1
C
C This segment prevents the overlapping of diagonal bonds when one
C node lies adjacent to a non attaching bond. OCUR is checked to
C disable the segment during chain and ring drawing.
        DIR1 = LMM(GOX,GIY)
        DIR2 = LMM(GIX,GOY)
        DIR3 = LMM(NOX,GIY)
        DIR4 = LMM(GIX,NOY)
        IF ((OCUR.EQ.1).AND.((MM(GIX,GIY).EQ.0).OR.(LMM(GIX,GIY).GT.256))
     *      .AND.(MOD(IBDIR,2).EQ.0).AND.
     *      (((DIR1.GE.256).AND.
     *      (MOD(IDIR(DIR1),2).EQ.0).AND.
```

```
     *    (MOD(IBDIR,4).NE.MOD(IDIR(DIR1),4))).OR.
     *    ((DIR2.GE.256).AND.
     *    (MOD(IDIR(DIR2),2).EQ.0).AND.
     *    (MOD(IBDIR,4).NE.MOD(IDIR(DIR2),4))).OR.
     *    ((DIR3.GE.256).AND.
     *    (MOD(IDIR(DIR3),2).EQ.0).AND.
     *    (MOD(IBDIR,4).NE.MOD(IDIR(DIR3),4))).OR.
     *    ((DIR4.GE.256).AND.
     *    (MOD(IDIR(DIR4),2).EQ.0).AND.
     *    (MOD(IBDIR,4).NE.MOD(IDIR(DIR4),4)))))
     *    XCROS = .TRUE.
C
C Diagonal overlaps are prevented.
          IF (PCROS) XCROS = .TRUE.
          DIR1 = LMM(GIX,GIY+INCX)
          DIR2 = LMM(GIX+INCX,GIY)
          IF ((MOD(IBDIR,2).EQ.0).AND.
     *    (((DIR1.GE.256).AND.
     *    (MOD(IDIR(DIR1),2).EQ.0).AND.
     *    (MOD(IBDIR,4).NE.MOD(IDIR(DIR1),4))).OR.
     *    ((DIR2.GE.256).AND.
     *    (MOD(IDIR(DIR2),2).EQ.0).AND.
     *    (MOD(IBDIR,4).NE.MOD(IDIR(DIR2),4)))))
     *    PCROS = .TRUE.
          IF (IBDIR.EQ.7) THEN
             GX = GIX - 1
          ELSE
             GX = GIX
          ENDIF
C
C Attempted overlap meets error message.
          IF (((MM(GX,GIY).NE.0).OR.(XCROS)).AND.((ISTATE.NE.9).OR.
     *    ((ISTATE.EQ.9).AND.(NEWBND.EQ.1)))) THEN
             DIR1 = LMM(GX,GIY)
             DIR2 = LMM(GX-2*INCX,GIY-2*INCY)
             IF (((DIR1.GE.256).AND.(MOD(IBDIR,4).NE.MOD(IDIR(DIR1),4)))
     *       .OR.XCROS) THEN
                IERR = 23
                CALL MYERR(IERR,IERR,IERR)
                IF (OCUR.EQ.0) GO TO 1239
                IF ((LMM(IX-INCX,IY-INCY).GE.256).AND.
     *          ((LMM(IX,IY).GE.256).OR.(MM(IX,IY).EQ.0))) THEN
                   JCHAR = 1
                   CALL DEL(KAR,IX,IY,INCX,INCY,0)
                   JCHAR = 2
                ELSE
                   IX = IOX
                   IY = IOY
                ENDIF
                KAR = MCHAR
                ICHAR = JCHAR
                IBDIR = JBDIR
                CALL SETLNS(1)
                ICUR = 1
                CALL CURSOR(IX,IY)
                RETURN
C Check for need of bond patching.
             ELSE IF ((DIR1.GE.256).AND.(DIR2.GE.256).AND.
     *       (MOD(IDIR(DIR1),4).EQ.MOD(IDIR(DIR2),4)).AND.
     *       ((DIR1/256.EQ.DIR2/256).OR.((DIR1/256+DIR2/256.EQ.13).AND.
     *       ((DIR1/256.EQ.6).OR.(DIR2/256.EQ.6))))) THEN
                IBTYPE = DIR2 / 256
                NBTYPE = DIR1 / 256
                MM(GX-INCX,GIY-INCY) = DIR2
                DBDIR = IDIR(DIR2)
                CALL DELTA(DBDIR,INCX,INCY)
                IBDIR = DBDIR
                DO 3400 LL = 1,MAXX
                   LX = GX - LL*INCX
                   LY = GIY - LL*INCY
                   IF ((MM(LX,LY).EQ.0).OR.(MM(LX,LY).EQ.46).OR.
     *             (MM(LX,LY).EQ.63).OR.((MM(LX,LY).GE.65).AND.
     *             (MM(LX,LY).LE.90))) THEN
                      IX = LX + INCX
```

```
                    IY = LY + INCY
                    GO TO 3410
                ENDIF
3400        CONTINUE
3410        CONTINUE
            RDBACK = .TRUE.
            CALL REDRAW(IX,IY,INCX,INCY,NBTYPE)
            CALL VALNCE(2,LX,LY,INCX,INCY)
            CALL SETLNS(1)
            ICUR = 1
            CALL CURSOR(IX,IY)
            RETURN
        ENDIF
1239    CONTINUE
        ENDIF
        GIX = GIX + INCX
        GIY = GIY + INCY
        IF ((GIX.EQ.DISTX+INCX).AND.(GIY.EQ.DISTY+INCY)) GO TO 1238
        IF ((MM(GIX,GIY).GT.0).AND.(MM(GIX,GIY).LT.256)) GO TO 1238
        GO TO 1237
1238    CONTINUE
        IF (DISTX.LT.LOX) THEN
            LOX = DISTX
        ELSE IF (DISTX.GT.HIX) THEN
            HIX = DISTX
        ENDIF
        IF (DISTY.LT.LOY) THEN
            LOY = DISTY
        ELSE IF (DISTY.GT.HIY) THEN
            HIY = DISTY
        ENDIF
1236    CONTINUE
        IF (NEWO) THEN
            IF (I.EQ.1) THEN
                GIX = DISTX
                GIY = DISTY
            ENDIF
            GO TO 778
        ENDIF
C Draw in jam mode, solid line.
        CALL SETMOD(4)    !Set JAM mode
        CALL SETLNS(1)
C Define & select dashed line--stereo
        IF (IBTYPE.EQ.5) CALL SETLNS(2)
C Scale to graphic coordinates
        NX = IX * MULTX -  8*IOFF
        NY = IY * MULTY - 11*IOFF
        IF (IBTYPE .EQ. 8) GO TO 77
C       Draw each segment separately
C
        DO 6 J=1,NLINES
            IF (MOD(JKM,2).EQ.1) THEN
                IF ((IBTYPE.EQ.6).AND.(JKM.EQ.1)) THEN
                    BND = 5
                ELSE IF ((IBTYPE.EQ.7).AND.(JKM.EQ.1)) THEN
                    BND = 4
                ELSE
                    BND = IBOND
                ENDIF
                IF ((JKM.EQ.5).AND.((IBTYPE.EQ.6).OR.(IBTYPE.EQ.7))) THEN
                    IF (IBOND.EQ.4) THEN
                        BND = 2
                    ELSE
                        BND = 1
                    ENDIF
                    I1X = NX + B(BND,J,1)
                    I2X = NX + B(BND,J,2)
                    I1Y = NY + B(BND,J,3)
                    I2Y = NY + B(BND,J,4)
                ELSE
C           Calculate plotting
                    I1X=NX + A(BND,J,JKL,1)
C           Coodinates;1=start
                    I2X=NX + A(BND,J,JKL,3)
C           2=end
```

```
                    I1Y=NY + A(BND,J,JKL,2)
                    I2Y=NY + A(BND,J,JKL,4)
                ENDIF
                CALL MOVABS(I1X,I1Y)
                CALL LNABS(I2X,I2Y)
            ELSE
                IF (JKL.EQ.2) THEN
                    JKJ = 4
                ELSE IF (JKL.EQ.4) THEN
                    JKJ = 2
                ENDIF
                I1X = NX + A(IBOND,J,JKJ,1)
                I2X = NX + A(IBOND,J,JKJ,3)
                I1Y = NY + A(IBOND,J,JKJ,2)
                I2Y = NY + A(IBOND,J,JKJ,4)
                CALL MOVABS(I1X,I1Y)
                CALL LNABS(I2X,I2Y)
            ENDIF
C Draw bond line segment
6       CONTINUE
        GO TO 777
C
C DRAWING OF TYPE 8 BOND - WIGGLY LINE
C Draw each segment separately
77      DO 66 J=1,3
            IF (J.EQ.1) CALL SETLNS(2)
            IF (J.EQ.2) CALL SETLNS(1)
            IF (J.EQ.3) CALL SETLNS(3)
            IF (MOD(JKM,2).EQ.1) THEN
C               Calculate plotting
                I1X=NX + A(3,J,JKL,1)
C               coodinates;1=start
                I2X=NX + A(3,J,JKL,3)
C               2=end
                I1Y=NY + A(3,J,JKL,2)
                I2Y = NY + A(3,J,JKL,4)
                CALL MOVABS(I1X,I1Y)
                CALL LNABS(I2X,I2Y)
            ELSE
                IF (JKL.EQ.2) THEN
                    JKJ = 4
                ELSE IF (JKL.EQ.4) THEN
                    JKJ = 2
                ELSE
                    JKJ = JKL
                ENDIF
                I1X = NX + A(3,J,JKJ,1)
                I2X = NX + A(3,J,JKJ,3)
                I1Y = NY + A(3,J,JKJ,2)
                I2Y = NY + A(3,J,JKJ,4)
                CALL MOVABS(I1X,I1Y)
                CALL LNABS(I2X,I2Y)
            ENDIF
66      CONTINUE
C
C Calculate 256(bond type1-8) + (bond direction) for storage in MM array.
C This is NOT the format required by the analysis program.
777     CONTINUE
        IF (IBTYPE.NE.4) THEN
C           Directional defaults for wedge bonds are set.
CXT         IF ((IBTYPE.EQ.6).AND.((INCX.LT.0).OR.
    *           (INCX+INCY.LT.0))) THEN
                ZBTYPE = 7
                ZBDIR = IBDIR + 4
                IF (ZBDIR.GT.8) ZBDIR = ZBDIR - 8
            ELSE IF ((IBTYPE.EQ.7).AND.((INCX.LT.0).OR.
    *           (INCX+INCY.LT.0))) THEN
                ZBTYPE = 6
                ZBDIR = IBDIR + 4
                IF (ZBDIR.GT.8) ZBDIR = ZBDIR - 8
            ELSE
                ZBTYPE = IBTYPE
                ZBDIR = IBDIR
            ENDIF
            MM(IX,IY) = 2**8*ZBTYPE + ZBDIR
        ELSE
```

```
              MM(IX,IY)=2**8*IBOND + IBDIR
            ENDIF
C Analysis pgm has direc UP=DOWN=0 & max 3 [here UP=1, max 8 incr clkwise]
C Analysis pgm recognizes only 3 incoming bond types:single,double;trple
C chain(5,6,7) and converts some to tautomer(8), ring(1-3) etc. Here,
C bond types include stereo wedge bonds (6,7), dotted stereo(5),etc.
C
7         CONTINUE
C Move location counters
778       IX = IX + INCX
          IY = IY + INCY
C
          IF (((IX.EQ.GIX).AND.(IY.EQ.GIY)).OR.(MM(IX,IY).GT.0)) THEN
            MLARGE = I
            IF (MM(IX,IY).GT.0) NOCHG = 0
            GO TO 5555
          ENDIF
C Close NLARGE loop
5         CONTINUE
C
C
5555      CONTINUE
C Restore H('s)
          CALL VALNCE(1,IX,IY,INCX,INCY)
7777      CONTINUE
C
CXT Bond type 0 overskipping an existing bond (from a non-marker) occurs.
          IF ((IBTYPE.NE.0).OR.(NEWO)) GOTO 7778
          ICUR = 0
          CALL CURSOR(IX,IY)
C Only erase bond if starting at marker
          DO 779 K=1,260
C
          IF ((IX-INCX.EQ.LABL(K,1)).AND.(IY-INCY.EQ.LABL(K,2)))
     *      THEN
            GO TO 780
          ELSE IF ((LABL(K,1).EQ.0).OR.(K.EQ.260)) THEN
            SKIP = .TRUE.
            GO TO 780
          ENDIF
779       CONTINUE
C This code skipped above
780       NBTYPE=LMM(IX,IY)/2**8
C
          IXX = KX + INCX
          IYY = KY + INCY
C When IBTYPE=0
          CALL REDRAW(IX,IY,INCX,INCY,NBTYPE)
          IF (OCUR.EQ.1) NOCHG = 0
          IF ((NBTYPE.GT.0).AND.(IBTYPE.EQ.0))
     *      CALL VALNCE(2,IXX,IYY,INCX,INCY)
C
7778      CONTINUE
          DO 1444 JJ = 0,MAXX
          IF ((MM(IX-JJ,IY).EQ.0).OR.(LMM(IX-JJ,IY).GE.256).OR.
     *      (IX-JJ.EQ.0)) THEN
            GO TO 1445
          ELSE IF (MM(IX-JJ,IY).EQ.42) THEN
            IERR = 25
            CALL MYERR(IERR,IERR,IERR)
            JCHAR = 1
            CALL DEL(KAR,IX,IY,INCX,INCY,0)
            JCHAR = 2
            KAR = MCHAR
            ICHAR = JCHAR
            IBDIR = JBDIR
            CALL SETLNS(1)
            ICUR = 1
            CALL CURSOR(IX,IY)
            RETURN
          ENDIF
1444      CONTINUE
1445      CONTINUE
```

```
C Following lines (through label 55) look for existing node @ end
C of newly drawn bond:
      IF (MM(IX,IY).EQ.0) GOTO 55
      MIX=IX
C SAVE OLD IX AND IY IN CASE WE CAN'T FIND NODE
      MIY=IY
56    LL=LMM(IX,IY)
      L2=LMM(IX+1,IY)
      L3 = LMM(IX+INCX,IY)
      IF ((LL.GT.0).AND.((LL.LE.48).AND.(LL.NE.46))) GO TO 5557
      IF ((LL.GE.97).AND.(LL.LE.122).AND.((MM(IX-1,IY).LT.65).OR.
     *    (MM(IX-1,IY).GT.90).OR.(IBDIR.NE.7)))
     *    GO TO 5557
C     Various ways to approach and identify node vs. non-node.
      IF (((LL.GE.65).AND.(LL.LE.90).AND.(LL.NE.72)) .OR. (LL.EQ.46)
     2    .OR. (LL.EQ.63) .OR. ((LL.EQ.72).AND.(L2.GE.97).AND.(L2.LE.
     3    122)).OR.(LL.GE.256)) GOTO 57
      IF ((LL.GE.49).AND.(LL.LE.57).AND.((IBDIR.NE.7).OR.
     *    (MM(IX-1,IY).NE.72))) GO TO 5557
      IF ((MOD(IBDIR,4).NE.3).AND.(MOD(IBDIR,4).NE.1)) GO TO 5557
      IF (((LL.GE.58).AND.(LL.LE.62)).OR.(LL.EQ.64).OR.
     *    ((LL.GE.91).AND.(LL.LE.96)).OR.(LL.GE.123)) GO TO 5557
      IF ((LL.EQ.72).OR.((LL.GE.49).AND.(LL.EQ.57))) THEN
          IF (IBDIR.EQ.7) THEN
              IF ((LL.GE.49).AND.(LL.LE.57)) THEN
                  II = 2
              ELSE
                  II = 1
              ENDIF
              IF ((MM(IX-II,IY).GE.65).AND.(MM(IX-II,IY).LE.122))
     *            THEN
                  GO TO 57
              ELSE
                  IX = IX + 1
                  GO TO 5557
              ENDIF
          ELSE IF (IBDIR.EQ.3) THEN
              DO 915 II = 1,2
                  IF ((MM(IX+II,IY).GE.65).AND.(MM(IX+II,IY).LE.90))
     *                GO TO 57
                  IF (MM(IX+II,IY).EQ.0) GO TO 5557
915           CONTINUE
              GO TO 5557
          ELSE IF (IBDIR.EQ.1) THEN
              IF ((MM(IX,IY-1).GE.65).AND.(MM(IX,IY-1).LE.90))
     *            THEN
                  IY = IY - 1
                  GO TO 57
              ELSE
                  IF ((MM(IX,IY+1).GE.65).AND.(MM(IX,IY+1).LE.90)) THEN
                      GO TO 55
                  ELSE
                      GO TO 5557
                  ENDIF
              ENDIF
          ELSE IF (IBDIR.EQ.5) THEN
              IF ((MM(IX,IY+1).GE.65).AND.(MM(IX,IY+1).LE.90))
     *            THEN
                  IY = IY + 1
                  GO TO 57
              ELSE
                  IF ((MM(IX,IY+1).GE.65).AND.(MM(IX,IY+1).LE.90)) THEN
                      GO TO 55
                  ELSE
                      GO TO 5557
                  ENDIF
              ENDIF
          ELSE
              GO TO 5557
          ENDIF
      ENDIF
      IX=IX+INCX
      IY=IY+INCY
```

```
              IF (IX.GE.1.AND.IX.LE.MAXX.AND.IY.GE.1.AND.IY.LE.MAXY)
     1        GO TO 56
5557          CONTINUE
              IERR = 45
C Found space conflict - ERROR MESSAGE
              CALL MYERR(IERR,KAR,KAR)
              IF (LMM(IX-INCX,IY-INCY).GE.256) THEN
                 JCHAR = 1
                 CALL DEL(KAR,IX,IY,INCX,INCY,0)
                 JCHAR = 2
              ELSE
                 IX = MIX
                 IY = MIY
              ENDIF
              GO TO 55
C Simulating IDENT as if this node were typed in
57            CONTINUE
              ICHAR=2
              IF (IBTYPE.NE.0) BONDEL = .TRUE.
              KAR=LL
C Tentative location after 'typing' node
              IX=IX+1
C Move cursor to new position
55            CONTINUE
              ICUR = 1
              CALL CURSOR(IX,IY)
              CALL HEADER
C Return to solid linetype (if nec)
              CALL SETLNS(1)
C End of normal bond drawing.
              RETURN
C
C Typed alphameric characters
10            CONTINUE
              ICUR = 1
              NOCHG = 0
              IF ((IX.GT.MAXX).OR.(IX.LT.1).OR.(IY.GT.MAXY).OR.(IY.LT.1))
     *        THEN
                 IF ((IX.GT.MAXX).AND.(IY.GE.1).AND.(IY.LE.MAXY).AND.
     *              (KAR.GE.65).AND.(KAR.LE.90).AND.(MM(MAXX,IY).EQ.46))
     *           GO TO 11111
                 CALL MYERR(36,KAR,KAR)
                 IX = IOX
                 IY = IOY
                 CALL CURSOR(IX,IY)
                 RETURN
              ENDIF
C Charges done in separate subroutine
              IF (IX.LT.LOX) THEN
                 LOX = IX
              ELSE IF (IX.GT.HIX) THEN
                 HIX = IX
              ENDIF
              IF (IY.LT.LOY) THEN
                 LOY = IY
              ELSE IF (IY.GT.HIY) THEN
                 HIY = IY
              ENDIF
11111         CONTINUE
              IF (ICHAR.NE.4) CALL CONTEX(KAR,IX,IY,INCX,INCY,IERR)
              IF (IX.GT.MAXX) THEN
                 IX = MAXX
              ELSE IF (IX.LT.1) THEN
                 IX = 1
              ENDIF
C Return bond type to 1 after any typed char(incl dot), unless it was 4,8,0:
              IF ((IBTYPE.NE.0).AND.(IBTYPE.NE.4).AND.(IBTYPE.NE.8)) IBTYPE=1
C Draw in jam mode
C 46 is Luhn dot--draw as 'fat dot'.
              IF (KAR.NE.IDOT) GOTO 14
              IF (MM(IX,IY).NE.0) GO TO 1144
              DO 12 I = -1,1
                 MX = IX + I
                 IF ((MX.LE.0).OR.(MX.GT.MAXX)) GO TO 12
```

```
              DO 1122 J = -1,1
              MY = IY + J
              IF ((MY.LE.0).OR.(MY.GT.MAXY)) GO TO 1122
              L = LMM(MX,MY)
              IF ((L.EQ.0).OR.(L.GE.256)) GO TO 1122
              IF ((L.EQ.34).OR.(MM(MX,MY).GT.8192).OR.
     *            ((L.GE.49).AND.(L.LE.57).AND.((LMM(MX-1,MY).EQ.
     *            43).OR.(LMM(MX-1,MY).EQ.45).OR.((IABS(I+J).NE.1)
     *            .AND.(MM(MX-1,MY).EQ.72)).AND.(MX-1.GE.0))))
     *           GO TO 1122
              GO TO 1144
1122        CONTINUE
12          CONTINUE
C Draw 3x3 fat dot
              I1X = IX * MULTX - 6
              I1Y = IY * MULTY - 4
              I3X = I1X + 3
              I3Y = I1Y - 3
              CALL BAR(I1X,I1Y,I3X,I3Y)
              MM(IX,IY)=IDOT
              IX=IX+1
              CALL CURSOR(IX,IY)
              RETURN
14          CONTINUE
              LL = LMM(IX,IY)
              IF ((KAR.LT.49).OR.((KAR.GT.57).AND.(KAR.LT.97)).OR.
     *           (KAR.GT.122)) THEN
                 IF (LL.EQ.0) THEN
                    GO TO 2222
                 ELSE
                    GO TO 1144
                 ENDIF
              ENDIF
C Space is found for 2nd letter of 2 letter atomic symbol.
              LLUP = MM(IX+1,IY-1)
              LLDN = MM(IX+1,IY+1)
              IF ((LLUP.GE.256).AND.(MOD(IDIR(LLUP),4).EQ.2)) GO TO 1898
              IF ((LLUP.GT.0).AND.(LLUP.NE.34).AND.(LLUP.NE.43).AND.
     *           (LLUP.NE.45).AND.(LLUP.LT.256)) GO TO 1898
              IF ((LLDN.GE.256).AND.(MOD(IDIR(LLDN),4).EQ.0)) GO TO 1898
              IF ((LLDN.GT.0).AND.(LLDN.NE.34).AND.(LLDN.NE.43).AND.
     *           (LLDN.NE.45).AND.(LLDN.LT.256)) GO TO 1898
              IF (((LL.EQ.0).OR.((LL.GE.256).AND.((IDIR(LL).EQ.3).OR.
     *           (IDIR(LL).EQ.7)))).AND.((LMM(IX+1,IY).GE.256).OR.
     *           (MM(IX+1,IY).EQ.0))) GO TO 2003
1898          FX = IX - 1
              CALL FTLOCA(IY,FX)
              CALL FTEXT('^ ^')
              MM(FX,IY) = 0
              IOX = IOX - 1
              GO TO 1144
2003        CONTINUE
              IELT = 0
              IF (IX-1.LE.0) GO TO 2008
C Element is identified.
              LET1 = LMM(IX-1,IY)
              IF ((KAR.GE.49).AND.(KAR.LE.57).AND.(((MM(IX-1,IY)
     *           .EQ.68).OR.(MM(IX-1,IY).EQ.77)).AND.(IX-1.GT.0))) THEN
                 LET2 = KAR + 63
              ELSE
                 LET2 = KAR
              ENDIF
              DO 2007 I = 1,126
                 IF ((LET1.EQ.IELEM(I,1)).AND.(LET2.EQ.IELEM(I,2))) GO TO 2323
2007        CONTINUE
2008        IERR = 11
              CALL MYERR(IERR,LET1,LET2)
              ICHAR = 30
              GO TO 1146
C
2323        CONTINUE
C Available space for 2nd letter of 2 letter element symbol is cleared.
              IF (ICHAR.EQ.4) THEN
                 IF (MM(IX,IY).NE.0) THEN
                    CALL FTLOCA(IY,IX)
```

```
              CALL FTEXT('  ')
          ENDIF
          GO TO 2333
        ENDIF
2222    CONTINUE
C
C Clear space for new node is verified.
        DO 2001 I = -1,1
          MX = IX + I
          IF ((MX.LE.0).OR.(MX.GT.MAXX)) GO TO 2001
          DO 2000 J = -1,1
            MY = IY + J
            IF ((MY.LE.0).OR.(MY.GT.MAXY)) GO TO 2000
            IF ((I.EQ.0).AND.(J.EQ.0)) GO TO 2000
            LL = LMM(MX,MY)
            IF (MX-1.LE.0) THEN
              LL2 = 0
            ELSE
              LL2 = LMM(MX-1,MY)
            ENDIF
            IF (LL.EQ.0) GO TO 2000
            IF ((MM(MX,MY).GT.8192).OR.(LL.EQ.34)) GO TO 2000
            IF ((LL.GE.49).AND.(LL.LE.57).AND.((MM(MX-1,MY).GT.
     *        8192).OR.((IABS(I+J).NE.1).AND.(LL2.EQ.72))))
     *        GO TO 2000
            IF (LL.GE.256) GO TO 2000
            GO TO 1144
2000      CONTINUE
2001    CONTINUE
2333    CALL CURSOR(IX,IY)
C
C Nodal or remaining character of atomic symbol is entered on screen.
        HALO(2) = CHAR(KAR)
        CALL TEXT(HALOE)
C
C Set H=J for storage so we won't have valence problems with H's
        IF (KAR .EQ. 72) KAR=74
C Translate D1-D9 and M1-M9 to Dp-Dx and Mp-Mx for internal storage.
        IF ((KAR.GE.49).AND.(KAR.LE.57).AND.(((MM(IX-1,IY)
     *     .EQ.68).OR.(MM(IX-1,IY).EQ.77)).AND.(IX-1.GT.0)))
     *     KAR = KAR + 63
        MM(IX,IY)=KAR
        IX=IX+1
        CALL CURSOR(IX,IY)
        RETURN
1144    CONTINUE
        IERR = 48
        CALL MYERR(IERR,IERR,IERR)
        ICHAR = JCHAR
        KAR = MCHAR
        IBDIR = JBDIR
1146    CONTINUE
        IX = IOX
        IY = IOY
        ICUR = 1
        CALL CURSOR(IX,IY)
        RETURN
        END
$STORAGE:2
        SUBROUTINE STRDRW(ISWIT)
        IMPLICIT INTEGER*2 (A-Z)
        REAL A,THETA,SLOPE,DELX,DELY,DTHETA,THETA2,DX,DY
        INTEGER*4 MM,IDTPIX,IPACK,LN
        CHARACTER*1 HALO(3)
        COMMON /CD/ MAXX,MAXY
        COMMON /RANGE/ LOX,HIX,LOY,HIY
        COMMON /IOFFST/IOFF
        COMMON /STRED/ IDTPIX(90,38),LABL(260,2),MRKCHN(260)
        COMMON /STRPIX/ LPIX,MM(90,38),LBLEN,LNGBND(100,5)
        COMMON /SIZZE/ MULTX,MULTY
        COMMON /HP/IHP
C       Relative coords for dwg bonds in 7x10 areas
        COMMON /BONDS/ A(5,3,4,4),B(2,3,4)
C       0,0 in lower left corner.
C       1st coord is bondtype (1=single,2=double,3=triple,4=wedge in,5=Out)
```

```
C       2nd coord is line segment # for dwg each bond (eg triple has 3segments)
C       3rd coord is bond direction, modulo 4 (up=1)
C       4th coord is Xstart,Ystart,Xend,Yend drawing coordinates.
        COMMON /CUR/ ICUR
C
        HALO(1) = '^'
        HALO(3) = '^'
C Counter for array LABL
        ICUR = 0
        CALL CURSOR(1,1)
        MRKLEN=0
        IGTEXT=1
C       If ISWIT = 0 markers are displayed
C       as Luhn dots - If ISWIT .NE. 0
C       markers are displayed as lower case letters
        IF (ISWIT .EQ. 0) GO TO 41
        DO 40 I=1,260
        IF (LABL(I,1).EQ.0) GO TO 40
        MRKLEN=MRKLEN+1
40      CONTINUE
C
41      DO 1000 IY= LOY,HIY
        DO 1000 IX= LOX,HIX
        IF (MM(IX,IY).EQ.0) GO TO 1000
        ISUBSC=1
C
C       UNPACK ARRAY
        IC=0
        IBDIR=0
        IBTYPE=0
        IPACK = MM(IX,IY)
        IF (IPACK.LT.256) GO TO 700
        IF ((LMM(IX,IY).EQ.43).OR.(LMM(IX,IY).EQ.45)) GO TO 800
C
C IDENTIFY BONDS
        IBDIR=MOD(IPACK,256)
        IBTYPE=(IPACK-IBDIR)/256
C Conversion of bond type to the first coordinate of 'A' (drawing coordin-
C ate array:
        IBOND=1
C IBOND is 1st coord of A; max 5
        IF (IBTYPE.LE.3) IBOND=IBTYPE
C We need 3 lines for type 8 bond
        IF (IBTYPE.EQ.8) IBOND=3
C Wedges:
        IF ((IBTYPE.EQ.6) .OR. (IBTYPE.EQ.7)) IBOND=IBTYPE-2
C
C Number of line segments req'd to draw the bond-Max 3
        NLINES=3
C single=1; double=2 line segments
        IF (IBOND.LE.2) NLINES=IBOND
C
C Correct direction error for wedge bond inherent in A array in DRAW:
        JKL=IBDIR
        JKM = IBDIR
        IF (JKL.GT.4) JKL=JKL-4
        IF ((IBOND.GE.4) .AND. (IBDIR.GT.4)) IBOND= 9 - IBOND
C
C Start drawing the bond:
        NX=IX*MULTX - 8*IOFF
C Screen coordinates of lower left corner of 7x10 area
        NY=IY*MULTY - 11*IOFF
C
        IPAT=1
        IF (IBTYPE.EQ.5) IPAT=5
C
C       Draw each segment separately
        DO 600 J=1,NLINES
            IF (MOD(JKM,2).EQ.1) THEN
                JKJ = JKL
                IF ((IBOND.EQ.5).AND.(JKM.EQ.1)) THEN
                    BND = 4
                ELSE IF ((IBOND.EQ.4).AND.(JKM.EQ.1)) THEN
                    BND = 5
                ELSE
```

```
                    BND = IBOND
                ENDIF
            ELSE
                BND = IBOND
                IF (JKL.EQ.2) THEN
                    JKJ = 4
                ELSE IF (JKL.EQ.4) THEN
                    JKJ = 2
                ENDIF
            ENDIF
            IF ((JKM.EQ.5).AND.((IBOND.EQ.4).OR.(IBOND.EQ.5))) THEN
                IF (IBOND.EQ.4) THEN
                    BND = 2
                ELSE
                    BND = 1
                ENDIF
                I1X = NX + B(BND,J,1)
                I2X = NX + B(BND,J,2)
                I1Y = NY + B(BND,J,3)
                I2Y = NY + B(BND,J,4)
            ELSE
C           Calc plotting coords
                I1X = NX + A(BND,J,JKJ,1)
C               I1X,I1Y = start
                I2X = NX + A(BND,J,JKJ,3)
C               I2X,I2Y = end
                I1Y = NY + A(BND,J,JKJ,2)
                I2Y = NY + A(BND,J,JKJ,4)
            ENDIF
            IF (IBTYPE.EQ.8) IPAT=IPAT+1
            CALL LINE(IGTEXT,IPAT,I1X,I1Y,I2X,I2Y)
600     CONTINUE
        GO TO 1000
C
C IDENTIFY CHARACTERS
700     CONTINUE
        NX=IX*MULTX - 8*IOFF
        NY=IY*MULTY - 2*IOFF
        IF (IPACK.EQ.46) GO TO 770
        IF (IPACK.LT.48.OR.IPACK.GT.57) GO TO 900
        IF (IX.LE.ISUBSC) GO TO 900
        LN = LMM(IX-ISUBSC,IY)
C       (LEFT NEIGHBOR)
        IF (LN.EQ.42) GO TO 900
        IF ((LN.EQ.43).OR.(LN.EQ.45)) GO TO 650
        IF((LN.GE.65.AND.LN.LE.90).OR.(LN.GE.97.AND.LN.LE.122))
     *      NY=NY-IHP*2
        IF (LN.GE.48.AND.LN.LE.57) GO TO 730
        GO TO 900
730     CONTINUE
        ISUBSC=ISUBSC+1
        GO TO 700
C
C       DIGIT ASSOCIATED WITH CHARGE
C       SEE IF CHARGE IS PART OF DOTDIS - IF SO RAISE DIGIT FOR DISPLAY
C
650     DO 652 I=IX-1,1,-1
            IF ((MM(I,IY).EQ.0).OR.(IY.EQ.1)) GO TO 900
            IF (MM(I,IY).EQ.42) GO TO 950
652     CONTINUE
        GO TO 900
C
C REENTER MARKERS
770     CONTINUE
C LUHN DOT - NOT MARKER
        IF (MRKLEN .EQ. 0) GO TO 750
        DO 780 K=1,MRKLEN
            IF (LABL(K,1).EQ.IX.AND.LABL(K,2).EQ.IY) GO TO 790
780     CONTINUE
C LUHN DOT - NOT MARKER
        GO TO 750
790     CONTINUE
        IPACK=MOD(K-1,26)+97
        GO TO 900
C
```

```
C       DRAW FAT DOT
750     CONTINUE
        IGTEXT = 0
        JX = (IX * MULTX) - 6
        JY = (IY * MULTY) - 4
        J3X = JX + 3
        J3Y = JY - 3
        CALL BAR(JX,JY,J3X,J3Y)
        GO TO 1000
C
C IDENTIFY CHARGES
800     CONTINUE
        NX=IX*MULTX - 8*IOFF
        NY=IY*MULTY - 2*IOFF
        IPACK=MOD(IPACK,2**13)
        IC=(MM(IX,IY)-IPACK)/2**13
C SEE IF CHARGE IS PART OF DOTDIS. IF SO RAISE
C CURSOR FOR DISPLAY
        DO 500 I=IX-1,1,-1
           IF (MM(I,IY).EQ.0) GO TO 900
           IF (MM(I,IY).EQ.42) GO TO 950
500     CONTINUE
        GO TO 900
C WE FOUND DOTDIS CHARGE
950     NY = NY +IHP*10
C
900     CONTINUE
        IGTEXT=1
C Display J's (which are stereo hydrogens) as H's
        IF (IPACK .EQ. 74) IPACK=72
        IF ((IPACK.GE.112).AND.(IPACK.LE.120).AND.
     *     ((MM(IX-1,IY).EQ.68).OR.(MM(IX-1,IY).EQ.77)))
     *     IPACK = IPACK - 63
        CALL MOVTCA(NX,NY)
        HALO(2) = CHAR(IPACK)
        CALL TEXT(HALO)
        IBOND=0
        IBTYPE=0
        IBDIR=0
        IC=0
1000    CONTINUE
C
C IDENTIFY LONG BONDS
        DO 2000 K=1,LBLEN
        IF (LNGBND(K,1).EQ.0) GO TO 2000
        IX1=LNGBND(K,1)
        IY1=LNGBND(K,2)
        IX2=LNGBND(K,3)
        IY2=LNGBND(K,4)
        IBTYPE=LNGBND(K,5)
C Now calculate bond endpoints, based on circle of rad 6 surrounding node
168     DX=MULTX*(IX2-IX1)
        DY=MULTY*(IY2-IY1)
        SLOPE = 0.0
        IF (IHP .NE. 1) THEN
        IF (DX.EQ.0.0) THEN
           IF (IY1.GT.IY2) THEN
              DELV1 = -4
              DELV2 = 8
           ELSE
              DELV1 = 8
              DELV2 = -4
           ENDIF
           DELX = 0.0
           DELY = 0.0
        ELSE
           DELV1 = 0
           DELV2 = 0
           SLOPE=DY/DX
           THETA=ATAN(SLOPE)
           IF ((THETA.LE.0.).AND.(DX.LT.0.0)) THETA = THETA - 3.14159265
C          Principal value problem
           IF ((THETA.GT.0.).AND.((DX.LT.0.0).OR.(DY.LT.0.0)))
     2        THETA = THETA + 3.14159265
```

```
C         Bond connects to circle of rad pixels from center of node
          DELX=6*COS(THETA)
          DELY=6*SIN(THETA)
       ENDIF
       JX1=IX1*MULTX - 4+DELX
       JY1=IY1*MULTY - 9 + DELY + DELV1
       JX2=IX2*MULTX - 4-DELX
       JY2=IY2*MULTY - 9 - DELY + DELV2
       IF ((SLOPE.LT.1.0).AND.(SLOPE.NE.0.0).AND.(SLOPE.GT.-1.0)) THEN
           JY2 = JY2 + 3
           JY1 = JY1 + 3
       ELSE IF (ABS(SLOPE).GT.1.0) THEN
           IF (JY1.GT.JY2) THEN
              JY1 = JY1 + 6
              JY2 = JY2 + 3
           ELSE
              JY1 = JY1 + 3
              JY2 = JY2 + 6
           ENDIF
       ELSE IF (ABS(SLOPE).EQ.1.0) THEN
           IF (JY1.GT.JY2) THEN
              JY1 = JY1 - 2
              JY2 = JY2 + 3
           ELSE
              JY1 = JY1 + 3
              JY2 = JY2 - 2
           ENDIF
       ELSE IF (DY.EQ.0.0) THEN
           JY1 = JY1 + 3
           JY2 = JY2 + 3
           IF (JX1.GT.JX2) JY2 = JY2 + 1
       ENDIF
       ELSE
       IF (DX .EQ. 0) THEN
       IF (IY2 .GT. IY1) THEN
       DELV1=6
       DELV2=-6
       THETA=1.571
       ELSE
       DELV1=-6
       DELV2=6
       THETA=-1.571
       ENDIF
       DELX=0
       DELY=0
       ELSE
       DELV1=0
       DELV2=0
           SLOPE = DY/DX
           THETA=ATAN(SLOPE)
           IF ((THETA.LE.0.) .AND. (DX.LT.0)) THETA = THETA - 3.14159265
C          Principal value problem
           IF ((THETA.GT.0.) .AND. ((DX.LT.0) .OR. (DY.LT.0)))
     2        THETA = THETA + 3.14159265
C          Bond connects to circle of rad 6 pixels from center of node
           DELX=6*COS(THETA)
           DELY=6*SIN(THETA)
       ENDIF
       JX1=IX1*MULTX+4+DELX
       JY1=IY1*MULTY+5+DELY+DELV1
       JX2=IX2*MULTX+4-DELX
       JY2=IY2*MULTY+5-DELY+DELV2
       ENDIF
C Now determine bond type to draw.
       IPAT=1
       IF (IBTYPE.EQ.5) IPAT=5
       IF (IBTYPE.EQ.8) IPAT=3
       IBOND=1
       IF (IBTYPE.LE.3) IBOND=IBTYPE
       IF (IBOND.EQ.1.OR.IBOND.EQ.3)
     2    CALL LINE(IGTEXT,IPAT,JX1,JY1,JX2,JY2)
       IF (IBTYPE .EQ. 8) GO TO 1700
C No more lines to draw
       IF (IBOND.EQ.1) GOTO 2000
C
```

```
C  Calculate side lines for double or triple bonds:
C  Use angle of +-.6 radians from center for side lines for triple;
C  .3 for double
1700    CONTINUE
        IF (IBOND.EQ.2) THEN
            DTHETA = .2
        ELSE IF ((IBOND.EQ.3).OR.(IBTYPE.EQ.8)) THEN
            DTHETA = .6
        ENDIF
C
C Change sign
        DO 1550 I=1,-1,-2
        IF (IHP .NE. 1) THEN
        IF (DX.EQ.0.0) THEN
            DELX = I * 2.0
            DELY = 0.0
            IF (IY1.GT.IY2) THEN
                DELV1 = -4
                DELV2 = 8
            ELSE
                DELV1 = 8
                DELV2 = -4
            ENDIF
        ELSE
            DELV1 = 0
            DELV2 = 0
            THETA2 = THETA + DTHETA*I
            DELX = (6*COS(THETA2))
            DELY=(6*SIN(THETA2))
        ENDIF
        JX1 = IX1 * MULTX - 4 + DELX
        JY1 = IY1 * MULTY - 9 + DELY + DELV1
        IF (DX.NE.0.0) THEN
            THETA2 = 3.14159265 + THETA - I*DTHETA
            DELX=(6*COS(THETA2))
            DELY=(6*SIN(THETA2))
        ENDIF
        JX2 = IX2 * MULTX - 4 + DELX
        JY2 = IY2 * MULTY - 9 + DELY + DELV2
        IF (IBTYPE.EQ.8) IPAT=3+I
        IF ((SLOPE.LT.1.0).AND.(SLOPE.NE.0.0).AND.(SLOPE.GT.-1.0)) THEN
            JY2 = JY2 + 3
            JY1 = JY1 + 3
        ELSE IF (ABS(SLOPE).GT.1.0) THEN
            IF (JY1.GT.JY2) THEN
                JY1 = JY1 + 6
                JY2 = JY2 + 3
            ELSE
                JY1 = JY1 + 3
                JY2 = JY2 + 6
            ENDIF
        ELSE IF (ABS(SLOPE).EQ.1.0) THEN
            IF (JY1.GT.JY2) THEN
                JY1 = JY1 - 2
                JY2 = JY2 + 3
            ELSE
                JY1 = JY1 + 3
                JY2 = JY2 - 2
            ENDIF
        ELSE IF (DY.EQ.0.0) THEN
            IF ((IBOND.EQ.3).OR.(IBTYPE.EQ.8)) THEN
                IF (DX.GT.0.0) THEN
                    IF (I.EQ.-1) THEN
                        JY1 = JY1 + 5
                        JY2 = JY2 + 5
                    ELSE
                        JY1 = JY1 + 2
                        JY2 = JY2 + 2
                    ENDIF
                ELSE
                    IF (I.EQ.-1) THEN
                        JY1 = JY1 + 2
                        JY2 = JY2 + 2
                    ELSE
                        JY1 = JY1 + 5
                        JY2 = JY2 + 5
```

```
              ENDIF
            ENDIF
          ELSE IF (IBOND.EQ.2) THEN
            JY1 = JY1 + 4
            JY2 = JY2 + 4
          ENDIF
        ENDIF
        IF ((SLOPE.NE.0.0).AND.((IBOND.EQ.3).OR.(IBTYPE.EQ.8))) THEN
          IF (SLOPE.GT.0.0) THEN
            IF (JY1.GT.JY2) THEN
              JY1 = JY1 + I
              JY2 = JY2 + I
            ELSE
              JY1 = JY1 - I
              JY2 = JY2 - I
            ENDIF
          ELSE
            IF (JY1.GT.JY2) THEN
              JY1 = JY1 - I
              JY2 = JY2 - I
            ELSE
              JY1 = JY1 + I
              JY2 = JY2 + I
            ENDIF
          ENDIF
        ENDIF
       ELSE
        THETA2 = THETA + DTHETA*I
        DELX= (6*COS(THETA2))
        DELY=(6*SIN(THETA2))
        JX1 = IX1 * MULTX + 4 + DELX
        JY1 = IY1 * MULTY + 5 + DELY
        THETA2 = 3.14159265 + THETA - I*DTHETA
        DELX=(6*COS(THETA2))
        DELY=(6*SIN(THETA2))
        JX2 = IX2 * MULTX + 4 + DELX
        JY2 = IY2 * MULTY + 5 + DELY
       ENDIF
       CALL LINE(IGTEXT,IPAT,JX1,JY1,JX2,JY2)
1550   CONTINUE
2000   CONTINUE
8500   CONTINUE
       ICUR = 1
       RETURN
       END
C
       SUBROUTINE LONG(KAR,IX,IY)
       IMPLICIT INTEGER*2 (A-Z)
       REAL THETA,DTHETA,THETA2,DELX,DELY,SLOPE,DX,DY
       INTEGER*4 MM,IDTPIX
       LOGICAL*2 RPLC
       CHARACTER*1 ISTAT
       COMMON /CD/ MAXX,MAXY
       COMMON /STRPIX/ LPIX,MM(90,38),LBLEN,LNGBND(100,5)
       COMMON /PARAMS/ JBDIR,NOCHG,LASTN,MCHAR,JCHAR,NLARGE,LEVEL
       COMMON /MODES/ JBTYPE,ICHAR,IBDIR,IBTYPE,ISMART,MODE,ISKILL,ISP
       COMMON /CHARS/IES, IDOT,ITAG,JUMP,LBOND,KAN,ISPACE
       COMMON /HEAD/ MW(12),ISTATE,PAGE
       COMMON /LABELS/ NR,NJLAST,NJNEXT
       COMMON /STRED/ IDTPIX(90,38),LABL(260,2),MRKCHN(260)
       COMMON /SIZZE/ MULTX,MULTY
       COMMON /ISTATE/ ISTAT
       COMMON /CUR/ ICUR
       COMMON /HP/ IHP
C
C This routine allows drawing of 'long bonds' between current location
C (if it is a marker) and any active marker.  The routine is called by
C entering a '%'.  Any number of calls to 'LEAP' can be made while in
C the routine.  When a second '%' is
C entered, a long bond is drawn between the initial node and the last
C marker jumped to.
C
C Long Bond state
       ICUR = 1
       ISTATE=7
```

```
              ISTAT='%'
              CALL HEADER
              IX2 = -99
              IY2 = -99
              IX1 = -99
              IY1 = -99
              RPLC = .FALSE.
       C
              K = 0
              IF (IX.GT.2) K = LMM(IX-1,IY)
              IF (K.EQ.46) GO TO 123
       C Return to previous state
              ISTATE=0
              KAR=0
              IF (MOD(IBTYPE,4).NE.0) IBTYPE=1
              LASTN=0
              CALL HEADER
              CALL CURSOR(IX,IY)
              CALL ERRMSG(0)
              RETURN
       C
       123    IX1 = IX - 1
              IY1 = IY
              CALL CURSOR(IX1,IY1)
       2      IKAR=KAR
       77     CALL INPUTX(KAR,IX,IY)
       C Second entry of '%'
              IF (KAR.EQ.LBOND) GOTO 3
              IF ((KAR.EQ.13).OR.(KAR.EQ.81)) GO TO 95
       C      These lines are commented out to lock out entry of elements in
       C      LONG.
       C Lowercase for jump
              IF ((KAR.GE.97).AND.(KAR.LE.122)) GOTO 4
       C digit = set bond type
              IF ((KAR .GE. 48) .AND. (KAR .LE. 57)) GO TO 21
       C '#' set marker
              IF (KAR.EQ.ITAG) GOTO 25
              CALL ERRMSG(KAR)
              GO TO 2
       51     IERR=9
              GO TO 96
       95     IERR=2
       96     CALL MYERR(IERR,KAR,KAR)
       5      LASTN=0
              ISTATE=0
              IF (MOD(IBTYPE,2).NE.0) IBTYPE=1
              CALL HEADER
              CALL CURSOR(IX,IY)
       C Erroneous input
              RETURN
       C
       C set marker after '#'
       25     CALL MARK(KAR,IX,IY)
              IX2=IX-1
              IY2=IY
              GOTO 2
       C
       700    ICHAR=4
       CLC AFTER $
              CALL DRAW(KAR,IX,IY,INCX,INCY)
              MCHAR=KAR
              JCHAR=ICHAR
              IX2=IX-2
              IY2=IY
              GO TO 2
       C
       900    ICHAR=2
       C      UC
              CALL DRAW(KAR,IX,IY,INCX,INCY)
              MCHAR=KAR
              JCHAR=ICHAR
              IX2=IX-1
              IY2=IY
              GO TO 2
       C
       C use digit to set bond type
```

```
21      IBTYPE=KAR-48
        CALL HEADER
C for more input
        GOTO 2
4       CALL LEAP(KAR,IX,IY)
        IX2=IX-1
        IY2=IY
        GOTO 2
C
C
C Zero-length bond
3       IF ((IX1.EQ.IX2) .AND. (IY1.EQ.IY2)) GOTO 51
C No endpoint specified
        IF (IX2.LE.0 .OR.IY2.LE.0) GOTO 51
C No starting point specified
        IF (IX1.LE. 0 .OR.IY1.LE.0) GO TO 51
        IF ((IBTYPE.EQ.4).OR.(IBTYPE.EQ.6).OR.(IBTYPE.EQ.7)) THEN
            IERR = 53
            CALL MYERR(IERR,KAR,MAR)
            IBTYPE = 1
        ENDIF
C
C   Actual drawing of long bond; hence ICHAR<10
        ICHAR=8
        JCHAR=8
C Put info into longbond array:
10      DO 9 I=1,100
        II = I
        IF ((LNGBND(I,1).EQ.IX1) .AND. (LNGBND(I,2).EQ.IY1) .AND.
     2      (LNGBND(I,3).EQ.IX2) .AND. (LNGBND(I,4).EQ.IY2)) THEN
            KX1 = IX1
            KY1 = IY1
            GOTO 166
C       If repeating an existing
C       long bond, don't re-enter into long bond table.
        ELSE IF ((LNGBND(I,1).EQ.IX2).AND.(LNGBND(I,2).EQ.IY2).AND.
     2      (LNGBND(I,3).EQ.IX1).AND.(LNGBND(I,4).EQ.IY1)) THEN
            KX1 = IX2
            KY1 = IY2
            GO TO 166
        ENDIF
        IF (LNGBND(I,1)+LNGBND(I,2)+LNGBND(I,3)+LNGBND(I,4).GT.0) GOTO 9
        IF (IBTYPE .EQ. 0) GO TO 5
        LNGBND(I,1)=IX1
        LNGBND(I,2)=IY1
        LNGBND(I,3)=IX2
        LNGBND(I,4)=IY2
        LNGBND(I,5)=IBTYPE
        ICUR = 0
        CALL CURSOR(IX,IY)
        GOTO 168
9       CONTINUE
C
166     IF (((LNGBND(II,5).EQ.IBTYPE).AND.(IBTYPE.NE.0)).OR.
     *      (MM(IX1,IY1).NE.46)) GO TO 5
C Don't redraw if bond type is the same or if initial
C point is not a marker
        IWHICH = II
        KXX = KX1
        KYY = KY1
        RPLC = .TRUE.
        CALL DEL(KAR,KXX,KYY,INCX,INCY,IWHICH)
C Set new bond type
        IF (IBTYPE .EQ. 0) GO TO 16
        LNGBND(II,5)=IBTYPE
        LNGBND(II,1) = KX1
C
C Now calculate bond endpoints, based on circle of rad 6 surrounding node
168     CONTINUE
        DX=MULTX*(IX2-IX1)
        DY=MULTY*(IY2-IY1)
        SLOPE = 0.0
        IF (IHP .NE. 1) THEN
        IF (DX.EQ.0.0) THEN
            IF (IY1.GT.IY2) THEN
                DELV1 = -4
```

```
            DELV2 = 8
        ELSE
            DELV1 = 8
            DELV2 = -4
        ENDIF
        DELX = 0.0
        DELY = 0.0
    ELSE
        DELV1 = 0
        DELV2 = 0
        SLOPE = DY/DX
        THETA=ATAN(SLOPE)
        IF ((THETA.LE.0.) .AND. (DX.LT.0)) THETA = THETA - 3.14159265
C       Principal value problem
        IF ((THETA.GT.0.) .AND. ((DX.LT.0) .OR. (DY.LT.0)))
    2       THETA = THETA + 3.14159265
C       Bond connects to circle of rad 6 pixels from center of node
        DELX=6*COS(THETA)
        DELY=6*SIN(THETA)
    ENDIF
    JX1=IX1*MULTX - 4+DELX
    JY1=IY1*MULTY - 9 + DELY + DELV1
    JX2=IX2*MULTX - 4-DELX
    JY2=IY2*MULTY - 9 - DELY + DELV2
    IF ((SLOPE.LT.1.0).AND.(SLOPE.NE.0.0).AND.(SLOPE.GT.-1.0)) THEN
        JY2 = JY2 + 3
        JY1 = JY1 + 3
    ELSE IF (ABS(SLOPE).GT.1.0) THEN
        IF (JY1.GT.JY2) THEN
            JY1 = JY1 + 6
            JY2 = JY2 + 3
        ELSE
            JY1 = JY1 + 3
            JY2 = JY2 + 6
        ENDIF
    ELSE IF (ABS(SLOPE).EQ.1.0) THEN
        IF (JY1.GT.JY2) THEN
            JY1 = JY1 - 2
            JY2 = JY2 + 3
        ELSE
            JY1 = JY1 + 3
            JY2 = JY2 - 2
        ENDIF
    ELSE IF (DY.EQ.0.0) THEN
        JY1 = JY1 + 3
        JY2 = JY2 + 3
        IF (JX1.GT.JX2) JY2 = JY2 + 1
    ENDIF
ELSE
    IF (DX .EQ. 0) THEN
        IF (IY2 .GT. IY1) THEN
            DELV1=6
            DELV2=-6
            THETA=1.571
        ELSE
            DELV1=-6
            DELV2=6
            THETA=-1.571
        ENDIF
        DELX=0
        DELY=0
    ELSE
        DELV1=0
        DELV2=0
        SLOPE = DY/DX
        THETA=ATAN(SLOPE)
        IF ((THETA.LE.0.) .AND. (DX.LT.0)) THETA = THETA - 3.14159265
C       Principal value problem
        IF ((THETA.GT.0.) .AND. ((DX.LT.0) .OR. (DY.LT.0)))
    2       THETA = THETA + 3.14159265
C       Bond connects to circle of rad 6 pixels from center of node
        DELX=6*COS(THETA)
        DELY=6*SIN(THETA)
    ENDIF
    JX1=IX1*MULTX+4+DELX
    JY1=IY1*MULTY+5+DELY+DELV1
```

```
              JX2=IX2*MULTX+4-DELX
              JY2=IY2*MULTY+5-DELY+DELV2
           ENDIF
C Now determine bond type to draw.
           IBOND=1
           IF (IBTYPE.LE.3) IBOND=IBTYPE
C Set mode, solid line
           CALL SETLNS(1)
CWIGGLY LINE - BOND TYPE 8
           IF (IBTYPE.EQ.5) CALL SETLNS(2)
C Single or triple: draw central line:
           IF ((IBOND.EQ.1).OR.(IBOND.EQ.3)) THEN
              CALL MOVABS(JX1,JY1)
              CALL LNABS(JX2,JY2)
           ENDIF
           IF (IBTYPE .EQ. 8) GO TO 70
C No more lines to draw
           IF (IBOND.EQ.1) GOTO 56
C
C  Calculate side lines for double or triple bonds:
C  Use angle of +-.6 radians from center for side lines for triple;
C  .3 for double
70         CONTINUE
           IF (IBOND.EQ.2) THEN
              DTHETA = .2
           ELSE IF ((IBTYPE.EQ.8).OR.(IBOND.EQ.3)) THEN
              DTHETA = .6
           ENDIF
C Change sign
           DO 55 I=1,-1,-2
              IF ((IBTYPE.EQ.8).AND.(I.EQ.1)) CALL SETLNS(2)
              IF ((IBTYPE.EQ.8).AND.(I.EQ.-1)) CALL SETLNS(3)
           IF (IHP .NE. 1) THEN
           IF (DX.EQ.0.0) THEN
              DELX = I * 2.0
              IF (IY1.GT.IY2) THEN
                 DELY = 0.0
                 DELV1 = -4
                 DELV2 = 8
              ELSE
                 DELY = 0.0
                 DELV1 = 8
                 DELV2 = -4
              ENDIF
           ELSE
              DELV1 = 0
              DELV2 = 0
              THETA2 = THETA + DTHETA*I
              DELX= (6*COS(THETA2))
              DELY=(6*SIN(THETA2))
           ENDIF
           JX1 = IX1 * MULTX - 4 + DELX
           JY1 = IY1 * MULTY - 9 + DELY + DELV1
           IF (DX.NE.0.0) THEN
              THETA2 = 3.14159265 + THETA - I*DTHETA
              DELX=(6*COS(THETA2))
              DELY=(6*SIN(THETA2))
           ENDIF
           JX2 = IX2 * MULTX - 4 + DELX
           JY2 = IY2 * MULTY - 9 + DELY + DELV2
           IF ((SLOPE.LT.1.0).AND.(SLOPE.NE.0.0).AND.(SLOPE.GT.-1.0)) THEN
              JY2 = JY2 + 3
              JY1 = JY1 + 3
           ELSE IF (ABS(SLOPE).GT.1.0) THEN
              IF (JY1.GT.JY2) THEN
                 JY1 = JY1 + 6
                 JY2 = JY2 + 3
              ELSE
                 JY1 = JY1 + 3
                 JY2 = JY2 + 6
              ENDIF
           ELSE IF (ABS(SLOPE).EQ.1.0) THEN
              IF (JY1.GT.JY2) THEN
                 JY1 = JY1 - 2
                 JY2 = JY2 + 3
```

```
            ELSE
                JY1 = JY1 + 3
                JY2 = JY2 - 2
            ENDIF
        ELSE IF (DY.EQ.0.0) THEN
            IF ((IBOND.EQ.3).OR.(IBTYPE.EQ.8)) THEN
                IF (DX.GT.0.0) THEN
                    IF (I.EQ.-1) THEN
                        JY1 = JY1 + 5
                        JY2 = JY2 + 5
                    ELSE
                        JY1 = JY1 + 2
                        JY2 = JY2 + 2
                    ENDIF
                ELSE
                    IF (I.EQ.-1) THEN
                        JY1 = JY1 + 2
                        JY2 = JY2 + 2
                    ELSE
                        JY1 = JY1 + 5
                        JY2 = JY2 + 5
                    ENDIF
                ENDIF
            ELSE IF (IBOND.EQ.2) THEN
                JY1 = JY1 + 4
                JY2 = JY2 + 4
            ENDIF

ENDIF
            IF ((SLOPE.NE.0.0).AND.((IBOND.EQ.3).OR.(IBTYPE.EQ.8))) THEN
                IF (SLOPE.GT.0.0) THEN
                    IF (JY1.GT.JY2) THEN
                        JY1 = JY1 + I
                        JY2 = JY2 + I
                    ELSE
                        JY1 = JY1 - I
                        JY2 = JY2.- I
                    ENDIF
                ELSE
                    IF (JY1.GT.JY2) THEN
                        JY1 = JY1 - I
                        JY2 = JY2 - I
                    ELSE
                        JY1 = JY1 + I
                        JY2 = JY2 + I
                    ENDIF
                ENDIF
            ENDIF
        ELSE
        THETA2 = THETA + DTHETA*I
        DELX= (6*COS(THETA2))
        DELY=(6*SIN(THETA2))
        JX1 = IX1 * MULTX + 4 + DELX
        JY1 = IY1 * MULTY + 5 + DELY
        THETA2 = 3.14159265 + THETA - I*DTHETA
        DELX=(6*COS(THETA2))
        DELY=(6*SIN(THETA2))
        JX2 = IX2 * MULTX + 4 + DELX
        JY2 = IY2 * MULTY + 5 + DELY
        ENDIF
        CALL MOVABS(JX1,JY1)
        CALL LNABS(JX2,JY2)
55      CONTINUE
56      CONTINUE
        IF (.NOT.RPLC) LBLEN = LBLEN + 1
16      CALL SETLNS(1)
C Solid line
C Following code is copied from DRAW & also appears in DEL:
C   ERASE ALL H's & SUBSCRIPTS:  **********
        KX=IX1
        KY=IY1
COnly@nodes
        IF ((LMM(KX,KY).LE.65) .OR. (LMM(KX,KY).GT.90)) GOTO 43
C
C Clear old valence hydrogens
        CALL CLRHYD(KX,KY)
```

```
              CALL VALNCE(2,IX1,IY1,0,0)
43            CONTINUE
              ICUR = 1
              CALL CURSOR(IX2+1,IY2)
972           IF(IBTYPE.NE.4 .AND. IBTYPE.NE.8 .AND. IBTYPE.NE.0) IBTYPE=1
              ISTATE=0
              CALL HEADER
              RETURN
              END
C     SUBROUTINE RELONG redraws all remaining long bonds after a bond
C     deletion to ensure that no long bond is only part visible.
C
              SUBROUTINE RELONG
              IMPLICIT INTEGER*2 (A-Z)
              REAL THETA,DTHETA,THETA2,DELX,DELY,SLOPE,DX,DY
              INTEGER*4 MM,IDTPIX
              COMMON /SIZZE/ MULTX,MULTY
              COMMON /CD/ MAXX,MAXY
              COMMON /STRPIX/ LPIX,MM(90,38),LBLEN,LNGBND(100,5)
              COMMON /STRED/ IDTPIX(90,38),LABL(260,2),MRKCHN(260)
C
              DO 1000 LB = 1,LBLEN
                 IF (LNGBND(LB,1).NE.0) THEN
                    IX1 = LNGBND(LB,1)
                    IY1 = LNGBND(LB,2)
                    IX2 = LNGBND(LB,3)
                    IY2 = LNGBND(LB,4)
                    KBTYPE = LNGBND(LB,5)
C                   Now calculate bond endpoints, based on circle of rad 6
C                   surrounding node.
                    DX=MULTX*(IX2-IX1)
                    DY=MULTY*(IY2-IY1)
                    SLOPE = 0.0
              IF (DX .EQ. 0) THEN
              IF (IY2 .GT. IY1) THEN
              DELV1=6
              DELV2=-6
              THETA=1.571
              ELSE
              DELV1=-6
              DELV2=6
              THETA=-1.571
              ENDIF
              DELX=0
              DELY=0
              ELSE
              DELV1=0
              DELV2=0
                    SLOPE = DY/DX
                    THETA=ATAN(SLOPE)
                    IF ((THETA.LE.0.) .AND. (DX.LT.0)) THETA = THETA - 3.14159265
C                   Principal value problem
                    IF ((THETA.GT.0.) .AND. ((DX.LT.0) .OR. (DY.LT.0)))
     2                 THETA = THETA + 3.14159265
C                   Bond connects to circle of rad 6 pixels from center of node
                    DELX=6*COS(THETA)
                    DELY=6*SIN(THETA)
              ENDIF
              JX1=IX1*MULTX+4+DELX
              JY1=IY1*MULTY+5+DELY+DELV1
              JX2=IX2*MULTX+4-DELX
              JY2=IY2*MULTY+5-DELY+DELV2
C
C                   Now determine bond type to draw.
                    IBOND=1
                    IF (KBTYPE.LE.3) IBOND=KBTYPE
C                   Set mode, solid line
                    CALL SETLNS(1)
C                   WIGGLY LINE - BOND TYPE 8
                    IF (KBTYPE.EQ.5) CALL SETLNS(2)
C                   Single or triple: draw central line:
                    IF ((IBOND.EQ.1).OR.(IBOND.EQ.3)) THEN
```

```
              CALL MOVABS(JX1,JY1)
              CALL LNABS(JX2,JY2)
           ENDIF
           IF (KBTYPE .EQ. 8) GO TO 70
C          No more lines to draw
           IF (IBOND.EQ.1) GOTO 100
C
C          Calculate side lines for double or triple bonds:
C          Use angle of +-.6 radians from center for side lines for triple;
C          .3 for double
70         CONTINUE
           IF (IBOND.EQ.2) THEN
              DTHETA = .2
           ELSE IF ((KBTYPE.EQ.8).OR.(IBOND.EQ.3)) THEN
              DTHETA = .6
           ENDIF
C          Change sign
           DO 55 I=1,-1,-2
              IF ((KBTYPE.EQ.8).AND.(I.EQ.1)) CALL SETLNS(2)
              IF ((KBTYPE.EQ.8).AND.(I.EQ.-1)) CALL SETLNS(3)
        THETA2 = THETA + DTHETA*I
        DELX= (6*COS(THETA2))
        DELY=(6*SIN(THETA2))
        JX1 = IX1 * MULTX + 4 + DELX
        JY1 = IY1 * MULTY + 5 + DELY
        THETA2 = 3.14159265 + THETA - I*DTHETA
        DELX=(6*COS(THETA2))
        DELY=(6*SIN(THETA2))
        JX2 = IX2 * MULTX + 4 + DELX
        JY2 = IY2 * MULTY + 5 + DELY
           CALL MOVABS(JX1,JY1)
           CALL LNABS(JX2,JY2)
55         CONTINUE
100        CONTINUE
           CALL SETLNS(1)
C          Solid line
        ENDIF
1000    CONTINUE
        RETURN
        END
C
        SUBROUTINE LINE(IGTEXT,IPAT,I1X,I1Y,I2X,I2Y)
        IMPLICIT INTEGER*2 (A-Z)
C
        IGTEXT=0
C Will print solid line.
        IF (IPAT.LE.0.OR.IPAT.GE.10) IPAT=1
C
        GO TO (100,200,300,400,500,100,100,100,100),IPAT
        GO TO 1000
C
100     CONTINUE
C Set mode, solid line
        CALL SETLNS(1)
        GO TO 1000
C
C       (ENTRIES 200-400 BELOW RESULT IN WIGGLY LINE)
200     CONTINUE
        CALL SETLNS(2)
        GO TO 1000
C
300     CONTINUE
CWIGGLY LINE - BOND TYPE 8
        CALL SETLNS(1)
        GO TO 1000
C
400     CONTINUE
        CALL SETLNS(3)
        GO TO 1000
C
500     CONTINUE
C Will print dashed line--stereo
        CALL SETLNS(2)
        GO TO 1000
C
```

```
1000      CONTINUE
          CALL MOVABS(I1X,I1Y)
          CALL LNABS(I2X,I2Y)
C Solid line
          CALL SETLNS(1)
          RETURN
          END
$STORAGE:2
C
          SUBROUTINE REPLCE(KX,KY,INKX,INKY,DLX,DLY,EDGE)
          IMPLICIT INTEGER*2 (A-Z)
          INTEGER*4 MM,IDTPIX
          CHARACTER*1 HALO(3)
          LOGICAL*2 RETR
          COMMON /CD/ MAXX,MAXY
          COMMON /STRPIX/ LPIX,MM(90,38),LBLEN,LNGBND(100,5)
          COMMON /PARAMS/ JBDIR,NOCHG,LASTN,MCHAR,JCHAR,NLARGE,LEVEL
          COMMON /MODES/ JBTYPE,ICHAR,IBDIR,IBTYPE,ISMART,MODE,ISKILL,ISP
          COMMON /CHARS/IES, IDOT,ITAG,JUMP,LBOND,KAN,ISPACE
          COMMON /LABELS/ NR,NJLAST,NJNEXT
          COMMON /STRED/ IDTPIX(90,38),LABL(260,2),MRKCHN(260)
          COMMON /SIZZE/ MULTX,MULTY
          COMMON /CUR/ ICUR
          COMMON /HP/IHP
CXT       RETR is set in SUBROUTINE RETRIEVE to ensure proper screen
CXT       screen replacement between arrays MM and IDTPIX.
          COMMON /RETDRW/ RETR
          COMMON /TEMP/ LLBOND(100,5),LLABL(260,2),MCHN(260)
C
C ERASE CELL(S) TO CLEAR BOND FRAGMENTS, AND RESTORE ANY CELL VALUES.
          ICUR = 0
          CALL CURSOR(KX,KY)
          IX = KX
          IY = KY
          INCX = INKX
          INCY = INKY
          IF (EDGE.EQ.0) THEN
              PASY2 = 0
          ELSE
          PASY2 = 1
          IF (EDGE.EQ.1) THEN
              IF (IABS(INCX*INCY).EQ.1 .AND. IHP .EQ.1) THEN
                  FX = IX - 2
                  CALL FTLOCA(IY,FX)
                  CALL FTEXT('^    ^')
              ELSE
                  CALL FTLOCA(IY,IX)
                  CALL FTEXT('^ ^')
              ENDIF
          IF (IHP .NE. 1) THEN
              IF (MOD((IY*10),40).EQ.0) THEN
                  IF ((IY.EQ.8).OR.(IY.EQ.28).OR.(IY.EQ.16)) THEN
                      FY = ((IY * 10) / 11) + 1
                      CALL FTSIZE(1,11)
                  ELSE
                      FY = ((IY * 10) / 9) + 1
                      CALL FTSIZE(1,9)
                  ENDIF
              ELSE
                  FY = ((IY * 10) / 8) + 1
                  CALL FTSIZE(1,8)
              ENDIF
              IF (IABS(INCX*INCY).EQ.1) THEN
                  CALL FTLOCA(FY,FX)
                  CALL FTEXT('^    ^')
                  CALL FTSIZE(1,10)
              ELSE
                  CALL FTLOCA(FY,IX)
                  CALL FTEXT('^ ^')
                  CALL FTSIZE(1,10)
              ENDIF
          ENDIF
          ENDIF
          ENDIF
          IF (IABS(INCX*INCY).EQ.1) THEN
              DO 4000 YY = IY,IY+PASY2
```

```
              IF (YY.LE.MAXY) THEN
              DO 3000 KKK = IX-2,IX+3
                IF (((MM(KKK,YY).GT.0).OR.RETR).AND.(KKK.GE.1).AND.
     *             (KKK.LE.MAXX)) THEN
                  IF (RETR) THEN
     *              IF ((IDTPIX(KKK,YY).NE.0).AND.(MM(KKK,YY).EQ.0))
                      THEN
                        MM(KKK,YY) = IDTPIX(KKK,YY)
                    ELSE
                        GO TO 3000
                    ENDIF
                ENDIF
                YYY = YY
                KKKK = KKK
                IF (MM(KKKK,YY).EQ.46) THEN
                    IF (RETR) THEN
                        DO 2019 LBL = 1,260
                          IF ((LLABL(LBL,1).EQ.KKKK).AND.
                              (LLABL(LBL,2).EQ.YY)) THEN
                              CALL CURSOR(KKKK,YYY)
                              IF (MOD(LBL,26).EQ.0) THEN
                                  HALO(2) = 'z'
                              ELSE
                                  HALO(2) = CHAR(MOD(LBL,26)+96)
                              ENDIF
                              CALL TEXT(HALO)
                              GO TO 2029
                          ELSE IF (((LLABL(LBL,1).EQ.0).AND.
     *                            (LLABL(LBL,2).EQ.0)).OR.(LBL.EQ.260))
     *                        THEN
                              JX = KKK * MULTX - 6
                              JY = YYY * MULTY - 4
                              J3X = JX + 3
                              J3Y = JY - 3
                              CALL BAR(JX,JY,J3X,J3Y)
                              GO TO 2029
                          ENDIF
2019                    CONTINUE
2029                    CONTINUE
                    ELSE
                        DO 2020 LBL = 1,260
                          IF ((LABL(LBL,1).EQ.KKKK).AND.(LABL(LBL,2)
     *                        .EQ.YY)) THEN
                              CALL CURSOR(KKKK,YYY)
                              IF (MOD(LBL,26).EQ.0) THEN
                                  HALO(2) = 'z'
                              ELSE
                                  HALO(2) = CHAR(MOD(LBL,26)+96)
                              ENDIF
                              CALL TEXT(HALO)
                              GO TO 2030
                          ELSE IF (((LABL(LBL,1).EQ.0).AND.
     *                            (LABL(LBL,2).EQ.0)).OR.(LBL.EQ.260))
     *                        THEN
                              JX = KKK * MULTX - 6
                              JY = YYY * MULTY - 4
                              J3X = JX + 3
                              J3Y = JY - 3
                              CALL BAR(JX,JY,J3X,J3Y)
                              GO TO 2030
                          ENDIF
2020                    CONTINUE
2030                    CONTINUE
                    ENDIF
                ELSE IF (LMM(KKKK,YYY).LT.256) THEN
                    IF ((MM(KKK,YY).GE.112).AND.(MM(KKK,YY).LE.
     *                  120).AND.((MM(KKK-1,YY).EQ.68).OR.
     *                  (MM(KKK-1,YY).EQ.77))) THEN
                        HALO(2) = CHAR(MM(KKK,YY) - 63)
                    ELSE
                        HALO(2) = CHAR(LMM(KKKK,YYY))
                        IF (HALO(2).EQ.'J') HALO(2) = 'H'
                    ENDIF
                    CALL CURSOR(KKKK,YYY)
                    IF ((MM(KKK,YY).GE.50).AND.(MM(KKK,YY).LE.57)
```

```
                   .AND.(((MM(KKK-1,YY).GE.65).AND.(MM(KKK-1,YY)
*                  .LE.90)).OR.((MM(KKK-1,YY).GE.97).AND.
*                  (MM(KKK-1,YY).LE.122)))) THEN
*                    CALL MOVTCR(0,2)
                     CALL TEXT(HALO)
                     CALL MOVTCR(0,-2)
                   ELSE IF (((LMM(KKKK,YYY).EQ.43).OR.(LMM(KKKK,YYY)
*                  .EQ.45)).OR.((MM(KKK,YYY).GE.49).AND.(MM(KKK,
*                  YYY).LE.57).AND.((LMM(KKK-1,YYY).EQ.43).OR.
*                  (LMM(KKK-1,YYY).EQ.45)))) THEN
                     DO 2060 LX = KKK,1,-1
                       IF (MM(LX,YYY).EQ.42) THEN
                         CALL MOVTCR(0,-10)
                         CALL TEXT(HALO)
                         CALL MOVTCR(0,10)
                         GO TO 2070
                       ELSE IF ((MM(LX,YYY).EQ.0).OR.(LX.EQ.1))
*                      THEN
                         CALL TEXT(HALO)
                         GO TO 2070
                       ENDIF
2060               CONTINUE
2070               CONTINUE
                 ELSE
                   CALL TEXT(HALO)
                 ENDIF
               ELSE IF ((KKK.NE.DLX).OR.(YY.NE.DLY)) THEN
                 MBOND = LMM(KKKK,YYY)
                 CALL DRAW2(KKKK,YYY,MBOND)
               ENDIF
               IF (RETR) MM(KKK,YY) = 0
             ENDIF
3000       CONTINUE
           ENDIF
4000     CONTINUE
       ELSE
         DO 5000 YY = IY,IY+PASY2
           IF (((MM(IX,YY).GT.0).OR.RETR).AND.(YY.LE.MAXY)) THEN
             YYY = YY
             IF (RETR) THEN
               IF ((IDTPIX(IX,YY).NE.0).AND.(MM(IX,YY).EQ.0))
*              THEN
                 MM(IX,YY) = IDTPIX(IX,YY)
               ELSE
                 GO TO 5000
               ENDIF
             ENDIF
             IF (MM(IX,YY).EQ.46) THEN
               IF (RETR) THEN
                 DO 4019 LBL = 1,260
                   IF ((LLABL(LBL,1).EQ.IX).AND.
*                  (LLABL(LBL,2).EQ.YY)) THEN
                     CALL CURSOR(IX,YYY)
                     IF (MOD(LBL,26).EQ.0) THEN
                       HALO(2) = 'z'
                     ELSE
                       HALO(2) = CHAR(MOD(LBL,26)+96)
                     ENDIF
                     CALL TEXT(HALO)
                     GO TO 4029
                   ELSE IF (((LLABL(LBL,1).EQ.0).AND.
*                  (LLABL(LBL,2).EQ.0)).OR.(LBL.EQ.260))
*                  THEN
                     JX = IX * MULTX - 6
                     JY = YY * MULTY - 4
                     J3X = JX + 3
                     J3Y = JY - 3
                     CALL BAR(JX,JY,J3X,J3Y)
                     GO TO 4029
                   ENDIF
4019             CONTINUE
4029             CONTINUE
               ELSE
                 DO 4020 LBL = 1,260
```

```
                        IF ((LABL(LBL,1).EQ.IX).AND.(LABL(LBL,2)
     *                      .EQ.YY)) THEN
                            CALL CURSOR(IX,YYY)
                            IF (MOD(LBL,26).EQ.0) THEN
                                HALO(2) = 'z'
                            ELSE
                                HALO(2) = CHAR(MOD(LBL,26)+96)
                            ENDIF
                            CALL TEXT(HALO)
                            GO TO 4030
                        ELSE IF (((LABL(LBL,1).EQ.0).AND.
     *                      (LABL(LBL,2).EQ.0)).OR.(LBL.EQ.260)) THEN
                            JX = IX * MULTX - 6
                            JY = YYY * MULTY - 4
                            J3X = JX + 3
                            J3Y = JY - 3
                            CALL BAR(JX,JY,J3X,J3Y)
                            GO TO 4030
                        ENDIF
 4020               CONTINUE
 4030           CONTINUE
                ENDIF
            ELSE IF (LMM(IX,YYY).LT.256) THEN
                CALL CURSOR(IX,YYY)
                IF ((MM(IX,YY).GE.112).AND.(MM(IX,YY).LE.
     *              120).AND.((MM(IX-1,YY).EQ.68).OR.
     *              (MM(IX-1,YY).EQ.77))) THEN
                    HALO(2) = CHAR(MM(IX,YY) - 63)
                ELSE
                    HALO(2) = CHAR(LMM(IX,YYY))
                    IF (HALO(2).EQ.'J') HALO(2) = 'H'
                ENDIF
                IF ((MM(IX,YY).GE.50).AND.(MM(IX,YY).LE.57).AND.
     *              (((MM(IX-1,YY).GE.65).AND.(MM(IX-1,YY).LE.90))
     *              .OR.((MM(IX-1,YY).GE.97).AND.(MM(IX-1,YY).LE.
     *              122)))) THEN
                    CALL MOVTCR(0,2)
                    CALL TEXT(HALO)
                    CALL MOVTCR(0,-2)
                ELSE IF (((LMM(IX,YYY).EQ.43).OR.(LMM(IX,YYY).EQ.
     *              45)).OR.((MM(IX,YY).GE.49).AND.(MM(IX,YY)
     *              .LE.57).AND.((LMM(IX-1,YYY).EQ.43).OR.(LMM(IX-1,
     *              YYY).EQ.45)))) THEN
                    DO 4060 LX = IX,1,-1
                        IF (MM(LX,YYY).EQ.42) THEN
                            CALL MOVTCR(0,-10)
                            CALL TEXT(HALO)
                            CALL MOVTCR(0,10)
                            GO TO 4070
                        ELSE IF ((MM(LX,YYY).EQ.0).OR.(LX.EQ.1)) THEN
                            CALL TEXT(HALO)
                            GO TO 4070
                        ENDIF
 4060               CONTINUE
 4070               CONTINUE
                ELSE
                    CALL TEXT(HALO)
                ENDIF
            ELSE IF ((IX.NE.DLX).OR.(YY.NE.DLY)) THEN
                MBOND = LMM(IX,YYY)
                CALL DRAW2(IX,YYY,MBOND)
            ENDIF
            IF (RETR) MM(IX,YYY) = 0
          ENDIF
 5000   CONTINUE
      ENDIF
      RETURN
      END
C
      SUBROUTINE DEL(KAR,IX,IY,INCX,INCY,IWHICH)
      IMPLICIT INTEGER*2 (A-Z)
      REAL SLOPE,DX,DY,THETA,ROUNDX,ROUNDY(2),DIAG
      INTEGER*4 MM,IDTPIX
      INTEGER*2 RTNX(10),RTNY(10)
      CHARACTER*1 HALO(3)
```

```
              LOGICAL*2 BONDEL
              COMMON /CD/ MAXX,MAXY
              COMMON /STRPIX/ LPIX,MM(90,38),LBLEN,LNGBND(100,5)
              COMMON /PARAMS/ JBDIR,NOCHG,LASTN,MCHAR,JCHAR,NLARGE,LEVEL
              COMMON /MODES/ JBTYPE,ICHAR,IBDIR,IBTYPE,ISMART,MODE,ISKILL,ISP
              COMMON /CHARS/IES, IDOT,ITAG,JUMP,LBOND,KAN,ISPACE
              COMMON /LABELS/ NR,NJLAST,NJNEXT
              COMMON /STRED/ IDTPIX(90,38),LABL(260,2),MRKCHN(260)
              COMMON /SIZZE/ MULTX,MULTY
              COMMON /IPLUS/ IHIGH(14,2)
              COMMON /D1/ IDNUM,IDS(9,6),NBD1,DSCNC(6,50)
              COMMON /CUR/ ICUR
              COMMON /HP/IHP
              COMMON /HEAD/ MW(12),ISTATE,PAGE
CXT           BONDEL = TRUE if a bond was last drawn between 2 nodes by
CXT           SUBROUTINE DRAW.
              COMMON /DELBND/ BONDEL
C
C  This subroutine handles, on input of a delete (ASCII 127), removal
C  of the most recently entered character, bond, or long bond.
C
              ICUR = 0
              CALL CURSOR(IX,IY)
              IF ((JCHAR.EQ.2).AND.BONDEL) THEN
                  IX = IX - 1
                  GO TO 11111
              ENDIF
C Erase bonds here, chars below.
              IF (JCHAR.NE.1) GOTO 1
11111         DLX = IX - INCX
              DLY = IY - INCY
              IF ((MM(DLX,DLY).EQ.46).OR.((MM(DLX,DLY).GE.65).AND.
     *            (MM(DLX,DLY).LE.122)).OR.((MM(DLX,DLY).GE.48).AND.
     *            (MM(DLX,DLY).LE.57))) THEN
                  IX = IX - INCX
                  IY = IY - INCY
                  GO TO 11111
C If there is nothing to delete, the cursor is left stationary.
              ELSE IF (MM(DLX,DLY).EQ.0) THEN
                  ICUR = 1
                  CALL CURSOR(IX,IY)
                  RETURN
              ENDIF
              BEGX = IX
              BEGY = IY
              IF (LMM(DLX,DLY).GE.256) THEN
                  BONDEL = .TRUE.
                  IF ((-INCY.NE.0).AND.(LMM(IX,IY).LT.256))
     *                CALL REPLCE(IX,IY,INCX,INCY,DLX,DLY,1)
              ELSE
                  BONDEL = .FALSE.
              ENDIF
              VHSCR = 0
C
C Back up one notch
2             CONTINUE
              IX = IX - INCX
              IY = IY - INCY
C
C Erase bonds and filler atoms until the next node:
              IF ((LMM(IX,IY).GT.256).OR.((MM(IX,IY).GE.50).AND.
     2            (MM(IX,IY).LE.57)) .OR. ((MM(IX,IY).EQ.72) .AND.
     3            ((MM(IX+1,IY).LT.97).OR.(MM(IX+1,IY).GT.122)))) THEN
                  IF ((INCX.EQ.0).AND.(MM(IX,IY).EQ.72)) THEN
                      IF ((MM(IX+1,IY).GE.50).AND.(MM(IX+1,IY).LE.57)) VHSCR = 1
                  ENDIF
22                CONTINUE
                  IF ((BONDEL).AND.(IABS(INCX*INCY).EQ.1)) THEN
                      IF (IHP .EQ. 1) THEN
                          CALL BERASE(IX,IY)
                      ELSE
                          FX = IX -1
                          CALL FTLOCA(IY,FX)
                          CALL FTEXT('^   ^')
                      ENDIF
```

```
              ELSE
                CALL FTLOCA(IY,IX)
            IF (IHP .EQ. 1) THEN
            CALL ERASE(IX,IY)
            ELSE
                CALL FTEXT('^  ^')
            ENDIF
              ENDIF
              IF (((MM(IX,IY).GE.50).AND.(MM(IX,IY).LE.57).AND.
      *         (LMM(IX-1,IY).NE.43).AND.(LMM(IX-1,IY).NE.45)).OR.
      *         (BONDEL)) THEN
                IF (MOD((IY*10),40).EQ.0) THEN
                    IF ((IY.EQ.8).OR.(IY.EQ.28).OR.(IY.EQ.16)) THEN
                        FY = ((IY * 10) / 11) + 1
                        CALL FTSIZE(1,11)
                    ELSE
                        FY = ((IY * 10) / 9) + 1
                        CALL FTSIZE(1,9)
                    ENDIF
                ELSE
                    FY = ((IY * 10) / 8) + 1
                    CALL FTSIZE(1,8)
                ENDIF
                IF((BONDEL).AND.(IABS(INCX*INCY).EQ.1))THEN
                    IF (IHP .EQ. 1) THEN
                    CALL BERASE(IX,IY)
                    ELSE
                    CALL FTLOCA(FY,FX)
                    CALL FTEXT('^    ^')
                    CALL FTSIZE(1,10)
                    ENDIF
                    MM(IX,IY) = 0
                    FY = IY - IHP
                    CALL REPLCE(IX,IY,INCX,INCY,IX,IY,0)
                    IF (INCY.LT.0) THEN
                        FX = IX - INCX
                        CALL REPLCE(IX,FY,INCX,INCY,FX,FY,0)
                    ELSE
                        CALL REPLCE(IX,FY,INCX,INCY,0,0,0)
                    ENDIF
                ELSE
                    CALL FTLOCA(FY,IX)
                    IF (IHP .EQ. 1) THEN
                    CALL ERASE(IX,IY)
                    ELSE
                    CALL FTEXT('^  ^')
                    ENDIF
                    CALL FTSIZE(1,10)
                    MM(IX,IY) = 0
                    IF (INCY.EQ.0) THEN
                        FY = IY -IHP
                        CALL REPLCE(IX,FY,INCX,INCY,0,0,0)
                    ENDIF
                ENDIF
              ENDIF
              IF (VHSCR.EQ.1) THEN
                IX = IX + 1
                VHSCR = 2
                GO TO 22
              ELSE IF (VHSCR.EQ.2) THEN
                FY = IY + 1
                CALL REPLCE(IX,FY,INCX,INCY,0,0,0)
                IX = IX - 1
                VHSCR = 0
              ENDIF
C Keep deleting this bond
            GOTO 2
            ENDIF
C
3           CONTINUE
            IF (INCY.NE.0) THEN
                CALL REPLCE(IX,IY,INCX,INCY,0,0,1)
                CALL REPLCE(BEGX,BEGY,INCX,INCY,0,0,1)
            ENDIF
            IF (LBLEN.GT.0) CALL RELONG
```

```
              IF (LEVEL.EQ.0) ICUR = 1
              CALL CURSOR(IX,IY)
              IF (MM(IX,IY).LE.0) GOTO 7
              K=LMM(IX,IY)
              IF (K.EQ.46) GOTO 23
C IF STEREO H IS ERASED, REPLACE WITH STEREO H, NOT INTERNALLY
C STORED J.
              IF (K .EQ. 74) K=72
C TRANSLATE Dp-Dx to D1-D9 and Mp-Mx to M1-M9 for redisplay.
              IF ((K.GE.112).AND.(K.LE.120).AND.((MM(IX-1,IY).EQ.
     *          68).OR.(MM(IX-1,IY).EQ.77))) K = K - 63
              HALO(2) = CHAR(K)
              CALL TEXT(HALO)
C retype letter
C RECONVERT Dp to D1 and Mp to M1.

IF ((K.GE.49).AND.(K.LE.57).AND.((MM(IX-1,IY).EQ.
     *          68).OR.(MM(IX-1,IY).EQ.77))) K = K + 63
              IF (K.NE.46) GOTO 10
C Loop to retype marker--not nec if dot only
23            DO 21 I=1,260
              IF (LABL(I,1).LT.0) GOTO 21
              IF (LABL(I,1).EQ.0) GO TO 5000
              IF ((LABL(I,1).NE.IX).OR.(LABL(I,2).NE.IY)) GOTO 21
C ASCII marker
              MARK=MOD(I,26)+96
              IF (MARK.EQ.96) MARK=122
              CALL CURSOR (IX,IY)
              HALO(2) = CHAR(MARK)
              CALL TEXT(HALO)
C retype marker
              GOTO 10
21            CONTINUE
5000          CONTINUE
              JX = IX * MULTX - 6
              JY = IY * MULTY - 4
              J3X = JX + 3
              J3Y = JY - 3
              CALL BAR(JX,JY,J3X,J3Y)
C       Identify cap, '.', AND '?'.
10            IF (.NOT.((K.EQ.46) .OR. (K.EQ.63) .OR. ((K.GE.65).AND.(K.LE.90)
     2          ))) GOTO 6
C identify as if this node was just typed.
              KAR=K
              ICHAR=2
              IX=IX+1
              GOTO 7
6             IF ((K.LT.97) .OR. (K.GT.122)) GOTO 7
              KAR=LMM(IX-1,IY)
              ICHAR=2
7             CONTINUE
              IF (IX.GT.MAXX) THEN
                  IX = MAXX
              ELSE IF (IX.LT.1) THEN
                  IX = 1
              ENDIF
              IF (IY.GT.MAXY) THEN
                  IY = MAXY
              ELSE IF (IY.LT.1) THEN
                  IY = 1
              ENDIF
              BONDEL = .FALSE.
              ICUR = 1
              CALL CURSOR (IX,IY)
              RETURN
C
1             IF (JCHAR.EQ.8) GOTO 60
              IF (JCHAR.EQ.6) GO TO 40
              IF (JCHAR.EQ.9) GO TO 140
              IX=IX-1
CXT
C If there is nothing to delete, the cursor is left stationary.
              IF (MM(IX,IY).EQ.0) THEN
                  IX = IX + 1
                  ICUR = 1
                  CALL CURSOR(IX,IY)
```

```
              RETURN
            ENDIF
C Delete prevous char

CALL FTLOCA(IY,IX)
            IF (IHP .EQ. 1) THEN      !Use this undrawing section if using
                                      !an HP terminal
            CALL ERASE(IX,IY)         !Erase pixel
            ELSE
            CALL FTEXT('^ ^')
            IF ((MM(IX,IY).EQ.46).OR.
     *          ((MM(IX,IY).GE.50).AND.(MM(IX,IY).LE.57).AND.
     *          (LMM(IX-1,IY).NE.43).AND.(LMM(IX-1,IY).NE.45)).OR.(MM(IX,
     *          IY).EQ.103).OR.(MM(IX,IY).EQ.106).OR.(MM(IX,IY).EQ.112)
     *          .OR.(MM(IX,IY).EQ.113).OR.(MM(IX,IY).EQ.121)) THEN
                IF (MOD((IY*10),40).EQ.0) THEN
                    IF ((IY.EQ.8).OR.(IY.EQ.28).OR.(IY.EQ.16)) THEN
                        FY = ((IY * 10) / 11) + 1
                        CALL FTSIZE(1,11)
                    ELSE
                        FY = ((IY * 10) / 9) + 1
                        CALL FTSIZE(1,9)
                    ENDIF
                ELSE
                    FY = ((IY * 10) / 8) + 1
                    CALL FTSIZE(1,8)
                ENDIF
                CALL FTLOCA(FY,IX)
                CALL FTEXT('^ ^')
                CALL FTSIZE(1,10)
                FY = IY + 1
                CALL REPLCE(IX,FY,0,0,0,0,0)
            ENDIF
            ENDIF
            CALL CURSOR(IX,IY)
            IF (MM(IX,IY).NE.46) GOTO 4
C Elim erased symbols from marker list
            DO 5 I=1,260
            IF (LABL(I,1)+LABL(I,2).EQ.0) GOTO 4
            IF ((LABL(I,1).NE.IX).OR.(LABL(I,2).NE.IY)) GOTO 5
            LABL(I,1)=-999
            LABL(I,2)=-999
            MRKCHN(I)=0
            GOTO 4
5           CONTINUE
C
4           MM(IX,IY)=0
            JX=IX-1
            K=LMM(JX,IY)
            IF (.NOT.((K.GE.30).AND.(K.LT.123))) GOTO 1110
            IX=IX-1
            GO TO 10
1110        NODE=0
            DO 50 IDIRX=-1,1
            DO 50 IDIRY=-1,1
            NEWX=IX+IDIRX
            NEWY=IY+IDIRY
            IF ((IDIRX.EQ.0).AND.(IDIRY.EQ.0)) GOTO 50
C Off edge
17          IF ((NEWX.LT.1) .OR. (NEWX.GT.MAXX)) GOTO 50
            IF ((NEWY.LT.1) .OR. (NEWY.GT.MAXY)) GOTO 50
C Blank space
            IF (MM(NEWX,NEWY).EQ.0) GOTO 50
C Bonds are > 256
            IF (LMM(NEWX,NEWY).LT.256) GOTO 14
C Bond extracted for type
            JBOND=LMM(NEWX,NEWY)/2**8
C Following 5 lines skip bonds not pointed to node being analyzed
C Bond direction
            JDIR=LMM(NEWX,NEWY) - JBOND*2**8
            IF ((IDIRX*IDIRY.EQ.-1).AND.(MOD(JDIR,4).NE.2)) GO TO 50
            IF ((IDIRX*IDIRY.EQ.1).AND.(MOD(JDIR,4).NE.0)) GO TO 50
            IF ((IDIRX.EQ.0) .AND. (MOD(JDIR,4).NE.1)) GOTO 50
```

```
              IF ((IDIRY.EQ.0) .AND. (MOD(JDIR,4).NE.3)) GOTO 50
              NODE=1
              GOTO 51
C
C H, lowercase, numerals, signs etc.
14            NEWX=NEWX+IDIRX
C This aboids endless loop.
              IF (IDIRX .EQ. 0) GO TO 50
              GOTO 17
50            CONTINUE
51            CONTINUE
C Picture boundary limits are adjusted.
              IF (IX.GT.MAXX) THEN
                  IX = MAXX
              ELSE IF (IX.LT.1) THEN
                  IX = 1
              ENDIF
              IF (IY.GT.MAXY) THEN
                  IY = MAXY
              ELSE IF (IY.LT.1) THEN
                  IY = 1
              ENDIF
              IF (NODE.LE.0) THEN
                  ICUR = 1
                  CALL CURSOR(IX,IY)
                  RETURN
              ENDIF
C
C BOND
              JCHAR=1
              ICHAR=1
              IBDIR=JDIR
              IBTYPE=JBOND
              KAR=LMM(NEWX,NEWY)
              IF (IX.GT.MAXX) THEN
                  IX = MAXX
              ELSE IF (IX.LT.1) THEN
                  IX = 1
              ENDIF
              IF (IY.GT.MAXY) THEN
                  IY = MAXY
              ELSE IF (IY.LT.1) THEN
                  IY = 1
              ENDIF
              ICUR = 1
              CALL CURSOR(IX,IY)
              RETURN
C We are deleting a charge
40            IX=IX-1
              IF(LMM(IX,IY).EQ.43 .OR. LMM(IX,IY).EQ.45)GO TO 45
C Charge at a node
              IIX=IX
              IF (MM(IX,IY).EQ.46.OR.MM(IX,IY).EQ.63.OR.
     1        (MM(IX,IY).GE. 65).AND.(MM(IX,IY) .LE.90)) GO TO 41
              IX=IX-1
              IF((MM(IX,IY).GE.65).AND.(MM(IX,IY).LE.90)) GOTO 41
C Can't find good node
              IERR=24
              CALL MYERR(IERR,KAR,KAR)
              IX=IIX+1
              ICUR = 1
              CALL CURSOR(IX,IY)
              RETURN
41            JX=IX+1
              JY = IY - 1
              IF((LMM(JX,JY).EQ.43.OR.LMM(JX,JY).EQ.45) .AND.
     1        (IX .EQ. (JX-IHIGH(IHMM(JX,JY),1))) .AND.
     2        (IY .EQ. (JY+IHP*IHIGH(IHMM(JX,JY),2)))) GO TO 47
              JY = IY + 1
              IF((LMM(JX,JY).EQ.43.OR.LMM(JX,JY).EQ.45) .AND.
     1        (IX .EQ. (JX-IHIGH(IHMM(JX,JY),1))) .AND.
     2        (IY .EQ. (JY+IHP*IHIGH(IHMM(JX,JY),2)))) GO TO 47
              JX=IX-1
              IF((LMM(JX,JY).EQ.43.OR.LMM(JX,JY).EQ.45) .AND.
     1        (IX .EQ. (JX-IHIGH(IHMM(JX,JY),1))) .AND.
     2        (IY .EQ. (JY+IHP*IHIGH(IHMM(JX,JY),2)))) GO TO 47
```

```
            JY = IY - 1
            IF((LMM(JX,JY).EQ.43.OR.LMM(JX,JY).EQ.45) .AND.
     1      (IX .EQ. (JX-IHIGH(IHMM(JX,JY),1))) .AND.
     2      (IY .EQ. (JY+IHP*IHIGH(IHMM(JX,JY),2)))) GO TO 47
            JX=JX-1
            IF((LMM(JX,JY).EQ.43.OR.LMM(JX,JY).EQ.45) .AND.
     1      (IX .EQ. (JX-IHIGH(IHMM(JX,JY),1))) .AND.
     2      (IY .EQ. (JY+IHP*IHIGH(IHMM(JX,JY),2)))) GO TO 47
            JY = IY + 1
            IF((LMM(JX,JY).EQ.43.OR.LMM(JX,JY).EQ.45) .AND.
     1      (IX .EQ. (JX-IHIGH(IHMM(JX,JY),1))) .AND.
     2      (IY .EQ. (JY+IHP*IHIGH(IHMM(JX,JY),2)))) GO TO 47
            IERR=24
            CALL MYERR(IERR,KAR,KAR)
C Can't find charge
            IX=IIX+1
            CALL CURSOR(IX,IY)
            IF (IX.GT.MAXX) THEN
                IX = MAXX
            ELSE IF (IX.LT.1) THEN
                IX = 1
            ENDIF
            IF (IY.GT.MAXY) THEN
                IY = MAXY
            ELSE IF (IY.LT.1) THEN
                IY = 1
            ENDIF
            ICUR = 1
            RETURN
C Clear cell
47          MM(JX,JY)=0
            CALL FTLOCA(JY,JX)
            CALL FTEXT('^ ^')
C Erase charge
            IF ((MM(JX+1,JY).GE.50).AND.(MM(JX+1,JY).LE.57)) THEN
C Clear cell
                MM(JX+1,JY)=0
                FX = JX + 1
                CALL FTLOCA(JY,FX)
                CALL FTEXT('^ ^')
            ENDIF
C Erase digit
            IX=IIX+1
            CALL CURSOR(IX,IY)
            KAR=LMM(IIX,IY)
            ICHAR=2
            IF((KAR.GE.97).AND.(KAR.LE.122))ICHAR=4
C Make it look like we just entered node
            IF (IX.GT.MAXX) THEN
                IX = MAXX
            ELSE IF (IX.LT.1) THEN
                IX = 1
            ENDIF
            IF (IY.GT.MAXY) THEN
                IY = MAXY
            ELSE IF (IY.LT.1) THEN
                IY = 1
            ENDIF
            ICUR = 1
            CALL CURSOR(IX,IY)
            RETURN
C Clear MM cell - we have a delocalized charge
45          MM(IX,IY)=0
            CALL FTLOCA(IY,IX)
            CALL FTEXT('^ ^')
C Erase charge
            IF((MM(IX+1,IY).LT.48) .OR. MM(IX+1,IY).GT.57) GO TO 46
C Charge is followed by digit - del that also
            IX=IX+1
```

```
C Clear cell
        MM(IX,IY)=0
        CALL FTLOCA(IY,IX)
        CALL FTEXT('^ ^')
C Erase digit
46      CALL CURSOR(IX,IY)
        KAR=13
        ICHAR=26
C Return witg kar = CARR RETURN - I.E. NOP
        MODE=1
        IF (IX.GT.MAXX) THEN
           IX = MAXX
        ELSE IF (IX.LT.1) THEN
           IX = 1
        ENDIF
        IF (IY.GT.MAXY) THEN
           IY = MAXY
        ELSE IF (IY.LT.1) THEN
           IY = 1
        ENDIF
        ICUR = 1
        CALL CURSOR(IX,IY)
        RETURN
C We are deleting a "
140     IX=IX-1
C At a node
        IIX=IX
        IF (MM(IX,IY).EQ.46.OR.MM(IX,IY).EQ.63.OR.
     1   (MM(IX,IY).GE. 65).AND.(MM(IX,IY) .LE.90)) GO TO 141
        IX=IX-1
        IF((MM(IX,IY).GE.65).AND.(MM(IX,IY).LE.90)) GOTO 141
C Can't find good node
        IERR=24
        CALL MYERR(IERR,KAR,KAR)
        IX=IIX+1
        ICUR = 1
        CALL CURSOR(IX,IY)
        RETURN
C
141     CONTINUE
        JX=IX+1
        JY = IY - 1
        IF ((MM(JX,JY).EQ.34).AND.(DSCNC(3,NBD1).EQ.IX).AND.
     *    (DSCNC(4,NBD1).EQ.IY)) GO TO 147
        JY = IY + 1
        IF ((MM(JX,JY).EQ.34).AND.(DSCNC(3,NBD1).EQ.IX).AND.
     *    (DSCNC(4,NBD1).EQ.IY)) GO TO 147
        JX= IX - 1
        IF ((MM(JX,JY).EQ.34).AND.(DSCNC(3,NBD1).EQ.IX).AND.
     *    (DSCNC(4,NBD1).EQ.IY)) GO TO 147
        JY = IY - 1
        IF ((MM(JX,JY).EQ.34).AND.(DSCNC(3,NBD1).EQ.IX).AND.
     *    (DSCNC(4,NBD1).EQ.IY)) GO TO 147
        IERR=24
        CALL MYERR(IERR,KAR,KAR)
C Can't cind "
        IX=IIX+1
        CALL CURSOR(IX,IY)
        IF (IX.GT.MAXX) THEN
           IX = MAXX
        ELSE IF (IX.LT.1) THEN
           IX = 1
        ENDIF
        IF (IY.GT.MAXY) THEN
           IY = MAXY
        ELSE IF (IY.LT.1) THEN
           IY = 1
        ENDIF
        ICUR = 1
        RETURN
C Clear cell
147     MM(JX,JY)=0
        CALL FTLOCA(JY,JX)
        CALL FTEXT('^ ^')
        DO 1444 K = 1,6
```

```
              DSCNC(K,NBD1) = 0
1444    CONTINUE
        NBD1 = NBD1 - 1
148     IX=IIX+1
        CALL CURSOR(IX,IY)
        KAR=LMM(IIX,IY)
        ICHAR=2
        IF((KAR.GE.97).AND.(KAR.LE.122))ICHAR=4
C Make it look like we just entered node.
        IF (IX.GT.MAXX) THEN
            IX = MAXX
        ELSE IF (IX.LT.1) THEN
            IX = 1
        ENDIF
        IF (IY.GT.MAXY) THEN
            IY = MAXY
        ELSE IF (IY.LT.1) THEN
            IY = 1
        ENDIF
        ICUR = 1
        CALL CURSOR(IX,IY)
        RETURN
145     MM(IX,IY)=0
        CALL FTLOCA(IY,IX)
        CALL FTEXT('^ ^')
        RETURN
C Following code (thru END) deletes last long bond entered:
C
C If IWHICH not 0 then delete long bond # IWHICH
60      LINE=IWHICH
        IF(IWHICH .NE. 0) GO TO 62
        LINE=0
C Find last long bond entered in LNGBND.
        DO 61 I=1,200
        IF (LNGBND(I,1).EQ.0) GOTO 62
        LINE=I
61      CONTINUE
C
62      CONTINUE
        IF (IHP .EQ. 1) THEN
        CALL HPLONG(LINE)
        ELSE
        IX1=LNGBND(LINE,1)
        IY1=LNGBND(LINE,2)
        IX2=LNGBND(LINE,3)
        IY2=LNGBND(LINE,4)
        IBOND=LNGBND(LINE,5)
        DY = IY2 - IY1
        IF (DY.GT.0) THEN
            DY = (-1) * DY
            BGX = IX2
            BGY = IY2
            FNX = IX1
            FNY = IY1
        ELSE
            BGX = IX1
            BGY = IY1
            FNX = IX2
            FNY = IY2
        ENDIF
        DX = FNX - BGX
        KX = BGX
        KY = BGY
        SLOPE = 0.0
        IF (DX.NE.0.0) THEN
            SLOPE = DY / DX
            THETA = ATAN(SLOPE)
            IF ((THETA.LE.0.).AND.(DX.LT.0.)) THETA = THETA - 3.14159265
C           Principal value problem
            IF ((THETA.GT.0.) .AND. ((DX.LT.0.) .OR. (DY.LT.0.)))
2               THETA = THETA + 3.14159265
        ENDIF
        IF (DX.GT.0.0) THEN
            INKX = 1
            ROUNDX = 0.0
```

```
         ELSE IF (DX.EQ.0.0) THEN
            INKX = 0
            ROUNDX = 0.0
         ELSE
            INKX = -1
            ROUNDX = 0.0
         ENDIF
         IF (DY.LT.0.0) THEN
            INKY = -1
            ROUNDY(1) = 1.0
            ROUNDY(2) = -1.0
         ELSE
            INKY = 0
         ENDIF
         DIAG = ABS(SLOPE)
         IF ((0.86666.LT.DIAG).AND.(DIAG.LT.1.15385)) THEN
            THRI = 0
            XL = 3
            XR = 4
            RY = BGY
         ELSE IF ((DX*DY.NE.0.0).AND.(ABS(DX).GT.ABS(DY))) THEN
            THRI = 0
            XL = 3
            XR = 4
         ELSE
            THRI = -1
            XL = 3
            XR = 5
         ENDIF
         NDDCHG = 0
2311     CONTINUE
         ICUR = 0
         IF (DX.EQ.0.0) THEN
            KY = KY + INKY
         ELSE IF (DY.EQ.0.0) THEN
            KX = KX + INKX
         ELSE IF ((0.86666.LT.DIAG).AND.(DIAG.LT.1.15385)) THEN
            IF (THRI.GT.0) THEN
               KY = RY + ROUNDY(THRI)
            ELSE
               KX = KX + INKX
               RY = RY + INKY
               KY = RY
            ENDIF
         ELSE IF (ABS(DX).GE.ABS(DY)) THEN
            IF (THRI.GT.0) THEN
               KY = RY + ROUNDY(THRI)
            ELSE
               KX = FLOAT(KX) + FLOAT(INKX)
               RY = (FLOAT(IABS(KX-BGX)) * SIN(THETA)) + FLOAT(BGY)
               KY = RY
            ENDIF
         ELSE IF (ABS(DX).LT.ABS(DY)) THEN
            KY = KY + INKY
            KX = (FLOAT(IABS(KY-BGY)) * COS(THETA)) + FLOAT(BGX)
         ENDIF
         IF (IABS(INKX*INKY).EQ.1) THEN
            IF (THRI.EQ.-1) THEN
               FX = KX - 3
               CALL FTLOCA(KY,FX)
               CALL FTEXT('^        ^')
            ELSE
               FX = KX - 3
               CALL FTLOCA(KY,FX)
               CALL FTEXT('^        ^')
            ENDIF
         ELSE
            FX = KX
            CALL FTLOCA(KY,FX)
            CALL FTEXT('^ ^')
         ENDIF
         IF (MOD((KY*10),40).EQ.0) THEN
            IF ((KY.EQ.8).OR.(KY.EQ.28).OR.(KY.EQ.16)) THEN
               FY = ((KY * 10) / 11) + 1
               CALL FTSIZE(1,11)
```

```
              ELSE
                  FY = ((KY * 10) / 9) + 1
                  CALL FTSIZE(1,9)
              ENDIF
          ELSE
              FY = ((KY * 10) / 8) + 1
              CALL FTSIZE(1,8)
          ENDIF
          IF (IABS(INKX*INKY).EQ.1) THEN
              CALL FTLOCA(FY,FX)
              CALL FTEXT('^        ^')
              CALL FTSIZE(1,10)
          ELSE
              CALL FTLOCA(FY,FX)
              CALL FTEXT('^ ^')
              CALL FTSIZE(1,10)
          ENDIF
C
          IF (IABS(INKX*INKY).EQ.1) THEN
              DO 4000 YY = KY,KY+1
                  DO 3000 KKK = KX-XL,KX+XR
                      IF (MM(KKK,YY).GT.0) THEN
                          YYY = YY
                          KKKK = KKK
                          IF (MM(KKKK,YY).EQ.46) THEN
                              DO 2020 LBL = 1,260
                                  IF ((LABL(LBL,1).EQ.KKKK).AND.(LABL(LBL,2)
                                  .EQ.YY)) THEN
                                      CALL CURSOR(KKKK,YYY)
                                      IF (MOD(LBL,26).EQ.0) THEN
                                          HALO(2) = 'z'
                                      ELSE
                                          HALO(2) = CHAR(MOD(LBL,26)+96)
                                      ENDIF
                                      CALL TEXT(HALO)
                                      GO TO 2030
                                  ELSE IF (((LABL(LBL,1).EQ.0).AND.
                                      (LABL(LBL,2).EQ.0)).OR.(LBL.EQ.260)) THEN
                                      JX = KKK * MULTX - 6
                                      JY = YYY * MULTY - 4
                                      J3X = JX + 3
                                      J3Y = JY - 3
                                      CALL BAR(JX,JY,J3X,J3Y)
                                      GO TO 2030
                                  ENDIF
2020                          CONTINUE
2030                      CONTINUE
                          ELSE IF (LMM(KKKK,YYY).LT.256) THEN
                              IF ((MM(KKK,YY).GE.112).AND.(MM(KKK,YY).LE.
                              120).AND.((MM(KKK-1,YY).EQ.68).OR.
                              (MM(KKK-1,YY).EQ.77))) THEN
                                  HALO(2) = CHAR(MM(KKK,YY) - 63)
                              ELSE
                                  HALO(2) = CHAR(LMM(KKKK,YYY))
                                  IF (HALO(2).EQ.'J') HALO(2) = 'H'
                              ENDIF
                              CALL CURSOR(KKKK,YYY)
                              IF ((MM(KKK,YY).GE.50).AND.(MM(KKK,YY).LE.57)
                              .AND.(((MM(KKK-1,YY).GE.65).AND.(MM(KKK-1,YY)
                              .LE.90)).OR.((MM(KKK-1,YY).GE.97).AND.
                              (MM(KKK-1,YY).LE.122)))) THEN
                                  CALL MOVTCR(0,2)
                                  CALL TEXT(HALO)
                                  CALL MOVTCR(0,-2)
                              ELSE IF (((LMM(KKK,YYY).EQ.43).OR.(LMM(KKK,YYY)
                                  .EQ.45)).OR.((MM(KKK,YY).GE.49).AND.(MM(KKK
                                  ,YY).LE.57).AND.((LMM(KKK-1,YYY).EQ.43).OR.
                                  (LMM(KKK-1,YYY).EQ.45)))) THEN
                                  DO 2060 LX = KKK,1,-1
                                      IF (MM(LX,YY).EQ.42) THEN
                                          DO 2050 LLXX = 1,NDDCHG
                                              IF ((RTNX(LLXX).EQ.KKK).AND.
                                              (RTNY(LLXX).EQ.YY)) GO TO 2070
2050                                      CONTINUE
                                          NDDCHG = NDDCHG + 1
```

```
                              RTNX(NDDCHG) = KKK
                              RTNY(NDDCHG) = YY
                              GO TO 2070
                          ELSE IF ((MM(LX,YY).EQ.0).OR.(LX.EQ.1))
*                              THEN
                              CALL TEXT(HALO)
                              GO TO 2070
                          ENDIF
2060              CONTINUE
2070          CONTINUE
              ELSE
                  CALL TEXT(HALO)
              ENDIF
          ELSE
              MBOND = LMM(KKKK,YYY)
              CALL DRAW2(KKKK,YYY,MBOND)
          ENDIF
      ENDIF
3000  CONTINUE
4000  CONTINUE
      ELSE
          DO 6000 YY = KY,KY+1
              IF (MM(KX,YY).GT.0) THEN
                  YYY = YY
                  IF (MM(KX,YY).EQ.46) THEN
                      DO 4020 LBL = 1,260
                          IF ((LABL(LBL,1).EQ.KX).AND.(LABL(LBL,2).EQ.YY))
*                              THEN
                              CALL CURSOR(KX,YYY)
                              IF (MOD(LBL,26).EQ.0) THEN
                                  HALO(2) = 'z'
                              ELSE
                                  HALO(2) = CHAR(MOD(LBL,26)+96)
                              ENDIF
                              CALL TEXT(HALO)
                              GO TO 4030
                          ELSE IF (((LABL(LBL,1).EQ.0).AND.(LABL(LBL,2)
*                              .EQ.0)).OR.(LBL.EQ.260)) THEN
                              JX = KX * MULTX - 6
                              JY = YYY * MULTY - 4
                              J3X = JX + 3
                              J3Y = JY - 3
                              CALL BAR(JX,JY,J3X,J3Y)
                              GO TO 4030
                          ENDIF
4020                  CONTINUE
4030              CONTINUE
                  ELSE IF (LMM(KX,YYY).LT.256) THEN
                      CALL CURSOR(KX,YYY)
                      IF ((MM(KX,YY).GE.112).AND.(MM(KX,YY).LE.
*                          120).AND.((MM(KX-1,YY).EQ.68).OR.
*                          (MM(KX-1,YY).EQ.77))) THEN
                          HALO(2) = CHAR(MM(KX,YY) - 63)
                      ELSE
                          HALO(2) = CHAR(LMM(KX,YYY))
                          IF (HALO(2).EQ.'J') HALO(2) = 'H'
                      ENDIF
                      IF ((MM(KX,YY).GE.50).AND.(MM(KX,YY).LE.57).AND.
*                          (((MM(KX-1,YY).GE.65).AND.(MM(KX-1,YY).LE.90))
*                          .OR.((MM(KX-1,YY).GE.97).AND.(MM(KX-1,YY).LE.
*                          122)))) THEN
                          CALL MOVTCR(0,2)
                          CALL TEXT(HALO)
                          CALL MOVTCR(0,-2)
                      ELSE IF (((LMM(KX,YYY).EQ.43).OR.(LMM(KX,YYY).EQ.
*                          45)).OR.((MM(KX,YY).GE.49).AND.(MM(KX,YY).LE.
*                          57).AND.((LMM(KX-1,YYY).EQ.43).OR.(LMM(KX-1,
*                          YYY).EQ.45)))) THEN
                          DO 4060 LX = KX,1,-1
                              IF (MM(LX,YYY).EQ.42) THEN
                                  DO 4050 LLXX = 1,NDDCHG
                                      IF ((RTNX(LLXX).EQ.KX).AND.
*                                         (RTNY(LLXX).EQ.YYY)) GO TO 4070
4050                              CONTINUE
                                  NDDCHG = NDDCHG + 1
                                  RTNX(NDDCHG) = KX
```

```
                            RTNY(NDDCHG) = YYY
                            GO TO 4070
                        ELSE IF ((MM(LX,YYY).EQ.0).OR.(LX.EQ.1)) THEN
                            CALL TEXT(HALO)
                            GO TO 4070
                        ENDIF
4060                CONTINUE
4070                CONTINUE
                ELSE
                    CALL TEXT(HALO)
                ENDIF
            ELSE
                MBOND = LMM(KX,YYY)
                CALL DRAW2(KX,YYY,MBOND)
            ENDIF
        ENDIF
6000    CONTINUE
    ENDIF
    IF ((((KX.GE.FNX-4).AND.(KX.LE.FNX+4).AND.(INKY.NE.0))
*       .OR.((KX.GE.FNX-1).AND.(KX.LE.FNX+1))).AND.((KY.EQ.FNY)
*       .OR.(KY.EQ.FNY-INKY))) GO TO 3368
*   IF ((KX.LT.0).OR.(KX.GT.MAXX).OR.(KY.LT.0).OR.(KY.GT.MAXY))
*       THEN
        CALL MYERR(24,KAR,KAR)
        GO TO 43
    ENDIF
    IF (THRI.EQ.2) THEN
        THRI = 0
    ELSE IF (THRI.GE.0) THEN
        THRI = THRI + 1
    ENDIF
    GO TO 2311
3368 CONTINUE
    CALL REPLCE(IX1,IY1,INKX,INKY,0,0,1)
    CALL REPLCE(IX2,IY2,INKX,INKY,0,0,1)
    IF (NDDCHG.GT.0) THEN
        DO 3369 I = 1,NDDCHG
            HALO(2) = CHAR(MM(RTNX(I),RTNY(I)))
            ICUR = 0
            CALL CURSOR(RTNX(I),RTNY(I))
            CALL MOVTCR(0,-10)
            CALL TEXT(HALO)
            CALL MOVTCR(0,10)
3369    CONTINUE
        ICUR = 1
        CALL CURSOR(IX1,IY1)
    ENDIF
ENDIF
C
C Now zero out the last line of LNGBND.
C       SKIP THIS "ZERO" CODE IF WE ARE GOING TO REDRAW A LONG BOND
107 CONTINUE
    LNGBND(LINE,1) = 0
    IF ((IWHICH.NE.0).AND.(IBTYPE.NE.0)) GO TO 666
    DO 63 I=2,5
        LNGBND(LINE,I) = 0
63  CONTINUE
    IF (LBLEN.GT.LINE) THEN
        DO 65 I = LINE,LBLEN
            IF (I.LT.100) THEN
                DO 64 J = 1,5
                    LNGBND(I,J) = LNGBND(I+1,J)
64              CONTINUE
            ENDIF
65      CONTINUE
    ENDIF
    LBLEN = LBLEN - 1
666 CONTINUE
    IF (LBLEN.GT.0) CALL RELONG
C ERASE ALL H's & SUBSCRIPTS:  **********
    KX=IX1
    KY=IY1
C Only@nodes
    IF ((MM(KX,KY).LE.65) .OR. (MM(KX,KY).GT.90)) GOTO 43
C
```

```
          CALL CLRHYD(KX,KY)
          CALL VALNCE(2,IX1,IY1,0,0)
43        CONTINUE
          ICUR = 1
          CALL CURSOR(IX2+1,IY2)
          RETURN
          END
$STORAGE:2
C
          SUBROUTINE ERRMSG(KAR)
          IMPLICIT INTEGER*2 (A-Z)
          CHARACTER*82 BLNK90
          CHARACTER*1 HALO(3)
          CHARACTER*3 HALOE
          EQUIVALENCE (HALOE,HALO(1))
          CHARACTER*1 KAN
          COMMON /CHARS/IES, IDOT,ITAG,IJUMP,LBOND,KAN,ISPACE
          COMMON /HEAD/ MW(12),ISTATE,PAGE
          COMMON /BLANK/ BLNK90
          COMMON /QTVLNC/ OERR,CHER
C
          CALL FTSIZE(2,18)
          IF (PAGE.EQ.0) THEN
              CALL FTLOCA(1,1)
              CALL FTEXT(BLNK90)
          ENDIF
          PAGE = 0
          IF (CHAR(KAR).NE.KAN) THEN
              HALO(1) = KAN
              HALO(3) = KAN
          ELSE
              HALO(1) = '/'
              HALO(3) = '/'
          ENDIF
          IF (KAR.EQ.0) GOTO 101
          CALL FTLOCA(4,1)
          IF (KAR.GE.128) THEN
            CALL FTEXT('^NON-RELEVANT KEY PRESSED. REENTER.^')
            GO TO 9
          ENDIF
          IF (KAR.EQ.13) GO TO 25
              HALO(2) = CHAR(KAR)
              CALL FTEXT(HALOE)
              CALL FTEXT('^ IS AN ILLEGAL INPUT. REENTER.^')
              GO TO 9
25        CONTINUE
          CALL FTEXT('^CR IS AN ILLEGAL INPUT. REENTER.^')
          GOTO 9
101       CONTINUE
          CALL FTLOCA(4,1)
          CALL FTEXT('^MUST BEGIN LONG BOND AT A MARKER! REENTER.^')
9         CONTINUE
          CALL FTSIZE(1,10)
          RETURN
          END
C
C         ERROR MESSAGE SUBROUTINE
C
          SUBROUTINE MYERR(IERR,KAR,MAR)
          IMPLICIT INTEGER*2 (A-Z)
          CHARACTER*82 BLNK90
          CHARACTER*54 MSBUF(61)
          CHARACTER*1 HALO(3)
          CHARACTER*3 HALOE
          EQUIVALENCE (HALOE,HALO(1))
          CHARACTER*1 KAN
          COMMON /CHARS/IES, IDOT,ITAG,JUMP,LBOND,KAN,ISPACE
          COMMON /HEAD/ MW(12),ISTATE,PAGE
          COMMON /BLANK/ BLNK90
          COMMON /WARN/ ERR
          COMMON /QTVLNC/ OERR,CHER
          DATA MSBUF(1)
     1    /'^NO SPACE AVAILABLE FOR CHAIN/GROUP-ENTER CMD OR ESC ^'/
          DATA MSBUF(2)
     1    /'^CMD STRING INTERRUPTED BY CR/Q - COMMAND ABORTED     ^'/
          DATA MSBUF(3)
```

```
 1    /'^BAD ENVIRONMENT FOR CHAIN OR GROUP-ENTER CMD OR ESC  ^'/
      DATA MSBUF(4)
 1    /'^ONLY 1 NONLOCAL CHARGE ALLOWED - CMD ABORTED          ^'/
      DATA MSBUF(5)
 1    /'^MUST ENTER BOND TYPE -OR- CR                          ^'/
      DATA MSBUF(6)
 1    /'^BAD/NO REPEAT CMD - REENTER CMD - (CR TO GND)         ^'/
      DATA MSBUF(7)
 1    /'^BAD BOND/NO BOND FOUND - REPEAT ABORTED               ^'/
      DATA MSBUF(8)
 1    /'^" BOND MARKER AND Dx NODE ARE NOT MATCHED             ^'/
      DATA MSBUF(9)
 1    /'^BAD LONG BOND - (0 LEN/NO ENDPOINT)- CMD ABORTED      ^'/
      DATA MSBUF(10)
 1    /'^INVALID CHARACTER                                     ^'/
      DATA MSBUF(11)
 1    /'^ ELEMENT DOES NOT EXIST IN ELEMENT TABLE              ^'/
      DATA MSBUF(12)
 1    /'^WARNING: TOO MANY BONDS FOR VALENCY                   ^'/
      DATA MSBUF(13)
 1    /'^CONTEXT ERROR - UNFORESEEN PROBLEM                    ^'/
      DATA MSBUF(14)
 1    /'^NO ROOM FOR FILLER HYDROGENS                          ^'/
      DATA MSBUF(15)
 1    /'^ERROR IN DECIDING WHERE TO PUT H''S                   ^'/
      DATA MSBUF(16)
 1    /'^ALL MARKERS USED- OR -NOT ENOUGH MARKERS FOR CHAIN    ^'/
      DATA MSBUF(17)
 1    /'^BAD ANGLE DATA FOR GROUP - CMD ABORTED                ^'/
      DATA MSBUF(18)
 1    /'^NULL CONNECTION TABLE                                 ^'/
      DATA MSBUF(19)
 1    /'^RETURNING TO NEW STRUCTURE MENU-DATA WILL BE LOST     ^'/
      DATA MSBUF(20)
 1    /'^DOT DISCONNECTED UNIT NOT STANDARD TO PROGRAM         ^'/
      DATA MSBUF(21)
 1    /'^PROBLEM HANDLING DOT DISCONNECTED STRUCTURE           ^'/
      DATA MSBUF(22)
 1    /'^SUM OF *M LENGTHS EXCEEDS MAXIMUM                     ^'/
      DATA MSBUF(23)
 1    /'^BAD BOND - USE LONGBOND TO CROSS BOND                 ^'/
      DATA MSBUF(24)
 1    /'^CAN''T FIND NODE/CHARGE IN DEL - CMD ABORTED          ^'/
      DATA MSBUF(25)
 1    /'^SPACE CONFLICT IN DOTDIS - CMD ABORTED                ^'/
      DATA MSBUF(26)
 1    /'^TOO MANY CONNECTIONS/NODE                             ^'/
      DATA MSBUF(27)
 1    /'^NO SUBSTRUCTURE FILES ON DISK - RETRIEVE ABORTED      ^'/
      DATA MSBUF(28)
 1    /'^CAN''T FIND NODE FOR(+-)WILL CALL IT DELOCALIZED      ^'/
      DATA MSBUF(29)
 1    /'^BAD VALUE FOR RING SIZE - ENTER CMD OR ESC            ^'/
      DATA MSBUF(30)
 1    /'^BAD ENVIRONMENT FOR RING - ENTER CMD OR ESC           ^'/
      DATA MSBUF(31)
 1    /'^NO SPACE FOR RING - ENTER CMD OR ESC                  ^'/
      DATA MSBUF(32)
 1    /'^NO GOOD ORIENTATION FOUND - ENTER NEW COMMAND         ^'/
      DATA MSBUF(33)
 1    /'^BOND WITH REDUNDANT LONG BOND BETWEEN SAME 2 NODES    ^'/
      DATA MSBUF(34)
 1    /'^NO NODE ADJACENT TO " - CMD ABORTED                   ^'/
      DATA MSBUF(35)
 1    /'^CONNECTION TABLE LIMITED TO 255 NODES                 ^'/
      DATA MSBUF(36)
 1    /'^ATTEMPT TO DRAW OFF SCREEN - CMD ABORTED              ^'/
      DATA MSBUF(37)
 1    /'^2 ATTEMPTS AT TRANSMISSION FAILED                     ^'/
      DATA MSBUF(38)
 1    /'^NODE ALLOWED ONLY 1 CHARGE - CMD ABORTED              ^'/
      DATA MSBUF(39)
 1    /'^ALREADY IN REQUESTED STATE                            ^'/
```

```
      DATA MSBUF(40)
    1 /'^ADJACENT NODES FOUND                             ^'/
      DATA MSBUF(41)
    1 /'^DANGLING BOND FOUND                              ^'/
      DATA MSBUF(42)
    1 /'^AMBIGUOUSLY ASSIGNED ENTRY - REPOSITION          ^'/
      DATA MSBUF(43)
    1 /'^ATTACHING BOND IN WRONG DIR - COMMAND ABORTED    ^'/
      DATA MSBUF(44)
    1 /'^NOT AT BOND OR MARKER - CAN''T ATTACH            ^'/
      DATA MSBUF(45)
    1 /'^BAD BOND - END IS NOT A NODE                     ^'/
      DATA MSBUF(46)
    1 /'^*M NODE AND DEFINITIONS ARE NOT MATCHED          ^'/
      DATA MSBUF(47)
    1 /'^NODE ALLOWED ONLY 1 " - CMD ABORTED              ^'/
      DATA MSBUF(48)
    1 /'^SPACE CONFLICT - CMD ABORTED                     ^'/
      DATA MSBUF(49)
    1 /'^ONLY NEW BOND MAY BE DELETED IN REPEAT           ^'/
      DATA MSBUF(50)
    1 /'^NOT AT A MARKER - CMD IGNORED                    ^'/
      DATA MSBUF(51)
    1 /'^TOO MANY CHARGES - LIBRARY CMD ABORTED           ^'/
      DATA MSBUF(52)
    1 /'^INVALID (STRUCTURE+DOTDIS) DETECTED - CMD ABORTED ^'/
      DATA MSBUF(53)
    1 /'^NO BOND TYPES 4, 6, OR 7 IN LONG - IBTYPE = 1    ^'/
      DATA MSBUF(54)
    1 /'^SUBSTRUCTURE TOO LONG FOR INPUT                  ^'/
      DATA MSBUF(55)
    1 /'^BAD BONDTYPE OR CHARGE VALUE - CMD ABORTED       ^'/
      DATA MSBUF(56)
    1 /'^BAD ENLARGE VALUE                                ^'/
      DATA MSBUF(57)
    1 /'^SUBSTRUCTURE MUST EMANATE FROM MARKER OR LUHN DOT ^'/
      DATA MSBUF(58)
    1 /'^NO SUBSTRUCTURE YET INPUT                        ^'/
      DATA MSBUF(59)
    1 /'^BAD INPUT CHAR - ENTER RETURN TWICE              ^'/
      DATA MSBUF(60)
    1 /'^AMBIGUOUSLY PLACED NONLOCAL CHARGE - REPOSITION  ^'/
      DATA MSBUF(61)
    1 /'^+ - " NOT ALLOWED ON 2 LETTER ELEMENT IN LIBRARY ^'/
C
      CALL FTSIZE(2,18)
      IF (CHER.EQ.2) THEN
         CALL SETSCR(1)
         PAGE = 1
         CALL DISPLA(1)
         IF (IERR.NE.18) THEN
            CALL SETCOL(0)
            CALL CLR
            CALL SETCOL(1)
            CALL FTLOCA(1,1)
         ELSE
            CALL FTLOCA(2,1)
         ENDIF
      ELSE
         IF (PAGE.EQ.0) THEN
            CALL FTLOCA(4,1)
            CALL FTEXT(BLNK90)
         ENDIF
         PAGE = 0
         CALL FTLOCA(4,1)
      ENDIF
      IF (IERR.EQ.11) GO TO 77
         CALL FTEXT(MSBUF(IERR))
         GO TO 9
 77   CONTINUE
         HALO(1) = KAN
         HALO(3) = KAN
         IF (KAR.NE.32) THEN
            EL1 = KAR
            EL2 = MAR
         ENDIF
```

```
              HALO(2) =CHAR(EL1)
              CALL FTEXT(HALOE)
              HALO(2) = CHAR(EL2)
              CALL FTEXT(HALOE)
              CALL FTEXT(MSBUF(IERR))
    9     CONTINUE
          IF (CHER.NE.2) CALL SETSCR(2)
          CALL FTSIZE(1,10)
          ERR = IERR
          RETURN
          END
C
          INTEGER*2 FUNCTION ILRRAY(IX,IY)
          IMPLICIT INTEGER*2 (A-Z)
          INTEGER*4 IARRAY
          COMMON /STRPIX/LPIX,IARRAY(90,38),LBLEN,LNGBND(100,5)
C     EXTRACT LOW ORDER PORTION OF WORD
          ILRRAY=MOD(IARRAY(IX,IY),2**13)
C     THIS ELIMINATES THE CHARGE LOC INFORMATION
          RETURN
          END
C
          INTEGER*2 FUNCTION IDIR(KAR)
          IMPLICIT INTEGER*2 (A-Z)
C     Set IDIR = -1
          IDIR=-1
C     Not a bond - return IDIR = -1
          IF (KAR .LT. 256) RETURN
          IDIR=KAR/256
          IDIR=KAR-IDIR*256
          RETURN
          END
C
          INTEGER*2 FUNCTION IHMM(IX,IY)
          IMPLICIT INTEGER*2 (A-Z)
          INTEGER*4 MM
          COMMON /STRPIX/ LPIX,MM(90,38),LBLEN,LNGBND(100,5)
C     EXTRACT HIGH ORDER PORTION OF WORD
          IHMM=MM(IX,IY)/2**13
C     THIS SHOULD YIELD A NUMBER FROM 0-14
C     THIS ASSOCIATES THE CHARGE WITH THE NODE
C     NOTE - 0 = DELOCALIZED CHARGE
          RETURN
          END
C
          INTEGER*2 FUNCTION LMM(IX,IY)
          IMPLICIT INTEGER*2 (A-Z)
          INTEGER*4 MM
          COMMON /STRPIX/ LPIX,MM(90,38),LBLEN,LNGBND(100,5)
C     EXTRACT LOW ORDER PORTION OF WORD
          LMM=MOD(MM(IX,IY),2**13)
C     THIS ELIMINATES THE CHARGE LOC INFORMATION
          RETURN
          END
C
          SUBROUTINE DOTDIS(KAR,IX,IY,IRESET,LFLAG)
          IMPLICIT INTEGER*2 (A-Z)
          INTEGER*4 MM
          LOGICAL*2 TERMN
          CHARACTER*1 HALO(3)
          CHARACTER*1 KAN
          CHARACTER*1 ISTAT
          COMMON /CD/ MAXX,MAXY
          COMMON /RANGE/ LOX,HIX,LOY,HIY
          COMMON /STRPIX/ LPIX,MM(90,38),LBLEN,LNGBND(100,5)
          COMMON /HEAD/ MW(12),ISTATE,PAGE
          COMMON /ISTATE/ ISTAT
          COMMON /CHARS/IES, IDOT,ITAG,JUMP,LBOND,KAN,ISPACE
          COMMON /BAD/ IBADX(9),IBADY(9)
          COMMON /CUR/ ICUR
          DIMENSION LIST(50)
C
          HALO(1) = KAN
          HALO(3) = KAN
          ISTATE=10
          KKAR=32
```

```
                ISTAT='*'
                MODE=1
                TERMN = .FALSE.
                CALL HEADER
                CALL CURSOR(IX,IY)
                CALL CELL(IX,IY,IGOOD)
                IF (IGOOD .NE.0) GO TO 55
                I=0
                DO 11 J = 1,50
                LIST(J)=0
 11             CONTINUE
C TYPE KAR
 14             CONTINUE
                HALO(2) = CHAR(KAR)
                CALL TEXT(HALO)
C STORE KAR
 35             MM(IX,IY)=KAR
                IF (IX.LT.LOX) THEN
                    LOX = IX
                ELSE IF (IX.GT.HIX) THEN
                    HIX = IX
                ENDIF
                IF (IY.LT.LOY) THEN
                    LOY = IY
                ELSE IF (IY.GT.HIY) THEN
                    HIY = IY
                ENDIF
                IF (KAR .NE. 43 .AND. KAR .NE. 45) GO TO 666
C CHARGE IN LOCATION 9 - 2 LETTER NODE
                IF(MM(IX-1,IY).GE.97 .AND. MM(IX-1,IY).LE.122)
     1          MM(IX,IY)=KAR + 9*2**13
C CHARGE IN LOCATION 8 - 1 LETTER NODE
                IF(MM(IX-1,IY).GE.65 .AND. MM(IX-1,IY) .LE. 90)
     1          MM(IX,IY)=KAR + 8*2**13
                IF (MM(IX,IY) .GT. 2**13) GO TO 666
                CALL FTSIZE(2,18)
C Charge not associated with node - cmd rejected
                CALL FTLOCA(1,1)
                CALL FTEXT('^ENTER DIGIT TO ASSIGN VALUE TO CHARGE^')
                CALL FTSIZE(1,10)
                PAGE = 0
C Delete charge
                MM(IX,IY)=0
                IF (IY.GT.1) THEN
                    FY = IY - 1
                ELSE
                    FY = IY
                ENDIF
                CALL FTLOCA(FY,IX)
                CALL FTEXT('^ ^')
                CALL CURSOR(IX,IY)
                GO TO 65
 666            I=I+1
                IX=IX+1
                CALL CURSOR(IX,IY)
                LIST(I)=KAR
                IF (I.EQ.50) GO TO 55
 65             CALL INPUTX(KAR,IX,IY)
                IF (KAR.EQ.42) THEN
                    IERR = 39
                    CALL MYERR(IERR,IERR,IERR)
                    GO TO 65
                ENDIF
C KAR = DEL?
                IF (KAR .EQ. 127) GO TO 90
                JX=IX+1
                CALL CELL(JX,IY,IGOOD)
                IF (IGOOD .NE. 0) GO TO 55
                IF (KAR .NE. 32 .AND. KAR .NE. 81) GO TO 44
                IX=IX+3
                CALL CURSOR(IX,IY)
C EXIT IF SPACE
                GO TO 50
C FOUND UC - NOW WHAT
C FOUND A ':' - GO PRINT IT
```

```
 44        IF (KAR.EQ.58) GO TO 14
           IF ((KAR.GE.65).AND.(KAR.LE.90)) GO TO 14
 20        IF(KAR .EQ. 47 .AND. (LIST(I).GE.48 .AND.
         1 LIST(I) .LE. 57)) GO TO 14
C DO WE HAVE DIGIT
           IF(KAR .LT. 48 .OR. KAR .GT. 57) GO TO 15
C OK IF PRECEEDED BY * OR /
           IF(LIST(I).EQ.47.OR.LIST(I).EQ.42)GO TO 14
C          PRECEEDED BY UC - THUS IS A SUBSCRIPT
C FOUND DIGIT PRECEEDED BY D OR M
           IF ((LIST(I).EQ.68).OR.(LIST(I).EQ.77)) GO TO 57
           IF(LIST(I) .GE.65 .AND. LIST(I).LE.90)GO TO 18
C          PRECEEDED BY A + OR - THUS IS A CHARGE
           IF(LIST(I) .EQ. 43 .OR. LIST(I) .EQ. 45) GO TO 222
C          PRECEEDED BY LC - THUS IS A SUBSCRIPT
           IF(LIST(I) .GE. 97 .AND. LIST(I) .LE. 122) GO TO 18
C IF BAD INPUT SEQUENCE, ISSUE MESSAGE.
           IF ((LIST(I).LT.48).OR.(LIST(I).GT.57)) GO TO 500
C IT'S A SUBSCRIPT.
           IF (((LIST(I-1).GE.65).AND.(LIST(I-1).LE.90)).OR.
         *    ((LIST(I-1).GE.97).AND.(LIST(I-1).LE.122)))GOTO 18
C IT'S A REGULAR INPUT
           GO TO 14
C WE HAVE A CHARGE
 15        IF (KAR .EQ. 43 .OR. KAR .EQ. 45) GO TO 222
           IF(KAR .EQ. 36) GO TO 65
C          WE HAVE VALID LC
           IF( (KAR .GE. 97 .AND. KAR .LE. 122).AND.
         1 (LIST(I).GE.65.AND.LIST(I).LE.90))GO TO 14
C BAD CHAR - ISSUE MESSAGE AND GET NEW INPUT
 500       CALL ERRMSG(KAR)
           GO TO 65
C DROP FOR A SUBSCRIPT
 18        CONTINUE
           ICUR = 0
           CALL CURSOR(IX,IY)
           CALL MOVTCR(0,2)
           HALO(2) = CHAR(KAR)
           CALL TEXT(HALO)
           CALL MOVTCR(0,-2)
           ICUR = 1
C RAISE FROM SUBSCRIPT
           GO TO 35
C NOTHING TO DEL
 90        IF(I .EQ. 0) GO TO 65
C DEC LIST COUNTER
           I=I-1
C DECREMENT CURSOR LOC
           IX=IX-1
C MOVE CURSOR BACK
           ICUR = 1
           CALL CURSOR(IX,IY)
C ZERO SPOT IN ARRAY
           IF (MM(IX,IY).EQ. 42) TERMN = .TRUE.
           MM(IX,IY)=0
C WHAT ARE WE TRYING TO DELETE
           J=LIST(I+1)
C IT'S A CHARGE
           IF (J .EQ. 43 .OR. J .EQ. 45) GO TO 95
           IF(J .GE.48 .AND. J .LE. 57) GO TO 98
C ERASE SPOT ON SCREEN
 91        CONTINUE
           CALL REPLCE(IX,IY,0,0,0,0,1)
           IF (TERMN) GO TO 50
C MOVE CURSOR BACK AGAIN
 66        CONTINUE
           ICUR = 1
           CALL CURSOR(IX,IY)
           GO TO 65
C RAISE FOR CHARGE
 95        CONTINUE
           IF (IY.GT.1) THEN
               FY = IY + 1
```

```
          ELSE
              FY = IY
          ENDIF
          CALL FTLOCA(FY,IX)
          CALL FTEXT('^ ^')
C ERASE CHARGE
C DROP FROM CHARGE
          GO TO 66
98        K=LIST(I)
C IT'S A CHARGE
          IF (K .EQ. 43 .OR. K .EQ. 45) GO TO 95
C IT'S A SUBSCRIPT
          IF (K .GE. 65 .AND. K .LE. 90) GO TO 97
C IT'S A SUBSCRIPT
          IF(K .GE. 97 .AND. K .LE. 122) GO TO 97
C IT'S JUST A REGULAR CHAR
          GO TO 91
C DROP FOR SUBSCRIPT
97        CONTINUE
          CALL REPLCE(IX,IY,0,0,0,0,1)
C ERASE SUBSCRIPT
C RAISE FROM SUBSCRIPT
          GO TO 66
C
C RAISE FOR CHARGE
222       CONTINUE
          HALO(2) = CHAR(KAR)
          IF (IY.GT.1) THEN
              CALL MOVTCR(0,-10)
              CALL TEXT(HALO)
              CALL MOVTCR(0,10)
          ELSE
              CALL TEXT(HALO)
          ENDIF
          GO TO 35
C TYPE KAR
C DROP FROM CHARGE
57        CONTINUE
          HALO(2) = CHAR(KAR)
          CALL TEXT(HALO)
          KAR = KAR + 63
          GO TO 35
55        IERR=25
          CALL MYERR(IERR,KAR,KAR)
50        ISTATE=0
          LFLAG=0
C RETURN AND PROCESS Q
          IF (KAR .EQ. 81) LFLAG=1
          CALL HEADER
10        CONTINUE
          RETURN
          END
C
          SUBROUTINE REPEAT(KAR,IX,IY,INCX,INCY,IRESET,LFLAG)
          IMPLICIT INTEGER*2 (A-Z)
          INTEGER*4 MM
          CHARACTER*1 CMD(3),HCMD,CHR,REPATM
          CHARACTER*1 ISTAT
          INTRINSIC ICHAR
          COMMON /STRPIX/ LPIX,MM(90,38),LBLEN,LNGBND(100,5)
          COMMON /PARAMS/ JBDIR,NOCHG,LASTN,MCHAR,JCHAR,NLARGE,LEVEL
          COMMON /MODES/ JBTYPE,ICHR,IBDIR,IBTYPE,ISMART,MODE,ISKILL,ISP
          COMMON /CHARS/ IES, IDOT,ITAG,JUMP,LBOND,KAN,ISPACE
          COMMON /HEAD/ MW(12),ISTATE,PAGE
          COMMON /ISTATE/ ISTAT
          COMMON /CUR/ ICUR
          COMMON /FROM/ LCHAR
          COMMON /REP/ HCMD(2)
          COMMON /REPBND/ NEWBND
          COMMON /MSKIP/ ISKIP
          COMMON /WARN/ ERR
          COMMON /STRED/ IDTPIX(90,38),LABL(260,2),MRKCHN(260)
          COMMON /PROB/ IPROB,JPROB
          COMMON /DFAULT/ REPATM(2)
C
```

```
C         SET STATE VARIABLES SO THAT HEADER WILL DISPLAY
C         THE HEADER FOR REPEAT STATE
C         CLEN = LENGTH OF COMMAND STRING
          OSTATE = ISTATE
          ISTATE=9
          ISTAT='a'
          HOLD=NLARGE
          IF ((IBTYPE.EQ.0).OR.(IBTYPE.EQ.4).OR.(IBTYPE.EQ.8)) THEN
              BHOLD = IBTYPE
          ELSE
              BHOLD = 1
          ENDIF
C
C         SAVE NLARGE AND SET TEMPORARILY TO 1
          NLARGE=1
          NOCHG = 1
          ISKIP = 1
          MODE=1
          KAR = 0
          CMD(1) = REPATM(1)
          HCMD(1) = CMD(1)
          IF (REPATM(2).NE.CHAR(0)) THEN
              CMD(2) = '$'
              CMD(3) = REPATM(2)
              CLEN = 3
          ELSE
              CMD(2) = '0'
              CMD(3) = '0'
              CLEN = 1
          ENDIF
          HCMD(2) = CMD(3)
          BTYPE = 50
          IBTYPE = BTYPE - 48
          NEWBND = 0
100       CONTINUE
          CALL HEADER
          ICUR = 1
          CALL CURSOR(IX,IY)
          OKAR = KAR
          CALL INPUTX(KAR,IX,IY)
1010      IF ((KAR.EQ.13).OR.(KAR.EQ.81)) GO TO 27
          IF ((KAR.LT.48).OR.(KAR.GT.56)) GO TO 10
          BTYPE = KAR
          IBTYPE = BTYPE - 48
          GO TO 100
C
10        IF ((KAR.LT.65).OR.(KAR.GT.90)) GO TO 20
          CLEN = 1
          CMD(1) = CHAR(KAR)
          HCMD(1) = CMD(1)
          CMD(2) = '0'
          CMD(3) = '0'
          HCMD(2) = CMD(3)
          GO TO 100
C
20        IF (KAR.NE.36) GO TO 30
          CMD(2) = CHAR(KAR)
          GO TO 100
30        IF ((KAR.LT. 97).OR.(KAR.GT.122)) GO TO 50
CXT
          IF (OKAR.NE.36) THEN
              IF (NEWBND.EQ.1) THEN
                  GO TO 1012
              ELSE
                  GO TO 40
              ENDIF
          ENDIF
          CMD(3) = CHAR(KAR)
          HCMD(2) = CMD(3)
          CLEN = 3
          GO TO 100
C
40        CALL IDENT(KAR,IX,IY,INCX,INCY,IRESET)
          IF (JPROB.EQ.1) GO TO 27
          GO TO 100
50        IF (KAR.NE.39) GO TO 60
```

```
            IF (MM(IX-1,IY).NE.46) GO TO 70
            DO 55 I = 1,CLEN
                CHR = CMD(I)
                ZAR = ICHAR(CHR)
                ERR = 0
                CALL IDENT(ZAR,IX,IY,INCX,INCY,IRESET)
                IF (JPROB.EQ.1) GO TO 27
                IF (ERR.EQ.48) THEN
                    CALL MARK(KAR,IX,IY,IERR)
                    GO TO 56
                ENDIF
55          CONTINUE
56          CONTINUE
            IF (IBTYPE.EQ.BTYPE-48) GO TO 100
            IBTYPE = BTYPE - 48
            CALL HEADER
            GO TO 100
C
70          IERR = 50
            CALL MYERR(IERR,KAR,MAR)
            GO TO 100
60          IF ((KAR.LT.22).OR.(KAR.GT.31)) GO TO 85
            ZAR = KAR
            CALL DELTA(ZAR,INCX,INCY)
            ZAR = LMM(IX+INCX-1,IY+INCY)
            IF (ZAR.LT.256) NEWBND = 1
            ZAR = BTYPE
            CALL IDENT(ZAR,IX,IY,INCX,INCY,IRESET)
            CALL IDENT(KAR,IX,IY,INCX,INCY,IRESET)
            IF (JPROB.EQ.1) GO TO 27
            IF ((MM(IX,IY).EQ.0).AND.(LMM(IX-INCX,IY-INCY).GE.256)) NEWBND=1
            OKAR = KAR
            CALL INPUTX(KAR,IX,IY)
            IF (KAR.NE.127) GO TO 1011
351             IF (NEWBND.EQ.1) CALL IDENT(KAR,IX,IY,INCX,INCY,IRESET)
            IF (JPROB.EQ.1) GO TO 27
            IF (NEWBND.EQ.0) THEN
                IERR = 49
                CALL MYERR(IERR,IERR,IERR)
            ENDIF
            NEWBND = 0
            GO TO 100
1011        IF (NEWBND.NE.1) GO TO 1010
            IF ((KAR.LT.97).OR.(KAR.GT.122)) GO TO 1010
1012        CONTINUE
            IF (MM(IX,IY).EQ.0) THEN
            IF (CLEN .EQ. 3) THEN
            ICK=LMM(IX+1,IY)
            JCK=LMM(IX+2,IY)
            KCK=LMM(IX+3,IY)
            IF((ICK .GE. 256) .AND. (ICK .NE. KCK)) THEN
            IF ((MM(IX-1,IY) .NE. 0 ).OR. (MM(IX-2,IY) .NE.0)) THEN
            IERR=48
            CALL MYERR(IERR,IERR,IERR)
            KAR=127
            GO TO 351
            ELSE IF (ICK .NE. JCK) THEN
            MM(IX,IY)=ICK
            IX=IX-1
            ENDIF
            ENDIF
            ENDIF
                DO 655 I = 1,CLEN
                    CHR = CMD(I)
                    ZAR = ICHAR(CHR)
                    CALL IDENT(ZAR,IX,IY,INCX,INCY,IRESET)
                    IF (JPROB.EQ.1) GO TO 27
655             CONTINUE
            ENDIF
            NEWBND = 0
            IF (IBTYPE.EQ.(BTYPE-48)) GO TO 40
            IBTYPE = BTYPE - 48
            CALL HEADER
            GO TO 40
```

```
 85     IF (KAR.NE.64) GO TO 80
        IERR = 39
        CALL MYERR(IERR,IERR,IERR)
        GO TO 100
 80     CALL ERRMSG(KAR)
        GO TO 100
C
 27     ISTATE = 0
        LEVEL = 0
        NLARGE = HOLD
        IBTYPE = BHOLD
        NOCHG = 0
        LFLAG = 1
        DO 4576 I = 1,12
4576       MW(I) = 999
        ISTATE = OSTATE
        ISKIP = 0
        CALL HEADER
        RETURN
        END
C
C
C This subroutine sets the parameter NLARGE (i.e. the enlargement
C factor). If an attempt is made to set the enlargment factor to
C 0 or a number > 99, and error message is issued, NLARGE is set to
C 1, and the subroutine is exited.
C
        SUBROUTINE SETLRG
        IMPLICIT INTEGER*2 (A-Z)
        CHARACTER*1 ISTAT
        COMMON /PARAMS/ JBDIR,NOCHG,LASTN,MCHAR,JCHAR,NLARGE,LEVEL
        COMMON /ISTATE/ ISTAT
        COMMON /HEAD/ MW(12),ISTATE,PAGE
        COMMON /ICUR/ CUR
CXT
CXT     MLARGE is used by SUBROUTINE VALNCE to determine the distance
CXT     between the end of the bond and the valence to be computed.
        COMMON /VLNPRV/ MLARGE
C
        ISTAT = '&'
        ICHAR = 15
        ISTATE = 13
        NLARGE = 0
        CALL HEADER
 50     CALL INPUTX(KAR,10,10)
        IF (KAR.EQ.38) GO TO 100
        IF ((KAR.LT.48).OR.(KAR.GT.57)) GO TO 90
C
C We have a digit - process it.
        NLARGE = 10 * NLARGE + (KAR - 48)
        IF ((NLARGE.GT.99).OR.(NLARGE.EQ.0)) GO TO 70
        CALL HEADER
        GO TO 50
C Bad input
 90     CALL ERRMSG(KAR)
        ICUR = 1
        GO TO 50
C Bad enlargement factor
 70     IERR = 56
        CALL MYERR(IERR,IERR,IERR)
        NLARGE = 1
        MLARGE = NLARGE
        LASTN = 0
        ISTATE = 0
        CALL HEADER
        RETURN
C
C Good enlargment factor
100     CONTINUE
        MLARGE = NLARGE
        IF (NLARGE.EQ.0) NLARGE = 1
        ISTATE = 0
        CALL HEADER
        RETURN
        END
```

```
$STORAGE:2
C       SUBROUTINE CELL sees if a 3*3 area is empty.
        SUBROUTINE CELL(IX,IY,IGOOD)
        IMPLICIT INTEGER*2 (A-Z)
        INTEGER*4 MM
        COMMON /BAD/ IBADX(9),IBADY(9)
        COMMON /STRPIX/ LPIX,MM(90,38),LBLEN,LNGBND(100,5)
        IGOOD=0
        DO 55 I=1,9
        IBADX(I)=0
        IBADY(I)=0
55      CONTINUE
        DO 10 I=-1,1
        DO 10 J=-1,1
        IVALX=IX+I
        IVALY = IY - J
        IF (MM(IVALX,IVALY) .EQ. 0) GO TO 10
        IGOOD=IGOOD+1
        IBADX(IGOOD)=IVALX
        IBADY(IGOOD)=IVALY
10      CONTINUE
        RETURN
        END
C
C       SUBROUTINE CELL2 sees if a 3*3 area is empty.
        SUBROUTINE CELL2(IX,IY,IGOOD)
        IMPLICIT INTEGER*2 (A-Z)
        INTEGER*4 IDTPIX
        COMMON /BAD/ IBADX(9),IBADY(9)
        COMMON /STRED/ IDTPIX(90,38),LABL(260,2),MRKCHN(260)
        IGOOD=0
        DO 55 I=1,9
        IBADX(I)=0
        IBADY(I)=0
55      CONTINUE
        DO 10 I=-1,1
        DO 10 J=-1,1
        IVALX=IX+I
        IVALY = IY - J
        IF (IDTPIX(IVALX,IVALY).EQ.0) GO TO 10
        IGOOD=IGOOD+1
        IBADX(IGOOD)=IVALX
        IBADY(IGOOD)=IVALY
10      CONTINUE
        RETURN
        END
C
C       SUBROUTINE SWITCH alters the bond direction back and forth for
C       chains of length 4 of greater.
        SUBROUTINE SWITCH(COMLEN)
        IMPLICIT INTEGER*2 (A-Z)
        COMMON /CHN/ CLARGE,CHBITS(65)
C       INTERCHANGE BONDS
        DO 9005 K=1,COMLEN
        KK=CHBITS(K)
        IF(KK.EQ. 35) GO TO 9005
        KK=KK-21
        IF(KK .GT.4) KK=KK-2
        IF (KK .EQ. 2 .OR. KK .EQ. 6) GO TO 9006
        KK=KK-2
        GO TO 9007
9006    KK=KK+2
9007    KK=KK+21
        IF (KK .GT. 25) KK=KK+2
        CHBITS(K)=KK
9005    CONTINUE
        RETURN
        END
        SUBROUTINE DOCHN - THIS SUBROUTINE DECIDES WHERE TO DRAW
C                          A CHAIN AND THEN DRAWS IT
C       THIS CODE WAS PULLED OUT OF SUBROUTINE CHAIN WHEN IT WAS
C       DECIDED TO TAKE THE GROUP FUNCTION OUT OF CHAIN AND MAKE GROUP
C       A SEPARATE SUBROUTINE AND ALLOW CHAINS TO BE DRAWN IN GROUP
        SUBROUTINE DOCHN(CLEN,CORF,MRKPNT,COMLEN,CBOND,IX,IY,IERR)
        IMPLICIT INTEGER*2 (A-Z)
        INTEGER*2 CB(2)
```

```
           INTEGER*4 MM,IDTPIX
           LOGICAL*2 BONDEL,BAR,BONDID
           COMMON /CINFO/ NDIRS(4),BDIRS(8,3)
           COMMON /BAD/ IBADX(9),IBADY(9)
           COMMON /MODES/ JBTYPE,ICHAR,IBDIR,IBTYPE,ISMART,MODE,ISKILL,ISP
           COMMON /CHARS/IES, IDOT,ITAG,JUMP,LBOND,KAN,ISPACE
           COMMON /PARAMS/ JBDIR,NOCHG,LASTN,MCHAR,JCHAR,NLARGE,LEVEL
           COMMON /STRPIX/ LPIX,MM(90,38),LBLEN,LNGBND(100,5)
           COMMON /STRED/ IDTPIX(90,38),LABL(260,2),MRKCHN(260)
           COMMON /CUR/ ICUR
           COMMON /DARK/ OCUR
           COMMON /CHN/ CLARGE,CHBITS(65)
           COMMON /CD/ MAXX,MAXY
           COMMON /HP/IHP
           COMMON /XBOND/ GOODB(2,9)
           COMMON /WARN/ ERR
CXT
CXT        BONDEL = TRUE indicates a bond has been drawn between 2 nodes
CXT        and subsequent deletion should delete the bond, not a node.
           COMMON /DELBND/ BONDEL
CXT
CXT        BAR is used in conjunction with NOCHG and BONDID to set bond
CXT        types in relation to default bond types.
           COMMON /BTPDIR/ BAR
C
           OCUR = 0
           CALL INITHC(3,3,OCUR)
           PDIR=0
C USED TO DETERMINE INITIAL BOND IN PUCKERED CHAIN
           CLARGE=NLARGE
CXT
CXT        BONDID is used in conjunction with BAR and NOCHG to set bond
CXT        types in relation to default bond types.
           BONDID = .FALSE.
C SAVE ENLARGE FACTOR FOR WE MAY TEMPORARILY
C CHANGE IT IF WE DRAW A STRAIGHT CHAIN
C
C THEN ESTABLISH CHAIN DIRECTION
C
           CALL NEW(SUM,IX,IY)
C ARE WE STARTING A NEW STRUCTURE
           IF (SUM .NE. 0) GO TO 23
           NODE=0
C YES-SET NODE AND BOND DIR ACCORDINGLY
           NEWS=1
C SET NEWS STRUCTURE CODE TO YES = 1
           IBDIR=3
           GO TO 25
C
C CAN WE FIND A CORRECT POINTER BOND
C
23         IF (MM(IX,IY) .NE.0) GO TO 22
C CAN'T BE A BOND - GO FIND NODE
           CALL FINDB(IBDIR,KBDIR,IX,IY)
           IF (IBDIR .EQ. -1) GO TO 22
C NOT AT A BOND - GO FIND NODE
           NODE = 0
C GOOD RETURN FROM FINDB - WE FOUND A BOND
           PDIR=KBDIR
           GO TO 25
22         DO 333 I=0,5
C WE'RE NOT AT A BOND - FIND THE NODE
           MX=IX-I
C LOOK LEFT
           LL=LMM(MX,IY)
           IF ((LL.NE.46).AND.(LL.NE.63).AND.((LL.LT.65).OR.(LL.GT.90)))
     2     GO TO 333
C NOT UPPERCASE OR DOT OR ?
           IF((LL.EQ.72).AND.((MM(MX+1,IY).LE.97).OR.(MM(MX+1,IY).GE.
     2        122))) GO TO 333
C SKIP OVER H WHICH IS NOT HE,HG, ETC.
           IX=IX-I
           CALL CNTBND(ICNT,IX,IY)
C HOW MANY BONDS AROUND NODE
           IF(ICNT .GT. 1) GO TO 9002
```

```
C MORE THAN ONE BOND AT NODE
C DON'T WORRY ABOUT INITIAL BOND IN PUCKERED CHAIN
        CALL FINDB(DUMMY,PDIR,IX,IY)
C WHAT IS THE DIR OF BOND COMING INTO NODE
9002    NODE=1
        ITRY=1
        NIX=IX
C SAVE INFO FOR SHARP ANGLE CHECK
        NIY=IY
        IBDIR=NDIRS(ITRY)
        IF (MM(IX+1,IY) .EQ. 0) GO TO 25
C NEXT SPACE IS EMPTY
C GO ON AND CHECK CELLS
        IF((MM(IX+1,IY) .GE. 97) .AND. (MM(IX+1,IY) .LE. 122)
     1    .AND. (MM(IX+2,IY) .EQ. 0)) GO TO 266
        IF (MM(IX+1,IY) .NE. 72) GO TO 974
C NEXT CHAR NOT H
C WE CAN'T DRAW A CHAIN IN THIS DIR
        IF(.NOT. (MM(IX+2,IY) .EQ. 0 .OR.
     1    (MM(IX+2,IY) .GE. 49 .AND. MM(IX+2,IY) .LE. 52
     2    .AND. MM(IX+3,IY) .EQ. 0))) GO TO 974
C WE CAN'T DRAW A CHAIN IN THIS DIR
        HYD=1
        CALL CLRHYD(IX,IY)
        GO TO 25
C FOUND THE NODE
333     CONTINUE
        IERR=3
        CALL MYERR(IERR,KAR,KAR)
C FOUND NO BOND OR NODE AND NOT NEW STRUCTURE
        OCUR = 1
        CALL INITHC(3,3,OCUR)
        ICUR = 1
        CALL CURSOR(IX,IY)
        RETURN
C THIS SHOULD NOT HAPPEN - PROBABLY PROGRAM ERROR
266     BIX=IX+1
        GO TO 270
25      CONTINUE
        BIX=IX
270     BIY=IY
475     IF (CLEN .LE. 4) GO TO 81
C CHAIN STRAIGHT OR PUCKERED?
        IF (NODE .EQ. 0) GO TO 742
        CB(1)=BDIRS(IBDIR,1)
C PUCKERED CHAIN - SET BOND DIRS
        CB(2)=BDIRS(IBDIR,2)
        GO TO 82
742     CB(1)=BDIRS(IBDIR,2)
        CB(2)=BDIRS(IBDIR,1)
        GO TO 82
81      CB(1)=BDIRS(IBDIR,3)
C STRAIGHT CHAIN - SET BONDS AND ENLARGE
        CB(2)=CB(1)
82      I=1
        DO 6 J=1,CLEN
C GENERATE COMMANDS FOR PROPOSED CHAIN
        IF(J .NE. 1) GO TO 55
        IF(NODE .EQ. 0) GO TO 60
55      CHBITS(I)=CB(MOD(J+1,2)+1)
        I=I+1
60      CHBITS(I)=ITAG
        I=I+1
6       CONTINUE
        COMLEN=I-1
        IF(NEWS .EQ. 1) GO TO 99
        FIRB=CHBITS(1)
C GET FIRST BOND OF CHAIN
        IF(FIRB.EQ.35) FIRB=CHBITS(2)
        FIRB=FIRB-21
        IF (FIRB .GT. 4) FIRB=FIRB-2
        IF(((FIRB.EQ.2.OR.FIRB.EQ.6) .AND.
     1    (PDIR.EQ.2 .OR. PDIR .EQ.6))) GO TO 9004
C IF BONDS ARE IN THE
```

```
C SAME DIR CHANGE BONDS IN CHAIN
       IF(.NOT.((FIRB.EQ.4 .OR. FIRB .EQ. 8) .AND.
     1 (PDIR .EQ. 4 .OR. PDIR .EQ. 8))) GO TO 9003
9004   CALL SWITCH(COMLEN)
C SWITCH BONDS IN CHAIN
C
C SEE IF THE CHAIN WE PROPOSE TO DRAW CREATES ANY OVERLAPS
C
9003   IF (NODE .EQ. 0) GO TO 89
       BOND=CHBITS(1)
       CALL DELTA(BOND,INCX,INCY)
       CALL SHARP(BOND,NIX,NIY,ISHARP)
C WILL THIS GENERATE A SHARP ANGLE
       IF (ISHARP .EQ. 0) GO TO 27
C NO SHARP ANGLE - GO AHEAD
       IF(CLEN .LE. 4) GO TO 974
C IF STRAIGHT CHAIN - THIS ONE IS NO GOOD
       CALL SWITCH(COMLEN)
C PUCKERED CHAIN - TRY PUCKERING THE OTHER WAY
       BOND=CHBITS(1)
       CALL DELTA(BOND,INCX,INCY)
       CALL SHARP(BOND,NIX,NIY,ISHARP)
C DO WE STILL HAVE A SHARP ANGLE
       IF( ISHARP .EQ. 1) GO TO 974
C IF STILL BAD - GO TO 974
27     BOND=CHBITS(1)
C WHAT BOND?
       CALL DELTA(BOND,INCX,INCY)
C CALCULATE INCX AND INCY
       BIX=BIX+INCX
       BIY=BIY+INCY
       IF (MM(BIX,BIY) .NE. 0) GO TO 974
       LAR=NLARGE
       IF (CLEN .LE. 4 .AND. (IBDIR .EQ. 3 .OR. IBDIR .EQ. 7))
     1 LAR=NLARGE*3
       DO 67 J=2,LAR+1
       BIX=BIX+INCX
       BIY=BIY+INCY
       CALL CHECK(BIX,BIY,ICHECK)
       IF (ICHECK .EQ. 1) GO TO 974
       CALL CELL(BIX,BIY,IGOOD)
       IF(IGOOD .NE. 0) GO TO 974
67     CONTINUE
       IF(COMLEN .LT.3) GO TO 99
       DO 68 J=3,COMLEN,2
       BOND=CHBITS(J)
       CALL DELTA(BOND,INCX,INCY)
       DO 699 I=1,LAR+1
       BIX=BIX+INCX
       BIY=BIY+INCY
       CALL CHECK(BIX,BIY,ICHECK)
       IF (ICHECK .EQ. 1) GO TO 974
       CALL CELL(BIX,BIY,IGOOD)
       IF (IGOOD .NE. 0) GO TO 974
699    CONTINUE
68     CONTINUE
       GO TO 99
974    ITRY=ITRY+1
       IF(ITRY .EQ. 5) GO TO 310
       IBDIR=NDIRS(ITRY)
       IF (HYD .EQ. 1 ) CALL VALNCE(2,IX,IY,0,0)
       IF (HYD .EQ. 1) HYD = 0
       BIX=IX
       BIY=IY
       IF (ITRY.EQ.3) BIY = IY -IHP
       IF (ITRY.EQ.4) BIY = IY +IHP
       IF (MM(BIX,BIY) .NE. 0 .AND. (ITRY .EQ. 3
     1 .OR. ITRY .EQ. 4)) GO TO 974
       IF (ITRY .NE. 2) GO TO 475
       HYD=0
       IF (MM(BIX-1,BIY) .EQ. 0) GO TO 475
       IF (LMM(BIX-1,BIY) .GE. 256) GO TO 974
       IF ((MM(BIX-1,BIY).EQ.72).AND.(MM(BIX-2,BIY).EQ.0)) GO TO 999
       IF (MM(BIX-2,BIY).EQ. 72 .AND. MM(BIX-3,BIY).EQ.0 .AND.
     1 (MM(BIX-1,BIY) .EQ. 51 .OR. MM(BIX-1,BIY) .EQ. 50)) GO TO 999
       GO TO 974
```

```
999     HYD=1
        CALL CLRHYD(IX,IY)
        GO TO 475
89      CALL CHECK(BIX,BIY,ICHECK)
        IF (ICHECK .EQ. 1) GO TO 310
        CALL CELL(BIX,BIY,IGOOD)
C THIS IS THE FIRST
C BOX CHECKED - WE
C SHOULD FIND ONLY ONE
C CELL OCCUPIED - THAT CELL
C CONTAINS THE POINTER BOND
        IF((IGOOD .EQ. 1) .AND. (NODE .EQ.0)) GO TO 301
310     IERR=1
C FOUND TOO MANY CELLS OCCUPIED - NO ROOM
        CALL MYERR(IERR,KAR,KAR)
C FOR CHAIN - ABORT CMD
        OCUR = 1
        CALL INITHC(3,3,OCUR)
        ICUR = 1
        CALL CURSOR(IX,IY)
        RETURN
301     IF(COMLEN .LT.2) GO TO 99
        DO 302 J=2,COMLEN,2
        BOND=CHBITS(J)
C CHECK THE REST OF THE CELLS- THEY SHOULD = 0
        CALL DELTA(BOND,INCX,INCY)
        LAR=NLARGE
        IF (CLEN .LE. 4 .AND. (IBDIR .EQ. 3 .OR. IBDIR .EQ. 7))
     1  LAR=NLARGE*3
        DO 302 I=1,LAR+1
        BIX=BIX+INCX
        BIY=BIY+INCY
        CALL CHECK(BIX,BIY,ICHECK)
        IF(ICHECK .EQ. 1) GO TO 310
        CALL CELL(BIX,BIY,IGOOD)
        IF (IGOOD .NE. 0) GO TO 310
302     CONTINUE
99      NEWS=0
        DO 90 M=1,260
        IF(LABL(M,1) .EQ. 0) GO TO 91
90      CONTINUE
7777    IERR=1
        CALL MYERR(IERR,KAR,KAR)
        OCUR = 1
        CALL INITHC(3,3,OCUR)
        ICUR = 1
        CALL CURSOR(IX,IY)
        RETURN
91      MRKPNT=M
        IF ((MRKPNT+CLEN) .GT. 260) GO TO 7777
        IF (CLEN .LE. 4 .AND. (IBDIR .EQ. 3 .OR. IBDIR .EQ. 7))
     1  NLARGE=NLARGE*3
        ICUR=1
        DO 45 I=1,COMLEN
        KAR=CHBITS(I)
        IF(CHBITS(I) .NE. ITAG) GO TO 93
        MRKCHN(MRKPNT)=1
        MRKPNT=MRKPNT+1
93      IF ((I.EQ.1.OR.I.EQ.2).AND.CHBITS(I).NE.ITAG) IBTYPE = CBOND
        ERR = 0
        IF ((KAR.GE.22).AND.(KAR.LE.31)) BONDID = .TRUE.
        CALL IDENT(KAR,IX,IY,INCX,INCY,IRESET)
        IF (BONDID) THEN
           NOCHG = 0
           BAR = .FALSE.
           BONDID = .FALSE.
           IF ((IBTYPE.NE.0).AND.(IBTYPE.NE.4).AND.(IBTYPE.NE.8))
     *     IBTYPE = 1
        ENDIF
        CBOND = IBTYPE
CXT
        IF (ERR.EQ.48) THEN
           IERR = 48
           STPLEN = I
           ICHAR = 1
```

```
              IX = IX
              IY = IY
              MRKPNT = MRKPNT - 1
              GO TO 46
          ENDIF
45        CONTINUE
46        CONTINUE
          IF (IERR.EQ.48) COMLEN = STPLEN - 1
CXT
          ICUR=0
          ICHAR=13
          CBOND=IBTYPE
          IF (IBTYPE .EQ. 2 .OR. IBTYPE .EQ. 3 .OR. IBTYPE.EQ.5
     1    .OR. IBTYPE .EQ. 6 .OR. IBTYPE .EQ. 7) CBOND=1
          NLARGE=CLARGE
          CORF=1
          OCUR = 1
          CALL INITHC(3,3,OCUR)
          ICUR = 1
          CALL CURSOR(IX,IY)
          RETURN
          END
C
          SUBROUTINE CHAIN(KAR,IX,IY,INCX,INCY,IRESET,LFLAG)
          IMPLICIT INTEGER*2 (A-Z)
          LOGICAL*2 BAR,BONDEL,BONDID
          INTEGER*4 MM,IDTPIX
          CHARACTER*1 ISTAT
          COMMON /CHARS/ IES, IDOT,ITAG,JUMP,LBOND,KAN,ISPACE
          COMMON /MODES/ JBTYPE,ICHAR,IBDIR,IBTYPE,ISMART,MODE,ISKILL,ISP
          COMMON /PARAMS/ JBDIR,NOCHG,LASTN,MCHAR,JCHAR,NLARGE,LEVEL
          COMMON /STRPIX/ LPIX,MM(90,38),LBLEN,LNGBND(100,5)
          COMMON /HEAD/ MW(12),ISTATE,PAGE
          COMMON /SIZZE/ MULTX,MULTY
          COMMON /STRED/ IDTPIX(90,38),LABL(260,2),MRKCHN(260)
          COMMON /XBOND/ GOODB(2,9)
          COMMON /PROB/ IPROB,JPROB
          COMMON /CD/ MAXX,MAXY
          COMMON /CHN/ CLARGE,CHBITS(65)
          COMMON /CUR/ ICUR
          COMMON /ISTATE/ ISTAT
          COMMON /FROM/ LCHAR
CXT
CXT       BAR is used in conjunction with NOCHG and BONDID to set bond
CXT       types in relation to default bond types.
          COMMON /BTPDIR/ BAR
CXT
CXT       BONDEL = TRUE indicates a bond has been drawn between 2 nodes
CXT       and subsequent deletion should delete the bond, not a node.
          COMMON /DELBND/ BONDEL
C
C         SET SOME VARIABLES
C
          IF (LCHAR.NE.13) LLCHAR = LCHAR
          BONDID = .FALSE.
10001     CONTINUE
          KKAR=0
          ISTAT='!'
          CBOND=IBTYPE
          IF((IBTYPE.NE.0).AND.(IBTYPE.NE.4).AND.(IBTYPE.NE.8).AND.
     1    (.NOT.BAR)) CBOND=1
          IF (BAR) NOCHG = 1
          HYD=0
          ISTATE=3
          MODE=1
          ICHAR = JCHAR
          CALL HEADER
          LFLAG=0
          NEWS=0
C SET NEW STRUCTURE CODE TO 0 = NOT NEW STRUCTURE
          CLARGE=NLARGE
100       OCHAR=KKAR
          CALL INPUTX(KAR,IX,IY)
          IF (KAR.EQ.27) THEN
              ICUR = 1
```

```
                CALL CURSOR(IX,IY)
                GO TO 100
            ENDIF
            IF (KAR.EQ.33) THEN
                IERR = 39
                CALL MYERR(IERR,IERR,IERR)
                GO TO 100
            ENDIF
            ICUR = 0
C GET INPUT CHARACTER
 101        KKAR=KAR
            IF (KAR .EQ. 13 .OR. KAR .EQ. 81) GO TO 900
C IS CHAR A CR OR Q - YES - QUIT OR RETURN TO GND LEVEL
            IF (KAR .NE. 124) GO TO 200

C **************************************************************
C
C                       # ENTRY CODE
C
C **************************************************************
C
C           CHAR WAS A VERTICAL LINE SO WE WILL BE SETTING
C                   NEW BOND TYPE OR CHARGE VALUE
C
            CALL NUMBER(KAR,IX,IY)
            IF (KAR.EQ.81) GO TO 900
            ISTAT = '!'
            ISTATE = 3
            CBOND = IBTYPE
            CALL HEADER
            GO TO 100
C **************************************************************
C                   END OF # ENTRY CODE
C **************************************************************
C
 200        IF (KAR.LT.49 .OR. KAR.GT.57) GO TO 300
            IF (.NOT.BAR) THEN
                NOCHG = 0
                IF ((IBTYPE.NE.0).AND.(IBTYPE.NE.4).AND.(IBTYPE.NE.8)) THEN
                    CBOND = 1
                    IBTYPE = 1
                ENDIF
            ENDIF
C KAR NOT DIGIT 1-9
C
C                   CHAIN DRAWING SECTION
C
C                   FIRST ESTABLISH CHAIN LENGTH
C
            CLEN=KAR-48
C CLEN = length of chain
            IERR=0
            BIX = IX
            BIY = IY
C Set error code to 0 - We will check it when we return from DOCHN
            CALL DOCHN(CLEN,CORF,MRKPNT,COMLEN,CBOND,IX,IY,IERR)
CXT
            IF (IERR.EQ.48) THEN
                KAR = 127
                ICHAR = 13
                GO TO 750
            ENDIF
CXT
C This is a chain command
C Determine where to draw chain and then draw it
            IF (IERR .EQ. 1) NLARGE=CLARGE
            IF (IERR .NE. 16) GO TO 100
            LFLAG=0
            GO TO 9501
 300        IF (KAR.GE.22 .AND. KAR.LE.31) THEN
                BONDID = .TRUE.
                GO TO 400
            ENDIF
C Bond command?
            IF (KAR .GE. 97 .AND. KAR .LE. 122) GO TO 400
```

```
C Lower case?
        IF (KAR .EQ. ITAG) GO TO 400
C Enlarge command?
        IF (KAR.EQ.38) GO TO 4123
C Marker command?
        IF (KAR .EQ. 63) GO TO 400
C Luhn dot?
        IF (KAR.EQ.46) GO TO 400
C Dumb mode
        IF ((KAR.EQ.21).OR.(KAR.EQ.32).OR.(KAR.EQ.8)) THEN
            IF (KAR.EQ.32) THEN
                JX = IX - 1
                CALL CURSOR(JX,IY)
                CALL CLRHYD(JX,IY)
                CALL VALNCE(2,JX,IY,0,0)
                IF (JPROB.EQ.1) GO TO 900
            ENDIF
            CALL SPACE(IX,IY)
            JCHAR = 2
            MCHAR = 0
            GO TO 10001
        ENDIF
        IF (KAR.EQ.34) GO TO 400
        IF ((KAR.EQ.43).OR.(KAR.EQ.45).OR.(KAR.EQ.61)) GO TO 400
C Question mark?
        IF (KAR .EQ. 36) GO TO 400
C Dollar sign?
        IF ((KAR.GE.65 .AND. KAR.LE.90).OR.(KAR.EQ.46)) GO TO 400
C Upper case?
        GO TO 600
CXT
400     CALL IDENT(KAR,IX,IY,INCX,INCY,IRESET)
        IF (BONDID) THEN
            BAR = .FALSE.
            BONDID = .FALSE.
        ENDIF
        CBOND = IBTYPE
        IF (JPROB.EQ.1) GO TO 900
        CALL HEADER
C Let IDENT process command if possible
        GO TO 100
C Set enlargement factor
4123    CALL IDENT(KAR,IX,IY,INCX,INCY,IRESET)
        ISTATE = 3
        IF (JPROB.EQ.1) GO TO 900
        CALL HEADER
        GO TO 100
C
C IF ITS A RING - SPACE - OR USER DEFINED COMMAND
C SET LFLAG = 1 SO WE NEXT GO TO IDENT AND NOT INPUT
600     IF (KAR.NE.94.AND.KAR.NE.60.AND.KAR.NE.32.AND.KAR.NE.95.AND.
       *    KAR.NE.58.AND.KAR.NE.42) GO TO 700
        GO TO 900
700     IF(KAR .NE. 64) GO TO 777
        CALL REPEAT(KAR,IX,IY,INCX,INCY,IRESET,LFLAG)
        LEVEL=1
        ISTATE=3
        ISTAT='C'
        JBDIR=IBDIR
        JBTYPE=IBTYPE
        JCHAR=ICHAR
        IF (JPROB.EQ.1) GO TO 900
        CALL HEADER
        IF (KAR .EQ. 13) GO TO 100
C IF KAR = CR GET NEXT CHAR
        OCHAR=KKAR
        GO TO 101
777     IF(KAR .NE. 37) GO TO 750
        CALL LONG(KAR,IX,IY)
C KAR WAS % - CALL LONG
        ISTAT='C'
        JBDIR=IBDIR
        JBTYPE=IBTYPE
        MCHAR=KAR
        JCHAR=ICHAR
```

```
989     ISTATE=3
        CALL HEADER
        IF(KAR .EQ. 81) GO TO 900
C LONG BOND CMD WAS INTERRUPTED
C BY Q - EXIT AND PASS Q ON
        GO TO 100
750     IF (KAR .NE. 127) GO TO 9981
CXT     IF (KAR .NE. OCHAR) GO TO 978
C 2 DEL'S IN ROW NOT ALLOWED
CXT     IERR=5
C TYPE ERR MSG AND GET NEXT CMD
CXT     CALL MYERR(IERR,KAR,KAR)
CXT     GO TO 100
978     IF (ICHAR .NE. 13) GO TO 781
        I=COMLEN
C DELETE THE LAST CHAIN
        MRKPNT=MRKPNT-1
CXT
        IF (IERR.EQ.48) THEN
            IERR = 0
            GO TO 988
        ENDIF
CXT
977     JCHAR=2
C DELETE MARKER
        IX=LABL(MRKPNT,1)+1
        IY=LABL(MRKPNT,2)
        MRKPNT=MRKPNT-1
        CALL DEL(KAR,IX,IY,INCX,INCY,0)
        JBTYPE=IBTYPE
        JBDIR=IBDIR
        I=I-1
CXT
988     IF (I.EQ.0) GO TO 110
C CHAIN DELETED - GO TO INPUT
        JCHAR=1
C PREPARE TO DELETE BOND
        BOND=CHBITS(I)
        CALL DELTA(BOND,INCX,INCY)
        CALL DEL(KAR,IX,IY,INCX,INCY,0)
        JBDIR=IBDIR
        JBTYPE=IBTYPE
        I=I-1
        IF (I .EQ. 0) GO TO 110
        GO TO 977
110     CONTINUE
        ICUR = 1
        IX = BIX
        IY = BIY
        CALL CURSOR(IX,IY)
        MCHAR=KAR
        JCHAR=ICHAR
        GO TO 100
781     IF (JCHAR .EQ. 1) CALL DELTA(MCHAR,INCX,INCY)
        CALL DEL(KAR,IX,IY,INCX,INCY,0)
C DEL LONG BOND OR LAST INPUT
        JCHAR=ICHAR
        MCHAR=KAR
        GO TO 100
9981    CALL ERRMSG(KAR)
C INVALID INPUT FOR CHAIN
        GO TO 100
C TYPE MESSAGE AND GET NEXT CMD
900     CONTINUE
        IF (KAR.EQ.13) THEN
            LCHAR = LLCHAR
            LFLAG=0
        ELSE
            LCHAR = 13
            LFLAG = 1
        ENDIF
9501    LEVEL=0
        ISTATE=0
        CALL HEADER
        ICUR = 1
800     RETURN
        END
```

```fortran
$STORAGE:2
      SUBROUTINE RING(KAR,IX,IY,INCX,INCY,IRESET,LFLAG)
      IMPLICIT INTEGER*2 (A-Z)
      INTEGER*4 MM,IDTPIX
      INTEGER*2 IPREF(5,10)
      INTEGER*2 PBRING(8,8,2)
      INTEGER*2 TEST(2),FBOND(2),T2BOND(8)
      LOGICAL*2 MATCH,BAR,BONDEL,BONDID
      CHARACTER*1 ISTAT
      COMMON /RINGY/ LBND(8,2),TSBOND(8),RHBIT(10),LAP(40,3),
     *   RINGS(16,2),RINGO(16,2)
      COMMON /BAD/ IBADX(9),IBADY(9)
      COMMON /CHARS/IES, IDOT,ITAG,JUMP,LBOND,KAN,ISPACE
      COMMON /MODES/ JBTYPE,ICHAR,IBDIR,IBTYPE,ISMART,MODE,ISKILL,ISP
      COMMON /PARAMS/ JBDIR,NOCHG,LASTN,MCHAR,JCHAR,NLARGE,LEVEL
      COMMON /STRPIX/ LPIX,MM(90,38),LBLEN,LNGBND(100,5)
      COMMON /HEAD/ MW(12),ISTATE,PAGE
      COMMON /RCAN/ CAN(10,10)
      COMMON /SIZZE/ MULTX,MULTY
      COMMON /STRED/ IDTPIX(90,38),LABL(260,2),MRKCHN(260)
      COMMON /CD/ MAXX,MAXY
      COMMON /FUSE/ ITIMES
      COMMON /ISTATE/ ISTAT
      COMMON /FROM/ LCHAR
      COMMON /XRNG/ NORDRW(8,8,2),SOFAR
      COMMON /WARN/ ERR
CXT   BAR is used in conjunction with NOCHG, BONDID, and LASTN
CXT   to control bond type drawing in relation to default bond types.
      COMMON /BTPDIR/ BAR
CXT   BONDEL = TRUE indicates that a bond has been drawn between 2
CXT   nodes so subsequent deletion will delete the bond, not a node.
      COMMON /DELBND/ BONDEL
      COMMON /PROB/ IPROB,JPROB
      DATA IPREF(1,3),IPREF(2,3),IPREF(3,3),IPREF(4,3) /7,3,5,1/
      DATA IPREF(1,4),IPREF(2,4),IPREF(3,4),IPREF(4,4) /1,2,3,4/
      DATA IPREF(1,5),IPREF(2,5),IPREF(3,5),IPREF(4,5)/1,5,3,7/
      DATA IPREF(1,6),IPREF(2,6),IPREF(3,6),IPREF(4,6)/4,6,8,2/
      DATA IPREF(1,7),IPREF(2,7),IPREF(3,7),IPREF(4,7)/2,6,4,8/
      DATA IPREF(1,8),IPREF(2,8) /1,2/
      DATA IPREF(1,9),IPREF(2,9),IPREF(3,9),IPREF(4,9)/1,3,5,7/
      DATA IPREF(1,10),IPREF(2,10),IPREF(3,10),IPREF(4,10)
     *   /2,4,6,8/
      DATA PBRING(3,1,1),PBRING(3,1,2),PBRING(3,2,1),PBRING(3,2,2),
     * PBRING(3,3,1),PBRING(3,3,2),PBRING(3,4,1),PBRING(3,4,2),
     * PBRING(3,5,1),PBRING(3,5,2),PBRING(3,6,1),PBRING(3,6,2),
     * PBRING(3,7,1),PBRING(3,7,2),PBRING(3,8,1),PBRING(3,8,2)
     *   /1,2,2,3,3,4,1,4,2,6,1,7,4,8,2,8/
      DATA PBRING(4,1,1),PBRING(4,1,2),PBRING(4,2,1),PBRING(4,2,2),
     * PBRING(4,3,1),PBRING(4,3,2),PBRING(4,4,1),PBRING(4,4,2),
     * PBRING(4,5,1),PBRING(4,5,2),PBRING(4,6,1),PBRING(4,6,2),
     * PBRING(4,7,1),PBRING(4,7,2),PBRING(4,8,1),PBRING(4,8,2)
     *   /2,2,1,3,2,4,1,5,2,6,1,7,2,8,1,1/
      DATA PBRING(5,1,1),PBRING(5,1,2),PBRING(5,2,1),PBRING(5,2,2),
     * PBRING(5,3,1),PBRING(5,3,2),PBRING(5,4,1),PBRING(5,4,2),
     * PBRING(5,5,1),PBRING(5,5,2),PBRING(5,6,1),PBRING(5,6,2),
     * PBRING(5,7,1),PBRING(5,7,2),PBRING(5,8,1),PBRING(5,8,2)
     *   /1,2,2,3,4,4,1,5,2,6,1,7,3,8,2,1/
      DATA PBRING(6,1,1),PBRING(6,1,2),PBRING(6,2,1),PBRING(6,2,2),
     * PBRING(6,3,1),PBRING(6,3,2),PBRING(6,4,1),PBRING(6,4,2),
     * PBRING(6,5,1),PBRING(6,5,2),PBRING(6,6,1),PBRING(6,6,2),
     * PBRING(6,7,1),PBRING(6,7,2),PBRING(6,8,1),PBRING(6,8,2)
     *   /1,2,1,4,2,4,1,5,1,6,1,8,2,8,1,1/
      DATA PBRING(7,1,1),PBRING(7,1,2),PBRING(7,2,1),PBRING(7,2,2),
     * PBRING(7,3,1),PBRING(7,3,2),PBRING(7,4,1),PBRING(7,4,2),
     * PBRING(7,5,1),PBRING(7,5,2),PBRING(7,6,1),PBRING(7,6,2),
     * PBRING(7,7,1),PBRING(7,7,2),PBRING(7,8,1),PBRING(7,8,2)
     *   /1,2,2,4,4,4,1,5,2,6,1,8,3,8,2,1/
      DATA PBRING(8,1,1),PBRING(8,1,2),PBRING(8,2,1),PBRING(8,2,2),
     * PBRING(8,3,1),PBRING(8,3,2),PBRING(8,4,1),PBRING(8,4,2),
     * PBRING(8,5,1),PBRING(8,5,2),PBRING(8,6,1),PBRING(8,6,2),
     * PBRING(8,7,1),PBRING(8,7,2),PBRING(8,8,1),PBRING(8,8,2)
     *   /1,3,1,4,1,5,2,5,1,6,1,8,1,8,1,1/
C Set a few variables
C
      ERR = 0
```

```
CXT
CXT       BONDID is used in conjnction with BAR, NOCHG and RBOND to control
CXT       bond type drawing in relation to default bond types.
          BONDID = .FALSE.
          IF (LCHAR.NE.12) LLCHAR = LCHAR
          LARGE = NLARGE
10001     CONTINUE
          KKAR=0
          ISTAT='^'
C Save bond type
          RBOND=IBTYPE
C Reset RBOND to 1 if bond
          IF ((IBTYPE .NE. 4).AND.(IBTYPE .NE. 8).AND.(IBTYPE.NE.0)
     *    .AND.(.NOT.BAR)) RBOND = 1
CXT  1    .AND. (LASTN .EQ. 0)) RBOND=1
C         Type is temporary type and it has been used once
C         Set header variable to RING state
888       ISTATE=5
C         Unless changed - upon exit we go to call next input
          LFLAG=0
          KAR1=0
          MODE=1
C         Display RING header
          CALL HEADER
100       OCHAR=KKAR
          ICUR = 1
          CALL CURSOR(IX,IY)
C         Get input char
1060      CALL INPUTX(KAR,IX,IY)
          IF (KAR.EQ.131) GO TO 1060
          IF (KAR.EQ.94) THEN
              IERR = 39
              CALL MYERR(IERR,IERR,IERR)
              GO TO 1060
          ENDIF
          KKAR=KAR
C         Not a valid digit - thus not a ring command
101       IF (KAR .LT. 48 .OR. KAR .GT. 56) GO TO 400
CXT
          IF (.NOT.BAR) THEN
              NOCHG = 0
              IF ((IBTYPE.NE.0).AND.(IBTYPE.NE.4).AND.(IBTYPE.NE.8)) THEN
                  RBOND = 1
                  IBTYPE = RBOND
              ENDIF
          ENDIF
C         Ring command - find environment
200       ENVIRN=-999
C         Count of bonds pointing to or away from node
          BCNT=0
C         Used to determine if all legal rings have been tried
          ITRY = 1
C         Implies that we are using the standard form of the ring
          IFROM = 0
C         RINGS version of NLARGE - we can't use NLARGE
          LARGE = NLARGE
C         in an automatic way for rings 3,5 and 7 so we do
C         it the hard way
          NLARGE=1
          DO 841 I=1,40
          DO 841 J=1,3
C         Zero overlap table
841       LAP(I,J)=0
C         Zero overlap table counter
          LCNT=0
          CALL CELL (IX,IY,IGOOD)
C         We are at an empty 3X3 area
          IF (IGOOD.NE.0) GO TO 7006
              ENVIRN=-1
              GO TO 207
7006      IF (MM(IX,IY).NE.0) GO TO 7001
          CALL FINDB(SLOB,BLOB,IX,IY)
          IF (SLOB.EQ.-1) GO TO 7001
```

```
              CALL DELTA(BLOB,INCX,INCY)
              IBDIR = BLOB
              ENVIRN = 0
              GO TO 207
 7001      KHAR=LMM(IX-1,IY)
C          WE ARE AT NODE
           IF(KHAR .EQ. 46 .OR. (KHAR .GE. 65 .AND.
     1     KHAR .LE.90) .OR. (KHAR .GE. 97 .AND.
     2     KHAR .LE. 122)) ENVIRN = 1
           IF(ENVIRN .NE. 1) GO TO 207
C
C          Find coordinates of node
C
           JJJ=0
           IF (KHAR .EQ. 46 .OR. KHAR .EQ. 81) JJJ=IX-1
           DO 428 I=0,-3,-1
           IF (((MM(IX+I,IY).GE.65).AND.(MM(IX+I,IY).LE.90).AND.
     2     (MM(IX+I,IY).NE.72)).OR.((MM(IX+I,IY).EQ.72).AND.
     3     (MM(IX+I+1,IY).GE.97).AND.(MM(IX+I+1,IY).LE.122))) THEN
           JJJ=IX+I
           GO TO 427
           ENDIF
 428       CONTINUE
 427       IF (JJJ .EQ. 0) ENVIRN=-999
 207       IF (ENVIRN .NE. -999) GO TO 201
C          Could not determine our environment
           IERR= 29
C          Issue error message and return to GND
           CALL MYERR(IERR,KAR,MAR)
           NLARGE = LARGE
           IF ((MM(IX,IY).EQ.46).OR.((MM(IX,IY).GE.65).AND.(MM(IX,IY).LE.
     *     90))) IX = IX + 1
           GO TO 10001
C          Set connection value to default
 201       CONN=ENVIRN
C          If chain (i.e. bond) CONN = 0
C          If ring (i.e. node) CONN = 1
C          If digit = 0,1,2 then set CONN to
           DIG=KAR-48
C          to explicitly requested connection type
C          -1 = unconnected
C          0 = SPIRO
C          1 = At least 1 side fused
C          2 = 2 sides fused
           COC=1
           IF (DIG .GE. 3) GO TO 202
C          Set connection type to explicitly requested type
           CONN=DIG
C          IS THIS A NEW COMMAND OR RETRY AFTER DELETE
 205       IF (KAR1 .EQ. 0) GO TO 2205
           KAR=KAR1
           KAR1=0
           GO TO 2105
 2205      OCHAR=KKAR
 1063      CALL INPUTX(KAR,IX,IY)
           IF (KAR.EQ.131) THEN
              ICUR = 1
              CALL CURSOR(IX,IY)
              NLARGE = LARGE
              GO TO 100
           ELSE IF (KAR.EQ.94) THEN
              IERR = 39
              CALL MYERR(IERR,IERR,IERR)
              GO TO 1063
           ENDIF
           KKAR=KAR
C          Get ring size
 2105      DIG=KAR-48
C          Go on if ring size 3 to 8
 202       IF (DIG .GE. 3 .AND. DIG .LE. 8) GO TO 203
           IF (DIG .NE. -35 ) GO TO 2020
           NLARGE=LARGE
           KAR1=0
           GO TO 100
 2020      IERR=30
```

```
C        Bad ring size - display error message
199      CALL MYERR(IERR,DIG,MAR)
C        and await reentry of ring size
         GO TO 205
C        Set ring size
203      RSIZE=DIG
C        Set default # of tries  to 1
         NTEST=1
         IF (CONN .NE. -1) GO TO 300
C
C        We are going to draw an unattached ring
C
         CALL MBIT(RSIZE)
C        Pick up first bond direction
         BONDF = IPREF(1,RSIZE)
C        Now generate full ring command table
         CALL MAKRNG(RSIZE,RCNT,ENVIRN,BONDF,LARGE,COC,1)
         FBOND(1) = BONDF
C
         GO TO 850
300      CONTINUE
         IF (CONN .NE. 0) GO TO 3100
C
C        Ring will have spiro connection
C
         IF (ENVIRN .EQ. 1) GO TO 305
C
C        Spiro connection - ring attached to bond
C
         KHAR=LMM(IX-INCX,IY-INCY)
         FINCX = INCX
         FINCY = INCY
         INBOND=KHAR/256
C        Ring will attach to bond of dir INBOND
         INBOND=KHAR-INBOND*256
C        Put pointer bond in table
         LAP(1,1)=IX-INCX
         LAP(1,2)=IY-INCY
         LCNT=1
         GO TO 308
C
C        Spiro connection - ring attached to node
C
305      KX=JJJ
         KY=IY
C        Clear hydrogens around node
         CALL CLRHYD(KX,KY)
C        so we can more easily find the
C        bonds around the node
C        Locate bonds around the node
         CALL LOCBND(JJJ,KY,BCNT)
C        Set X value
         IX=JJJ
         LAP(1,1)=JJJ
C        Put node in overlap table
         LAP(1,2)=KY
         LCNT=1
9999     IF (BCNT .NE. 0) GO TO 310
C
C        No bonds - draw ring in normal shape and orientation with node
C        incorporated in ring
C
C        Set up ring definition and first bond
         BONDF = IPREF(1,RSIZE)
         CALL MBIT(RSIZE)
         CALL MAKRNG(RSIZE,RCNT,ENVIRN,BONDF,LARGE,COC,1)
         FBOND(1) = BONDF
         GO TO 850
310      IF (BCNT .NE. 1) GO TO 315
C
C        One bond - draw ring with existing node in ring and determine
C        orientation using pointer bond logic
C
C        Pick up bond
         INBOND=LBND(1,1)
C        Reverse pointer bond
317      INBOND=MOD(INBOND+4,8)
```

```
              IF (INBOND .EQ. 0) INBOND=8
              GO TO 308
      C
      C
      C       2 or more bonds at node - determine pseudo pointer bond
      315     MAXI=0
              TEST(1)=0
              TEST(2)=0
              MAXGAP=0
      C       Find biggest gap
              DO 20 I=1,BCNT
              IF (LBND(I,2) .LE. MAXGAP) GO TO 20
              MAXI=I
              MAXGAP=LBND(I,2)
      20      CONTINUE
      C
      C       Found biggest gap - now calculate pseudo pointer bond
      C
              INBOND=MOD((LBND(MAXI,1)+MAXGAP/2),8)
              IF (INBOND .EQ. 0) INBOND = 8
      C       If gap = 4
              IF (BCNT .NE.2 .OR. MAXGAP .NE. 4) GO TO 309
      C       and there are only 2 bonds on node - there are 2
      C       'equal' positions - set TEST(1) and TEST(2) such
      C       that rings are positoned in the following order
      C       right - left - down - up
              TEST(1)=INBOND
              IF(INBOND .LT. 3 .OR. INBOND .GT. 6) TEST(2)=INBOND
              INBOND=MOD(INBOND+4,8)
              IF(INBOND .EQ. 0) INBOND=8
              IF (INBOND .LT.3 .OR. INBOND .GT. 6) TEST(2)=INBOND
              IF (INBOND .GE.3 .AND. INBOND.LE. 6) TEST(1)=INBOND
              IF (TEST(1) .EQ. 5 .AND. TEST(2) .EQ. 1) THEN
              TEST(1)=1
              TEST(2)=5
              ENDIF            !Fix so ring goes down before up
              INBOND=TEST(1)
              NTEST=2
      C       If MAXGAP is not an
      309     IF (MOD(MAXGAP,2).EQ.0) GO TO 308
      C       even number - we have 2 positions to try
              TEST(1)=INBOND
              INBOND=INBOND+1
              IF(INBOND .GT. 8) INBOND = 1
              TEST(2)=INBOND
              if (mod(inbond,2).eq. 0) then
              ihold=test(1)
              test(1)=test(2)
              test(2)=ihold
              endif
              INBOND=TEST(1)
              NTEST=2
      C       First bond in ring will have dir FFBOND
      308     FFBOND=PBRING(RSIZE,INBOND,1)
              FFBOND=IPREF(FFBOND,RSIZE)
      330     CALL MBIT(RSIZE)
              CALL MAKRNG(RSIZE,RCNT,ENVIRN,FFBOND,LARGE,COC,0)
              BONDF = PBRING(RSIZE,INBOND,2)
      C       Convert bond dir to bond command
              CALL MKBND(BONDF)
              FBOND(1) = BONDF
              DO 409 I=1,RCNT
      C       See if we have the needed bond
              ISTART = I
              IF (FBOND(1).EQ.RINGO(I,1)) GO TO 410
      409     CONTINUE
      C       Can't find needed bond - go try next orientation
              GO TO 937
      410     CONTINUE
              IF (ISTART .EQ. 1 .AND. ENVIRN .EQ. 0) ISTART=RCNT+1
              IF (ISTART .NE. 1 .AND. ENVIRN .EQ. 0)ISTART=ISTART-1
              DO 411 I=1,RCNT
```

```
C            Copy RING to RINGS so commands are
             RINGS(I,1)=RINGO(ISTART,1)
C            in the right order for DRING
             RINGS(I,2) = RINGO(ISTART,2)
             ISTART=ISTART+1
             IF (ISTART .GT. RCNT) ISTART=1
411     CONTINUE
C
850     KX=IX
        KY=IY
        BIX=IX
C            Start to check if there is room for ring
C            without creating unacceptable collisions
C
852     J=1
        RG1 = RINGS(1,1)
        RG2 = RINGS(2,1)
        BLOB=MIN0(RG1,RG2)
        CALL DELTA(BLOB,INCX,INCY)
C            Pick up ring command
985     BLOB=RINGS(J,1)
C            If it is a marker
        IF (BLOB .EQ. 35) GO TO 854
C            Its a bond - get incs
        CALL DELTA(BLOB,INCX,INCY)
C            Get bond length
        LAR = RINGS(J,2)
        SLOB=BLOB
        DO 990 IK=1,LAR
        KX=KX+INCX
        KY=KY+INCY
C            Check cell
8888    CALL LOOK(KX,KY,ICHECK,LCNT,BLOB)
        RG1 = RINGS(J,2)
        IF (BLOB .EQ. -1) RINGS(J,2) = -IABS(RG1)
C            Not = 0 means invalid conflict
        IF (ICHECK .NE. 0) GO TO 937
        BLOB=SLOB
990     CONTINUE
C            Bond OK - go get next command
        GO TO 971
C
854     IF (J .EQ. 1 .AND. ENVIRN .EQ. 0) GO TO 8854
        KX=KX+INCX
        KY=KY+INCY
C            Check cell
8854    CALL LOOK(KX,KY,ICHECK,LCNT,BLOB)
        RG2 = RINGS(J,2)
        IF (BLOB.EQ.-1) RINGS(J,2) = -IABS(RG2)
C            If bad conflict - go to 937
        IF (ICHECK .NE. 0) GO TO 937
C            OK so far - go check next one
971     J=J+1
C            OK so far - get next command
        IF( J .LE. RCNT) GO TO 985
C
999     BIX=IX
        BIY=IY
C            Now draw ring
        ERR = 0
        CALL DRING(RCNT,IX,IY,TX,TY,RBOND,CONN)
        NLARGE=LARGE
        OCHAR=KKAR
        IF (ERR.EQ.23) THEN
CXT          Crossing diagonal bonds not allowed - delete ring.
             ERR = 0
             KAR = 127
             GO TO 1074
        ELSE IF (ERR.EQ.48) THEN
CXT          Adjacent nodal values not allowed - delete ring.
             KAR = 127
             GO TO 1084
        ENDIF
C            GET INPUT TO CHECK FOR DELETE
```

```
1064    CALL INPUTX(KAR,TX,TY)
        IF (KAR.EQ.131) THEN
            ICUR = 1
            CALL CURSOR(TX,TY)
            GO TO 1064
        ELSE IF (KAR.EQ.94) THEN
            IERR = 39
            CALL MYERR(IERR,IERR,IERR)
            GO TO 1064
        ENDIF
1074    CONTINUE
1084    IDEL=0
        KKAR=KAR
        KAR1=0
C       NOT DEL - GO PROCESS COMMAND
        IF (KAR .NE. 127) THEN
            IF ((MM(TX,TY).EQ.46).OR.((MM(TX,TY).GE.65).AND.(MM(TX,TY)
     *         .LE.90))) THEN
                IX = TX + 1
            ELSE
                IX = TX
            ENDIF
            IY = TY
            GO TO 101
        ENDIF
        CALL CURSOR(IX,IY)
C THIS VARIABLE IS USED TO TRIGGER 'NO GOOD ORIENTATION' MESSAGE
        IDEL=1
        IF ((RINGS(1,1).EQ.35).AND.(ERR.NE.48)) IX=IX-1
C DELETE RINGS
        CALL RNGDEL(RCNT,IX,IY)
        IF (ERR.EQ.48) THEN
            IX = BIX
            IY = BIY
            CALL CURSOR(IX,IY)
            ERR = 0
        ENDIF
C WE DELETED FREE STANDING
        IF (ENVIRN .EQ. -1) GO TO 100
C RING - GO GET NEXT COMMAND
        OCHAR=KKAR
C WE DID A DELETE - DO WE TRY IT AGAIN
1065    CALL INPUTX(KAR,IX,IY)
        IF (KAR.EQ.131) THEN
            ICUR = 1
            CALL CURSOR(IX,IY)
            GO TO 1065
        ELSE IF (KAR.EQ.94) THEN
            IERR = 39
            CALL MYERR(IERR,IERR,IERR)
            GO TO 1065
        ENDIF
        KKAR=KAR
        IF(KAR .LT. 48 .OR. KAR .GT.56) GO TO 400
        OCONN=CONN
        CONN=-999
        ORSIZE=RSIZE
        DIG=KAR-48
        IF (DIG .GE. 3) GO TO 1202
        CONN=DIG
1205    OCHAR=KKAR
1066    CALL INPUTX(KAR1,IX,IY)
        IF (KAR1.EQ.131) THEN
            ICUR = 1
            CALL CURSOR(IX,IY)
            GO TO 1066
        ELSE IF (KAR1.EQ.94) THEN
            IERR = 39
            CALL MYERR(IERR,IERR,IERR)
            GO TO 1066
        ENDIF
        KKAR=KAR1
C GET NEW CONN AND RING SIZE
        DIG=KAR1-48
1202    IF (DIG .GE. 3 .AND. DIG .LE. 8) GO TO 1203
        IERR=30
```

```
              CALL MYERR(IERR,DIG,MAR)
              GO TO 1205
1203    RSIZE=DIG
              IF (CONN .EQ. -999) CONN=ENVIRN
              IF ((IX.NE.BIX).OR.(IY.NE.BIY)) GO TO 7017
              IF (ORSIZE .EQ. RSIZE .AND. CONN .EQ. OCONN) GO TO 937
C IF SAME SIZE AND CONNECTION - TRY NEXT ORIENTATION
C IF NOT - TRY NEW RING
7017    INCX = FINCX
              INCY = FINCY
              NLARGE = LARGE
              GO TO 101
C       We've tried everything - all failed - issue error and get next command
937     IF (ITRY.EQ.NTEST) THEN
                 INCX = FINCX
                 INCY = FINCY
                 GO TO 973
              ENDIF
              ITRY=ITRY+1
              IX=BIX
C Pick up next INBOND and try again
              INBOND=TEST(ITRY)
              GO TO 308
3100    KX=IX
              KY=IY
              IF(ENVIRN .EQ. 1) KX=JJJ
              MX=KX
              MY=KY
              JL=KX+1
              ITIMES=CONN
              IALT=1
C Start loop for alternate ring forms if ring size = 3 or 5.
              IF (RSIZE .EQ. 3 .OR. RSIZE .EQ. 5) IALT=2
C Get all into bonds
              CALL GETABD(JL,KY,TSCNT)
C No bond - too bad
              IF (TSCNT .EQ. 0) GO TO 947
CXT
CXT     Variables used to prevent redrawing of symmetrical rings are
CXT     (re)initiallized.
              IF ((MOD(RSIZE,2).EQ.0).AND.(SOFAR.GT.0)) THEN
                 DO 1053 IM = 1,SOFAR
                    DO 1052 IN = 1,8
                       NORDRW(IM,IN,1) = 0
                       NORDRW(IM,IN,2) = 0
1052                CONTINUE
1053             CONTINUE
              ENDIF
              SOFAR = 0
CXT
CXT     Two passes can be made, the first for 2 sided fuses, the second
CXT     for fuses of more than 2 sides, if the operator does not accept
CXT     any 2 sided fuses.  The count of the passes and the count of
CXT     fuses with more then 2 sides are initiallized.
              ATTMPT = 0
              FUSE3 = 0
1061    CONTINUE
              ATTMPT = ATTMPT + 1
CXT
              DO 1001 IKK=1,IALT
              DO 1000 IK=1,TSCNT
              KX=MX
              KY=MY
              LCNT=0
C 0 implies we are at the end of a bond
              IF (ENVIRN .EQ. 0) GO TO 957
              LCNT=LCNT+1
              LAP(LCNT,1)=KX
C Put node in overlap table
              LAP(LCNT,2)=KY
C Get bond dir
957     BDIR=TSBOND(IK)
              CALL DELTA(BDIR,INCX,INCY)
              KX=KX-INCX
              KY=KY-INCY
```

```
C Put bond in overlap table
        BND=LMM(KX,KY)
968     LCNT=LCNT+1
        IF(LCNT .GT. 40) GO TO 947
        LAP(LCNT,1)=KX
        LAP(LCNT,2)=KY
        KX=KX-INCX
        KY=KY-INCY
        GND=LMM(KX,KY)
        IF(GND .EQ. BND) GO TO 968
967     BLEN=LCNT-1
        IF (BLEN .EQ. 0) BLEN=1
        IF(GND .NE. 46) GO TO 947
        LCNT=LCNT+1
        IF(LCNT .GT. 40) GO TO 947
C Put marker in overlap table
        LAP(LCNT,1)=KX
        LAP(LCNT,2)=KY
        LLCNT=LCNT
C Set first bond
4000    FBOND(1)=BDIR
        BONDF1 = FBOND(1)
        FBOND(2)=MOD(FBOND(1)+4,8)
C REVERSE BOND
        IF (FBOND(2) .EQ. 0) FBOND(2)=8
        BONDF2 = FBOND(2)
C Convert bond dir to bond command
        CALL MKBND(BONDF1)
        CALL MKBND(BONDF2)
        FBOND(1) = BONDF1
        FBOND(2) = BONDF2
        DO 991 K=1,4
        DO 8809 IROT=1,2
        COC=1
        RRSIZE=RSIZE
        IF (RSIZE .EQ. 3 .AND. IKK .EQ. 2) RRSIZE=9
        IF (RSIZE .EQ. 5 .AND. IKK .EQ. 2) RRSIZE=10
        FFBOND=IPREF(K,RRSIZE)
C       If no new orientations - try next 'into' bond
        IF (FFBOND .EQ. 0) GO TO 8809
        CALL MBIT(RRSIZE)
        CALL MAKRNG(RSIZE,RCNT,ENVIRN,FFBOND,LARGE,COC,0)
        DO 809 I=1,RCNT
        II = I
        IF(FBOND(IROT).EQ.RINGO(I,1).AND.BLEN.EQ.RINGO(I,2)) GO TO 810
C Can we match bond dir and len
809     CONTINUE
C No - go try next orientation
        GO TO 8809
810     ISTART=II
        IF (IROT .EQ. 2) GO TO 8111
        ISTART=MOD(ISTART+2,RCNT)
        IF (ISTART .EQ. 0) ISTART=RCNT
8111    IF (ISTART .EQ. 1 .AND. ENVIRN .EQ. 0) ISTART=RCNT+1
        IF (ISTART .NE. 1 .AND. ENVIRN .EQ. 0) ISTART=ISTART-1
C Copy RING to RINGS so commands are in
        DO 811 I=1,RCNT
C the right order for DRING
        RINGS(I,1)=RINGO(ISTART,1)
        RINGS(I,2)=RINGO(ISTART,2)
        ISTART=ISTART+1
        IF (ISTART .GT. RCNT) ISTART=1
811     CONTINUE
        J=1
        KX=MX
        KY=MY
        BLOB=MINO(RINGS(1,1),RINGS(2,1))
        CALL DELTA(BLOB,INCX,INCY)
C Pick up ring command
9850    BLOB=RINGS(J,1)
        IF (BLOB .EQ. 35) GO TO 8540
C Its a bond - get incs
994     CALL DELTA(BLOB,INCX,INCY)
C Get bond length
        LAR = RINGS(J,2)
        SLOB=BLOB
```

```
              DO 9990 IM=1,LAR
              KX=KX+INCX
              KY=KY+INCY
C Check cell
              CALL LOOK(KX,KY,ICHECK,LCNT,BLOB)
              IF (BLOB .EQ. -1) RINGS(J,2)=-IABS(RINGS(J,2))
C Not = 0 means invalid conflict
              IF (ICHECK .NE. 0) GO TO 992
              BLOB=SLOB
9990          CONTINUE
C Bond OK - go get next command
              GO TO 9710
C
8540          IF (J.EQ.1 .AND. ENVIRN.EQ.0 ) GO TO 8585
              KX=KX+INCX
              KY=KY+INCY
C Check cell
8585          CALL LOOK(KX,KY,ICHECK,LCNT,BLOB)
              RG2 = RINGS(J,2)
              IF (BLOB .EQ. -1) RINGS(J,2)=-IABS(RG2)
C NEQ NUM IN RINGS(*,2) MEANS FUSED SO DON'T
C REALLY DO THIS COMMAND
C If bad conflict - go to 992
              IF (ICHECK .NE. 0) GO TO 992
C OK so far - go check next one
9710          J=J+1
C OK so far - get next command
              IF( J .LE. RCNT) GO TO 9850
C Reset LCNT for next try
              LCNT=LLCNT
              DO 995  IM=1,LLCNT
              IF (LAP(IM,3) .EQ. 0) GO TO 8809
995           CONTINUE
              IF(ITIMES .EQ. 1) GO TO 9050
              L=0
              LB=0
              DO 714 IM=1,RCNT
              IF (RINGS(IM,2).LT.0) L=L+1
              IF (RINGS(IM,1) .NE. 35 .AND. RINGS(IM,2) .LT.0) LB=LB+1
714           CONTINUE
              ITEST=4
              IF (ENVIRN .EQ.0) ITEST=3
              IF (L .LT. ITEST .OR. LB .LT. 2) GO TO 8809
              IF (L .EQ. RCNT) GO TO 8809
CXT
CXT           If the current number of fuses found by the original algorithm
CXT           is greater than 2 and this is the 1st pass, skip drawing it -or-
CXT           If the current number of fused found by the original algorithm
CXT           equals 2 and this is the second pass, skip the drawing.
              IF ((LB.GT.2).AND.(ATTMPT.EQ.1)) THEN
                 FUSE3 = FUSE3 + 1
                 GO TO 8809
              ELSE IF ((LB.EQ.2).AND.(ATTMPT.EQ.2)) THEN
                 GO TO 8809
              ENDIF
CXT
9050          CONTINUE
CXT
CXT           The next symmetrical ring drawing is compared to previous
CXT           symmetrical drawings to see if it is a duplicate.  X and
CXT           Y coordinates of nodes are computed by tracing bonds and
CXT           compared.
              IF ((MOD(RSIZE,2).EQ.0).AND.(SOFAR.GT.0)) THEN
                 DO 9075 IL = 1,SOFAR
                    LX = MX
                    LY = MY
                    MATCH = .FALSE.
                    DO 9074 IM = 1,RCNT
                       IF (IABS(RINGS(IM,1)).EQ.35) THEN
                          DO 9072 IN = 1,8
                             IF ((LX.EQ.NORDRW(IL,IN,1)).AND.
                                 (LY.EQ.NORDRW(IL,IN,2))) THEN
                                MATCH = .TRUE.
                                GO TO 9073
                             ENDIF
```

```
9072            CONTINUE
                MATCH = .FALSE.
                GO TO 9075
             ELSE IF (RINGS(IM,1).NE.0) THEN
                DRDIR = IABS(RINGS(IM,1))
                IF (DRDIR.GT.25) DRDIR = DRDIR - 2
                DRDIR = DRDIR - 21
                IF ((DRDIR.EQ.1).OR.(DRDIR.EQ.5)) THEN
                   INCKX = 0
                ELSE IF ((DRDIR.GE.2).AND.(DRDIR.LE.4)) THEN
                   INCKX = 1
                ELSE IF (DRDIR.GE.6) THEN
                   INCKX = -1
                ENDIF
                IF ((DRDIR.EQ.8).OR.(DRDIR.LE.2)) THEN
                   INCKY = -1
                ELSE IF ((DRDIR.EQ.3).OR.(DRDIR.EQ.7)) THEN
                   INCKY = 0
                ELSE IF ((DRDIR.GE.4).AND.(DRDIR.LE.6)) THEN
                   INCKY = 1
                ENDIF
                LX = LX + (IABS(RINGS(IM,2)) * INCKX) + INCKX
                LY = LY + (IABS(RINGS(IM,2)) * INCKY) + INCKY
             ELSE
                GO TO 9075
             ENDIF
9073         CONTINUE
9074      CONTINUE
          IF (MATCH) GO TO 8809
9075   CONTINUE
       ENDIF
CXT
       CIX=IX
       CIY=IY
       BX=MX
       BY=MY
       TIMES = ITIMES
       ERR = 0
       CALL DRING(RCNT,BX,BY,TX,TY,RBOND,TIMES)
       NLARGE=LARGE
       OCHAR=KKAR
       IF (ERR.EQ.23) THEN
CXT       Crossing diagonal bonds not allowed - delete ring.
          ERR = 0
          KAR = 127
          GO TO 1077
       ELSE IF (ERR.EQ.48) THEN
CXT       Adjacent nodal values not allowed - delete ring.
          KAR = 127
          IX = BX
          IY = BY
          GO TO 1088
       ENDIF
C GET INPUT TO CHECK FOR DELETE
1067   CALL INPUTX(KAR,TX,TY)
       IF (KAR.EQ.131) THEN
          ICUR = 1
          CALL CURSOR(TX,TY)
          GO TO 1067
       ELSE IF (KAR.EQ.94) THEN
          IERR = 39
          CALL MYERR(IERR,IERR,IERR)
          GO TO 1067
       ENDIF
1077   CONTINUE
1088   IDEL=0
       KKAR=KAR
       KAR1=0
C NOT DEL - GO PROCESS COMMAND
       IF (KAR.NE.127) THEN
          IF ((MM(TX,TY).EQ.46).OR.((MM(TX,TY).GE.65).AND.(MM(TX,TY)
     *       .LE.90))) THEN
             IX = TX + 1
          ELSE
             IX = TX
          ENDIF
```

```
              IY = TY
              GO TO 101
           ENDIF
           CALL CURSOR(IX,IY)
C THIS VARIABLE TRIGGERS THE 'NO GOOD ORIENTATION' MESSAGE
           IDEL=1
CXT        IF (RINGS(RCNT,1).EQ.35) IX = IX - 1
           IF ((RINGS(RCNT,1).EQ.35).AND.(ERR.NE.48)) IX = IX - 1
C DELETE RINGS
           CALL RNGDEL(RCNT,IX,IY)
           ERR = 0
           IX=CIX
           IY=CIY
           IF (IBTYPE.NE.0) THEN
               IF ((MM(IX,IY).GT.0).AND.(MM(IX,IY).LT.256)) IX = IX + 1
               CALL CURSOR(IX,IY)
           ENDIF
           OCHAR=KKAR
C WE DID A DELETE - DO WE TRY IT AGAIN
1068       CALL INPUTX(KAR,IX,IY)
           IF (KAR.EQ.131) THEN
               ICUR = 1
               CALL CURSOR(IX,IY)
               GO TO 1068
           ELSE IF (KAR.EQ.94) THEN
               IERR = 39
               CALL MYERR(IERR,IERR,IERR)
               GO TO 1068
           ENDIF
           KKAR=KAR
           IF(KAR .LT. 48 .OR. KAR .GT.56) GO TO 400
           OCONN=CONN
           CONN=-999
           ORSIZE=RSIZE
           DIG=KAR-48
           IF (DIG .GE. 3) GO TO 3202
           CONN=DIG
3205       OCHAR=KKAR
1069       CALL INPUTX(KAR1,IX,IY)
           IF (KAR1.EQ.131) THEN
               ICUR = 1
               CALL CURSOR(IX,IY)
               GO TO 1069
           ELSE IF (KAR1.EQ.94) THEN
               IERR = 39
               CALL MYERR(IERR,IERR,IERR)
               GO TO 1069
           ENDIF
           KKAR=KAR1
C GET NEW CONN AND RING SIZE
           DIG=KAR1-48
3202       IF (DIG .GE. 3 .AND. DIG .LE. 8) GO TO 3203
           IERR=30
           CALL MYERR(IERR,DIG,MAR)
           GO TO 3205
3203       RSIZE=DIG
           IF.(CONN .EQ. -999) CONN=ENVIRN
           IF ((IX.NE.CIX).OR.(IY.NE.CIY)) GO TO 70017
           IF (ORSIZE .EQ. RSIZE .AND. CONN .EQ. OCONN) GO TO 992
C IF SAME SIZE AND CONNECTION - TRY NEXT ORIENTATION
C IF NOT - TRY NEW RING
70017      NLARGE = LARGE
           GO TO 101
992        DO 993 IM=1,40
           LAP(IM,3)=0
993        CONTINUE
           DO 904 IM=1,16
           RG2 = RINGS(IM,2)
904        RINGS(IM,2)=IABS(RG2)
8809       CONTINUE
991        CONTINUE
1000       CONTINUE
1001       CONTINUE
CXT
CXT        If fuses of more than 2 sides have been found possible,
```

```
      CXT    attempt pass 2.
             IF ((FUSE3.GT.0).AND.(ATTMPT.EQ.1)) GO TO 1061
      CXT
      C  Can't draw ring - issue error message
      973    IF (IDEL .EQ. 1) GO TO 974
             IERR=31
      C      Issue error message - reset NLARGE command and get next command
             CALL MYERR(IERR,KAR,MAR)
             NLARGE=LARGE
             KAR1=0
             GO TO 100
      974    IDEL=0
             IERR=32
             CALL MYERR(IERR,IERR,IERR)
             KAR1=0
             NLARGE = LARGE
             GO TO 100
      C      Bad connections for ring - issue error message - reset NLARGE
      C      - get next cmd
      947    IERR=29
             CALL MYERR(IERR,IERR,IERR)
             NLARGE=LARGE
             KAR1=0
             IF ((MM(IX,IY).EQ.46).OR.((MM(IX,IY).GE.65).AND.(MM(IX,IY).LE.
           *   90))) IX = IX + 1
             GO TO 10001
      CXT
      C Check for bond
      400    IF (KAR.GE.22 .AND. KAR.LE.31) THEN
                BONDID = .TRUE.
                GO TO 700
             ELSE
                NOCHG = 0
             ENDIF
      CXT
             IF (KAR.EQ.13 .OR. KAR .EQ. 81) GO TO 900
      C If KAR = CR or Q - Quit or return to GND level
             IF ((KAR.EQ.21).OR.(KAR.EQ.32).OR.(KAR.EQ.8)) THEN
                IF (KAR.EQ.32) THEN
                   JX = IX - 1
                   CALL CURSOR(JX,IY)
                   CALL CLRHYD(JX,IY)
                   CALL VALNCE(2,JX,IY,0,0)
                   IF (JPROB.EQ.1) GO TO 900
                ENDIF
                CALL SPACE(IX,IY)
                JCHAR = 2
                MCHAR = 0
                NLARGE = LARGE
                GO TO 10001
             ENDIF
             IF (KAR.EQ.33 .OR. KAR.EQ.95 .OR .KAR.EQ.58) GO TO 900
             IF (KAR.EQ.42) GO TO 900
      C If KAR is chain, space or backspace (i.e. DUMB) set LFLAG
      C so that we exit and go to IDENT not INPUTX
             IF (KAR .EQ. 64 .OR. KAR .EQ. 37) GO TO 800
      C We have a REPEAT or LONGBOND command
      C Check to UC
             IF ((KAR.GE.65 .AND. KAR.LE.90).OR.(KAR.EQ.46)) GO TO 700
      C Check for $
             IF (KAR .EQ. 36) GO TO 700
      C Check for &
             IF (KAR.EQ.38) GO TO 71234
      C Check for lc
             IF (KAR .GE. 97 .AND. KAR .LE. 122) GO TO 700

CXT
      C Check for marker command
             IF (KAR .EQ. 35) GO TO 700
      C Check for luhn dot command
             IF (KAR.EQ.46) GO TO 700
      C Go to DELETE section
             IF (KAR .EQ. 127) GO TO 700
      C Go to NUM ENTRY section
             IF (KAR .EQ. 124) GO TO 600
```

```
        IF ((KAR.EQ.43).OR.(KAR.EQ.45).OR.(KAR.EQ.61)) GO TO 700
        IF (KAR.EQ.34) GO TO 700
        CALL ERRMSG(KAR)
        NLARGE = LARGE
C Invalid RING command - display error message and go try again
        GO TO 100
C
C xxxxxxxxxxxxxxxxxxxxxxxxxxxxxxxxxxxxxxxxxxxxxxxxxxxxxxxxxxx
C
C                     # ENTRY CODE
C
C xxxxxxxxxxxxxxxxxxxxxxxxxxxxxxxxxxxxxxxxxxxxxxxxxxxxxxxxxxx
C
C           CHAR WAS A VERTICAL LINE SO WE WILL BE SETTING
C               A NEW BOND TYPE OR CHARGE VALUE
C
600     OCHAR=KKAR
        CALL CURSOR(IX,IY)
        CALL NUMBER(KAR,IX,IY)
        IF (KAR.EQ.81) GO TO 900
        KKAR = KAR
        ISTATE = 5
        ISTAT = '^'
        RBOND = IBTYPE
        CALL HEADER
        GO TO 100
C xxxxxxxxxxxxxxxxxxxxxxxxxxxxxxxxxxxxxxxxxxxxxxxxxxxxxxxxxxx
C                   END OF # ENTRY CODE
C xxxxxxxxxxxxxxxxxxxxxxxxxxxxxxxxxxxxxxxxxxxxxxxxxxxxxxxxxxx
C       Process command that IDENT can handle
700     CALL IDENT(KAR,IX,IY,INCX,INCY,IRESET)
CXT
        IF (BONDID) THEN
            BONDID = .FALSE.
            BAR = .FALSE.
        ENDIF
        RBOND = IBTYPE
C Get next command
        NLARGE = LARGE
        IF (JPROB.EQ.1) GO TO 900
        CALL HEADER
        GO TO 100
C Set enlargement factor
71234   CALL IDENT(KAR,IX,IY,INCX,INCY,IRESET)
        LARGE = NLARGE
        IF (JPROB.EQ.1) GO TO 900
        ISTATE = 5
        CALL HEADER
        GO TO 100
C Call REPEAT
800     IF (KAR .EQ. 64)
     1  CALL REPEAT(KAR,IX,IY,INCX,INCY,IRESET,LFLAG)
        IF (JPROB.EQ.1) GO TO 900
C Call LONGBOND
        IF (KAR .EQ. 37) CALL LONG(KAR,IX,IY)
C If we returned with
        IF (KAR .EQ. 81) GO TO 900
C a Q - Quit
C Reset variables and get next command
1310    CONTINUE
        LEVEL=1
        ISTATE=5
        ISTAT='^'
        JBDIR=IBDIR
        JBTYPE=IBTYPE
        JCHAR=ICHAR
C Call HEADER to display RING header
        CALL HEADER
        ICUR = 1
        CALL CURSOR(IX,IY)
        NLARGE = LARGE
        GO TO 100
C Set return flag to go to IDENT not INPUTX
900     CONTINUE
```

```
C If CR - then go to INPUTX
        IF (KAR .EQ. 13) THEN
            LCHAR = LLCHAR
            LFLAG=0
        ELSE
            LCHAR = 12
            LFLAG = 1
        ENDIF
        LEVEL=0
        ISTATE=0
C Set LEVEL and ISTATE to GND and call HEADER
        CALL HEADER
        ICUR = 1
        RETURN
        END
$STORAGE:2
C       SUBROUTINE LOCBND(IX,IY,LBND,BCNT)
C
C       THIS SUBROUTINE LOOKS AROUND A NODE AND COUNTS THE
C       BONDS POINTING TO OR FROM THE NODE - INPUT IS IX, IY
C       THE X AND Y COORDINATES OF THE NODE - OUTPUT IS BCNT
C       THE COUNT OF BONDS POINTING TO OR FROM THE NODE AND
C       LBND(1-8), WHICH IS SET TO 1 FOR THOSE LOCATIONS WHICH
C       HAVE EXISTING BONDS - I E - LBND(1) IS SET IF THE CELL
C       WHICH WOULD BE OCCUPIED BY ENTERING A DIR=1 BOND FROM
C       THE NODE CURRENTLY CONTAINS A BOND OF DIRECTION 1 OR 5
C
        SUBROUTINE LOCBND(IX,IY,BCNT)
        IMPLICIT INTEGER*2 (A-Z)
        INTEGER*4 MM
        INTEGER*2 CBOND(8)
        COMMON /RINGY/ LBND(8,2),TSBOND(8),RHBIT(10),LAP(40,3),
     *      RINGS(16,2),RINGO(16,2)
        COMMON /STRPIX/ LPIX,MM(90,38),LBLEN,LNGBND(100,5)
        DATA CBOND /8,1,2,7,3,6,5,4/
C
C Zero LBND
C
        DO 10 I=1,8
        DO 10 J=1,2
10      LBND(I,J)=0
9999    INDEX=1
C
C See if location contains a bond pointing to or from the node
C
        DO 11 J = -1,1
        DO 11 I=-1,1
C
C Skip node position
C
        IF (I .EQ. 0 .AND. J .EQ. 0) GO TO 11
        KAR = LMM(IX+I,IY+J)
C
C Consider case of 2 letter element code
C
        IF (I .EQ. 1 .AND. J .EQ. 0   .AND.
     1  (MM(IX+I,IY+J) .GE. 97 .AND. MM(IX+I,IY+J).LE.122))
     2  KAR = LMM(IX+I+1, IY+J)
C
C See if KAR is a bond and if so extract dir
C
        DIR = IDIR(KAR)
C Not a bond - go on
        IF(DIR .EQ. -1) GO TO 9
        IF(MOD(DIR,4).EQ. MOD(CBOND(INDEX),4))
     1  LBND(CBOND(INDEX),1)=CBOND(INDEX)
9       INDEX=INDEX+1
11      CONTINUE
C
C COUNT # OF GOOD BONDS FOUND
C
        BCNT=0
        DO 14 I=1,8
        IF(LBND(I,1) .NE. 0) BCNT=BCNT+1
14      CONTINUE
C
C Compress list - so that bond numbers are at the top on the list
```

```
C and 0's are at the bottom
C
        IF (BCNT .EQ. 0) RETURN
        I=1
        DO 15 J=1,8
        IF(LBND(J,1) .EQ. 0) GO TO 15
        LBND(I,1)=LBND(J,1)
        IF (I .NE. J) LBND(J,1)=0
        I=I+1
15      CONTINUE
        IF (BCNT .EQ. 1) RETURN
C
C Now set up LBND so that LBND(I,1) = first bond of gap
C                         LBND(I,2) = width of gap
C
        DO 16 I=2,BCNT
        LBND(I-1,2)=LBND(I,1)-LBND(I-1,1)
16      CONTINUE
        LBND(BCNT,2)=8-LBND(BCNT,1)+LBND(1,1)
C
        RETURN
        END
C
        SUBROUTINE GETABD(IX,IY,TSCNT)
        IMPLICIT INTEGER*2 (A-Z)
        INTEGER*2 GETB(8,3)
        INTEGER*4 MM
        COMMON /RINGY/ LBND(8,2),TSBOND(8),RHBIT(10),LAP(40,3),
     *      RINGS(16,2),RINGO(16,2)
        COMMON /STRPIX/ LPIX,MM(90,38),LBLEN,LNGBND(100,5)
        DATA GETB /-1,0,0,0,-1,-2,-2,-2,1,1,0,-1,-1,-1,0,1,
     *      5,6,7,8,1,2,3,4/
        DO 100 I=1,8
100     TSBOND(I)=0
        TSCNT=0
        DO 10 I=1,8
        KX=IX+GETB(I,1)
        KY = IY - GETB(I,2)
        K=LMM(KX,KY)
        KBTYPE=K/256
        KBDIR=K-KBTYPE*256
        IF(KBDIR .NE. GETB(I,3)) GO TO 10
        TSCNT=TSCNT+1
        TSBOND(TSCNT)=KBDIR
10      CONTINUE
        RETURN
        END
C
C       SUBROUTINE MAKRNG(RSIZE,RCNT,ENVIRN,FBOND,LARGE,COC,WCHRNG)
C
C       This subroutine will take the raw data in RHBIT and generate
C       a table of ring commands  - RINGS(I,1) will be the actual
C       ring commands - i.e. markers or bond commands - RINGS(I,2)
C       will give the length of the bonds desired - We do not use
C       NLARGE in an automatic way in RINGS because of multiplicative
C       problems in rings or size 3, 5, and 7. We temporarily set NLARGE
C       to 1 and let RINGS(I,2) represent the actual length on the bonds
C       RSIZE = size of ring - i.e. 3 to 8
C       RCNT = length of RINGS table
C       ENVIRN = type of environment -
C                   -1 = We are at an empty 3X3 area
C                    1 = We are at a node
C                    0 = We are at a bond
C       FBOND = direction of first bond of ring
C       LARGE = pseudo NLARGE
        SUBROUTINE MAKRNG(RSIZE,RCNT,ENVIRN,FBOND,LARGE,COC,WCHRNG)
        IMPLICIT INTEGER*2 (A-Z)
        COMMON /HP/IHP
        COMMON /RINGY/ LBND(8,2),TSBOND(8),RHBIT(10),LAP(40,3),
     *      RINGS(16,2),RINGO(16,2)
        DIMENSION TBOND(8)
        DATA TBOND/5,4,3,2,1,8,7,6/
        RCNT = 1
        DO 101 I=1,16
```

```
C Clear RINGS array
            IF (WCHRNG.EQ.1) THEN
                RINGS(I,1)=0
C Default len is 1
                RINGS(I,2)=1
            ELSE
                RINGO(I,1)=0
                RINGO(I,2)=1
            ENDIF
101     CONTINUE
C
C Generate ring definitions - i.e. markers and bonds
C
        I=1
        DO 6 J=1,RSIZE
C Skip first marker if we are doing SPIRO connection at a node
        IF (ENVIRN .EQ. 1 .AND. J .EQ. 1) GO TO 7
C Marker command
        IF (WCHRNG.EQ.1) THEN
            RINGS(I,1)=35
        ELSE
            RINGO(I,1) = 35
        ENDIF
        I=I+1
C Insert raw bond command
7       CONTINUE
        IF (WCHRNG.EQ.1) THEN
            RINGS(I,1)=RHBIT(J)
        ELSE
            RINGO(I,1) = RHBIT(J)
        ENDIF
        I=I+1
6       CONTINUE
C Length of RINGS table
        RCNT=I-1
        IF(ENVIRN .NE. 1) GO TO 40
        RCNT=RCNT+1
        IF (WCHRNG.EQ.1) THEN
            RINGS(RCNT,1)=35
        ELSE
            RINGO(RCNT,1) = 35
        ENDIF
C
C Now start to convert raw bond command to IDENT acceptable
C commands - i.e. 22-31 - and load RINGS(I,2) with bond length
C
40      PIT = 0
        BIT = FBOND
        DO 111 J=1,RCNT
C No work needed for marker command
        IF (WCHRNG.EQ.1) THEN
            IF(RINGS(J,1) .EQ. 35) GO TO 111
        ELSE
            IF (RINGO(J,1).EQ.35) GO TO 111
        ENDIF
        BIT=BIT+COC*PIT
        IF (BIT .EQ. 0) BIT = 8
        IF (BIT .LT. 0) BIT=BIT+8
        IF (BIT .GT. 8) BIT = BIT - 8
        IT=BIT
        IF (IHP .EQ. 1) IT=TBOND(IT)
        IT=IT+21
        IF (IT .GT. 25) IT=IT+2
        IF (WCHRNG.EQ.1) THEN
            PIT=RINGS(J,1)
        ELSE
            PIT = RINGO(J,1)
        ENDIF
        LEN = (PIT+4)/4
        IF(LEN .GT. 1) PIT=PIT-((LEN-1)*4)
        LEN = LEN*LARGE
        IF (WCHRNG.EQ.1) THEN
            RINGS(J,1)=IT
            RINGS(J,2)=LEN
```

```
              ELSE
                  RINGO(J,1) = IT
                  RINGO(J,2) = LEN
              ENDIF
111       CONTINUE
          IF (LARGE .EQ. 1) GO TO 12
          IF (RSIZE .NE. 3 .AND. RSIZE .NE. 5) GO TO 70
C
C Alter longest bond if size is 3 or 5 and LARGE > 1
C
          MAXI = 0
          MAXLEN = 0
          DO 15 I=1,RCNT
              IF (WCHRNG.EQ.1) THEN
                  IF(RINGS(I,2) .LT.  MAXLEN) GO TO 15
                  MAXLEN = RINGS(I,2)
              ELSE
                  IF(RINGO(I,2) .LT.  MAXLEN) GO TO 15
                  MAXLEN = RINGO(I,2)
              ENDIF
              MAXI=I
15        CONTINUE
              IF (WCHRNG.EQ.1) THEN
                  RINGS(MAXI,2)=RINGS(MAXI,2)-(LARGE-1)
              ELSE
                  RINGO(MAXI,2)=RINGO(MAXI,2)-(LARGE-1)
              ENDIF
C
70        IF(RSIZE .NE. 7) GO TO 12
C
C Adjust ring of size 7 if LARGE>1
C
          MAXI=0
          MAXLEN=LARGE
          DO 16 I=1,RCNT
              IF (WCHRNG.EQ.1) THEN
                  IF(RINGS(I,2) .LT. MAXLEN) GO TO 16
                  MAXLEN=RINGS(I,2)
              ELSE
                  IF(RINGO(I,2) .LT. MAXLEN) GO TO 16
                  MAXLEN=RINGO(I,2)
              ENDIF
              MAXI=I
16        CONTINUE
          INDEX = MAXI + 6
          IF (WCHRNG.EQ.1) THEN
          IF (INDEX.GT.RCNT.AND.RINGS(MAXI-2,2).NE.MAXLEN)INDEX=MAXI-6
          IF(INDEX.GT.RCNT.AND.RINGS(MAXI-2,2).EQ.MAXLEN)INDEX=MAXI-8
          RINGS(INDEX,2)=LARGE*2-1
          ELSE
          IF (INDEX.GT.RCNT.AND.RINGO(MAXI-2,2).NE.MAXLEN)INDEX=MAXI-6
          IF(INDEX.GT.RCNT.AND.RINGO(MAXI-2,2).EQ.MAXLEN)INDEX=MAXI-8
          RINGO(INDEX,2)=LARGE*2-1
          ENDIF
12        CONTINUE
          RETURN
          END
C
          SUBROUTINE DRING(SIZE,IX,IY,RMXCUR,LMYCUR,RBOND,TIMES)
          IMPLICIT INTEGER*2 (A-Z)
          INTEGER*2 REALR(4)
          INTEGER*4 IDTPIX,MM
          LOGICAL*2 DUPSTR,BAR,OPNBAR,BONDEL,BONDID
          COMMON /RINGY/ LBOND(8,2),TSBOND(8),RHBIT(10),LAP(40,3),
         *    RINGS(16,2),RINGO(16,2)
          COMMON /MODES/ JBTYPE,ICHAR,IBDIR,IBTYPE,ISMART,MODE,ISKILL,ISP
          COMMON /PARAMS/ JBDIR,NOCHG,LASTN,MCHAR,JCHAR,NLARGE,LEVEL
          COMMON /STRED/ IDTPIX(90,38),LABL(260,2),MRKCHN(260)
          COMMON /STRPIX/ LPIX,MM(90,38),LBLEN,LNGBND(100,5)
          COMMON /CUR/ ICUR
          COMMON /DARK/ OCUR
          COMMON /XRNG/ NORDRW(8,8,2),SOFAR
CXT       BAR is used in conjunction with NOCHG, OPNBAR, and BONDID to
CXT       control bond type determination in relation to default bond types.
          COMMON /BTPDIR/ BAR
```

```
CXT         BONDEL = TRUE indicates a bond has been drawn between 2 nodes so
CXT         subsequent deletion can delete the bond, not a node.
            COMMON /DELBND/ BONDEL
            COMMON /WARN/ ERR
C
            RSIZE = SIZE / 2
            OPNBAR = .TRUE.
            OBTYPE = IBTYPE
C
C           Each ring drawing is recorded to bypass later duplication.
            IF ((TIMES.GT.0).AND.(MOD(RSIZE,2).EQ.0)) THEN
                SOFAR = SOFAR + 1
                L = 0
                DUPSTR = .TRUE.
            ELSE
                DUPSTR = .FALSE.
            ENDIF
C
C           The cursor coordinates are initialized to allow cursor end up
C           at lower right corner node of ring.
            RMXCUR = 1
            LMYCUR = 1
            CALL INITHC(3,3,0)
            OCUR = 0
            OLARGE=NLARGE
            DO 11 I = 1,SIZE
            KAR =RINGS(I,1)
            K=KAR
C
C           The x and y coordinates of the ring being drawn are recorded.
            IF ((DUPSTR).AND.(KAR.EQ.35)) THEN
                L = L + 1
                IF ((MM(IX,IY).NE.46).AND.(MM(IX-1,IY).EQ.46)) THEN
                    NORDRW(SOFAR,L,1) = IX - 1
                ELSE
                    NORDRW(SOFAR,L,1) = IX
                ENDIF
                NORDRW(SOFAR,L,2) = IY
            ENDIF
            IF (KAR.NE.35 .AND.(I.EQ.1.OR.I.EQ.2)) IBTYPE = RBOND
            LEN = RINGS(I,2)
C
C           Test is made for lower rightmost node of ring.
            IF ((KAR.EQ.35).AND.(IX.GE.RMXCUR)) THEN
                IF (IX.GT.RMXCUR) THEN
                    LMYCUR = IY
                ELSE IF (IY.GT.LMYCUR) THEN
                    LMYCUR = IY
                ENDIF
                RMXCUR = IX
            ENDIF
            IF (LEN.LT.0 .AND. KAR.EQ.35) GO TO 111
            IF (LEN .LT. 0) GO TO 15
            IF(KAR .EQ. 35 .AND. MM(IX-1,IY).EQ.46.AND.I.GT.1)GO TO 11
            NLARGE=LEN
C Draw part of ring here
            IF ((KAR.GE.22).AND.(KAR.LE.31)) BONDID = .TRUE.
            CALL IDENT(KAR,IX,IY,INCX,INCY,IRESET)
            RBOND = IBTYPE
            IF (BONDID) THEN
                BONDID = .FALSE.
                OPNBAR = .FALSE.
                NOCHG = 0
            ENDIF
            IF (ERR.EQ.48) THEN
                STPSZE = I
                GO TO 12
            ENDIF
            IF (K .EQ. 35) GO TO 11
            REALR(1)=K
            REALR(2)=IX
            REALR(3)=IY
            REALR(4)=NLARGE
            GO TO 11
 111        BIX=IX
            IF (MM(BIX,IY) .NE.46 .AND. MM(BIX-1,IY).EQ.46)BIX=BIX-1
C WE HAVE INCORPORATED A CHAIN MARKER IN A RING
```

```
            DO 20 JJ=1,260
C DELETE IT FROM THE CHAIN MARKER TEST
            IF (LABL(JJ,1).EQ.0) GO TO 11
            IF (LABL(JJ,1).NE.BIX.OR.LABL(JJ,2).NE.IY) GO TO 20
            MRKCHN(JJ)=0
            GO TO 11
20          CONTINUE
            GO TO 11
C
C           This section retraces an existing bond - Set bondtype
C           so that existing bonds are not changed
C
15          KX=IX
            KY=IY
            IF(MM(KX,KY).NE.46 .AND. MM(KX-1,KY).EQ.46)KX=KX-1
            IBND=KAR
            CALL DELTA(IBND,INCX,INCY)
C Get existing bond
            OBND=LMM(KX+INCX,KY+INCY)
            OBND=OBND/256
            KBOND=IBTYPE
CXT
            IBTYPE = OBND
            NOCHG = 1
            BAR = .FALSE.
            CALL IDENT(KAR,IX,IY,INCX,INCY,IRESET)
C Restore bond type
            IBTYPE=KBOND
            IF (OPNBAR) THEN
               BAR = .TRUE.
            ELSE
               NOCHG = 0
            ENDIF
            IF (ERR.EQ.48) THEN
               STPSZE = I
               GO TO 12
            ENDIF
11          CONTINUE
12          CONTINUE
C SUPPRESS CURSOR DISPLAY WHEN DRAWING RING
            ICUR=0
            RBOND=IBTYPE
            IF (IBTYPE .EQ. 2 .OR. IBTYPE .EQ. 3 .OR. IBTYPE.EQ.5
        1      .OR. IBTYPE .EQ. 6 .OR. IBTYPE .EQ. 7) RBOND=1
            NLARGE=OLARGE
C           THE FOLLOWING CODE IS USED FOR ALTERNATING BONDS
C           IT SOMETIMES HAPPENS THAT 2 DOUBLE BONDS ARE
C           DRAWN TOGETHER - PARTICULARLY WHEN RINGS ARE
C           FUSED - THIS CODE EXAMINES THE LAST BOND DRAWN
C           IF IT IS A DOUBLE BOND - IT EXAMINES THE OTHER
C           BONDS AROUND THE NODE AND CHANGES THE LAST DRAWN
C           BOND TO SINGLE IF - 1 THERE IS ANOTHER DOUBLE
C           BOND FROM THAT NODE - OR 2 THE TOTAL BOND
C           COUNT EXCEEDS 4
            IF (IBTYPE .NE. 4) THEN
               OCUR = 1
               CALL INITHC(3,3,OCUR)
               ICUR = 1
               IF (ERR.EQ.48) THEN
                  SIZE = STPSZE - 1
                  CALL CURSOR(IX,IY)
               ELSE
                  CALL CURSOR(RMXCUR,LMYCUR)
               ENDIF
               IBTYPE = OBTYPE
               RETURN
            ENDIF
            NBOND=REALR(1)
            R1 = REALR(1)
            CALL DELTA(R1,INCX,INCY)
            REALR(1) = R1
            JX=REALR(2)-1-INCX
            JY=REALR(3)-INCY
C IS THE LAST BOND A DOUBLE BOND
            MMM=LMM(JX,JY)/256
```

```
C NO - RETURN - NO PROBLEM
        IF (MMM.EQ.1) THEN
            OCUR = 1
            CALL INITHC(3,3,OCUR)
            ICUR = 1
            CALL CURSOR(RMXCUR,LMYCUR)
            RETURN
        ENDIF
        MX=REALR(2)-1
C GET BONDS AROUND NODE
        R2 = REALR(3)
        CALL LOCBND(MX,R2,BCNT)
        REALR(3) = R2
C ONLY ONE BOND - NO PROBLEM
        IF (BNCT .EQ. 1) THEN
            OCUR = 1
            CALL INITHC(3,3,OCUR)
            ICUR = 1
            CALL CURSOR(RMXCUR,LMYCUR)
            RETURN
        ENDIF
        IDOB=0
        CNT=0
        MY=REALR(3)
        DO 40 I=1,BCNT
        DIR=LBOND(I,1)
        CALL DELTA(DIR,INCX,INCY)
        MMM=LMM(MX+INCX,MY+INCY)/256
        IF (MMM .EQ. 2) IDOB=IDOB+1
        IF (MMM .GT. 3) MMM=1
        CNT=CNT+MMM
40      CONTINUE
        DO 400 I=0,2,2
        DO 4141 J=1,100
        IF (LNGBND(J,I+1) .EQ. 0) GO TO 400
        IF ((LNGBND(J,I+1) .NE. MX) .OR.
     1  (LNGBND(J,I+2) .NE. MY)) GO TO 4141
        MMM=LNGBND(J,5)
        IF (MMM .EQ. 2 ) IDOB=IDOB+1
        IF (MMM .GT. 3) MMM=1
        CNT=CNT+MMM
        GO TO 444
4141    CONTINUE
400     CONTINUE
444     IF (IDOB .LE.1 .AND. CNT .LE.4) THEN
            OCUR = 1
            CALL INITHC(3,3,OCUR)
            ICUR = 1
            CALL CURSOR(RMXCUR,LMYCUR)
            RETURN
        ENDIF
        DIR=REALR(1)+4
        IF (DIR .GT. 8) DIR = DIR -8
        DIR=DIR+21
        IF (DIR .GT. 25) DIR = DIR + 2
C REPLACE BOND
        R1 = REALR(2)
        R2 = REALR(3)
        CALL IDENT(DIR,R1,R2,INCX,INCY,IRESET)
        IBTYPE=1
        CALL IDENT(NBOND,R1,R2,INCX,INCY,IRESET)
        NOCHG = 0
        REALR(2) = R1
        REALR(3) = R2
        IBTYPE=4
        OCUR = 1
        CALL INITHC(3,3,OCUR)
        ICUR = 1
        CALL CURSOR(RMXCUR,LMYCUR)
        RETURN
        END
C
C       SUBROUTINE RNGDEL(RINGS,RCNT,IX,IY)
C
C       THIS SUBROUTINE DELETES A RING - INPUT IS THE ARRAY RINGS
C       WHICH CONTAINS THE RING GENERATING COMMAND - AND IX AND IY
```

```
C         WHICH ARE THE COORDINATES OF THE STARTING POINT FOR THE RING
C         RCNT = # OF COMMANDS IN RINGS
C
          SUBROUTINE RNGDEL(RCNT,IX,IY)
          IMPLICIT INTEGER*2 (A-Z)
          INTEGER*4 MM
          LOGICAL*2 BONDEL
          COMMON /RINGY/ LBND(8,2),TSBOND(8),RHBIT(10),LAP(40,3),
     *       RINGS(16,2),RINGO(16,2)
          COMMON /MODES/ JBTYPE,ICHAR,IBDIR,IBTYPE,ISMART,MODE,ISKILL,ISP
          COMMON /PARAMS/ JBDIR,NOCHG,LASTN,MCHAR,JCHAR,NLARGE,LEVEL
          COMMON /STRPIX/ LPIX,MM(90,38),LBLEN,LNGBND(100,5)
          COMMON /CUR/ ICUR
          COMMON /WARN/ ERR
          COMMON /DELBND/ BONDEL
          ICUR=0
          ITYPE=0
          IF (IBTYPE .EQ. 4) ITYPE=1
          KX=IX
C INITIAL COORDINATES
          KY=IY
          DO 100 I=RCNT,1,-1
C GET COMMAND
          COM=RINGS(I,1)
          C=COM
C GO TO 200 FOR MARKER
          IF (COM .EQ. 35) GO TO 200
          IF (MM(KX,KY).NE.46 .AND. MM(KX-1,KY).EQ.46 .AND.
     *       (ERR.NE.48 .OR. I.NE.RCNT)) KX=KX-1
C GET READY TO DEL BOND
          JCHAR=1
          BOND=COM
C GET DELTAS FOR BOND
          CALL DELTA(BOND,INCX,INCY)
          JBTYPE=IBTYPE
C SET BOND DIR
          IBDIR=BOND
          JBDIR=IBDIR
C IF NEG - SKIP BOND DEL
          IF ((RINGS(I,2).LT.0).OR.(IBTYPE.EQ.0)) GO TO 300
C AND JUST SLIDE ALONG BOND TO NODE
C DEL BOND
          CALL DEL(COM,KX,KY,INCX,INCY,0)
          GO TO 100
300       LEN = IABS(RINGS(I,2))
          DO 400 K=1,LEN+1
          KX=KX-INCX
          KY=KY-INCY
400       CONTINUE
          GO TO 100
C IF NEG - SKIP DEL MARKER COMMAND
200       IF (RINGS(I,2) .LT. 0) GO TO 100
          JCHAR=2
C MOVE CURSOR JUST TO LEFT OF MARKER
          IF (MM(KX,KY).EQ. 46)KX=KX+1
          BONDEL = .FALSE.
          CALL DEL(COM,KX,KY,INCX,INCY,0)
100       CONTINUE
          IF (ICHAR .LE. 10) MCHAR=COM
          IF (ICHAR .LE. 10) JCHAR=ICHAR
C Reset to 4 if we entered with bondtype = 4
          IF (ITYPE .EQ. 1) IBTYPE=4
          JBTYPE=IBTYPE
          JBDIR=IBDIR
          ICUR=1
          CALL CURSOR(IX,IY)
          RETURN
          END
C
C
          SUBROUTINE LOOK(IX,IY,ICHECK,IBADX,IBADY,LAP,LCNT,BLOB)
C
C
          THIS SUBROUTINE CHECKS A 3 x 3 CELL CENTERED AT IX & IY
C
C         ICHECK = 0      THAT IS OK - IF
C
C                                     1. THE MM SUBSCRIPTS ARE GOOD
```

```
C                                    2. THE CELL IS EMPTY - OR - THE
C                                       OVERLAPS ARE VALID OVERLAPS
C                                       FOUND IN THE LAP TABLE
C       ICHECK NOT = 0 MEANS THAT BAD CONFLICTS AROSE
C
        SUBROUTINE LOOK(IX,IY,ICHECK,LCNT,BLOB)
        IMPLICIT INTEGER*2 (A-Z)
        COMMON /RINGY/ LBND(8,2),TSBOND(8),RHBIT(10),LAP(40,3),
     *      RINGS(16,2),RINGO(16,2)
        COMMON /BAD/ IBADX(9),IBADY(9)
        COMMON /FUSE/ ITIMES
C Cell is OK until proven otherwise
        ICHECK=0
C Check MM subscritps
        CALL CHECK(IX,IY,ICHECK)
C Bad subscripts - set error and return
777     IF (ICHECK .EQ.1) GO TO 10
C Space is empty - go check surrounding area
        WHAT=LMM(IX,IY)
        IF (WHAT .EQ. 0) GO TO 800
        IF (WHAT .EQ. 46 .AND. BLOB .EQ. 35) GO TO 856
        W=IABS(MOD(WHAT,256)-BLOB)
        IF (W .EQ. 0 .OR. W .EQ. 4) GO TO 856
        GO TO 851
C Novalid overlaps - set error and exit
856     IF (LCNT .EQ. 0) GO TO 10
        DO 850 I=1,LCNT
        IF (LAP(I,1) .EQ. IX .AND. LAP(I,2).EQ.IY) LAP(I,3)=1
        IF (LAP(I,1).EQ. IX .AND. LAP(I,2).EQ.IY) BLOB=-1
        IF(LAP(I,1) .EQ. IX .AND. LAP(I,2) .EQ.IY) GO TO 855
850     CONTINUE
C OK IS 2 OR MORE SIDES TO BE FUSED
        IF (ITIMES .NE. 2) GO TO 851
        IF (LCNT.GE.40) GO TO 851
        BLOB=-1
        LCNT=LCNT+1
        LAP(LCNT,1)=IX
        LAP(LCNT,2)=IY
        LAP(LCNT,3)=1
        GO TO 855
C Center of cell ocupied by valid overlap - no need to check further
851     ICHECK=1
855     CONTINUE
        RETURN
800     IF(ITIMES .EQ. 2)  RETURN
        CALL CELL(IX,IY,ICHECK)
C No problem - good cell - ICHECK=0 and return
        IF (ICHECK.EQ.0) RETURN
        DO 982 I=1,ICHECK
        DO 980  J=1,LCNT
        IF(IBADX(I).EQ.LAP(J,1) .AND. IBADY(I) .EQ. LAP(J,2)) GO TO 982
980     CONTINUE
C Overlap was not in LAP table
        BX = IBADX(I)
        BY = IBADY(I)
        A = LMM(BX,BY)
C Was it a legal overlap - i.e.
C bond - not pointing to cell
C or cell would contain bond
C and overlap is marker and cell bond
C does not pointer to marker
C A = contents of offending cell
        IF (BLOB .EQ. 35) GO TO 20
C A is a bond - is it an OK bond
        IF (A .GE. 256) GO TO 11
C A is not a bond or marker - can't be any good
        IF (A .NE. 46) GO TO 10
        B=BLOB
C       Cell will contain bond - does it point to marker
        CALL DELTA(B,INCX,INCY)
C If bond points to marker - it is no good
        IF (((IBADX(I).EQ.(IX+INCX)).AND.(IBADY(I).EQ.(IY+INCY)))
     1  .OR. ((IBADX(I).EQ. (IX-INCX)).AND.(IBADY(I).EQ.(IY-INCY))))
```

```
       2  GO TO 10
C If not - it is OK
          GO TO 982
C Not a bond - can't be OK
20        IF (A .LT. 256) GO TO 10
C Get bond direction
11        B=IDIR(A)
C Get bond deltas
          CALL DELTA(B,INCX,INCY)
          IF((((IBADX(I)+INCX).EQ. IX) .AND.((IBADY(I)+INCY).EQ.IY))
     1    .OR. (((IBADX(I)-INCX).EQ.IX).AND.((IBADY(I)-INCY).EQ.IY)))
     2    GO TO 10
C If it point to bond or marker - it is no good
982       CONTINUE
C Overlap was valid - cell OK
          ICHECK=0
C Valid overlap - return
          RETURN
10        ICHECK=1
C Bad overlap - return with error set
          RETURN
          END
C
C         SUBROUTINE MBIT(RSIZE,RHBIT)
C
C         THIS SUBROUTINE FILLS THE RHBIT ARRAY STARTING WITH CAN(SR,RSIZE)
          SUBROUTINE MBIT(RSIZE)
          IMPLICIT INTEGER*2 (A-Z)
          COMMON /RINGY/ LBND(8,2),TSBOND(8),RHBIT(10),LAP(40,3),
     *    RINGS(16,2),RINGO(16,2)
          COMMON /RCAN/ CAN(10,10)
          RSIZ=RSIZE
          IF (RSIZE .EQ. 9) RSIZ=3
          IF (RSIZE .EQ. 10) RSIZ = 5
          DO 450 K=1,RSIZ
          RHBIT(K)= CAN(K,RSIZE)
450       CONTINUE
          RETURN
          END
C
          SUBROUTINE DELTA(BOND,INCX,INCY)
          IMPLICIT INTEGER*2 (A-Z)
          COMMON/ITERM/ITER
          IF (BOND .LE. 8) GO TO 10
          BOND=BOND-21
          IF(BOND .GT. 4) BOND=BOND-2
C DETERMINE DELTA X AND DELTA Y
10        INCY = -1  * ITER
C
          IF ((BOND.GE.4).AND.(BOND.LE.6)) INCY = 1 *ITER
          IF(MOD(BOND,4) .EQ. 3) INCY = 0
          INCX=1
          IF ((BOND.GE.6) .AND.(BOND .LE.8)) INCX=-1
          IF(MOD(BOND,4) .EQ. 1) INCX=0
          RETURN
          END
C
C         SUBROUTINE MKBND(FBOND)
C
C         THIS SUBROUTINE CONVERTS A BOND DIRECTION (1-8) TO A
C         BOND COMMAND (22-25;28-31)
C
          SUBROUTINE MKBND(FBOND)
          IMPLICIT INTEGER*2 (A-Z)
          FBOND=FBOND+21
          IF (FBOND .GT. 25) FBOND=FBOND+2
          RETURN
          END
C         SUBROUTINE NEW sees if the chain is starting with a new structure.
          SUBROUTINE NEW(SUM,IX,IY)
          IMPLICIT INTEGER*2 (A-Z)
          INTEGER*4 MM
          COMMON /STRPIX/ LPIX,MM(90,38),LBLEN,LNGBND(100,5)
          SUM=0
          DO 10 I=-1,1
```

```
              DO 10 J=-1,1
              SUM=SUM + LMM(IX+I, IY+J)
10            CONTINUE
              RETURN
              END
C
C             SUBROUTINE FINDB finds a correct pointer bond.
              SUBROUTINE FINDB(IBDIR,KBDIR,IX,IY)
              IMPLICIT INTEGER*2 (A-Z)
              INTEGER*4 MM
              LOGICAL*2 CHEK67
              COMMON /STRPIX/ LPIX,MM(90,38),LBLEN,LNGBND(100,5)
              COMMON /XBOND/ GOODB(2,9)
              CHEK67 = .TRUE.
              IB=0
              DO 24 J = -1,1
              DO 24 I=-1,1
              IB=IB+1
              KX=IX+I
              KY=IY+J
CIF NOT BOND - SKIP THIS ONE
              IF (LMM(KX,KY) .LT. 256) GO TO 24
              KBTYPE=LMM(KX,KY)/256
              KBDIR=LMM(KX,KY) - KBTYPE*256
21            IF (KBDIR .EQ. GOODB(1,IB)) GO TO 26
              IF ((KBTYPE.EQ.6).OR.(KBTYPE.EQ.7)) THEN
                  IF (CHEK67) THEN
                      KBDIR = KBDIR + 4
                      IF (KBDIR.GT.8) KBDIR = KBDIR - 8
                      CHEK67 = .FALSE.
                      GO TO 21
                  ELSE
                      CHEK67 = .TRUE.
                  ENDIF
              ENDIF
24            CONTINUE
CWE DID NOT FIND A BOND - SET BOND
              IBDIR=-1
CDIRECTION TO -1 AND RETURN
              RETURN
CFOUND GOOD POINTER BOND
26            IBDIR=GOODB(2,IB)
              RETURN
              END
C
C             CNTBND counts the number of bonds of a node.
C
              SUBROUTINE CNTBND(ICNT,IX,IY)
              IMPLICIT INTEGER*2 (A-Z)
              INTEGER*4 MM
              COMMON /STRPIX/ LPIX,MM(90,38),LBLEN,LNGBND(100,5)
              ICNT=0
              DO 24 J=1,-1,-1
              DO 24 I=-1,1
              KX=IX+I
              KY=IY+J
              IF((I.EQ.1) .AND. (J.EQ.0) .AND.
     1        (MM(KX,KY).GE.97 .AND. MM(KX,KY).LE. 122))KX=KX+1
              IF (LMM(KX,KY).LT.256) GO TO 24
              ICNT=ICNT+1
24            CONTINUE
              RETURN
              END
C
              SUBROUTINE CHECK(IX,IY,ICHECK)
              IMPLICIT INTEGER*2 (A-Z)
              COMMON /CD/ MAXX,MAXY
              ICHECK=0
C             CHECK=0 IMPLIES INDICIES ARE OK. CHECK=1 IMPLIES INDICIES ARE BAD.
              IF(IX .LE. 0 .OR. IX .GT. MAXX .OR.
     1        IY .LE. 0 .OR. IY .GT. MAXY) ICHECK=1
              RETURN
              END
C
```

```fortran
      SUBROUTINE SHARP(IBDIR,IX,IY,ISHARP)
      IMPLICIT INTEGER*2 (A-Z)
      INTEGER*2 WHERE(8,4)
      INTEGER*4 MM
      COMMON /STRPIX/LPIX,MM(90,38),LBLEN,LNGBND(100,5)
      DATA WHERE /-1,-1,0,0,-1,0,0,1,0,0,1,1,0,1,1,0,
     *    1,0,0,-1,1,1,0,0,0,-1,-1,0,0,0,-1,-1/
      ISHARP=0
      INBOND=IBDIR
      CALL DELTA(INBOND,KNCX,KNCY)
      KX=IX+KNCX
      KY=IY+KNCY
      WX = KX + WHERE(INBOND,1)
      WY = KY - WHERE(INBOND,2)
      K = LMM(WX,WY)
      IF(K.LT.256) GO TO 24
      GO TO 26
C
24    CONTINUE
      WX = KX + WHERE(INBOND,3)
      WY = KY - WHERE(INBOND,4)
      K = LMM(WX,WY)
      IF (K .LT. 256) GO TO 27
      GO TO 26
27    CONTINUE
      RETURN
26    CONTINUE
      ISHARP=1
      RETURN
      END
C
      SUBROUTINE GETBD(IX,IY,KBDIR,KX,KY)
      IMPLICIT INTEGER*2 (A-Z)
      INTEGER*4 MM
      COMMON /STRPIX/ LPIX,MM(90,38),LBLEN,LNGBND(100,5)
      DIMENSION GETB(8,3)
      DATA GETB /-1,0,0,0,-1,-2,-2,-2,1,1,0,-1,-1,-1,0,1,
     *    5,6,7,8,1,2,3,4/
      DO 10 I=1,8
      KX=IX+GETB(I,1)
      KY = IY - GETB(I,2)
      K=LMM(KX,KY)
      KBTYPE=K/256
      KBDIR=K-KBTYPE*256
      IF(KBDIR .NE. GETB(I,3)) GO TO 10
      RETURN
10    CONTINUE
      KBDIR=-1
      END
$STORAGE:2
C
C     SUBROUTINE SITE(IX,IY,ACHAR,BCHAR,TER,ICNT)
C     ACHAR=PRIMARY TERMINATOR CHAR
C     BCHAR=ALTERNATE TERMINATOR CHAR
C     TER=TERMINATOR CHARACTER ACTUALLY RECEIVED
C     This subroutine obtains the connecting or exiting site
C     It should be a marker or a bond end
C     The type of site is not checked in this subroutine - it
C     is checked back in LIBRA
      SUBROUTINE SITE(IX,IY,ACHAR,BCHAR,TER,ICNT,REST)
      IMPLICIT INTEGER*2(A-Z)
      INTEGER*4 MM
      CHARACTER*1 HLO(3)
      CHARACTER*3 HLOE
      EQUIVALENCE (HLOE,HLO(1))
      COMMON /ISTATE/ ISTAT
      CHARACTER*1 ISTAT
      COMMON /HEAD/ MW(12),ISTATE,PAGE
      COMMON /STRPIX/ LPIX,MM(90,38),LBLEN,LNGBND(100,5)
      COMMON /MODES/ JBTYPE,ICHAR,IBDIR,IBTYPE,ISMART,MODE,ISKILL,ISP
      COMMON /CHARS/IES, IDOT,ITAG,JUMP,LBOND,KAN,ISPACE
      OKAR=97
C Set last char to lc
      KAR=13
      IRESET = 0
```

```
100     CALL INPUTX(IKAR,IX,IY)
        IF (IKAR.EQ.95) THEN
           IERR = 39
           CALL MYERR(IERR,IERR,IERR)
           GO TO 100
        ELSE IF (IKAR.EQ.131) THEN
           REST = IKAR
           RETURN
        ELSE IF ((REST.EQ.1).AND.(IKAR.NE.69).AND.(IKAR.NE.83).AND.
     *     (IKAR.NE.13)) THEN
           CALL FTSIZE(2,18)
           CALL FTLOCA(6,1)
           CALL FTEXT('^Move cursor to connecting site - Type E to finalize
     * position^')
        ELSE IF ((REST.EQ.2).AND.(IKAR.NE.83).AND.(IKAR.NE.13)) THEN
           CALL FTSIZE(2,18)
           CALL FTLOCA(6,1)
           CALL FTEXT('^Move cursor to exit site - Type S to finalize posit
     *ion       ^')
        ENDIF
        PAGE = 0
        CALL FTSIZE(1,10)
        IIKAR=IKAR
C       Save char before call to IDENT because IDENT
C       may change char
C       Marker preceeded by marker or DEL = OK
        IF ((IKAR .GE. 97 .AND. IKAR .LE. 122) .AND. ((OKAR .GE. 97
     1  .AND. OKAR .LE. 122) .OR. OKAR .EQ. 127)) GO TO 1000
        IF (IKAR .GE. 48 .AND. IKAR .LE. 56) GO TO 1000
C Set bond type cmd = OK
        IF (IKAR.EQ.127.AND. (OKAR .GE. 22 .AND.OKAR .LE. 31)) GO TO 1000
C DEL preceeded by bond = OK
        IF (IKAR.GE.21 .AND. IKAR.LE.31) GO TO 1000
C Bond cmd = OK
        IF (IKAR.EQ.ACHAR.OR.IKAR .EQ. BCHAR .OR. IKAR .EQ. 13) GO TO 500
C Terminator = ACHAR or BCHAR or CR = OK = EXIT
        ICNT= ICNT+1
        CALL FTSIZE(2,18)
        CALL FTLOCA(4,1)
        CALL FTEXT('^Invalid response: ^')
        HLO(2) = CHAR(IKAR)
        CALL FTEXT(HLOE)
        CALL FTEXT('^       Enter bond, bond type, DEL(bond) or terminator
     *^')
        CALL FTSIZE(1,10)
        PAGE = 0
        GO TO 100
1000    CALL IDENT(IKAR,IX,IY,INCX,INCY,IRESET)
        IF (IKAR.EQ.21) THEN
        IF ((REST.EQ.1).AND.(IKAR.NE.69).AND.(IKAR.NE.83).AND.
     *     (IKAR.NE.13)) THEN
           CALL FTSIZE(2,18)
           CALL FTLOCA(6,1)
           CALL FTEXT('^Move cursor to connecting site - Type E to finalize
     * position^')
        ELSE IF ((REST.EQ.2).AND.(IKAR.NE.83).AND.(IKAR.NE.13)) THEN
           CALL FTSIZE(2,18)
           CALL FTLOCA(6,1)
           CALL FTEXT('^Move cursor to exit site - Type S to finalize posit
     *ion       ^')
        ENDIF
        PAGE = 0
        CALL FTSIZE(1,10)
        ENDIF
        ISTATE = 11
        CALL HEADER
        OKAR=IIKAR
C Save last command
        GO TO 100
C Go get next command
500     TER=IKAR
        IF (OKAR .GE. 48 .AND. OKAR .LE. 56)
     1  CALL IDENT(KAR,IX,IY,INCX,INCY,IRESET)
C We had an incomplete bond type - bond cycle
C Terminate it with CR
        RETURN
```

```
      END
C
C     THIS SUBROUTINE CONVERTS LUHN DOTS TO NON-CHAIN MARKERS
C     AND CHx'S TO CHAIN MARKERS
C
      SUBROUTINE REMARK(IERR)
      IMPLICIT INTEGER*2 (A-Z)
      INTEGER*4 MM,IDTPIX
      COMMON /STRPIX/ LPIX,MM(90,38),LBLEN,LNGBND(100,5)
      COMMON /PARAMS/ JBDIR,NOCHG,LASTN,MCHAR,JCHAR,NLARGE,LEVEL
      COMMON /MODES/ JBTYPE,ICHAR,IBDIR,IBTYPE,ISMART,MODE,ISKILL,ISP
      COMMON /LABELS/ NR,NJLAST,NJNEXT
      COMMON /STRED/ IDTPIX(90,38),LABL(260,2),MRKCHN(260)
      COMMON /RANGE/ LOX,HIX,LOY,HIY
      COMMON /CD/ MAXX,MAXY
C
C     ZERO MARKER ARRAYS AND POINTER NJNEXT AND ERROR FLAG IERR
C
      IERR=0
C     DEFAULT VALUE - 0 IMPLIES NO ERROR
      NJNEXT=0
      DO 50 I=1,260
         LABL(I,1)=0
         LABL(I,2)=0
         MRKCHN(I)=0
50    CONTINUE
C
C     GO THROUGH THE MM ARRAY - CHANGE LUHN DOTS (46) TO NON-CHAIN
C     MARKERS AND CHx'S TO CHAIN MARKERS
C
      DO 100 I = LOX,HIX
      DO 100 J = LOY,HIY
         IF (MM(I,J) .EQ. 46) GO TO 60
         IF (MM(I,J).NE.67 .OR. (MM(I,J).EQ.67 .AND. (MM(I+1,J).GE.
     1      97.AND.MM(I+1,J).LE.122))) GO TO 100
C
C     CLEAR HYDROGENS AROUND CARBON
C     DELETE CARBON - INSERT MARKER - MARK MARKER AS CHAIN MARKER
C
         DO 1444 K = 1,MAXX
            IF ((MM(I-K,J).EQ.0).OR.(LMM(I-K,J).GE.256).OR.
     *         (I-K.LE.0)) THEN
               GO TO 1445
            ELSE IF (MM(I-K,J).EQ.42) THEN
               GO TO 100
            ENDIF
1444     CONTINUE
1445     CONTINUE
      NJNEXT=NJNEXT+1
      IF (NJNEXT .GT. 260) GO TO 99
      II=I
      JJ = J
      CALL CLEARH(1,II,JJ)
      MM(I,J)=46
      LABL(NJNEXT,1)=I
      LABL(NJNEXT,2)=J
      MRKCHN(NJNEXT)=1
      GO TO 100
C
C     DELETE LUHN DOT AND ENTER MARKER HERE
C
60    NJNEXT=NJNEXT+1
      IF (NJNEXT .GT. 260) GO TO 99
C     HAVE WE RUN OUT OF MARKERS?
      LABL(NJNEXT,1)=I
      LABL(NJNEXT,2)=J
100   CONTINUE
      RETURN
99    IERR=16
      CALL MYERR(IERR,IERR,IERR)
      RETURN
      END
C
      SUBROUTINE CLEARH(WHICH,KX,KY)
      IMPLICIT INTEGER*2 (A-Z)
```

```
      INTEGER*4 MM,IDTPIX
      COMMON /CHARS/IES, IDOT,ITAG,JUMP,LBOND,KAN,ISPACE
      COMMON /STRPIX/ LPIX,MM(90,38),LBLEN,LNGBND(100,5)
      COMMON /STRED/ IDTPIX(90,38),LABL(260,2),MRKCHN(260)
C This subroutine clears valence hydrogens from the vicinity of nodes
C and extends bonds as needed, before re-calculation of valences.
C This is a simplified version of CLRHYD - It changes the MM array
C but it does not change the screen
C
C       Most of this code is lifted from CLRHYD
C
      IF (WHICH.EQ.1) THEN
1     IF (MM(KX-1,KY) .EQ. 46) RETURN
C     DO NOTHING IF AT A MARKER OR DOT
C     First look right for H's & subscripts & eliminate them:
      INC=1
C     Increment for looking across for H & subscripts
      MBOND=0
      IF ((MM(KX+1,KY).GE.97).AND.(MM(KX+1,KY).LE.122)) INC=2
C     2 let element
      IF (MM(KX+INC,KY).NE.72) GOTO 40
      MBOND = MAX0(MOD(MM(KX+INC+1,KY),2**13),MOD(MM(KX+INC+2,KY),
     *   2**13))
C Bond on rt of H
      LBLOB=MOD(MBOND,256)
      IF (LBLOB .NE. 3 .AND. LBLOB .NE. 7) MBOND=0
      MM(KX+INC,KY)=MBOND
C     Reinstall bond
      IF ((MM(KX+INC+1,KY).LT.50).OR.(MM(KX+INC+1,KY).GT.57))
     *   GO TO 43
      CALL CURSOR(KX+INC+1,KY)
      MM(KX+INC+1,KY)=MBOND
      GOTO 43
C     Here completh undrawing H's & subscripts on right
C     Now look on left for H & subscripts:
40    MBOND=0
      DO 42 INC=-3,-1
C     Look left for H, subscript, MBOND to copy
      IF ((MM(KX-1,KY).LT.50) .OR. (MM(KX-1,KY).GT.72)) GOTO 43
      IF (MOD(MM(KX+INC,KY),2**13).GT.256)
     *   MBOND = MOD(MM(KX+INC,KY),2**13)
      IF (MM(KX+INC,KY).NE.72) GOTO 42
      LBLOB = MOD(MBOND,256)
      IF (LBLOB.NE.3 .AND. LBLOB.NE.7) MBOND=0
      MM(KX+INC,KY)=MBOND
C     Replace H with bond
C     Look for number to right of H, on left of node
      IF ((MM(KX+INC+1,KY).LT.50) .OR. (MM(KX+INC+1,KY).GT.57))
2    *   GOTO 43
C     If No number, skip out of loop: done here
      MM(KX+INC+1,KY)=MBOND
42    CONTINUE
43    CONTINUE
C     At this point, filler H's are removed
C
C     Look above and below to remove H's.
      DO 50 I = -1,1,2
         FY = KY + I
         IF (MM(KX,FY).EQ.72) THEN
            MM(KX,FY) = 0
            FX = KX + 1
            IF ((MM(FX,FY).GE.50).AND.(MM(FX,FY).LE.57))
     *         MM(FX,FY) = 0
            MBOND = LMM(KX,FY+I)
            IF ((MBOND.GE.256).AND.(MOD(IDIR(MBOND),4).EQ.1))
     *         MM(KX,FY) = MBOND
         ENDIF
50    CONTINUE
      RETURN
C
      ELSE
101   IF (IDTPIX(KX-1,KY) .EQ. 46) RETURN
C     DO NOTHING IF AT A MARKER OR DOT
C     First look right for H's & subscripts & eliminate them:
      INC=1
C     Increment for looking across for H & subscripts
      MBOND=0
```

```
          IF ((IDTPIX(KX+1,KY).GE.97).AND.(IDTPIX(KX+1,KY).LE.122)) INC=2
C         2 let element
          IF (IDTPIX(KX+INC,KY).NE.72) GOTO 140
          MBOND = MAX0(MOD(IDTPIX(KX+INC+1,KY),2**13),
        *      MOD(IDTPIX(KX+INC+2,KY),2**13))
C Bond on rt of H
          LBLOB=MOD(MBOND,256)
          IF (LBLOB .NE. 3 .AND. LBLOB .NE. 7) MBOND=0
          IDTPIX(KX+INC,KY)=MBOND
C         Reinstall bond
          IF ((IDTPIX(KX+INC+1,KY).LT.50).OR.(IDTPIX(KX+INC+1,KY).GT.57))
        *    GO TO 143
          CALL CURSOR(KX+INC+1,KY)
          IDTPIX(KX+INC+1,KY)=MBOND
          GOTO 143
C         Here completh undrawing H's & subscripts on right
C         Now look on left for H & subscripts:
140       MBOND=0
          DO 142 INC=-3,-1
C         Look left for H, subscript, MBOND to copy
          IF ((IDTPIX(KX-1,KY).LT.50) .OR. (IDTPIX(KX-1,KY).GT.72))
        *     GO TO 143
          IF (MOD(IDTPIX(KX+INC,KY),2**13).GT.256)
        *      MBOND = MOD(IDTPIX(KX+INC,KY),2**13)
          IF (IDTPIX(KX+INC,KY).NE.72) GO TO 142
          LBLOB = MOD(MBOND,256)
          IF (LBLOB.NE.3 .AND. LBLOB.NE.7) MBOND=0
          IDTPIX(KX+INC,KY)=MBOND
C         Replace H with bond
C         Look for number to right of H, on left of node
          IF ((IDTPIX(KX+INC+1,KY).LT.50).OR.(IDTPIX(KX+INC+1,KY).GT.57))
        2    GO TO 143
C         If No number, skip out of loop: done here
          IDTPIX(KX+INC+1,KY) = MBOND
142       CONTINUE
C         At this point, filler H's are removed
143       CONTINUE
C
C         Look above and below to remove H's.
          DO 150 I = -1,1,2
             FY = KY + I
             IF (IDTPIX(KX,FY).EQ.72) THEN
                IDTPIX(KX,FY) = 0
                FX = KX + 1
                IF ((IDTPIX(FX,FY).GE.50).AND.(IDTPIX(FX,FY).LE.57))
        *          IDTPIX(FX,FY) = 0
                MBOND = MOD(IDTPIX(KX,FY+I),2**13)
                IF ((MBOND.GE.256).AND.(MOD(IDIR(MBOND),4).EQ.1))
        *          IDTPIX(KX,FY) = MBOND
             ENDIF
150       CONTINUE
          RETURN
          ENDIF
          END
C
C
C
C         VERSION 1 - JAN 15, 1985
C
C This subroutine is called by MOVEIT and MOVEFL
C It places charges in MM - (Used by RETRIEVE)
C It does not display them
C
          SUBROUTINE ZHARGE(KAR,IX,IY,NCHRG,IERR)
          IMPLICIT INTEGER*2(A-Z)
          INTEGER*4 MM
          COMMON /CHARS/IES, IDOT,ITAG,JUMP,LBOND,KAN,ISPACE
          COMMON /STRPIX/ LPIX,MM(90,38),LBLEN,LNGBND(100,5)
          COMMON /CD/ MAXX,MAXY
          COMMON /HP/IHP
          COMMON /RANGE/ LOX,HIX,LOY,HIY
C This subroutine, called when a +,-, or = sign is entered, searches for
C a diagonal location for the charge, and types it in.
          IERR=0
          IC=0
          JJJ=IX
          IF (MM(IX,IY) .EQ. 0) GO TO 430
```

```
C This should be a delocalized charge
C Search back for the node, if any:
C look for space for charge up & to the right:
        IF ((JJJ+2.GT.MAXX).OR.(IY+2*IHP.LE.0) .OR. (IY+2*IHP .GT.MAXY))
      * GO TO 431
        IF (MM(JJJ+1,IY+IHP)+MM(JJJ+2,IY+IHP)+MM(JJJ+2,IY+2*IHP)
      * +MM(JJJ+1,IY+2*IHP) .NE.0) GO TO 431
            IF (JJJ+3.LE.MAXX) THEN
                IF (MM(JJJ+3,IY+IHP).NE.0) GO TO 431
            ENDIF
            JX=JJJ+1
            JY=IY +IHP
            IF (JX.GT.HIX) HIX = JX
        IF (IHP .EQ. 1 .AND. JY .GT. HIY) HIY=JY
        IF (IHP .NE. 1 .AND. JY .LT. LOY) LOY=JY
        IC=4
        GOTO 450
C Look down & right:
431     IF ((JJJ+2.GE.MAXX).OR.(IY-2*IHP.GE.MAXY)
      * .OR. (IY-2*IHP.LE.0)) GO TO 118
        IF (MM(JJJ+1,IY-IHP)+MM(JJJ+2,IY-IHP)+MM(JJJ+2,IY-2*IHP)
      * + MM(JJJ+1,IY-2*IHP) .NE.0) GO TO 118
            IF (JJJ+3.LE.MAXX) THEN
                IF (MM(JJJ+3,IY-IHP).NE.0) GO TO 118
            ENDIF
            JX=JJJ+1
            JY=IY - IHP
            IF (JX.GT.HIX) HIX = JX
        IF (IHP .EQ. 1 .AND. JY .LT. LOY) LOY=JY
        IF (IHP .NE. 1 .AND. JY .GT. HIY) HIY=JY
        IC=13
        GOTO 450
C Look up & left:
118     IF ((JJJ-2.LE.0).OR.(IY+2*IHP.LE.0)
      * .OR. (IY+2*IHP .GT. MAXY)) GO TO 433
        IF (MM(JJJ-2,IY+IHP)+MM(JJJ-1,IY+IHP)+MM(JJJ-1,IY+2*IHP).NE.0)
      * GO TO 433
            IF (JJJ-3.GT.0) THEN
                IF (MM(JJJ-3,IY+2*IHP)+MM(JJJ-3,IY+IHP).NE.0) GO TO 433
            ENDIF
            JX=JJJ-2
            JY=IY +IHP
            IF (JX.LT.LOX) LOX = JX
        IF (IHP .EQ. 1 .AND. JY .GT. HIY) HIY=JY
        IF (IHP .NE. 1 .AND. JY .LT. LOY) LOY=JY
        IC=1
        IF (NCHRG.LE.1) JX=JX+1
        IF (NCHRG .LE.1) IC=2
        GOTO 450
C Look down and left:
433     IF ((JJJ-2.LE.0).OR.(IY-2*IHP.GT.MAXY)
      * .OR. (IY-2*IHP .LE.0)) GO TO 434
        IF (MM(JJJ-2,IY-IHP)+MM(JJJ-1,IY-IHP)+MM(JJJ-1,IY-2*IHP)
      * +MM(JJJ-2,IY-2*IHP).NE.0) GO TO 434
            IF (JJJ-3.GT.0) THEN
                IF (MM(JJJ-3,IY-IHP)+MM(JJJ-3,IY-2*IHP).NE.0) GO TO 434
            ENDIF
            JX=JJJ-2
            JY=IY -IHP
            IF (JX.LT.LOX) LOX = JX
        IF (IHP .EQ. 1 .AND. JY .LT. LOY) LOY=JY
        IF (IHP .NE. 1 .AND. JY .GT. HIY) HIY=JY
        IC=10
        IF (NCHRG.LE.1) JX=JX+1
        IF (NCHRG.LE.1) IC=11
        GOTO 450
434     IERR=1
C       No place for charge - set error return and exit
        RETURN
C       Enter charge in MM
450     MM(JX,JY)=KAR +IC * 2**13
C       STORE LOC OF CHARGE IN HIGH ORDER PART OF MM
        IF (NCHRG.LE.1) GOTO 60
        KHAR=NCHRG
        MM(JX+1,JY)=KHAR
60      RETURN
```

```
      430   JJJ=IX
      C           Delocalized charge--find clear area:
      493   M=0
            DO 223 I=JJJ-1,JJJ+2
            DO 223 J=IY-1,IY+1
            M=M + LMM(I,J)
      223   CONTINUE
            IF (M.LE.0) GOTO 432
            JJJ=JJJ+1
            IF (JJJ .GT. MAXX) GO TO 434
      C           No place for charge - bail out
            GOTO 493
      432   MM(JJJ,IY)=KAR
            IF (NCHRG.LE.1) GOTO 60
            KHAR=NCHRG
            MM(JJJ+1,IY)=KHAR
            GOTO 60
            END
$STORAGE:2
      C           SUBROUTINE GETIT(IX,IY,LFLAG,KAR)
      C
      C           This subroutine will retrieve a stand alone structure
      C           or a partial structure from the disk.  The position
      C           of the stand alone structure can be controlled by setting
      C           the cursor to the desired location of the lower left corner of
      C           the structure - Partial structures are attached to the existing
      C           structure at the point indicated by the cursor. If the cursor is
      C           at the end of a bond, the partial structure must be placed using
      C           that bond. If that can't be done, the command is aborted. If the
      C           cursor is at a node, the program will try 4 orientations of the
      C           partial structure around the node before aborting the command
      C           Available commands are :
      C                  ' - retrieve
      C                  V - view disk structure
      C                  Del - delete - delete the result of the last command
      C                        executed (i.e. structure, marker or bond)
      C                  Bond - draw a bond
      C                  # - enter a marker
      C                  1c - jump to a marker
      C                  | - go to NUMBER ENTRY state
      C                  CR - return to calling state
            SUBROUTINE GETIT(IX,IY,LFLAG,KAR)
      C
            IMPLICIT INTEGER*2 (A-Z)
            INTEGER*4 MM,IDTPIX,CONNEC,DELET(2000),COPYB
            INTEGER*2 LIBMAX(2)
            LOGICAL*2 EXIST,PNODE,RETR,LATEH3,VNODE,DIRECT
            LOGICAL PMESS
            CHARACTER*10 FILE,LFILE
            CHARACTER*8 LIBRET,HLO8
            CHARACTER*5 KSC(2),NSC,LSC
            CHARACTER*1 NSC10(10),HALO(12),HLO(3)
            CHARACTER*12 HALOE
            CHARACTER*3 HLOE
            EQUIVALENCE (HALOE,HALO(1))
            EQUIVALENCE (HLOE,HLO(1))
            CHARACTER*1 KAN
            CHARACTER*1 ISTAT
            CHARACTER*1 NAMSTR(6)
            COMMON /HP/IHP
            COMMON /LIB/ LIBRET(640),NLIBS
            COMMON /IPLUS/ IHIGH(14,2)
            COMMON /RET/ SYM,NSC(2)
            COMMON /BAKLIB/ LSC(2)
            COMMON /ISTATE/ ISTAT
            COMMON /STRDEF/ NNODE,TABLE(255,43)
            COMMON /STRPIX/ LPIX,MM(90,38),LBLEN,LNGBND(100,5)
            COMMON /MODES/ JBTYPE,ICHAR,IBDIR,IBTYPE,ISMART,MODE,ISKILL,ISP
            COMMON /LABELS/ NR,NJLAST,NJNEXT
            COMMON /HEAD/ MW(12),ISTATE,PAGE
            COMMON /CHARS/IES, IDOT,ITAG,JUMP,LBOND,KAN,ISPACE
            COMMON /STRED/ IDTPIX(90,38),LABL(260,2),MRKCHN(260)
            COMMON /TEMP/ LLBOND(100,5),LLABL(260,2),MCHN(260)
            COMMON /PARAMS/ JBDIR,NOCHG,LASTN,MCHAR,JCHAR,NLARGE,LEVEL
            COMMON /CD/ MAXX,MAXY
```

```
      COMMON /FROM/ LCHAR
      COMMON /BAD/ IBADX(9),IBADY(9)
      COMMON /LAPE/ LAP(5,2)
      COMMON /ENTRAR/ CONNEC(2001)
      COMMON /RANGE/ LOX,HIX,LOY,HIY
      COMMON /CUR/ ICUR
      COMMON /MKSKP/ ISKIP
      COMMON /PROB/ IPROB,JPROB
      COMMON /RETLIB/OVRWRT
CXT
CXT   PNODE = TRUE is passed to SUBROUTINE VLNCE when VLNCE need only
CXT   search array MM for nodal adjacency. DELH is assigned the attached
CXT   node's hydrogen information so it can be had for any subsequent
CXT   substructure deletion. V.NODE = TRUE indicates the substructure
CXT   is being drawn by the VIEW SECTION of SUBROUTINE GETIT.
      COMMON /VALH/ PNODE,DELH(2,3),VNODE
CXT
CXT   RETR = TRUE for calls in which SUBROUTINE REPLCE must deal with
CXT   both array MM and IDTPIX.
      COMMON /RETDRW/ RETR
      EQUIVALENCE (FILE,NSC),(NSC,NSC10),(CONNEC(2001),DELET(1))
      DIMENSION THETA(8,8)
      DATA THETA /-1,-1,2,-1,1,-1,4,-1,
     2             -1,-1,-1,1,-1,5,-1,3,
     3              2,-1,-1,-1,4,-1,3,-1,
     4             -1,1,-1,-1,-1,3,-1,5,
     5              1,-1,4,-1,-1,-1,2,-1,
     6             -1,5,-1,3,-1,-1,-1,1,
     7              4,-1,3,-1,2,-1,-1,-1,
     8             -1,3,-1,5,-1,1,-1,-1/
      DATA READS /0/, APOS /39/, IU /1/, LFILE /'                    '/
C***************************************************************
C
C     This section sets some parameters - clears the arrays IDTPIX
C     and LLBOND clears possible text from the screen and calls HEADER
C     The parameters MODE, ISTAT, and ISTATE are used by HEADER
C     LCHAR = indicates if we came from CHAIN or RING - It is used
C     to determine if we should return to CHAIN or RING instead
C     of GROUND
C     NODE will indicate whether we are at a marker or a bond or neither
C     It is used when we are trying to attach to an existing structure
C     IFLIP and IROT are used to indicate the rotation or reflection
C     operators needed
C***************************************************************
      IF (NLIBS.EQ.0) THEN
          CALL MYERR(27,27,27)
          GO TO 6777
      ENDIF
      HALO(1) = KAN
      HALO(12) = KAN
      HLO(1) = KAN
      HLO(3) = KAN
      VNODE = .FALSE.
      ALONE = 0
      ISKIP = 1
      KCHAR = LCHAR
      COPY = 0
      XCHAR = 1
      KCHAR=LCHAR
      OCHAR=0
C     Parameter which decides when to use default origin for stand
C     alone structure
      CALL CLRPIX(2)
C     Clear IDTPIX and LLBOND
122   NODE=-1
      ISTAT=':'
      SYM = 1
C Default symmetry = 1 = axial
      MW(7)=999
C Force new heading
      MW(8)=999
      MW(9)=999
      ISTATE=12
      CALL HEADER
```

```
        IF (((FILE.NE.LFILE).OR.(OVRWRT)) .AND.(FILE.NE.'         '))
   1    THEN
        OVRWRT=.FALSE.
           DIRECT = .TRUE.
           KSC(1) = LSC(1)
           KSC(2) = LSC(2)

DO 222 I = 1,10
              HALO(I+1) = NSC10(I)
 222       CONTINUE
           GO TO 8737
        ELSE
           DIRECT = .FALSE.
        ENDIF
C Go get first file name - then await next command
C***********************************************************************
C        This section reads the next command - clears some screen dialog
C        decodes the command and goes to the appropriate section to execute
C        the command - If an invalid command is given, an error message
C        will be given and the program will wait for a valid command
C***********************************************************************
 305    CONTINUE
        IF (JPROB.NE.0) GO TO 6777
        IERR = 0
        ICUR = 1
        CALL CURSOR(IX,IY)
        CALL INPUTX(KKAR,IX,IY)
        IF (KKAR.EQ.58) THEN
           IERR = 39
           CALL MYERR(IERR,IERR,IERR)
           GO TO 305
        ENDIF
        IF (KKAR.NE.127) XCHAR = 1
C
C Read command
C
C Dumb mode
        IF ((KKAR.EQ.21) .OR. (KKAR .EQ. 32) .OR. (KKAR .EQ.8)) THEN
           GO TO 4911
C Delete structure
        ELSE IF (KKAR .EQ. 127) THEN
           GO TO 650
C ' - Retrieve next structure
        ELSE IF (KKAR.EQ.39) THEN
           IF (FILE.EQ.'       ') THEN
              IERR = 58
              CALL MYERR(IERR,IERR,IERR)
              GO TO 305
           ELSE
              GO TO 87
           ENDIF
C Bond command
        ELSE IF (KKAR.GE.22 .AND. KKAR.LE.31) THEN
           COPY=0
           GO TO 793
C Enter marker command or set new enlargement factor
        ELSE IF (KKAR .EQ. 35 .OR. KKAR.EQ.38) THEN
           IF (KKAR .EQ. 35) COPY =0
           GO TO 793
C Jump to marker
        ELSE IF (KKAR.GE.97 .AND. KKAR.LE.122) THEN
           GO TO 793
C Charge (+,- or =)
        ELSE IF ((KKAR.EQ.43).OR.(KKAR.EQ.45).OR.(KKAR.EQ.61)) THEN
           COPY=0
           GO TO 793
C Set symmetry to axial
        ELSE IF (KKAR .EQ. 65) THEN
           GO TO 955
C Set symmetry to point symmetry
        ELSE IF (KKAR .EQ. 80) THEN
           GO TO 966
C Get file name
        ELSE IF (KKAR .EQ. 70) THEN
           GO TO 4923
```

```
C VIEW structure
            ELSE IF (KKAR .EQ. 86) THEN
                GO TO  4949
C Return or Quit
            ELSE IF (KKAR .EQ. 13 .OR. KKAR .EQ. 81) THEN
                GO TO 6777
C Set new bond type
            ELSE IF (KKAR.EQ.124) THEN
                GO TO 3561
            ENDIF
C LIST substructures
            IF (KKAR.NE.76) GO TO 202
201         CALL SETSCR(1)
            IF (IHP .EQ. 1) THEN
            CALL CLEAR
            CALL GRAOFF
            ENDIF
                PAGE = 1
                CALL DISPLA(1)
                CALL FTSIZE(1,10)
                IF (NLIBS.GT.320) THEN
                    LIBMAX(1) = 320
                    LIBMAX(2) = NLIBS - 320
                    SCROLL = 2
                ELSE
                    LIBMAX(1) = NLIBS
                    SCROLL = 1
                ENDIF
                DO 3040 I = 1,SCROLL
                    FX = 1
                    FY = 1
                    DO 3030 J = 1,LIBMAX(I)
                        CALL FTLOCA(FY,FX)
                        HLO8 = LIBRET(J+((SCROLL-1)*320))
                        CALL FTEXT(HLO8)
                        IF (FX.GE.71) THEN
                            FY = FY + 1
                            FX = 1
                        ELSE
                            FX = FX + 7
                        ENDIF
3030                CONTINUE
                    CALL FTSIZE(2,18)
                    FY = FY + 2
                    CALL FTLOCA(FY,1)
                    CALL FTEXT('^Press RETURN to continue^')
                    CALL FTSIZE(1,10)
                    KKAR = GETCHR()
                    CALL SETCOL(0)
                    CALL CLR
                    CALL SETCOL(1)
3040            CONTINUE
                CALL SETSCR(2)
                PAGE = 2
                CALL DISPLA(2)
                DO 7932 I=1,12   !Force tidy call to Header
                MW(I)=999
7932            CONTINUE
                CALL HEADER
                GO TO 305
202         CONTINUE
            IF (KKAR.EQ.131) GO TO 305
            CALL FTSIZE(2,18)
            CALL FTLOCA(4,1)
            CALL FTEXT('^Invalid response: ^')
            HLO(2) = CHAR(KKAR)
            CALL FTEXT(HLOE)
            PAGE = 0
            CALL FTSIZE(1,10)
C Return to GROUND
            GO TO 305
```

```
C***********************************************************
C       This section will (VIEW) display the last structure read into
C       memory - that is the structure whose file name was last entered
C       The view is terminated by the input of any character - At that
C       point the screen is cleared and the original structure is restored
C       to the screen and to the MM array.
C***********************************************************
C If the picture is in MM - copy it to IDTPIX
4949    IF (COPY .EQ. 0) CALL SHIF(1,MC,LC)
        COPY = 1
C Copy = 1 implies current picture is in IDTPIX
        ICUR = 0
        SIX=IX  !Save cursor values
        SIY=IY
        CALL CURSOR(IX,IY)
        CALL SETCOL(0)
        CALL CLR
        CALL SETCOL(1)
        VLOX = LOX
        VHIX = HIX
        VLOY = LOY
        VHIY = HIY
        LOX = 1
        HIX = MAXX
        LOY = 1
        HIY = MAXY
        CALL CLRPIX(1)
C Clear MM and LNGBND
        IROT=1
        DX=0
        DY=0
C Set origin to default
        CALL MOVEIT(DX,DY,LENP,LENM,LLLEN,LENC,LEND,ABX,ABY,IROT,IERR)
C Move picture from CONNEC to MM with translation
        IF (DOT .EQ. 1) GO TO 5512
C Skip VLNCE if we have a call to DOTDIS
C       Fill in valence hydrogens
        PNODE = .TRUE.
        VNODE = .TRUE.
        IERR=0
        DO 5910 I = LOX,HIX
        DO 5910 J = LOY,HIY
        II=I
        JJ=J
        IF (MM(I,J) .GE. 65 .AND. MM(I,J) .LE. 90
     1   .AND. (MM(I,J) .NE. 72 .OR. (MM(I,J) .EQ. 72
     2   .AND. MM(I+1,J) .GE. 97 .AND. MM(I+1,J) .LE. 122)))
     3   CALL VLNCE(2,II,JJ,0,0,IERR)
        IF (IERR.EQ.12) IERR = 0
        IF (IERR .NE. 0) GO TO 5512
5910    CONTINUE
        ISWIT = 1
C Call STRDRW with markers displayed as markers
        LBLEN=LLLEN
        CALL STRDRW(ISWIT)
5512    PNODE = .FALSE.
        VNODE = .FALSE.
C View (display) the structure
        CALL FTSIZE(2,18)
        IF (JPROB.EQ.0) THEN
        IF (IHP .EQ.1) CALL CLEAR
            CALL FTLOCA(1,1)
            CALL FTEXT('^VIEW of ^')
            CALL FTEXT(HALOE)
            CALL FTEXT('^ - Enter RETURN to end VIEW^')
            PAGE = 0
            CALL FTSIZE(1,10)
            CALL INPUTX(KKAR,IX,IY)
C Await terminator character
            CALL SETCOL(0)
            CALL CLR
            CALL SETCOL(1)
        ENDIF
        ICUR = 1
        CALL CURSOR(IX,IY)
```

```
C Clear screen
        CALL SHIF(2,MC,LC)
        LOX = VLOX
        HIX = VHIX
        LOY = VLOY
        HIY = VHIY
        LBLEN=LC
        NJNEXT=MC
        ISWIT=1
        CALL STRDRW(ISWIT)
        DO 6565 I=1,12
C Force tidy call to header
        MW(I)=999
6565    CONTINUE
        CALL HEADER
        IF (IHP .EQ. 1)THEN
        IX=SIX
        IY=SIY
        ENDIF
        GO TO 305
C*****************************************************************
C       This section accesses DUMB MODE.
C*****************************************************************
4911    CONTINUE
        CALL SPACE(IX,IY)
        JCHAR = 2
        MCHAR = 0
        ISTATE = 12
        ISTAT = ':'
        COPY=0
        CALL HEADER
        GO TO 305
C*****************************************************************
C       This section reserves a channel - sets some graphic switches
C       requests the file name - concatenates the extension .LIB
C       to the file name - senses the current cursor location
C       and uses that as the lower left corner of the display if the
C       structure to be retrieved is a stand alone structure
C       A file name = CR causes a return to the calling program
C       to be used again.
C       If the requested file does not exist, an error message
C       is issued and another file name is requested.
C*****************************************************************
C
C       THIS SECTION RETRIEVES A STRUCTURE FROM THE LIBRARY
C
4923    CONTINUE
        CALL SETSCR(1)
        PAGE = 1
        CALL DISPLA(1)
        CALL FTSIZE(2,18)
4924    READS = READS + 1
C Request file name
520     CONTINUE
C
        FY = 9
        FYY = 7
        LSC(1) = NSC(1)
        LSC(2) = NSC(2)
        LFILE = FILE
565     CONTINUE
        FILE = '        '
        CALL FTLOCA(8,28)
        CALL FTEXT('^Enter 1 to 6 character file name^')
        IF (READS.GE.2) THEN
            CALL FTLOCA(9,28)
            CALL FTEXT('^or '' for previous file^')
            FY = 10
        ENDIF
C Read file name
        IF (IHP .EQ. 1) THEN
        CALL ALPCUR
        ACCEPT 691,(NAMSTR(I),I=1,6)
691     FORMAT(6A1)
        ENDIF
```

```
            CALL FTLOCA(FY,FX)
            J = 0
            DO 4445 I = 1,60
                J = J + 1
                FX = 27 + J
 1445           CONTINUE
            IF (IHP .EQ. 1) THEN
            A=ICHAR(NAMSTR(J))
            IF (A .GE. 97) A=A-32
            ELSE
                A = GETCHR()
            ENDIF
                IF (A.EQ.APOS) THEN
                    IF (READS.LT.2) THEN
                        CALL FTLOCA(FYY,28)
                        CALL FTEXT('^No previous files input^')
                        GO TO 565
                    ENDIF
                    NSC10(1) = CHAR(A)
                    HLO(2) = CHAR(A)
                        IF (IHP .NE. 1) THEN
                    CALL FTLOCA(FY,28)
                    CALL FTEXT(HLOE)
                        ENDIF
                    GO TO 4447
                ENDIF
                IF (A.EQ.8) THEN
                    IF (J.GT.1) J = J - 1
                    FX = 27 + J
                    CALL FTLOCA(FY,FX)
                    CALL FTEXT('^ ^')
                    NSC10(J) = ' '
                    GO TO 1445
                ENDIF
                HLO(2) = CHAR(A)
            IF (IHP .NE. 1) THEN
                CALL FTLOCA(FY,FX)
                CALL FTEXT(HLOE)
            ENDIF
                IF (((A.GE.48).AND.(A.LE.57)).OR.((A.GE.65).AND.
  *                (A.LE.90)).OR.((A.GE.97).AND.(A.LE.122)).OR.
  *                ((A.EQ.34).AND.(I.EQ.1))) THEN
                    NSC10(J) = CHAR(A)
                ELSE IF (A.EQ.13 .OR. A .EQ. 32) THEN
                    GO TO 4447
                ELSE
                    NSC10(J) = ' '
                ENDIF
                IF (J.EQ.6) GO TO 4447
 4445       CONTINUE
 4447       CONTINUE
            IF (IHP .EQ. 1) THEN
            CALL LINE4
            CALL ACLEAR
            ELSE
            CALL SETCOL(0)
            CALL CLR
            CALL SETCOL(1)
            ENDIF
            IF (NSC(1) .EQ. '       ') THEN
                CALL SETSCR(2)
                PAGE = 2
                CALL DISPLA(2)
                CALL FTSIZE(1,10)
                FILE = LFILE
                READS = READS - 1
                GO TO 305
            ELSE IF (NSC10(1).EQ.CHAR(APOS)) THEN
                IF (KSC(1).NE.'       ') THEN
                    NSC(1) = KSC(1)
                    NSC(2) = KSC(2)
                ELSE
                    NSC(1) = LSC(1)
                    NSC(2) = LSC(2)
                ENDIF
```

```
            ELSE
C           CONCATENATE .LIB EXTENSION TO FILE NAME
                NSC10(7) = '.'
                NSC10(8) = 'S'
                NSC10(9) = 'T'
                NSC10(10) = 'R'
            ENDIF
            KSC(1) = LSC(1)
            KSC(2) = LSC(2)
            DO 8334 I = 1,10
                HALO(I+1) = NSC10(I)
8334        CONTINUE
            CALL FTLOCA(7,28)
            CALL FTEXT('^Input from file: ^')
            CALL FTEXT(HALOE)
            CALL FTLOCA(8,28)
            CALL FTEXT('^Press RETURN to clear screen^')
            A = GETCHR()
            IF (IHP .EQ. 1) THEN
            CALL LINE4
            CALL ACLEAR
            ELSE
            CALL SETCOL(0)
            CALL CLR
            CALL SETCOL(1)
            ENDIF
8737        INQUIRE(FILE=FILE,EXIST=EXIST)
            IF (.NOT.EXIST) THEN
                IF (DIRECT) THEN
                    CALL SETSCR(1)
                    PAGE = 1
                    CALL DISPLA(1)
                    CALL FTSIZE(2,18)
                    DIRECT = .FALSE.
                ENDIF
                CALL FTLOCA(6,28)
                CALL FTEXT('^File doesn''t exist/file empty - ^')
                CALL FTLOCA(7,28)
                CALL FTEXT('^Try another name or CR to recover^')
                FY = 9
                FYY = 10
                GO TO 565
            ENDIF
507         OPEN(IU,FILE=FILE,STATUS='OLD')
            IF (.NOT.DIRECT) THEN
                CALL SETSCR(2)
                PAGE = 2
                CALL DISPLA(2)
                CALL FTSIZE(1,10)
            ELSE
                READS = READS + 1
            ENDIF
            ICUR = 1
            CALL CURSOR(IX,IY)
            CALL HEADER
C***********************************************************************
12          READ (IU,100,END=5777,ERR=5776) ABX,ABY,BDIR,BLEN,DOT,LBX,LBY
C           ABX ABY = coordinates of attaching bond
C           BDIR = attaching bond direction
C           BLEN = attaching bond length
C           LBX LBY = coordinates for final cursor position
100         FORMAT(7I4)
            READ(IU,100,END=5777,ERR=5776) LENP
C           LENP = # of cells used in MM
            IF (LENP .EQ. 0) GO TO 5776
            IF (3*LENP .GT. 2000) GO TO 999
C           We will be using CONNEC array temporarily to store X's, Y's, contents
C           marker coordinates and long bond info
C           This is a bounds check for CONNEC
            J=1
C           Read structure into CONNEC
            DO 51 I=1,LENP
            READ(IU,400,END=5777,ERR=5776) CONNEC(J),CONNEC(J+1),CONNEC(J+2)
C           Read X, Y and MM(X,Y)
            J=J+3
```

```
51      CONTINUE
        READ (IU,100,END=5777,ERR=5776) LENM
C       LENM = # of markers in structure
        IF (LENM .EQ. 0) GO TO 54
        IF (3*(LENM+LENP) .GT. 2000) GO TO 999
C       Bounds check
        DO 52 I=1,LENM
400     FORMAT(2I4,I10)
        READ(IU,100,END=5777,ERR=5776) CONNEC(J),CONNEC(J+1),CONNEC(J+2)
C       Read coordinates of marker and type of marker (chain or non chain)
        J=J+3
52      CONTINUE
54      READ (IU,100,END=5777,ERR=5776) LLLEN
C       LLLEN = # of long bonds
        IF (LLLEN .EQ. 0) GO TO 5666
        IF ((3*(LENP+LENM)+5*LLLEN) .GT. 2000) GO TO 999
        DO 57 I=1,LLLEN
        READ (IU,100,END=5777,ERR=5776) (CONNEC(J+K),K=0,4)
C       Read initial and final coordinates of long bond and bond type
        J=J+5
57      CONTINUE
C       LENC = # of charges
5666    READ(IU,100,END=5777,ERR=5776) LENC
        IF (LENC.EQ.0) GO TO 5611
        IF ((3*(LENP+LENM) + 5 * LLLEN + 4 * LENC).GT.2000) GO TO 999
        DO 5577 I = 1,LENC
            READ(IU,100,END=5777,ERR=5776) (CONNEC(J+K),K=0,3)
            J = J + 4
5577    CONTINUE
5611    CONTINUE
        READ(IU,100,END=5777,ERR=5776) LEND
        IF (LEND.EQ.0) GO TO 56
        IF ((3*(LENP+LENM)+5*LLLEN+4*LENC+2*LEND).GT.2000) GO TO 999
        DO 5612 I = 1,LEND
            READ(IU,100,END=5777,ERR=5776) CONNEC(J),CONNEC(J+1)
            J = J + 2
5612    CONTINUE
        GO TO 56
5776    CONTINUE
        CLOSE(IU)
        CALL FTSIZE(2,18)
        CALL FTLOCA(1,1)
        CALL FTEXT('^INPUT FILE DATA FORMAT ERROR ENCOUNTERED^')
        PAGE = 0
        CALL FTSIZE(1,10)
        GO TO 305
5777    CONTINUE
        CLOSE(IU)
        CALL FTSIZE(2,18)
        CALL FTLOCA(1,1)
        CALL FTEXT('^ERROR - END OF INPUT FILE ENCOUNTERED^')
        PAGE = 0
        CALL FTSIZE(1,10)
        GO TO 305
56      CLOSE(IU)
C       Close file
        DIRECT = .FALSE.
        GO TO 305
C Get next command
C************************************************************
C       Start of RETRIEVE code - Clear dialog - Save coordinates -
C       Set parameters
C************************************************************
37      CONTINUE
        LX=IX
C Save these coordinates in case we do a RETRIEVE followed
C by a DELETE - We will then reset the cursor to these coordinates
        LY=IY
        IROT=1
C Set rotation angle to a default of 0
        IFLIP=-1
C Set reflection code to default value 0 = equals no reflection
```

```
C***********************************************************
C       This section shifts the current MM array to IDTPIX.
C       It also moves the marker array LABL to LLABL and
C       the long bond array LNGBND to LLBOND.
C       MC = count of markers moved.
C       LC = count of long bonds moved.
C       It also does a bounds check on the marker and long bond arrays.
C       It also determines whether we are dealing with a stand alone
C       structure (ABX and ABY = 0) or an attaching structure.
C***********************************************************
        CALL SHIF(1,MC,LC)
        COPY = 1
        IF ((MC+LENM) .GT. 260 .OR. (LLLEN+LC) .GT. 100) GO TO 333
C       Bail out - We have too many markers or longbonds
C       This section determines whether we are dealing with a standalone
C       or attaching structure. If the cursor is at a 3X3 clear area
C       (node=-2) we have as standalone.
C       Node = -1 = error - not at bond, node or empty space
C       Node = 1 = attach group to node
C       Node = 0 = attach group to bond
C***********************************************************
        ICUR = 0
        PNODE = .FALSE.
        FIX=IX
C       Save current cursor position because MAP could alter IX if we are
C       at a non marker node
        FIY=IY
        CALL MAP(IX,IY,NODE,OBDIR)
        IF (NODE.EQ.-2) GO TO 200
        IF (BLEN.EQ.0) GO TO 200
        IF (DOT.EQ.1) GO TO 200
        IF (NODE .NE. -1) GO TO 71
        IERR = 48
C       We are not at a marker or bond - can't attach here
        CALL MYERR(IERR,KAR,KAR)
C       Issue error message
        IX=FIX
C       Restore IX and IY
        IY=FIY
        CALL SHIF(2,MC,LC)
C       Shift old picture back to MM etc.
        COPY = 0
        GO TO 305
C       Go await new command
71      IF(NODE .EQ. 1) GO TO 711
C       If NODE = 1 go to node code
C***********************************************************
C       This section tries to attach a structure to a pointer bond
C       It determines the direction of the dangling bond on the
C       structure on disk - If the bond directions match (i.e.
C       ABS(difference in bond directions) = 4 no rotation or reflection
C       is needed - If the difference in bond directions is odd, we can
C       not attach this group to the pointer bond, for only reflections
C       around the X and Y axes and rotations of 90, 180, and 270 degrees
C       are allowed. If the difference in bond directions is even, we
C       determine the transformation necessary. We prefer to do reflections
C       because they tend to result in fewer distorted nodes.
C       After the transformation has been performed and the picture has
C       been moved into MM, we check for collisions and for nodes that
C       have been distorted. If no collisions occur and all distorted
C       nodes can be corrected, we go to 240 to display the structure.
C       If collisions occur or distorted nodes cannot be corrected, we
C       issue an appropriate error message, restore the old picture and
C       await entry of a new command
C
C***********************************************************
        KX=IX
        KY=IY
        PX = IX
        PY = IY
C       Get delta values for current bond
        CALL DELTA(OBDIR,INCX,INCY)
        KX=KX-INCX
        KY=KY-INCY
        IVAL=LMM(KX,KY)
        OBTYPE=IVAL/256
```

```
      C       Bond type of current bond
              DO 601 I=1,MAXX
              OBLEN = I
              KX=KX-INCX
              KY=KY-INCY
              IF (LMM(KX,KY) .NE. IVAL) GO TO 602
              IF ((KX.GE.MAXX-1).OR.(KX.LE.1).OR.(KY.GE.MAXY-1).OR.(KY.LE.1))
             *    GO TO 602
      601     CONTINUE
      602     CONTINUE
      C       OBLEN = length of bond of currently displayed structure
              DIFF = OBLEN - BLEN
      C       SUB is used to calculate translation value
              PIX=KX
              PIY=KY
      CXT     Use in program until VALENCED node attached end nodes are approved.
              IF (MM(PIX,PIY).NE.46) THEN
                  IERR = 57
                  CALL MYERR(IERR,KAR,MAR)
      C           Shift old picture back to MM etc.
                  IX = FIX
                  IY = FIY
                  CALL CURSOR(IX,IY)
                  CALL SHIF(2,MC,LC)
                  COPY = 0
                  GO TO 305
              ENDIF
              OBX=KX+INCX
      C       X coordinate for start of old bond
              OBY=KY+INCY
      C       Y coordinate for start of old bond
      C       Get dangling bond
              ADIR=BDIR
      C       BDIR = Bond direction of stored dangling bond
              IF (IABS(BDIR-OBDIR) .EQ. 4) GO TO 78
      C       Attaching bond in correct direction - No transformation other
      C       than translation needed
              IF (MOD(IABS(BDIR-OBDIR),2) .EQ. 0) GO TO 79
      C       Acceptable bond but transformation + translation needed
      C
      C       We can't attach to this bond
      C       Issue an error message - shift the old picture back to MM
      C       Abort command and await new command
      C
              IERR = 43
      C       Bad attaching bond - Bail out
              CALL MYERR(IERR,KAR,KAR)
              CALL SHIF(2,MC,LC)
              COPY = 0
              GO TO 305
      C       Abort command and await new command
      C
      C       Determine what transformation is needed
      79      NBOND=OBDIR+4
      C       NBOND = dir of needed attaching bond
              IF (NBOND .GT. 8) NBOND=NBOND-8
              IF (SYM.EQ.1) GO TO 8633
              DO 862 I=1,8
              II = I
      C       Calculate the rotation needed to make attaching bond right
              ADIR=ADIR+1
              IF (ADIR .GT. 8) ADIR=ADIR-8
              IF (ADIR .EQ. NBOND) GO TO 863
      862     CONTINUE
      863     IROT= (II / 2) + 1
              IF (IROT.EQ.2) THEN
                  IROT = 4
              ELSE IF (IROT.EQ.4) THEN
                  IROT = 2
              ENDIF
              IF (IROT.EQ.5) IROT = 1
      C
      C
      C       If no rotation is needed (IROT=1) or bond direction is odd
      C       and rotation is not 180  go to 78
```

```
              IF (SYM .EQ. 2) GO TO 78
C             If symmetry is point - skip next section
C             Determine needed reflection
8633          CONTINUE
              IFLIP = THETA(BDIR,NBOND)
              IF (IFLIP.EQ.2) THEN
                  IFLIP = 4
              ELSE IF (IFLIP.EQ.4) THEN
                  IFLIP = 2
              ENDIF
C
C             Calculate translation values
C
78            CALL DELTA(OBDIR,KNCX,KNCY)
              OX = ABX + BLEN*KNCX
              OY = ABY + BLEN*KNCY
              DX=OX-IX
              DY=OY-IY
C             Move picture into MM after performing necessary transformations
C
              CALL CLRPIX(1)
              IF ((IFLIP.EQ.-1).AND.(SYM.EQ.1)) IROT = 1
              IF ((SYM.EQ.1).AND.(IFLIP.NE.-1))
     1        CALL MOVEFL(DX,DY,LENP,LENM,LLLEN,LENC,LEND,ABX,ABY,IFLIP,IERR)
C             Move picture from CONNEC to MM with translation and reflection
              IF ((SYM.EQ.2).OR.((SYM.EQ.1).AND.(IFLIP.EQ.-1)))
     *        CALL MOVEIT(DX,DY,LENP,LENM,LLLEN,LENC,LEND,ABX,ABY,IROT,IERR)
C             Move picture from CONNEC to MM with translation to new origin
C
C             If IERR=1 we have a bounds problem and we will go to 546
              IF (IERR.NE.0) GO TO 546
C
C             Erase the old bond in IDTPIX
C             Erase the old bond from the screen
C             Copy the new bond into MM
              COPYB=MM(ABX-DX,ABY-DY)
              LE = 0
              DO 605 I=1,OBLEN+1
                  MX = OBX + (I-1)*INCX
                  MY = OBY + (I-1)*INCY
                  IF (IDTPIX(MX,MY).EQ.0) GO TO 605
                  IF (MOD(IDTPIX(MX,MY),2**13).LT.256) GO TO 805
                  LE = I
C                 Erase old bond in IDTPIX
                  IDTPIX(MX,MY)=0
                  MM(MX,MY)=COPYB
605           CONTINUE
805           CONTINUE
              IF (DIFF.LT.0) THEN
C             Erase excess bond if bond on disk was longer than bond on screen
                  IEND=-DIFF
                  DO 123 I=1,IEND
                      MX=OBX-(I*INCX)
                      MY=OBY-(I*INCY)
                      IF (MM(MX,MY).GT.256) MM(MX,MY)=0
123               CONTINUE
              ENDIF
              IF (OBLEN.LT.BLEN) THEN
                  MX = PX - (OBLEN*INCX)
                  MY = PY - (OBLEN*INCY)
              ELSE
                  MX = ABX - DX
                  MY = ABY - DY
              ENDIF
              DO 504 I = 1,LE
                  MX = MX + INCX
                  MY = MY + INCY
                  IF (LMM(MX,MY).LT.256) THEN
                      FX = MX
                      FY = MY
                      MX = MX - INCX
                      MY = MY - INCY
                      GO TO 515
                  ENDIF
504           CONTINUE
              FX = MX + INCX
```

```
              FY = MY + INCY
515       CONTINUE
          IBDIR = OBDIR + 4
          IF (IBDIR.GT.8) IBDIR = IBDIR - 8
          IBTYPE = 0
          MBTYPE = COPYB / 256
          LNCX = -1 * INCX
          LNCY = -1 * INCY
          RETR = .TRUE.
          CALL REDRAW(MX,MY,LNCX,LNCY,MBTYPE)
          IBTYPE = 1
          IF (IABS(INCX*INCY).EQ.0) THEN
              IF (IDTPIX(MX,MY).EQ.0) THEN
                  CALL FTLOCA(MY,MX)
                  CALL FTEXT('^ ^')
              ELSE
                  CALL REPLCE(MX,MY,0,0,0,0,0)
              ENDIF
              IF (IDTPIX(FX,FY).EQ.0) THEN
                  CALL FTLOCA(FY,FX)
                  CALL FTEXT('^ ^')
                ELSE
                  CALL REPLCE(FX,FY,0,0,0,0,0)
              ENDIF
          ELSE
              LATEH3 = .FALSE.
              DO 607 JY = MY,FY,INCY
                  DO 606 J = -3,4
                      IF ((J.EQ.0).AND.(JY.NE.MY).AND.(JY.NE.FY))
     *                   GO TO 606
                      JX = MX + J
                      IF ((IDTPIX(JX,JY).EQ.0).AND.(MM(JX,JY).NE.0)) THEN
                          CALL FTLOCA(JY,JX)
                          CALL FTEXT('^ ^')
                          IF (MOD((JY*10),40).EQ.0) THEN
                              IF ((JY.EQ.8).OR.(JY.EQ.28).OR.(JY.EQ.16)) THEN
                                  FYY = ((JY * 10) / 11) + 1
                                  CALL FTSIZE(1,11)
                              ELSE
                                  FYY = ((JY * 10) / 9) + 1
                                  CALL FTSIZE(1,9)
                              ENDIF
                          ELSE
                              FYY = ((JY * 10) / 8) + 1
                              CALL FTSIZE(1,8)
                          ENDIF
              IF (IHP .EQ. 1) FYY=JY
                          CALL FTLOCA(FYY,JX)
                          CALL FTEXT('^ ^')
                          CALL FTSIZE(1,10)
                      ELSE IF (IDTPIX(JX,JY).NE.0) THEN
                          CALL REPLCE(JX,JY,0,0,0,0,0)
                          IF (LATEH3) MM(JX-1,JY) = 0
                          IF (((IDTPIX(JX+1,JY).LT.50).OR.(IDTPIX(JX+1,JY)
     *                       .GT.57)).OR.(JX+1.GT.MX+3)) THEN
                              LATEH3 = .FALSE.
                          ELSE
                              MM(JX,JY) = IDTPIX(JX,JY)
                              LATEH3 = .TRUE.
                          ENDIF
                      ENDIF
606               CONTINUE
                  MX = MX + INCX
607           CONTINUE
          ENDIF
          RETR = .FALSE.
          IF ((MBTYPE.EQ.6).OR.(MBTYPE.EQ.7)) THEN
              IF (((BDIR.EQ.3).AND.((OBDIR.EQ.3).OR.(OBDIR.EQ.5))).OR.
     *           (BDIR.EQ.2).OR.(BDIR.EQ.4).OR.((BDIR.EQ.5).AND.
     *           ((OBDIR.EQ.5).OR.(OBDIR.EQ.7).OR.(OBDIR.EQ.3)))) THEN
                  IF (MBTYPE.EQ.6) THEN
                      MBTYPE = 7
                  ELSE
                      MBTYPE = 6
                  ENDIF
                  COPYB = MBTYPE * 256 + OBDIR
```

```
              ENDIF
              IF (((BDIR.EQ.1).AND.((OBDIR.EQ.7).OR.(OBDIR.EQ.1)))
     *          .OR.((BDIR.EQ.5).AND.(OBDIR.EQ.7))
     *          .OR.((BDIR.EQ.7).AND.((OBDIR.EQ.1).OR.(OBDIR.EQ.7)))
     *          .OR.(((BDIR.EQ.2).OR.(BDIR.EQ.4)).AND.((OBDIR.EQ.6).OR.
     *          (OBDIR.EQ.8)))
     *          .OR.((BDIR.EQ.6).AND.((OBDIR.EQ.6).OR.(OBDIR.EQ.8)))
     *          .OR.((BDIR.EQ.8).AND.((OBDIR.EQ.6).OR.(OBDIR.EQ.8))))
     *          THEN
                 CBDIR = OBDIR + 4
                 IF (CBDIR.GT.8) CBDIR = CBDIR - 8
                 IF (MBTYPE.EQ.6) THEN
                    COPYB = 7 * 256 + CBDIR
                 ELSE
                    COPYB = 6 * 256 + CBDIR
                 ENDIF
              ENDIF
           ENDIF
           DO 609 I = 1,LE
              MX = PX - I*INCX
              MY = PY - I*INCY
              IF (MM(MX,MY).GT.0) GO TO 610
              MM(MX,MY) = COPYB
609        CONTINUE
610        CONTINUE
C
C          See if there are collisions between the new group and old
C          structure
C          Erase excess bond if bond on disk was longer than bond on screen
1234       CALL FIXUP(IERR)
C Fix up any bad node caused by rotations and reflections
           IF (IERR .EQ. 0 ) GO TO 2401
C If FIXUP OK -then go add valence hydrogens
2403       IERR=17
C We have a distorted node problem - bail out
           GO TO 173
C
C          Fill in valence hydrogens
2401       ierr=0
           DO 2402 I = LOX,HIX
           DO 2402 J = LOY,HIY
           ii=i
           jj=j
           LL = LMM(I,J)
           IF ((LL.EQ.46).OR.((LL.GE.65).AND.(LL.LE.90)).OR.
     *         ((LL.GE.95).AND.(LL.LE.122)).OR.((LL.GE.50).AND.
     *         (LL.LE.57).AND.(MM(I-1,TY).EQ.72))) THEN
              DO 1012 X = -1,1
                 MX = I + X
                 IF ((MX.LE.0).OR.(MX.GT.MAXX)) GO TO 1012
                 DO 1122 Y = -1,1
                    MY = J + Y
                    IF ((MY.LE.0).OR.(MY.GT.MAXY)) GO TO 1122
                    L = MOD(IDTPIX(MX,MY),2**13)
                    IF ((L.EQ.0).OR.(L.GE.256)) GO TO 1122
                    IF ((L.EQ.34).OR.(L.EQ.43).OR.(L.EQ.45).OR.
     *                 (((L.GE.50).AND.(L.LE.57)).AND.((MOD(IDTPIX(MX-1,
     *                 MY),2**13).EQ.43).OR.(MOD(IDTPIX(MX-1,MY),2**13)
     *                 .EQ.45).OR.((IABS(X+Y).NE.1).AND.(IDTPIX(MX-1,MY)
     *                 .EQ.72))).AND.(MX-1.GT.0))) GO TO 1122
                    IERR = 48
                    GO TO 5663
1122             CONTINUE
1012          CONTINUE
              if ((MM(I,J).EQ.46).OR.(mm(i,j).ge.65.and.mm(i,j).le.90
     1           .and. (mm(i,j).ne.72 .or. (mm(i,j).eq.72
     2           .and. mm(i+1,j).ge.97 .and. mm(i+1,j).le.122))))
     3           call vlnce(2,ii,jj,0,0,ierr)
           ENDIF
5663       IF (IERR.EQ.12) THEN
              IERR = 0
              EX = II
              EY = JJ
           ELSE if (ierr .ne. 0) THEN
              DO 2705 L = 1,260
```

```
                    IF (LABL(L,1).EQ.0) THEN
                       LOW =  L - LENM
                       DO 2703 LL = LOW,L-1
                          LABL(LL,1) = 0
                          LABL(LL,2) = 0
2703                   CONTINUE
                       GO TO 546
                    ENDIF
2705             CONTINUE
                 GO TO 546
             ENDIF
2402     continue
C        See if there are collisions between the new group and the old
C        structure.
         LAP(1,1)=PIX
         LAP(1,2)=PIY
         LCNT=1
         CALL CURSOR(LOX,LOY)
         DO 710 I = LOX,HIX
         DO 710 J = LOY,HIY
         II = I
         JJ = J
         IF (MM(I,J).EQ.0) GO TO 710
         IF ((I.EQ.PIX).AND.(J.EQ.PIY)) GO TO 710
C        Empty space - no collision worry
         BLOB=LMM(I,J)
C        This is used to see if a possible collision is acceptable
         CALL LOOKR(II,JJ,ICHECK,LCNT,BLOB)
C        Check for conflicts
C
         IF (ICHECK .NE. 0) THEN
            DO 705 L = 1,260
               IF (LABL(L,1).EQ.0) THEN
                  LOW =  L - LENM
                  DO 703 LL = LOW,L-1
                     LABL(LL,1) = 0
                     LABL(LL,2) = 0
703               CONTINUE
                  GO TO 546
               ENDIF
705         CONTINUE
            GO TO 546
         ENDIF
C        ICHECK not = 0 indicate collision - bail out
710      CONTINUE
         GO TO 240
C
C        We have a problem - bounds, collision or irreparably distorted node
C        Issue error message - shift old picture back to MM etc.
C        Then we go to 683 to redraw the pointer bond and go await
C        new command
546      IERR=48
173      IF (JPROB.EQ.0) CALL MYERR(IERR,KAR,KAR)
C        Issue message
         CALL CLRPIX(1)
C        Clear picture array
         CALL SHIF(2,MC,LC)
         COPY = 0
C        Restore old picture
         GO TO 683
C        Go to redraw pointer bond
C
C
C
C**************************************************************
C        This section handles attaching a structure to a node
C**************************************************************
711      NIX=IX
C        Save node coordinates
         LY=IY
         NIY=IY
         LX=IX-1
         LAP(1,1)=NIX
         LAP(1,2)=NIY
         LCNT=1
         IF (LMM(NIX,NIY) .EQ. 46) GO TO 306
```

```
C       If we are at a marker go to 306
        IERR = 57
C       Not at marker or bond - exit to calling state
        CALL MYERR(IERR,KAR,MAR)
C       Shift old picture back to MM etc.
        IX = FIX
        IY = FIY
        CALL CURSOR(IX,IY)
        CALL SHIF(2,MC,LC)
        COPY = 0
        GO TO 305
306     ITRY = 1
C       We will try 4 orientations of the attaching group before
C       we give up - We will try the unrotated and unreflected
C       group first because it is likely to look the best
        ADIR=BDIR
        IFLIP=-1
        IROT=1
310     CALL DELTA(ADIR,INCX,INCY)
C Get delta values so you can calculate where to attach the bond
        DX=ABX-NIX+INCX
        DY=ABY-NIY+INCY
        IF (ITRY .GT. 1) CALL FIXMRK(1,MC)
C Eliminate debris from LABL and MRKCHN
        CALL CLRPIX(1)
C Clear the MM array
        IF (SYM .EQ. 2 .OR. (SYM .EQ. 1 .AND. IFLIP .EQ. -1))
     1  CALL MOVEIT(DX,DY,LENP,LENM,LLLEN,LENC,LEND,ABX,ABY,IROT,IERR)
C Move picture from CONNEC to MM with translation to new origin plus rotation
        IF (IHP .NE. 1) THEN
        IF (IROT.EQ.4) THEN
            IROT = 2
        ELSE IF (IROT.EQ.2) THEN
            IROT = 4
        ENDIF
        ENDIF
        IF (SYM .EQ.1 .AND. IFLIP .NE. -1)
     1  CALL MOVEFL(DX,DY,LENP,LENM,LLLEN,LENC,LEND,ABX,ABY,IFLIP,IERR)
C Move picture from CONNEC to MM with translation and reflection
        IF (IERR .NE. 0) GO TO 300
C If the move didn't work - bail out
        CALL FIXUP(IERR)
C Fix up any bad node caused by rotations or reflections
        IF (IERR .EQ. -1) GO TO 300
C Irreparable node - bail out or try new orientation
        ierr=0
        DO 3402 I = LOX,HIX
        DO 3402 J = LOY,HIY
        ii=i
        jj=j
        LL = LMM(I,J)
        IF ((LL.EQ.46).OR.((LL.GE.65).AND.(LL.LE.90)).OR.
     *      ((LL.GE.95).AND.(LL.LE.122)).OR.((LL.GE.50).AND.
     *      (LL.LE.57).AND.(MM(I-1,TY).EQ.72))) THEN
            DO 112 X = -1,1
            MX = I + X
            IF ((MX.LE.0).OR.(MX.GT.MAXX)) GO TO 112
            DO 1212 Y = -1,1
                MY = J + Y
                IF ((MY.LE.0).OR.(MY.GT.MAXY)) GO TO 1212
                L = MOD(IDTPIX(MX,MY),2**13)
                IF ((L.EQ.0).OR.(L.GE.256)) GO TO 1212
                IF ((L.EQ.34).OR.(L.EQ.43).OR.(L.EQ.45).OR.
     *              (((L.GE.50).AND.(L.LE.57)).AND.((MOD(IDTPIX(MX-1,
     *              MY),2**13).EQ.43).OR.(MOD(IDTPIX(MX-1,MY),2**13)
     *              .EQ.45).OR.((IABS(X+Y).NE.1).AND.(IDTPIX(MX-1,MY)
     *              .EQ.72))).AND.(MX-1.GT.0))) GO TO 1212
                IERR = 48
                GO TO 3033
1212        CONTINUE
112         CONTINUE
            if ((MM(I,J).EQ.46).OR.(mm(i,j).ge.65 .and. mm(i,j).le.90
     1         .and. (mm(i,j).ne.72 .or. (mm(i,j).eq.72
     2         .and. mm(i+1,j).ge.97 .and. mm(i+1,j).le.122))))
     3         call vlnce(2,ii,jj,0,0,ierr)
        ENDIF
```

```
3033        IF (IERR.EQ.12) THEN
                IERR = 0
                EX = II
                EY = JJ
            ELSE if (ierr.ne. 0) THEN
                DO 3705 L = 1,260
                    IF (LABL(L,1).EQ.0) THEN
                        LOW =   L - LENM
                        DO 3703 LL = LOW,L-1
                            LABL(LL,1) = 0
                            LABL(LL,2) = 0
3703                    CONTINUE
                        GO TO 300
                    ENDIF
3705            CONTINUE
                go to 300
            ENDIF
3402    continue
        CALL CURSOR(LOX,LOY)
        DO 301 I = LOX,HIX
        DO 301 J = LOY,HIY
        II = I
        JJ = J
        IF (MM(I,J) .EQ. 0) GO TO 301
        IF ((I.EQ.NIX).AND.(J.EQ.NIY)) GO TO 301
C Spot is empty - no collision problem
C       Not is empty - no collision problem
        BLOB=LMM(I,J)
C       This is used to see if a possible collision is acceptable
        CALL LOOKR(II,JJ,ICHECK,LCNT,BLOB)
C       Check for conflicts
C
        IF (ICHECK .NE. 0) THEN
            DO 1705 L = 1,260
                IF (LABL(L,1).EQ.0) THEN
                    LOW =   L - LENM
                    DO 1703 LL = LOW,L-1
                        LABL(LL,1) = 0
                        LABL(LL,2) = 0
1703                CONTINUE
                    GO TO 300
                ENDIF
1705        CONTINUE
            GO TO 300
        ENDIF
C       Bad conflict - bail out or try new orientation
301     CONTINUE
        MX = ABX - DX
        MY = ABY - DY
        MBTYPE = MM(MX,MY) / 256
        IF ((MBTYPE.EQ.6).OR.(MBTYPE.EQ.7)) THEN
            IF (((BDIR.EQ.1).AND.((ADIR.EQ.1).OR.(ADIR.EQ.5))).OR.
     *          (BDIR.EQ.6).OR.(BDIR.EQ.8).OR.
     *          ((BDIR.EQ.1).AND.(ADIR.EQ.3)).OR.
     *          ((BDIR.EQ.7).AND.((ADIR.EQ.3).OR.(ADIR.EQ.5)))) THEN
                IF (MBTYPE.EQ.6) THEN
                    MBTYPE = 7
                ELSE
                    MBTYPE = 6
                ENDIF
                COPYB = MBTYPE * 256 + ADIR
                DO 2998 I = 1,BLEN
                    IF (LMM(MX,MY).LT.256) GO TO 2999
                    MM(MX,MY) = COPYB
                    MX = MX - INCX
                    MY = MY - INCY
2998            CONTINUE
2999            CONTINUE
            ENDIF
            MX = ABX - DX
            MY = ABY - DY
            IF (((BDIR.EQ.1).AND.(ADIR.EQ.1))
     *          .OR.((BDIR.EQ.5).AND.((ADIR.EQ.7).OR.(ADIR.EQ.1)))
     *          .OR.((BDIR.EQ.3).AND.((ADIR.EQ.6).OR.(ADIR.EQ.1)))
     *          .OR.((BDIR.EQ.6).AND.((ADIR.EQ.6).OR.(ADIR.EQ.8)))
     *          .OR.((BDIR.EQ.8).AND.((ADIR.EQ.6).OR.(ADIR.EQ.8)))
     *          .OR.((BDIR.EQ.2).AND.((ADIR.EQ.6).OR.(ADIR.EQ.8)))
     *          .OR.((BDIR.EQ.4).AND.((ADIR.EQ.6).OR.(ADIR.EQ.8))))
```

```
      *           THEN
                  CBDIR = ADIR + 4
                  IF (CBDIR.GT.8) CBDIR = CBDIR - 8
                  IF (MBTYPE.EQ.6) THEN
                      COPYB = 7 * 256 + CBDIR
                  ELSE
                      COPYB = 6 * 256 + CBDIR
                  ENDIF
                  DO 8998 I = 1,BLEN
                      IF (LMM(MX,MY).LT.256) GO TO 8999
                      MM(MX,MY) = COPYB
                      MX = MX - INCX
                      MY = MY - INCY
 8998             CONTINUE
 8999             CONTINUE
              ENDIF
          ENDIF
C         Irreparable node - bail out or try new orientation
          IF (IOP .EQ. 1) IFLIP=0
C         Prepare for possible delete and go draw group
          IF (IHP .NE. 1) THEN
          IF (IROT.EQ.2) THEN
              IROT = 4
          ELSE IF (IROT.EQ.4) THEN
              IROT = 2
          ENDIF
          ENDIF
          GO TO 240
C         No collisions - go draw it
 300      ITRY=ITRY+1
          IF (ITRY .GT. 4) GO TO 5460
          JPROB = 0
C         Bail out - we can't do it
          IROT=IROT+1
          ADIR=BDIR + (IROT-1)*2
          IF (IHP .EQ. 1 .AND. IROT .EQ. 2) ADIR = ADIR + 4
          IF (IHP .EQ. 1 .AND. IROT .EQ. 4) ADIR=ADIR-4
C         Halo y axis direction is opposite HP and requires rotational
C         substitution.
          IF (IHP .NE. 1) THEN
          IF (IROT.EQ.2) THEN
              IROT = 4
          ELSE IF (IROT.EQ.4) THEN
              IROT = 2
          ENDIF
          ENDIF
          IF (ADIR .GT. 8) ADIR=ADIR-8
C
          IFLIP = THETA(BDIR,ADIR)
          IF (IFLIP.EQ.2) THEN
              IFLIP = 4
          ELSE IF (IFLIP.EQ.4) THEN
              IFLIP = 2
          ENDIF
C Get reflection value
          GO TO 310
C Try next orientation
C         Try next orientation
 5460     IERR=48
C         No space or distorted node - issue error message
          IF (JPROB.EQ.0) CALL MYERR(IERR,KAR,KAR)
          CALL SHIF(2,MC,LC)
          COPY = 0
          GO TO 305
C         Await new command
```

```
C************************************************************
C       This section tries to display a stand alone structure
C       It defines the origin for the new structure - Determines the
C       minimum X and Y coordinates in the new structure - Calculates
C       the translation values needed and checks to see if the new
C       structure collides with the current structure. If no collision
C       occurs, the MM and LNGBND arrays are cleared and the new picture
C       is moved (with the necessary translation to the new origin)
C       into MM. If there is a bounds problem encountered while copying
C       the picture to MM, an error message is issued, the old picture
C       array is copied back into MM and the program awaits entry of a
C       new command.
C************************************************************
200     ALONE = 1
        IF (OCHAR .NE. 68) GO TO 211
C       Set new origin to 0 if KAR = D
        DX=0
        DY=0
        GO TO 212
211     OX=IX
C       We are doing a stand alone structure
        OY=IY
C       Set new origin
C       Find min X and min Y in structure we're going to retrieve
        MX=10000
        MY=10000
        J=1
        DO 13 I=1,LENP
        IF (CONNEC(J) .LT. MX) MX=CONNEC(J)
        IF (CONNEC(J+1) .LT. MY) MY=CONNEC(J+1)
        J=J+3
13      CONTINUE
C
C       Calculate translation value
C
        DX=MX-OX
        DY=MY-OY
C
C       See if new structure at new origin collides with current structure
C
212     J=1
        DO 261  I=1,LENP
        JX=CONNEC(J)-DX
        JY=CONNEC(J+1)-DY
        CALL CELL2(JX,JY,IGOOD)
        IF (IGOOD .NE. 0) GO TO 480
C       IGOOD .NE. 0 implies there is a collision
        J=J+3
261     CONTINUE
        GO TO 260
C
C       We have a collision - issue error messages  - go to await
C       entry of new command
C
480     CONTINUE
C       Type error message
        CALL FTSIZE(2,18)
        CALL FTLOCA(4,1)
        CALL FTEXT('^New structure collides with old structure - ^')
        PMESS=.TRUE.
        GO TO 491
C
C       No collision - clear MM and LNGBND
C
260     CALL CLRPIX(1)
250     IROT=1
C Set rotation to 0 degree rotation
        IFLIP=-1
        CALL MOVEIT(DX,DY,LENP,LENM,LLLEN,LENC,LEND,ABX,ABY,IROT,IERR)
C Move picture from CONNEC to MM with translation to new origin
        IF (IERR .NE. 0) GO TO 490
C If there is a bounds problem - bail out
C       Fill in valence hydrogens
        IF (DOT .EQ. 1) GO TO 6512
```

```
C Skip valence call if we have a DOTDIS
      IERR=0
      DO 4910 I = LOX,HIX
      DO 4910 J = LOY,HIY
      II=I
      JJ=J
      LL = LMM(I,J)
      IF ((LL.EQ.46).OR.((LL.GE.65).AND.(LL.LE.90)).OR.
     *    ((LL.GE.95).AND.(LL.LE.122)).OR.((LL.GE.50).AND.
     *    (LL.LE.57).AND.(MM(I-1,TY).EQ.72))) THEN
         DO 113 X = -1,1
           MX = I + X
           IF ((MX.LE.0).OR.(MX.GT.MAXX)) GO TO 113
           DO 1313 Y = -1,1
             MY = J + Y
             IF ((MY.LE.0).OR.(MY.GT.MAXY)) GO TO 1313
             L = MOD(IDTPIX(MX,MY),2**13)
             IF ((L.EQ.0).OR.(L.GE.256)) GO TO 1313
             IF ((L.EQ.34).OR.(L.EQ.43).OR.(L.EQ.45).OR.
     *          ((L.GE.50).AND.(L.LE.57)).AND.((MOD(IDTPIX(MX-1,
     *          MY),2**13).EQ.43).OR.(MOD(IDTPIX(MX-1,MY),2**13)
     *          .EQ.45).OR.((IABS(X+Y).NE.1).AND.(IDTPIX(MX-1,MY)
     *          .EQ.72))).AND.(MX-1.GT.0))) GO TO 1313
             IERR = 48
             GO TO 4040
1313       CONTINUE
113        CONTINUE
         if ((MM(I,J).EQ.46).OR.(mm(i,j).ge.65 .and. mm(i,j).le.90
     1      .and. (mm(i,j).ne.72 .or. (mm(i,j).eq.72
     2      .and. mm(i+1,j).ge.97 .and. mm(i+1,j).le.122))))
     3      call vlnce(2,ii,jj,0,0,ierr)
      ENDIF
4040  IF (IERR.EQ.12) THEN
         IERR = 0
         EX = II
         EY = JJ
      ELSE IF (IERR.NE.0) THEN
         DO 4705 L = 1,260
           IF (LABL(L,1).EQ.0) THEN
             LOW = L - LENM
             DO 4703 LL = LOW,L-1
               LABL(LL,1) = 0
               LABL(LL,2) = 0
4703         CONTINUE
             GO TO 3305
           ENDIF
4705     CONTINUE
         GO TO 3305
      ENDIF
4910  CONTINUE
      GO TO 6512
3305  CALL CLRPIX(1)
      CALL SHIF(2,MC,LC)
      COPY = 0
      GO TO 305
6512  CONTINUE
      DO 492 I = LOX,HIX
      DO 492 J = LOY,HIY
      II = I
      JJ = J
      IF (MM(I,J) .EQ. 0) GO TO 492
      CALL CELL2(I,J,IGOOD)
      IF (IGOOD .NE. 0 ) THEN
         DO 5705 L = 1,260
           IF (LABL(L,1).EQ.0) THEN
             LOW = L - LENM
             DO 5703 LL = LOW,L-1
               LABL(LL,1) = 0
               LABL(LL,2) = 0
5703         CONTINUE
             GO TO 490
           ENDIF
5705     CONTINUE
         GO TO 490
```

```
          ENDIF
492       CONTINUE
          GO TO 240
C         If there is no bounds problem - go to 240 where we will display
C         the picture.  If we have a bounds problem, shift old picture back
C         to MM etc.  Type error message - and go to await new command.
C
490       CONTINUE
491       CALL SHIF(2,MC,LC)
          CALL FTSIZE(2,18)
          IF (IHP .EQ. 1 .AND. PMESS .EQ. .TRUE.) THEN
                         PMESS=.FALSE.
                    ELSE
          CALL FTLOCA(4,1)
          ENDIF
          COPY = 0
C         Type error message
          CALL FTEXT('^Bad origin requested ^')
          PAGE = 0
          IF (OCHAR.EQ.68) THEN
             CALL FTEXT('^                                          ^')
             CALL FTSIZE(1,10)
             GO TO 9222
          ENDIF
C Have we tried default origin
          OCHAR=68
          IF (IHP .EQ. 1) CALL FTLOCA(5,1)
          CALL FTEXT('^- Will try default origin.^')
          IF (IHP .EQ. 1) THEN
                   CALL DELAY
                   CALL DELAY
                   CALL FTLOCA(5,1)
                   CALL FTEXT('^                                     ^')
                   ENDIF
          CALL FTSIZE(1,10)
          GO TO 200
9222      OCHAR=0
C We've tried default - give up
          GO TO 305
C*********************************************************************
C         This section displays the retrieved structure.
C         It defines the parameters LBLEN (# of long bonds) and
C         NJNEXT (last marker index used) - displays the structure -
C         Sets XCHAR = 0 (This indicates that we just did a retrieve)
C         Sets OCHAR = 0 (This indicates that the origin is not the
C         default origin.
C         It then adds the old picture back to the new picture (MM) and
C         adds the old long bonds to the new long bonds (LNGBND).
C         It then clears screen dialog and moves the cursor to the
C         requested final cursor position. The cursor position is
C         adjusted by SYNCH if it is not at a valid position.
C*********************************************************************
240       CONTINUE
          NJNEXT=LENM+MC
          ISWIT=1
C         Call STRDRW with markers displayed as markers
          LBLEN=LLLEN
          do 2562,ii=1,maxx
          do 2562,jj=1,maxy
2562      continue
          CALL STRDRW(ISWIT)
          ICUR = 1
C         Display retrieved structure
C
C         Move the structure back to CONNEC - We may have called FIXUP
C         which may have moved nodes - thus we need a good copy in
C         CONNEC in case we have to do a delete
C
          K=1
          DO 94 I = LOX,HIX
          DO 94 J = LOY,HIY
          IF (MM(I,J) .EQ. 0) GO TO 94
          DELET(K)=I
          DELET(K+1)=J
```

```
              DELET(K+2)=MM(I,J)
              K=K+3
94            CONTINUE
              DENP = K / 3
              XCHAR=0
C             XCHAR = 0 implies that we just did a retrieve
              OCHAR=0
C             Reset origin character to not default
              CALL ADDBCK
C             Add old picture to new picture
              CALL ADDLNG(LC,LLLEN)
C             Add old long bonds to new long bonds
              COPY=0
C Current picture is in MM
C Erase dialog
              SSYM = SYM
              CALL FINDXY(IX,IY,LBX,LBY,DX,DY,ABX,ABY,IROT,IFLIP,SSYM)
              SYM = SSYM
C Calculate final cursor values
              IF (ALONE .EQ. 0 ) GO TO 5687
              ALONE=0
              IF (BLEN .EQ. 0) GO TO 5687
              CALL DELTA(BDIR,KNCX,KNCY)
C Delete dangling bond if structure is stand alone and has dangling bond.
              KX=ABX-DX+KNCX
              KY=ABY-DY+KNCY
              JCHAR=1
              ICHAR=1
              CALL DEL(KAR,KX,KY,KNCX,KNCY,IWHICH)
CXT
CXT           The valence hydrogens of the attached node are computed.
              PNODE = .TRUE.
              DELH(1,3) = 0
              DELH(2,3) = 0
              SXX = KX - 1
              CALL CLRHYD(SXX,KY)
              CALL VLNCE(1,SXX,KY,0,0,IERR)
              PNODE = .FALSE.
CXT           The valence hydrogens of the attached node are made deletable.
              DO 5369 I = 1,2
                 IF (DELH(I,3).NE.0) THEN
                    DELET(K) = DELH(I,1)
                    DELET(K+1) = DELH(I,2)
                    DELET(K+2) = DELH(I,3)
                    DENP = DENP + 1
                    K = K + 3
                 ENDIF
5369          CONTINUE
CXT
C Delete bond
              IF (IERR.EQ.12) THEN
                 IX = EX
                 IY = EY
              ENDIF
              IF (IABS(ABX-LBX).GT.1 .OR. IABS(ABY-LBY).GT.1) GO TO 4568
C If beginning site
C equals leaving site equals bond and we have deleted bond
C set cursor to node at end of erased bond
              IX=KX
              IY=KY
5687          IF (IERR.EQ.12) THEN
                 IX = EX
                 IY = EY
              ENDIF
              IF (NODE .NE. 0 ) GO TO 4567
              IF (DIFF .GE. 0) GO TO 4567
              IF (IABS(ABX-LBX).GT.1 .OR. IABS(ABY-LBY).GT.1) GO TO 4567
              IX=OBX
C The bond on disk is longer than the bond on screen
              IY=OBY
C Adjust the final cursor position so that it is really
C at the end of the screen bond
4567          IF (DOT .NE. 1) GO TO 4568
```

```
          IX=IX-1
C Skip SYNCH call if this is a DOTDIS
          GO TO 305
4568      CALL SYNCH(KAR,IX,IY)
C Adjust and display final cursor position
          GO TO 305
C
CXXXXXXXXXXXXXXXXXXXXXXXXXXXXXXXXXXXXXXXXXXXXXXXXXXXXXXXXXXXXXXXXX
C         This section will call IDENT to handle bond entry commands -
C         marker entry commands and jump to marker commands
C         It then sets XCHAR to 1 to indicate that we just called IDENT
C         and did not just do a retrieve - This parameter is used by the delete sect
CXXXXXXXXXXXXXXXXXXXXXXXXXXXXXXXXXXXXXXXXXXXXXXXXXXXXXXXXXXXXXXXXX
793       CALL IDENT(KKAR,IX,IY,INCX,INCY,IRESET)
          IF ((KKAR.GE.22).AND.(KKAR.LE.31)) NOCHG = 0
C         Do bond-enter marker-or-jump to marker
          XCHAR=1
C         XCHAR=1 implies that we just did a call to IDENT - not a retrieve
          IF (KKAR.NE.38) GO TO 305
          ISTATE = 12
          MW(7) = 999
          MW(8) = 999
          MW(9) = 999
          CALL HEADER
          GO TO 305
C         Go get next command
CXXXXXXXXXXXXXXXXXXXXXXXXXXXXXXXXXXXXXXXXXXXXXXXXXXXXXXXXXXXXXXXXX
C         This section sets the type of symmetry to axial
CXXXXXXXXXXXXXXXXXXXXXXXXXXXXXXXXXXXXXXXXXXXXXXXXXXXXXXXXXXXXXXXXX
955       SYM=1
          CALL HEADER
          GO TO 305
CXXXXXXXXXXXXXXXXXXXXXXXXXXXXXXXXXXXXXXXXXXXXXXXXXXXXXXXXXXXXXXXXX
C         This section sets the symmetry to point
CXXXXXXXXXXXXXXXXXXXXXXXXXXXXXXXXXXXXXXXXXXXXXXXXXXXXXXXXXXXXXXXXX
966       SYM=2
          CALL HEADER
          GO TO 305
CXXXXXXXXXXXXXXXXXXXXXXXXXXXXXXXXXXXXXXXXXXXXXXXXXXXXXXXXXXXXXXXXX
C         This section sets a bondtype and does a bond command or
C         sets a charge value and enters a charge.
CXXXXXXXXXXXXXXXXXXXXXXXXXXXXXXXXXXXXXXXXXXXXXXXXXXXXXXXXXXXXXXXXX
3561      CALL CURSOR(IX,IY)
          CALL NUMBER(KKAR,IX,IY)
          IF (KKAR.EQ.81) GO TO 6777
          MW(7) = 999
          MW(8) = 999
          MW(9) = 999
          ISTAT = ':'
          ISTATE = 12
          CALL HEADER
          GO TO 305
CXXXXXXXXXXXXXXXXXXXXXXXXXXXXXXXXXXXXXXXXXXXXXXXXXXXXXXXXXXXXXXXXX
C         This section deletes the result of the last operation
C         If XCHAR = 0, we delete the last retrieved structure
C         If XCHAR = 1, we delete the last bond or marker entered
CXXXXXXXXXXXXXXXXXXXXXXXXXXXXXXXXXXXXXXXXXXXXXXXXXXXXXXXXXXXXXXXXX
650       IF (XCHAR .NE. 0) GO TO 728
C         If XCHAR = 1 we will go delete a bond or marker
C
C         We will be deleting the structure just drawn
C
          J=1
          BX=KX
          BY=KY
C         This loop picks up the X and Y coordinates from DELETE
C         ZAP is called to erase from the screen the character or bond at KX,KY
C
          ICUR = 0
          CALL CURSOR(KX,KY)
          DO 527 I=1,DENP
          KX=DELET(J)
          KY=DELET(J+1)
528       CALL ZAP(KX,KY)
C         Erase the character or bond at KX,KY
```

```
529         J=J+3
527         CONTINUE
C
C           Erase current pointer bond
            IF (NODE.NE.0) GO TO 7529
            DO 545 I=1,OBLEN
                MX=OBX + (I-1)*INCX
                MY=OBY + (I-1)*INCY
                CALL ZAP(MX,MY)
545         CONTINUE
            SXX = MX - INCX
            SYY = MY - INCY
            CALL CLRHYD(SXX,SYY)
            CALL VALNCE(2,SXX,SYY,0,0)
C
C           Now delete the long bonds from the new structure
C
7529        IF (LLLEN .EQ. 0) GO TO 980
            OCHAR=JCHAR
C           Save old JCHAR
            JCHAR=8
C           Set JCHAR so that we will delete longbond
            DO 64 I=1,LLLEN
            CALL DEL(KAR,IX,IY,INCX,INCY,0)
C           Del last longbond drawn
64          CONTINUE
C
C           Delete the last LLLEN longbonds from LLBOND before SHIFT is
C           called.
            DO 984 I = LLLEN+LC,LC+1,-1
            DO 984  J=1,5
            LLBOND(I,J)=0
984         CONTINUE
            LBLEN = LC
C
C           Now move old picture back to MM etc.
C
980         CONTINUE
            CALL SHIF(2,MC,LC)
            COPY = 0
            NJNEXT=MC
            LABL(NJNEXT+1,1) = 0
C           Index of last used label
            JCHAR=OCHAR
C           Restore JCHAR
            ICUR = 1
            CALL CURSOR(IX,IY)
C
C           Redraw pointer bond if we were attaching to bond not node
C
            IF (NODE .NE. 0) GO TO 444
683         OTYPE=IBTYPE
C           Save old bond type and enlarge factor
            OLARGE=NLARGE
            NOCHG = 1
            IBTYPE = OBTYPE
C           Set bond type for pointer bond
            NLARGE=OBLEN
C           Set bond length for pointer bond
            ICHAR=2
            JCHAR=2
C           Set JCHAR to 'just entered a node'
            CMD=OBDIR+21
C           Set CMD to bond command
            IF (CMD .GT. 25) CMD=CMD+2
            PPIX = PIX + 1
            PPIY = PIY
            CALL IDENT(CMD,PPIX,PPIY,INCX,INCY,IRESET)
C           Redraw bond
            NLARGE=OLARGE
C           Reset NLARGE and IBTYPE
            NOCHG=0
            IBTYPE=OTYPE
444         IX=LX
C           Reset coordinates as they were when we started RETRIEVE
            IY=LY
```

```
              CALL SYNCH(KAR,IX,IY)
              XCHAR = 1
C             Adjust and display cursor position
              GO TO 305
C             Delete last bond or marker
728           COPY=0
              CALL IDENT(KKAR,IX,IY,INCX,INCY,IRESET)
              GO TO 305
C*********************************************************************
C
C             We found too many markers or longbonds - Issue error message
C             Shift old picture back to MM etc.  -  Then exit
C
C*********************************************************************
333           CONTINUE
              CALL FTSIZE(2,18)
              CALL FTLOCA(4,1)
              CALL FTEXT('^Command aborted - Too many markers or longbonds^')
              PAGE = 0
              CALL FTSIZE(1,10)
C
C             Shift old picture back to MM etc.
C
              CALL SHIF(2,MC,LC)
              COPY = 0
              GO TO 6777
C*********************************************************************
C             We found a bounds problem in CONNEC - Close the file
C             Release the channel - Issue an error message and prepare
C             to exit.
C*********************************************************************
999           IERR = 54
              CALL MYERR(IERR,KAR,MAR)
C             Bounds problem with CONNEC
67            CLOSE(IU)
C             Close file
              GO TO 305
C*********************************************************************
C             This section prepares to exit from GETIT
C             The screen dialog is erased.
C             If we came from Ground level - call HEADER to display
C             Ground level heading and return to Ground level
C             If we came from RING or CHAIN, then display the
C             appropriate heading and return to RING or CHAIN
C             respectively
C*********************************************************************
6777          CONTINUE
              IF (FILE.NE.'            ') LFILE = FILE
              LCHAR=KCHAR
              KAR=KKAR
              ISTATE=0
              IF ((LCHAR .EQ. 12 .OR. LCHAR .EQ.13).and.kkar.ne.81) GO TO 2000
              LFLAG=0
              IF (KKAR .EQ. 81) LFLAG=1
              LEVEL=0
              DO 6789 I=1,12
6789          MW(I)=999
C FORCE A COMPLETE NEW HEADING
              ISKIP = 0
              CALL HEADER
C             SET LEVEL AND ISTATE TO GROUND AND CALL HEADER
              RETURN
2000          LFLAG=1
              LEVEL=1
              ICHAR=LCHAR
              IF (ICHAR .EQ. 12) KAR = 94
              IF (ICHAR .EQ. 13) KAR = 33
              DO 9898 I = 1,12
9898          MW(I) = 999
              ISKIP = 0
              CALL HEADER
              RETURN
              END
$STORAGE:2
C
```

```
C       SUBROUTINE MAP(IX,IY,NODE,BDIR)
C
C       This subroutine examines the neighborhood of point MM(IX,IY)
C       to determine if the point is a node or a bond or neither
C
C       NODE = 0  implies that we are at the end of a bond
C       NODE = 1  implies that we are at a node
C       NODE = -1 implies that we are not at a node or a bond or a
C          3X3 clear space
C       NODE = -2 implies we are at a 3X3 clear space
C       BDIR = bond direction of bond if NODE = 0
C       Beware - MAP may change IX - If IX,IY is near a node -
C       i.e. at 2 or H of CH2 - IX will be altered so that it
C       is at the C
        SUBROUTINE MAP(IX,IY,NODE,BDIR)
        IMPLICIT INTEGER*2 (A-Z)
        INTEGER*4 MM
        COMMON /STRPIX/ LPIX,MM(90,38),LBLEN,LNGBND(100,5)
C
C       Determine if we are at a 3X3 blank space
C
        NODE = -2
        CALL NEW(SUM,IX,IY)
C       SUM = 0  implies we are at a 3X3 blank space - i.e. not bond or node
        IF (SUM .EQ. 0) THEN
        RETURN
        ENDIF
C
C       We are not at a 3X3 blank area - See if we are at a bond
C
        IF (MM(IX,IY) .NE. 0) GO TO 12
C       MM(IX,IY) not equal 0 implies we are not at the end of a bond
C       because the cursor is positioned at empty cell just
C       beyond bond after a bond is entered
        CALL FINDB(IBDIR,KBDIR,IX,IY)
C       See if there is a bond around MM(IX,IY)
        IF (IBDIR .EQ. -1) GO TO 12
C       IBDIR=-1 implies that we are not at a bond
        NODE = 0
C       We are at the end of a bond - Set NODE=0 and BDIR to bond direction
        BDIR=KBDIR
        GO TO 13
C
C       Determine if we are at a node
C
12      KX=IX
        DO 30 I=0,5
C       See if we are at a node - Node = marker, ?, or upper case
        MX=KX-I
        LL=LMM(MX,IY)
        IF ((LL .NE. 46) .AND. (LL .NE. 63) .AND. ((LL .LT. 65) .OR.
     1  (LL .GT. 90))) GO TO 30
        IF (LL .EQ. 72 .AND. ((MM(MX+1,IY) .LE. 97 .OR. (MM(MX+1,IY))
     1    .GE. 122))) GO TO 30
        IX=MX
        CALL CURSOR(IX,IY)
        NODE=1
C       We are at a node
        GO TO 13
30      CONTINUE
C
C       We are not at a node or a bond
C
11      NODE=-1
C       We aren't at a bond or a node
13      CONTINUE
        RETURN
        END
C
C       SUBROUTINE MOVEIT(DX,DY,LENP,LENM,LLLEN,LENC,LEND,ABX,ABY,IROT,
C      IERR)
C       THIS SUBROUTINE MOVES THE PICTURE FROM ITS TEMPORARY STORAGE
C       PLACE IN CONNEC TO MM - IN THE PROCESS IT TRANSLATES THE
C       PICTURE TO THE NEW ORIGIN BY USING THE DELTA VALUES DX AND DY
C       IF NECESSARY (IN THE CASE OF AN ATTACHING GROUP) IT ALSO ROTATES
```

```
C       THE GROUP AROUND THE GROUPS ATTACHING BOND AT ABX,ABY
C       THE ANGLE OF ROTATION IS SPECIFIED BY IROT
C       IROT=1 = ANGLE 0    IROT=2 = ANGLE 90    IROT=3 = ANGLE 180
C       IROT=4 = ANGLE 270
C
        SUBROUTINE MOVEIT(DX,DY,LENP,LENM,LLLEN,LENC,LEND,ABX,ABY,IROT,
     *      IERR)
        IMPLICIT INTEGER*2(A-Z)
        INTEGER*4 MM,IDTPIX,CONNEC,LL
        COMMON /STRPIX/ LPIX,MM(90,38),LBLEN,LNGBND(100,5)
        COMMON /STRED/ IDTPIX(90,38),LABL(260,2),MRKCHN(260)
        COMMON /CD/ MAXX,MAXY
        COMMON /RANGE/ LOX,HIX,LOY,HIY
        COMMON /ENTRAR/ CONNEC(2001)
        DIMENSION KSIN(4),KCOS(4)
        DATA KSIN /0,1,0,-1/
        DATA KCOS /1,0,-1,0/
        IERR=0
C       Return code - IERR will be set to 1 if we have bounds problems
        IF (IROT.EQ.2) THEN
            ROT = 4
        ELSE IF (IROT.EQ.4) THEN
            ROT = 2
        ELSE
            ROT = IROT
        ENDIF
        DELT = (ROT - 1) * 2
        J=1
        DO 200 I=1,LENP
        TX=((CONNEC(J)-ABX)*KCOS(IROT)+(CONNEC(J+1)-ABY)*KSIN(IROT))
     1  +ABX-DX
        TY=-(CONNEC(J)-ABX)*KSIN(IROT)+(CONNEC(J+1)-ABY)*KCOS(IROT)
     1  +ABY-DY
        IF (TX .GT. 0 .AND. TX .LE. MAXX .AND. TY .GT. 0
     1  .AND. TY .LE. MAXY) GO TO 201
225     IF (TX .GT. 0 .AND. TX .LE. MAXX .AND. TY .GT. 0
     1  .AND. TY .LE. MAXY) GO TO 201
55      IERR = 48
C       We found a bounds problem
        RETURN
201     CONTINUE
        IF (TX.LT.LOX) THEN
            LOX = TX
        ELSE IF (TX.GT.HIX) THEN
            HIX = TX
        ENDIF
        IF (TY.LT.LOY) THEN
            LOY = TY
        ELSE IF (TY.GT.HIY) THEN
            HIY = TY
        ENDIF
        LL=CONNEC(J+2)
C       Translate values to new origin and store in MM
        MM(TX,TY)=LL
        IF (LMM(TX,TY).LT.256) GO TO 203
C
C       If LL is a bond - rotate it and then store in MM
C
        BDIR=IDIR(LL)
C       Extract bond dir from bond
        LL=LL-BDIR
        BDIR=BDIR+DELT
C       Rotate bond
        IF (BDIR .GT. 8) BDIR=BDIR-8
        LL=LL+BDIR
        MM(TX,TY)=LL
C       Store rotated bond in MM
203     J=J+3
200     CONTINUE
        IF (LENM .EQ. 0) GO TO 207
        DO 40 I=1,260
        II = I
        IF (LABL(I,1) .EQ. 0) GO TO 50
40      CONTINUE
50      LABLEN = II-1
```

```
C       Find end of LABL ARRAY
        IF (LABLEN+LENM .GT. 260) THEN
            IERR = 48
            RETURN
        ENDIF
C       Bounds problem with LABL array
        DO 206 I=LABLEN+1,LABLEN+LENM
C       Copy markers to end of present marker array
        LABL(I,1)=((CONNEC(J)-ABX)*KCOS(IROT)+(CONNEC(J+1)-ABY)
     1  *KSIN(IROT))+ABX-DX
        LABL(I,2)=-(CONNEC(J)-ABX)*KSIN(IROT)+(CONNEC(J+1)-ABY)
     1  *KCOS(IROT)+ABY-DY
        MRKCHN(I)=CONNEC(J+2)
        J=J+3
206     CONTINUE
207     IF (LLLEN.EQ.0) GO TO 2088
C       Set up
        DO 209 I=1,LLLEN
        LNGBND(I,1)=((CONNEC(J)-ABX)*KCOS(IROT)+
     1  (CONNEC(J+1)-ABY)*KSIN(IROT))+ABX-DX
        LNGBND(I,2)=-(CONNEC(J)-ABX)*KSIN(IROT)+
     1  (CONNEC(J+1)-ABY)*KCOS(IROT)+ABY-DY
        LNGBND(I,3)=((CONNEC(J+2)-ABX)*KCOS(IROT)+
     1  (CONNEC(J+3)-ABY)*KSIN(IROT))+ABX-DX
        LNGBND(I,4)=-(CONNEC(J+2)-ABX)*KSIN(IROT)+
     1  (CONNEC(J+3)-ABY)*KCOS(IROT)+ABY-DY
        LNGBND(I,5)=CONNEC(J+4)
        J=J+5
209     CONTINUE
C
2088    IF (LENC .EQ. 0) GO TO 2081
C Handle charges if there are any
        DO 1200 I=1,LENC
        TX=((CONNEC(J)-ABX)*KCOS(IROT)+(CONNEC(J+1)-ABY)*KSIN(IROT))
     1  +ABX-DX
        TY=-(CONNEC(J)-ABX)*KSIN(IROT)+(CONNEC(J+1)-ABY)*KCOS(IROT)
     1  +ABY-DY
        IF (TX .GT. 0 .AND. TX .LE. MAXX .AND. TY .GT. 0
     1  .AND. TY .LE. MAXY) GO TO 1201
5555    IERR=48
C We found a bounds problem
        RETURN
1201    CONTINUE
        KAR=CONNEC(J+2)
C Get sign of charge
        NCHRG=CONNEC(J+3)
C Get digit associated with charge
        CALL ZHARGE(KAR,TX,TY,NCHRG,IERR)
C Position charge
        IF (IERR .NE. 0) GO TO 5555
C Couldn't place charge - bail out
1203    J=J+4
1200    CONTINUE
2081    IF (LEND.EQ.0) GO TO 208
        DO 1205 I = 1,LEND
        TX = ((CONNEC(J)-ABX)*KCOS(IROT)+(CONNEC(J+1)-ABY)*
     *      KSIN(IROT)) + ABX - DX
        TY = -(CONNEC(J)-ABX)*KSIN(IROT)+(CONNEC(J+1)-ABY)*
     *      KCOS(IROT) + ABY - DY
        IF ((TX.GT.0).AND.(TY.LE.MAXX).AND.(TY.GT.0).AND.(TY.LE.
     *      MAXY)) GO TO 1202
5556    IERR = 1
        RETURN
1202    KAR = 34
        IDRAW = 1
        CALL IND1(KAR,TX,TY,IDRAW,IERR)
        IF (IERR.NE.0) GO TO 5556
        J = J + 2
1205    CONTINUE
208     CONTINUE
        RETURN
        END
C
C       SUBROUTINE MOVEFL(DX,DY,LENP,LENM,LLLEN,LENC,LEND,ABX,ABY,IFLIP,
C       IERR)
```

```
C
C       THIS SUBROUTINE MOVES THE PICTURE FROM ITS TEMPORARY STORAGE
C       PLACE IN CONNEC TO MM - IN THE PROCESS IT TRANSLATES THE
C       PICTURE TO THE NEW ORIGIN BY USING THE DELTA VALUES DX AND DY
C       AND REFLECTS THE PICTURE AROUND THE X AND/OR Y AXIS ACCORDING TO
C       THE VALUE OF IFLIP
C       IFLIP=1 (REFLECT AROUND X AXIS)
C       IFLIP=2 (REFLECT AROUND LINE MAKING 45 DEGREE ANGLE WITH X AXIS
C       IFLIP=3 (REFLECT AROUND Y AXIS)
C       IFLIP=4 (REFLECT AROUND LINE MAKING 135 DEGREE ANGLE WITH X AXIS
C       IFLIP=5 (REFLECT AROUND X AND Y AXES)
C
        SUBROUTINE MOVEFL(DX,DY,LENP,LENM,LLLEN,LENC,LEND,ABX,ABY,
     *      IFLIP,IERR)
        IMPLICIT INTEGER*2(A-Z)
        INTEGER*4 MM,IDTPIX,CONNEC,LL
        COMMON /STRPIX/ LPIX,MM(90,38),LBLEN,LNGBND(100,5)
        COMMON /STRED/ IDTPIX(90,38),LABL(260,2),MRKCHN(260)
        COMMON /CD/ MAXX,MAXY
        COMMON /RANGE/ LOX,HIX,LOY,HIY
        COMMON /ENTRAR/ CONNEC(2001)
        DIMENSION FLIPBD(8,5),KSIN(4),KCOS(4)
        DATA FLIPBD /5,4,3,2,5,8,7,6,
     *               7,6,5,4,3,6,1,8,
     *               1,8,7,6,5,4,3,2,
     *               3,2,1,8,7,6,5,4,
     *               5,6,7,8,1,2,3,4/
        DATA KSIN /0,1,0,-1/, KCOS /1,0,-1,0/
C
        IERR=0
C       Return code - IERR will be set to 1 if we have bounds problems
        J=1
        DO 200 I=1,LENP
        IF (IFLIP.NE.5) GO TO 219
            TX = -CONNEC(J) + 2 * ABX - DX
            TY = -CONNEC(J+1) + 2 * ABY - DY
            GO TO 225
219     CONTINUE
            TX = ((CONNEC(J)-ABX) * KCOS(IFLIP) + (CONNEC(J+1)-ABY) *
     *          KSIN(IFLIP)) + ABX - DX
            TY = ((CONNEC(J)-ABX) * KSIN(IFLIP) - (CONNEC(J+1)-ABY) *
     *          KCOS(IFLIP)) + ABY - DY
225     IF ((TX.GT.0).AND.(TX.LE.MAXX).AND.(TY.GT.0).AND.(TY.LE.
     *      MAXY)) GO TO 201
55      IERR=48
C       We found a bounds problem
        RETURN
201     CONTINUE
        IF (TX.LT.LOX) THEN
            LOX = TX
        ELSE IF (TX.GT.HIX) THEN
            HIX = TX
        ENDIF
        IF (TY.LT.LOY) THEN
            LOY = TY
        ELSE IF (TY.GT.HIY) THEN
            HIY = TY
        ENDIF
        LL=CONNEC(J+2)
C       Translate values to new origin and store in MM
        MM(TX,TY)=LL
        IF (LMM(TX,TY).LT. 256) GO TO 203
C
C       If LL is a bond - flip it and then store in MM
C
        BDIR=IDIR(LL)
C       Extract bond dir from bond
        LL=LL-BDIR
        BDIR=FLIPBD(BDIR,IFLIP)
C       Flip bond as necessary
        IF (BDIR .GT. 8) BDIR=BDIR-8
        LL=LL+BDIR
C       Store flipped bond in MM
        MM(TX,TY)=LL
203     J=J+3
```

```
200     CONTINUE
        IF (LENM .EQ. 0) GO TO 207
        DO 40 I=1,260
        II = I
        IF (LABL(I,1) .EQ. 0) GO TO 50
40      CONTINUE
50      LABLEN = II-1
C       Find end of LABL ARRAY
        IF (LABLEN+LENM .GT. 260) THEN
            IERR = 49
            RETURN
        ENDIF
C       Bounds problem with LABL array
        DO 206  I=LABLEN+1,LABLEN+LENM
C       Copy markers to end of present marker array
        IF (IFLIP .NE. 5 ) GO TO 406
        LABL(I,1)=-CONNEC(J)+2*ABX-DX
        LABL(I,2)=-CONNEC(J+1)+2*ABY-DY
        MRKCHN(I)=CONNEC(J+2)
        GO TO 407
406     LABL(I,1)=((CONNEC(J)-ABX)*KCOS(IFLIP)+(CONNEC(J+1)-ABY)
     1  *KSIN(IFLIP))+ABX-DX
        LABL(I,2)=((CONNEC(J)-ABX)*KSIN(IFLIP)-(CONNEC(J+1)-ABY)
     2  *KCOS(IFLIP))+ABY-DY
        MRKCHN(I)=CONNEC(J+2)
407     J=J+3
206     CONTINUE
207     IF (LLLEN .EQ. 0) GO TO 2088
C Set up LNGBND
        DO 209 I=1,LLLEN
        IF (IFLIP .NE. 5) GO TO 607
        LNGBND(I,1)=-CONNEC(J)+2*ABX-DX
        LNGBND(I,2)=-CONNEC(J+1)+2*ABY-DY
        LNGBND(I,3)=-CONNEC(J+2)+2*ABX-DX
        LNGBND(I,4)=-CONNEC(J+3)+2*ABY-DY
        GO TO 608
607     LNGBND(I,1)=((CONNEC(J)-ABX)*KCOS(IFLIP)+
     1  (CONNEC(J+1)-ABY)*KSIN(IFLIP))+ABX-DX
        LNGBND(I,2)=((CONNEC(J)-ABX)*KSIN(IFLIP)-
     1  (CONNEC(J+1)-ABY)*KCOS(IFLIP))+ABY-DY
        LNGBND(I,3)=((CONNEC(J+2)-ABX)*KCOS(IFLIP)+
     1  (CONNEC(J+3)-ABY)*KSIN(IFLIP))+ABX-DX
        LNGBND(I,4)=(CONNEC(J+2)-ABX)*KSIN(IFLIP)-
     1  (CONNEC(J+3)-ABY)*KCOS(IFLIP)+ABY-DY
608     LNGBND(I,5)=CONNEC(J+4)
        J=J+5
209     CONTINUE
2088    IF (LENC .EQ. 0) GO TO 2081
C Do charges if there are any
        DO 2000 I=1,LENC
        IF (IFLIP .NE. 5) GO TO 309
        TX=-CONNEC(J)+2*ABX-DX
        TY=-CONNEC(J+1)+2*ABY-DY
        GO TO 310
309     TX=((CONNEC(J)-ABX)*KCOS(IFLIP)+(CONNEC(J+1)-ABY)*KSIN(IFLIP))
     1  +ABX-DX
        TY=((CONNEC(J)-ABX)*KSIN(IFLIP)-(CONNEC(J+1)-ABY)*KCOS(IFLIP))
     1  +ABY-DY
310     IF (TX .GT. 0 .AND. TX .LE. MAXX .AND. TY .GT. 0
     1  .AND. TY .LE. MAXY) GO TO 2011
5555    IERR=48
C We found a bounds problem
        RETURN
2011    CONTINUE
        KAR=CONNEC(J+2)
C Get sign of charge
        NCHRG=CONNEC(J+3)
C Get digit associated with charge
        CALL ZHARGE(KAR,TX,TY,NCHRG,IERR)
        IF (IERR .NE. 0) GO TO 5555
        J=J+4
2000    CONTINUE
2081    IF (LEND.EQ.0) GO TO 208
        DO 1205 I = 1,LEND
```

```
          IF (IFLIP.EQ.5) THEN
             TX = -CONNEC(J)+ 2*ABX - DX
             TY = -CONNEC(J+1) + 2*ABY - DY
          ELSE
             TX = ((CONNEC(J)-ABX)*KCOS(IFLIP)+(CONNEC(J+1)-ABY)*
     *            KSIN(IFLIP)) + ABX - DX
             TY = -((CONNEC(J)-ABX)*KSIN(IFLIP)+(CONNEC(J+1)-ABY)*
     *            KCOS(IFLIP)) + ABY - DY
          ENDIF
          IF ((TX.GT.0).AND.(TY.LE.MAXX).AND.(TY.GT.0).AND.(TY.LE.
     *       MAXY)) GO TO 1202
5556      IERR = 1
          RETURN
1202      KAR = 34
          IDRAW = 1
          CALL IND1(KAR,TX,TY,IDRAW,IERR)
          IF (IERR.NE.0) GO TO 5556
          J = J + 2
1205   CONTINUE
208    CONTINUE
       RETURN
       END
C
C      SUBROUTINE CLRPIX(A,LB)
C
C      THIS WILL CLEAR THE PICTURE ARRAYS - MM &  LNGBND
C                      OR  - IDTPIX & LLBOND
       SUBROUTINE CLRPIX(WHICH)
       IMPLICIT INTEGER*2 (A-Z)
       INTEGER*4 MM,IDTPIX
       COMMON /CD/ MAXX,MAXY
       COMMON /RANGE/ LOX,HIX,LOY,HIY
       COMMON /STRPIX/ LPIX,MM(90,38),LBLEN,LNGBND(100,5)
       COMMON /STRED/ IDTPIX(90,38),LABL(260,2),MRKCHN(260)
       COMMON /TEMP/ LLBOND(100,5),LLABL(260,2),MCHN(260)
C
       IF (WHICH.EQ.1) THEN
          DO 10 I = LOX,HIX
          DO 10 J = LOY,HIY
10        MM(I,J)=0
          DO 12 I=1,100
          IF (LNGBND(I,1).EQ.0) GO TO 30
          DO 12 J=1,5
12        LNGBND(I,J)=0
       ELSE IF (WHICH.EQ.2) THEN
          DO 20 I = LOX,HIX
          DO 20 J = LOY,HIY
20        IDTPIX(I,J)=0
          DO 22 I=1,100
          IF (LLBOND(I,1).EQ.0) GO TO 30
          DO 22 J=1,5
22        LLBOND(I,J)=0
       ENDIF
30     CONTINUE
       RETURN
       END
C
C      SUBROUTINE ADDLNG(MCNT,LLLEN)
C
C      Move the new longbonds to the end of the temporary longbond
C      array LLBOND - Then copy LLBOND back to LNGBND
C      This must be done because the new longbonds must be at the
C      end for longbond delete to work correctly
C
       SUBROUTINE ADDLNG(MCNT,LLLEN)
       IMPLICIT INTEGER*2 (A-Z)
       INTEGER*4 MM
       COMMON /STRPIX/ LPIX,MM(90,38),LBLEN,LNGBND(100,5)
       COMMON /TEMP/ LLBOND(100,5),LLABL(260,2),MCHN(260)
       IF (LLLEN .EQ. 0) GO TO 100
       FIRST=MCNT+1
       K=1
       DO 10 I=FIRST,FIRST+LLLEN-1
          DO 11 J=1,5
             LLBOND(I,J)=LNGBND(K,J)
```

```
11          CONTINUE
            K=K+1
10       CONTINUE
100      IF ((MCNT + LLLEN) .EQ. 0) RETURN
         K=1
         DO 13 I=1,MCNT+LLLEN
            DO 12 J=1,5
               LNGBND(I,J)=LLBOND(K,J)
12          CONTINUE
            K=K+1
13       CONTINUE
         LBLEN = MCNT + LLLEN
         RETURN
         END
C
C        SUBROUTINE ADDBCK
C
C        Add old picture (stored in IDTPIX) to new picture (stored in MM)
         SUBROUTINE ADDBCK
         IMPLICIT INTEGER*2 (A-Z)
         INTEGER*4 MM,IDTPIX
         COMMON /CD/ MAXX,MAXY
         COMMON /STRPIX/ LPIX,MM(90,38),LBLEN,LNGBND(100,5)
         COMMON /STRED/ IDTPIX(90,38),LABL(260,2),MRKCHN(260)
         COMMON /RANGE/ LOX,HIX,LOY,HIY
         DO 10 I = LOX,HIX
         DO 10 J = LOY,HIY
10       MM(I,J)=MM(I,J)+IDTPIX(I,J)
         RETURN
         END
C
C        SUBROUTINE SHIFT(A,B,C,D,E,F,G,H,MCNT,LCNT)
C
C        THIS SUBROUTINE SHIFTS ARRAYS A TO B
C                         C TO D AND E TO F UNTIL 0 ENTRY IS FOUND IN C
C                         G TO H UNTIL 0 ENTRY FOUND
C        MCNT = COUNT OF MARKERS MOVED
C        LCNT = COUNT OF LONGBONDS MOVED
C
         SUBROUTINE SHIF(WHICH,MCNT,LCNT)
         IMPLICIT INTEGER*2 (A-Z)
         INTEGER*4 MM,IDTPIX
         COMMON /CD/ MAXX,MAXY
         COMMON /STRPIX/ LPIX,MM(90,38),LBLEN,LNGBND(100,5)
         COMMON /STRED/ IDTPIX(90,38),LABL(260,2),MRKCHN(260)
         COMMON /TEMP/ LLBOND(100,5),LLABL(260,2),MCHN(260)
         COMMON /RANGE/ LOX,HIX,LOY,HIY
         IF (WHICH.EQ.1) THEN
         DO 10 I = LOX,HIX
         DO 10 J = LOY,HIY
10          IDTPIX(I,J) = MM(I,J)
C        Move A to B
            DO 11 I=1,260
               IF (LLABL(I,1).EQ.0) GO TO 14
               DO 12 J=1,2
12             LLABL(I,J)=0
C           Clear D and F
               MCHN(I)=0
11          CONTINUE
14          CONTINUE
            DO 13 I=1,260
               II = I
               IF (LABL(I,1) .EQ. 0) GO TO 20
C           Move C to D and E to F until 0 entry is found in C
               LLABL(I,1) = LABL(I,1)
               LLABL(I,2) = LABL(I,2)
               MCHN(I) = MRKCHN(I)
13          CONTINUE
20          MCNT = II-1
C           MCNT = # of markers moved
            DO 50 I=1,100
            IF (LLBOND(I,1).EQ.0) GO TO 51
            DO 50 J=1,5
50          LLBOND(I,J)=0
51          CONTINUE
```

```
C           Move G to H until 0 entry is found in G
            DO 35 I=1,100
            II = I
            IF (LNGBND(I,1) .EQ. 0) GO TO 40
            DO 35 J=1,5
            LLBOND(I,J) = LNGBND(I,J)
35          CONTINUE
40          LCNT = II - 1
C           LCNT = # of longbonds moved
            ELSE IF (WHICH.EQ.2) THEN
            DO 100 I = LOX,HIX
            DO 100 J = LOY,HIY
100         MM(I,J) = IDTPIX(I,J)
C           Move A to B
            DO 110 I=1,260
            IF (LABL(I,1).EQ.0) GO TO 111
            DO 120 J=1,2
120         LABL(I,J)=0
C           Clear D and F
            MRKCHN(I)=0
110         CONTINUE
111         CONTINUE
            DO 130 I=1,260
            II = I
            IF (LLABL(I,1) .EQ. 0) GO TO 200
C           Move C to D and E to F until 0 entry is found in C
            LABL(I,1) = LLABL(I,1)
            LABL(I,2) = LLABL(I,2)
            MRKCHN(I) = MCHN(I)
130         CONTINUE
200         MCNT = II - 1
C           MCNT = # of markers moved
            DO 500 I=1,100
            IF (LNGBND(I,1).EQ.0) GO TO 501
            DO 500 J=1,5
500         LNGBND(I,J)=0
501         CONTINUE
C           Move G to H until 0 entry is found in G
            DO 350 I = 1,100
            II = I
            IF (LLBOND(I,1) .EQ. 0) GO TO 400
            DO 350 J=1,5
            LNGBND(I,J) = LLBOND(I,J)
350         CONTINUE
400         LCNT = II - 1
C           LCNT = # of longbonds moved
            ENDIF
            RETURN
            END
C
C
C
C           SUBROUTINE ZAP(IX,IY)
C
C           THIS SUBROUTINE WILL ERASE SCREEN LOCATION IX,IY
            SUBROUTINE ZAP(IX,IY)
            IMPLICIT INTEGER*2 (A-Z)
            INTEGER*4 MM,IDTPIX
            COMMON /STRPIX/ LPIX,MM(90,38),LBLEN,LNGBND(100,5)
            COMMON /STRED/ IDTPIX(90,38),LABL(260,2),MRKCHN(260)
            COMMON /HP/IHP
            COMMON /CUR/ ICUR
            ICUR = 0
            CALL CURSOR(IX,IY)
            LL = LMM(IX,IY)
            IF ((LL.GE.256).AND.(MOD(IDIR(LL),4).NE.3)) THEN
            FX = IX - 1
            IF (IHP .EQ. 1) THEN
      CALL BERASE(IX,IY)
      ELSE
            CALL FTLOCA(IY,FX)
            CALL FTEXT('^   ^')
      ENDIF
            IF ((MM(FX,IY).NE.0).OR.(IDTPIX(FX,IY).NE.0))
*           CALL REPLCE(FX,IY,1,1,0,0,0)
```

```
              FX = IX + 1
              IF ((MM(FX,IY).NE.0).OR.(IDTPIX(FX,IY).NE.0))
*                 CALL REPLCE(FX,IY,1,1,0,0,0)
          ELSE
              CALL FTLOCA(IY,IX)
              CALL FTEXT('^  ^')
          ENDIF
          IF ((MM(IX,IY).EQ.46).OR.(LL.GE.256).OR.
*            ((MM(IX,IY).GE.50).AND.(MM(IX,IY).LE.57).AND.
*            (LMM(IX-1,IY).NE.43).AND.(LMM(IX-1,IY).NE.45)).OR.
*            (MM(IX,IY).EQ.103).OR.(MM(IX,IY).EQ.106).OR.(MM(IX,IY).EQ
*            .112).OR.(MM(IX,IY).EQ.113).OR.(MM(IX,IY).EQ.121).OR.
*            (MM(IX,IY).EQ.95)) THEN
              IF (MOD((IY*10),40).EQ.0) THEN
                  IF ((IY.EQ.8).OR.(IY.EQ.28).OR.(IY.EQ.16)) THEN
                      FY = ((IY * 10) / 11) + 1
                      CALL FTSIZE(1,11)
                  ELSE
                      FY = ((IY * 10) / 9) + 1
                      CALL FTSIZE(1,9)
                  ENDIF
              ELSE
                  FY = ((IY * 10) / 8) + 1
                  CALL FTSIZE(1,8)
              ENDIF
              IF ((LL.GE.256).AND.(MOD(IDIR(LL),4).NE.3)) THEN
                  FX = IX - 1
                  IF (IHP .EQ. 1) THEN
                  CALL BERASE(IX,IY)
                  ELSE

CALL FTLOCA(FY,FX)
                  CALL FTEXT('^  ^')
                  CALL FTSIZE(1,10)
                  ENDIF
                  FY = IY - IHP
                  IF ((MM(FX,FY).NE.0).OR.(IDTPIX(FX,FY).NE.0))
*                     CALL REPLCE(FX,FY,1,1,0,0,0)
                  IF ((MM(IX,FY).NE.0).OR.(IDTPIX(IX,FY).NE.0))
*                     CALL REPLCE(IX,FY,1,1,0,0,0)
                  FX = IX + 1
                  IF ((MM(FX,FY).NE.0).OR.(IDTPIX(FX,FY).NE.0))
*                     CALL REPLCE(FX,FY,1,1,0,0,0)
              ELSE
      IF (IHP .EQ. 1) THEN
      CALL ERASE(IX,IY)
      ELSE
                  CALL FTLOCA(FY,IX)
                  CALL FTEXT('^  ^')
                  CALL FTSIZE(1,10)
      ENDIF
                  FY = IY - IHP
                  IF ((MM(IX,FY).NE.0).OR.(IDTPIX(IX,FY).NE.0))
*                     CALL REPLCE(IX,FY,0,0,0,0,0)
                  ENDIF
              ENDIF
              IF ((LL.GE.256).AND.(MOD(IDIR(LL),4).NE.3)) THEN
                  MM(IX,IY) = 0
                  FY = IY - 1
                  CALL REPLCE(IX,FY,1,1,0,0,1)
                  FY = IY + 1
                  CALL REPLCE(IX,FY,1,1,0,0,1)
              ELSE
                  MM(IX,IY) = 0
              ENDIF
          RETURN
          END
C
C
C
C         SUBROUTINE FIXMRK(A,B,C,D,MCNT)
C
C         This subroutine will zero array B and D and copy A to B
C         and C to D until a zero entry is found in A
C         It is used to tidy up the LABL and MRKCHN so that spurious
C         markers are not left in them after an unsuccessful RETRIEVE
C         attempt
```

```
        SUBROUTINE FIXMRK(WHICH,MCNT)
        IMPLICIT INTEGER*2(A-Z)
        INTEGER*4 IDTPIX
        COMMON /STRED/ IDTPIX(90,38),LABL(260,2),MRKCHN(260)
        COMMON /TEMP/ LLBOND(100,5),LLABL(260,2),MCHN(260)
        IF (WHICH.EQ.1) THEN
            DO 10 I=1,260
                LLABL(I,1) = 0
                LLABL(I,2) = 0
                MCHN(I)=0
10          CONTINUE
            DO 11 I=1,260
                II = I
                IF (LABL(I,1) .EQ. 0) GO TO 20
                LLABL(I,1) = LABL(I,1)
                LLABL(I,2) = LABL(I,2)
                MCHN(I) = MRKCHN(I)
11          CONTINUE
20          MCNT= II - 1
        ELSE
            DO 100 I=1,260
                LABL(I,1) = 0
                LABL(I,2) = 0
                MRKCHN(I)=0
100         CONTINUE
            DO 110 I=1,260
                II = I
                IF (LABL(I,1) .EQ. 0) GO TO 200
                LABL(I,1) = LLABL(I,1)
                LABL(I,2) = LLABL(I,2)
                MRKCHN(I) = MCHN(I)
110         CONTINUE
200         MCNT = II-1
        ENDIF
        RETURN
        END
C
C
C       SUBROUTINE SYNCH(KAR,KX,KY)
C
C       This subroutine adjusts the cursor (initially positioned at KX,KY) so
C       positioned at a node or at the end of a bond. It sets the
C       argument variable KAR and the COMMON variables ICHAR and JCHAR to refl
C       (just drew a bond - or - just entered a node) If cursor
C       can't be positioned at a nearby node or bond, the cursor
C       position will be moved to a 3X3 empty space  and JCHAR and ICHAR,
C       will be set to 0 and KAR will be set to 13 (i.e. CR)
        SUBROUTINE SYNCH(KAR,KX,KY)
        IMPLICIT INTEGER*2 (A-Z)
        INTEGER*4 MM
        COMMON /STRPIX/ LPIX,MM(90,38),LBLEN,LNGBND(100,5)
        COMMON /PARAMS/ JBDIR,NOCHG,LASTN,MCHAR,JCHAR,NLARGE,LEVEL
        COMMON /MODES/ JBTYPE,ICHAR,IBDIR,IBTYPE,ISMART,MODE,ISKILL,ISP
        COMMON /CD/ MAXX,MAXY
        COMMON /RANGE/ LOX,HIX,LOY,HIY
C
        KAR=13
        ICHAR=0
        JCHAR=0
C       First check that X and Y are in bounds
        IF (KX .GT. 0 .AND. KX .LE. MAXX .AND. KY .GT. 0 .AND. KY
     1      .LE. MAXY) GO TO 710
C       Bounds problems
        KX=10
C       Set X and Y to valid coordinates and then move cursor
        KY=10
C       to clear area and exit
710     CALL NEW(IGOOD,KX,KY)
C       See if we are at A 3x3 empty area
        IF (IGOOD .NE. 0) GO TO 70
        CALL CURSOR(KX,KY)
        RETURN
C       If so return with  KAR=13 ICHAR=0 JCHAR=0
70      L=LMM(KX,KY)
        IF (L .NE. 0) GO TO 10
C
C       Cell is empty
```

```
C
        IIBDIR = IBDIR
        CALL FINDB(IIBDIR,KBDIR,KX,KY)
        IBDIR = IIBDIR
C       Are we at the end of a bond?
        IF (IBDIR .EQ. -1) GO TO 20
C
C       We're at the end of a bond
C
        ICHAR = 1
        CALL MKBND(KBDIR)
C       Convert bond direction to bond command
        KAR=KBDIR
C                  (22-25;28-31)
        GO TO 100
C
C       Cell was empty, but we weren't at a bond
C       Look alternately left and right 3 times for non empty cell
C       Then give up and RETURN with parameters ICHAR & JCHAR set to zero & cursor at
C       a 3X3 empty area and KAR=13
20      IX=KX
        DO 30 I=1,3
        DO 35 J=1,2
        IF (J .EQ. 1) THEN
            EDIR = -1
        ELSE
            EDIR = 1
        ENDIF
        KX = IX + EDIR * I
CXT
        IF ((KX.LE.0).OR.(KX.GT.MAXX)) GO TO 35
CXT
        L=LMM(KX,KY)
        IF ( L .NE. 0) GO TO 10
35      CONTINUE
30      CONTINUE
C       Cells to left are empty and cells to right are empty - give up
C       Set cursor to 3X3 empty area and exit
        GO TO 500
C
C       Cell was not empty - What kind is it?
C
10      IF (L .GE. 256 .AND. (MM(KX-1,KY) .NE. 0) .AND.
     1     (LMM(KX-1,KY) .LT. 256)) KX=KX-1
C       If cell holds bond and cell to left is not empty and not a bond
C       shift pointer to left for it is likely to be our node
        IF (LMM(KX,KY) .LT. 256) GO TO 25
C       It should be a node - go see if it is
C       Cell to left of bond is empty or a bond - trace bond to end
C
        IIBDIR = IBDIR
        CALL BSLIDE(KX,KY,IIBDIR)
        IBDIR = IIBDIR
C
C       If we couldn't find the end of the bond - give up
C       Return with cursor at 3X3 empty area and parameters
C       set to zero
C
        IF (IBDIR .EQ. -1) GO TO 500
C
C       If we traced bond to end and found a blank at the end - then
C       set parameters and ICHAR and KAR and prepare to exit
C
        IF (MM(KX,KY) .NE. 0) GO TO 25
        ICHAR=1
        IIBDIR = IBDIR
        CALL MKBND(IIBDIR)
        IBDIR = IIBDIR
        KAR=IBDIR
C       KAR = bond command
        GO TO 100
C
C       We are near a node  -  Find correct X position for cursor
C
25      CALL FNODEB(KX,KY,JX)
```

```
              IF (JX .EQ. 0) GO TO 500
C     Can't find X position for node - give up
              KX=JX
C     KX = correct X position for cursor
              KAR=LMM(KX-1,KY)
              ICHAR=2
C     Set ICHAR to "we just entered a node"
C
C     We found node or bond - set cursor and parameters and RETURN
C
100           CALL CURSOR(KX,KY)
              JCHAR=ICHAR
              MCHAR=KAR
              RETURN
C
C     We couldn't find the node or bond so we are going to
C     place the cursor at an empty 3X3 area
C
500           I1=MIN0(KX,(MAXX-1))
              J1=MIN0(KY,(MAXY-1))
              DO 501 I=I1,MAXX-1
              II = I
C     NOTE - I LOOK FOR A 3x3 EMPTY CELL
              DO 501 J=J1,MAXY-1
              JJ = J
C     NEAR THE CURRENT X,Y POSITION
              CALL NEW(IGOOD,II,JJ)
              IF (IGOOD .EQ. 0) GO TO 502
501           CONTINUE
502           KX=II
              KY=JJ
              CALL CURSOR(KX,KY)
              RETURN
              END
C
C     SUBROUTINE FNODE(IX,IY,KX,IDIR)
C
C
C     This subroutine will look for a node in the MM array
C     starting with loc IX, IY and looking left 3 spaces if IDIR = -1
C     and looking right 3 spaces if IDIR = 1
C     Output is KX which is the proper X coordinate for the node
              SUBROUTINE FNODE (IX,IY,KX,EDIR)
              IMPLICIT INTEGER*2 (A-Z)
              INTEGER*4 MM
              COMMON /STRPIX/ LPIX,MM(90,38),LBLEN,LNGBND(100,5)
              IEND = EDIR * 3
              IDELTA = EDIR
              KX=0
C
C     An empty cell or a bond containing cell causes ABORT with KX = 0
C
              IF (MM(IX,IY) .EQ. 0 .OR. LMM(IX,IY) .GT. 256) RETURN
              DO 10 I=0,IEND,IDELTA
              II = I
              M=LMM(IX+I,IY)
              MP1=LMM(IX+I+1,IY)
              IF (M .EQ. 63 .OR. M .EQ. 46) GO TO 11
C     Is it a ? or a FAT DOT?
              IF (M .GE. 65 .AND. M .LE. 90 .AND. M .NE. 72) GO TO 11
C     Is it a non-H UC letter?
              IF (M.EQ.72 .AND.(MP1.GE.97 .AND. MP1.LE.122)) GO TO 11
C     Is it a H followed by a lower case letter?
10            CONTINUE
              RETURN
C     Didn't find it - Return with KX = 0
11            KX = IX + II + 1
C     Position X correctly
              RETURN
              END
C
C     Subroutine FNODEB(IX,IY,KX)
C
C     This subroutine will look for a node by first looking in the 3 spaces to th
C     left of MM(IX,IY) - If that is not successful - it will then
```

```fortran
C           look in the 3 spaces to the right
C           If that is not successful - it will abort with KX=0
            SUBROUTINE FNODEB(IX,IY,KX)
            IMPLICIT INTEGER*2 (A-Z)
            EDIR = -1
            CALL FNODE(IX,IY,KX,EDIR)
            IF (KX .NE. 0) RETURN
            EDIR = 1
            CALL FNODE(IX,IY,KX,EDIR)
            RETURN
            END
C
C           SUBROUTINE BSLIDE(IX,IY,IBDIR)
C
C           This subroutine finds the end of the bond passing through MM(IX,IY)
C           Inputs to this subroutine are the X and Y coordinates of the bond in MM
C           If the end of the bond is found IX and IY are set to the cell
C           just beyond the end of the bond in the bond direction
C           If not, IX and IY are not changed
C           If the end of the bond can't be found IBDIR is set to -1
C           If the end is found, IBDIR is set to the bond direction
            SUBROUTINE BSLIDE(IX,IY,IBDIR)
            IMPLICIT INTEGER*2 (A-Z)
            INTEGER*4 MM
            COMMON /STRPIX/ LPIX,MM(90,38),LBLEN,LNGBND(100,5)
            COMMON /CD/ MAXX,MAXY
C
            KX=IX
            KY=IY
            L=LMM(IX,IY)
            IBDIR=IDIR(L)
C           L=bond direction
            CALL DELTA(IBDIR,INCX,INCY)
C           Get deltas for bond
            DO 10 I=1,100
            IX=IX+INCX
            IY=IY+INCY
            IF (IX.LE.0 .OR. IX.GT.MAXX .OR. IY.LE.0 .OR. IY.GT.MAXY)
        1   GO TO 100
C           Are coordinates out of bounds?
            IF (LMM(IX,IY) .LT. 256) RETURN
C           Found end of bond - RETURN
 10         CONTINUE
 100        IBDIR=-1
C           Couldn't find end of bond - Set coordinates to 0 and RETURN
            IX=KX
C           Reset X and Y to their values at time of input
            IY=KY
            RETURN
            END
C
C           SUBROUTINE FINDXY(IX,IY,KX,KY,DX,DY,ABX,ABY,IROT,IFLIP,SYM)
C
C           This subroutine calculates the appropriate X and Y values
C           using the appropriate translation, rotation and reflection
C           operators
C
C           Input is KX and KY - the unoperated coordinates
C             DX and DY  - the translation values
C             ABX & ABY  - the coordinates of the end of the attaching bond
C             IROT       - indicates what rotation, if any, is necessary
C             IFLIP      - indicates what reflection, if any, is necessary
            SUBROUTINE FINDXY(IX,IY,KX,KY,DX,DY,ABX,ABY,IROT,IFLIP,SYM)
            IMPLICIT INTEGER*2 (A-Z)
            DIMENSION KSIN(4),KCOS(4)
            DATA KSIN/0,1,0,-1/
            DATA KCOS/1,0,-1,0/
C
            IF ((SYM.EQ.2).OR.((SYM.EQ.1).AND.(IFLIP.EQ.-1))) GO TO 100
            IF (IFLIP .NE. 5) GO TO 200
            IX=-KX+2*ABX-DX
            IY=-KY+2*ABY-DY
            RETURN
C
C           We need to do a reflection
C
```

```
 200    IX=(KX-ABX)*KCOS(IFLIP)+(KY-ABY)*KSIN(IFLIP)+ABX-DX
        IY=(KX-ABX)*KSIN(IFLIP)-(KY-ABY)*KCOS(IFLIP)+ABY-DY
        RETURN
C
C       We need to do a rotation
C
 100    IX=(KX-ABX)*KCOS(IROT) + (KY-ABY)*KSIN(IROT) + ABX-DX
        IY=-(KX-ABX)*KSIN(IROT)+(KY-ABY) * KCOS(IROT) + ABY -DY
        RETURN
        END
C
C       SUBROUTINE LOOKR(IX,IY,MM,ICHECK,IBADX,IBADY,LAP,LCNT,BLOB)
C
C       THIS SUBROUTINE CHECKS A 3 x 3 CELL CENTERED AT IX & IY
C       ICHECK = 0      THAT IS OK - IF
C
C                                       1. THE MM SUBSCRIPTS ARE GOOD
C                                       2. THE CELL IS EMPTY - OR - THE
C                                          COLLISIONS ARE VALID COLLISIONS
C
C       ICHECK NOT = 0 MEANS THAT BAD CONFLICTS AROSE
C
        SUBROUTINE LOOKR(IX,IY,ICHECK,LCNT,BLOB)
        IMPLICIT INTEGER*2 (A-Z)
        INTEGER*4 MM,IDTPIX,WHAT,A
        COMMON /STRED/ IDTPIX(90,38),LABL(260,2),MRKCHN(260)
        COMMON /STRPIX/ LPIX,MM(90,38),LBLEN,LNGBND(100,5)
        COMMON /BAD/ IBADX(9),IBADY(9)
        COMMON /LAPE/ LAP(5,2)
        COMMON /CD/ MAXX,MAXY
        ICHECK=0
C       Cell is OK until proven otherwise
        CALL CHECK(IX,IY,ICHECK)
C       Check IDTPIX subscripts
 777    IF (ICHECK .EQ.1) GO TO 10
C       Bad subscripts - set error and return
        WHAT = IDTPIX(IX,IY)
        IF (WHAT .NE. 0) GO TO 10
C       Space is occupied - set error and return
        CALL CELL2(IX,IY,ICHECK)
C       Space is empty - check surrounding area
        IF (ICHECK .EQ. 0) RETURN
C       No problem - good cell - ICHECK = 0 and return
        DO 982 I=1,ICHECK
        DO 980 J=1,LCNT
        IF (IBADX(I).EQ.LAP(J,1) .AND. IBADY(I).EQ.LAP(J,2)) GO TO 982
 980    CONTINUE
        A = IDTPIX(IBADX(I),IBADY(I))
C       Was it a legal collision? Was it a legal overlap - i.e.
C       bond - not pointing to cell or cell would contain bond
C       and overlap is node and cell bond does not point to node
C       A = contents of offending cell
        IF ((BLOB.EQ.43).OR.(BLOB.EQ.45).OR.(A.EQ.43).OR.(A.EQ.45))
      *    GO TO 10
C       If it is a collision with a charge - it is bad
        IF (BLOB .LT. 46) GO TO 20
C       Blob is a node
        IF (A .GE. 256) GO TO 11
C       A is a bond - is it an OK bond
        B=BLOB
        CALL DELTA(B,INCX,INCY)
C       Cell will contain bond - does it point to node
        IF (((IBADX(I).EQ.(IX+INCX)).AND.(IBADY(I).EQ.(IY+INCY)))
      1 .OR.((IBADX(I).EQ.(IX-INCX)).AND.(IBADY(I).EQ.(IY-INCY))))
      2    GO TO 10
C       If bond points to node - it is no good
        GO TO 982
C       If not - it is OK
 20     IF (A .LT. 256) GO TO 10
C       Not a bond - can't be OK
 11     B=IDIR(A)
C       Get bond direction
        CALL DELTA(B,INCX,INCY)
```

```
C       Get bond deltas
        IF((((IBADX(I)+INCX).EQ. IX) .AND.((IBADY(I)+INCY).EQ.IY))
     1  .OR. (((IBADX(I)-INCX).EQ.IX).AND.((IBADY(I)-INCY).EQ.IY)))
     2  GO TO 10
C       If it points to bond or node - it is no good
982     CONTINUE
        ICHECK=0
C       Overlap was valid - cell OK
        RETURN
C       Valid overlap - return
10      ICHECK=1
        RETURN
C       Bad overlap - return with error set
        END
C
        SUBROUTINE CKNOD2(I,J,IVAL,IERR)
        IMPLICIT INTEGER*2(A-Z)
        INTEGER*4 MM
        COMMON /STRPIX/ LPIX,MM(90,38),LBLEN,LNGBND(100,5)
        IERR=0
        IVAL=LMM(I,J)
        IF (IVAL .LT. 97 .OR. IVAL .GT. 122) RETURN
        IVALL=LMM(I-1,J)
        IF (IVALL .GE. 65 .AND. IVALL .LE. 90) RETURN
        IERR=1
        RETURN
        END
C
        SUBROUTINE VLNCE(II,IX,IY,INCX,INCY,IERR)
        IMPLICIT INTEGER*2 (A-Z)
        INTEGER*4 MM,IDTPIX
        LOGICAL*2 PNODE,VNODE
        CHARACTER*1 HALO(3)
        CHARACTER*1 KAN
        COMMON /ELECHR/ IELEM(126,5)
        COMMON /CD/ MAXX,MAXY
        COMMON /RANGE/ LOX,HIX,LOY,HIY
        COMMON /STRPIX/ LPIX,MM(90,38),LBLEN,LNGBND(100,5)
C       MM(I,J) CONTAINS BOND OR ATOM TYPE, & BOND DIRECTION
C       FOR EACH OF MAXX * MAXY LOCATIONS.
        COMMON /CHARS/IES, IDOT,ITAG,JUMP,LBOND,KAN,ISPACE
        COMMON /PARAMS/ JBDIR,NOCHG,LASTN,MCHAR,JCHAR,NLARGE,LEVEL
        COMMON /MODES/ JBTYPE,ICHAR,IBDIR,IBTYPE,ISMART,MODE,ISKILL,ISP
        COMMON /PROB/ IPROB,JPROB
        COMMON /IPLUS/ IHIGH(14,2)
        COMMON /LABELS/ NR,LJLAST,NJNEXT
        COMMON /STRED/ IDTPIX(90,38),LABL(260,2),MRKCHN(260)
        COMMON /QTVLNC/ OERR,CHER
        COMMON /HP/IHP
CXT
CXT     PNODE = TRUE is passed by SUBROUTINE GETIT if only array MM need
CXT     be searched for nodal adjacency. DELH is assigned the attached
CXT     node's hydrogen information so it can be had for any subsequent
CXT     substructure deletion. VNODE = TRUE indicates the substructure
CXT     is being drawn by the VIEW SECTION of SUBROUTINE GETIT.
        COMMON /VALH/ PNODE,DELH(2,3),VNODE
        COMMON /CUR/ ICUR
C
        ICUR = 0
        HALO(1) = KAN
        HALO(3) = KAN
        MAR=0
C Filler atoms not triggered by bond.
        IF (II.GT.2) GO TO 1000
C Look at grid space BEFORE bond.
        JX=IX-(NLARGE+1)*INCX
C (NLARGE+1) removes incrementing done in DRAW.
        JY=IY-(NLARGE+1)*INCY
        IF (II.LT.2) GOTO 23
C If overdrawing an existing bond, II=2.
        JX=IX-INCX
        JY=IY-INCY
C If to right of element, skip back over lower case second letter:
23      IF ((MM(JX,JY).GT.96) .AND. (MM(JX,JY).LT.123)) JX=JX-1
C If bond didn't originate at a (non-dot) node (i.e. cap letter), return
```

```
            IF(MM(JX,JY).EQ.46) GO TO 63
            IF ((MM(JX,JY).LT.65) .OR. (MM(JX,JY).GT.90)) RETURN
            GO TO 87
C IS THIS A MARKER OR FAT DOT
63          DO 64 I=1,NJNEXT
            IF(JX .EQ. LABL(I,1) .AND. JY .EQ. LABL(I,2))RETURN
64          CONTINUE
            MAR=1
C IF FAT DOT SET PARAMS FOR CARBON
            LET1=67
            LET2=0
            IELT=1
            GO TO 800
C First letter of symbol
87          LET1=LMM(JX,JY)
            LET2=0
C Second letter, if 2-letter symbol
            IF ((MM(JX+1,JY).GE.97) .AND. (MM(JX+1,JY).LE.122))
     2          LET2=MM(JX+1,JY)
C Dont check H2,ETC
            IF((LET1.EQ.72) .AND. (LET2.EQ.0)) RETURN
C Count of OCCUPIED valence positions
            IVALNC=0
C Element number of node at JX,JY
            IELT=0
C
C Search for element in element table
                DO 1 I=1,125
                    IF ((LET1.NE.IELEM(I,1)) .OR. (LET2.NE.IELEM(I,2)))
     2                  GOTO 1
C Records row number of correct element
                    IELT=I
C No valence in table
                    IF (IELEM(IELT,3).EQ.0) RETURN
                    GOTO 2
1               CONTINUE
C
2           IF (IELT.NE.0) GO TO 800
C ELEMENT NOT FOUND - ISSUE MESSAGE AND CONTINUE
            IERR=11
            CALL MYERR(IERR,LET1,LET2)
C BEWARE I DON'T KNOW ALL THE IMPLICATIONS OF THIS RETURN
            RETURN
C
C Now search around node for bonds, charges, for 'valence users'.
C
800         CONTINUE
C                where to put filler H's if there is room on both sides.
C           BEWARE - VAA MODIFIED LOOP 3 - THE MODIFICATION IS TO DETECT
C           CHARGES ON THE RIGHT DIAGONALS OF THE SECOND LETTER OF A 2
C           LETTER ELEMENT NAME
C Count of bonds 'used'.
            IVALNC=0
C search around node - LOOP CHANGED TO 2 BY VAA
            DO 3 IDIRX=-1,2
            DO 3 IDIRY=-1,1
            IF ((IDIRX.EQ.0) .AND. (IDIRY.EQ.0)) GOTO 3
            IF((IDIRX .EQ. 2) .AND. (IDIRY .EQ.0)) GO TO 3
C WE DON'T NEED TO CHECK THIS ONE
C WE WILL CATCH A CHARGE AT THIS LOCATION
C WHEN X=1 AND Y=0
C Nearby array location to look for bonds
            NEWX=JX + IDIRX
            NEWY=JY + IDIRY
C Off the edge
7           IF ((NEWX.LT.1) .OR. (NEWX.GT.MAXX)) GOTO 3
            IF ((NEWY.LT.1) .OR. (NEWY.GT.MAXY))  GOTO 3
C Blank space
            IF (MM(NEWX,NEWY).EQ.0) GOTO 3
C Bonds are >256
            IF (LMM(NEWX,NEWY).LT.256)  GOTO 4
C WE ARE ONLY LOOKING FOR CHARGES AT THIS PLACE - NOT BONDS
            IF (IDIRX .EQ. 2) GO TO 3
C Bond extracted for type
            JBOND=LMM(NEWX,NEWY)/2**8
C Following 5 lines skip bonds not pointed to node being analyzed:
```

```
C Direction of bond
        JDIR=LMM(NEWX,NEWY)-JBOND*2**8
        IF ((IDIRX*IDIRY.EQ.-1).AND.(MOD(JDIR,4).NE.2)) GOTO 3
        IF ((IDIRX*IDIRY.EQ.1).AND.(MOD(JDIR,4).NE.0)) GOTO 3
        IF ((IDIRX.EQ.0) .AND. (MOD(JDIR,4).NE.1)) GOTO 3
        IF ((IDIRY.EQ.0) .AND. (MOD(JDIR,4).NE.3)) GOTO 3
C Useful for bondtypes 1-3 others revised below
        IVAL = JBOND
C Stereo bonds are single.
        IF (JBOND.GT.3) IVAL=1
        IVALNC = IVALNC + IVAL
C Only if a valence-using bond is on this side.
        GOTO 3
C Charges
4       IF ((LMM(NEWX,NEWY).NE.43) .AND. (LMM(NEWX,NEWY).NE.45))GOTO 5
4444    LOC=IHMM(NEWX,NEWY)
        IFX=NEWX-IHIGH(LOC,1)
        IFY=NEWY+IHP*IHIGH(LOC,2)
C IS CHARGE ASSOCIATED WITH THIS NODE
        IF(JX.NE.IFX .OR.JY.NE.IFY) GO TO 5
C Set the sign from ASCII char
        ISIGN = 44 - LMM(NEWX,NEWY)
        IF ((MM(NEWX+1,NEWY).LT.50).OR.(MM(NEWX+1,NEWY).GT.57)) GOTO 6
C       Number of charges>1
        ISIGN = ISIGN * (LMM(NEWX+1,NEWY) - 48)
C       Correct # of valencies used for chg
6       IVALNC=IVALNC + IABS(ISIGN)
        ISIGN=0
C Only if a valence-using bond is on this side.
        GOTO 3
C
C H, lowercase, numerals, etc, keep looking
5       NEWX = NEWX + IDIRX
C H, lc, OR NUMERAL CAN'T
        IF (IDIRX .EQ. 0) GO TO 3
C CONTRIBUTE TO VALENCE IN THIS LOC
C BEWARE CHANGED BY VAA - TO FIX
C ENDLESS LOOP FOUND BY GREG
        GOTO 7
C Close loop of looking around each node.
3       CONTINUE
C
C Following code (through label 200) adds to IVALNC those bonds 'used'
C by long bonds:
C Beginning & ending nodes of long bond
        DO 200 I=0,2,2
C Up to 100 long bonds stored
        DO 201 J=1,100
C Done with this column of node
        IF (LNGBND(J,I+1).EQ.0) GOTO 200
C Check if current nodeJX,JY is listed as a node of a long bond:
        IF ((LNGBND(J,I+1).NE.JX) .OR. (LNGBND(J,I+2).NE.JY)) GOTO 201
C Use of valence from this long bond
        IVAL = 1
        IF (LNGBND(J,5).EQ.2) IVAL=2
        IF (LNGBND(J,5).EQ.3) IVAL=3
        IVALNC = IVALNC + IVAL
201     CONTINUE
200     CONTINUE
C
C Number of H's required at this node. Neg no for test
        IHYD=-7
C Elect smallest valence from IELEM which would satisfy all existing bonds.
        DO 10 M=3,5
C
        IF(IELEM(IELT,M).LT.IVALNC) GOTO 10
        IHYD = IELEM(IELT,M) - IVALNC
        GOTO 11
10      CONTINUE
C Now draw hydrogens
11      CONTINUE
        IF (IHYD.GE.0 .AND. MAR .EQ. 0) GO TO 1000
        IF(IHYD .GE. 0 .AND. MAR .EQ. 1) RETURN
C TOO MANY BONDS FOR VALENCY
        IERR=12
        OERR = IERR
```

```
              CALL MYERR(IERR,IVALNC,KAR)
1000          CONTINUE
              IF (MM(JX,JY).EQ.46) RETURN
C
C Now look left & right to determine where filler atoms can fit:
C
C Done if no filler atoms needed.
              IF (IHYD) 111,111,30
C =1 means there IS room for H('s) on left
30            ILEFT=1
C similarly
              IRIGHT=1
C
C Look right to see if there is room for H('s):
C MX is first position to right of node.
              MX=JX+1
C Two-letter symbol
              IF (LET2.GT.0) MX=JX+2
C Number of chars needed for H('s):=1 or 2
              KHYD=1
              IF (IHYD.GT.1) KHYD = 2
CXT
C
C Edge of screen problems are checked.
              IF (MX+1.GT.MAXX) THEN
                  DG = LMM(JX-KHYD,JY)
                  IF (((DG.LT.256).AND.(DG.GT.0)).OR.((DG.GE.256).AND.
     *            (MOD(IDIR(DG),4).NE.3))) GO TO 9394
                  IF (.NOT.PNODE) THEN
                      DG = MOD(IDTPIX(JX-KHYD,JY),2**13)
                      IF (((DG.LT.256).AND.(DG.GT.0)).OR.((DG.GE.256).AND.
     *                (MOD(IDIR(DG),4).NE.3))) GO TO 9394
                  ENDIF
                  GO TO 42
              ELSE IF (JX-2.LT.1) THEN
                  DG = LMM(JX+KHYD,JY)
                  IF (((DG.LT.256).AND.(DG.GT.0)).OR.((DG.GE.256).AND.
     *            (MOD(IDIR(DG),4).NE.3))) GO TO 9394
                  IF (.NOT.PNODE) THEN
                      DG = MOD(IDTPIX(JX+KHYD,JY),2**13)
                      IF (((DG.LT.256).AND.(DG.GT.0)).OR.((DG.GE.256).AND.
     *                (MOD(IDIR(DG),4).NE.3))) GO TO 9394
                  ENDIF
                  GO TO 43
              ENDIF
C
C             If CHER = 1, SUBROUTINE QUIT is converting chain markers to "C"s.
C             Check for bad bonds coming in on the left diagonals.
              L1 = LMM(MX-1,JY-1)
              L2 = LMM(MX-1,JY+1)
              IF (((L1.EQ.0).OR.((L1.GT.256).AND.(MOD(IDIR(L1),4).NE.0)))
     *        .AND.((L2.EQ.0).OR.((L2.GT.256).AND.(MOD(IDIR(L2),4).NE.
     *        2)))) GO TO 522
              IF (.NOT.PNODE) THEN
                  L3 = LMM(MX-1,JY-1)
                  L4 = LMM(MX-1,JY+1)
                  IF (((L3.EQ.0).OR.((L3.GT.256).AND.(MOD(IDIR(L3),4).NE.0)))
     *            .AND.((L4.EQ.0).OR.((L4.GT.256).AND.(MOD(IDIR(L4),4).NE.
     *            2)))) GO TO 522
              ENDIF
              IRIGHT = 0
              GO TO 34
C
C The actual search-right algorithm loop.
522           DO 33 I=0,KHYD
                  IF (((PNODE).AND.(MM(MX+I,JY).EQ.0)).OR.((.NOT.PNODE)
     *            .AND.(MM(MX+I,JY).EQ.0).AND.(IDTPIX(MX+I,JY).EQ.0)))
     *            THEN
                      GO TO 330
                  ELSE IF ((LMM(MX+I,JY).LT.256).OR.((IDTPIX(MX+I,JY)
     *            .NE.0).AND.(.NOT.PNODE))) THEN
                      GO TO 400
                  ENDIF
```

```
                    ITEST=LMM(MX+I,JY)/256
                    ITEST=LMM(MX+I,JY)-ITEST*256
C                   CHECK FOR BOND IN LEFT OR RIGHT DIR
                    IF (ITEST.EQ.3 .OR. ITEST.EQ.7) GO TO 330
C If non-blank or non-bond on right within
400                 IRIGHT=0
C KHYD+1 to right of node, can't put H('s)there
                    GOTO 34
330                 CONTINUE
                    L1 = LMM(MX+I,JY-1)
                    L2 = LMM(MX+I,JY+1)
                    L3 = LMM(MX+I,JY-1)
                    L4 = LMM(MX+I,JY+1)
                    IF ((PNODE).AND.(L1.EQ.0).AND.(L2.EQ.0)) GO TO 33
                    IF ((.NOT.PNODE).AND.(L1.EQ.0).AND.(L2.EQ.0).AND.(L3.EQ.0)
     *              .AND.(L4.EQ.0)) GO TO 33
                    IF (I.LE.2) THEN
                       IF ((L1.EQ.46).OR.((L1.GE.65).AND.(L1.LE.90))) GO TO 400
                       IF ((L2.EQ.46).OR.((L2.GE.65).AND.(L2.LE.90))) GO TO 400
                    ENDIF
                    IF ((I.EQ.KHYD).AND.(((L1.GT.256).AND.
     *              (MOD(IDIR(L1),4).EQ.2)).OR.((L2.GT.256)
     *              .AND.(MOD(IDIR(L2),4).EQ.0)))) GO TO 400
                    IF ((KHYD.EQ.1).AND.(I.EQ.0).AND.((
     *              (L1.GE.256).AND.(MOD(IDIR(L1),4).EQ.1)).OR.(
     *              (L2.GT.256).AND.(MOD(IDIR(L2),4).EQ.1)))) GO TO 400
                    IF ((KHYD.EQ.2).AND.(I.EQ.0).AND.((
     *              (L1.GE.256).AND.((MOD(IDIR(L1),4).EQ.1).OR.
     *              (MOD(IDIR(L1),4).EQ.0))).OR.(
     *              (L2.GT.256).AND.((MOD(IDIR(L2),4).EQ.1).OR.
     *              (MOD(IDIR(L2),4).EQ.2)))) GO TO 400
                    IF ((KHYD.EQ.2).AND.(I.EQ.1).AND.((
     *              (L1.GE.256).AND.((MOD(IDIR(L1),4).EQ.1).OR.
     *              (MOD(IDIR(L1),4).EQ.2))).OR.(
     *              (L2.GT.256).AND.((MOD(IDIR(L2),4).EQ.1).OR.
     *              (MOD(IDIR(L2),4).EQ.0)))) GO TO 400
                    IF (.NOT.PNODE) THEN
                       IF (I.LT.2) THEN
                          IF ((L3.EQ.46).OR.((L3.GE.65).AND.(L3.LE.90)))
     *                    GO TO 400
                          IF ((L4.EQ.46).OR.((L4.GE.65).AND.(L4.LE.90)))
     *                    GO TO 400
                       ENDIF
                       IF ((I.EQ.KHYD).AND.(((L3.GT.256).AND.
     *                 (MOD(IDIR(L3),4).EQ.2)).OR.((L4.GT.256)
     *                 .AND.(MOD(IDIR(L4),4).EQ.0)))) GO TO 400
                       IF ((KHYD.EQ.1).AND.(I.EQ.0).AND.((
     *                 (L3.GE.256).AND.(MOD(IDIR(L3),4).EQ.1)).OR.(
     *                 (L4.GT.256).AND.(MOD(IDIR(L4),4).EQ.1)))) GO TO 400
                       IF ((KHYD.EQ.2).AND.(I.EQ.0).AND.((
     *                 (L3.GE.256).AND.((MOD(IDIR(L3),4).EQ.1).OR.
     *                 (MOD(IDIR(L3),4).EQ.0))).OR.(
     *                 (L4.GT.256).AND.((MOD(IDIR(L4),4).EQ.1).OR.
     *                 (MOD(IDIR(L4),4).EQ.2)))) GO TO 400
                       IF ((KHYD.EQ.2).AND.(I.EQ.1).AND.((
     *                 (L3.GE.256).AND.((MOD(IDIR(L3),4).EQ.1).OR.
     *                 (MOD(IDIR(L3),4).EQ.2))).OR.(
     *                 (L4.GT.256).AND.((MOD(IDIR(L4),4).EQ.1).OR.
     *                 (MOD(IDIR(L4),4).EQ.0)))) GO TO 400
                    ENDIF
33                  CONTINUE
                    IF (IRIGHT.EQ.1) GO TO 36
C Now look left to see if filler atoms can be put there:
C Look left for non-blank,non-bonds.
34                  L1 = LMM(JX,JY-1)
                    L2 = LMM(JX,JY+1)
                    L3 = LMM(JX,JY-1)
                    L4 = LMM(JX,JY+1)
                    IF (((L1.EQ.0).OR.((L1.GT.256).AND.(MOD(IDIR(L1),4).NE.2)))
     *              .AND.((L2.EQ.0).OR.((L2.GT.256).AND.(MOD(IDIR(L2),4)
     *              .NE.0)))) GO TO 3441
                    IF (.NOT.PNODE) THEN
                       L3 = LMM(JX,JY-1)
                       L4 = LMM(JX,JY+1)
```

```
                         IF (((L3.EQ.0).OR.((L3.GT.256).AND.(MOD(IDIR(L3),4).NE.
     *                       2))).AND.((L4.EQ.0).OR.((L4.GT.256).AND.(MOD(IDIR(L4)
     *                       ,4).NE.0)))) GO TO 3441
                         ENDIF
                         ILEFT = 0
                         GO TO 36
3441                     DO 35 I=1,KHYD+1
                         IF ((PNODE).AND.(MM(JX-I,JY).EQ.0)) GO TO 3555
                         IF ((.NOT.PNODE).AND.(MM(JX-I,JY).EQ.0).AND.
     *                       (IDTPIX(JX-I,JY).EQ.0)) GO TO 3555
                         IF ((LMM(JX-I,JY).LT.256).OR.((IDTPIX(JX-I,JY).NE.0)
     *                       .AND.(.NOT.PNODE))) GO TO 401
                         ITEST=LMM(JX-I,JY)/256
                         ITEST=LMM(JX-I,JY)-ITEST*256
                         IF (ITEST.EQ.3 .OR. ITEST.EQ.7) GO TO 3555
401                      ILEFT=0
                         GOTO 36
3555                     L1 = LMM(JX-I,JY-1)
                         L2 = LMM(JX-I,JY+1)
                         L3 = LMM(JX-I,JY-1)
                         L4 = LMM(JX-I,JY+1)
                         IF ((PNODE).AND.(L1.EQ.0).AND.(L2.EQ.0)) GO TO 35
                         IF ((.NOT.PNODE).AND.(L1.EQ.0).AND.(L2.EQ.0).AND.(L3.EQ.0)
     *                       .AND.(L4.EQ.0)) GO TO 35
                         IF ((L1.EQ.46).OR.((L1.GE.65).AND.(L1.LE.90))) GO TO 401
                         IF ((L2.EQ.46).OR.((L2.GE.65).AND.(L2.LE.90))) GO TO 401
                         IF ((I.EQ.KHYD+1).AND.(((L1.GT.256).AND.
     *                       (MOD(IDIR(L1),4).EQ.0)).OR.((L2.GT.256)
     *                       .AND.(MOD(IDIR(L2),4).EQ.2)))) GO TO 401
                         IF ((KHYD.EQ.1).AND.(I.EQ.1).AND.((
     *                       (L1.GE.256).AND.(MOD(IDIR(L1),4).EQ.1)).OR.(
     *                       (L2.GT.256).AND.(MOD(IDIR(L2),4).EQ.1)))) GO TO 401
                         IF ((KHYD.EQ.2).AND.(I.EQ.2).AND.((
     *                       (L1.GE.256).AND.((MOD(IDIR(L1),4).EQ.1).OR.
     *                       (MOD(IDIR(L1),4).EQ.0))).OR.(
     *                       (L2.GT.256).AND.((MOD(IDIR(L2),4).EQ.1).OR.
     *                       (MOD(IDIR(L2),4).EQ.2)))))  GO TO 401
                         IF ((KHYD.EQ.2).AND.(I.EQ.1).AND.((
     *                       (L1.GE.256).AND.((MOD(IDIR(L1),4).EQ.1).OR.
     *                       (MOD(IDIR(L1),4).EQ.2))).OR.(
     *                       (L2.GT.256).AND.((MOD(IDIR(L2),4).EQ.1).OR.
     *                       (MOD(IDIR(L2),4).EQ.0))))) GO TO 401
                         IF (.NOT.PNODE) THEN
                         IF ((L3.EQ.46).OR.((L3.GE.65).AND.(L3.LE.90))) GO TO 401
                         IF ((L4.EQ.46).OR.((L4.GE.65).AND.(L4.LE.90))) GO TO 401
                         IF ((I.EQ.KHYD+1).AND.(((L3.GT.256).AND.
     *                       (MOD(IDIR(L3),4).EQ.0)).OR.((L4.GT.256)
     *                       .AND.(MOD(IDIR(L4),4).EQ.2)))) GO TO 401
                         IF ((KHYD.EQ.1).AND.(I.EQ.1).AND.((
     *                       (L3.GE.256).AND.(MOD(IDIR(L3),4).EQ.1)).OR.(
     *                       (L4.GT.256).AND.(MOD(IDIR(L4),4).EQ.1)))) GO TO 401
                         IF ((KHYD.EQ.2).AND.(I.EQ.2).AND.((
     *                       (L3.GE.256).AND.((MOD(IDIR(L3),4).EQ.1).OR.
     *                       (MOD(IDIR(L3),4).EQ.0))).OR.(
     *                       (L4.GT.256).AND.((MOD(IDIR(L4),4).EQ.1).OR.
     *                       (MOD(IDIR(L4),4).EQ.2)))))  GO TO 401
                         IF ((KHYD.EQ.2).AND.(I.EQ.1).AND.((
     *                       (L3.GE.256).AND.((MOD(IDIR(L3),4).EQ.1).OR.
     *                       (MOD(IDIR(L3),4).EQ.2))).OR.(
     *                       (L4.GT.256).AND.((MOD(IDIR(L4),4).EQ.1).OR.
     *                       (MOD(IDIR(L4),4).EQ.0))))) GO TO 401
                         ENDIF
35                   CONTINUE
C
C See if ILEFT, IRIGHT, or both equal 1. If one is, insert H('s) there.
C If both equal 1, use criteria to decide which side to put H('s) on.
C If neither equals 1, call error message that there is no room for H.
C
36                   CONTINUE
                     IF (ILEFT+IRIGHT.NE.0) THEN
                         IF (IRIGHT.EQ.0) THEN
                             GO TO 42
                         ELSE
                             GO TO 43
                         ENDIF
```

```
            ENDIF
CXT
CXT     Placement attached hydrogens vertical to the node is attempted.
9394    CONTINUE
        DO 9395 IN = IHP,-IHP,-IHP*2
            FY = JY + IN
            IF (((PNODE).AND.((MM(JX,FY).EQ.0).OR.(LMM(JX,FY).GE.256)))
     *         .OR.((.NOT.PNODE).AND.((MM(JX,FY).EQ.0).OR.
     *         (LMM(JX,FY).GE.256)).AND.(IDTPIX(JX,FY).EQ.0))) THEN
                DO 939 KK = -1,2
                    IF ((KK.EQ.2).AND.(KHYD.LE.1)) GO TO 939
                    DO 938 JJ = 0,1
                        IL = JX + KK
                        JL = FY + (JJ * IN)
                        IF ((MM(IL,JL).GT.0).AND.(LMM(IL,JL).LT.256).AND.
     *                     (MM(IL,JL).NE.34).AND.(LMM(IL,JL).NE.43).AND.
     *                     (LMM(IL,JL).NE.45)) GO TO 9395
                        IF ((.NOT.PNODE).AND.(IDTPIX(IL,JL).GT.0).AND.
     *                     (MOD(IDTPIX(IL,JL),2**13).LT.256).AND.
     *                     (IDTPIX(IL,JL).NE.34).AND.(MOD(IDTPIX(IL,JL),
     *                     2**13).NE.43).AND.(MOD(IDTPIX(IL,JL),2**13)
     *                     .NE.45)) GO TO 9395
938                 CONTINUE
939             CONTINUE
                IF (KHYD.GT.1) THEN
                    FX = JX + 1
                    IF (((PNODE).AND.(MM(FX,FY).EQ.0)).OR.
     *                 ((.NOT.PNODE).AND.(MM(FX,FY).EQ.0).AND.
     *                 (IDTPIX(FX,FY).EQ.0))) THEN
                        MM(JX,FY) = 72
                        MM(FX,FY) = IHYD + 48
                        IF ((PNODE).AND.(.NOT.VNODE)) THEN
                            IF (MM(JX,FY).GE.256) THEN
                                CALL FTLOCA(FY,JX)
                                CALL FTEXT('^ ^')
                            ENDIF
                            CALL CURSOR(JX,FY)
                            HALO(2) = 'H'
                            CALL TEXT(HALO)
                            CALL CURSOR(FX,FY)
                            IF (MM(FX,FY).GE.256) THEN
                                CALL FTLOCA(FY,FX)
                                CALL FTEXT('^ ^')
                            ENDIF
                            IJ = IHYD + 48
                            HALO(2) = CHAR(IJ)
                            CALL MOVTCR(0,2)
                            CALL TEXT(HALO)
                            CALL MOVTCR(0,-2)
                            DELH(1,1) = JX
                            DELH(1,2) = FY
                            DELH(1,3) = 72
                            DELH(2,1) = FX
                            DELH(2,2) = FY
                            DELH(2,3) = IJ
                        ENDIF
                        IF (FX.GT.HIX) HIX = FX
                        GO TO 9396
                    ELSE
                        GO TO 9395
                    ENDIF
                ELSE
                    MM(JX,FY) = 72
                    IF ((PNODE).AND.(.NOT.VNODE)) THEN
                        DELH(1,1) = JX
                        DELH(1,2) = FY
                        DELH(1,3) = 72
                        IF (MM(JX,FY).GE.256) THEN
                            CALL FTLOCA(FY,JX)
                            CALL FTEXT('^ ^')
                        ENDIF
                        CALL CURSOR(JX,FY)
                        HALO(2) = 'H'
                        CALL TEXT(HALO)
                    ENDIF
```

```
                  GO TO 9396
              ENDIF
          ENDIF
9395  CONTINUE
      GO TO 9397
9396  CONTINUE
          IF (FY.LT.LOY) THEN
              LOY = FY
          ELSE IF (FY.GT.HIY) THEN
              HIY = FY
          ENDIF
          CALL CURSOR(JX,JY)
          RETURN
9397  IERR=14
      JPROB=1
C ERROR IN DECIDING WHERE TO PUT H'S
      CHER = 2
      CALL MYERR(IERR,KAR,KAR)
      CHER = 0
      RETURN
C
C     Draw H on left:
C Saved for possible extension of bond
42    MBOND=LMM(JX-1,JY)
C Move to H location
      CALL CURSOR(JX-KHYD,JY)
C ASCII H into array
      MM(JX-KHYD,JY)=72
      IF ((PNODE).AND.(.NOT.VNODE)) THEN
          IF (MM(JX-KHYD,JY).GE.256) THEN
              FX = JX  - KHYD
              CALL FTLOCA(JY,FX)
              CALL FTEXT('^ ^')
          ENDIF
          HALO(2) = 'H'
          CALL TEXT(HALO)
          DELH(1,1) = JX - KHYD
          DELH(1,2) = JY
          DELH(1,3) = 72
      ENDIF
C Insert H here
      IF ((JX-2).LT.LOX) LOX = MINO(JX-2,1)
C Skip subscript if not necessary.
      IF (KHYD.LE.1) GOTO 45
C Move to cursor position: one left of node.
      CALL CURSOR(JX-1,JY)
C ASCII for typing
      IJ=IHYD+48
C backspace
      IBACK=8
C ASCII of numeral into array
      MM(JX-1,JY)=IJ
      IF ((PNODE).AND.(.NOT.VNODE)) THEN
          IF (MM(JX-1,JY).GE.256) THEN
              FX = JX - 1
              CALL FTLOCA(JY,FX)
              CALL FTEXT('^ ^')
          ENDIF
          HALO(2) = CHAR(IJ)
          CALL MOVTCR(0,2)
          CALL TEXT(HALO)
          CALL MOVTCR(0,-2)
          DELH(2,1) = JX - 1
          DELH(2,2) = JY
          DELH(2,3) = IJ
      ENDIF
C
C If blank now to the left of H, extend whatever bond was covered over
C by the H and/or subscript,if any.(If MBOND=0,there was no bond there):
45    IF (MM(JX-KHYD-1,JY).NE.0) GOTO 111
C Move cursor
      IF ((IBDIR.EQ.7) .AND. (ILEFT.EQ.1)) IX=JX-KHYD-2
      IF (MBOND.GT.256) ICHAR=1
C beyond the end of the extended bond.
C Done with valence after left insertion.
      CALL CURSOR (IX,IY)
```

```
111     CONTINUE
        RETURN
C
C  Insert (H's) on right:
C Position for H on right of node
43      MX = JX + 1
        IF (LET2.GT.0) MX=JX+2
C Save for possible bond extension.
        MBOND = LMM(MX,JY)
        CALL CURSOR(MX,JY)
C Insert H.
        IF ((JX+2).GT.HIX) HIX = MAX0(JX+2,MAXX)
C ASCII H into array
        MM(MX,JY)=72
        IF ((PNODE).AND.(.NOT.VNODE)) THEN
            IF (MM(MX,JY).GE.256) THEN
                CALL FTLOCA(JY,MX)
                CALL FTEXT('^ ^')
            ENDIF
            HALO(2) = 'H'
            CALL TEXT(HALO)
            DELH(1,1) = MX
            DELH(1,2) = JY
            DELH(1,3) = 72
        ENDIF
C No subscript needed
        IF (KHYD.LE.1) GOTO 44
C Position of subscript
        CALL CURSOR(MX+1,JY)
C ASCII for subscript
        IJ=IHYD+48
        IBACK=8
C ASCII of numeral into array
        MM(MX+1,JY)=IJ
        IF ((PNODE).AND.(.NOT.VNODE)) THEN
            IF (MM(MX+1,JY).GE.256) THEN
                FX = MX + 1
                CALL FTLOCA(JY,FX)
                CALL FTEXT('^ ^')
            ENDIF
            HALO(2) = CHAR(IJ)
            CALL MOVTCR(0,2)
            CALL TEXT(HALO)
            CALL MOVTCR(0,-2)
            DELH(2,1) = MX+1
            DELH(2,2) = JY
            DELH(2,3) = IJ
        ENDIF
C If H and subscript covered over all of bond (if any), replace with one length
C of bond, using DRAW2:
44      IF(MM(MX+KHYD,JY).NE.0) GOTO 115
        IF ((IBDIR.EQ.3) .AND. (IRIGHT.EQ.1)) IX=MX+KHYD+1
115     CONTINUE
        CALL CURSOR(IX,IY)
C Completed with insertion of H on right
        RETURN
        END
$STORAGE:2
C       SUBROUTINE NSEW(I,J,ORIENT)
C       This subroutine determines if we are dealing with groups that
C       are vertically bonded or horizontally. Vertically bonded groups
C       are defined as groups in which the components H, digits, or lower
C       case letters are bracketed on the left and right by blanks
C       or by diagonal bonds.
C       Inputs are I and J - the coordinates of the element in MM
C       Output is the variable ORIENT - ORIENT = 1 = vertically bonded
C                                              = 0 = horizontally bonded
        SUBROUTINE NSEW(I,J,ORIENT)
        IMPLICIT INTEGER*2 (A-Z)
        INTEGER*4 MM
        COMMON /STRPIX/ LPIX,MM(90,38),LBLEN,LNGBND(100,5)
        ORIENT=0
C
C       Set to default 'horizontally bonded'
        IVAL1=LMM(I-1,J)
```

```
            IVAL1A = LMM(I-1,J-1)
            IVAL1B = LMM(I-1,J+1)
            IVAL2=LMM(I+1,J)
            IVAL2A = LMM(I+1,J-1)
            IVAL2B = LMM(I+1,J+1)
            IF ((IVAL1.EQ.0 .OR. (IVAL1A.GE.256 .AND. MOD(IDIR(IVAL1A),2)
          2   .EQ.0) .OR. (IVAL1B.GE.256 .AND. MOD(IDIR(IVAL1B),2).EQ.0))
          3   .AND. (IVAL2.EQ.0 .OR. (IVAL2A.GE.256 .AND.
          4   MOD(IDIR(IVAL2A),2).EQ.0) .OR. (IVAL2B.GE.256 .AND.
          5   MOD(IDIR(IVAL2B),2).EQ.0))) ORIENT=1
    C     If there is a blank or a diagonal bond
    C     on the left and right
    C     then the component is 'vertically bonded'
            RETURN
            END
    C
    C
    C           SUBROUTINE GLEN(I,J,ORIENT,LEN,START)
    C
    C
    C       This subroutine determines the X or Y coordinate of the start
    C       Inputs are I and J - the coordinates of the element in MM
    C             ORIENT = the parameter which indicates vertical
    C                      or horizontal bonds
    C       Outputs are LEN (the length of the group) and START
    C       START = minimum X coordinate in a horizontally bonded group
    C             = minimum Y coordinate in a vertically bonded group
    C       If there is a problem finding the ends of the group LEN is set to -1
            SUBROUTINE GLEN(I,J,ORIENT,LEN,START)
            IMPLICIT INTEGER*2 (A-Z)
            INTEGER*4 MM
            COMMON /STRPIX/ LPIX,MM(90,38),LBLEN,LNGBND(100,5)
    C
            IF (ORIENT .EQ. 1) GO TO 20
    C
    C       We are dealing with a horizontal node.
            DO 40 L=0,5
               LL = L
               IF (MM(I-L,J) .EQ. 0 .OR. LMM(I-L,J) .GE. 256) GO TO 41
    40      CONTINUE
            GO TO 99
    C       Something is wrong - set LEN = -1 and abort
    41      START = I - LL + 1
            DO 60 L=1,5
               LL = L
               IF (MM(START+L,J).EQ.0.OR.LMM(START+L,J).GE.256) GO TO 61
    60      CONTINUE
            GO TO 99
    C       Something is wrong - set LEN = -1 and abort
    61      LEN=LL
            RETURN
    C       We are dealing with a vertical node
    20      DO 10 L=0,5
               LL = L
               IF (MM(I,J-L) .EQ. 0 .OR. LMM(I,J-L) .GE. 256) GO TO 11
    CXT        IF (MM(I,J+L).EQ.0.OR.LMM(I,J+L).GE.256) GO TO 11
    10      CONTINUE
            GO TO 99
    C       Something is wrong - set LEN = -1 and abort
    11      START=J-L+1
    CXT11      START = J + LL - 1
            DO 12 L=1,5
               LL = L
               IF (MM(I,START+L).EQ.0.OR.LMM(I,START+L).GE.256) GO TO 130
    CXT        IF (MM(I,START-L).EQ.0.OR.LMM(I,START-L).GE.256) GO TO 130
    12      CONTINUE
            GO TO 99
    C       Something is wrong - set LEN = -1 and abort
    130     LEN = LL
            RETURN
    99      IERR=-1
            RETURN
            END
    C
    C           SUBROUTINE BRANCH(I,J,LEN,ORIENT,RESULT)
```

```
C
C       This subroutine determines if the node starting at MM(I,J) is
C       branched
C       Inputs are I, J, LEN and ORIENT
C       I & J = coordinates of the start of the node
C       LEN = the length of the node
C       ORIENT = indicates if the node is horizontally or vertically bonded
C
C       OUTPUT = RESULT
C              = 0 = no horizontal bonds on a vertically bonded group
C                      or no vertical bonds on a horizontally bonded group
C              = 1 if a horizontally bonded group has a bond coming in
C                    from below or if a vertically bonded group has a bond
C                    coming in from the left
C              = 2 if a horizontally bonded group has a bond coming in
C                    from above or if a vertically bonded group has a bond
C                    coming in from the right
C              = 3 if a horizontally bonded group has a bond coming in
C                    from below AND above or if a vertically bonded group
C                    has a bond coming in from the right AND from the left
        SUBROUTINE BRANCH(I,J,LEN,ORIENT,RESULT)
        IMPLICIT INTEGER*2 (A-Z)
        INTEGER*4 MM
        COMMON /STRPIX/ LPIX,MM(90,38),LBLEN,LNGBND(100,5)
C
        LOW=0
        HIGH=0
        IF (ORIENT .EQ. 1) GO TO 100
C
C       Here we deal with horizontally bonded groups
        DO 10 II=-1,LEN
C!!         IVAL1=LMM(I+II,J-1)
C!!         IVAL2=LMM(I+II,J+1)
            IVAL1 = LMM(I+II,J+1)
            IVAL2 = LMM(I+II,J-1)
            IF (II .NE. -1 .AND. II .NE. LEN) GO TO 2
            IF (II .EQ. -1.AND.(IVAL1.GE.256.AND.(IDIR(IVAL1).EQ.2
     1         .OR. IDIR(IVAL1) .EQ. 6))) LOW = 1
            IF (II.EQ.-1.AND.(IVAL2.GE.256.AND.(IDIR(IVAL2).EQ.4
     1         .OR. IDIR(IVAL2) .EQ. 8))) HIGH=1
            IF (II.EQ.LEN.AND.(IVAL1 .GE.256.AND.(IDIR(IVAL1).EQ.4
     1         .OR. IDIR(IVAL1) .EQ. 8))) LOW=1
            IF (II.EQ.LEN.AND.(IVAL2.GE.256.AND.(IDIR(IVAL2).EQ.2
     1         .OR. IDIR(IVAL2) .EQ. 6))) HIGH=1
            GO TO 10
2           IF (IVAL1 .GE. 256) LOW=1
            IF (IVAL2 .GE. 256) HIGH=1
10      CONTINUE
        GO TO 200
C
C       Here we deal with vertically bonded groups
C
100     DO 20 JJ=-1,LEN
            IVAL1=LMM(I-1,J+JJ)
            IVAL2=LMM(I+1,J+JJ)
            IF (JJ .NE. -1 .AND. JJ .NE. LEN) GO TO 4
CXT         IF (JJ .NE. 1 .AND. JJ .NE. -LEN) GO TO 4
CXT         IF (JJ.EQ.1.AND.(IVAL1.GE.256.AND.(IDIR(IVAL1).EQ.2
C!!         IF (JJ.EQ.-1.AND.(IVAL1.GE.256.AND.(IDIR(IVAL1).EQ.2
C!!  1         .OR. IDIR(IVAL1) .EQ. 6))) LOW=1
            IF (JJ.EQ.-1.AND.(IVAL1.GE.256.AND.(IDIR(IVAL1).EQ.4
     1         .OR. IDIR(IVAL1) .EQ. 8))) LOW=1
CXT         IF (JJ.EQ.1.AND.(IVAL2.GE.256.AND.(IDIR(IVAL2).EQ.4
C!!         IF (JJ.EQ.-1.AND.(IVAL2.GE.256.AND.(IDIR(IVAL2).EQ.4
C!!  1         .OR.IDIR(IVAL2).EQ.8))) HIGH=1
            IF (JJ.EQ.-1.AND.(IVAL2.GE.256.AND.(IDIR(IVAL2).EQ.2
     1         .OR.IDIR(IVAL2).EQ.6))) HIGH=1
CXT         IF (JJ.EQ.-LEN.AND.(IVAL2.GE.256.AND.(IDIR(IVAL1).EQ.4
C!!         IF (JJ.EQ.LEN.AND.(IVAL2.GE.256.AND.(IDIR(IVAL1).EQ.4
C!!  1         .OR.IDIR(IVAL2).EQ.8))) LOW=1
            IF (JJ.EQ.LEN.AND.(IVAL2.GE.256.AND.(IDIR(IVAL1).EQ.2
     1         .OR.IDIR(IVAL2).EQ.6))) LOW=1
CXT         IF (JJ.EQ.-LEN.AND.(IVAL2.GE.256.AND.(IDIR(IVAL2).EQ.2
C!!         IF (JJ.EQ.LEN.AND.(IVAL2.GE.256.AND.(IDIR(IVAL2).EQ.2
C!!  1         .OR.IDIR(IVAL2).EQ.6))) HIGH=1
```

```
         IF (JJ.EQ.LEN.AND.(IVAL2.GE.256.AND.(IDIR(IVAL2).EQ.4
1          .OR.IDIR(IVAL2).EQ.8))) HIGH=1
           GO TO 20
4       IF(IVAL1 .GE. 256) LOW=1
        IF (IVAL2 .GE. 256) HIGH=1
20      CONTINUE
200     RESULT = LOW + 2*HIGH
        RETURN
        END
C
C       SUBROUTINE BRAKIT(I,J,LEN,ORIENT,LOW,HIGH)
C
C       This subroutine returns the bracketing values of the group
C       (i.e. the values at the ends of the group)
C       Inputs are I, J, LEN, and ORIENT
C
C       I & J are the coordinates of the start of the group
C       LEN = length of the group
C       ORIENT = indicates whether the group is vertically or horizontally bonded
C
C       Outputs are LOW and HIGH
C
C       LOW = array value to the left of a horizontally bonded group
C             or below vertically bonded group
C       HIGH = array value to the right of a horizontally bonded group
C              or above a vertically bonded group
        SUBROUTINE BRAKIT(I,J,LEN,ORIENT,LOW,HIGH)
        IMPLICIT INTEGER*2 (A-Z)
        INTEGER*4 MM
        COMMON /STRPIX/ LPIX,MM(90,38),LBLEN,LNGBND(100,5)
C
        IF (ORIENT .EQ. 1) GO TO 200
C
C          Here we handle horizontally bonded groups
C
           LOW=LMM(I-1,J)
           HIGH=LMM(I+LEN,J)
           RETURN
C
C          Here we handle vertically bonded groups
C
200        LOW=LMM(I,J-1)
           HIGH=LMM(I,J+LEN)
CXT200     LOW=LMM(I,J+1)
CXT        HIGH=LMM(I,J-LEN)
        RETURN
        END
C
C       SUBROUTINE COPY(I,J,LEN,ORIENT,NODE)
C
C
C       This subroutine copies the node in MM to the vector NODE
C
C
C       Inputs are I, J, LEN, and ORIENT
C       I & J = coordinates of the group in MM
C       LEN = length of the group
C       ORIENT = indicates if the group is a horizontally or vertically bonded gr
C       Output is the vector NODE
        SUBROUTINE COPY(I,J,LEN,ORIENT)
        IMPLICIT INTEGER*2 (A-Z)
        INTEGER*4 MM,NODE
        COMMON /STRPIX/ LPIX,MM(90,38),LBLEN,LNGBND(100,5)
        COMMON /KNOD/ NODE(4)
C       Zero NODE
C
        DO 5 K=1,4
5          NODE(K)=0
        IF (ORIENT .EQ. 1) GO TO 100
C
C          Here we handle a horizontally bonded group
C
           DO 10 K=1,LEN
              NODE(K)=MM(I+K-1,J)
10         CONTINUE
           RETURN
```

```
C
C         Here we handle vertically bonded groups
C
100       DO 30 K=1,LEN
          NODE(K)=MM(I,J+K-1)
CXT       NODE(K)=MM(I,J-K+1)
30        CONTINUE
          RETURN
       END
C
C      SUBROUTINE RORDER(NODE,LEN,LC,DIG)
C
C      This subroutine will reorder the NODE so that the characters
C      appear in the following order
C                   UC - lc - H - digit
C      Inputs are NODE (the 4 element array) and LEN (the # of Characters in NODE)
C      Outputs are the reordered NODE, LC, and DIG
C      LC = the lower case char in NODE if there is one
C         = 0 if the NODE contains no lower case character
C      DIG = the digit in NODE if there is one
C          = 0 if the NODE contains no digit
       SUBROUTINE RORDER(LEN,LC,DIG)
       IMPLICIT INTEGER*2 (A-Z)
       INTEGER*4 MM,NODE
       COMMON /STRPIX/ LPIX,MM(90,38),LBLEN,LNGBND(100,5)
       COMMON /KNOD/ NODE(4)
C
       H=0
       LC=0
       DIG=0
       UC=0
       DO 10 K=1,LEN
          IF (NODE(K) .EQ. 72) H=72
          IF ((NODE(K).GE.65.AND.NODE(K).LE.90).AND.NODE(K).NE.72)
      1       UC=NODE(K)
          IF (NODE(K) .GE. 49 .AND. NODE(K) .LE. 57) DIG=NODE(K)
          IF (NODE(K) .GE. 97 .AND. NODE(K) .LE. 122) LC=NODE(K)
10     CONTINUE
       FULL=0
       IF (H .NE. 0) FULL=FULL+1
       IF (LC .NE. 0) FULL=FULL+1
       IF (DIG .NE. 0) FULL=FULL+1
       IF (UC .NE. 0) FULL=FULL+1
       IF (UC .EQ. 0) UC=72
C      UC = H if no other UC found
       IF (FULL .GT. LEN) H=0
       I=1
       NODE(I)=UC
       I=I+1
       IF (LC .EQ. 0) GO TO 500
       NODE(I)=LC
       I=I+1
500    IF (H .EQ. 0) GO TO 600
          NODE(I)=H
          I=I+1
          IF (DIG .EQ. 0) GO TO 600
          NODE(I)=DIG
600    RETURN
       END
C
C      SUBROUTINE ORDER2(NODE,LEN,IERR)
C
C      This subroutine is used to reorder the NODE if we are trying
C      to copy the node to the left not the right
C      Consider NODE=CH3 - ORDER2 will change it so that NODE=C3H
C      Then when node is copied to the right (in reverse) it will appear as H3C
C      Inputs are NODE and LEN - LEN is the length of NODE
C
C      Outputs are the reordered NODE and the error return IERR
C      This reordering can't be done if the NODE includes a 2 letter element
C      In that case IERR=1  -   If the reordering is successful IERR=0
       SUBROUTINE ORDER2(LEN,IERR)
       IMPLICIT INTEGER*2 (A-Z)
       INTEGER*4 NODE
       COMMON /KNOD/ NODE(4)
```

```
      IERR=1
C
C     Bail out if we find a lower case char
      DO 10 I=1,LEN
         IF (NODE(I) .GE. 97 .AND. NODE(I) .LE. 122) RETURN
10    CONTINUE
      IERR=0
C
C     If there is no digit - just return
C
      IF (NODE(LEN) .LT. 49 .OR. NODE(LEN) .GT. 57) RETURN
      HOLD=NODE(LEN)
      NODE(LEN)=NODE(LEN-1)
      NODE(LEN-1)=HOLD
      RETURN
      END
C
C     SUBROUTINE MOVE1(I,J,LEN,NODE)
C
C
C
C     This subroutine copies the contents of NODE into the horizontally
C     bonded node of length LEN starting at MM(I,J)
      SUBROUTINE MOVE1(I,J,LEN)
      IMPLICIT INTEGER*2 (A-Z)
      INTEGER*4 MM,NODE
      COMMON /STRPIX/ LPIX,MM(90,38),LBLEN,LNGBND(100,5)
      COMMON /RANGE/ LOX,HIX,LOY,HIY
      COMMON /KNOD/ NODE(4)
      DO 10 K=0,LEN-1
         MM(I+K,J)=NODE(K+1)
10    CONTINUE
      IF (HIX .LT.(I+LEN-1)) HIX=I+LEN-1
      RETURN
      END
C
C     SUBROUTINE MOV2(I,J,LEN1,K,M,LEN,NODE,REP)
C
C     This subroutine will replace LEN1 chars of the vertically bonded node
C     starting at MM(I,J) with the value in REP (REP will be a 0
C     or a bond) It will then copy the node of length LEN stored in NODE into
C     MM starting at coordinates K and L and continuing to the right
      SUBROUTINE MOV2(I,J,LEN1,K,M,LEN,REP)
      IMPLICIT INTEGER*2 (A-Z)
      INTEGER*4 MM,NODE
      COMMON /STRPIX/ LPIX,MM(90,38),LBLEN,LNGBND(100,5)
      COMMON /RANGE/ LOX,HIX,LOY,HIY
      COMMON /KNOD/ NODE(4)
      IF (LEN1 .EQ. 0) GO TO 15
      DO 10 N=0,LEN1-1
      MM(I,J+N)=REP
CXT      MM(I,J-N) = REP
10    CONTINUE
15    DO 11 N=0,LEN-1
         MM(K+N,M) = NODE(N+1)
11    CONTINUE
      IF (HIX .LT. (K+LEN-1)) HIX=K+LEN-1
      RETURN
      END
C
C     SUBROUTINE MOV3(I,J,LEN1,K,M,LEN,NODE,REP)
C
C
C     This subroutine will replace LEN1 chars of the vertically bonded node
C     starting at MM(I,J) with the value in REP (REP will be a 0
C     or a bond) It will then copy the node of length LEN stored in NODE into
C     MM starting at coordinates K and L and continuing to the left
      SUBROUTINE MOV3(I,J,LEN1,K,M,LEN,REP)
      IMPLICIT INTEGER*2 (A-Z)
      INTEGER*4 MM,NODE
      COMMON /STRPIX/ LPIX,MM(90,38),LBLEN,LNGBND(100,5)
      COMMON /KNOD/ NODE(4)
      COMMON /RANGE/LOX,HIX,LOY,HIY
C
      IF (LEN1 .EQ. 0) GO TO 15
      DO 10 N=0,LEN1-1
```

```
              MM(I,J+N)=REP
CXT           MM(I,J-N) = REP
10         CONTINUE
15         DO 11 N=0,LEN-1
              MM(K-N,M) = NODE(N+1)
11         CONTINUE
           IF (LOX .GT. (K-(LEN-1))) LOX=K-(LEN-1)
           RETURN
           END

C
C          SUBROUTINE MOV4(I,J,K,M,LEN,NODE,REP)
C
C          This subroutine will replace the horizontally bonded node of length
C          LEN starting at MM(I,J) with the value in REP (REP will be a 0
C          or a bond) It will then copy the node stored in NODE into
C          MM starting at coordinates K and L and continuing to the right
           SUBROUTINE MOV4(I,J,K,M,LEN,REP)
           IMPLICIT INTEGER*2 (A-Z)
           INTEGER*4 MM,NODE
           COMMON /STRPIX/ LPIX,MM(90,38),LBLEN,LNGBND(100,5)
           COMMON /KNOD/ NODE(4)
           COMMON /RANGE/ LOX,HIX,LOY,HIY
           DO 10 N=1,LEN
              MM(I+N-1,J)=REP
10         CONTINUE
           DO 11 N=0,LEN-1
              MM(K+N,M)=NODE(N+1)
11         CONTINUE
           IF (HIX .LT. (K+LEN-1)) HIX=K+LEN-1
           RETURN
           END C
C          SUBROUTINE SCAN(I,J,IERR)
C
C          This subroutine will scan IDTPIX and MM for space conflicts
C
C          This subroutine will scan MM(I,J), MM(I,J-1) and MM(I,J+1)
C          and the corresponding elements in IDTPIX.
C          It will return IERR = 0 if IDTPIX(I,J) is empty and MM(I,J)
C          is empty or contains a horizonal bond and
C          MM(I,J-1), IDTPIX(I,J-1), IDTPIX(I,J+1) and MM(I,J+1)
C          are empty or contain a diagonal bond
C          Else it will return IERR = 1.
C
           SUBROUTINE SCAN(I,J,IERR)
           IMPLICIT INTEGER*2 (A-Z)
           INTEGER*4 MM,IDTPIX
           COMMON /STRPIX/ LPIX,MM(90,38),LBLEN,LNGBND(100,5)
           COMMON /STRED/ IDTPIX(90,38),LABL(260,2),MRKCHN(260)
C
           IERR=1
           IVAL1=MM(I,J-1)
           IVAL2=MM(I,J+1)
           IVAL3=IDTPIX(I,J-1)
           IVAL4=IDTPIX(I,J+1)
C          IF ((MM(I,J) .EQ. 0  .AND. (IVAL1 .EQ. 0 .OR. (IVAL1 .GE. 256
C        1     .AND. (MOD(IDIR(IVAL1),2) .EQ. 0))) .AND. (IVAL2 .EQ.0 .OR.
C        2     (IVAL2 .GE. 256 .AND. (MOD(IDIR(IVAL2),2) .EQ.0))))
           IF (((MM(I,J).EQ.0 .OR. IDIR(LMM(I,J)).EQ.3 .OR. IDIR(LMM(I,J))
         1     .EQ.7) .AND. (IVAL1.EQ.0 .OR. (IVAL1.GE.256 .AND.
         2     (MOD(IDIR(IVAL1),2).EQ.0))) .AND. (IVAL2 .EQ.0 .OR.
         2     (IVAL2 .GE. 256 .AND. (MOD(IDIR(IVAL2),2) .EQ.0))))
         3     .AND.
         4     (IDTPIX(I,J) .EQ. 0 .AND. (IVAL3 .EQ. 0 .OR. (IVAL3 .GE.256
         5     .AND. (MOD(IDIR(IVAL3),2).EQ.0))) .AND. (IVAL4 .EQ. 0 .OR.
         6     (IVAL4 .GE. 256 .AND. (MOD(IDIR(IVAL4),2) .EQ. 0)))))
         7     IERR=0
           RETURN
           END C
C          SUBROUTINE FINDX(I,J,IVAL,LEN,INODE)
C
C          This subroutine will search LEN cells of the array MM for the
C          value IVAL starting at coordinates I & J and looking to the right
C          It will return the X coordinate in INODE if the value is found
```

```
C       If the value is not found INODE will be set to -1
C
        SUBROUTINE FINDX(I,J,IVAL,LEN,INODE)
        IMPLICIT INTEGER*2 (A-Z)
        INTEGER*4 MM
        COMMON /STRPIX/ LPIX,MM(90,38),LBLEN,LNGBND(100,5)
        DO 10 K=0,LEN-1
            KK = K
            IF (IVAL .EQ. MM(I+K,J)) GO TO 25
10      CONTINUE
        INODE=-1
        RETURN
25      INODE = I + KK
        RETURN
        END
C
C       SUBROUTINE BLEN(I,J,IVAL,LEN)
C
C       There should be a horizontal bond of type IVAL starting at MM(I,J)
C       This subroutine will determine the length of the bond and
C       return it in LEN - If the bond is not found the LEN will be 0
        SUBROUTINE BLEN(I,J,IVAL,LEN)
        IMPLICIT INTEGER*2 (A-Z)
        INTEGER*4 MM
        COMMON /STRPIX/ LPIX,MM(90,38),LBLEN,LNGBND(100,5)
        LEN=0
        DO 10 K=0,100
            IF (MM(I+K,J) .NE. IVAL) GO TO 100
            LEN=LEN+1
10      CONTINUE
100     CONTINUE
        RETURN
        END
C
C       SUBROUTINE FINDY(I,J,IVAL,LEN,INODE)
C
C       This subroutine will search LEN cells of the array MM for the
C       value IVAL starting at coordinates I & J and looking up
C       It will return the Y coordinate in INODE if the value is found
C       If the value is not found INODE will be set to -1
C
        SUBROUTINE FINDY(I,J,IVAL,LEN,INODE)
        IMPLICIT INTEGER*2 (A-Z)
        INTEGER*4 MM
        COMMON /STRPIX/ LPIX,MM(90,38),LBLEN,LNGBND(100,5)
        DO 10 K=0,LEN-1
            KK = K
        IF (IVAL .EQ. MM(I,J+K)) GO TO 25
CXT     IF (IVAL .EQ. MM(I,J-K)) GO TO 25
10      CONTINUE
        INODE=-1
        RETURN
25      INODE = J + KK
        RETURN
        END
C
C       SUBROUTINE FIXUP(IERR)
C
C       This subroutine will examine nodes in MM - If the node is not
C       in the proper order due to rotations or reflections, FIXUP
C       will try to reorder the node - If it can, the node will be reordered
C       and IERR will be set to 0 - If it can't, IERR will be set to -1
C
        SUBROUTINE FIXUP(IERR)
        IMPLICIT INTEGER*2 (A-Z)
        INTEGER*4 MM,NODE
        COMMON /CD/ MAXX,MAXY
        COMMON /STRPIX/ LPIX,MM(90,38),LBLEN,LNGBND(100,5)
        COMMON /KNOD/ NODE(4)
        COMMON /RANGE/ LOX,HIX,LOY,HIY
        COMMON /CUR/ ICUR
C
C       Start looking through the array
C
        DO 10 I = LOX,HIX
```

```
            DO 10 J = LOY,HIY
               IF (MM(I,J).EQ.0) GO TO 10
               II = I
               JJ = J
               ICUR = 0
               CALL CURSOR(II,JJ)
               CALL CKNOD2(II,JJ,IVAL,IERR)
C              Is there a problem with this node.
               IF (IERR .EQ. 0) GO TO 10
C              IERR=0 means node is OK
C
C
C              Node is bad - See if we can fix it
C
               CALL NSEW(II,JJ,ORIENT)
C              Get node orientation
               CALL GLEN(II,JJ,ORIENT,LEN,START)
C              Get length of node and starting location of node
               IF (ORIENT .EQ. 0) GO TO 500
C
C           Here we handle vertical nodes
            CALL COPY (II,START,LEN,ORIENT)
C           Copy node in MM into NODE
            CALL RORDER(LEN,LC,DIG)
C           Reorder the node
            CALL BRAKIT(II,START,LEN,ORIENT,LOW,HIGH)
C           Get the values above and below the node
            NOD = NODE(1)
            CALL FINDY(II,START,NOD,LEN,INODE)
            NODE(1) = NOD
C           Find Y coordinate for start of UC element of node
            L=INODE-START
            LEND=LEN-L-1
            IF (LEND .EQ. 0) GO TO 22
            DO 20 K=1,LEND
C              Extend bond value or blank value from above the node downward.
20             MM(I,INODE+K)=HIGH
CXT20          MM(I,INODE-K)=HIGH
C
C              Try to extend node to the right
22          DO 61 K=1,LEN
C              See if room for node on the right
               M=I + K
               CALL SCAN(M,INODE,IERR)
               IF (IERR .EQ. 1) GO TO 80
C              No room on this side but we can try other side
61          CONTINUE
            CALL MOV2(II,START,L,II,INODE,LEN,LOW)
C           Copy node to MM
            GO TO 10
80          DO 75 K=1,LEN
               M=I - K
C              Do we have room on the left
               CALL SCAN(M,INODE,IERR)
               IF (IERR .EQ. 1) GO TO 900
C              No room - bail out
75          CONTINUE
            CALL ORDER2(LEN,IERR)
C           Reorder node for left side
            IF (IERR .EQ. -1) GO TO 900
C           Can't reorder - bail out
C
C
C           Extend node to the left
C
            CALL MOV3(II,START,L,II,INODE,LEN,LOW)
C           Copy node to MM
            GO TO 10
C
C           We are dealing with a horizontal node
500         CALL BRANCH(START,JJ,LEN,ORIENT,RESULT)
C           Determine if the node is branched
            CALL COPY(START,JJ,LEN,ORIENT)
C           Copy node in MM into NODE
            CALL RORDER(LEN,LC,DIG)
C           Reorder the node
            CALL BRAKIT(START,JJ,LEN,ORIENT,LOW,HIGH)
```

```
C       Get the values to the left and right of the node
        IF (RESULT .NE. 0) GO TO 600
C
C       We are dealing with an unbranched node
C
        CALL MOVE1(START,JJ,LEN)
C       Copy node into MM
        GO TO 10
C
C       We are dealing with a branched node
C
600     NOD = NODE(1)
        CALL FINDX(II,JJ,NOD,LEN,INODE)
        NODE(1) = NOD
C       Find position where node should start
        IF (INODE .EQ. -1) GO TO 900
C       Can't find starting char - abort
        IVAL=HIGH
C       IVAL = value of bond to right of node
        IF (IVAL .EQ. 0) GO TO 800
C       If IVAL=0 - call SCAN to see if we have room to extend
C       node on the right
        END=START+LEN
C       END = X coordinate just beyond end of node
        CALL BLEN(END,JJ,IVAL,BONDL)
C       Get bond length of bond to right of node
        IF (BONDL .EQ. 0) GO TO 900
C       Bad bond - abort
        IF (BONDL .LT. LEN) GO TO 900
C       Bond too short - abort
        GO TO 700
800     DO 83 K=1,LEN
        M=INODE+K
        CALL SCAN(M,JJ,IERR)
C       SCAN to right to see if we have room for node
        IF (IERR .EQ. 1) GO TO 900
83      CONTINUE
700     CALL MOV4(START,JJ,INODE,JJ,LEN,LOW)
C       Move node into MM and pad to the left of the new node with value
C       LOW (from BRAKIT)
10      CONTINUE
        IERR=0
C       Set error code IERR to 0 = OK
        RETURN
900     IERR=-1
        RETURN
        END $STORAGE:2
        SUBROUTINE BOND(IERR,IX,IY)
C This program converts the 90x31 arrays which contain graphic
C structures of chemical compounds to connection tables.
C In addition, long bond information is read from a separate file
C and merged with the bond information from the standard data to form
C a complete connection table.
C
C
        IMPLICIT INTEGER*2 (A-Z)
        COMMON /NDE/ NODE(255,3),IATOM
C       SET ERROR FLAG = 0 = OK FOR NOW
        IERR=0
        CALL READD(IERR,IX,IY)
C       RETURN TO STRINP IF BAD RETURN FROM READ
        IF (IERR .NE. 0 ) RETURN
        CALL NOD(IERR,IX,IY)
C       RETURN TO STRINP ON BAD RETURN FROM NOD
        IF (IERR .NE. 0) RETURN
        CALL CONNET(IERR,IX,IY)
C       RETURN TO STRINP ON BAD RETURN FROM CONNET
        IF (IERR .NE. 0) RETURN
        CALL CHGHYD(IERR,IX,IY)
        IF (IERR.NE.0) RETURN
        IF(IATOM .NE. 0) GO TO 40
        IERR=18
C       NULL CONNECTION TABLE - RETURN TO DIS WITH NO DATA
```

```
           CALL MYERR(IERR,KAR,KAR)
           RETURN
40         CONTINUE
           CALL TBLOUT(IERR,IX,IY)
           RETURN
           END
C
C
C          SUBROUTINE READD(IERR,JX,JY)
           IMPLICIT INTEGER*2 (A-Z)
           INTEGER*4 IARRAY
           COMMON /CD/ MAXX,MAXY
           COMMON /RANGE/ LOX,HIX,LOY,HIY
           COMMON /STRPIX/ LPIX,IARRAY(90,38),LBLEN,LNGBND(100,5)
           COMMON /D1/ IDNUM,IDS(9,6),NBD1,DSCNC(6,50)
           COMMON /CUR/ ICUR
C
C          Variable MNUM contains the number of *M structures and array
C          IMS contains the following items for each *M structure:
C             1 - The multiplier of the structure.
C             2 - The M1 identifying ordinal value.
C             3,4 - The x and y coordinates of the *M.
C             5 - The length of the *M conection table entry.
C             6 - The length of the formula to follow.
C             7 - The divisor of the multiplier (if fractional).
C             8 thru 90 - The molecular formula of the M1 structure.
           COMMON /M1/ MNUM,IMS(90,5)
           COMMON /DTDS/ DTN,DTX(30),DTY(30),DTN1(30),DTN2(30)
C          # of D1's - coordinates - multiplier-1 and node #
           DIMENSION ISTRNG(20),ISTRUC(7,5),JSTRUC(5)
C          READS IN ARRAY OF GRAPHICAL INFORMATION
C          Each element of IARRAY(IX,IY) contains a part
C          of the graph of the chemical compound.  An integer
C          less than 256 indicates an ASCII character (Cap or l.c.)
C          --symbol of an element {O, Ca, etc or a dot[Carbon]},
C          a numeral, + or - sign). An integer >256 indicates a bond.
C          IARRAY(IX,IY) Mod 256 indicates the direction (0--3), while
C          the greatest integer in IARRAY(IX,IY)/256 indicates
C          the bond type, according to a code.
           DATA ISTRUC/72,78,78,67,67,72,0,67,97,97,
     *         108,108,43,0,108,0,43,0,45,0,0,0,0,0,0,0,0,0,
     *         0,0,0,0,0,0,0/
C structures:  HCl,Na,Na+,Cl,Cl-,H+
C
           MNUM = 0
           M1MAX = 14
           DTN = 0
           DO 21 I= LOX,HIX
           DO 21 J= LOY,HIY
           IF (IARRAY(I,J).NE.42) GOTO 2211
           JX = I
           JY = J
           DTN = DTN + 1
           IF (DTN.GT.30) THEN
               CALL FTSIZE(2,18)
               CALL FTLOCA(1,1)
               CALL FTEXT('^DOTDIS STRUCTURES EXCEED MAXIMUM OF 30^')
               IERR = 200
               PAGE = 0
               DTN = 30
               CALL FTSIZE(1,10)
               GO TO 37
           ENDIF
           DTX(DTN) = I
           DTY(DTN) = J
           NUMTOR = 0
           K=0
C Routine to handle dot_disconnects;K=no of char in number or fraction
           M=1
           IDIGIT=0
           IFRAC=0
C Set fraction indicator to no
C *=dot-disconn struc follows
           IF (IARRAY(I+M,J).EQ.0) GOTO 56
C blank after *: skip
```

```
CXT       IARRAY(I,J)=0
C Eliminate '*' from array
          IF (ILRRAY(I+M,J).EQ.43 .OR. ILRRAY(I+M,J).EQ.45) GO TO 56
C Not a + or - so go on
C We found a + or - so erase the entire dot-disconnected structure
CXT       IEND=MAXX - I
CXT       DO 61 L=1,IEND
CXT       IF (IARRAY(I+L,J) .EQ. 0) GO TO 21
CXT       IARRAY(I+L,J)=0
C Erase all dot-disconnect until space is found
CXT61     CONTINUE
CXT       GO TO 21
          IF (IARRAY(I+M,J).GE.97 .AND. IARRAY(I+M,J).LE.122) GO TO 56
C Do we have a lower case letter
C Dot disconnect is of the form nHCl - Eliminate the n
CXT       IARRAY(I+M,J)=0
CXT       M=M+1
C Get next character
70        CONTINUE
          VAL = 1
          IF (IARRAY(I+M,J).LT.48 .OR. IARRAY(I+M,J).GT.57) GO TO 80
C Is it a digit?
C We found a digit
          IDIGIT=M+I
          VAL = ILRRAY(IDIGIT,J) - 48
          DTN1(DTN) = VAL
C Location of first digit in number
          K=K+1
C # of characters in # or fraction
          M=M+1
75        IF (IARRAY(I+M,J) .LT. 48 .OR. IARRAY(I+M,J) .GT. 57) GO TO 80
C We found another digit
          VAL = (VAL * 10) + IARRAY(I+M,J) - 48
          IF (VAL.GE.1000) GO TO 56
          IF (IFRAC.EQ.0) THEN
             DTN1(DTN) = VAL
          ELSE IF (IFRAC.EQ.1) THEN
             DTN1(DTN) = NUMTOR
             DTN2(DTN) = VAL
          ENDIF
          K=K+1
C Increase character count
          M=M+1
C Get next character
C M+I>103 implies we went off the edge
          IF ((M+I).LE.MAXX) GO TO 75
          GO TO 56
C Issue error message and return
80        IF (IARRAY(I+M,J) .NE. 47) GO TO 85
C 47 = /
C We found a /  We have a fraction
          IFRAC = IFRAC + 1
          IF (IFRAC.GT.1) GO TO 56
          NUMTOR = VAL
          VAL = 0
C Set fraction indicator to yes
          K=K+1
C Increase character count
          M=M+1
C Get next character
          IF ((I+M).LE.MAXX) GO TO 75
          GO TO 56
C We went off the edge - issue msg and return
85        CONTINUE
          IF ((IFRAC.EQ.1).AND.(VAL.EQ.0)) GO TO 56
          IF (IARRAY(I+M,J).NE.77.OR.IARRAY(I+M+1,J).LT.112.OR.
     *    IARRAY(I+M+1,J).GT.120) GO TO 88
C Is it a D1 or M1 structure
C We found an M1 or D1
          DTX(DTN) = 0
          DTY(DTN) = 0
          DTN1(DTN) = 0
          DTN2(DTN) = 0
          DTN = DTN - 1
          MNUM = MNUM + 1
```

```
            IF ((MNUM.GT.5).OR.(IARRAY(I+M+2,J).NE.58)) GO TO 56
            IF (IFRAC.EQ.0) THEN
                IMS(1,MNUM) = VAL
            ELSE IF (IFRAC.EQ.1) THEN
                IMS(7,MNUM) = VAL
                IMS(1,MNUM) = NUMTOR
            ENDIF
            IMS(2,MNUM) = ILRRAY(I+M+1,J)
            IMS(3,MNUM) = I + M
            IMS(4,MNUM) = J
C           If more than of the same M1 structure definitions exist,
C           differing only in the multiplication factor, the duplicate
C           definitions are not entered into the connection table.
            DO 6350 KK = 1,MNUM-1
                IF (IMS(2,KK).EQ.IMS(2,MNUM)) THEN
                    JX = IMS(3,MNUM)
                    JY = IMS(4,MNUM)
                    IERR = 46
                    CALL MYERR(IERR,IERR,IERR)
                    ICUR = 1
                    CALL CURSOR(JX,JY)
                    RETURN
                ENDIF
6350        CONTINUE
C           It is a M1 - Count its length and erase it all for it should
C           not appear in the connection table
            IEND = MAXX - I
            DO 6351 KK = 2,IEND
                IF (IARRAY(I+M+KK,J).EQ.0) GO TO 6352
                IMS(5,MNUM) = IMS(5,MNUM) + 1
                IMS(6+KK,MNUM) = ILRRAY(I+M+KK,J)
6351        CONTINUE
6352        CONTINUE
            IMS(6,MNUM) = IMS(5,MNUM)
C
C           Length of formula including multiplier, x and y coordinates,
C           and their delimiters is computed and assigned.
            IF (IMS(1,MNUM).GT.1) THEN
                IMS(5,MNUM) = IMS(5,MNUM) + 2
                IF (IMS(1,MNUM).GE.10) THEN
                    IMS(5,MNUM) = IMS(5,MNUM) + 1
                    IF (IMS(1,MNUM).GE.100) IMS(5,MNUM) =
     *                  IMS(5,MNUM) + 1
                ENDIF
            ENDIF
            IF (IMS(7,MNUM).GT.0) THEN
                IMS(5,MNUM) = IMS(5,MNUM) + 2
                IF (IMS(7,MNUM).GE.10) THEN
                    IMS(5,MNUM) = IMS(5,MNUM) + 1
                    IF (IMS(7,MNUM).GE.100) IMS(5,MNUM) = IMS(5,MNUM) + 1
                ENDIF
            ENDIF
            IMS(5,MNUM) = IMS(5,MNUM) + 6
            IF (IMS(3,MNUM).GE.10) THEN
                IMS(5,MNUM) = IMS(5,MNUM) + 1
                IF (IMS(3,MNUM).GE.100) IMS(5,MNUM) = IMS(5,MNUM) + 1
            ENDIF
            IF (IMS(4,MNUM).GE.10) THEN
                IMS(5,MNUM) = IMS(5,MNUM) + 1
                IF (IMS(4,MNUM).GE.100) IMS(5,MNUM) = IMS(5,MNUM) + 1
            ENDIF
            M1MAX = M1MAX + IMS(5,MNUM) + 2
            IF (M1MAX.GT.160) THEN
                JX = IMS(3,MNUM)
                JY = IMS(4,MNUM)
                IERR = 22
                CALL MYERR(IERR,IERR,IERR)
                ICUR = 1
                CALL CURSOR(JX,JY)
                RETURN
            ENDIF
            DO 89 KK=0,IEND
            IF (IARRAY(I+KK,J) .EQ. 0) GO TO 21
            IARRAY(I+KK,J)=0
89          CONTINUE
```

```
          GO TO 21
C
C
C
C We found a D1
CXT90     IF (IFRAC .EQ. 1) GO TO 56
C D1 with fractional multiplier not allowed
C No multiplier = no problem
CXT       IF (K .GT. 5) GO TO 56
C Multiplier with > 5 digits is not allowed
C Convert numeric characters to integer
C Multiplier = 1 implies no problem
CXT       IDNUM=IDNUM+1
C # of D1 structures found
CXT       IF (IDNUM .GT. 9) GO TO 56
C No more than 9 D1's allowed
CXT       IDS(IDNUM,1)=I+M
C X coordinate of D1
CXT       IDS(IDNUM,2)=J
C Y coordinate of D1
CXT       IDS(IDNUM,3) = VAL
C # of additional times D1 will have to be copied into connection table
CXT       IDS(IDNUM,4)=0
C Will eventually be set to node #
CXT       GO TO 21
C Regular dot-disconnect - See if it is allowed
88        M=M-1
          DO 32 L=1,5
          JSTRUC(L)=0
C used to match structure to library file
32        CONTINUE
          DO 33 L=1,5
          IF (IARRAY(I+M+L,J).EQ.74) IARRAY(I+M+L,J) = 72
          IF (IARRAY(I+M+L,J).EQ.0 ) GOTO 34
          JSTRUC(L)=ILRRAY(I+M+L,J)
C Copy structure from array to JSTRUC
33        CONTINUE
34        CONTINUE
          DO 35 K=1,7
          DO 36 L=1,5
          IF (JSTRUC(L).NE.ISTRUC(K,L)) GOTO 35
36        CONTINUE
          GOTO 21
C Successful match to library in ISTRUC
35        CONTINUE
39        IERR=20
C SET ERROR FLAG
          CALL MYERR(IERR,KAR,KAR)
37        CONTINUE
          JX = I + M
          JY = J
          ICUR = 1
          CALL CURSOR(JX,JY)
C TYPE DOT-DISCONNECTED UNIT NOT ON FILE IN SUB READ
          RETURN
2211      IF (IARRAY(I,J).GT.0) THEN
            IF (ILRRAY(I,J).LT.256) THEN
              IF (IARRAY(I,J).NE.46) THEN
                IF ((IARRAY(I,J).LT.65).OR.(IARRAY(I,J).GT.90)) THEN
                  IF ((IARRAY(I,J).LT.48).OR.(IARRAY(I,J).GT.57)) THEN
                    IF ((IARRAY(I,J).LT.97).OR.(IARRAY(I,J).GT.122))
     *              THEN
                      IF ((ILRRAY(I,J).NE.43).AND.(ILRRAY(I,J)
     *                .NE.45))THEN
                        IF ((IARRAY(I,J).NE.63).AND.
     *                  (IARRAY(I,J).NE.34)) THEN
                          IF (IARRAY(I,J).NE.47) THEN
                            IERR = 10
                            CALL MYERR(IERR,IERR,IERR)
                            JX = I
                            JY = J
                            RETURN
                          ENDIF
                        ENDIF
                      ENDIF
                    ENDIF
```

```
              ENDIF
             ENDIF
            ENDIF
           ENDIF
          ENDIF
 21       CONTINUE
C Search thru array
          GOTO 57
C To end
 56       IERR=21
          CALL MYERR(IERR,KAR,KAR)
          ICUR = 1
          CALL CURSOR(JX,JY)
C Problem handling dot disconnected structure
 57       RETURN
          END
C
C
          SUBROUTINE NOD(IERR,JX,JY)
          IMPLICIT INTEGER*2 (A-Z)
          INTEGER*4 IARRAY
          COMMON /CD/ MAXX,MAXY
          COMMON /RANGE/ LOX,HIX,LOY,HIY
          COMMON /HP/IHP
          COMMON /NDE/ NODE(255,3),IATOM
C         NODE(255,3) stores the X, Y, and chem element code for up to 255
C         nodes (junctions of bonds) for the compound under study.
          COMMON /STRPIX/ LPIX,IARRAY(90,38),LBLEN,LNGBND(100,5)
C         IARRAY(I,J) CONTAINS BOND OR ATOM TYPE, & BOND DIRECTION
C         FOR EACH OF MAXX * MAXY LOCATIONS.
C         DNUM is the # of D1 structures found
          COMMON /D1/ IDNUM,IDS(9,6),NBD1,DSCNC(6,50)
C         IDS(1) = x-coordinate of D1 structure
C         IDS(2) = y-coordinate of of D1 structure
C         IDS(3) = multiplier - 1 (i.e. # of additional times D1 must be
C            copied into connection table)
C         IDS(4) = NODE # for the node
C         IDS(5) = NODE # for the last node in the fragment
C         IDS(6) = NNODE = # of nodes before fragment was replicated in
C            connection table.
          COMMON /ELECHR/ IELEM(126,5)
          COMMON /CUR/ ICUR
          COMMON /M1/ MNUM,IMS(90,5)
          COMMON /LNGOUT/ LNGNDE(100,2)
          COMMON /WARN/ ERR
          COMMON /QTVLNC/ OERR,CHER
          COMMON /HEAD/ MW(12),ISTATE,PAGE
          COMMON /DTDS/ DTN,DTX(30),DTY(30),DTN1(30),DTN2(30)
          COMMON /GPRNT/ KHAR
          COMMON /ELENOD/ IELT
C
          IATOM=0
C         Fill NODE by searching through IARRAY:
          DO 999 I= LOX,HIX
          DO 999 J= LOY,HIY
C         Lowercase and non'.' are not nodes.
          IF(((IARRAY(I,J).LE.62).OR.(IARRAY(I,J).GE.91))
     2      .AND.(IARRAY(I,J).NE.46)) GO TO 999
C  H's not followed by a lowercase letter are not nodes.
          IF ((IARRAY(I,J).EQ.72).AND.(((IARRAY(I+1,J).LT.97).OR.
     2      (IARRAY(I+1,J).GT.122)).AND.(((IARRAY(I-1,J).NE.42).AND.
     3      (IARRAY(I-1,J).LT.48).AND.(IARRAY(I-1,J).GT.57)).OR.
     3      (ILRRAY(I+1,J).NE.43)))) GOTO 999
          IATOM=IATOM + 1
CXT       M = 33
          IF (IATOM.GT.255) THEN
C Too many nodes - i.e. greater than 255
          IERR=35
          CALL MYERR(IERR,KAR,KAR)
          RETURN
          ENDIF
C X,Y of node are equal to I,J
          NODE(IATOM,1)=I
          NODE (IATOM,2)=J
C         Dot (ASCII 46) is a Carbon atom.
```

```
                IF (IARRAY(I,J).EQ.46) GO TO 921
CXT             IF (IARRAY(I,J).NE.46) GOTO 950
C LTR1, LTR2 are ASCII codes for first, second letter of chem element.
C Blank second characters are set to ASCII zero.
CXT950          CONTINUE
                LTR1=ILRRAY(I,J)
                LTR2=0
                IF ((IARRAY(I+1,J).LT.123).AND.(IARRAY(I+1,J).GT.96))
      2         LTR2=ILRRAY(I+1,J)
                IF ((LTR1.EQ.77).AND.(LTR2.GE.112).AND.(LTR2.LE.120)) GO TO 945
                IF ((LTR1.EQ.68).AND.(LTR2.GE.112).AND.(LTR2.LE.120)) GO TO 943
C Search element array to find element code from node's ASCII code.
                DO 444 JJ = 1,MAXX
                    IF ((IARRAY(I-JJ,J).EQ.0).OR.(ILRRAY(I-JJ,J).GE.256).OR.
      *                 (I-JJ.EQ.0)) THEN
                        GO TO 921
                    ELSE IF (IARRAY(I-JJ,J).EQ.42) THEN
                        DO 1 KK = 1,107
                            IF ((LTR1.NE.IELEM(KK,1)).OR.
      *                         (LTR2.NE.IELEM(KK,2))) GO TO 1
                            M = KK
                            GO TO 930
   1                    CONTINUE
                        IERR = 11
                        CALL MYERR(LTR1,LTR2,IERR)
                        ICUR = 1
                        JX = I + 1
                        JY = J
                        CALL CURSOR(JX,JY)
                        RETURN
                    ENDIF
 444            CONTINUE
 921        CONTINUE
            JX = I
            JY = J
            ERR = 0
            PAGE = 2
            ICUR = 0
            CALL CURSOR(JX,JY)
            CALL CLRHYD(JX,JY)
            CHER = 1
            CALL VALNCE(3,JX,JY,0,0)
            M = IELT
            IF (ERR.NE.0) THEN
                IERR = ERR
                P = 0
                IF (IERR.EQ.12) THEN
                    ICUR = 1
                    CALL CURSOR(JX,JY)
                    CALL FTSIZE(2,18)
                    CALL FTLOCA(1,37)
                    CALL FTEXT('^-Enter "C" to edit structure -or- "S" ^')
                    CALL FTEXT('^to continue.^')
                    CALL FTSIZE(1,10)
                    PAGE = 0
                    CALL INPUTX(P,JX,JY)
                ENDIF
                IF ((P.NE.83).AND.(P.NE.115)) THEN
                    IF (IERR.NE.12) THEN
                        CHER = 2
                        CALL MYERR(IERR,IERR,IERR)
                    ELSE
                        CHER = 0
                        CALL REMARK(DIERR)
                        CALL SETCOL(0)
                        CALL CLR
                        CALL SETCOL(1)
                        ISWIT = 1
                        CALL STRDRW(ISWIT)
                        IF (IERR.EQ.11) THEN
                            ICUR = 1
                            JX = I + 1
                            JY = J
                            CALL CURSOR(JX,JY)
                        ELSE
```

```
                    IERR = 12
                ENDIF
            ENDIF
            RETURN
        ELSE
            IERR = 0
        ENDIF
    ENDIF
    CHER = 2
    GO TO 930
C
945 CONTINUE
C   The *M node is prepared for entry into the connection table.
    DO 9466 POS = 117,125
        IF (IELEM(POS,2).EQ.LTR2) THEN
            M = POS
            DO 3036 KK = 1,MNUM
                IF (IMS(2,KK).EQ.LTR2) GO TO 930
3036        CONTINUE
            ICUR = 1
            JX = I + 1
            JY = J
            CALL CURSOR(JX,JY)
            IERR = 46
            CALL MYERR(IERR,IERR,IERR)
            RETURN
        ENDIF
9466 CONTINUE
    GO TO 930
C   Convert D1's to atom type 33 - i.e. unkn - store Node # in IDS(*,4)
C
943 CONTINUE
C   Dummy atom code
    DO 946 POS = 108,116
        IF (IELEM(POS,2).EQ.LTR2) M = POS
946 CONTINUE
C   No D1's with multiplier in this structure
    IF (IDNUM.EQ.0) GO TO 930
    DO 942 K = 1,IDNUM
        IF ((IDS(K,1).NE.I).OR.(IDS(K,2).NE.J)) GO TO 942
        IDS(K,4) = IATOM
        GO TO 930
942 CONTINUE
C   D1 not in table because it has no multiplier - ok - go on
930 NODE(IATOM,3)=M
999 CONTINUE
C
    ICUR = 0
    CALL CURSOR(JX,JY)
    IF (LBLEN.GT.0) CALL RELONG
    IF (KHAR.EQ.71) THEN
        CALL GPRINT
    IF (IHP .EQ. 1) THEN
    CALL FTLOCA(1,1)
    CALL FTEXT('^      ^')
    ENDIF
        CALL FTSIZE(2,18)
        CALL FTLOCA(3,1)
        CALL FTEXT('^CONNECTION TABLE IS BEING PROCESSED^')
        CALL FTSIZE(1,10)
    ENDIF
C
    DO 1910 I = 1,MNUM
        DO 1905 J = 1,IATOM
            IF ((IMS(2,I).EQ.IELEM(NODE(J,3),2)).AND.
     *          (IELEM(NODE(J,3),1).EQ.77)) GO TO 1910
1905    CONTINUE
        JX = IMS(3,I)
        JY = IMS(4,I)
        ICUR = 1
        CALL CURSOR(JX,JY)
        IERR = 46
        CALL MYERR(IERR,IERR,IERR)
        RETURN
1910 CONTINUE
```

```
C
C Zero fill balance of NODE
      DO 920 I=IATOM+1,255
         NODE(I,1)=0
         NODE(I,2)=0
         NODE(I,3)=0
920   CONTINUE
C
C Now that node table is available, the XY's in the long bond table
C can be converted to node numbers. The node number for X1,Y1 is
C placed in the first column of the row; that for X2,Y2 is placed in
C column 3. Columns 2 and 4 are zeroed out, while column 5, the bond
C type, is not changed:
C
C Rows of LNGBND
      DO 20 I=1,LBLEN
         II = I
C Beginning node, ending node
      DO 20 J=1,3,2
         JJ = J
         IF (J.EQ.3) THEN
            PLC = 2
         ELSE
            PLC = 1
         ENDIF
C All long bonds analyzed
C Search thru node table
         DO 22 K=1,IATOM
            IF (NODE(K,1).LE.0) GO TO 25
C Check for XY match
            IF ((NODE(K,1).NE.LNGBND(I,J)) .OR. (NODE(K,2).NE.
     2         LNGBND(I,J+1))) GOTO 22
C NODE # of XY is row # within array NODE
            LNGNDE(I,PLC) = K
C Go from beginning node to end node of longbd,
            GOTO 20
C                 or from end node to next long bond
22       CONTINUE
20    CONTINUE
21    RETURN
25    IERR = 9
C LONG BOND NODE NOT IN NODE
      CALL MYERR(IERR,KAR,KAR)
      JX = LNGBND(II,JJ)
      JY = LNGBND(II,JJ+1)
      ICUR = 1
      CALL CURSOR(JX,JY)
      RETURN
      END
C
C
      SUBROUTINE CHGHYD(IERR,JX,JY)
      IMPLICIT INTEGER*2 (A-Z)
      INTEGER*4 IARRAY
      LOGICAL*2 LOCH
      COMMON /H/ MOBILE(255,2)
      COMMON /NDE/ NODE(255,3),IATOM
      COMMON /STRPIX/ LPIX,IARRAY(90,38),LBLEN,LNGBND(100,5)
      COMMON /CONNCT/ IBOND(255,16),KBOND(255,16)
      COMMON /KHARGE/ ICHRGE(50,4),NCHG
      COMMON /IPLUS/ IHIGH(14,2)
      COMMON /CD/ MAXX,MAXY
      COMMON /RANGE/ LOX,HIX,LOY,HIY
      COMMON /D1/ IDNUM,IDS(9,6),NBD1,DSCNC(6,50)
      COMMON /CUR/ ICUR
      COMMON /HP/IHP
C
C Counts the number of potentially mobile hydrogens and - charges
C for each node. Used only for tautomer analysis.
C
C Now search IARRAY for H, D, T, -, +, ":
C      SITES OF INDETERMINATE LINK TO A 'D' STRUCTURE SYMBOLS (").
C      ARE IDENTIFIED.
      DO 111 I = 1,IATOM
```

```
               IF ((NODE(I,3).GE.108).AND.(NODE(I,3).LE.116).AND.
     *            (NBD1.NE.0)) GO TO 113
               IF ((NODE(I,3).GE.108).AND.(NODE(I,3).LE.116).AND.
     *            (NBD1.EQ.0)) THEN
                  JX = NODE(I,1) + 1
                  JY = NODE(I,2)
                  GO TO 112
               ENDIF
111         CONTINUE
            IF (NBD1.EQ.0) GO TO 113
            JX = DSCNC(3,1)
            JY = DSCNC(4,1)
112         IERR = 8
            CALL MYERR(IERR,IERR,IERR)
            ICUR = 1
            CALL CURSOR(JX,JY)
            GO TO 7777
113         CONTINUE
            DO 3333 I = 1,NBD1
               DO 2222 J = 1,IATOM
                  IF ((NODE(J,1).EQ.DSCNC(3,I)).AND.(NODE(J,2).EQ.
     *               DSCNC(4,I))) THEN
                     IF (IARRAY(DSCNC(5,I),DSCNC(6,I)).EQ.34) THEN
                        DSCNC(1,I) = J
                        DO 1111 K = 1,I-1
                           IF (DSCNC(1,K).EQ.J) THEN
                              IERR = 47
                              CALL MYERR(IERR,IERR,IERR)
                              ICUR = 1
                              JX = DSCNC(3,K)
                              JY = DSCNC(4,K)
                              GO TO 7777
                           ENDIF
1111                    CONTINUE
                        GO TO 3333
                     ELSE
                        GO TO 2223
                     ENDIF
                  ENDIF
2222           CONTINUE
2223           CONTINUE
               DSCNC(1,I) = 0
3333        CONTINUE
C
            NCHG = 0
            DO 3 I = LOX,HIX
            DO 3 J = LOY,HIY

ISIGN = 1
            IF ((IARRAY(I,J).NE.72) .AND. (IARRAY(I,J).NE.68) .AND.
     2         (IARRAY(I,J).NE.84) .AND. (ILRRAY(I,J).NE.45) .AND.
     3         (ILRRAY(I,J).NE.43))    GOTO 3
C
C If first letter is H, D, T, but second is lowercase, you have a node,
C not a hydrogen--mobile group:
            IF ((IARRAY(I+1,J).GT.96).AND.(IARRAY(I+1,J).LT.128)) GOTO 3
            IF ((IARRAY(I,J).EQ.72).AND.((IARRAY(I-1,J).EQ.42).OR.
     *         ((IARRAY(I-1,J).GE.48).AND.(IARRAY(I-1,J).LE.57))).AND.
     *         (ILRRAY(I+1,J).EQ.43)) GO TO 3
C Take care of + sign (ISIGN=-1) and NUM:
            IF (ILRRAY(I,J).EQ.45) ISIGN = -1
            NUM = 1
            IF ((IARRAY(I+1,J).GE.50) .AND. (IARRAY(I+1,J).LE.57))
     2         NUM = IARRAY(I+1,J) - 48
            IF ((ILRRAY(I,J).NE.43).AND.(ILRRAY(I,J).NE.45))GO TO 60
C
C     WE HAVE A CHARGE - NOW FIND ITS NODE
C
            ICRNR = 0
            LINE=0
C     CHARGE IS DELOCALIZED
            IGH = IARRAY(I,J) / 2**13
            IF (IGH.EQ.0) THEN
            DO 15 IK = I-1,I+2
            DO 14 JK = J-1,J+1
```

```
              IF ((IARRAY(IK,JK) .EQ. 46).OR.((IARRAY(IK,JK).GE.65)
     *          .AND. (IARRAY(IK,JK).LE.90)).OR.((IARRAY(IK,JK).GE.
     *          97) .AND.(IARRAY(IK,JK).LE.122))) THEN
              IF ((K .EQ. I+2).AND.((IARRAY(IK+1,JK).LT.50).AND.
     *          (IARRAY(IK+1,JK).LE.57))) GO TO 14
              IERR=60
              CALL MYERR(IERR,IERR,IERR)
              JX=I
              JY=J
              GO TO 7777
              ENDIF
14            CONTINUE
15            CONTINUE
              GO TO 133
              ENDIF
              IX = I - IHIGH(IGH,1)
              IY = J +IHP* IHIGH(IGH,2)
C
          DO 17 K=1,IATOM
C           THE RELATIVE POSITON OF THE CHARGE IS NOTED FOR THE CONNECTION
C           TABLE. THE 8 CORNER POSITIONS ARE U=1, UR=2, R=3,
C           DR=4, D=5, DL=6, L=7, UL=8.
              IF ((IX.EQ.NODE(K,1)).AND.(IY.EQ.NODE(K,2))) THEN
                 LINE = K
                 IF (IGH.EQ.3) THEN
                    ICRNR = 1
                 ELSE IF (IGH.EQ.4) THEN
                    ICRNR = 2
                 ELSE IF (IGH.EQ.5) THEN
                    ICRNR = 12
                 ELSE IF (IGH.EQ.8) THEN
                    ICRNR = 3
                 ELSE IF (IGH.EQ.9) THEN
                    ICRNR = 13
                 ELSE IF (IGH.EQ.13) THEN
                    ICRNR = 4
                 ELSE IF (IGH.EQ.14) THEN
                    ICRNR = 14
                 ELSE IF (IGH.EQ.12) THEN
                    ICRNR = 5
                 ELSE IF (IGH.EQ.10) THEN
                    ICRNR = 16

ELSE IF (IGH.EQ.11) THEN
                    ICRNR = 6
                 ELSE IF (IGH.EQ.6) THEN
                    ICRNR = 17
                 ELSE IF (IGH.EQ.7) THEN
                    ICRNR = 7
                 ELSE IF (IGH.EQ.1) THEN
                    ICRNR = 18
                 ELSE IF (IGH.EQ.2) THEN
                    ICRNR = 8
                 ENDIF
                 DO 16 L = 1,NCHG
                    IF (LINE.EQ.ICHRGE(L,1)) THEN
                       IERR = 38
                       CALL MYERR(IERR,IERR,IERR)
                       ICUR = 1
                       JX = IX
                       JY = IY
                       CALL CURSOR(JX,JY)
                       GO TO 7777
                    ENDIF
16               CONTINUE
                 GO TO 133
              ENDIF
17        CONTINUE
C
C  The relative positions of attached hydrogens are noted for
C  the connection table.
C  First look left for node associated with IARRAY(I,J):
60        CONTINUE
          LOCH = .FALSE.
          IX = I - 1
          IF ((IX.LT.1).OR.(IARRAY(IX,J).LT.65).OR.(IARRAY(IX,J).GE.122))
```

```
    *         GO TO 4
C   If its lower case, move one more to left:
          IF (IARRAY(IX,J).GT.96) IX = IX -1
          LINE = 0
          DO 5 K=1,IATOM
          IF ((IX.EQ.NODE(K,1)) .AND. (J.EQ.NODE(K,2))) LINE = K
          IF (LINE.GT.0) GOTO 7
5         CONTINUE
          IF(LINE.EQ.0) GOTO 4
7         MOBILE(LINE,1) = NUM
          MOBILE(LINE,2) = 3
          LOCH = .TRUE.
C
C   Try looking on the right of the sign for a node:
C
4         IX = I + 1
          IF (NUM.GT.1) IX = IX + 1
          IF ((IARRAY(IX,J).LT.65).OR.(IARRAY(IX,J).GT.90).OR.(IX.GT.
     *       MAXX)) GO TO 10
          IF (IARRAY(IX,J).EQ.72) GO TO 10
          IF (LOCH) THEN
             IERR = 42
             CALL MYERR(IERR,IERR,IERR)
             JX = IX
             JY = J
             GO TO 7777
          ENDIF
          LINE = 0
          DO 8 K=1,IATOM
          IF ((IX.EQ.NODE(K,1)).AND.(J.EQ.NODE(K,2))) LINE = K
          IF (LINE.GT.0) GOTO 9
8         CONTINUE
          IF (LINE.EQ.0) GOTO 10
9         MOBILE(LINE,1) = NUM
          MOBILE(LINE,2) = 7
10        CONTINUE
C
C       Up
          IY = J + IHP
          IF ((IY.LE.1).OR.(ILRRAY(I,IY).LT.65).OR.(ILRRAY(I,IY).GT.90))
     *       GO TO 500
          IF (IARRAY(I,IY).EQ.72) GO TO 500
          IF (LOCH) THEN
             IERR = 42
             CALL MYERR(IERR,IERR,IERR)
             JX = I
             JY = IY
             GO TO 7777
          ENDIF
          DO 410 LINE = 1,IATOM
             IF ((I.EQ.NODE(LINE,1)).AND.(IY.EQ.NODE(LINE,2))) THEN
                MOBILE(LINE,1) = NUM
                MOBILE(LINE,2) = 5
                LOCH = .TRUE.
                GO TO 500
             ENDIF
410       CONTINUE
500       CONTINUE
C
C       Down
          IY = J - IHP
          IF ((IY.GE.MAXY).OR.(ILRRAY(I,IY).LT.65).OR.
     *       (ILRRAY(I,IY).GT.90)) GO TO 3
          IF (LOCH) THEN
             IERR = 42
             CALL MYERR(IERR,IERR,IERR)
             JX = I
             JY = IY
             GO TO 7777
          ENDIF
          DO 710 LINE = 1,IATOM
             IF ((I.EQ.NODE(LINE,1)).AND.(IY.EQ.NODE(LINE,2))) THEN
                MOBILE(LINE,1) = NUM
                MOBILE(LINE,2) = 1
                GO TO 3
```

```
            ENDIF
710     CONTINUE
        IERR = 15
        CALL MYERR(IERR,IERR,IERR)
        JX = I
        JY = J
        GO TO 7777
133     CONTINUE
C
        IF ((ILRRAY(I,J).NE.45).AND.(ILRRAY(I,J).NE.43)) GOTO 3
        NCHG = NCHG + 1
C       CHARGE NODE NUMBER AND VALUE IS ASSIGNED.
125     ICHRGE(NCHG,1) = LINE
        ICHRGE(NCHG,2) = ISIGN*NUM
C       NONLOCAL CHARGE X & Y COORDINATES ARE
C       ASSIGNED.
        IF ((ICRNR.EQ.0).AND.(LINE.EQ.0)) THEN
            ICHRGE(NCHG,3) = I
            ICHRGE(NCHG,4) = J
            GO TO 3
        ENDIF
C       LOCAL CHARGE RELATIVE POSITION IS ASSIGNED.
        ICHRGE(NCHG,3) = ICRNR
3       CONTINUE
        GO TO 8888
C**     DO 991 I = 1,IATOM
C**         WRITE(10,444) (NODE(I,J),J=1,3),(MOBILE(I,J),J=1,2)
C**991  CONTINUE
C**     DO 888 I=1,20
C**         WRITE(10,444) I,ICHRGE(I,1),ICHRGE(I,2),ICHRGE(I,3)
C**444  FORMAT(10I8)
C**888     CONTINUE
7777    CONTINUE
        DO 8004 I = 1,IATOM
            DO 8002 J = 1,16
                IBOND(I,J) = 10000
                KBOND(I,J) = 10000
8002        CONTINUE
8004    CONTINUE
8888    RETURN
        END
C
C
        SUBROUTINE CONNET(IERR,JX,JY)
        IMPLICIT INTEGER*2 (A-Z)
        INTEGER*4 IARRAY
        COMMON /NDE/ NODE(255,3),IATOM
        COMMON /STRPIX/ LPIX,IARRAY(90,38),LBLEN,LNGBND(100,5)
C  IBOND lists up to 16 node numbers to which a given node is bonded.  The
C  row of IBOND is the node under consideration, while the contents of
C  the array elements 1-->10 are the numbers of those nodes to which it
C  is bonded.  Unused spaces are filled with integer 10000.
C  KBOND contains bond types associated with same element of IBOND.
        COMMON /CONNCT/ IBOND(255,16),KBOND(255,16)
        COMMON /CD/ MAXX,MAXY
        COMMON /D1/ IDNUM,IDS(9,6),NBD1,DSCNC(6,50)
        COMMON /M1/ MNUM,IMS(90,5)
        COMMON /CUR/ ICUR
        COMMON /LNGOUT/ LNGNDE(100,2)
C
        DO 999 I=1,IATOM
C       Search for bonds around each node. Search direction is:
C       IDIRX   left, center, right
C       IDIRY   below, center, above
            DO 990 IDIRX=-1,1
            DO 990 IDIRY=-1,1
            IF ((IDIRX.EQ.0) .AND. (IDIRY.EQ.0)) GOTO 990
C   NEWX & NEWY are nearby array elements to search for bondings.
            NEWX=NODE(I,1)
            NEWY=NODE(I,2)
234         NEWY=NEWY + IDIRY
            IF((NEWY.LT.1).OR.(NEWY.GT.MAXY))  GOTO 990
            NEWX=NEWX + IDIRX
            IF ((NEWX.LT.1) .OR. (NEWX.GT.MAXX)) GOTO 990
C           Blank, +, and - signs cannot be in bonding direction. Try
```

```
C                next direction.
C
C   JDIR is the direction a bond must have if it attaches at NODE(I,*)
            IF (IDIRX*IDIRY.EQ.1) THEN
               IF (IDIRX.GT.0) THEN
                  JDIR = 4
               ELSE
                  JDIR = 8
               ENDIF
            ELSE IF (IDIRX*IDIRY.EQ.-1) THEN
               IF (IDIRX.GT.IDIRY) THEN
                  JDIR = 2
               ELSE
                  JDIR = 6
               ENDIF
            ELSE IF (IABS(IDIRX).GT.IABS(IDIRY)) THEN
               IF (IDIRX.GT.IDIRY) THEN
                  JDIR = 3
               ELSE
                  JDIR = 7
               ENDIF
            ELSE
               IF (IDIRX.GT.IDIRY) THEN
                  JDIR = 1
               ELSE
                  JDIR = 5
               ENDIF
            ENDIF
C   If direction is ok and it is a bond, assume a link and follow it:
            IF ((MOD(JDIR,4).EQ.MOD(MOD(ILRRAY(NEWX,NEWY),2**8),4)).AND.
     2          (ILRRAY(NEWX,NEWY).GT.255)) GOTO 1000
C   A SYMBOL must have been found. LOOK FURTHER one link at line 234:
            IF (((IARRAY(NEWX,NEWY).EQ.72).OR.((IARRAY(NEWX,NEWY)
     *          .GE.49).AND.(IARRAY(NEWX,NEWY).LE.57)).AND.
     *          (IDIRY.EQ.0)).OR.((IARRAY(NEWX,NEWY).EQ.72).AND.
     *          (IDIRX.EQ.0)).OR.((IARRAY(NEWX,NEWY).GE.97).AND.
     *          (IARRAY(NEWX,NEWY).LE.122).AND.(IDIRX.EQ.1).AND.
     *          (IDIRY.EQ.0))) THEN
               GOTO 234
            ELSE
               GO TO 990
            ENDIF
C       Follow an acceptable bond to its other node & save bondtype:
1000        IBDTYP=ILRRAY(NEWX,NEWY)/2**8
            IBDT = IARRAY(NEWX,NEWY)
            DIR = IDIR(IBDT)
            DO 1010 K=1,MAXX
            NEWX=NEWX+IDIRX
            IF ((NEWX.GT.MAXX).OR.(NEWX.LT.1)) GOTO 990
            NEWY= NEWY + IDIRY
            IF ((NEWY.GT.MAXY).OR.(NEWY.LT.1)) GOTO 990
C   Search through node table to find second node of this bond:
            IF (ILRRAY(NEWX,NEWY).GE.256) GO TO 1010
            IF (((ILRRAY(NEWX,NEWY).LE.48).AND.(IARRAY(NEWX,NEWY)
     *          .NE.46)).OR.((ILRRAY(NEWX,NEWY).GE.256).AND.
     *          (IARRAY(NEWX,NEWY).NE.IBDT).AND.
     *          (IABS(IARRAY(NEWX,NEWY)-IBDT).NE.4)).OR.

*          ((IARRAY(NEWX,NEWY).GE.49).AND.(IARRAY(NEWX,NEWY)
     *          .LE.57).AND.((MOD(DIR,4).NE.3).OR.(IARRAY(NEWX-1,
     *          NEWY).NE.72)))) GO TO 1111
            IF ((IARRAY(NEWX,NEWY).GE.97).AND.
     *          (IARRAY(NEWX,NEWY).LE.122).AND.((MOD(DIR,4).NE.3).OR.
     *          (IARRAY(NEWX-1,NEWY).LT.65).OR.(IARRAY(NEWX-1,NEWY)
     *          .GT.90))) GOTO 1111
            GO TO 2222
1111        CONTINUE
            IERR = 41
            CALL MYERR(IERR,IERR,IERR)
            ICUR = 1
            JX = NEWX
            JY = NEWY
            CALL CURSOR(JX,JY)
            GO TO 777
2222        CONTINUE
            DO 1020 L=1,IATOM
```

```
                        M=L
C                       Skip hanging (open) bond.
                        IF ((NODE(L,1).EQ.NEWX).AND.(NODE(L,2).EQ.NEWY))
     *                  GO TO 1101
1020            CONTINUE
1010        CONTINUE
C  There is a connection between nodes I & M.
C  Store M on next available column of Ith row of IBOND.
1101            DO 666 J = 1,16
                    IF (IBOND(I,J).NE.10000) GOTO 666
                    IBOND(I,J)=M
                    KBOND(I,J)=IBDTYP
                    GOTO 990
666             CONTINUE
C FOUND TOO MANY CONNECTIONS / NODE - ABORT
         IERR=26
         CALL MYERR(IERR,KAR,KAR)
         ICUR = 1
         CALL CURSOR(NEWX,NEWY)
777      CONTINUE
         DO 1004 L1 = 1,I
             DO 1002 L2 = 1,16
                 IBOND(L1,L2) = 10000
                 KBOND(L1,L2) = 10000
1002         CONTINUE
1004     CONTINUE
         RETURN
990        CONTINUE
999        CONTINUE
C
C Next piece of code (thru label 29) takes long bonds in LNGBND (which
C have beginning and ending node numbers in column 1 and 3 respecively,
C and bond type in column 5; columns 2 & 4 and unused rows zero-filled)
C and incorporates them into the bond tables IBOND and KBOND:
C for reversing "to" and "from"
         DO 29 M=1,2
C            Rows of LNGBND
             DO 20 I=1,LBLEN
                 IF (M.GT.1) GOTO 25
C                Node# becomes line# in IBOND
                 LINE = LNGNDE(I,1)
C                "to" node ITO = LNGNDE(I,2)
                 GOTO 26
C                Reverse of above: both directions must be added to bond tables
25               LINE = LNGNDE(I,2)
                 ITO = LNGNDE(I,1)

C
C                Now, put "to" node in numerical order on the LINE'th
C                line of IBOND; similarly for KBOND. Skip across the
C                row of IBOND until ITO > IBOND(LINE,J); move the balance
C                up one column and insert the new one.
C
26               JJ=0
                 DO 21 J = 1,16
                 IF (ITO.GT.IBOND(LINE,J)) GOTO 21
                     IF (ITO.EQ.IBOND(LINE,J)) THEN
                         IERR = 33
                         CALL MYERR(IERR,IERR,IERR)
                         ICUR = 1
                         JX = LNGBND(I,1) + 1
                         JY = LNGBND(I,2)
                         CALL CURSOR(JX,JY)
                         DO 1008 L1 = 1,IATOM
                             DO 1006 L2 = 1,16
                                 IBOND(L1,L2) = 10000
                                 KBOND(L1,L2) = 10000
1006                         CONTINUE
1008                     CONTINUE
                         RETURN
                     ENDIF
                     JJ=J
C                    Move higher ones up
                     DO 22 K = 16,JJ+1,-1
                         IBOND(LINE,K) = IBOND (LINE,K-1)
```

```
                  KBOND(LINE,K) = KBOND (LINE,K-1)
22              CONTINUE
                GOTO 23
21            CONTINUE
C             Fill in nodes of long bonds in place
23          . IBOND(LINE,JJ)=ITO
C             Fill in bond type
              KBOND(LINE,JJ) = LNGBND(I,5)
20        CONTINUE
29      CONTINUE
C At this point in Subroutine CONNET, INODE contains IX, IY, Element type of
C each node (connecting atom, excluding H). IBOND contains list of
C connections between nodes. The row in IBOND corresponds to the row
C in INODE for the 'primary' end of each bond, the contents of each column
C (up to ten columns) contains the 'other' node which the bond
C is attached to. At this point, each bond is represented twice.
C KBOND contains the numerical bondtype for each bond in IBOND.
C Unused matrix elements of K- and IBOND have been filled with 10000.
C Note also that rows of IBOND are already sorted in numerical order
C of node number, due to direction of node numbering, and careful
C placing of long bonds in K- and IBOND rows.
C
C       The bond elements are duplicated with 2 way pointers.
        DO 8000 I = 1,IATOM
           DO 7000 J = 1,16
              IF (IBOND(I,J).LT.10000) THEN
                 IF (IBOND(I,J).LT.I) THEN
                    DO 6000 K = 1,16
                       IF (IBOND(IBOND(I,J),K).EQ.I) GO TO 6100
                       IF (IBOND(IBOND(I,J),K).EQ.10000) THEN
                          IBOND(IBOND(I,J),K) = I
                          IF ((KBOND(I,J).LT.6).OR.(KBOND(I,J).GT.7))
     *                       THEN
                             KBOND(IBOND(I,J),K) = KBOND(I,J)
                          ELSE
                             IF (KBOND(I,J).EQ.6) THEN
                                KBOND(IBOND(I,J),K) = 7
                             ELSE
                                KBOND(IBOND(I,J),K) = 6
                             ENDIF
                          ENDIF
                          GO TO 6100
                       ENDIF
6000                CONTINUE
6100                CONTINUE
                 ENDIF
              ENDIF
7000       CONTINUE
8000    CONTINUE
C
CXT     DEBUG DUMP WRITES
C**     DO 1234 I=1,IATOM
C**        WRITE(10,444) I,NODE(I,1),NODE(I,2),NODE(I,3)
C**1234  CONTINUE
C**444   FORMAT (16I5)
C**     WRITE(10,444) IATOM
C**     DO 1235 I = 1,IATOM
C**        WRITE(10,444) I,(IBOND(I,J),J=1,8)
C**        WRITE(10,444) I,(KBOND(I,J),J=1,8)
C**1235  CONTINUE
C**     WRITE(10,444) IDNUM
C**     DO 1236 I = 1,IDNUM
C**        WRITE(10,444) (IDS(I,J),J=1,6)
C**1236  CONTINUE
C**     WRITE(10,444) NBD1
C**     DO 1237 I = 1,NBD1
C**        WRITE(10,444) (DSCNC(J,I),J=1,2)
C**1237  CONTINUE
C**     WRITE(10,444) MNUM
C**     DO 1238 I = 1,MNUM
C**        WRITE(10,444) (IMS(J,I),J=1,16)
C**1238  CONTINUE
C
C       Bonds of types 5-8 are changed to bond types 4-7 respectively.
        DO 5000 I = 1,IATOM
```

```
              DO 4500 J = 1,16
                 IF (KBOND(I,J).GE.5) KBOND(I,J) = KBOND(I,J) - 1
 4500         CONTINUE
 5000      CONTINUE
           RETURN
           END
$STORAGE:2
C          SUBROUTINE TBLOUT creates the connection table according
C          to the output format developed for IBM XT preprocessing.
C
C          ORI   Paul Broderick   July, 1984
C
           SUBROUTINE TBLOUT(IERR,JX,JY)
           IMPLICIT INTEGER*2 (A-Z)
           DIMENSION CA(16),CB(16)
C
C          Array MOBILE contains each node's number of attached
C          hydrogens and the code for the graphic position of the
C          hydrogen value. The positional code used for the hydrogen
C          as well as for the charge and indeterminate bond site marker is:
C          U=1; UR=2; R=3; LR=4; DR=5; D=6; DL=7; L=8; UL=8.
           COMMON /H/ MOBILE(255,2)
C
C          The following variables are the output of SUBROUTINE
C          TBLOUT. NNODE contains the number of nodes in the
C          chemical structure. Array TABLE comprises the connection
C          table.
           COMMON /STRDEF/ NNODE,TABLE(255,43)
C
C          Array NODE contains 3 columns: column 3 contains the
C          numeric element code that maps to the chemical symbol
C          array. Columns 1 and 2 contain the x and y graphic coordinates,
C          respectively. Variable IATOM contians the number of nodes.
           COMMON /NDE/ NODE(255,3),IATOM
C
C          Array IBOND contains, for each node, the sequence numbers of
C          up to 16 connected nodes.  Array KBOND contains the
C          corresponding bond types.
           COMMON /CONNCT/ IBOND(255,16),KBOND(255,16)
C
C          Array IELEM contains the chemical symbols for 106
C          elements plus lower case c to be output for luhn dots.
           COMMON /ELECHR/ IELEM(126,5)
C
C          Array ICHRGE contains 4 columns: column 1 contains the
C          node number to which the entry is attached. If the charge is
C          nonlocalized, the value in column 1 is 0. Column 2 contains
C          the charge value. Column 3 contains either the charge's
C          positional code relative to its node, or if the charge is
C          nonlocalized, the graphic x-coordinate of the charge. If the
C          charge is nonlocalized, column 4 contains the y-coordinate;
C          otherwise column 4 is valueless.
           COMMON /KHARGE/ ICHRGE(50,4),NCHG
C
C          Variable NBD1 contains the number of nodes which may be bonded
C          to *D structures.
           COMMON /D1/ IDNUM,IDS(9,6),NBD1,DSCNC(6,50)
           COMMON /M1/ MNUM,IMS(90,5)
           COMMON /DTDS/ DTN,DTX(30),DTY(30),DTN1(30),DTN2(30)
C
           COMMON /CUR/ ICUR
           DATA NODENO,EL,XCOOR,YCOOR,CHG,RELCGP,NHYD,RLHYDP,MASS,
         *   NCON/1,2,4,5,6,7,8,9,10,11/, MULT /6/
           DATA CA /12,14,16,18,20,22,24,26,28,30,32,34,36,38,40,42/
           DATA CB /13,15,17,19,21,23,25,27,29,31,33,35,37,39,41,43/
C
C          SUBROUTINE OUD1 is called to provide bond information arrays
C          information at the nodes of uncertain connection.  This
C          information constsits of pointers to all *D structures, and
C          relative positions of graphical uncertain bond markers.
           IF (NBD1.GT.0) CALL OUD1
C
C
           DO 100 I = 1,DTN
              TABLE(I,NODENO) = I
```

```
              TABLE(I,EL) = 42
              TABLE(I,EL+1) = 32
              TABLE(I,XCOOR) = DTX(I)
              TABLE(I,YCOOR) = DTY(I)
              TABLE(I,CHG) = DTN1(I)
              TABLE(I,RELCGP) = DTN2(I)
100       CONTINUE
C
C         The number of nodes in the structure is assigned to the table.
          NNODE = IATOM + DTN
C
C         Assignments are made for each node.
          DO 500 I = DTN+1,NNODE
C
              II = I - DTN
C             The node's sequence number is assigned to the table.
              TABLE(I,NODENO) = I
C
C             The element's chemical symbol is assigned to the table.
              TABLE(I,EL) = IELEM(NODE(II,3),1)
              TABLE(I,EL+1) = IELEM(NODE(II,3),2)
              IF (TABLE(I,EL+1).EQ.0) TABLE(I,EL+1) = 32
              IF (TABLE(I,EL).EQ.74) TABLE(I,EL) = 72
C
C             The element's graphic coordinates are assigned to the table.
              TABLE(I,XCOOR) = NODE(II,1)
              TABLE(I,YCOOR) = NODE(II,2)
C
C             The connections between nodes are searched and each
C             bond to a node of higher sequence number is entered
C             into the table.  The corresponding bond types are
C             also entered.  The number of connections added to the
C             table is counted.
              NUMCON = 0
              N = 1
              IF ((TABLE(I,EL).EQ.68).AND.((TABLE(I,EL+1).GE.112).AND.
     *            (TABLE(I,EL+1).LE.120))) THEN
                  SUB = 4
              ELSE IF ((TABLE(I,EL).EQ.77).AND.((TABLE(I,EL+1).GE.112)
     *            .AND.(TABLE(I,EL+1).LE.120))) THEN
                  SUB = 5
              ELSE
                  SUB = 0
              ENDIF
              DO 200 J = 1,16
                  IF ((IBOND(II,J).EQ.10000).OR.(IBOND(II,J).LE.II))
     *            THEN
                      TABLE(I,CA(J)-SUB) = 0
                      TABLE(I,CB(J)-SUB) = 0
                  ELSE
                      TABLE(I,CA(N)-SUB) = IBOND(II,J) + DTN
                      TABLE(I,CB(N)-SUB) = KBOND(II,J)
                      NUMCON = NUMCON + 1
                      N = N + 1
                  ENDIF
200           CONTINUE
C
C             The number of connections entered into the table is
C             assigned to the table.
              TABLE(I,NCON-SUB) = NUMCON
C
C             The node's charge value and graphic relative position are
C             initialized to 0.
              IF (SUB.NE.5) THEN
                  TABLE(I,CHG) = 0
                  IF (SUB.NE.4) TABLE(I,RELCGP) = 0
              ENDIF
              IF (SUB.EQ.0) THEN
C
C                 The node's number of attached hydrogens and their graphic
C                 relative position are assigned to the table.
                  TABLE(I,NHYD) = MOBILE(II,1)
                  TABLE(I,RLHYDP) = MOBILE(II,2)
C
C                 The abnormal mass value is set to 0.
```

```
                  TABLE(I,MASS) = 0
              ELSE IF (SUB.EQ.4) THEN
C
C                 The D1 structure multiplication factor is assigned.
                  DO 450 J = 1,IDNUM
                      IF (IDS(J,4).EQ.II) THEN
                          TABLE(I,MULT) = IDS(J,3)
                          GO TO 460
                      ENDIF
450               CONTINUE
460               CONTINUE
              ENDIF
500       CONTINUE
C
C         With chemical symbol lengths convenient, a search for adjacent
C         nodes is made.
          DO 600 I = DTN+1,NNODE
              DO 550 J = I+1,NNODE
                  DY = IABS(TABLE(I,YCOOR)-TABLE(J,YCOOR))
                  DX = TABLE(I,XCOOR) - TABLE(J,XCOOR)
                  IF (DY.LE.1) THEN
                      IF (DX.EQ.0) THEN
                          OFFSET = 0
                      ELSE IF (IABS(DX).LE.2) THEN
                          IF ((TABLE(I,EL+1).EQ.32).OR.(DX.GT.0)) THEN
                              OFFSET = DX / IABS(DX)
                          ELSE
                              OFFSET = 2 * DX / IABS(DX)
                          ENDIF
                      ENDIF
                      IF ((OFFSET.EQ.2).AND.(TABLE(I,XCOOR)-TABLE(J,XCOOR)
     *                  .EQ.1)) GO TO 525
                      IF ((OFFSET.EQ.-2).AND.(TABLE(I,XCOOR)-TABLE(J,XCOOR)
     *                  .EQ.-1)) GO TO 525
                      IF (TABLE(I,XCOOR)-TABLE(J,XCOOR).EQ.OFFSET) GO TO 525
                      DX = TABLE(J,XCOOR) - TABLE(I,XCOOR)
                      IF (DX.EQ.0) THEN
                          OFFSET = 0
                      ELSE IF (IABS(DX).LE.2) THEN
                          IF ((TABLE(J,EL+1).EQ.32).OR.(DX.GT.0)) THEN
                              OFFSET = DX / IABS(DX)
                          ELSE
                              OFFSET = 2 * DX / IABS(DX)
                          ENDIF
                      ENDIF
                      IF ((OFFSET.EQ.2).AND.(TABLE(J,XCOOR)-TABLE(I,XCOOR)
     *                  .EQ.1)) GO TO 525
                      IF ((OFFSET.EQ.-2).AND.(TABLE(J,XCOOR)-TABLE(I,XCOOR)
     *                  .EQ.-1)) GO TO 525
                      IF (TABLE(J,XCOOR)-TABLE(I,XCOOR).NE.OFFSET) GO TO 550
                  ELSE
                      GO TO 550
                  ENDIF
525               CONTINUE
                  ICUR = 1
                  JX = TABLE(I,XCOOR)
                  JY = TABLE(I,YCOOR)
                  CALL CURSOR(JX,JY)
                  IERR = 40
                  CALL MYERR(IERR,IERR,IERR)
                  DO 540 K = 1,NNODE
                      DO 530 L = 1,16
                          IBOND(K,L) = 10000
                          KBOND(K,L) = 10000
530                   CONTINUE
540               CONTINUE
                  RETURN
550           CONTINUE
600       CONTINUE
C
C         All node values have been assigned except for possible
C         charge values and their graphic positions or possible
C         connection pointers to D structures and the relative graphic
C         position of the marker. Any such values are now sought and,
C         if found, are assigned to their node's table entry. If a
```

```
C       a nonlocalized charge is found, a node is created for it as
C       the last node and the number of nodes is adjusted.
        DO 700 I = 1,NCHG
            IF (ICHRGE(I,1).EQ.0) THEN
                NNODE = NNODE + 1
                TABLE(NNODE,NODENO) = NNODE
C
C               Nonlocalized charge value is assigned.
                IF (ICHRGE(I,2).GT.0) THEN
                    TABLE(NNODE,EL) = 43
                ELSE
                    TABLE(NNODE,EL) = 45
                ENDIF
                TABLE(NNODE,EL+1) = IABS(ICHRGE(I,2)) + 48
C
C               Nonlocalized graphic x and y locations are assigned.
                TABLE(NNODE,XCOOR) = ICHRGE(I,3)
                TABLE(NNODE,YCOOR) = ICHRGE(I,4)
            ELSE
C
C               Either the localized charge and relative position or
C               the identifying value of the bonded D structure and
C               the marker's relative position are assigned.
                TABLE(ICHRGE(I,1)+DTN,CHG) = ICHRGE(I,2)
                TABLE(ICHRGE(I,1)+DTN,RELCGP) = ICHRGE(I,3)
            ENDIF
700     CONTINUE
C
C       The connection table is passed to SUBROUTINE TBLCHR to be
C       converted to character strings for transmission.
        CALL TBLCHR(IERR)
C
        RETURN
        END
C
C       SUBROUTINE OUD1 places bond information for nodes which are
C       potentially, but uncertainly bonded with *D structures.  For each
C       such node, the node number representation of the *D site pointed
C       to is placed in the next available 2nd cell of array ICHRGE, the
C       relative position of its uncertain location bond marker is placed
C       in the corresponding 3rd cell, while the nod number of the node
C       itself is placed in the 1st cell.
C
C       ORI    Paul Broderick    August, 1984
C
        SUBROUTINE OUD1
        IMPLICIT INTEGER*2 (A-Z)
        COMMON /D1/ IDNUM,IDS(9,6),NBD1,DSCNC(6,50)
        COMMON /KHARGE/ ICHRGE(50,4),NCHG
C
        IDN = 1
        DO 500 I = 1,NBD1
            IF (DSCNC(1,I).NE.0) THEN
                NCHG = NCHG + 1
                ICHRGE(NCHG,1) = DSCNC(1,I)
                ICHRGE(NCHG,2) = IDN + 100
                IF (IDN.LT.IDNUM) IDN = IDN + 1
                ICHRGE(NCHG,3) = DSCNC(2,I)
            ENDIF
500     CONTINUE
        RETURN
        END
C
C       SUBROUTINE NUMCHR assigns the ASCII representation of a passed
C       decimal integer value of 1 - 3 digits to the transmission string.
C
C       ORI    Paul Broderick    July, 1984
C
        SUBROUTINE NUMCHR(VALUE,RET,NDGT)
        IMPLICIT INTEGER*2 (A-Z)
        CHARACTER*1 DIGIT(3),RET(3)
C
        IF ((VALUE.GT.999).OR.(VALUE.LT.-99)) THEN
            NDGT = 0
            RETURN
```

```fortran
            ENDIF
            VAL = IABS(VALUE)
            DO 100 I = 1,3
                DIVD = MOD(VAL,10)
                VAL = VAL / 10
                DIGIT(I) = CHAR(DIVD + 48)
                NDGT = I
                IF (VAL.EQ.0) GO TO 110
100         CONTINUE
110         CONTINUE
C
            IF (VALUE.LT.0) THEN
                NDGT = NDGT + 1
                DIGIT(NDGT) = '-'
            ENDIF
            N = 1
            DO 200 I = NDGT,1,-1
                RET(N) = DIGIT(I)
                N = N + 1
200         CONTINUE
C
            RETURN
            END
C
C
C  SUBROUTINE CHKGEN computes the check digit for each transmission
C  string.
C
C  ORI    Paul Broderick    July, 1984
C
            SUBROUTINE CHKGEN(POS,CHK)
            IMPLICIT INTEGER*2 (A-Z)
            CHARACTER*1 TRANS,CHK,CHR,TMP,MSK
            COMMON /TRNS/ TRANS(80)
            EQUIVALENCE (CHR,ICHR),(TMP,ITMP),(MSK,IMSK)
            DATA ADD /32/, IMSK /63/
            ICHR = 0
            ITMP = 0
C
            DO 100 I = 1,POS
                CHR = TRANS(I)
C
                ITMP = IEOR(ITMP,ICHR)
C
100         CONTINUE
C
            ITMP = IAND(ITMP,IMSK)
C
            ITMP = ITMP + ADD
            IF (ITMP.EQ.32) ITMP = 33
            CHK = TMP
C
            RETURN
            END
```

```
!       This file contains the DUMMY files which replace some of
!       Paul's FASTTEXT files.

!       It also contains the terminal dependent graphic routines
!       needed for the HP terminal !       Subroutine SETSCR(IARG)

!       This is a dummy subroutine - In Paul's version this sets
!       the screen number where 1 = interactive screen used for
!       prompts and 2 = graphic screen where molecules are displayed SUBROUTINE SETSCR(IARG)
        RETURN
        END
!       Subroutine SETCOL(IARG)

!       This is a dummy subroutine - In Paul's version this sets
!       the color of screen to black (0) or white (1)
```

```
          SUBROUTINE SETCOL(IARG)
          RETURN
          END

!   Subroutine FTSIZE(IARG1,IARG2)

!   This is a dummy subroutine - In Paul's version this
!   sets the size of the character used

SUBROUTINE FTSIZE(IARG1,IARG2)
          RETURN
          END

!   This subroutine sets the Y and X locations for subsequent
!   calls to FTEXT SUBROUTINE FTLOCA(IY,IX)
          COMMON /FTLOC/IFTY,IFTX,IOFTY,IOFTX
          COMMON /CHARS/ IES,IDOT,ITAG,JUMP,LBOND,KAN,ISPACE
          IFTY=IY-1
          IFTX=IX-1
          IOFTY=-1
          TYPE 100,IES
100       FORMAT('+',R1,'*dR',$)
          RETURN
          END !   This subroutine sets IndHNDSHK(G) = Yes
!                        IndDC2(H) = Yes
!                        Compatibility = Off SUBROUTINE HNDOFF
          COMMON /CHARS/ IES,IDOT,ITAG,JUMP,LBOND,KAN,ISPACE
          TYPE 21, IES
21        FORMAT('+',r1,'&s1g1h0p0Q',$)
          RETURN
          END !   This subroutine gets the device ID SUBROUTINE DEVICE (MODEL)
          COMMON /CHARS/ IES,IDOT,ITAG,JUMP,LBOND,KAN,ISPACE
          TYPE 22,IES
22        FORMAT('+',R1,'*s1^',$)
          ACCEPT 33,MODEL
33        FORMAT(A5)
          RETURN
          END !   This is terminal dependent code
!   This subroutine downloads the special function keys F1 to F8

SUBROUTINE DOWNLO
          COMMON/KEYS/ICODE(8)
          COMMON/CHARS/IES,IDOT,ITAG,JUMP,LBOND,KAN,ISPACE
          COMMON/MOD/MODEL
          TYPE 1999,IES ! DC1,DC2 off
1999      FORMAT('+',R1,'&s1g1h0p0Q',$)

IF (MODEL.EQ.'2647A') GOTO 3
C *** The following sequence is required for the HP-2623A
          TYPE 11,IES
11        FORMAT('+',R1,'&ja')

TYPE 112,IES,ICODE(8)
112       FORMAT('+',R1,'&f0a1k6d1L     UP ',R1,$)
          TYPE 113,IES,ICODE(4)
113       FORMAT ('+',R1,'&f0a2k14d1L UP  &    RIGHT',R1,$)
          TYPE 114,IES,ICODE(3)
114       FORMAT ('+',R1,'&f0a3k14d1L           RIGHT',R1,$)
          TYPE 115,IES,ICODE(2)
115       FORMAT ('+',R1,'&f0a4k14d1L DOWN &   RIGHT',R1,$)
          TYPE 116,IES,ICODE(1)
116       FORMAT ('+',R1,'&f0a5k6d1L   DOWN',R1,$)
          TYPE 117,IES,ICODE(5)
```

```
117     FORMAT ('+',R1,'&f0a6k14d1L DOWN &     LEFT',R1,$)
        TYPE 118,IES,ICODE(6)
118     FORMAT ('+',R1,'&f0a7k14d1L           LEFT',R1,$)
        TYPE 119,IES,ICODE(7)
119     FORMAT ('+',R1,'&f0a8k14d1L  UP &     LEFT',R1,$)
        TYPE 22,IES
22      FORMAT('+',R1,'&jB')
        RETURN
3       ICR=13 ! Carriage return
C    Following code to download keys onto 2647A terminal:

TYPE 112,IES,ICODE(8)
        TYPE 213,IES,ICODE(4)
213     FORMAT('+',R1,'&f0a2k8d1LUP&RIGHT',R1,$)
        TYPE 214,IES,ICODE(3)
214     FORMAT('+',R1,'&f0a3k6d1L RIGHT',R1,$)
        TYPE 215,IES,ICODE(2)
215     FORMAT('+',R1,'&f0a4k8d1LDN&RIGHT',R1,$)
        TYPE 116,IES,ICODE(1)
        TYPE 217,IES,ICODE(5)
217     FORMAT('+',R1,'&f0a6k8d1LDN &LEFT',R1,$)
        TYPE 218,IES,ICODE(6)
218     FORMAT('+',R1,'&f0a7k6d1L   LEFT',R1,$)
        TYPE 219,IES,ICODE(7)
219     FORMAT('+',R1,'&f0a8k8d1LUP &LEFT',R1,$)
        TYPE 220,IES,ICR ! Display labels on 2647A terminal+
220     FORMAT('+',R1,',cDIsplay Window #7',R1,$)
        RETURN
        END !       This is terminal dependent code
!       This subroutine gets a character (in I3 form - i.e. if A
!       is typed on the keyboard, KAR=065) from the keyboard
!       and the X and Y coordinates SUBROUTINE GETCR(KAR,IX,IY)
        COMMON /CHARS/IES,IDOT,ITAG,JUMP,LBOND,KAN,ISPACE
        COMMON /SIZZE/MULTX,MULTY
        COMMON/OLD/IOX,IOY
        TYPE 20,IES
20      FORMAT('+',R1,'&k0C',$) !Caps lock off
        TYPE 21,IES
21      FORMAT('+',R1,'&k0P',$) !Caps mode disabled
        TYPE 5,IES
5       FORMAT('+',R1,'*dK',$) ! Graphics cursor on
106     TYPE 1,IES
1       FORMAT('+',R1,'b',$) ! Enable keyboard
        TYPE 2,IES
2       FORMAT('+',R1,'*s4^') ! Read cursor position & wait for kbd input
        IREADU=5        !Set read unit
        READ(IREADU,3,ERR=100)NX,NY,KAR  ! Read cursor coordinates, keystoke.i
C                    (KAR=decimal # of ASCII char)
3       FORMAT (I6,1XI6,1XI3)
c       TYPE 4,IES
4       FORMAT('+',R1,'c',$)   ! Disable keyboard
C    CLEAR PREVIOUS ERROR MESSAGE(formats 10-13)
        TYPE 10,IES
        TYPE 11,IES
        TYPE 12,IES
        TYPE 13,IES
10      FORMAT ('+',R1,'m',$) ! memory lock off
11      FORMAT('+',R1,'&a4r1C',$) ! Alpha cursor to 4th line
12      FORMAT('+',R1,'K',$)   ! Clear line
13      FORMAT('+',R1,'l',$)   ! Memory lock on
        IX=NX/MULTX  ! Scale to array coordinates
        IY=NY/MULTY  !  from graphic coordinates.
        IF ((IX*MULTX.NE.NX) .OR. (IY*MULTY.NE.NY))
     2  CALL CURSOR(IX,IY) ! Move cursor to corner if moved
        TYPE 14,IES
14      FORMAT('+',R1,'*dL',$) ! Graphics cursor off
        IF (KAR .EQ. 27) KAR=131        !Set KAR = 131 if KAR = ESC
        RETURN
100     IERR=59
        CALL MYERR(IERR,KAR,KAR)
        TYPE 5, IES
```

```
        ACCEPT 9,A
        GO TO 106
9       FORMAT(R1)
        END

!       FUNCTION GETCHR

!       This function will return the character entered from the
!       keyboard using a Fortran ACCEPT statement with an A1 FORMAT.

INTEGER FUNCTION GETCHR()
        CHARACTER*1 KAR
        COMMON /FTLOC/IFTY,IFTX,IOFTY,IOFTX
        DATA IES/"33/
        IF (IOFTY .EQ. -1) THEN
                        IFFTY=IFTY
                        IFFTX=IFTX
        ELSE
                        IFFTY=IOFTY
                        IFFTX=IOFTX
        ENDIF
        IFFTX=IFFTX+1
        TYPE 50, IES,IFFTY,IFFTX
50      FORMAT('+',R1,'&a',I3,'r',I3,'C',$)

ACCEPT 100,KAR
100     FORMAT(A1)
        GETCHR=ICHAR(KAR)
        IF (GETCHR .EQ. 32) GETCHR = 13 !Set GETCHR to CR if it is blank
        RETURN
        END !       Subroutine CLOSEG !       This is a dummy subroutine - In Paul's version this terminates
!       HALO environment and restores 'host' environment.

SUBROUTINE CLOSEG
        RETURN
        END

!       Subroutine SETTCL(IARG1,IARG2)

!       This is a dummy subroutine - In Paul's version this defines
!       stroke text line and internal color.

SUBROUTINE SETTCL(IARG1,IARG2)
        RETURN
        END

!       INITTC

!       This is a dummy subroutine. In Paul's version it initializes
!       the text cursor

SUBROUTINE INITTC
        RETURN
        END

!       INITHC

!       This is a dummy subroutine. In Paul's version it initializes
!       the cross hair cursor.
        SUBROUTINE INITHC
        RETURN
        END

!       SETTEX

!       This is a dummy subroutine. In Paul's version this sets some
!       text attributes.

SUBROUTINE SETTEX(I1,I2,I3,I4)
        RETURN
        END
```

```
!       SETDEG

!       This is a dummy subroutine. In Paul's version this sets the
!       angle definition to degrees or radians.

SUBROUTINE SETDEG(I1)
        RETURN
        END

!       SETIEE

!       This is a dummy subroutine. In Paul's version this sets the
!       floating font format

SUBROUTINE SETIEE(I1)
        RETURN
        END

!       FTCOLO

!       This is a dummy routine. In Paul's version this sets the character
!       and box colors for FASTTEXT

SUBROUTINE FTCOLO(IARG1,IARG2)
        RETURN
        END

!       This is a set of graphics routines for the HP

!       SETMOD(IARG)

!       This routine sets the drawing mode
!       Input is IARG. It must be in the range 1-4
!       Values out of range are ignored SUBROUTINE SETMOD(IARG)
        IMPLICIT INTEGER(A-Z)
        COMMON /DRAWIT/DRWMOD
        DATA IES/"33/
        IF (IARG .LE. 0 .OR. IARG .GE. 5) RETURN   !Do nothing
                                                   !if IARG is out
                                                   !of range
        IF (IARG .EQ. 1) TYPE 10, IES    !MODE = CLEAR
        IF (IARG .EQ. 2) TYPE 20, IES    !MODE = SET
        IF (IARG .EQ. 3) TYPE 30, IES    !MODE = COMPLEMENT
        IF (IARG .EQ. 4) TYPE 40, IES    !MODE = JAM
        DRWMOD=IARG      !Save drawing mode
10      FORMAT('+',R1,'*m1A',$)
20      FORMAT('+',R1,'*m2A',$)
30      FORMAT('+',R1,'*m3A',$)
40      FORMAT('+',R1,'*m4A',$)
        RETURN
        END

!       SETLNS(IARG)

!       This subroutine sets the line type.
!       Input is IARG. Currently it must be in the range 1-3.
!       If IARG is outside the range, line type will be set
!       to 1 (solid).

SUBROUTINE SETLNS(IARG)
        DATA IES/"33/
        IF (IARG .EQ. 2) THEN
                TYPE 20,IES               !Dashed line
        ELSE IF (IARG .EQ. 3) THEN
                TYPE 30, IES              !Dotted line
        ELSE
                TYPE 10,IES               !Solid line
                ENDIF 10      FORMAT('+',R1,'*m1B',$)
20      FORMAT('+',R1,'*m 170 2 c 2 B',$)
30      FORMAT('+',R1,'*m 85 1 c 2 B',$)
```

```
        RETURN
        END

!       MOVABS(INITX,INITY)

!       This subroutine replaces Paul's MOVABS. It does not cause an
!       actual move with PEN UP to (INITX,INITY). It merely save the
!       X and Y coordinates in INX and INY. This subroutine must
!       be used in conjunction with LNABS(IFINX,IFINY). A call to
!       MOVABS followed by a call to LNABS results in the drawing of
!       a vector from (INITX,INITY) to (IFINX,IFINY) in the mode
!       last set by SETMOD and in the line style last set by SETLNS.

SUBROUTINE MOVABS(INITX,INITY)
        COMMON /VECT/INX,INY
        INX=INITX
        INY=INITY
        RETURN
        END

!       LNABS(IFINX,IFINY)

!       This subroutine will cause a vector to be drawn from
!       (INX,INY) - set by MOVABS - to (IFINX,IFINY) in the mode last
!       set by SETMOD and in the line style last set by SETLNS.

SUBROUTINE LNABS(IFINX,IFINY)
        COMMON /VECT/INX,INY
        DATA IES/"33/
        TYPE 10, IES, INX,INY, IFINX,IFINY
10      FORMAT('+',R1,'*pa',4I4,'A',$)
        RETURN
        END

!       HOME

!       This subroutine moves the alpha cursor home. The 'home'
!       command is different depending on the HP model we are
!       using. Therefore MODEL in the named COMMON MOD must be
!       set to '2623A' or '2647A' before HOME is called. It can
!       be set by calling the subroutine DEVICE

SUBROUTINE HOME
        COMMON /MOD/MODEL
        DATA IES/"33/

IF (MODEL .EQ. '2623A' ) THEN
                        TYPE 10, IES
                        ELSE
                        TYPE 20,IES
                        ENDIF
10      FORMAT('+',R1,'H')
20      FORMAT('+',R1,'h',$)
        RETURN
        END

!       ACLEAR

!       This subroutine will clear the alpha display from the current
!       location of the alpha cursor to the end of memory SUBROUTINE ACLEAR
        DATA IES/"33/
        TYPE 10,IES
10      FORMAT('+',R1,'J')
        RETURN
        END

!       INITGR(IARG)

!       This substitutes for Paul's version of INITGR. This does not
!       really do all that INITGR does. It turns graphic display on,
!       turns alpha display on, turns graphic text mode off and clears
```

```
!       graphic memory. It unlocks alpha memory and moves alpha cursor
!       to HOME position. It clears the alpha screen. IARG is a dummy
!       argument.
        SUBROUTINE INITGR(IARG)
        COMMON /MOD/ MODEL
        DATA IES/"33/
        CALL MEMOFF
        CALL HOME
        CALL ACLEAR
        TYPE 10, IES
10      FORMAT('+',R1,'*dcetA')
        RETURN
        END !       SETGPR
!       This is a dummy subroutine. In Paul's version this sets
!       the hard copy output device

SUBROUTINE SETGPR(I1)
        RETURN
        END

!       FTINIT

!       This is a dummy subroutine. In Paul's version this initializes
!       FASTTEXT

SUBROUTINE FTINIT
        RETURN
        END

!       GPRINT

!       This subroutine makes a hard copy of the current graphic display
        SUBROUTINE GPRINT
        COMMON/CHARS/IES,IDOT,ITAG,JUMP,LBOND,KAN,ISPACE
        COMMON /MOD/MODEL
        CALL CLEAR      !Clear alpha display
722     FORMAT(A5)
        IF (MODEL.EQ.'2623A') TYPE 724,IES ! Print graphics on 2623A
724     FORMAT('+',R1,'&p7s6dF', $)
        IF (MODEL.EQ.'2623A') ACCEPT 722,MD ! S U or F sent by term
        ICR=13 ! Carriage return
        IF (MODEL.EQ.'2647A') TYPE 726,IES,ICR !Print graphics on 2647A
726     FORMAT('+',R1,',c TRansfer File from Graphics to Hp-ib#1',R1,$)
        RETURN
        END

!       MEMOFF

!       This subroutine unlocks the memory

SUBROUTINE MEMOFF
        COMMON/CHARS/IES,IDOT,ITAG,JUMP,LBOND,KAN,ISPACE
        TYPE 4,IES
4       FORMAT('+',R1,'m',$)
        RETURN
        END

!       CLEAR

!       This subroutine clears all the alpha memory including the
!       first few lines which are usually locked SUBROUTINE CLEAR
        CALL MEMOFF     !Unlock memory
        CALL HOME       !Move alpha cursor to home position
        CALL ACLEAR     !Clear screen
        RETURN
        END

!       BAR

!       This replaces Paul's version of BAR. His version draws a
```

!      fat dot with borders defined by JX JY J3X J3Y.

SUBROUTINE BAR(JX,JY,J3X,J3Y)
       IMPLICIT INTEGER(A-Z)
       COMMON /DRAWIT/DRWMOD
       COMMON /CHARS/IES,IDOT,ITAG,JUMP,LBOND,KAN,ISPACE
       JJX=JX+8           !TEST FOR OFFSET
       JJY=JY+8
       OLDMOD=DRWMOD    !Save current drawing mode
       CALL SETMOD(4)   !Set JAM mode
       TYPE 15,IES,JJX,JJY
15     FORMAT('+',R1,'*pa',2i4,'g 0 2 2 0 0 -2 -1 0 0 1 aZ',$)
       CALL SETMOD(OLDMOD)     !Reset old drawing mode
       RETURN
       END

!      CLR

!      This clears the alpha display if IDIS=<1. If not,
!      it clears graphics memory SUBROUTINE CLR
       IMPLICIT INTEGER(A-Z)
       COMMON/HEAD/ MW(12),ISTATE,PAGE
       COMMON /DISPL/IDIS
       COMMON/CHARS/IES,IDOT,ITAG,JUMP,LBOND,KAN,ISPACE
       IF (IDIS .LE. 1) THEN
               CALL CLEAR       !Clear alpha display ELSE
               TYPE 100,IES     !Clear graphics memory
100            FORMAT('+',R1,'*dA',$)
               ENDIF
       RETURN
       END

!      FTEXT

!      This program will display the message in the string S
!      (without the terminator characters) The first and last characters
!      are assumed to be the terminator characters. If the message is
!      a-blank-a where a's are terminators, ERASE is called to erase
!      a single graphics pixel.

!      The message is comprised of all characters encountered after
!      the first delimiter character and before the next delimiter
!      character. The string will be displayed starting at row IFTY
!      and col IFTX. This are set by the subroutine FTLOCA.

SUBROUTINE FTEXT(S)
       CHARACTER S*(*)
       CHARACTER SS(98)*1
       CHARACTER*1 LIM,DELIM
       COMMON /FTLOC/ IFTY,IFTX,IOFTY,IOFTX
       COMMON /CHARS/IES,IDOT,ITAG,JUMP,LBOND,KAN,ISPACE
       DATA IES/"33/
       IF (IOFTY .EQ. -1 ) THEN
                       IFFTY=IFTY
                       IFFTX=IFTX
       ELSE
                       IFFTY=IOFTY
                       IFFTX=IOFTX
       ENDIF
       DELIM = S(1:1)
       DO 10 I=2,98
       LIM=S(I:I)
       IF (LIM .EQ. DELIM) GO TO 12
10     CONTINUE
       I=98
12     L=I
       DO 90 I=2,L-1
       SS(I-1)=S(I:I)
90     CONTINUE
       IF (L .EQ. 3 .AND. SS(1) .EQ. ' ') THEN !We are really trying to
                       ITX=IFFTX+1

```
                    ITY=IFFTY+1
                    CALL ERASE(ITX,ITY)      !erase a pixel
          ELSE
          TYPE 80,IES
80        FORMAT('+',R1,'m',$)       !Memory lock off
          TYPE 134,IES,IFFTY,IFFTX,(SS(I),I=1,L-2)
134       FORMAT('+',R1,'&a',I3,'r',I3,'C',98A1,$)
          ENDIF
          IOFTX=IFFTX+L-2 !This shifts the X value to end of message
          IOFTY=IFFTY
                          !just typed
          RETURN
          END
```

!   MEMDSK

!   This is a dummy subroutine. At the moment it sets the variables
!   BPSECT, SPCLUS and CPDISK to 1 and CLUSTS to 50,000.

```
          SUBROUTINE MEMDSK(CLUSTS,CPDISK,BPSECT,SPCLUS)
          IMPLICIT INTEGER (A-Z)
          CLUSTS=50000
          CPDISK=1
          BPSECT=1
          SPCLUS=1
          RETURN
          END
```

!   MOVTCA

!   This subroutine positions the text cursor (graphics cursor)
!   absolutely.

```
          SUBROUTINE MOVTCA(INTX,INTY)
          DATA IES/"33/
```

!   Graphics text mode off - Position graphics cursor absolutely
!   Turn off graphics cursor

```
          TYPE 111, IES,INTX,INTY
111       FORMAT('+',R1,'xdt',I4,',',I4,'oL',$)
          RETURN
          END
```

!   MOVTCR
!   This subroutine positions the graphics cursor relatively.

```
          SUBROUTINE MOVTCR(INTX,INTY)
          DATA IES/"33/
```

!   Turn off graphic text mode - Position graphic cursor relatively
!   It changes the sign of the Y coordinate to account
!   for the difference in Y addressing.
!   Turn off graphic cursor

```
          MINTY=-INTY
          TYPE 111, IES,INTX,MINTY
111       FORMAT('+',R1,'xdt',I4,',',I4,'pL',$)
          RETURN
          END
```

!   MOVHCA

!   This is a dummy subroutine

```
          SUBROUTINE MOVHCA(INTX,INTY)
          RETURN
          END
```

!   STARTG(IARG)

!   This substitutes for Paul's version of STARTG. This does not
!   really do all that STARTG does. It turns graphic display on,
!   turns alpha display on and turns graphic text mode off. IARG is
!   a dummy argument.

```
        SUBROUTINE STARTG(IARG)
        DATA IES/"33/
        TYPE 10, IES
10      FORMAT('+',R1,'*dceT')
        RETURN
        END

!       DISPLA

!       This subroutine will turn on the display. If IARG is 1, the
!       alpha display will be turned on. If IARG is 2, the graphics
!       display will be turned on.

SUBROUTINE DISPLA(IARG)
        COMMON /DISPL/IDIS
        DATA IES/"33/
        IDIS=IARG
        IF (IARG .EQ. 1) THEN
        TYPE 10,IES
10      FORMAT('+',R1,'*dE',$)    !Turn on alpha display
        ELSE
        TYPE 20,IES
20      FORMAT('+',R1,'*dcT',$)   !Turn on graphics display and
                                  !turn off graphics text mode
        ENDIF
        RETURN
        END

!       TEXT

!       This subroutine will display a single character at the current
!       graphics cursor position

SUBROUTINE TEXT(A)
        IMPLICIT INTEGER (A-Z)
        COMMON /DRAWIT/DRWMOD

CHARACTER A(3)*1
        COMMON/CUR/ICUR
        DATA IES/"33/
        OLDMOD=DRWMOD     !Save old drawing mode
        CALL SETMOD(4)    !Set JAM mode
              IF (ICUR .EQ. 0) THEN
                    TYPE 12,IES,A(2),IES
12                  FORMAT('+',R1,'*dkS',A1,R1,'*dlT',$)    !Graphic text on
                                 !graphics cursor on - type character - graphic
                                 !text off ELSE
                    TYPE 122, IES,A(2),IES
122                 FORMAT('+',R1,'*dS',A1,R1,'*dlT',$)     !Graphic text on
                                 !type character - graphics text off
              ENDIF
        CALL SETMOD(OLDMOD)      !Reset drawing mode
        RETURN
        END

!       MEMON

!       This subroutine locks the memory

SUBROUTINE MEMON
        COMMON/CHARS/IES,IDOT,ITAG,JUMP,LBOND,KAN,ISPACE
        TYPE 4,IES
4       FORMAT('+',R1,'l',$)
        RETURN
        END

!       LINE4

!       This subroutine moves the alpha cursor to X=1 Y=4

SUBROUTINE LINE4
        COMMON /CHARS/IES,IDOT,ITAG,JUMP,LBOND,KAN,ISPACE
```

```
            TYPE 50,IES        !Graphics text mode off
50          FORMAT('+',R1,'*dT',$)
            TYPE 100,IES       !Memory lock off
100         FORMAT('+',R1,'m',$)
            TYPE 87,IES
87          FORMAT('+',R1,'&a4r1C',$)          !Alpha cursor to 4th line
            TYPE 200, IES
200         FORMAT('+',R1,'l',$)    !Memory lock on
            RETURN
            END

!      ERASE

!      This will erase a pixel. If the pixel has address IX,IY,
!      this subroutine will erase area with diagonals defined
!      by (IX*MULTX,IY*MULTY)(IX*MULTX+7,IY*MULTY+10)

SUBROUTINE ERASE(IX,IY)
       IMPLICIT INTEGER(A-Z)
       COMMON /DRAWIT/DRWMOD
       COMMON /CHARS/ IES,IDOT,ITAG,JUMP,LBOND,KAN,ISPACE
       COMMON /SIZZE/MULTX,MULTY
       KX=IX*MULTX
       KY=IY*MULTY
       TYPE 30,IES,KX,KY         !Erase block - See HP manual p10-10
30     FORMAT('+',R1,'*m1a1b',2I4,'j 0 0 7 10 F',$)
       CALL SETMOD(DRWMOD)       !Reset drawing mode
       RETURN
       END

!      ALPOFF

!      This subroutine turns off the ALPHA display

SUBROUTINE ALPOFF
       DATA IES/"33/
       TYPE 100,IES
100    FORMAT('+',R1,'*dF',$)
       RETURN
       END

!      GRAOFF

!      This subroutine turns off the GRAPHIC display

SUBROUTINE GRAOFF
       DATA IES/"33/
       TYPE 100,IES
100    FORMAT('+',R1,'*dD',$)
       RETURN
       END

!      ALPCUR

!      This subroutine moves the alpha cursor to
!      (IFTX+1,IFTY) if IOFTY is -1
!      and sets it to
!      (IOFTX+1,IOFTY) if IOFTY is not -1
!      NOTE: These variables are set by FTLOCA SUBROUTINE ALPCUR
       COMMON /FTLOC/IFTY,IFTX,IOFTY,IOFTX
       DATA IES/"33/
       IF (IOFTY .EQ. -1) THEN
                     IFFTY=IFTY
                     IFFTX=IFTX
       ELSE
                     IFFTY=IOFTY
                     IFFTX=IOFTX
       ENDIF
       IFFTX=IFFTX+1
       TYPE 50, IES,IFFTY,IFFTX
50     FORMAT('+',R1,'&a',I3,'r',I3,'C',$)
       RETURN
       END
```

```
!       This subroutine causes a 1 second delay

SUBROUTINE DELAY
        DATA IES/"33/
        TYPE 100,IES
100     FORMAT('+',R1,'a')
        RETURN
        END

!       This subroutine turns on the Alpha cursor

SUBROUTINE ALPCON
        DATA IES/"33/
        TYPE 100, IES
100     FORMAT('+',R1,'*dQ',$)
        RETURN
        END

!       ISENSE

!       This subroutine will sense the location of the grpahics cursor
!       It will return the coordinates in IX and IY.

SUBROUTINE ISENSE(IX,IY)
        COMMON/CHARS/IES,IDOT,ITAG,JUMP,LBOND,KAN,ISPACE
        COMMON /SIZZE/MULTX,MULTY

TYPE 1,IES
1       FORMAT('+',R1,'&s1g1h0p0Q',$)
C       TYPE 112,IES
112     FORMAT('+',R1,'*dT')
5       TYPE 111,IES
111     FORMAT('+',R1,'*s3^',$)
        continue
        IREADU=5
        READ(IREADU,3,ERR=100) NX,NY      !Sense cursor position
3       FORMAT(I6,1X,I6)
        IX=NX/MULTX
        IY=NY/MULTY
        RETURN
100     GO TO 5              !Bad read of cursor - try again
        RETURN
        END !This subroutine will move the graphics cursor to IX,IY SUBROUTINE GRACUR(IX,IY)
        COMMON/CHARS/IES,IDOT,ITAG,JUMP,LBOND,KAN,ISPACE
        COMMON /SIZZE/MULTX,MULTY C       CONVERT COORDINATES TO RASTER
        INTX=IX*MULTX
        INTY=IY*MULTY
        TYPE 111,IES,INTX,INTY
111     FORMAT('+',R1,'*dt',I4,',',I4,'oL',$)
C       (Cursor will not position correctly unless graphic text mode is
C       turned off)
        RETURN
        END

!       HPLONG(LB)

!       This subroutine contains the HP code for deleting a LONGBOND
!       It deletes long bond with index HP in the LNGBND table SUBROUTINE HPLONG(LB)
        IMPLICIT INTEGER*2 (A-Z)
        REAL THETA,DTHETA,THETA2,DELX,DELY,SLOPE,DX,DY
        INTEGER*4 MM,IDTPIX
```

```
      COMMON /SIZZE/ MULTX,MULTY
       COMMON/DRAWIT/DRWMOD
      COMMON /CD/ MAXX,MAXY
      COMMON /STRPIX/ LPIX,MM(90,38),LBLEN,LNGBND(100,5)
      COMMON /STRED/ IDTPIX(90,38),LABL(260,2),MRKCHN(260)
C
      OLDDRW=DRWMOD
      CALL SETMOD(1)   !Set mode to clear
           IX1 = LNGBND(LB,1)
           IY1 = LNGBND(LB,2)
           IX2 = LNGBND(LB,3)
           IY2 = LNGBND(LB,4)
           KBTYPE = LNGBND(LB,5)
C          Now calculate bond endpoints, based on circle of rad 6
C          surrounding node.
           DX=MULTX*(IX2-IX1)
           DY=MULTY*(IY2-IY1)
           SLOPE = 0.0
      IF (DX .EQ. 0) THEN
      IF (IY2 .GT. IY1) THEN
      DELV1=6
      DELV2=-6
      THETA=1.571
      ELSE
      DELV1=-6
      DELV2=6
      THETA=-1.571
      ENDIF
      DELX=0
      DELY=0
      ELSE
      DELV1=0
      DELV2=0
          SLOPE = DY/DX
          THETA=ATAN(SLOPE)
          IF ((THETA.LE.0.) .AND. (DX.LT.0)) THETA = THETA - 3.14159265
C         Principal value problem
          IF ((THETA.GT.0.) .AND. ((DX.LT.0) .OR. (DY.LT.0)))
     2        THETA = THETA + 3.14159265
C         Bond connects to circle of rad 6 pixels from center of node
          DELX=6*COS(THETA)
          DELY=6*SIN(THETA)
      ENDIF
      JX1=IX1*MULTX+4+DELX
      JY1=IY1*MULTY+5+DELY+DELV1
      JX2=IX2*MULTX+4-DELX
      JY2=IY2*MULTY+5-DELY+DELV2
C
C         Now determine bond type to draw.
          IBOND=1
          IF (KBTYPE.LE.3) IBOND=KBTYPE
C         Set mode, solid line
          CALL SETLNS(1)
C         WIGGLY LINE - BOND TYPE 8
          IF (KBTYPE.EQ.5) CALL SETLNS(2)
C         Single or triple: draw central line:
          IF ((IBOND.EQ.1).OR.(IBOND.EQ.3)) THEN
              CALL MOVABS(JX1,JY1)
              CALL LNABS(JX2,JY2)
          ENDIF
          IF (KBTYPE .EQ. 8) GO TO 70
C         No more lines to draw
          IF (IBOND.EQ.1) GOTO 100
C
C         Calculate side lines for double or triple bonds:
C         Use angle of +-.6 radians from center for side lines for triple;
C         .3 for double
70        CONTINUE
          IF (IBOND.EQ.2) THEN
              DTHETA = .2
          ELSE IF ((KBTYPE.EQ.8).OR.(IBOND.EQ.3)) THEN
              DTHETA = .6
          ENDIF
C         Change sign
          DO 55 I=1,-1,-2
```

```
            IF ((KBTYPE.EQ.8).AND.(I.EQ.1)) CALL SETLNS(2)
            IF ((KBTYPE.EQ.8).AND.(I.EQ.-1)) CALL SETLNS(3)
         THETA2 = THETA + DTHETA*I
         DELX= (6*COS(THETA2))
         DELY=(6*SIN(THETA2))
         JX1 = IX1 * MULTX + 4 + DELX
         JY1 = IY1 * MULTY + 5 + DELY
         THETA2 = 3.14159265 + THETA - I*DTHETA
         DELX=(6*COS(THETA2))
         DELY=(6*SIN(THETA2))
         JX2 = IX2 * MULTX + 4 + DELX
         JY2 = IY2 * MULTY + 5 + DELY
            CALL MOVABS(JX1,JY1)
            CALL LNABS(JX2,JY2)
55          CONTINUE
100         CONTINUE
            CALL SETLNS(1)
C           Solid line
1000    CONTINUE
         CALL SETMOD(OLDDRW)      !Restore old drawing mode
         RETURN
         END
!       BERASE
!
!       This will erase a pixel. If the pixel has address IX,IY,
!       this subroutine will erase area with diagonals defined
!       by (IX*MULTX-2,IY*MULTY-3)(IX*MULTX+10,IY*MULTY+12)
         SUBROUTINE BERASE(IX,IY)
         IMPLICIT INTEGER(A-Z)
         COMMON /DRAWIT/DRWMOD
         COMMON /CHARS/ IES,IDOT,ITAG,JUMP,LBOND,KAN,ISPACE
         COMMON /SIZZE/MULTX,MULTY
         KX=IX*MULTX
         KY=IY*MULTY
         TYPE 30,IES,KX,KY        !Erase block - See HP manual p10-10
30       FORMAT('+',R1,'*m1a1b',2I4,'j -2 -3 10 12 F',$)
         CALL SETMOD(DRWMOD)      !Reset drawing mode
         RETURN
         END
```

What is claimed is:

1. A computer-operated method for minimizing the number of keystrokes required to be entered at a data entry keyboard to display two-dimensional figures on a display controlled by a computer, which display is subdivided into multiple two-dimensionally arrayed grid locations, said figures being made up of plural individual segments to be entered from said keyboard and displayed in individual display grid locations, some of said segments taking the form of alphanumeric characters corresponding to keys of said keyboard, others of said segments taking the form of directional symbols having forward and rearward ends and which, when displayed, link displayed alphanumeric characters and extend in respective horizontal, vertical and diagonal directions on said display, the method comprising the steps of:

(a) entering into the computer signals representing individual graphic figure segments actuated in succession on said keyboard;

(b) storing within said computer a stored array of entered characters with locations corresponding to respective grid locations on said display;

(c) establishing a movable cursor grid location on said display;

(d) providing a plurality of selectable operating states for said computer, in each of which said plural operating states said component will interpret key entries on said keyboard differently;

(e) for each of said plural operating states, providing a protocol of preferred display element orientations each having an order of preference;

(f) storing within said computer a plurality of display elements each having a plurality of permissible orientations;

(g) in response to the entry of a display element recall code, examining in said computer said entered display element recall code and determining the identity of a corresponding stored display element to be recalled;

(h) recalling said identified stored display element;

(i) applying said respective protocol of permissible display element orientations to said identified recalled display element; and (j) orienting the recalled display element relative to a grid location on said display according to said respective protocol.

2. A computer-operated method as claimed in claim 1, wherein said plural operating states comprise a ring state corresponding to the displaying of ringed chemical structural symbols and a chain state corresponding to the displaying of chained chemical structural symbols.

3. The computer-operated method according to claim 1, wherein said display element recall code further comprises a connection code.

4. The computer-operated method according to claim 3, further comprising the steps of:

specifying markers for each said display element for indicating the location of atoms of chemical structures represented by said display elements; and identifying the location of each marker in each said recalled display element according to a predetermined sequence, said predetermined sequence beginning at a point therealong determined from the marker most recently used on said display prior to recall of each said stored display element.

5. The computer-operated method according to claim 1, wherein said display element recall code selectively contains a connection code;

and further comprising the step of examining said display element recall code to determine the presence of a connection code;

in response to the presence of a connection code, connecting said display element in accordance with said connection code; and if the absence of a connection code is detected, applying a default connection code to determine connection of said display element.

6. The computer-operated method according to claim 5, wherein said connection code selectively specifies a connection by a joined bond attachment between chemical structures to be displayed, a connection by fusion of one side between chemical structures to be displayed, and a connection by fusion of two sides between chemical structures to be displayed.

7. The computer-operated method according to claim 1, wherein the recalled said display element, once oriented, can be re-oriented in accordance with the respective said protocol by entry of a re-orientation command.

8. The computer-operated method according to claim 7, further comprising the step of entering a flip command to provide a mirror-image orientation of a recalled asymmetrical display element about a predetermined point.

9. The computer-operated method according to claim 1, wherein at least some of said stored display elements have a specified merging bond attachment site associated therewith at which merging bond attachment sites said respective display elements may be connected to other display elements on said display.

10. A computer-operated method for data-entry at a keyboard to display two-dimensional figures on a display controlled by said computer, comprising the steps of:

(a) storing within a computer a plurality of stored display elements, each said stored display element corresponding to a respective system operating state in each which respective system operating state key entries are differently interpreted by said computer to cause graphic figures to be displayed in corresponding different ways on said display;

(b) establishing a movable cursor grid location on said display;

(c) entering into the computer signals representing individual graphic figure segments actuated in succession at said keyboard;

(d) in response to entry at said keyboard of a display element recall code, recalling one of said plurality of stored display elements corresponding thereto; and (e) orienting said recalled display element according to a connection code protocol corresponding to a respective said system operating state.

11. A computer-operated method as claimed in claim 10, wherein said respective system operating state includes a chain state for displaying of chained chemical structural symbols and a ring state for displaying of ringed chemical structural symbols.

12. A computer-operated method as claimed in claim 11, wherein said connection code protocol includes spiro, hinged and jointed chemical bond attachment interfaces having specified predetermined permissible display orientations.

13. A computer-operated method of claim 10, wherein a plurality of system operating states are provided, including a chain state for displaying of chained chemical structural symbols, a ring state for displaying of ringed chemical structural symbols, a ground state for displaying display elements on said display as entered at said keyboard, and a retrieve state for retrieving from said computer stored user-defined graphic figures.

14. The computer-operated method of claim 10, further comprising the step just prior to step (a) of specifying a connecting site on at least some of said plurality of stored display elements.

15. The computer-operated method of claim 10, wherein said connection code protocol includes a preferred, ordered set of angle-pairs, and of preferred angles of rotation.

16. A computer-operated method for data entry at a keyboard to display two-dimensional figures at a display controlled by said computer, comprising the steps of:

(a) storing within said computer a plurality of stored display elements, each display element having nodes;

(b) establishing a predetermined marker sequence and ;

(c) in response to recall of a display element, recalling one of said plurality of figures and determining the position in said predetermined sequence of a last marker used for designating an atom;

said figure having markers arranged according to said predetermined sequence beginning from said last marker used.

17. The computer-operated display of claim 16, further including the steps of:

in response to the presence of an alphanumeric character in the present cursor display grid location and to an entered figure segment corresponding to a directional symbol: moving the cursor grid location under computer control to a new cursor grid location one grid space in the direction of the entered directional symbol segment.

18. The computer-operated method according to claim 16, further comprising the steps of:

in response to the presence of two alphanumeric characters supplied from a data-input means, supplying a directional symbol between the two alphanumeric characters.

19. The computer-operated method of claim 16, further comprising the steps of:

supplying a signal by an input means to said computer to indicate completion of a diagram;

wherein in response to said completion symbol, supplying under computer control all remaining markers with a symbol most commonly occurring in diagrams.

20. The computer-operated method of claim 18, wherein said symbol is the chemical symbol for a carbon atom.

21. The computer-operated method of claim 16, wherein said predetermined sequence is permitted to repeat;

further comprising the steps of:

in response to inputting a symbol when the present cursor display grid location corresponds to a marker location, replacing said marker with said symbol;

in response to inputting a marker symbol, moving the cursor grid location under computer control to a new cursor grid location corresponding to the last said marker used; and in response to input of a command signal which indicates that another marker in a previous sequence was to have been identified, moving the cursor grid location under computer control to a new cursor grid location corresponding to an immediately preceding said marker in an immediately preceding said predetermined sequence.

* * * * *